US008575135B2

(12) United States Patent
Bacon et al.

(10) Patent No.: US 8,575,135 B2
(45) Date of Patent: Nov. 5, 2013

(54) ANTIVIRAL COMPOUNDS

(71) Applicant: Gilead Sciences, Inc., Foster City, CA (US)

(72) Inventors: Elizabeth M. Bacon, Burlingame, CA (US); Jeromy J. Cottell, Redwood City, CA (US); Ashley Anne Katana, San Mateo, CA (US); Darryl Kato, San Francisco, CA (US); Evan S. Krygowski, Washington, DC (US); John O. Link, San Francisco, CA (US); James Taylor, San Mateo, CA (US); Chinh Viet Tran, San Diego, CA (US); Teresa Alejandra Trejo Martin, Union City, CA (US); Zheng-Yu Yang, Palo Alto, CA (US); Sheila Zipfel, San Mateo, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 13/783,056

(22) Filed: Mar. 1, 2013

(65) Prior Publication Data
US 2013/0177530 A1 Jul. 11, 2013

Related U.S. Application Data

(63) Continuation of application No. 13/679,874, filed on Nov. 16, 2012.

(60) Provisional application No. 61/560,654, filed on Nov. 16, 2011.

(51) Int. Cl.
A01N 43/16 (2006.01)
A01N 33/18 (2006.01)
A01N 33/24 (2006.01)
A61K 31/35 (2006.01)
A61K 31/04 (2006.01)
C07D 207/46 (2006.01)
C07D 295/00 (2006.01)

(52) U.S. Cl.
USPC ............ 514/92; 514/894; 514/741; 514/453; 548/571

(58) Field of Classification Search
USPC .......................... 514/894, 741, 453; 548/571
See application file for complete search history.

(56) References Cited

FOREIGN PATENT DOCUMENTS

| WO | WO-2008/021927 | 2/2008 |
|---|---|---|
| WO | WO-2008/021928 | 2/2008 |
| WO | WO-2008/021936 | 2/2008 |
| WO | WO-2009/102318 | 8/2009 |
| WO | WO-2009/102325 | 8/2009 |
| WO | WO-2009/102633 | 8/2009 |
| WO | WO-2010/062821 | 6/2010 |
| WO | WO-2010/065681 | 6/2010 |
| WO | WO-2010/096777 | 8/2010 |
| WO | WO-2010/099527 | 9/2010 |
| WO | WO-2010/132601 | 11/2010 |
| WO | WO-2010/138368 | 12/2010 |
| WO | WO-2011/028596 | 3/2011 |
| WO | WO-2011/066241 | 6/2011 |
| WO | WO-2011/075439 | 6/2011 |
| WO | WO-2011/087740 | 7/2011 |
| WO | WO-2011/112429 | 9/2011 |
| WO | WO-2011/146401 | 11/2011 |
| WO | WO-2012/027712 | 3/2012 |
| WO | WO-2012/048421 | 4/2012 |
| WO | WO-2012/068234 | 5/2012 |
| WO | WO-2012/087976 | 6/2012 |

OTHER PUBLICATIONS

U.S. Appl. No. 13/679,862, filed Nov. 16, 2012, Bacon et al.
U.S. Appl. No. 13/679,874, filed Nov. 16, 2012, Bacon et al.
International Search Report and Written Opinion for PCT/US2011/060966 dated Sep. 19, 2012.
International Search Report and Written Opinion for PCT/US2012/065681 dated Jan. 25, 2013.

Primary Examiner — Jeffrey S. Lundgren
Assistant Examiner — Chris Simmons
(74) Attorney, Agent, or Firm — Sheppard, Mullin, Richter & Hampton LLP; Lorna L. Tanner

(57) ABSTRACT

The disclosure is related to anti-viral compounds, compositions containing such compounds, and therapeutic methods that include the administration of such compounds, as well as to processes and intermediates useful for preparing such compounds.

7 Claims, No Drawings

ANTIVIRAL COMPOUNDS

CROSS REFERENCE TO RELATED APPLICATIONS

This application is a continuation of U.S. application Ser. No. 13/679,874, filed Nov. 16, 2012, which application claims the benefit under 35 U.S.C. §119(e) of U.S. Provisional Application No. 61/560,654 filed on Nov. 16, 2011, which applications are hereby incorporated by reference in their entirety.

BACKGROUND

Hepatitis C is recognized as a chronic viral disease of the liver which is characterized by liver disease. Although drugs targeting the liver are in wide use and have shown effectiveness, toxicity and other side effects have limited their usefulness. Inhibitors of hepatitis C virus (HCV) are useful to limit the establishment and progression of infection by HCV as well as in diagnostic assays for HCV.

There is a need for new HCV therapeutic agents. In particular, there is a need for HCV therapeutic agents that have broad activity against HCV genotypes (e.g. genotypes 1a, 1b, 2a, 3a, 4a). There is also a particular need for agents that are less susceptible to viral resistance. Resistance mutations to inhibitors have been described for HCV NSSA for genotypes 1a and 1b in Antimicrobial Agents and Chemotherapy, September 2010, Volume 54, p. 3641-3650.

SUMMARY

In one embodiment the disclosure provides a compound of the disclosure which is a compound of formula (I):

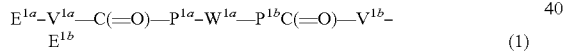

(1)

wherein:
$W^{1a}$ is

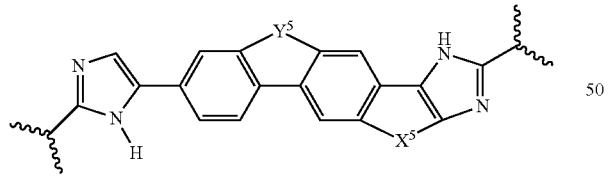

and $W^{1a}$ is optionally substituted with one or more groups independently selected from halo, alkyl, haloalkyl, or cyano;

$Y^5$ is —O—CH$_2$—, or —CH$_2$—O—; $X^5$ is —CH$_2$—CH$_2$— or —CH=CH—;

$E^{1a}$ is —N(H)(alkoxycarbonyl), —N(H)(cycloalkylcarbonyl) or —N(H)(cycloalkyloxycarbonyl); or $E^{1a}$-$V^{1a}$ taken together are $R^{9a}$;

$E^{1b}$ is —N(H)(alkoxycarbonyl), —N(H)(cycloalkylcarbonyl) or —N(H)(cycloalkyloxycarbonyl); or $E^{1b}$-$V^{1b}$ taken together are $R^{9b}$;

$V^{1a}$ and $V^{1b}$ are each independently selected from:

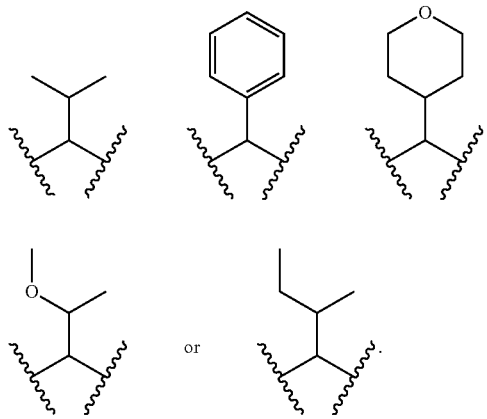

$P^{1a}$ is selected from:

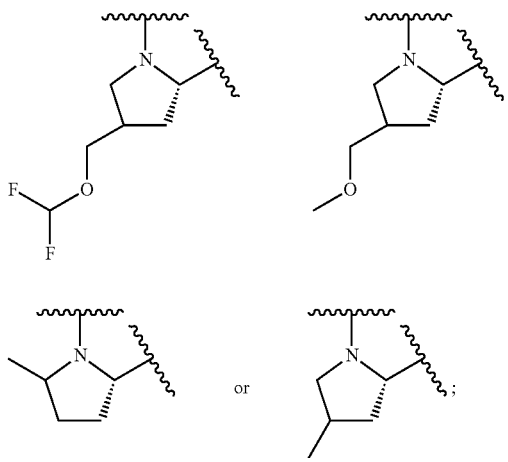

$P^{1b}$ is selected from:

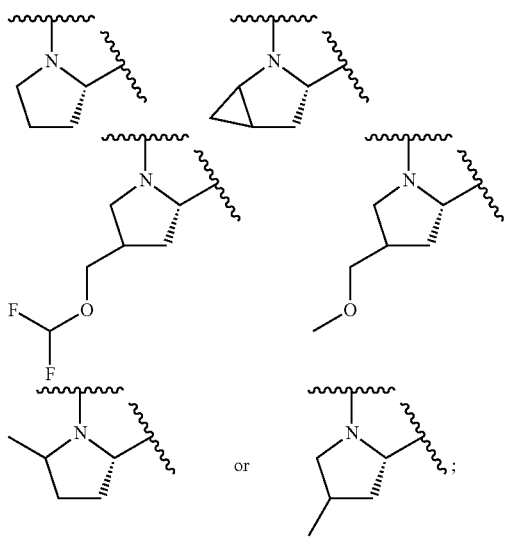

and
R$^{9a}$ and R$^{9b}$ are each independently:

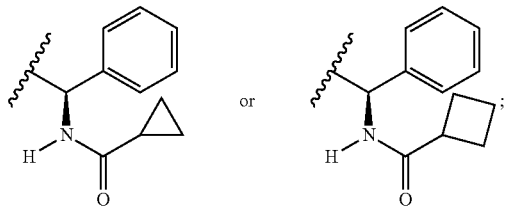 [SMILES: *[C@H](NC(=O)C1CC1)c1ccccc1 ; *[C@H](NC(=O)C1CCC1)c1ccccc1]

or a pharmaceutically acceptable salt or prodrug thereof.

The disclosure also provides isotopically enriched compounds that are compounds of the disclosure that comprise an enriched isotope at one or more positions in the compound.

The present disclosure also provides a pharmaceutical composition comprising a compound of the disclosure or a pharmaceutically acceptable salt or prodrug thereof and at least one pharmaceutically acceptable carrier.

The present disclosure also provides a pharmaceutical composition for use in treating hepatits C(HCV). In one embodiment the composition comprises at least one additional therapeutic agent for treating HCV. In one embodiment, the therapeutic agent is selected from ribavirin, an NS3 protease inhibitor, a nucleoside or nucleotide inhibitor of HCV NS5B polymerase, an alpha-glucosidase 1 inhibitor, a hepatoprotectant, a non-nucleoside inhibitor of HCV polymerase, or combinations thereof. In one embodiment, composition further comprises a nucleoside or nucleotide inhibitor of HCV NS5B polymerase. In one embodiment, the nucleoside or nucleotide inhibitor of HCV NS5B polymerase is selected from ribavirin, viramidine, levovirin, a L-nucleoside, or isatoribine.

In one embodiment is provided a pharmaceutical composition comprising a compound as described herein and at least one nucleoside or nucleotide inhibitor of HCV NS5B polymerase, and at least one pharmaceutically acceptable carrier. In one embodiment, the composition further comprises an interferon, a pegylated interferon, ribavirin or combinations thereof. In one embodiment, the compound is the compound exemplified in Example PY. In one embodiment the nucleoside or nucleotide inhibitor of HCV NS5B polymerase is sofosbuvir.

The present disclosure also provides a pharmaceutical composition further comprising an interferon or pegylated interferon.

The present disclosure also provides a pharmaceutical composition further comprising a nucleoside analog.

The present disclosure also provides for a pharmaceutical composition wherein said nucleoside analogue is selected from ribavirin, viramidine, levovirin, an L-nucleoside, and isatoribine and said interferon is α-interferon or pegylated α-interferon.

The present disclosure also provides for a method of treating hepatitis C, said method comprising administering to a human patient a pharmaceutical composition which comprises a therapeutically effective amount of a compound of the disclosure.

The present disclosure also provides a method of inhibiting HCV, comprising administering to a mammal afflicted with a condition associated with HCV activity, an amount of a compound of the disclosure, effective to inhibit HCV.

The present disclosure also provides a compound of the disclosure for use in medical therapy (e.g. for use in inhibiting HCV activity or treating a condition associated with HCV activity), as well as the use of a compound of the disclosure for the manufacture of a medicament useful for inhibiting HCV or the treatment of a condition associated with HCV activity in a mammal.

The present disclosure also provides synthetic processes and novel intermediates disclosed herein which are useful for preparing compounds of the disclosure. Some of the compounds of the disclosure are useful to prepare other compounds of the disclosure.

In another aspect the disclosure provides a compound of the disclosure, or a pharmaceutically acceptable salt or prodrug thereof, for use in the prophylactic or therapeutic treatment of hepatitis C or a hepatitis C associated disorder.

In another aspect the disclosure provides a method of inhibiting HCV activity in a sample comprising treating the sample with a compound of the disclosure.

Compounds of formula (I) have been found to possess useful activity against HCV genotypes. Additionally certain compounds of formula (I) have significant potency against resistant variants in GT1.

Accordingly, certain compounds of formula (I) possess beneficial pharmacological properties that make them well suited to fulfill the current need for HCV agents with such beneficial properties.

In one embodiment the disclosure provides a compound having improved inhibitory or pharmacokinctic properties, including enhanced activity against development of viral resistance, improved oral bioavailability, greater potency (for example, in inhibiting HCV activity) or extended effective half-life in vivo. Certain compounds of the disclosure may have fewer side effects, less complicated dosing schedules, or be orally active.

DETAILED DESCRIPTION

Reference will now be made in detail to certain embodiments of the disclosure, examples of which are illustrated in the accompanying structures and formulas. While the disclosure will be described in conjunction with the enumerated embodiments, it will be understood that they are not intended to limit the disclosure to those embodiments. On the contrary, the disclosure is intended to cover all alternatives, modifications, and equivalents, which may be included within the scope of the present disclosure as defined by the embodiments.

Compounds

The compounds of the disclosure exclude compounds heretofore known. However, it is within the disclosure to use compounds that previously were not known to have antiviral properties for antiviral purposes (e.g. to produce an anti-viral effect in an animal). With respect to the United States, the compounds or compositions herein exclude compounds that are anticipated under 35 USC §102 or that are obvious under 35 USC §103.

Whenever a compound described herein is substituted with more than one of the same designated group, e.g., "R$^1$" or "A$^3$", then it will be understood that the groups may be the same or different, i.e., each group is independently selected.

"Absent"—Some groups are defined such that they can be absent. When a group is absent it becomes a bond connector. The two groups that would otherwise be connected to that absent group are connected to each other through a bond.

The "P" groups (e.g. P$^{1a}$ and P$^{1b}$) defined for formula (I) herein have one bond to a —C(=O)— of formula (I) and one bond to a W$^{1a}$ group. It is to be understood that a nitrogen of the P group is connected to the —C(=O)— group of formula (I) and that a carbon of the P group is connected to the $W^{1a}$ group.

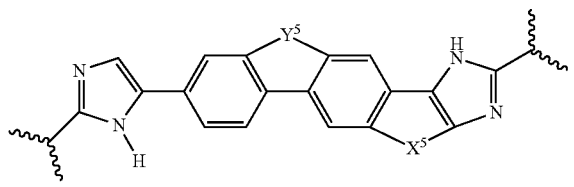

In the $W^{1a}$ group a $Y^5$ group is present. When that $Y^5$ group is defined as —O—CH$_2$—, or —CH$_2$—O— group, those $Y^5$ groups have a directionality. The $Y^5$ group is connected to the $W^{1a}$ group in the same left to right directionality that each is drawn. So for example, when $Y^5$ is —O—CH$_2$—, the directly following structure is intended:

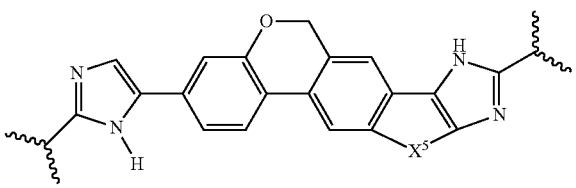

For example, when $Y^5$ is —CH$_2$—O—, the directly following structure is intended:

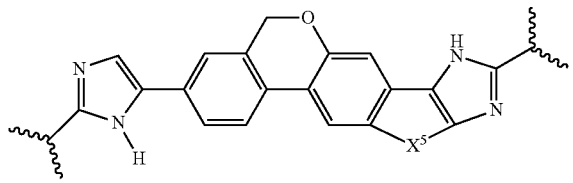

In the structure I, the $W^{1a}$ group has a left-to-right directionality as depicted in I and $W^{1a}$ as drawn.

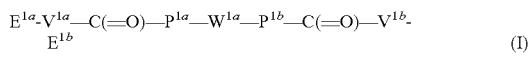

wherein:
$W^{1a}$ is

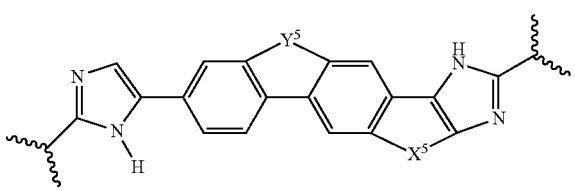

For example, the $P^{1a}$ group is connected to the imidazole group of $W^{1a}$, and the $P^{1b}$ group is connected to the pentacyclic ring system of $W^{1a}$.

"Alkyl" is C$_1$-C$_{18}$ hydrocarbon containing normal, secondary, tertiary or cyclic carbon atoms. Examples are methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$, and cyclopropylmethyl

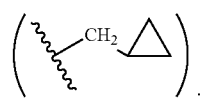

"Alkenyl" is C$_2$-C$_{18}$ hydrocarbon containing normal, secondary, tertiary or cyclic carbon atoms with at least one site of unsaturation, i.e. a carbon-carbon, sp$^2$ double bond. Examples include, but are not limited to, ethylene or vinyl (—CH=CH$_2$), allyl (—CH$_2$CH=CH$_2$), cyclopentenyl (—C$_5$H$_7$), and 5-hexenyl (—CH$_2$CH$_2$CH$_2$CH$_2$CH=CH$_2$).

"Alkynyl" is C$_2$-C$_{18}$ hydrocarbon containing normal, secondary, tertiary or cyclic carbon atoms with at least one site of unsaturation, i.e. a carbon-carbon, sp triple bond. Examples include, but are not limited to, acetylenic (—C≡CH) and propargyl (—CH$_2$C≡CH).

"Alkylene" refers to a saturated, branched or straight chain or cyclic hydrocarbon radical of 1-18 carbon atoms, and having two monovalent radical centers derived by the removal of two hydrogen atoms from the same or two different carbon atoms of a parent alkane. Typical alkylene radicals include, but are not limited to, methylene (—CH$_2$—) 1,2-ethyl (—CH$_2$CH$_2$—), 1,3-propyl (—CH$_2$CH$_2$CH$_2$—), 1,4-butyl (—CH$_2$CH$_2$CH$_2$CH$_2$—), and the like.

"Alkenylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkene. Typical alkenylene radicals include, but are not limited to, 1,2-ethylene (—CH=CH—).

"Alkynylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkyne. Typical alkynylene radicals include, but are not limited to, acetylene (—C≡C—), propargyl (—CH$_2$C≡C—), and 4-pentynyl (—CH$_2$CH$_2$CH$_2$C≡CH).

The term "alkoxy" or "alkyloxy," as used herein, refers to an alkyl group attached to the parent molecular moiety through an oxygen atom.

The term "alkoxycarbonyl," as used herein, refers to an alkoxy group attached to the parent molecular moiety through a carbonyl group.

The term "cycloalkyl," as used herein, refers to a saturated monocyclic, hydrocarbon ring system having three to seven carbon atoms and zero heteroatoms. Representative examples of cycloalkyl groups include, but are not limited to, cyclopropyl, cyclopentyl, and cyclohexyl. The cycloalkyl groups of the present disclosure are optionally substituted with one, two, three, four, or five substituents independently selected from alkoxy, alkyl, aryl, cyano, halo, haloalkoxy, haloalkyl, heterocyclyl, hydroxy, hydroxyalkyl, nitro, and —NR$^x$R$^y$ wherein the aryl and the heterocyclyl are further optionally substituted with one, two, or three substituents independently selected from alkoxy, alkyl, cyano, halo, haloalkoxy, haloalkyl, hydroxy, and nitro.

The term "cycloalkylcarbonyl," as used herein, refers to a cycloalkyl group attached to the parent molecular moiety through a carbonyl group.

The term "cycloalkyloxy," as used herein, refers to a cycloalkyl group attached to the parent molecular moiety through an oxygen atom.

The term "cycloalkyloxycarbonyl," as used herein, refers to a cycloalkyloxy group attached to the parent molecular moiety through a carbonyl group.

"Aryl" means a monovalent aromatic hydrocarbon radical of 6-20 carbon atoms derived by the removal of one hydrogen atom from a single carbon atom of a parent aromatic ring system. Typical aryl groups include, but are not limited to, radicals derived from benzene, substituted benzene, naphthalene, anthracene, biphenyl, and the like.

"Arylalkyl" refers to an acyclic alkyl radical in which one of the hydrogen atoms bonded to a carbon atom, typically a terminal or sp$^3$ carbon atom, is replaced with an aryl radical. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl group comprises 6 to 20 carbon atoms, e.g., the alkyl moiety, including alkanyl, alkenyl or alkynyl groups, of the arylalkyl group is 1 to 6 carbon atoms and the aryl moiety is 5 to 14 carbon atoms.

"Substituted alkyl", "substituted aryl", and "substituted arylalkyl" mean alkyl, aryl, and arylalkyl respectively, in which one or more hydrogen atoms are each independently replaced with a non-hydrogen substituent. Typical substituents include, but are not limited to: halo (e.g. F, Cl, Br, I), —R, —OR, —SR, —NR$_2$, —CF$_3$, —CCl$_3$, —OCF$_3$, —CN, —NO$_2$, —N(R)C(=O)R, —C(=O)R, —OC(=O)R, —C(O)OR, —C(=O)NRR, —S(=O)R, —S(=O)$_2$OR, —S(=O)$_2$R, —OS(=O)$_2$OR, —S(=O)$_2$NRR, and each R is independently —H, alkyl, aryl, arylalkyl, or heterocycle. Alkylene, alkenylene, and alkynylene groups may also be similarly substituted.

The term "optionally substituted" in reference to a particular moiety of the compound of formula I, (e.g., an optionally substituted aryl group) refers to a moiety having 0, 1, 2, or more substituents.

The symbol "====" in a ring structure means that a bond is a single or double bond. In a non-limiting example,

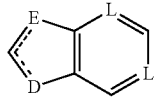

can be

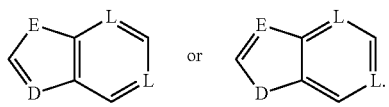

"Haloalkyl" as used herein includes an alkyl group substituted with one or more halogens (e.g. F, Cl, Br, or I). Representative examples of haloalkyl include trifluoromethyl, 2,2,2-trifluoroethyl, and 2,2,2-trifluoro-1-(trifluoromethyl)ethyl.

"Heterocycle" or "heterocyclyl" as used herein includes by way of example and not limitation these heterocycles described in Paquette, Leo A.; Principles of Modern Heterocyclic Chemistry (W.A. Benjamin, New York, 1968), particularly Chapters 1, 3, 4, 6, 7, and 9; The Chemistry of Heterocyclic Compounds, A Series of Monographs" (John Wiley & Sons, New York, 1950 to present), in particular Volumes 13, 14, 16, 19, and 28; and J. Am. Chem. Soc. (1960) 82:5566. In one specific embodiment, "heterocycle" includes a "carbocycle" as defined herein, wherein one or more (e.g. 1, 2, 3, or 4) carbon atoms have been replaced with a heteroatom (e.g. O, N, or S). The term heterocycle also includes "heteroaryl" which is a heterocycle wherein at least one heterocyclic rings is aromatic.

Examples of heterocycles include by way of example and not limitation pyridyl, dihydropyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4H-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl oxazolidinyl, benzotriazolyl, benzisoxazolyl, oxindolyl, benzoxazolinyl, isatinoyl, and bis-tetrahydrofuranyl:

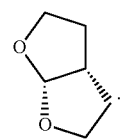

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Carbocycle" refers to a saturated, unsaturated or aromatic ring having up to about 25 carbon atoms. Typically, a carbocycle has about 3 to 7 carbon atoms as a monocycle, about 7 to 12 carbon atoms as a bicycle, and up to about 25 carbon atoms as a polycycle. Monocyclic carbocycles typically have 3 to 6 ring atoms, still more typically 5 or 6 ring atoms. Bicyclic carbocycles typically have 7 to 12 ring atoms, e.g., arranged as a bicyclo[4,5], [5,5], [5,6] or [6,6] system, or 9 or 10 ring atoms arranged as a bicyclo[5,6] or [6,6] system. The term carbocycle includes "cycloalkyl" which is a saturated or unsaturated carbocycle. Examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl, spiryl and naphthyl.

The term "amino," as used herein, refers to $-NH_2$.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

The term "treatment" or "treating," to the extent it relates to a disease or condition includes preventing the disease or condition from occurring, inhibiting the disease or condition, eliminating the disease or condition, and/or relieving one or more symptoms of the disease or condition.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., Stereochemistry of Organic Compounds (1994) John Wiley & Sons, Inc., New York. Many organic compounds exist in optically active forms, i.e., they have the ability to rotate the plane of plane-polarized light. In describing an optically active compound, the prefixes (D and L) or (R and S) are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity. The disclosure includes all stereoisomers of the compounds described herein.

Prodrugs

The term "prodrug" as used herein refers to any compound that when administered to a biological system generates a compound of the disclosure that inhibits HCV activity ("the active inhibitory compound"). The compound may be formed from the prodrug as a result of: (i) spontaneous chemical reaction(s), (ii) enzyme catalyzed chemical reaction(s), (iii) photolysis, and/or (iv) metabolic chemical reaction(s).

"Prodrug moiety" refers to a labile functional group which separates from the active inhibitory compound during metabolism, systemically, inside a cell, by hydrolysis, enzymatic cleavage, or by some other process (Bundgaard, Hans, "Design and Application of Prodrugs" in A Textbook of Drug Design and Development (1991), P. Krogsgaard-Larsen and H. Bundgaard, Eds. Harwood Academic Publishers, pp. 113-191). Enzymes which are capable of an enzymatic activation mechanism with the prodrug compounds of the disclosure include, but are not limited to, amidases, esterases, microbial enzymes, phospholipases, cholinesterases, and phosphases. Prodrug moieties can serve to enhance solubility, absorption and lipophilicity to optimize drug delivery, bioavailability and efficacy. A prodrug moiety may include an active metabolite or drug itself.

Exemplary prodrug moieties include the hydrolytically sensitive or labile acyloxymethyl esters $-CH_2OC(=O)R^{99}$ and acyloxymethyl carbonates $-CH_2C(=O)OR^{99}$ where $R^{99}$ is $C_1$-$C_6$ alkyl, $C_1$-$C_6$ substituted alkyl, $C_6$-$C_{20}$ aryl or $C_6$-$C_{20}$ substituted aryl. The acyloxyalkyl ester was first used as a prodrug strategy for carboxylic acids and then applied to phosphates and phosphonates by Farquhar et al. (1983) J. Pharm. Sci. 72: 324; also U.S. Pat. Nos. 4,816,570, 4,968, 788, 5,663,159 and 5,792,756. Subsequently, the acyloxyalkyl ester was used to deliver phosphonic acids across cell membranes and to enhance oral bioavailability. A close variant of the acyloxyalkyl ester, the alkoxycarbonyloxyalkyl ester (carbonate), may also enhance oral bioavailability as a prodrug moiety in the compounds of the combinations of the disclosure. An exemplary acyloxymethyl ester is pivaloyloxymethoxy, (POM) $-CH_2C(=O)C(CH_3)_3$. An exemplary acyloxymethyl carbonate prodrug moiety is pivaloyloxymethylcarbonate (POC) $-CH_2C(=O)OC(CH_3)_3$.

Aryl esters of phosphorus groups, especially phenyl esters, are reported to enhance oral bioavailability (De Lombaert et al. (1994) J. Med. Chem. 37: 498). Phenyl esters containing a carboxylic ester ortho to a phosphate have also been described (Khamnei and Torrence, (1996) J. Med. Chem. 39:4109-4115). Benzyl esters are reported to generate parent phosphonic acids. In some cases, substituents at the ortho- or para-position may accelerate the hydrolysis. Benzyl analogs with an acylated phenol or an alkylated phenol may generate the phenolic compound through the action of enzymes, e.g., esterases, oxidases, etc., which in turn undergoes cleavage at the benzylic C—O bond to generate phosphoric acid and a quinone methide intermediate. Examples of this class of prodrugs are described by Mitchell et al. (1992) J. Chem. Soc. Perkin Trans. II 2345; Glazier WO 91/19721. Still other benzylic prodrugs have been described containing a carboxylic ester-containing group attached to the benzylic methylene (Glazier WO 91/19721). Thio-containing prodrugs are reported to be useful for the intracellular delivery of phosphonate drugs. These proesters contain an ethylthio group in which the thiol group is either esterified with an acyl group or combined with another thiol group to form a disulfide. Deesterification or reduction of the disulfide generates the free thio intermediate which subsequently breaks down to the phosphoric acid and episulfide (Puech et al. (1993) *Antiviral Res.*, 22: 155-174; Benzaria et al. (1996) *J. Med. Chem.* 39: 4958).

Protecting Groups

In the context of the present disclosure, protecting groups include prodrug moieties and chemical protecting groups.

"Protecting group" refers to a moiety of a compound that masks or alters the properties of a functional group or the properties of the compound as a whole. Chemical protecting groups and strategies for protection/deprotection are well known in the art. See e.g., Protective Groups in Organic Chemistry, Theodora W. Greene, John Wiley & Sons, Inc., New York, 1991. Protecting groups are often utilized to mask the reactivity of certain functional groups, to assist in the efficiency of desired chemical reactions, e.g., making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive.

Protected compounds may also exhibit altered, and in some cases, optimized properties in vitro and in vivo, such as passage through cellular membranes and resistance to enzymatic degradation or sequestration. In this role, protected compounds with intended therapeutic effects may be referred to as prodrugs. Another function of a protecting group is to convert the parental drug into a prodrug, whereby the parental drug is released upon conversion of the prodrug in vivo. Because active prodrugs may be absorbed more effectively than the parental drug, prodrugs may possess greater potency in vivo than the parental drug. Protecting groups are removed either in vitro, in the instance of chemical intermediates, or in vivo, in the case of prodrugs. With chemical intermediates, it is not particularly important that the resulting products after deprotection, e.g., alcohols, be physiologically acceptable, although in general it is more desirable if the products are pharmacologically innocuous.

Protecting groups are available, commonly known and used, and are optionally used to prevent side reactions with the protected group during synthetic procedures, i.e. routes or methods to prepare the compounds of the disclosure. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis. PGs do not need to be, and generally are not, the same if the compound is substituted with multiple PGs. In general, PG will be used to protect functional groups such as carboxyl, hydroxyl, thio, or amino groups and to thus prevent side reactions or to otherwise facilitate the synthetic efficiency. The order of deprotection to yield free deprotected groups is dependent upon the intended direction of the synthesis and the reaction conditions to be encountered, and may occur in any order as determined by the artisan.

Various functional groups of the compounds of the disclosure may be protected. For example, protecting groups for —OH groups (whether hydroxyl, carboxylic acid, phosphonic acid, or other functions) include "ether- or ester-forming groups". Ether- or ester-forming groups are capable of functioning as chemical protecting groups in the synthetic schemes set forth herein. However, some hydroxyl and thio protecting groups are neither ether- nor ester-forming groups, as will be understood by those skilled in the art, and are included with amides, discussed below.

A very large number of hydroxyl protecting groups and amide-forming groups and corresponding chemical cleavage reactions are described in Protective Groups in Organic Synthesis, Theodora W. Greene (John Wiley & Sons, Inc., New York, 1991, ISBN 0-471-62301-6) ("Greene"). See also Kocienski, Philip J.; Protecting Groups (Georg Thieme Verlag Stuttgart, New York, 1994), which is incorporated by reference in its entirety herein. In particular Chapter 1, Protecting Groups: An Overview, pages 1-20, Chapter 2, Hydroxyl Protecting Groups, pages 21-94, Chapter 3, Diol Protecting Groups, pages 95-117, Chapter 4, Carboxyl Protecting Groups, pages 118-154, Chapter 5, Carbonyl Protecting Groups, pages 155-184. For protecting groups for carboxylic acid, phosphonic acid, phosphonate, sulfonic acid and other protecting groups for acids see Greene as set forth below.

By way of example and not limitation, variables described herein may recursive substituents in certain embodiments. Typically, each of these may independently occur 20, 19, 18, 17, 16, 15, 14, 13, 12, 11, 10, 9, 8, 7, 6, 5, 4, 3, 2, 1, or 0, times in a given embodiment. More typically, each of these may independently occur 12 or fewer times in a given embodiment. Whenever a compound described herein is substituted with more than one of the same designated group, e.g., "$R^1$" or "$R^3$", then it will be understood that the groups may be the same or different, i.e., each group is independently selected. Wavy lines indicate the site of covalent bond attachments to the adjoining groups, moieties, or atoms.

In one embodiment of the disclosure, the compound is in an isolated and purified form. Generally, the term "isolated and purified" means that the compound is substantially free from biological materials (e.g. blood, tissue, cells, etc.). In one specific embodiment of the disclosure, the term means that the compound or conjugate of the disclosure is at least about 50 wt. % free from biological materials; in another specific embodiment, the term means that the compound or conjugate of the disclosure is at least about 75 wt. % free from biological materials; in another specific embodiment, the term means that the compound or conjugate of the disclosure is at least about 90 wt. % free from biological materials; in another specific embodiment, the term means that the compound or conjugate of the disclosure is at least about 98 wt. % free from biological materials; and in another embodiment, the term means that the compound or conjugate of the disclosure is at least about 99 wt. % free from biological materials. In another specific embodiment, the disclosure provides a compound or conjugate of the disclosure that has been synthetically prepared (e.g., ex vivo).

Stereoisomers

The compounds of the disclosure may have chiral centers, e.g., chiral carbon or phosphorus atoms. The compounds of the disclosure thus include racemic mixtures of all stereoisomers, including enantiomers, diastereomers, and atropisomers. In addition, the compounds of the disclosure include enriched or resolved optical isomers at any or all asymmetric, chiral atoms. In other words, the chiral centers apparent from the depictions are provided as the chiral isomers or racemic mixtures. Both racemic and diastereomeric mixtures, as well as the individual optical isomers isolated or synthesized, substantially free of their enantiomeric or diastereomeric partners, are all within the scope of the disclosure. The racemic mixtures are separated into their individual, substantially optically pure isomers through well-known techniques such as, for example, the separation of diastereomeric salts formed with optically active adjuncts, e.g., acids or bases followed by conversion back to the optically active substances. In most instances, the desired optical isomer is synthesized by means of stereospecific reactions, beginning with the appropriate stereoisomer of the desired starting material.

The compounds of the disclosure can also exist as tautomeric isomers in certain cases. Although only one tautomer may be depicted, all such forms are contemplated within the scope of the disclosure. For example, ene-amine tautomers can exist for purine, pyrimidine, imidazole, guanidine, amidine, and tetrazole systems and all their possible tautomeric forms are within the scope of the disclosure.

Salts and Hydrates

Examples of physiologically or pharmaceutically acceptable salts of the compounds of the disclosure include salts derived from an appropriate base, such as an alkali metal (for example, sodium), an alkaline earth metal (for example, magnesium), ammonium and $NX_4^+$ (wherein X is $C_1$-$C_4$ alkyl). Physiologically acceptable salts of a hydrogen atom or an amino group include salts of organic carboxylic acids such as acetic, benzoic, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, sulfuric, phosphoric and sulfamic acids. Physiologically acceptable salts of a compound of a hydroxy group include the anion of said compound in combination with a suitable cation such as $Na^+$ and $NX_4^+$ (wherein X is independently selected from H or a $C_1$-$C_4$ alkyl group).

For therapeutic use, salts of active ingredients of the compounds of the disclosure will typically be physiologically acceptable, i.e. they will be salts derived from a physiologically acceptable acid or base. However, salts of acids or bases which are not physiologically acceptable may also find use, for example, in the preparation or purification of a physiologically acceptable compound. All salts, whether or not derived from a physiologically acceptable acid or base, are within the scope of the present disclosure.

Metal salts typically are prepared by reacting the metal hydroxide with a compound of this disclosure. Examples of metal salts which are prepared in this way are salts containing $Li^+$, $Na^+$, and $K^+$. A less soluble metal salt can be precipitated from the solution of a more soluble salt by addition of the suitable metal compound.

In addition, salts may be formed from acid addition of certain organic and inorganic acids, e.g., HCl, HBr, $H_2SO_4$, $H_3PO_4$ or organic sulfonic acids, to basic centers, typically amines, or to acidic groups. Finally, it is to be understood that the compositions herein comprise compounds of the disclosure in their un-ionized, as well as zwitterionic form, and combinations with stoichiometric amounts of water as in hydrates.

Also included within the scope of this disclosure are the salts of the parental compounds with one or more amino acids. Any of the natural or unnatural amino acids are suitable, especially the naturally-occurring amino acids found as protein components, although the amino acid typically is one bearing a side chain with a basic or acidic group, e.g., lysine, arginine or glutamic acid, or a neutral group such as glycine, serine, threonine, alanine, isoleucine, or leucine.

Methods of Inhibition of HCV

Another aspect of the disclosure relates to methods of inhibiting the activity of HCV comprising the step of treating a sample suspected of containing HCV with a compound or composition of the disclosure.

Compounds of the disclosure may act as inhibitors of HCV, as intermediates for such inhibitors or have other utilities as described below. The inhibitors will generally bind to locations on the surface or in a cavity of the liver. Compounds binding in the liver may bind with varying degrees of reversibility. Those compounds binding substantially irreversibly are ideal candidates for use in this method of the disclosure. Once labeled, the substantially irreversibly binding compounds are useful as probes for the detection of HCV. Accordingly, the disclosure relates to methods of detecting NS3 in a sample suspected of containing HCV comprising the steps of: treating a sample suspected of containing HCV with a composition comprising a compound of the disclosure bound to a label; and observing the effect of the sample on the activity of the label. Suitable labels are well known in the diagnostics field and include stable free radicals, fluorophores, radioisotopes, enzymes, chemiluminescent groups and chromogens. The compounds herein are labeled in conventional fashion using functional groups such as hydroxyl or amino. In one embodiment the disclosure provides a compound of any one of formulae (I) and (A1)-(A4) that comprises or that is bound or linked to one or more detectable labels. Within the context of the disclosure samples suspected of containing HCV include natural or man-made materials such as living organisms; tissue or cell cultures; biological samples such as biological material samples (blood, serum, urine, cerebrospinal fluid, tears, sputum, saliva, tissue samples, and the like); laboratory samples; food, water, or air samples; bioproduct samples such as extracts of cells, particularly recombinant cells synthesizing a desired glycoprotein; and the like. Typically the sample will be suspected of containing HCV. Samples can be contained in any medium including water and organic solvent/water mixtures. Samples include living organisms such as humans, and man made materials such as cell cultures.

The treating step of the disclosure comprises adding the compound of the disclosure to the sample or it comprises adding a precursor of the composition to the sample. The addition step comprises any method of administration as described above.

If desired, the activity of HCV after application of the compound can be observed by any method including direct and indirect methods of detecting HCV activity. Quantitative, qualitative, and semiquantitative methods of determining HCV activity are all contemplated. Typically one of the screening methods described above are applied, however, any other method such as observation of the physiological properties of a living organism are also applicable.

Many organisms contain HCV. The compounds of this disclosure are useful in the treatment or prophylaxis of conditions associated with HCV activation in animals or in man.

However, in screening compounds capable of inhibiting HCV activity it should be kept in mind that the results of enzyme assays may not always correlate with cell culture assays. Thus, a cell based assay should typically be the primary screening tool.

Pharmaceutical Formulations

The compounds of this disclosure are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic.

All formulations will optionally contain excipients such as those set forth in the Handbook of Pharmaceutical Excipients (1986). Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 3 to about 11, but is ordinarily about 7 to 10. Typically, the compound will be administered in a dose from 0.01 milligrams to 2 grams. In one embodiment, the dose will be from about 10 milligrams to 450 milligrams. In another embodiment, the dosage will be from about 25 to about 250 milligrams. In another embodiment, the dosage will be about 50 or 100 milligrams. In one embodiment, the dosage will be about 100 milligrams. It is contemplated that the compound may be administered once, twice or three times a day.

While it is possible for the active ingredients to be administered alone it may be preferable to present them as pharmaceutical formulations. The formulations, both for veterinary and for human use, of the disclosure comprise at least one active ingredient, as above defined, together with one or more acceptable carriers therefor and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present disclosure suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

For administration to the eye or other external tissues e.g., mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this disclosure may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the disclosure include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present disclosure comprise one or more compounds of the disclosure together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the disclosure contain the active materials in admixture with excipients suitable for the manufacture of aqueous suspensions. Such excipients include a suspending agent, such as sodium carboxymethylcellulose, methylcellulose, hydroxypropyl methyl celluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the disclosure suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the disclosure may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the disclosure may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for administration to the eye include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments such as 0.5 microns, 1 micron, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of conditions associated with HCV activity.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this disclosure may include other agents conventional in the art having regard to the type of formulation in question, for example those suitable for oral administration may include flavoring agents.

The disclosure further provides veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the disclosure can also be formulated to provide controlled release of the active ingredient to allow less frequent dosing or to improve the pharmacokinetic or toxicity profile of the active ingredient. Accordingly, the disclosure also provides compositions comprising one or more compounds of the disclosure formulated for sustained or controlled release.

Effective dose of active ingredient depends at least on the nature of the condition being treated, toxicity, whether the compound is being used prophylactically (lower doses), the method of delivery, and the pharmaceutical formulation, and will be determined by the clinician using conventional dose escalation studies.

Routes of Administration

One or more compounds of the disclosure (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this disclosure is that they are orally bioavailable and can be dosed orally.

HCV Combination Therapy

In another embodiment, non-limiting examples of suitable combinations include combinations of one or more compounds of formula (I) and (A1-A4) with one or more interferons, ribavirin or its analogs, HCV NS3 protease inhibitors, alpha-glucosidase 1 inhibitors, hepatoprotectants, nucleoside or nucleotide inhibitors of HCV NS5B polymerase, non-nucleoside inhibitors of HCV NS5B polymerase, HCV NS5A inhibitors, TLR-7 agonists, cyclophillin inhibitors, HCV IRES inhibitors, pharmacokinetic enhancers, and other drugs or therapeutic agents for treating HCV.

More specifically, one or more compounds as described herein may be combined with one or more compounds selected from the group consisting of:

1) interferons, e.g., pegylated rIFN-alpha 2b (PEG-Introit), pegylated rIFN-alpha 2a (Pegasys), rIFN-alpha 2b (IntronA), rIFN-alpha 2a (Roferon-A), interferon alpha (MOR-22, OPC-18, Alfaferone, Alfanative, Multiferon, subalin), interferon alfacon-1 (Infergen), interferon alpha-nl (Wellferon), interferon alpha-n3 (Alferon), interferon-beta (Avonex, DL-8234), interferon-omega (omega DUROS, Biomed 510), albinterferon alpha-2b (Albuferon), IFN alpha-2b XL, BLX-883 (Locteron), DA-3021, glycosylated interferon alpha-2b (AVI-005), PEG-Infergen, PEGylated interferon lambda-1 (PEGylated IL-29), and belerofon;

2) ribavirin and its analogs, e.g., ribavirin (Rebetol, Copegus), and taribavirin (Viramidine);

3) HCV NS3 protease inhibitors, e.g., boceprevir (SCH-503034, SCH-7), telaprevir (VX-950), TMC435350, BI-1335, BI-1230, MK-7009, VBY-376, VX-500, GS-9256, GS-9451, BMS-605339, PHX-1766, AS-101, YH-5258, YH5530, YH5531, ABT-450, ACH-1625, ITMN-191, MK5172, MK6325, and MK2748;

4) alpha-glucosidase 1 inhibitors, e.g., celgosivir (MX-3253), Miglitol, and UT-231B;

5) hepatoprotectants, e.g., emericasan (IDN-6556), ME-3738, GS-9450 (LB-84451), silibilin, and MitoQ;

6) nucleoside or nucleotide inhibitors of HCV NS5B polymerase, e.g., R1626, R7128 (R4048), IDX184, IDX-102, BCX-4678, valopicitabine (NM-283), MK-0608, sofosbuvir (GS-7977 (formerly PSI-7977)), and INX-189 (now BMS986094);

7) non-nucleoside inhibitors of HCV NS5B polymerase, e.g., PF-868554, VCH-759, VCH-916, JTK-652, MK-3281, GS-9190, VBY-708, VCH-222, A848837, ANA-598, GL60667, GL59728, A-63890, A-48773, A-48547, BC-2329, VCH-796 (nesbuvir), GSK625433, BILN-1941, XTL-2125, ABT-072, ABT-333, GS-9669. PSI-7792, and GS-9190;

8) HCV NS5A inhibitors, e.g., AZD-2836 (A-831), BMS-790052, ACH-3102, ACH-2928, MK8325, MK4882, MK8742, PSI-461, IDX719, and A-689;

9) TLR-7 agonists, e.g., imiquimod, 852A, GS-9524, ANA-773, ANA-975, AZD-8848 (DSP-3025), and SM-360320;

10) cyclophillin inhibitors, e.g., DEBIO-025, SCY-635, and NIM811;

11) HCV IRES inhibitors, e.g., MCI-067;

12) pharmacokinetic enhancers, e.g., BAS-100, SPI-452, PF-4194477, TMC-41629, GS-9350, GS-9585, and roxythromycin; and 13) other drugs for treating HCV, e.g., thymosin alpha 1 (Zadaxin), nitazoxanide (Alinea, NTZ), BIVN-401 (virostat), PYN-17 (altirex), KPE02003002, actilon (CPG-10101), GS-9525, KRN-7000, civacir, GI-5005, XTL-6865, BIT225, PTX-111, ITX2865, TT-033i, ANA 971, NOV-205, tarvacin, EHC-18, VGX-410C, EMZ-702, AVI 4065, BMS-650032, BMS-791325, Bavituximab, MDX-1106 (ONO-4538), Oglufanide, and VX-497 (merimepodib).

More specifically, one or more compounds as described herein may be combined with one or more compounds selected from the group consisting of non-nucleoside inhibitors of HCV NS5B polymerase (ABT-072 and ABT-333), HCV NS5A inhibitors (ACH-3102 and ACH-2928) and HCV NS3 protease inhibitors(ABT-450 and ACH-1625).

In yet another embodiment, the present application discloses pharmaceutical compositions comprising a compound as described herein, or a pharmaceutically acceptable salt, solvate, and/or ester thereof, in combination with at least one additional therapeutic agent, and a pharmaceutically acceptable carrier or excipient.

According to one embodiment, the therapeutic agent used in combination with the compound as described herein can be any agent having a therapeutic effect when used in combination with the compound as described herein. For example, the therapeutic agent used in combination with the compound as described herein can be interferons, ribavirin analogs, NS3 protease inhibitors, NS5b polymerase inhibitors, alpha-glucosidase 1 inhibitors, hepatoprotectants, non-nucleoside inhibitors of HCV, and other drugs for treating HCV.

In another embodiment, the present application provides pharmaceutical compositions comprising a compound of formula (I), or a pharmaceutically acceptable salt, solvate, and/or ester thereof, in combination with at least one additional therapeutic agent selected from the group consisting of pegylated rIFN-alpha 2b, pegylated rIFN-alpha 2a, rIFN-alpha 2b, IFN alpha-2b XL, rIFN-alpha 2a, consensus IFN alpha, infergen, rebif, locteron, AVI-005, PEG-infergen, pegylated IFN-beta, oral interferon alpha, feron, reaferon, intermax alpha, r-IFN-beta, infergen+actimmune, IFN-omega with DUROS, albuferon, rebetol, copegus, levovirin, VX-497, viramidine (taribavirin), A-831, A-689, NM-283, valopicitabine, R1626, PSI-6130 (R1656), HCV-796, BILB 1941, MK-0608, NM-107, R7128, VCH-759, PF-868554, GSK625433, XTL-2125, SCH-503034 (SCH-7), VX-950 (Telaprevir), ITMN-191, and BILN-2065, MX-3253 (celgosivir), UT-231B, IDN-6556, ME 3738, MitoQ, and LB-84451, benzimidazole derivatives, benzo-1,2,4-thiadiazine derivatives, and phenylalanine derivatives, zadaxin, nitazoxanide (alinea), BIVN-401 (virostat), DEBIO-025, VGX-410C, EMZ-702, AVI 4065, bavituximab, oglufanide, PYN-17, KPE02003002, actilon (CPG-10101), KRN-7000, civacir, GI-5005, ANA-975 (isatoribine), XTL-6865, ANA 971, NOV-205, tarvacin, EHC-18, and NIM811 and a pharmaceutically acceptable carrier or excipient.

In yet another embodiment, the present application provides a combination pharmaceutical agent comprising:

a) a first pharmaceutical composition comprising a compound of formula (I), or a pharmaceutically acceptable salt, solvate, or ester thereof; and b) a second pharmaceutical composition comprising at least one additional therapeutic agent selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, interferons, ribavirin analogs, NS3 protease inhibitors, alpha-glucosidase 1 inhibitors, hepatoprotectants, non-nucleoside inhibitors of HCV, and other drugs for treating HCV, and combinations thereof.

In another embodiment is provided a pharmaceutical composition comprising a compound of formula (I) as described herein and a nucleoside or nucleotide inhibitors of HCV NS5B polymerase and optionally an interferon or ribavirin. In one embodiment, the compound is methyl{(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate having the formula:

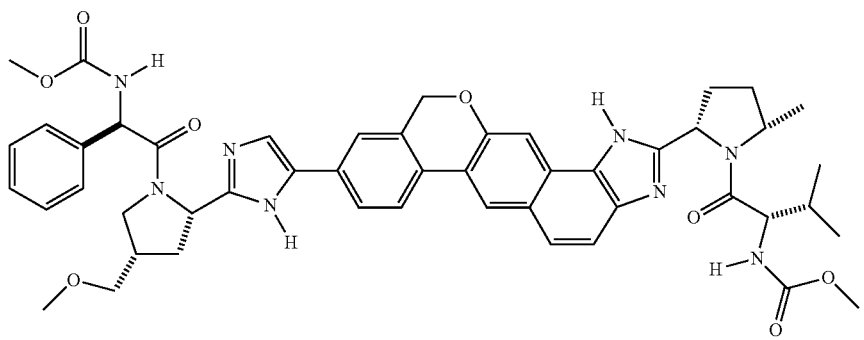

and the inhibitor is sofosbuvir.

Combinations of the compounds of formula I and additional active therapeutic agents may be selected to treat patients infected with HCV and other conditions such as HIV infections. Accordingly, the compounds of formula I may be combined with one or more compounds useful in treating HIV, for example HIV protease inhibiting compounds, non-nucleoside inhibitors of HIV reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, interferons, ribavirin analogs, NS3 protease inhibitors, NS5b polymerase inhibitors, alpha-glucosidase 1 inhibitors, hepatoprotectants, non-nucleoside inhibitors of HCV, and other drugs for treating HCV.

More specifically, one or more compounds of formula (I) or (A1)-(A4) may be combined with one or more compounds selected from the group consisting of 1) HIV protease inhibitors, e.g., amprenavir, atazanavir, fosamprenavir, indinavir, lopinavir, ritonavir, lopinavir+ritonavir, nelfinavir, saquinavir, tipranavir, brecanavir, darunavir, TMC-126, TMC-114, mozenavir (DMP-450), JE-2147 (AG1776), AG1859, DG35, L-756423, RO0334649, KNI-272, DPC-681, DPC-684, and GW640385X, DG17, PPL-100, 2) a HIV non-nucleoside inhibitor of reverse transcriptase, e.g., capravirine, emivirine, delaviridine, efavirenz, nevirapine, (+) calanolide A, etravirine, GW5634, DPC-083, DPC-961, DPC-963, MIV-150, and TMC-120, TMC-278 (rilpivirine), efavirenz, BILR 355 BS, VRX 840773, UK-453,061, RDEA806, 3) a HIV nucleoside inhibitor of reverse transcriptase, e.g., zidovudine, emtricitabine, didanosine, stavudine, zalcitabine, lamivudine, abacavir, amdoxovir, elvucitabine, alovudine, MIV-210, racivir (±-FTC), D-d4FC, emtricitabine, phosphazide, fozivudine tidoxil, fosalvudine tidoxil, apricitibine (AVX754), amdoxovir, KP-1461, abacavir+lamivudine, abacavir+lamivudine+zidovudine, zidovudine+lamivudine, 4) a HTV nucleotide inhibitor of reverse transcriptase, e.g., tenofovir, tenofovir disoproxil fumarate+emtricitabine, tenofovir disoproxil fumarate+ emtricitabine+efavirenz, and adefovir, 5) a HIV integrase inhibitor, e.g., curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), L-870812, and L-870810, MK-0518 (raltcgravir), BMS-707035, MK-2048, BA-011, BMS-538158, GSK364735C, 6) a gp41 inhibitor, e.g., enfuvirtide, sifuvirtide, FB006M, TRI-1144, SPC3, DES6, Locus gp41, CovX, and REP 9, 7) a CXCR4 inhibitor, e.g., AMD-070, 8) an entry inhibitor, e.g., SP01A, TNX-355, 9) a gp120 inhibitor, e.g., BMS-488043 and BlockAide/CR, 10) a G6PD and NADH-oxidase inhibitor, e.g., immunitin, 11) a CCR5 inhibitor, e.g., aplaviroc, vicriviroc, 1NCB9471, PRO-140, INCB15050, PF-232798, CCR5mAb004, and maraviroc, 12) an interferon, e.g., pegylated rIFN-alpha 2b, pegylated rIFN-alpha 2a, rIFN-alpha 2b, IFN alpha-2b XL, rIFN-alpha 2a, consensus IFN alpha, infergen, rebif, locteron, AVI-005, PEG-infergen, pegylated IFN-beta, oral interferon alpha, feron, reaferon, intermax alpha, r-IFN-beta, infergen+ actimmune, IFN-omega with DUROS, and albuferon, 13) ribavirin analogs, e.g., rebetol, copegus, levovirin, VX-497, and viramidine (taribavirin), 14) NS5a inhibitors, e.g., A-831, A-689, and BMS-790052, 15) NS5b polymerase inhibitors, e.g., NM-283, valopicitabine, R1626, PSI-6130 (R1656), HCV-796, BILB 1941, MK-0608, NM-107, R7128, VCH-759, PF-868554, GSK625433, and XTL-2125, 16) NS3 protease inhibitors, e.g., SCH-503034 (SCH-7), VX-950 (Telaprevir), ITMN-191, and BILN-2065, 17) alpha-glucosidase 1 inhibitors, e.g., MX-3253 (celgosivir) and UT-231B, 18) hepatoprotectants, e.g., IDN-6556, ME 3738, MitoQ, and LB-84451, 19) non-nucleoside inhibitors of HCV, e.g., benzimidazole derivatives, benzo-1,2,4-thiadiazine derivatives, and phenylalanine derivatives, 20) other drugs for treating Hepatitis C, e.g., zadaxin, nitazoxanide (alinea), BIVN-401 (virostat), DEBIO-025, VGX-410C, EMZ-702, AV1 4065, bavituximab, oglufanide, PYN-17, KPE02003002, actilon (CPG-10101), KRN-7000, civacir, GI-5005, ANA-975 (isatoribine), XTL-6865, ANA 971, NOV-205, tarvacin, EHC-18, and NIM811, 20) pharmacokinetic enhancers, e.g., BAS-100 and SPI452, 21) RNAsc H inhibitors, e.g., ODN-93 and ODN-112, 22) other anti-HIV agents, e.g., VGV-1, PA-457 (bevirimat), ampligen, HRG214, cytolin, polymun, VGX-410, KD247, AMZ 0026, CYT 99007, A-221 HIV, BAY 50-4798, MDX010 (iplimumab), PBS119, ALG889, and PA-1050040.

It is contemplated that the second therapeutic agent will be administered in a manner that is known in the art and the dosage may be selected by someone of skill in the art. For example, the second agent may be administered in a dose from about 0.01 milligrams to about 2 grams per day.

Metabolites of the Compounds

Also falling within the scope of this disclosure are the in vivo metabolic products of the compounds described herein. Such products may result for example from the oxidation, reduction, hydrolysis, amidation, esterification and the like of the administered compound, primarily due to enzymatic processes. Accordingly, the disclosure includes compounds produced by a process comprising contacting a compound of this disclosure with a mammal for a period of time sufficient to yield a metabolic product thereof. Such products typically are identified by preparing a radiolabelled (e.g., $C^{14}$ or $H^3$) compound of the disclosure, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the disclosure even if they possess no HCV-inhibitory activity of their own.

Methods for determining stability of compounds in surrogate gastrointestinal secretions are known.

Exemplary Methods of Making the Compounds

The disclosure also relates to methods of making the compositions of the disclosure. The compositions are prepared by any of the applicable techniques of organic synthesis. Many such techniques are well known in the art. However, many of the known techniques are elaborated in Compendium of Organic Synthetic Methods (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6, Michael B. Smith; as well as March, J., Advanced Organic Chemistry, Third Edition, (John Wiley & Sons, New York, 1985), Comprehensive Organic Synthesis. Selectivity, Strategy & Efficiency in Modern Organic Chemistry. In 9 Volumes, Barry M. Trost, Editor-in-Chief (Pergamon Press, New York, 1993 printing). Other methods suitable for preparing compounds of the disclosure are described in International Patent Application Publication Number WO 2006/020276.

A number of exemplary methods for the preparation of the compositions of the disclosure are provided in the schemes and examples below. These methods are intended to illustrate the nature of such preparations and are not intended to limit the scope of applicable methods.

Generally, the reaction conditions such as temperature, reaction time, solvents, work-up procedures, and the like, will be those common in the art for the particular reaction to be performed. The cited reference material, together with material cited therein, contains detailed descriptions of such conditions. Typically the temperatures will be −100° C. to 200° C., solvents will be aprotic or protic, and reaction times will be 10 seconds to 10 days. Work-up typically consists of quenching any unreacted reagents followed by partition between a water/organic layer system (extraction) and separating the layer containing the product.

Oxidation and reduction reactions are typically carried out at temperatures near room temperature (about 20° C.), although for metal hydride reductions frequently the temperature is reduced to 0° C. to −100° C., solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures (0° C. to −100° C.) are also common Solvents can be either protic (common in equilibrating reactions) or aprotic (common in kinetically controlled reactions).

Standard synthetic techniques such as azeotropic removal of reaction by-products and use of anhydrous reaction conditions (e.g., inert gas environments) are common in the art and will be applied when applicable.

The terms "treated", "treating", "treatment", and the like, when used in connection with a chemical synthetic operation, mean contacting, mixing, reacting, allowing to react, bringing into contact, and other terms common in the art for indicating that one or more chemical entities is treated in such a manner as to convert it to one or more other chemical entities. This means that "treating compound one with compound two" is synonymous with "allowing compound one to react with compound two", "contacting compound one with compound two", "reacting compound one with compound two", and other expressions common in the art of organic synthesis for reasonably indicating that compound one was "treated", "reacted", "allowed to react", etc., with compound two. For example, treating indicates the reasonable and usual manner in which organic chemicals are allowed to react. Normal concentrations (0.01M to 10M, typically 0.1M to 1M), temperatures (−100° C. to 250° C., typically −78° C. to 150° C., more typically −78° C. to 100° C., still more typically 0° C. to 100° C.), reaction vessels (typically glass, plastic, metal), solvents, pressures, atmospheres (typically air for oxygen and water insensitive reactions or nitrogen or argon for oxygen or water sensitive), etc., are intended unless otherwise indicated. The knowledge of similar reactions known in the art of organic synthesis is used in selecting the conditions and apparatus for "treating" in a given process. In particular, one of ordinary skill in the art of organic synthesis selects conditions and apparatus reasonably expected to successfully carry out the chemical reactions of the described processes based on the knowledge in the art.

Modifications of each of the exemplary schemes and in the Examples (hereafter "exemplary schemes") leads to various analogs of the specific exemplary materials produced. The above-cited citations describing suitable methods of organic synthesis are applicable to such modifications.

In each of the exemplary schemes it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium, and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point, and molecular weight in distillation and sublimation, presence or absence of polar functional groups in chromatography, stability of materials in acidic and basic media in multiphase extraction, and the like. One skilled in the art will apply techniques most likely to achieve the desired separation.

A single stereoisomer, e.g., an enantiomer, substantially free of its stereoisomer may be obtained by resolution of the racemic mixture using a method such as formation of di astereomers using optically active resolving agents (Stereochemistry of Carbon Compounds, (1962) by E. L. Eliel, McGraw Hill; Lochmuller, C. H., (1975) *J. Chromatogr.*, 113, 3) 283-302). Racemic mixtures of chiral compounds of the disclosure can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions.

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (Eliel, E. and Wilen, S. (1994) Stereochemistry of Organic Compounds, John Wiley & Sons, Inc., p. 322). Diastereomeric compounds can be formed by reacting asymmetric compounds with enantiomerically pure chiral derivatizing reagents, such as menthyl derivatives, followed by separation of the diastereomers and hydrolysis to yield the free, enantiomerically enriched substrate. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III. (1982) *J. Org. Chem.* 47:4165), of the racemic mixture, and analyzing the NMR spectrum for the presence of the two atropisomeric diastereomers. Stable diastereomers of atropisomeric compounds can be separated and isolated by normal- and reverse-phase chromatography following methods for separation of atropisomeric naphthyl-isoquinolines (Hoye, T., WO 96/15111). By method (3), a racemic mixture of two enantiomers can be separated by chromatography using a chiral stationary phase (Chiral Liquid Chromatography (1989) W. J. Lough, Ed. Chapman and Hall, New York; Okamoto, (1990) *J. of Chromatogr.* 513:375-378). Enriched or purified enantiomers can be distinguished by methods used to distinguish other chiral molecules with asymmetric carbon atoms, such as optical rotation and circular dichroism.

SCHEMES AND EXAMPLES

General aspects of these exemplary methods are described below and in the Examples. Each of the products of the following processes is optionally separated, isolated, and/or purified prior to its use in subsequent processes.

A number of exemplary methods for the preparation of compounds of the disclosure are provided herein, for example, in the Examples below. These methods are intended to illustrate the nature of such preparations and are not intended to limit the scope of applicable methods. Certain compounds of the disclosure can be used as intermediates for the preparation of other compounds of the disclosure. In the exemplary methods described herein, the fragment E-V— can also be written as R9-. PG represents a protecting group common for the given functional group that it is attached. The installation and removal of the protecting group can be accomplished using standard techniques, such as those described in Wuts, P. G. M., Greene, T. *Protective Groups in Organic Synthesis,* 4th ed.; John Wiley & Sons, Inc.: Hoboken, N.J., 2007.

Scheme 1. Representative synthesis of
E—V—C(═O)—P—W—P—C(═O)—V—E

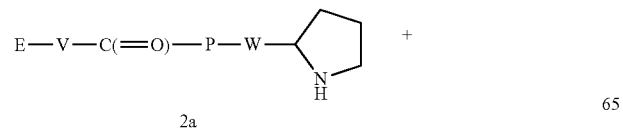

Scheme 1 shows a general synthesis of an E-V—C(═O)—P—W—P—C(═O)—V-E molecule of the disclosure wherein, for illustrative purposes, E is methoxycarbonylamino. The treatment of either 1a or 1c with one or two equivalents respectively of methyl chloroformate under basic conditions (e.g. sodium hydroxide) provides the molecule 1b or 1d.

Scheme 2. Representative synthesis of
E—V—C(═O)—P—W—P—C(═O)—V—E

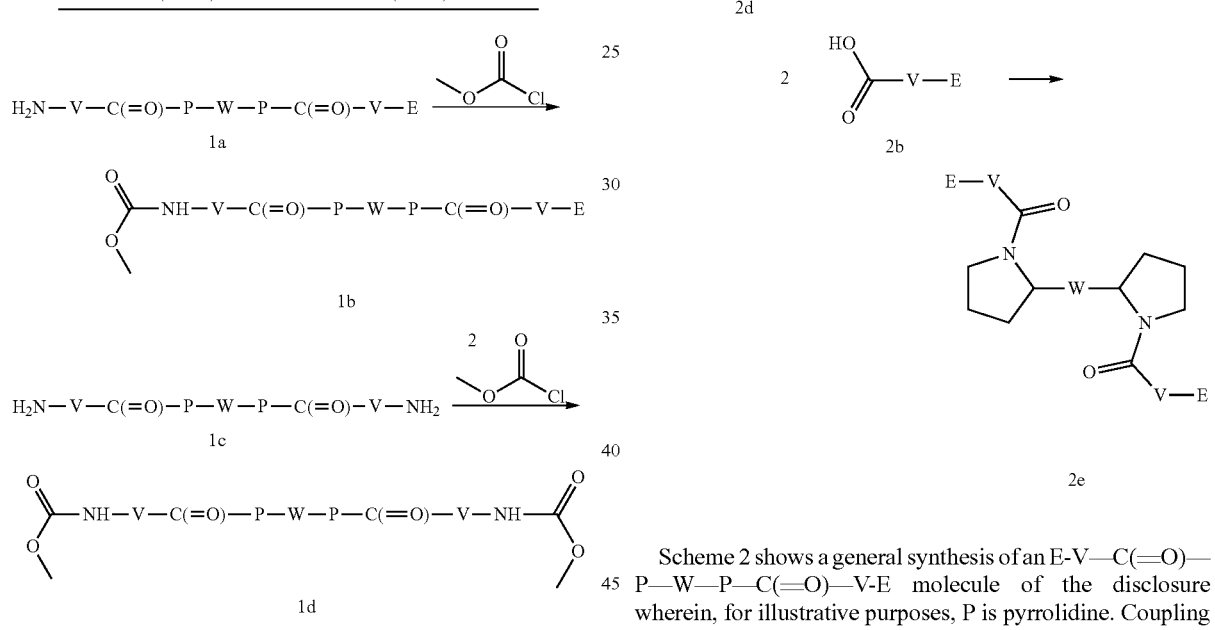

Scheme 2 shows a general synthesis of an E-V—C(═O)—P—W—P—C(═O)—V-E molecule of the disclosure wherein, for illustrative purposes, P is pyrrolidine. Coupling of amine 2a with acid 2b is accomplished using a peptide coupling reagent (e.g. HATU) to afford 2c. Alternatively, amine 2d is coupled with two equivalents of 2b under similar conditions to provide 2e.

Scheme 6. Representative synthesis of
R¹—V—C(═O)—P—R²

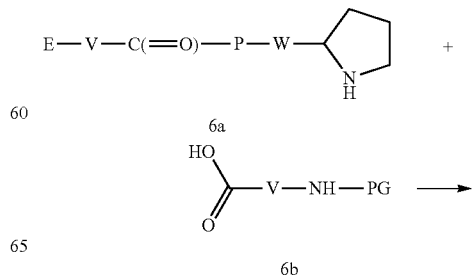

Scheme 6 shows a general synthesis of an R¹—V—C(=O)—P—R² intermediate wherein, for illustrative purposes, P is pyrrolidine, $R^1$ is a generic group that is depicted as either -E or a amino protecting group, and $R^2$ is a generic group that is depicted as —W—P—C(=O)—V-E, —W—P—C(=O)—V—NH-PG, —W—P—NH-PG, or —W—NH-PG. Coupling of amine 6a (or 6d, 6h, 6k) with acid 6b or 6e is accomplished using a peptide coupling reagent (e.g. HATU) to afford 6c (or 6f, 6g, 6i, 6j, 6l, 6m) respectively.

7c, 7e, 7g, 7i) with methyl chloroformate under basic conditions (e.g. sodium hydroxide) provides the molecule 7b (or 7d, 7f, 7h, 7j).

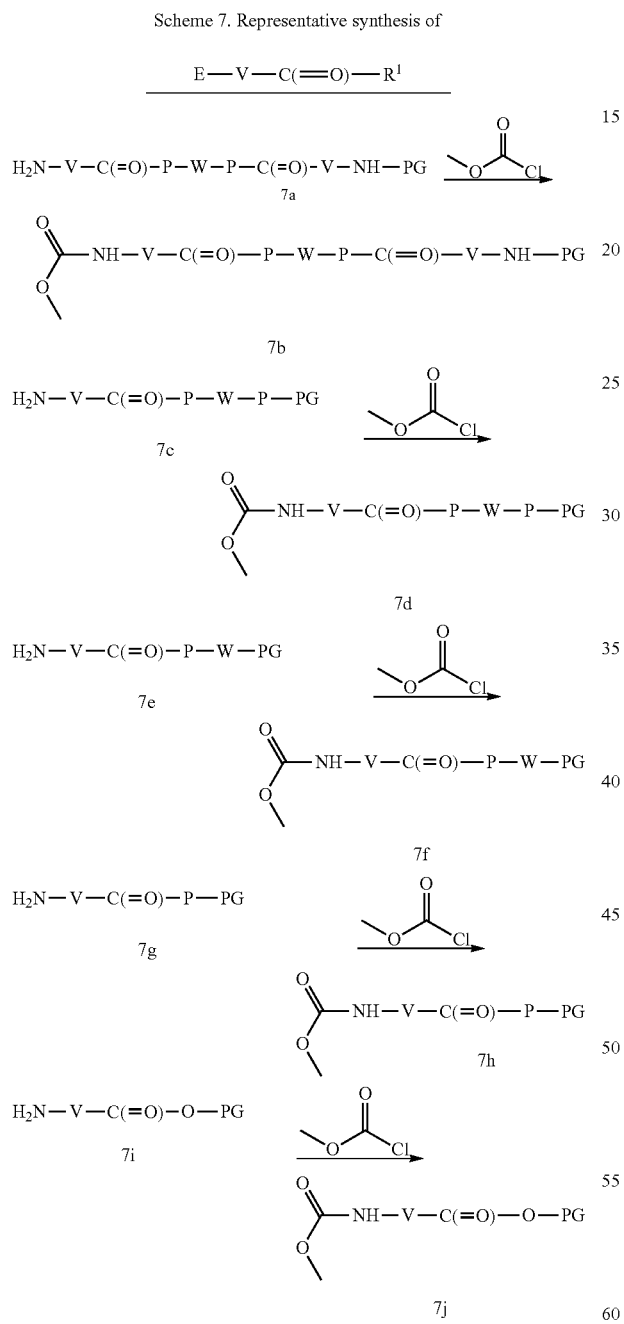

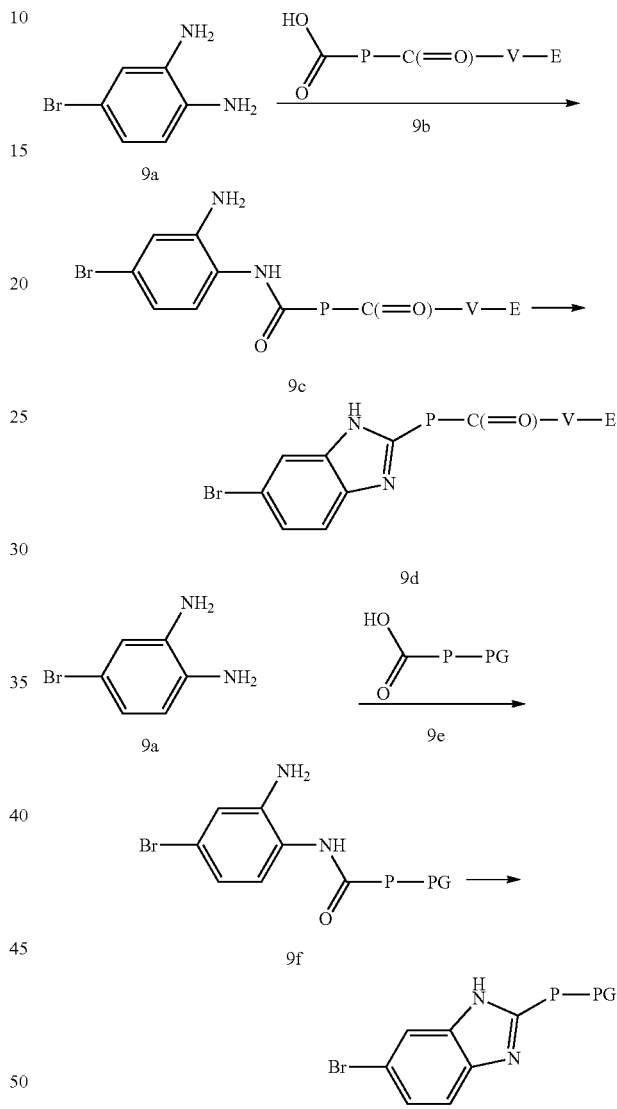

Scheme 9 shows a general synthesis of an $R^1$—P—$R^2$ intermediate wherein, for illustrative purposes, $R^1$ is —C(=O)—V-E or a protecting group and $R^2$ is a substituted benzimidazole. The formation of the benzimidazole is accomplished by coupling the acid 9b or 9e with an arylamine 9a, using a peptide coupling reagent such as HATU, to afford 9c or 9f. Cyclization of the amide in the presence of an acid (such as acetic acid) affords the benzimidazole containing molecule 9d or 9g.

The formation of multiple benzimidazoles is performed in the same manner, starting with a bis-diamine to provide the corresponding bis-benzimidazole.

Scheme 7 shows a general synthesis of an E—V—C(=O)—$R^1$ intermediate wherein, for illustrative purposes, E is methoxycarbonylamino and $R^1$ is a generic group that is depicted as either —P—W—P—C(=O)—V—NH-PG, —P—W—P-PG, —P—W-PG, —P-PG, or —O-PG. Treatment of 7a (or

Scheme 20. Representative synthesis
$$R^1\text{—}P\text{—}W\text{—}P\text{—}R^2$$

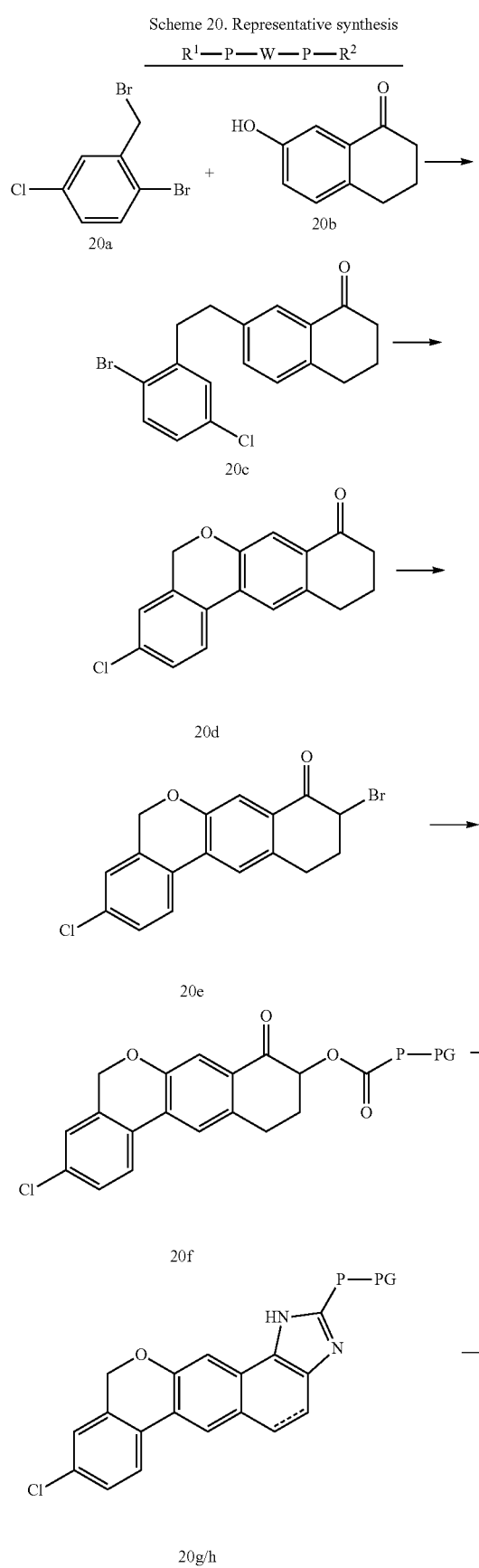

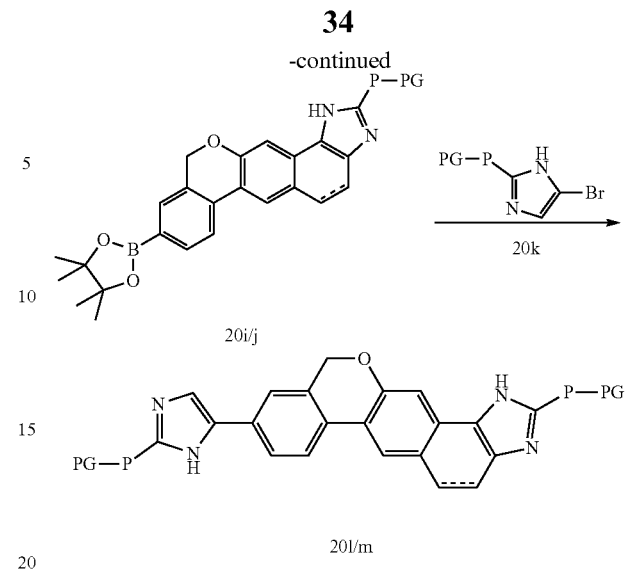

Scheme 20 shows a general synthesis of an $R^1$—P—W—P—$R^2$ intermediate of the disclosure wherein, for illustrative purposes, $R^1$ and $R^2$ are independent protecting groups and W is a two aromatic ring unit constructed via a transition metal mediated cyclization. Alkylation of phenol 20b with an alkyl bromide, such as 20a, provides the ether 20c. Cyclization of the aromatic rings in the presence of a palladium catalyst provides the compound 20d. Treatment of 20d with $CuBr_2$ provides the α-haloketone 20e, which provides 20f upon addition of an acid under basic conditions (e.g. $Et_3N$). Reaction of 20f with an amine or amine salt (e.g. ammonium acetate) affords the imidazole containing molecule 20g. Oxidation of 20g, 20i, or 20l can be accomplished by heating in the presence of $MnO_2$ to provide 20h, 20j, or 20m, respectively. Conversion of 20g or 20h with a palladium catalyst, such as $Pd_2dba_3$ and X-Phos, and a boron source such as bis(pinacolato)diboron provides the boronic ester 20i or 20j. The boronic ester is coupled with an appropriate coupling partner (e.g. 20k) using a palladium catalyst, such as $Pd(PPh_3)_4$ or $PdCl_2(dppf)$, to afford 20l or 20m. For each transition metal mediated cross-coupling reaction, the roles of the nucleophile and electrophile can be reversed to provide the same coupling product. Other transition metal mediated cross couplings that enable the construction of W, but employ alternative coupling partners and reagents, include, but are not limited to, the Negishi, Kumada, Stille, and Ullman couplings. For the preparation of alternate two aromatic ring containing W groups, this general scheme can be applied through the appropriate choice of the starting reagents.

Scheme 21. Representative synthesis
$$R^1\text{—}P\text{—}W\text{—}P\text{—}R^2$$

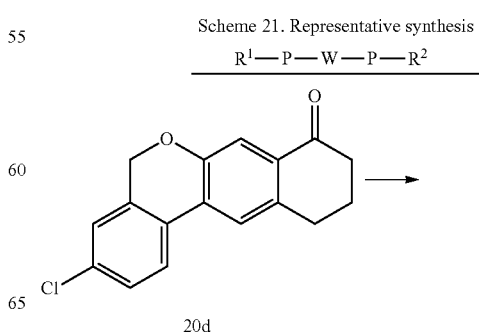

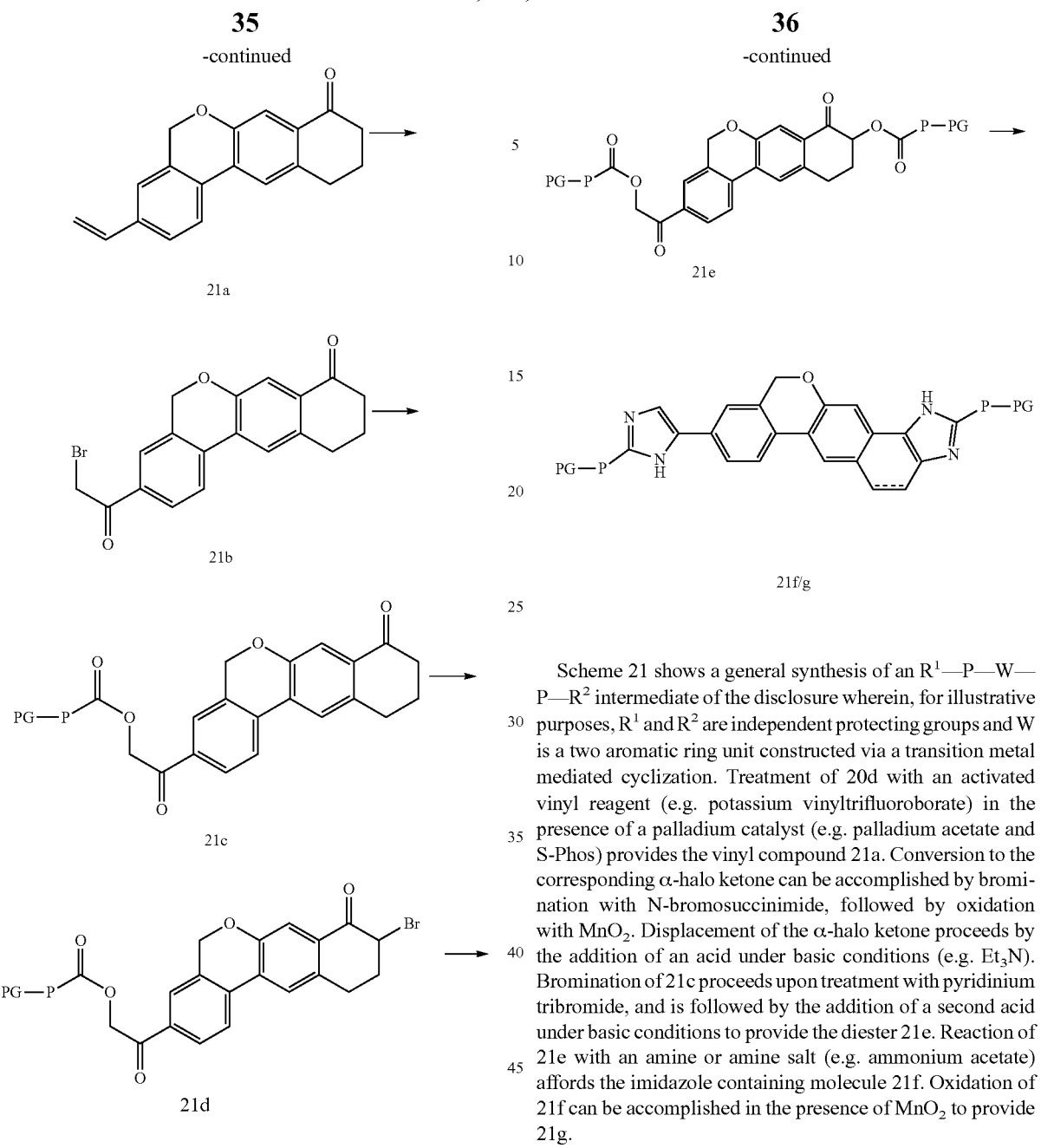

Scheme 21 shows a general synthesis of an $R^1$—P—W—P—$R^2$ intermediate of the disclosure wherein, for illustrative purposes, $R^1$ and $R^2$ are independent protecting groups and W is a two aromatic ring unit constructed via a transition metal mediated cyclization. Treatment of 20d with an activated vinyl reagent (e.g. potassium vinyltrifluoroborate) in the presence of a palladium catalyst (e.g. palladium acetate and S-Phos) provides the vinyl compound 21a. Conversion to the corresponding α-halo ketone can be accomplished by bromination with N-bromosuccinimide, followed by oxidation with $MnO_2$. Displacement of the α-halo ketone proceeds by the addition of an acid under basic conditions (e.g. $Et_3N$). Bromination of 21c proceeds upon treatment with pyridinium tribromide, and is followed by the addition of a second acid under basic conditions to provide the diester 21e. Reaction of 21e with an amine or amine salt (e.g. ammonium acetate) affords the imidazole containing molecule 21f. Oxidation of 21f can be accomplished in the presence of $MnO_2$ to provide 21g.

Scheme 22. Representative synthesis of

E—V—C(=O)—P—W—P—R

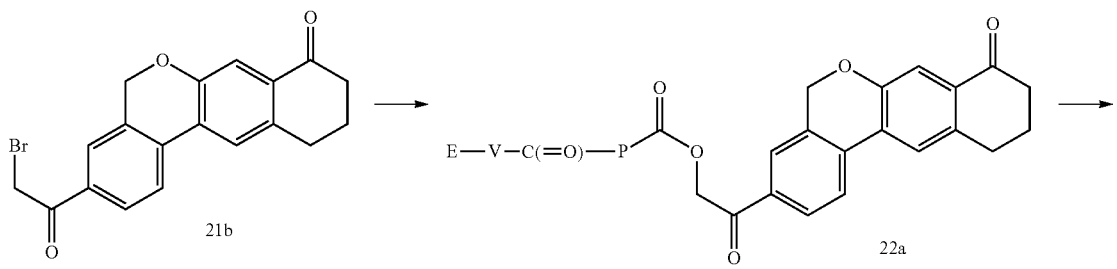

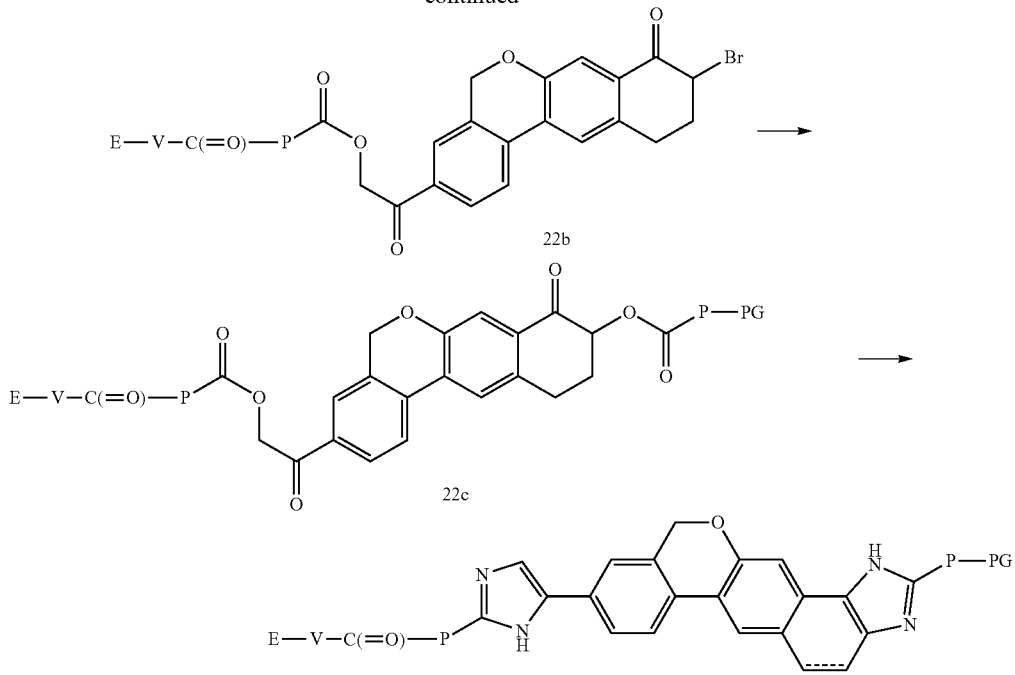

22b

22c 22 d/e

Scheme 22 shows a general synthesis of an E-V—C(=O)—P—W—P—R intermediate of the disclosure wherein, for illustrative purposes, R is a protecting group and W is a two aromatic ring unit. Displacement of the α-halo ketone 21b proceeds by the addition of an acid under basic conditions (e.g. Et₃N). Bromination of 22a proceeds upon treatment with pyridinium tribromide, and is followed by the addition of a second acid under basic conditions to provide the diester 22c. Reaction of 22c with an amine or amine salt (e.g. ammonium acetate) affords the imidazole containing molecule 22d. Oxidation of 22d can be accomplished in the presence of MnO₂ to provide 22e.

Scheme 23. Representative synthesis of
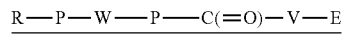

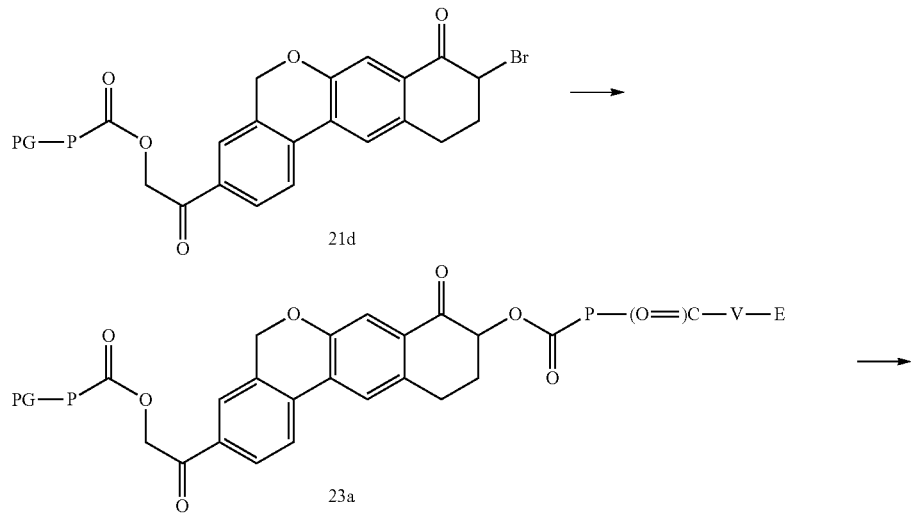

21d

23a

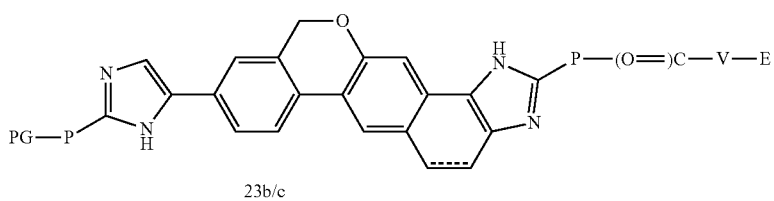

23b/c

Scheme 23 shows a general synthesis of an E-V—C(=O)—P—W—P—R intermediate of the disclosure wherein, for illustrative purposes, R is a protecting group and W is a two aromatic ring unit. Displacement of the α-halo ketone 21d proceeds by the addition of an acid under basic conditions (e.g. $Et_3N$). Reaction of 23a with an amine or amine salt (e.g. ammonium acetate) affords the imidazole containing molecule 23b. Oxidation of 23b can be accomplished in the presence of $MnO_2$ to provide 23c.

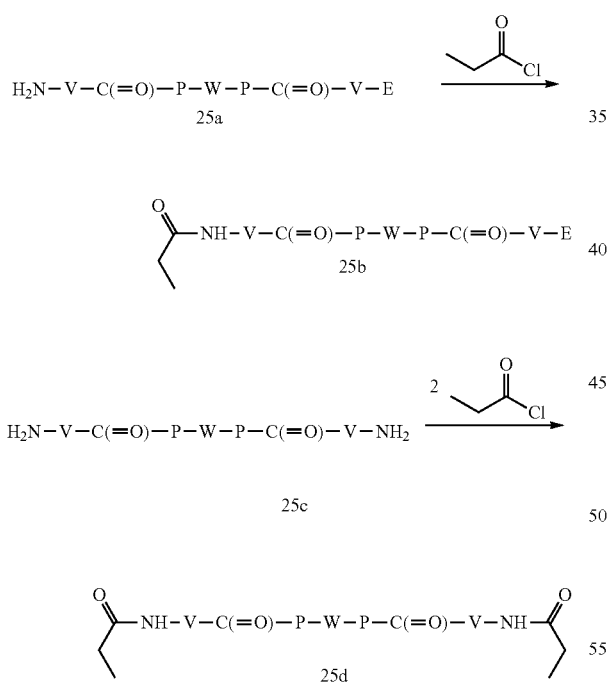

Scheme 25 shows a general synthesis of an E-V—C(=O)—P—W—P—C(=O)—V-E molecule of the disclosure wherein, for illustrative purposes, E is ethylcarbonylamino. The treatment of either 25a or 25c with one or two equivalents respectively of propionyl chloride under basic conditions (e.g. sodium hydroxide) provides the molecule 25b or 25d.

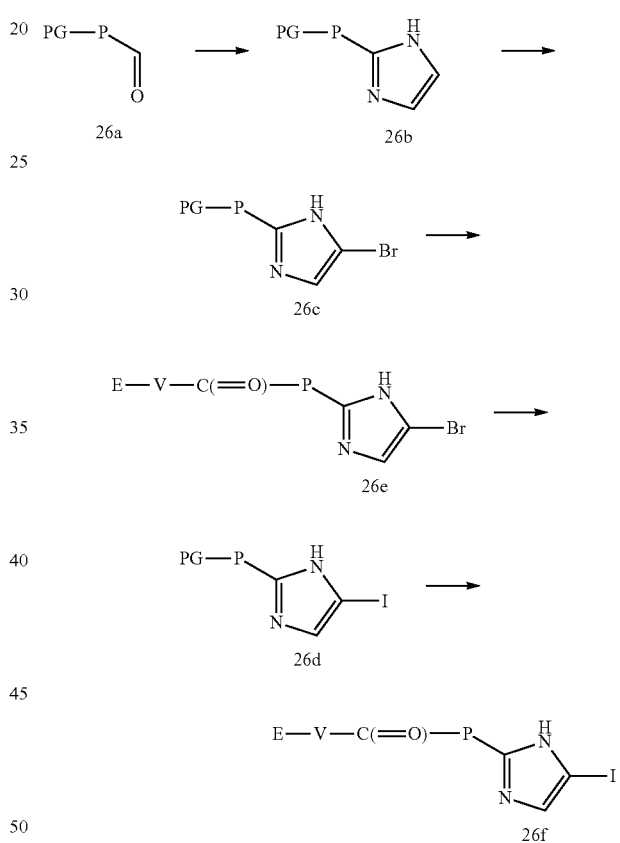

Scheme 26 shows a general synthesis of an E-V—C(=O)—P—R and an $R^1$—P—R molecule of the disclosure wherein, for illustrative purposes R is a haloimidazole. Treatment of the aldehyde 26a with glyoxal, in the presence of ammonium hydroxide provides the imidazole 26b. Treatment with either N-bromosuccinamide or iodine provides the corresponding haloimidazole 26c and 26d respectively. Separation from the corresponding bis-halogenated compound can be accomplished by preparative HPLC chromatography. The conversion of the bis-haloimidazole to the mono-haloimidazole can also be accomplished upon heating in the presence of sodium sulfite. Further functionalization of the P group can be accomplished upon removal of the protecting group and coupling with an appropriate acid (E-V—C(=O)—OH).

Scheme 27. Representative synthesis of $$R^1-P-W-P-R^2$$

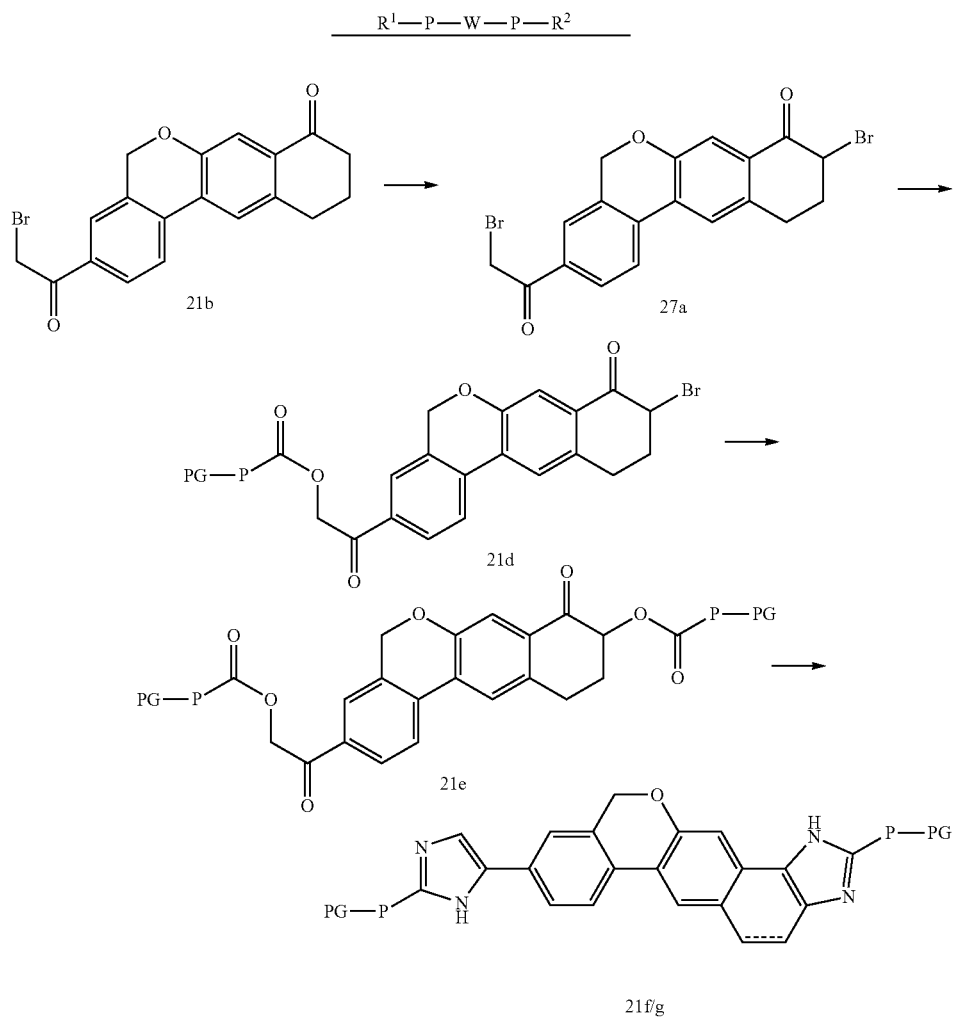

Scheme 27 shows an alternate general synthesis of an $R^1$—P—W—P—$R^2$ intermediate of the invention wherein, for illustrative purposes, $R^1$ and $R^2$ are independent protecting groups and W is a two aromatic ring unit constructed via a transition metal mediated cyclization. Bromination of 21b with a brominating agent (i.e. pyridinium tribromide) provides the dibromide 27a. Displacement of the primary bromide then proceeds by the addition of an acid under basic conditions (e.g. $K_2CO_3$) to provide 21d. Conversion to 21f or 21g can be accomplished following methods described in Scheme 21.

Scheme 28. Representative synthesis of $$E-V-C(=O)-P-W-P-R$$

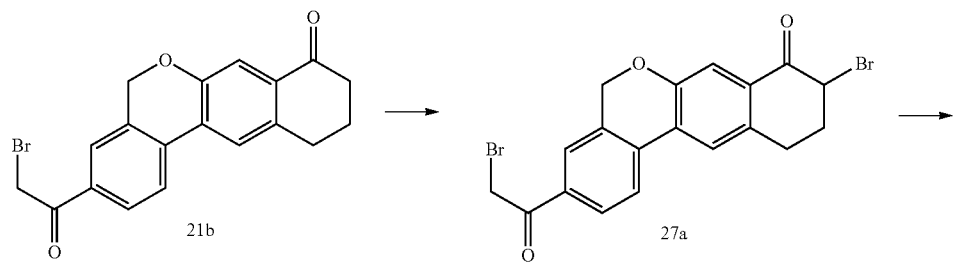

-continued

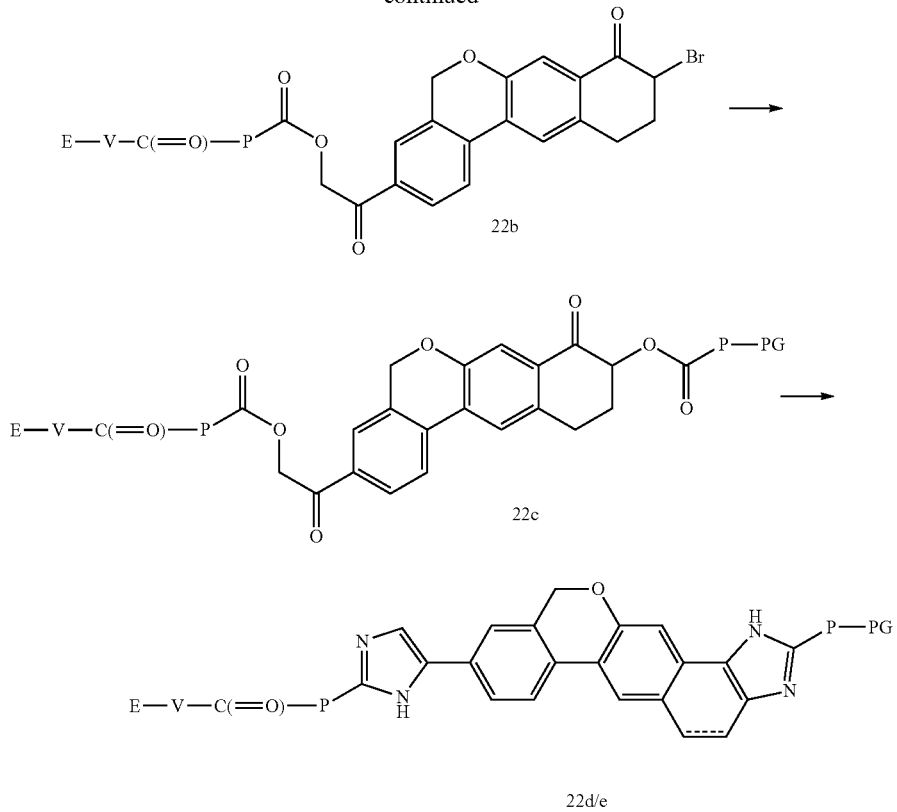

Scheme 28 shows an alternate general synthesis of an E-V—C(=O)—P—W—P—R intermediate of the invention wherein, for illustrative purposes, R is a protecting group and W is a two aromatic ring unit. Bromination of 21b with a brominating agent (i.e. pyridinium tribromide) provides the dibromide 27a. Displacement of the primary bromide then proceeds by the addition of an acid under basic conditions (e.g. $K_2CO_3$) to provide 22d. Conversion to 22d or 22e can be accomplished following methods described in Scheme 22.

Specific Embodiments

In one embodiment the disclosure provides a compound which has formula:

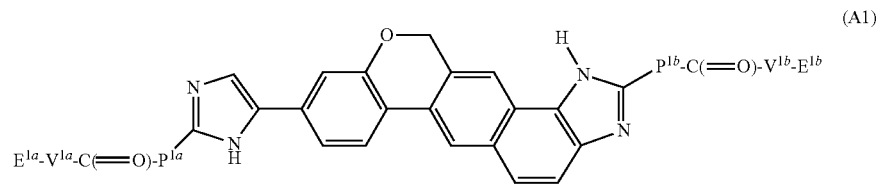

(A1)

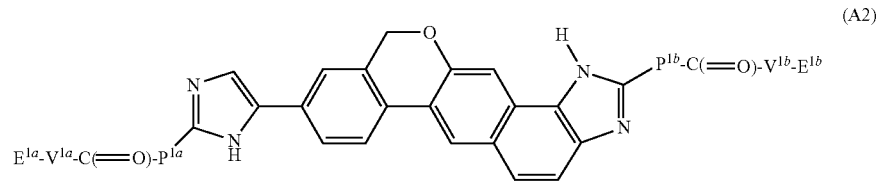

(A2)

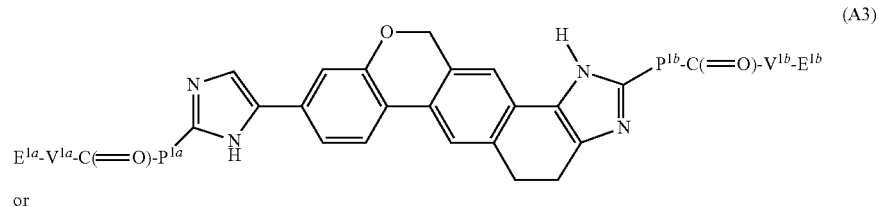

(A3)

or

-continued

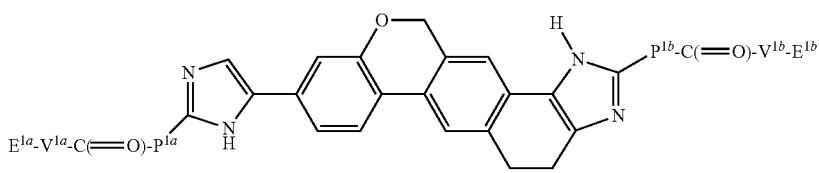
(A4)

wherein the imidazole ring shown in formula A1, A2, A3, and A4 is optionally substituted with one or more groups independently selected from halo, haloalkyl, cyano, or alkyl;

or a pharmaceutically acceptable salt or prodrug thereof.

In one embodiment the disclosure provides a compound which has formula:

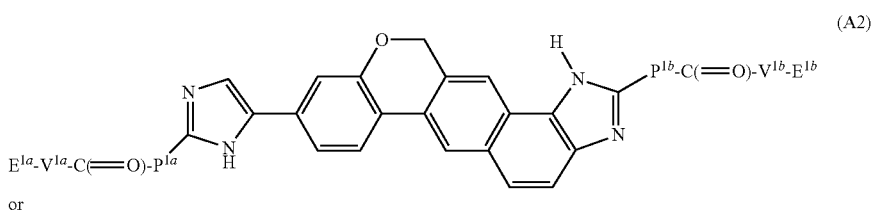
(A2)

or

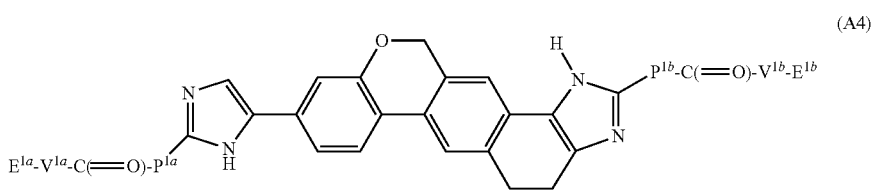
(A4)

wherein the imidazole ring shown in formula A2 and A4 is optionally substituted with one or more groups independently selected from halo, haloalkyl, cyano, or alkyl;

or a pharmaceutically acceptable salt or prodrug thereof.

In one embodiment at least one of $E^{1a}$ and $E^{1b}$ is —N(H)(alkoxycarbonyl).

In one embodiment at least one of $E^{1a}$ and $E^{1b}$ is —N(H)C(=O)OMe.

In one embodiment both of $E^{1a}$ and $E^{1b}$ are —N(H)C(=O)OMe.

In one embodiment at least one of $E^{1a}$ and $E^{1b}$ is —N(H)(cycloalkylcarbonyl) or —N(H)(cycloalkyloxycarbonyl).

In one embodiment at least one of $E^{1a}$ and $E^{1b}$ is cyclopropylcarbonylamino, cyclobutylcarbonylamino, cyclopropyloxycarbonylamino or cyclobutyloxycarbonylamino In one embodiment $E^{1a}$ and $E^{1b}$ are each independently selected from cyclopropylcarbonylamino, cyclobutylcarbonylamino, cyclopropyloxycarbonylamino or methoxycarbonylamino.

In one embodiment at least one of $V^{1a}$ and $V^{1b}$ is:

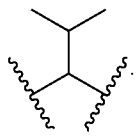

In one embodiment $E^{1a}$-$V^{1a}$ taken together are $R^{9a}$ or wherein $E^{1b}$-$V^{1b}$ taken together are $R^{9b}$.

In one embodiment at least one of $P^{1a}$ and $P^{1b}$ is selected from:

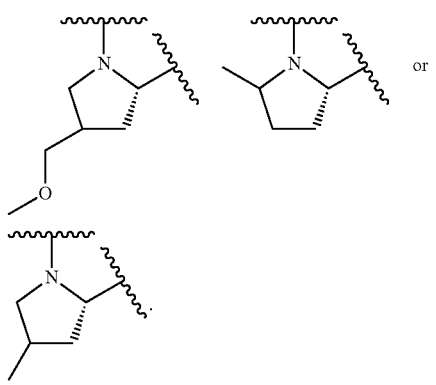

In one embodiment $P^{1a}$ and $P^{1b}$ are each independently selected from:

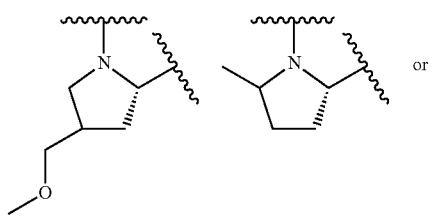

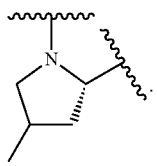

In one embodiment one of $P^{1a}$ and $P^{1b}$ is:

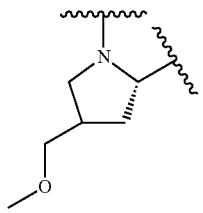

and the other of $P^{1a}$ and $P^{1b}$ is:

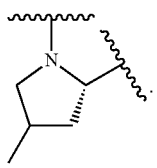

In one embodiment one of $P^{1a}$ and $P^{1b}$ is:

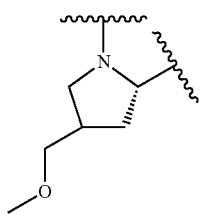

and the other of $P^{1a}$ and $P^{1b}$ is:

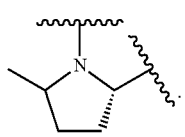

In one embodiment at least one of $P^{1a}$ and $P^{1b}$ is:

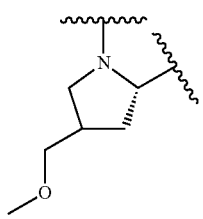 or 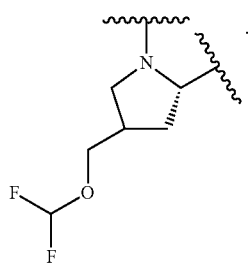

In one embodiment at least one of $P^{1a}$ and $P^{1b}$ is:

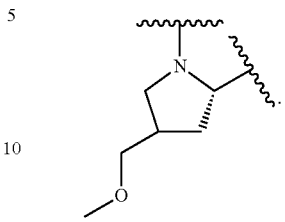

In one embodiment at least one of —$V^{1a}$—C(=O)—$P^{1a}$— and —$P^{1b}$—C(=O)—$V^{1b}$— is:

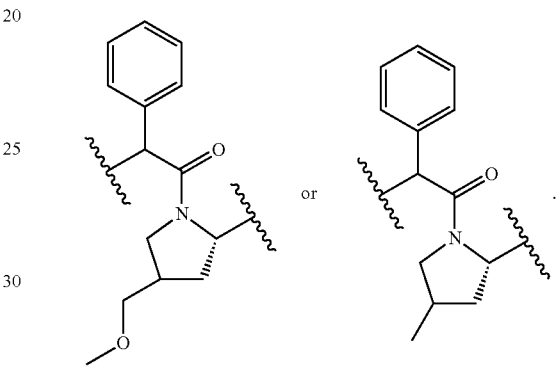

In one embodiment at least one of —$V^{1a}$—C(=O)—$P^{1a}$— and —$P^{1b}$—C(=O)—$V^{1b}$— is:

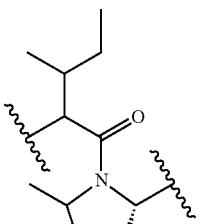 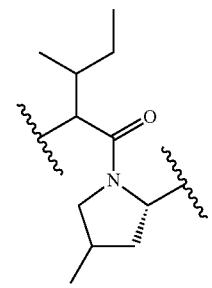

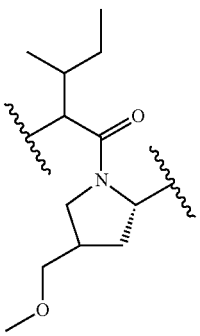 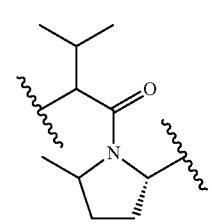

-continued
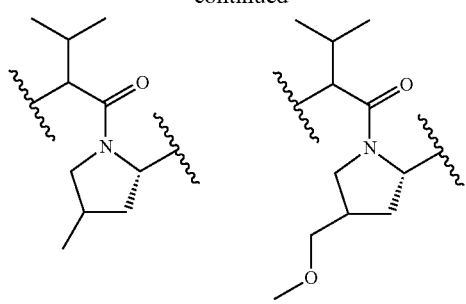
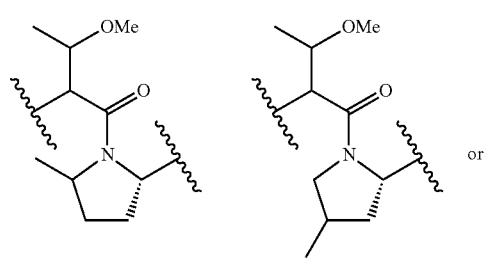
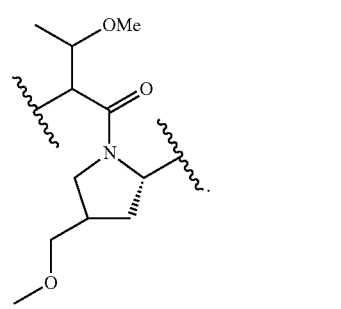
-continued
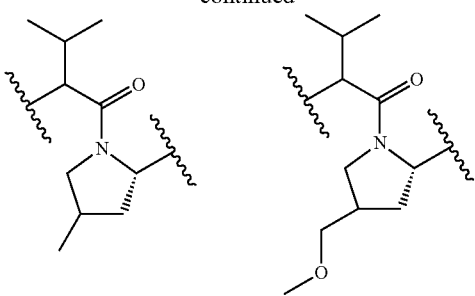
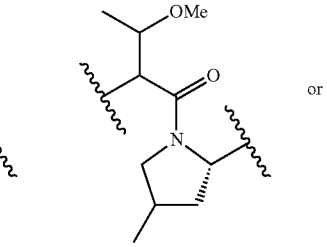
In one embodiment both of —$V^{1a}$—C(=O)—$P^{1a}$— and —$P^{1b}$—C(=O)—$V^{1b}$— are independently selected from:
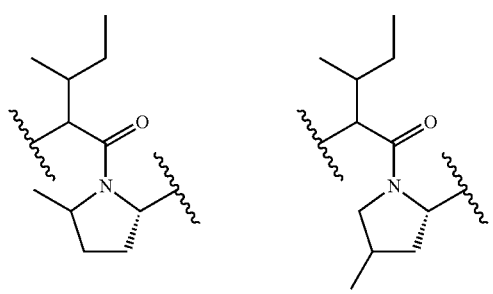
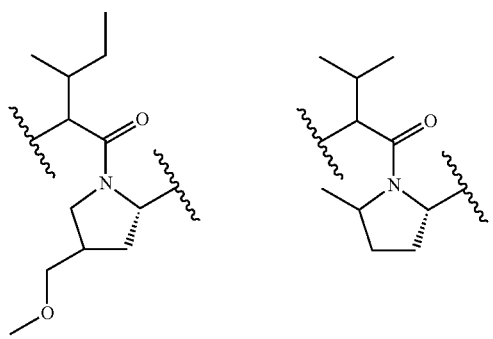
In one embodiment one of —$V^{1a}$—C(=O)—$P^{1a}$— and —$P^{1b}$—C(=O)—$V^{1b}$— is:
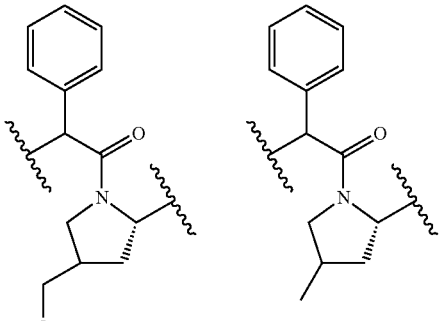
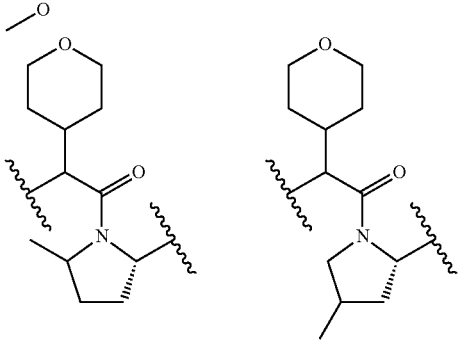

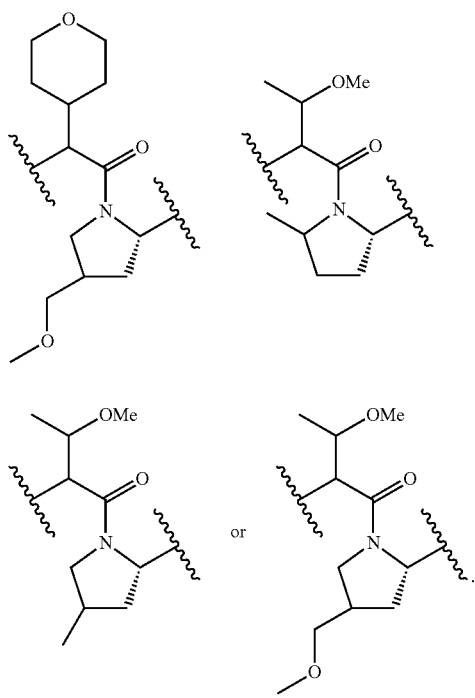
and the other of —V$^{1a}$—C(=O)—P$^{1a}$— and —P$^{1b}$—C(=O)—V$^{1b}$— is:
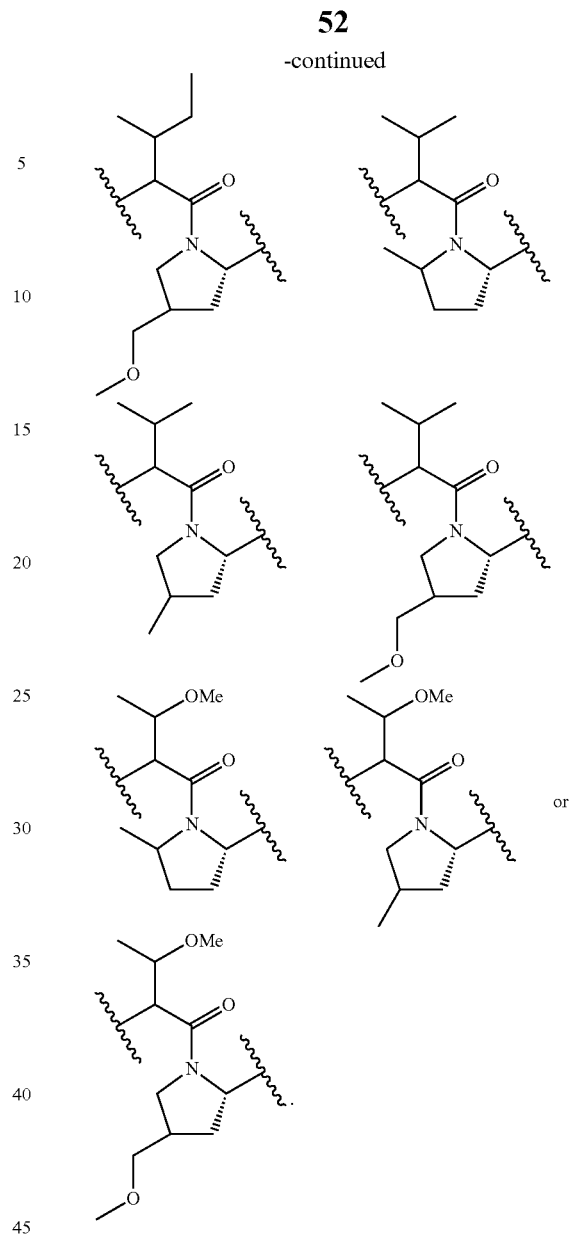
In one embodiment the disclosure provides a compound of formula:
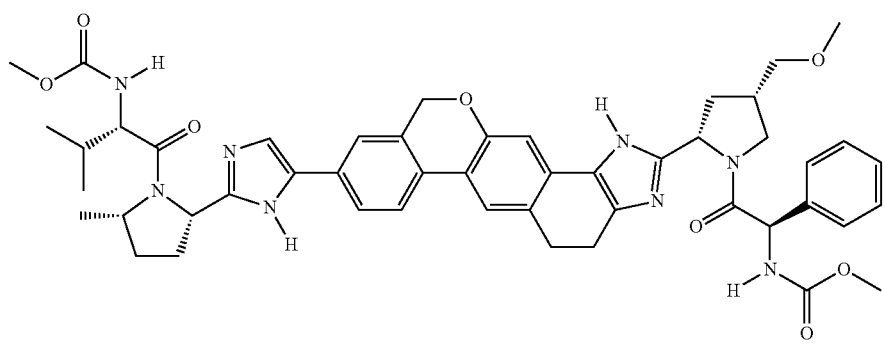

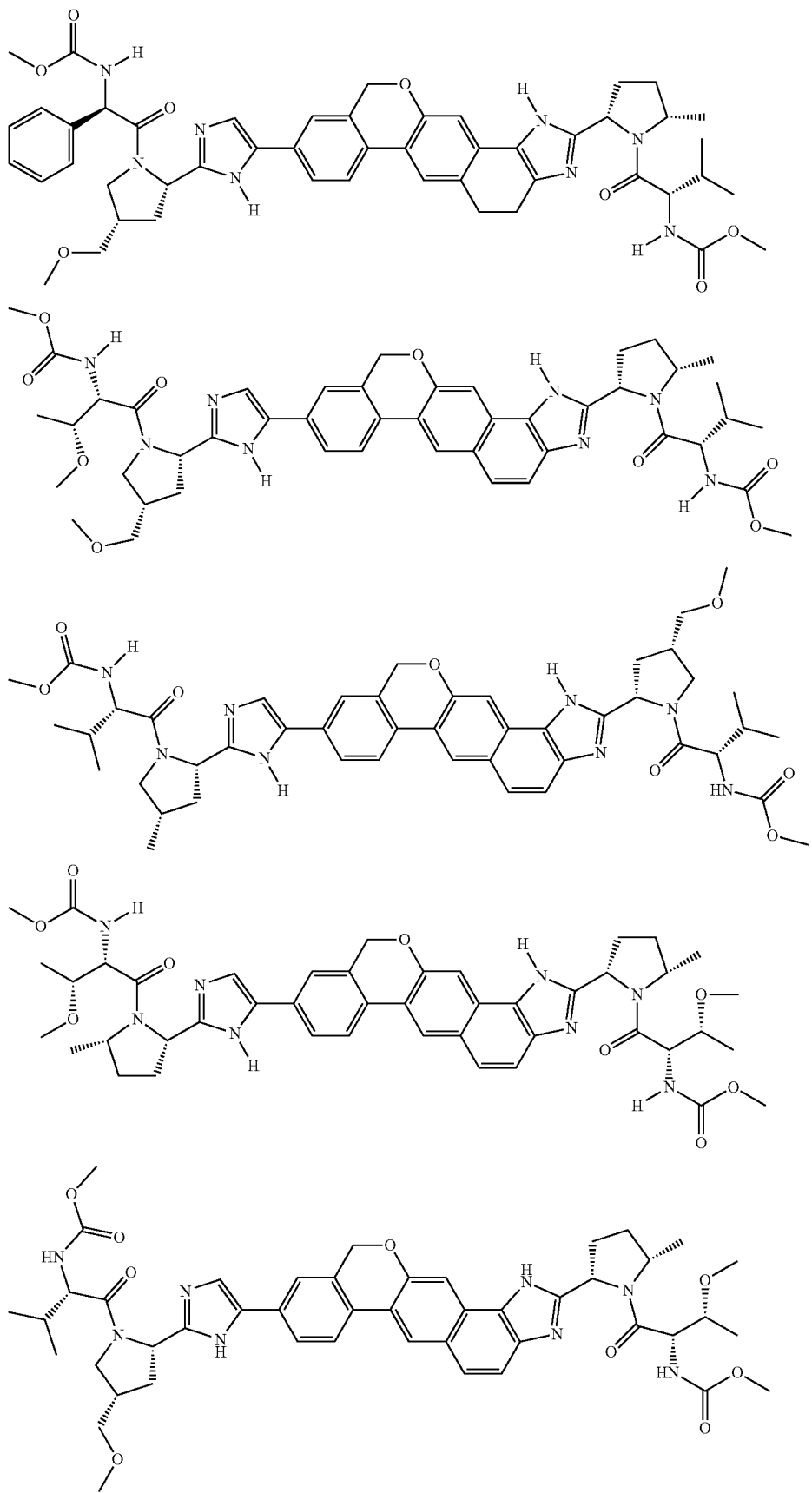

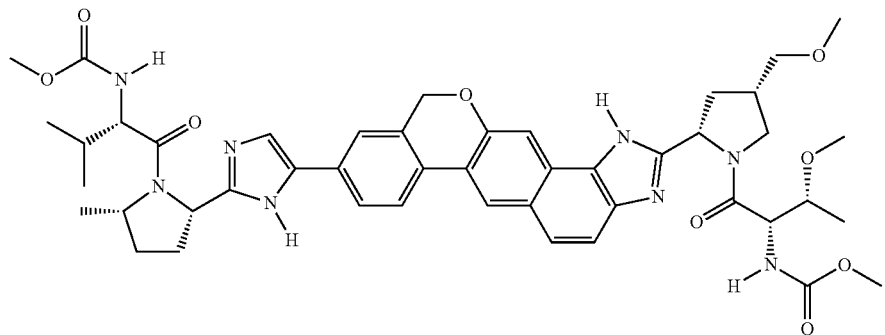
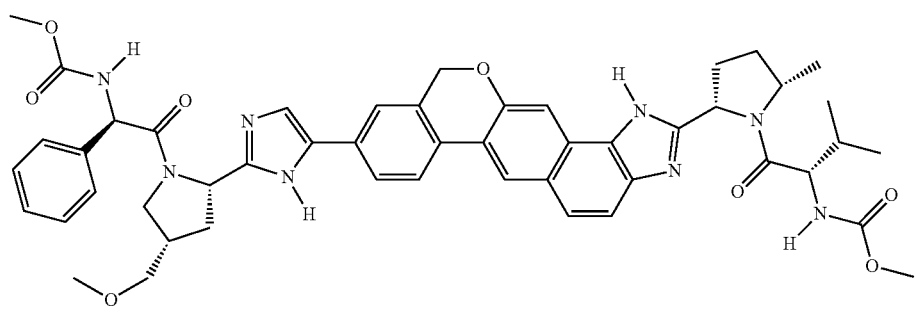
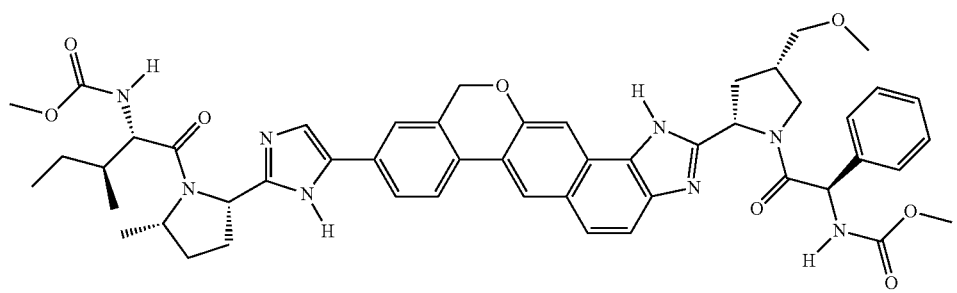
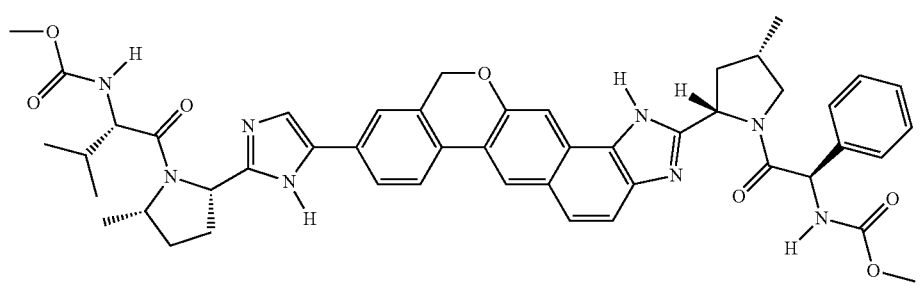
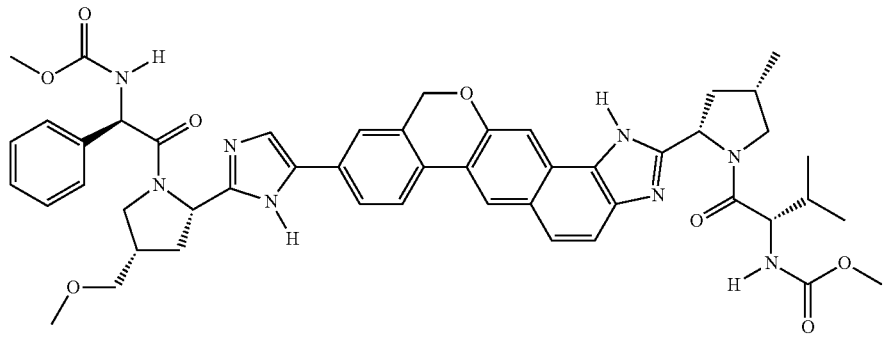

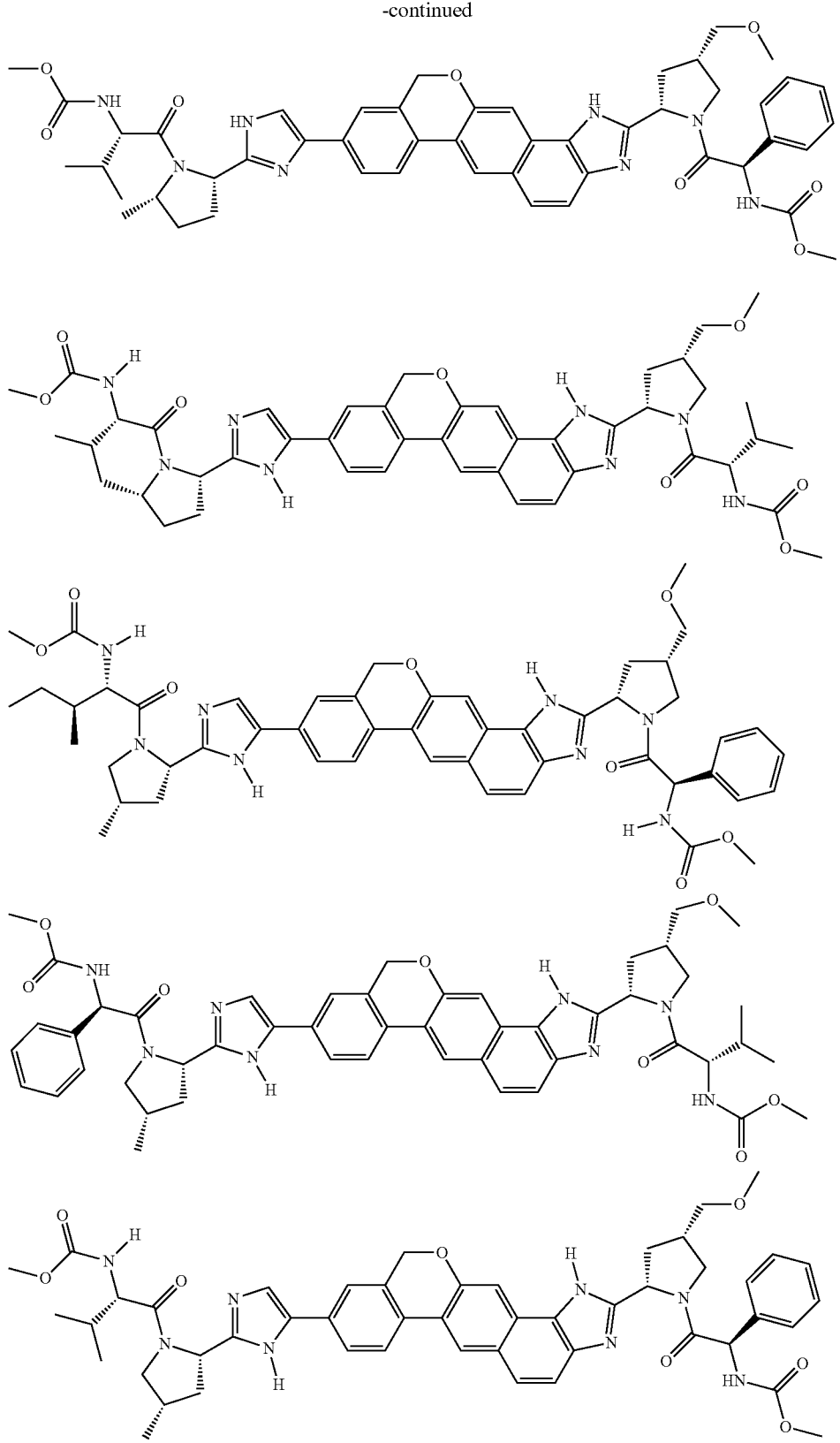
or a pharmaceutically acceptable salt or prodrug thereof.
In one embodiment the disclosure provides a compound of formula:

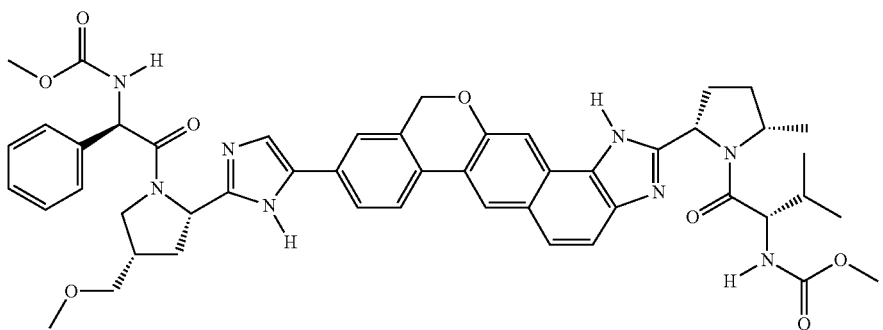 [SMILES: COC[C@H]1C[C@@H](c2ncc(-c3ccc4c(c3)COc3cc5c(ccc6nc([C@@H]7CC[C@H](C)N7C(=O)[C@@H](NC(=O)OC)C(C)C)[nH]c65)cc3-4)[nH]2)N(C(=O)[C@H](NC(=O)OC)c2ccccc2)C1]
or a pharmaceutically acceptable salt or prodrug thereof.
 In one embodiment the disclosure provides a compound of formula:
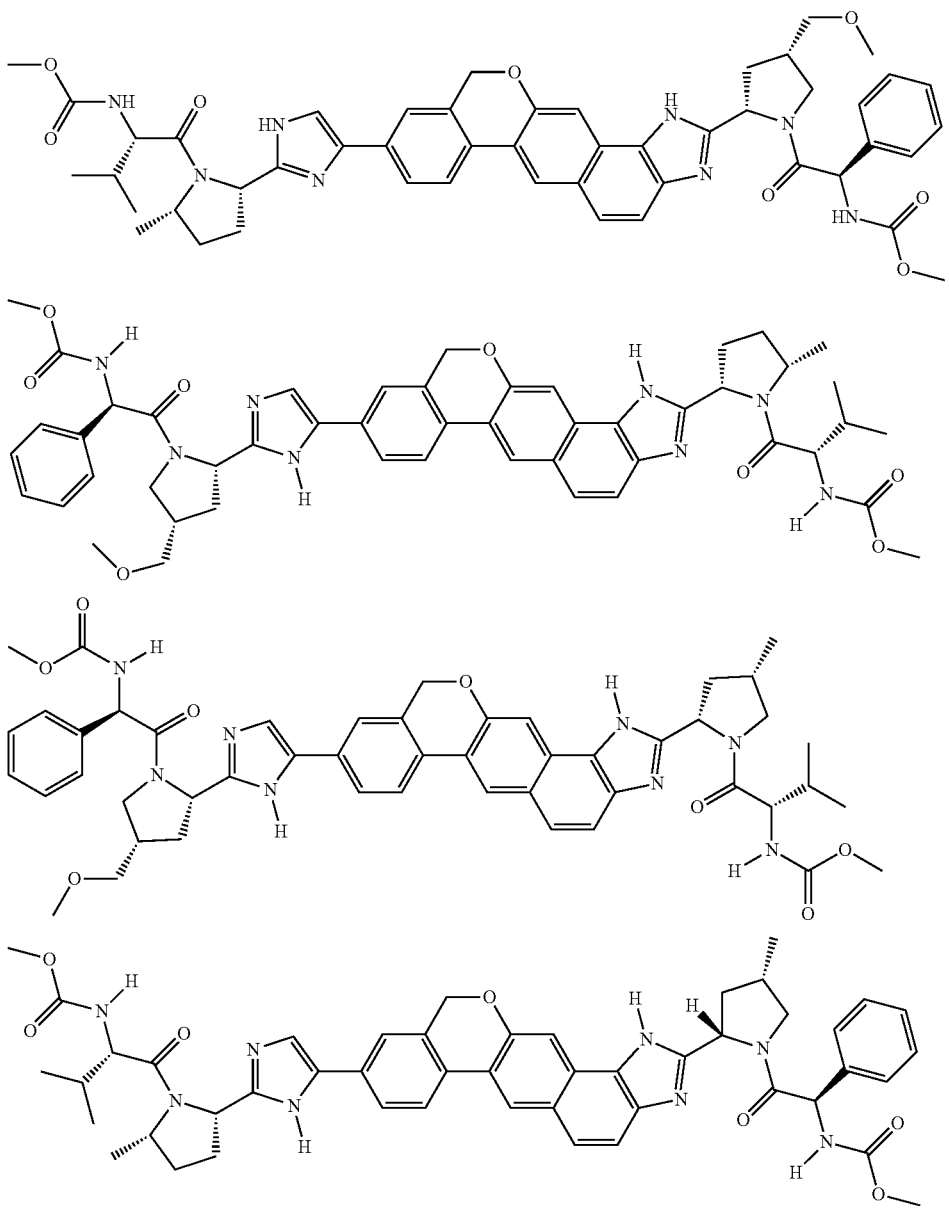

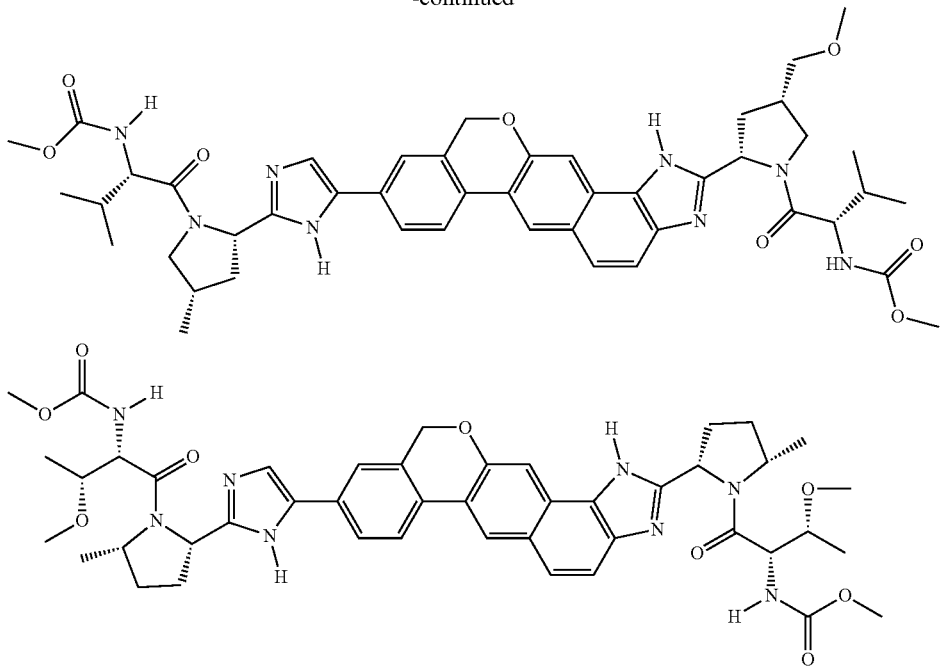

or a pharmaceutically acceptable salt or prodrug thereof.

The disclosure will now be illustrated by the following non-limiting Examples. The following abbreviations are used throughout the specification, including the Examples.

| | |
|---|---|
| (aq) | Aqueous |
| (g) | Gas |
| (s) | Solid |
| ° C. | Degree Celsius |
| Ac | Acetate |
| ACN | Acetonitrile |
| apprx | Approximate |
| Bis-pinB/(Bpin)$_2$/ (pinB)$_2$ | Bis(pinacolato)diboron |
| BOC/Boc | tert-Butoxycarbonyl |
| calc'd | Calculated |
| CC$_{50}$ | 50% Cytotoxicity concentration |
| COMU | 1-[(1-(Cyano-2-ethoxy-2-oxoethylideneaminooxy) dimethylaminomorpholino)] uronium hexafluorophosphate |
| d | Doublet |
| dba | dibenzalacetone |
| DCM | Dichloromethane |
| dd | Doublet of doublets |
| ddd | Doublet of doublet of doublets |
| DIPEA/DIEA | N,N-Diisopropylethylamine |
| DMA | N,N-Dimethylacetamide |
| DMAP | 4-Dimethylaminopyridine |
| DME | Dimethoxyethane |
| DMEM | Eagle's minimal essential medium |
| DMF | Dimethylformamide |
| DMSO/dmso | Dimethylsulfoxide |
| dppf | 1,1'-bis(diphenylphosphanyl) ferrocene |
| dt | Doublet of triplets |
| EC$_{50}$ | Half maximal effective concentration |
| ESI | Electrospray ionization |
| Et | Ethyl |
| ext. | External |
| FBS | Fetal bovine serum |
| g | Gram |
| HATU | 2-(1H-7-Azabenzotriazol-1-yl)-1,1,3,3-tetramethyl uronium hexafluorophosphate Methanaminium |
| HPLC | High performance liquid chromatography |
| hr/h | Hour |
| Hz | Hertz |
| J | Coupling constant |
| LCMS | Liquid chromatography mass spectrometry |
| M | Molar |
| m | Multiplet |
| m/z | Mass to charge |
| M+ | Mass peak |
| Me | Methyl |
| mg | Milligram |
| MHz | Megahertz |
| min | Minute |
| mL | Milliliter |
| mmol | Millimole |
| Moc | Methoxycarbonyl |
| MS | Mass spectrometry |
| MTBE | Methyl tert-butyl ether |
| N | Normal |
| NADPH | Nicotinamide adenine dinucleotide phosphate |
| NBS | N-Bromosuccinimide |
| NMM | N-Methylmorpholine |
| NMR | Nuclear magnetic resonance |
| o/n | Over night |
| Papp | Apparent permeability |
| PBS | Phosphate buffer system |
| Pd/C | Palladium on carbon |
| Ph | Phenyl |
| Phg/PhGly | Phenyl glycine |
| Piv | Pivalate |
| Pro | Proline |
| pyr | Pyridine |
| q | Quartet |
| qd | Quartet of doublets |
| quant | Quantitative |
| quint | Quintet |
| rt/RT | Room temperature |
| s | Singlet |
| SPhos | 2-Dicyclohexylphosphino-2',6'-dimethoxybiphenyl |
| t | Triplet |
| t-Bu | tert-Butyl |

-continued

| | |
|---|---|
| TEMPO | (2,2,6,6-Tetramethyl-piperidin-1-yl)oxyl |
| Tf | Trifluoromethanesulfonate |
| TFA | Trifluoroacetic acid |
| THF | Tetrahydrofuran |
| Thr | Threonine |
| TLC | Thin layer chromatography |
| tol. | Toluene |
| UV | Ultraviolet |
| Val | Valine |
| w/v | Weight to volume |
| w/w | Weight to weight |
| X-Phos/XPOS/ Xphos | 2-Dicyclohexylphosphino-2',4',6'-triisopropylbiphenyl |
| δ | Chemical shift |
| μg | Microgram |
| μL | Microliter |

Examples

Example LQ

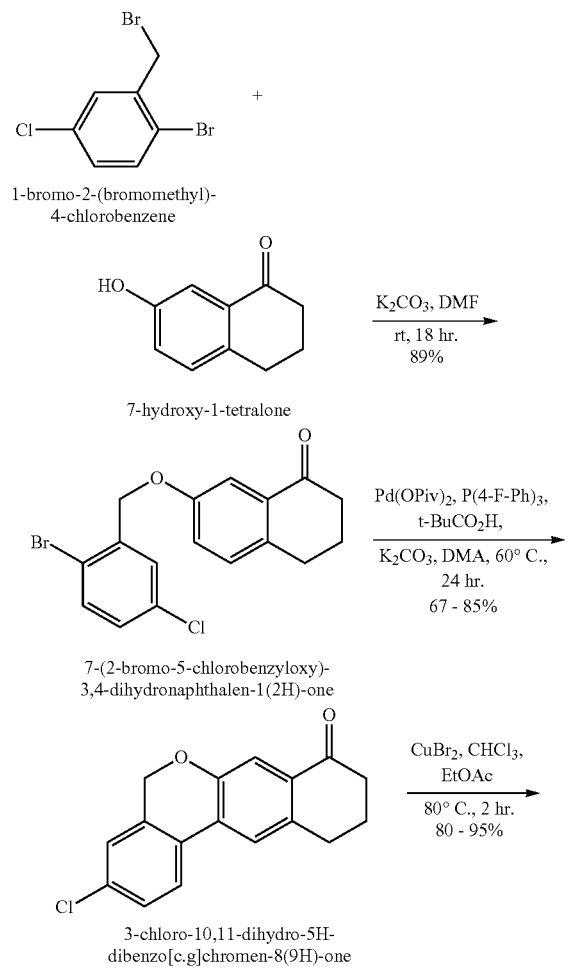

7-hydroxy-1-tetralone 7-(2-bromo-5-chlorobenzyloxy)-3,4-dihydronaphthalen-1(2H)-one 3-chloro-10,11-dihydro-5H-dibenzo[c,g]chromen-8(9H)-one

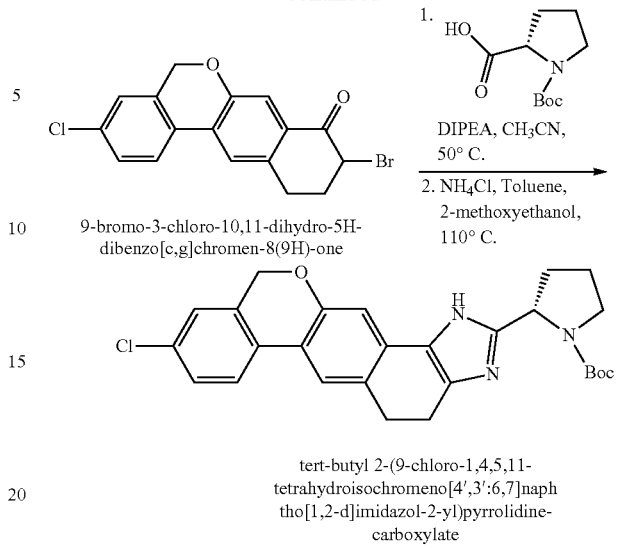

9-bromo-3-chloro-10,11-dihydro-5H-dibenzo[c,g]chromen-8(9H)-one tert-butyl 2-(9-chloro-1,4,5,11-tetrahydroisochromeno[4',3':6,7]naphtho[1,2-d]imidazol-2-yl)pyrrolidine-carboxylate 7-(2-bromo-5-chlorobenzyloxy)-3,4-dihydronaphthalen-1(2H)-one To a stirred solution of 7-hydroxy-1-tetralone (13.9 g, 85.7 mmol) and 1-bromo-2-(bromomethyl)-4-chlorobenzene (25.6 g, 90 0 mmol) in dimethylformamide (850 mL) was added potassium carbonate (24 g, 172 mmol). The reaction was stirred under argon for 18 hours then diluted with ethyl acetate (1 L). The organics were washed three times with water and once with brine. The organic layer was then dried with magnesium sulfate, filtered and concentrated. To the resulting oil was added methanol (500 mL) and the suspension was agitated for thirty minutes. 7-(2-bromo-5-chlorobenzyloxy)-3,4-dihydronaphthalen-1(2H)-one (27.8 g, 89% yield) was isolated by filtration.

3-chloro-10,11-dihydro-5H-dibenzo[c,g]chromen-8(9H)-one

To a 1 L flask containing palladium(11) pivalate (1.18 g, 3 8 mmol), tri(4-fluorophenyl)phosphine (1.20 g, 3.8 mmol), pivalic acid (2.33 g, 22.8 mmol) and potassium carbonate (31.8 g, 228 mmol) was added a solution of 7-(2-bromo-5-chlorobenzyloxy)-3,4-dihydronaphthalen-1(2H)-one (27.8 g, 76.2 mmol) in dimethylacetamide (380 mL). The flask was evacuated and backfilled with argon 5 times and then stirred under argon at 60° C. for 24 hours. The reaction was cooled to room temperature and diluted with MTBE and water. The resulting biphasic mixture was stirred for 3 hours and filtered through Celite, rinsing with MTBE. The organic layer of the filtrate was separated and then washed twice with water and once with brine. The organics were then dried with magnesium sulfate, filtered, concentrated and purified by flash column chromatography (Hexanes/DCM) to yield 3-chloro-10,11-dihydro-5H-dibenzo[c,g]chromen-8(9H)-one (14.4 g, 67% yield) as an off-white solid.

9-bromo-3-chloro-10,11-dihydro-5H-dibenzo[c,g]chromen-8(9H)-one

To a mixture of 3-chloro-10,11-dihydro-5H-dibenzo[c,g]chromen-8(9H)-one (14.8 g, 52 mmol) in chloroform (50 mL) and ethyl acetate (50 mL) was added copper(II) bromide (24.3 g, 104 mmol). The reaction was heated to 80° C. for 2 hours and then cooled to room temperature. The mixture was diluted with dichloromethane and washed twice with a 5:1 solution of saturated aqueous ammonium chloride and aqueous ammonium hydroxide (~38%), and washed once with water. The organic layer was dried with magnesium sulfate, filtered and concentrated to yield 9-bromo-3-chloro-10,11-dihydro-5H-dibenzo[c,g]chromen-8(9H)-one (18.5 g, >95% yield) with >95% purity.

Note: This reaction is not always this clean. Sometimes there is over-bromination and sometimes there is significant starting material. These impurities can be removed by flash column chromatography.

tert-Butyl 2-(9-chloro-1,4,5,11-tetrahydroisochromeno[4',3':6,7]naphtho[1,2-d]imidazol-2-yl)pyrrolidine-1-carboxylate To a solution of (1R)-2-(tert-butoxycarbonyl)cyclopentanecarboxylic acid (10.17 g, 47.25 mmol) and 9-bromo-3-chloro-10,11-dihydro-6H-naphtho[2,3-c]chromen-8(9H)-one (5.7 mg, 15.7 mmol) in acetonitrile (50 mL) was added diisopropylethylamine (11.11 mL, 64 mmol). The reaction was stirred at 50° C. for 4 hours and was then diluted with ethyl acetate. The organics were washed with water and brine, dried (MgSO$_4$) and concentrated. The resulting crude residue was purified by flash chromatography to yield (2S)-1-tert-butyl 2-(3-chloro-8-oxo-8,9,10,11-tetrahydro-5H-naphtho[c,g]chromen-9-yl)pyrrolidine-1,2-dicarboxylate (4.52 g, 58%). To a solution of (2S)-1-tert-butyl 2-(3-chloro-8-oxo-8,9,10,11-tetrahydro-6H-naphtho[2,3-c]chromen-9-yl)pyrrolidine-1,2-dicarboxylate (3.27 mg, 6.56 mmol) in a mixture of toluene (11 mL) and 2-methoxyethanol (0.7 mL) was added ammonium acetate (5.06 g, 65.6 mmol). The reaction mixture was heated to 110° C. for 3 hours, cooled to room temperature and diluted with ethyl acetate. The organics were washed with water and brine, dried (Na$_2$SO$_4$), and concentrated. The crude residue was purified by flash chromatography to yield tert-butyl 2-(9-chloro-1,4,5,11-tetrahydroisochromeno[4',3':6,7]naphtho[1,2-d]imidazol-2-yl)pyrrolidine-1-carboxylate (1.95 g, 61%). LCMS-ESI$^+$: calculated for C27H28ClN$_3$O3$_{42}$: 477.98; observed [M+1]$^+$: 478.47 tert-Butyl 2-(9-chloro-1,11-dihydroisochromeno[4',3':6,7]naphtho[1,2-d]imidazol-2-yl)pyrrolidine-1-carboxylate To a solution of tert-butyl 2-(9-chloro-1,4,5,11-tetrahydroisochromeno[4',3':6,7]naphtho[1,2-d]imidazol-2-yl)pyrrolidine-1-carboxylate (1.9 g, 3.96 mmol) in dichloromethane (35 mL) was added manganese(IV) oxide (17 g, 198 mmol). The reaction mixture was stirred at room temperature for 18 hours, diluted with ethyl acetate. The organics were washed with water and brine, dried (Na$_2$SO$_4$), and concentrated. The crude residue was purified by flash chromatography to yield tert-butyl 2-(9-chloro-1,11-dihydroisochromeno[4',3':6,7]naphtho[1,2-d]imidazol-2-yl)pyrrolidine-1-carboxylate (1.52 g, 81%). LCMS-ESI$^+$: calculated for C27H26ClN3O3: 475.9; observed [M+1]$^+$: 476.45.

tert-Butyl 2-[9-(4,4,5,5-tetramethyl-1,3,2-dioxaborolan-2-yl)-1,11-dihydroisochromeno[4',3':6,7]naphtho[1,2-d]imidazol-2-yl]pyrrolidine-1-carboxylate A degassed mixture of tert-butyl 2-(9-chloro-1,11-dihydroisochromeno[4',3':6,7]naphtho[1,2-d]imidazol-2-yl)pyrrolidine-1-carboxylate (1.52 g, 3.17 mmol), bis(pinacolato) diboron (1.21 g, 4.75 mmol), potassium acetate (934 mg, 9.52 mmol), tris(dibenzylideneacetone)palladium (116 mg, 0.13 mmol) and 2-dicyclohexylphosphino-2',4',6'-tri-i-propyl-1,1'-biphenyl (121 mg, 0.08 mmol) in 1,4-dioxane (16 mL) was heated to 90° C. for 1.5 hours, cooled to room temperature and diluted with ethyl acetate. The organics were washed with water and brine, dried (Na$_2$SO$_4$), and concentrated. The crude residue was purified by flash chromatography to yield tert-butyl 2-[9-(4,4,5,5-tetramethyl-1,3,2-dioxaborolan-2-yl)-1,11-dihydroisochromeno[4',3':6,7]naphtho[1,2-d]imidazol-2-yl]pyrrolidine-1-carboxylate (1.7 g, 94%)

tert-Butyl 2-[9-(2-{1-[N-(methoxycarbonyl)valyl]pyrrolidin-2-yl}-1H-imidazol-5-yl)-1,11-dihydroisochromeno[4',3':6,7]naphtho[1,2-d]imidazol-2-yl]pyrrolidine-1-carboxylate To a solution of methyl(S)-1-((S)-2-(5-bromo-1H-imidazol-2-yl)pyrrolidin-1-yl)-3-methyl-1-oxobutan-2-ylcarbamate (1.48 g, 3.97 mmol), tert-butyl 2-[9-(4,4,5,5-tetramethyl-1,3,2-dioxaborolan-2-yl)-1,11-dihydroisochromeno[4',3':6,7]naphtho[1,2-d]imidazol-2-yl]pyrrolidine-1-carboxylate (1.88 g, 1.48 mmol), tetrakis(triphenyl phosphine)palladium (0) (191 mg, 0.16 mmol) and dichloro[1,1'-bis(diphenylphosphino) ferrocene]palladium(II) (242 mg, 0.33 mmol) in a mixture of 1,2-dimethoxyethane (37.0 mL) and dimethylformamide (6 mL) was added a solution of potassium carbonate (2M in water, 5 mL, 9.93 mmol). The resulting mixture was degassed and then heated to 85° C. under argon for 18 hours. After cooling to room temperature, the reaction was diluted with ethyl acetate. The organics were washed with water and brine, dried (Na$_2$SO$_4$), and concentrated. The crude residue was purified by flash chromatography to yield tert-butyl 2-[9-(2-{1-[N-(methoxycarbonyl)valyl]pyrrolidin-2-yl}-1H-imidazol-5-yl)-1,11-dihydroisochromeno[4',3':6,7]naphtho[1,2-d]imidazol-2-yl]pyrrolidine-1-carboxylate (1.45 mg, 59%). LCMS-ESI$^+$: calculated for C41H47N7O6$_{73}$ 733.86; observed [M+1]$^+$: 734.87.

[1-(2-{5-[2-(1-{[(Methoxycarbonyl)amino](phenyl)acetyl}pyrrolidin-2-yl)-1,11-dihydroisochromeno[4',3':6,7]naphtho[1,2-d]imidazol-9-yl]-1H-imidazol-2-yl}pyrrolidin-1-yl)-3-methyl-1-oxobutan-2-yl]carbamic acid A solution of tert-butyl 2-[9-(2-{1-[N-(methoxycarbonyl)valyl]pyrrolidin-2-yl}-1H-imidazol-5-yl)-1,11-dihydroisochromeno[4',3':6,7]naphtho[1,2-d]imidazol-2-yl]pyrrolidine-1-carboxylate (462 mg, 0.63 mmol), ethanol (6 mL) and concentrated HCl (2 mL) was heated to 60° C. for 1 hour. The reaction was concentrated and the crude material dissolved in DCM (6 mL). This solution was concentrated and to this material was added a solution of (R)-2-(methoxycarbonylamino)-2-phenylacetic acid (172 mg, 0.82 mmol) and COMU (311 mg, 073 mmol) in DMF (6 mL). To the resulting solution was added diisopropylethylamine (330 μL, 1.89 mmol). After stirring for 18 hours at room temperature, the reaction was diluted with ethyl acetate, washed with water and brine, dried (Na$_2$SO$_4$), concentrated and purified by preparative reverse phase HPLC (Gemini, 15 to 45% ACN/H$_2$O+ 0.1% TFA). The product fractions were lyophilized to give [1-(2-{5-[2-(1-{[(methoxycarbonyl)amino](phenyl)acetyl}pyrrolidin-2-yl)-1,11-dihydroisochromeno[4',3':6,7]naphtho[1,2-d]imidazol-9-yl]-1H-imidazol-2-yl}pyrrolidin- 1-yl)-3-methyl-1-oxobutan-2-yl]carbamic acid (231 mg, 45%). LCMS-ESI⁺: calculated for $C_{46}H_{48}N_8O_{7S}$: 824.92; observed [M+1]⁺: 826.00.

Example LR

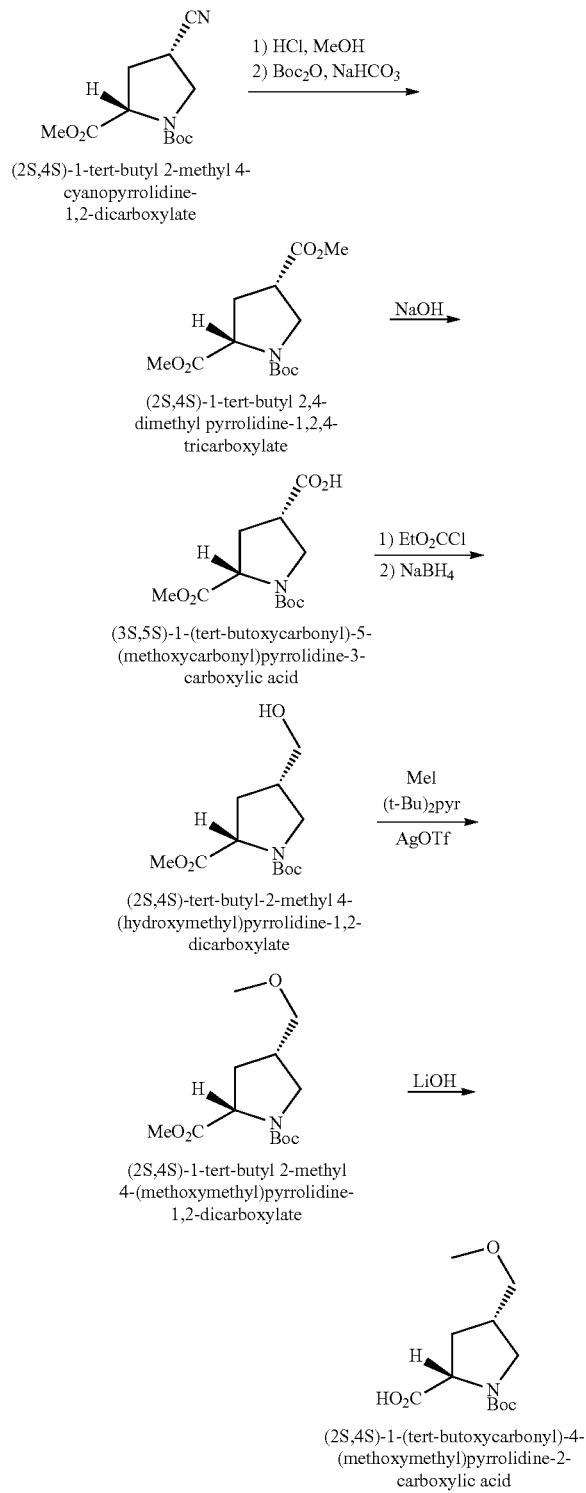

(2S,4S)-1-tert-butyl 2,4-dimethyl pyrrolidine-1,2,4-tricarboxylate

To a solution of (2S,4S)-1-tert-butyl 2-methyl 4-cyanopyrrolidine-1,2-dicarboxylate (9.0 g, 35.4 mmol) in MeOH (196 mL) was added HCl (4M in 1,4-dioxane, 100 mL, 403 mmol). The solution was stirred at room temperature for 16 h and concentrated in vacuo. The crude intermediate was dissolved in EtOAc (180 mL) and basified with aqueous bicarbonate (sat.). Di-tert-butyl dicarbonate (8.5 g, 38.9 mmol) was added and the biphasic solution was stirred at room temperature for 12 h. The layers were then separated and the aqueous layer was backextracted with EtOAc. The combined organic layers were washed with brine, dried over $Na_2SO_4$, and concentrated. The crude oil was purified by silica gel chromatography (15% to 40% to 100% EtOAc/Hexanes) to provide (2S,4S)-1-tert-butyl 2,4-dimethylpyrrolidine-1,2,4-tricarboxylate (9.56 g, 94%).

(3S,5S)-1-(tert-butoxycarbonyl)-5-(methoxycarbonyl)pyrrolidine-3-carboxylic acid To a solution of (2S,4S)-1-tert-butyl 2,4-dimethylpyrrolidine-1,2,4-tricarboxylate (9.56 g, 33.3 mmol) in THF (70 mL) at 0° C. (external temperature, ice bath) was added NaOH (1N aqueous, 33 mL, 33.3 mmol) dropwise over 15 min. The solution was stirred at 0° C. for 5 h before acidification with HCl (1N). The solution was extracted with EtOAc (3×). The combined organic layers were dried over $Na_2SO_4$ and concentrated. The crude oil was purified by silica gel chromatography (2% to 5% to 10% $MeOH/CH_2Cl_2$) to provide (3S,5S)-1-(tert-butoxycarbonyl)-5-(methoxycarbonyl)pyrrolidine-3-carboxylic acid (6.38 g, 70%).

(2S,4S)-1-tert-butyl 2-methyl 4-(hydroxymethyl) pyrrolidine-1,2-dicarboxylate

To a solution of (3S,5S)-1-(tert-butoxycarbonyl)-5-(methoxycarbonyl)pyrrolidine-3-carboxylic acid (6.38 g, 23.3 mmol) in THF (116 mL) at 0° C. (external temperature, ice bath) was added $Et_3N$ (4.9 mL, 35.0 mmol) and ethyl chloroformate (2.7 mL, 28.0 mmol). The resulting solution was stirred at 0° C. for 45 min, during which time a white precipitate forms. The reaction mixture was filtered through celite and concentrated.

The crude intermediate was dissolved in THF (59 mL) and cooled to 0° C. (external temperature, ice bath). $NaBH_4$ (4.41 g, 116.7 mmol) in $H_2O$ (59 mL) was slowly added and the resulting solution was stirred at 0° C. for 2 h. The reaction mixture was diluted with EtOAc and washed with $H_2O$. The aqueous layer was backextracted with EtOAc. The combined organic layers were dried over $Na_2SO_4$ and concentrated. The crude oil was purified by silica gel chromatography (42% to 69% to 100% EtOAc/Hexanes) to provide (2S,4S)-1-tert-butyl 2-methyl 4-(hydroxymethyl)pyrrolidine-1,2-dicarboxylate (3.63 g, 60%).

(2S,4S)-1-tert-butyl 2-methyl 4-(methoxymethyl) pyrrolidine-1,2-dicarboxylate

To a solution of (2S,4S)-1-tert-butyl 2-methyl 4-(hydroxymethyl)pyrrolidine-1,2-dicarboxylate (2.57 g, 9.9 mmol) in $CH_2Cl_2$ (50 mL) was added AgOTf (4.07 g, 15.8 mmol) and 2,6-di-tert-butylpyridine (4.4 mL, 19.8 mmol). The reaction mixture was cooled to 0° C. (external temperature, ice bath) and MeI (0.98 mL, 15.8 mmol) was slowly added. The resulting slurry was stirred at 0° C. for 1.5 h and at room temperature for 1.5 h. The slurry was diluted with CH$_2$Cl$_2$ and filtered through celite. The filtrate was concentrated to dryness, dissolved in Et$_2$O, and washed with HCl (1N) and brine. The aqueous layers were backextracted with Et$_2$O and the combined organic layers were dried over Na$_2$SO$_4$ and concentrated. The crude oil was purified by silica gel chromatography (10% to 75% to 100% EtOAc/Hexanes) to provide (2S,4S)-1-tert-butyl 2-methyl 4-(methoxymethyl)pyrrolidine-1,2-dicarboxylate (2.11 g, 78%). $^1$H-NMR: 400 MHz, (CDCl$_3$) δ: (mixture of rotamers, major reported) 4.20 (t, 1H), 3.71 (s, 3H), 3.67 (m, 1H), 3.34 (m, 2H), 3.30 (s, 3H), 3.16 (t, 1H), 2.43 (m, 2H), 1.74 (m, 1H), 1.38 (s, 9H).

(2S,4S)-1-(tert-butoxycarbonyl)-4-(methoxymethyl)pyrrolidine-2-carboxylic acid

To a solution of (2S,4S)-1-tert-butyl 2-methyl 4-(methoxymethyl)pyrrolidine-1,2-dicarboxylate (2.11 g, 7.7 mmol) in a mixture of THF (38 mL) and MeOH (15 mL) was added LiOH (2.5 M aqueous, 15 mL, 38.6 mmol). The resulting solution was stirred at room temperature for 2 h, and acidified with aqueous HCl (1N). The desired product was extracted with CH$_2$Cl$_2$ (4×). The combined organic layers were dried over Na$_2$SO$_4$ and concentrated to provide (2S,4S)-1-(tert-butoxycarbonyl)-4-(methoxymethyl)pyrrolidine-2-carboxylic acid (2.0 g, 99%). $^1$H-NMR: 400 MHz, (CDCl$_3$) δ: (mixture of rotamers, major reported) 4.33 (t, 1H), 3.65 (m, 1H), 3.35 (m, 2H), 3.32 (s, 3H), 3.16 (t, 1H), 2.45 (m, 2H), 2.12 (m, 1H), 1.46 (s, 9H).

Example LR-1

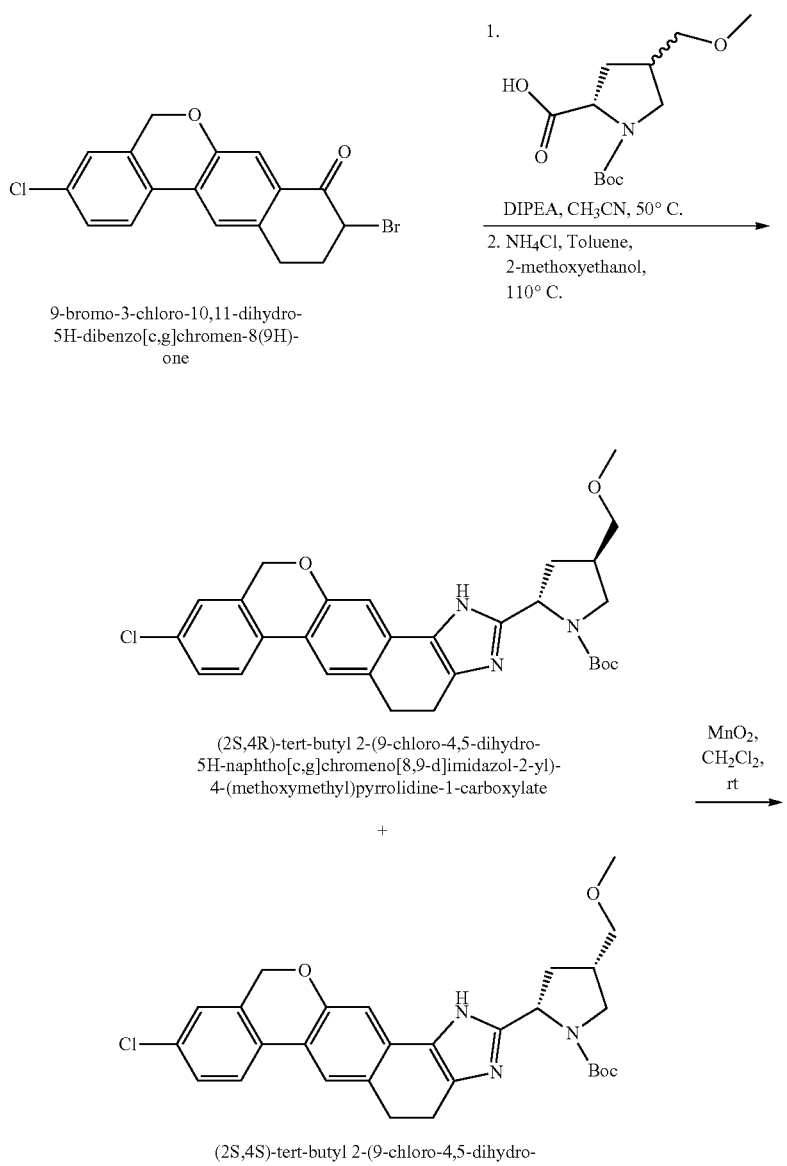

-continued

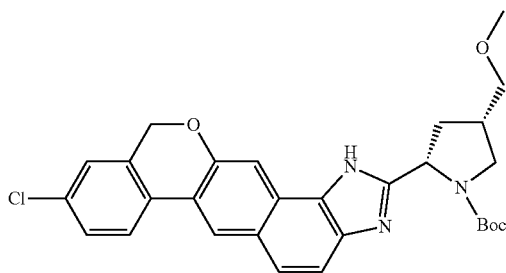 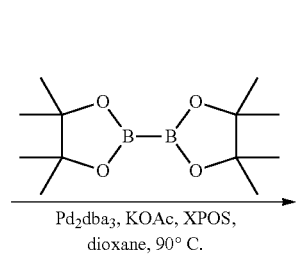

(2S,4S)-tert-butyl 2-(9-chloro-5H-naphtho
[c,g]chromeno[8,9-d]imidazol-2-yl)-4-
(methoxymethyl)pyrrolidine-1-carboxylate Pd$_2$dba$_3$, KOAc, XPOS,
dioxane, 90° C.

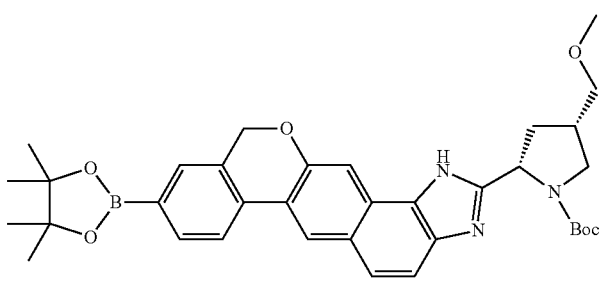 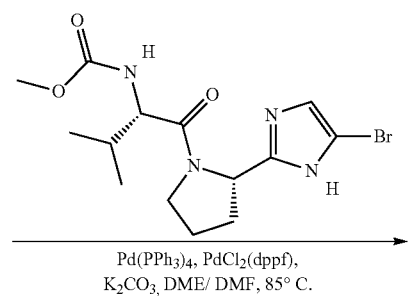

(2S,4S)-tert-butyl 4-(methoxymethyl)-2-(9-(4,4,5,5-
tetramethyl-1,3,2-dioxaborolan-2-yl)-5H-naphtho
[c,g]chromeno[8,9-d]imidazol-2-yl)pyrrolidine-
1-carboxylate Pd(PPh$_3$)$_4$, PdCl$_2$(dppf),
K$_2$CO$_3$, DME/ DMF, 85° C.

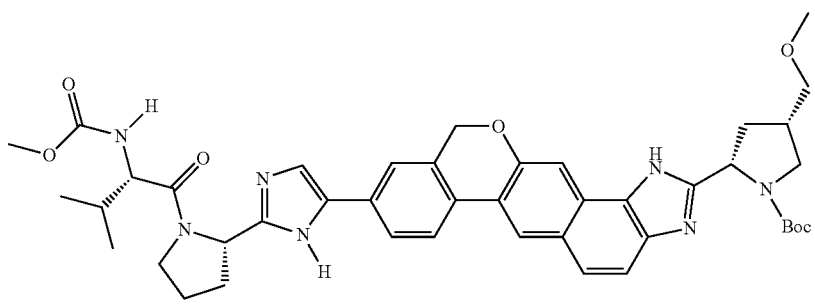 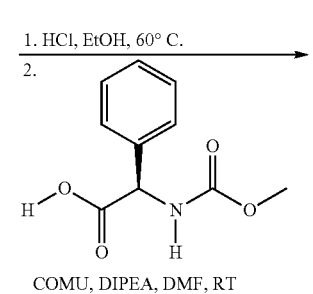

(2S,4S)-tert-butyl 2-(9-(2-((S)-2-(methoxycarbonylamino)-3-
methylbutanoyl)pyrrolidin-2-yl)-1H-imidazol-5-yl)-5H-napto
[c,g]chromeno[8,9-d]imidazol-2-yl)-4-(methoxymethyl)pyrrolidine-1-
carboxylate 1. HCl, EtOH, 60° C.
2.

COMU, DIPEA, DMF, RT

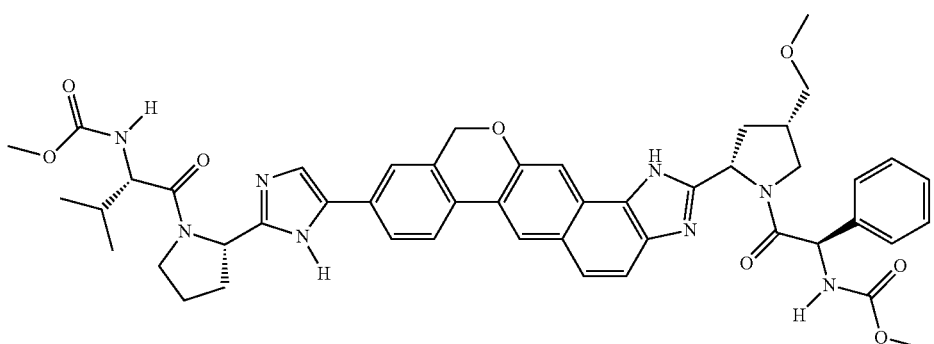

methyl {2-[2-{9-[2-(1-{2-[(methoxycarbonyl)amino]-3-
methylbutanoyl}pyrrolidin-2-yl)-1H-imidazol-5-yl]-1,11-
dihydroisochromeno[4',3':6,7]naptho[1,2-d]imidazol-2-yl}-
4-(methoxymethyl)pyrrolidin-1-yl]-2-oxo-1-
phenylethyl}carbamate

(2S,4S)-tert-butyl-2-(9-chloro-4,5-dihydro-5H-naphtho[2,3-c]chromeno[8,9-d]imidazol-2-yl)-4-(methoxymethyl)pyrrolidine-1-carboxylate To a solution of ((S)-1-(tert-butoxycarbonyl)-4-(methoxymethyl)pyrrolidine-2-carboxylic acid (5.9 g, 23.1 mmol) and 9-bromo-3-chloro-10,11-dihydro-5H-naphtho[c,g]chromen-8(9H)-one (5.6 mg, 15.4 mmol) in acetonitrile (60 mL) was added diisopropylethylamine (5.35 mL, 30.8 mmol). The reaction was stirred at 50° C. for 18 hours and was then diluted with ethyl acetate. The organics were washed with water and brine, dried (MgSO$_4$) and concentrated. The resulting crude residue was purified by flash chromatography to yield (2S)-1-tert-butyl-2-(3-chloro-8-oxo-8,9,10,11-tetrahydro-6H-naphtho[2,3-c]chromen-9-yl)-4(methoxymethyl)pyrrolidine-1,2-dicarboxylate (5.12 g, 61%). To a solution of (2S)-1-tert-butyl-2-(3-chloro-8-oxo-8,9,10,11-tetrahydro-6H-naphtho[2,3-c]chromen-9-yl)-4 (methoxymethyl)pyrrolidine-1,2-dicarboxylate (5.11 mg, 9.42 mmol) in a mixture of toluene (94 mL) and 2-methoxyethanol (0.1 mL) was added ammonium acetate (23.5 g, 304 mmol). The reaction mixture was heated to 110° C. for 18 hours, cooled to room temperature and diluted with ethyl acetate. The organics were washed with water and brine, dried (Na$_2$SO$_4$), and concentrated. The crude residue was purified by flash chromatography to yield (2S,4R)-tert-butyl 2-(9-chloro-4,5-dihydro-5H-naphtho[c,g]chromeno[8,9-d]imidazol-2-yl)-4-(methoxymethyl)pyrrolidine-1-carboxylate (1.05 g, 21%) and (2S,4S)-tert-butyl-2-(9-chloro-4,5-dihydro-6H-naphtho[2,3-c]chromeno[8,9-d]imidazol-2-yl)-4-(methoxymethyl)pyrrolidine-1-carboxylate (2.0 g, 41%). LCMS-ESI$^+$: calculated for $C_{29}H_{32}ClN_3O_{42}$: 522.0; observed [M+1]$^+$: 522.2.

(2S,4S)-tert-butyl-2-(9-chloro-5H-naphtho[c,g]chromeno[8,9-d]imidazol-2-yl)-4-(methoxymethyl)pyrrolidine-1-carboxylate To a solution of (2S,4S)-tert-butyl-2-(9-chloro-4,5-dihydro-5H-naphtho[c,g]chromeno[8,9-d]imidazol-2-yl)-4-(methoxymethyl)pyrrolidine-1-carboxylate (1.99 g, 3.82 mmol) in dichloromethane (30 mL) was added manganese (IV) oxide (10 g, 115 mmol). The reaction mixture was stirred at room temperature for 18 hours, diluted with ethyl acetate. The organics were washed with water and brine, dried (Na$_2$SO$_4$), and concentrated. The crude residue was purified by flash chromatography to yield(2S,4S)-tert-butyl-2-(9-chloro-6H-naphtho[2,3-c]chromeno[8,9-d]imidazol-2-yl)-4-methoxymethyl)pyrrolidine-1-carboxylate (1.05 g, 21%) and (2S,4S)-tert-butyl-2-(9-chloro-4,5-dihydro-6H-naphtho[2,3-c]chromeno[8,9-d]imidazol-2-yl)-4-(methoxymethyl)pyrrolidine-1-carboxylate (1.64 g, 82%). LCMS-ESI$^+$: calculated for $C_{29}H_{30}ClN_3O_{42}$: 520.02; observed [M+1]$^+$: 520.97.

(2S,4S)-tert-butyl-4-(methoxymethyl)-2-(9-(4,4,5,5-tetramethyl-1,3,2-dioxaborolan-2-yl)-5H-naphtho[c,g]chromeno[8,9-d]imidazol-2-yl)pyrrolidine-1-carboxylate A degassed mixture of -(2S,4S)-tert-butyl-2-(9-chloro-5H-naphtho[c,g]chromeno[8,9-d]imidazol-2-yl)-4-(methoxymethyl)pyrrolidine-1-carboxylate (649 mg 1.25 mmol), bis(pinacolato)diboron (635 mg, 2.5 mmol), potassium acetate (368 mg, 3.7 mmol), tris(dibenzylideneacetone)palladium (46 mg, 0.05 mmol) and 2-dicyclohexylphosphino-2',4',6'-tri-i-propyl-1,1'-biphenyl (60 mg, 0.12 mmol) in 1,4-dioxane (7 mL) was heated to 90° C. for 3 hours, cooled to room temperature and diluted with ethyl acetate. The organics were washed with water and brine, dried (Na$_2$SO$_4$), and concentrated. The crude residue was purified by flash chromatography to yield (2S,4S)-tert-butyl 4-(methoxymethyl)-2-(9-(4,4,5,5-tetramethyl-1,3,2-dioxaborolan-2-yl)-5H-naphtho[c,g]chromeno[8,9-d]imidazol-2-yl)pyrrolidine-1-carboxylate (467 mg, 61%) LCMS-ESI$^i$: calculated for $C_{35}H_{42}BN_3O_6$: 611.54; observed [M+1]$^+$: 612.96.

(2S,4S)-tert-butyl 2-(9-(2-((S)-1-((S)-2-(methoxycarbonylamino)-3-methylbutanoyl)pyrrolidin-2-yl)-1H-imidazol-5-yl)-5H-naphtho[c,g]chromeno[8,9-d]imidazol-2-yl)-4(methoxymethyl)pyrrolidine-1-carboxylate To a solution of (2S,4S)-tert-butyl 4-(methoxymethyl)-2-(9-(4,4,5,5-tetramethyl-1,3,2-dioxaborolan-2-yl)-5H-naphtho[c,g]chromeno[8,9-d]imidazol-2-yl)pyrrolidine-1-carboxylate (467 mg, 0.76 mmol), methyl(S)-1-((S)-2-(5-bromo-1H-imidazol-2-yl)pyrrolidin-1-yl)-3-methyl-1-oxobutan-2-ylcarbamate (342 mg, 0.92 mmol), tetrakis(triphenylphosphine) palladium(0) (44 mg, 0.04 mmol) and dichloro[1,1'-bis(diphenylphosphino)ferrocene]palladium (II) (56 mg, 0.07 mmol) in a mixture of 1,2-dimethoxyethane (11.0 mL) and dimethylformamide (1.9 mL) was added a solution of potassium carbonate (2M in water, 1.15 mL, 2.29 mmol). The resulting mixture was degassed and then heated to 85° C. under argon for 18 hours. After cooling to room temperature, the reaction was diluted with ethyl acetate. The organics were washed with water and brine, dried (Na$_2$SO$_4$), and concentrated. The crude residue was purified by flash chromatography to yield (2S,4S)-tert-butyl 2-(9-(2-((S)-1-((S)-2-(methoxycarbonylamino)-3-methylbutanoyl)pyrrolidin-2-yl)-1H-imidazol-5-yl)-5H-naphtho[c,g]chromeno[8,9-d]imidazol-2-yl)-4-(methoxymethyl)pyrrolidine-1-carboxylate (180 mg, 67%). LCMS-ESI$^+$: calculated for $C_{43}H_{51}N_7O_{73}$ 777.91; observed [M+1]$^+$: 778.84.

methyl{2-[2-{9-[2-(1-{2-[(methoxycarbonyl)amino]-3-methylbutanoyl}pyrrolidin-2-yl)-1H-imidazol-5-yl]-1,11-dihydroisochromeno[4',3':6,7]naphtho[1,2-d]imidazol-2-yl}-4-(methoxymethyl)pyrrolidin-1-yl]-2-oxo-1-phenylethyl}carbamate A solution of (2S,4S)-tert-butyl 2-(9-(2-((S)-1-((S)-2-(methoxycarbonylamino)-3-methylbutanoyl)pyrrolidin-2-yl)-1H-imidazol-5-yl)-5H-naphtho[c,g]chromeno[8,9-d]imidazol-2-yl)-4-(methoxymethyl)pyrrolidine-1-carboxylate (196 mg, 0.25 mmol), ethanol (3 mL) and concentrated HCl (1 mL) was heated to 60° C. for 1 hour. The reaction was concentrated and the crude material dissolved in DCM (6 mL). This solution was concentrated and to this material was added a solution of (R)-2-(methoxycarbonylamino)-2-phenylacetic acid (69 mg, 0.33 mmol) and COMU (124 mg, 029 mmol) in DMF (4 mL). To the resulting solution was added diisopropylethylamine (130 μL, 0.76 mmol). After stirring for 2 hours at room temperature, the reaction was diluted with ethyl acetate, washed with water and brine, dried (Na$_2$SO$_4$), concentrated and purified by preparative reverse phase HPLC (Gemini, 15 to 45% ACN/H$_2$O+0.1% TFA). The product fractions were lyophilized to give methyl{2-[2-{9-[2-(1-{2-[(methoxycarbonyl)amino]-3-methylbutanoyl}pyrrolidin-2-yl)-1H-imidazol-5-yl]-1,11-dihydroisochromeno[4',3':6,7]naphtho[1,2-d]imidazol-2-yl}-4-(methoxymethyl)pyrrolidin-1-yl]-2-oxo-1-phenylethyl}carbamate (84 mg, 39%). LCMS-ESI$^+$: calculated for $C_{48}H_{52}N_8O_8$: 868.98; observed [M+1]$^+$: 870.11

Example LS

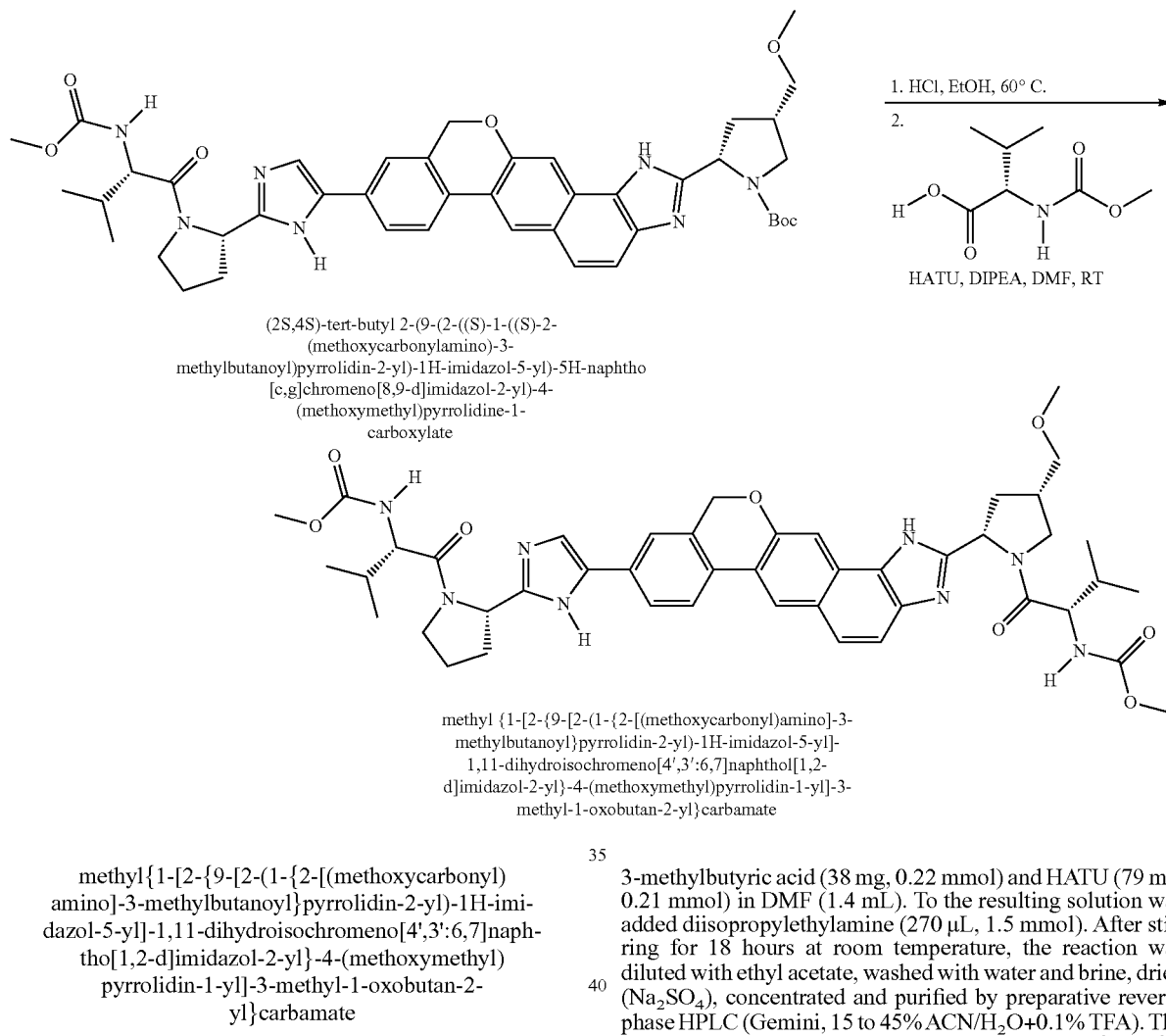
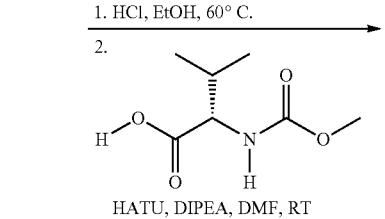

(2S,4S)-tert-butyl 2-(9-(2-((S)-1-((S)-2-(methoxycarbonylamino)-3-methylbutanoyl)pyrrolidin-2-yl)-1H-imidazol-5-yl)-5H-naphtho[c,g]chromeno[8,9-d]imidazol-2-yl)-4-(methoxymethyl)pyrrolidine-1-carboxylate methyl {1-[2-{9-[2-(1-{2-[(methoxycarbonyl)amino]-3-methylbutanoyl}pyrrolidin-2-yl)-1H-imidazol-5-yl]-1,11-dihydroisochromeno[4',3':6,7]naphtho[1,2-d]imidazol-2-yl}-4-(methoxymethyl)pyrrolidin-1-yl]-3-methyl-1-oxobutan-2-yl}carbamate methyl{1-[2-{9-[2-(1-{2-[(methoxycarbonyl)amino]-3-methylbutanoyl}pyrrolidin-2-yl)-1H-imidazol-5-yl]-1,11-dihydroisochromeno[4',3':6,7]naphtho[1,2-d]imidazol-2-yl}-4-(methoxymethyl)pyrrolidin-1-yl]-3-methyl-1-oxobutan-2-yl}carbamate A solution of (2S,4S)-tert-butyl 2-(9-(2-((S)-1-((S)-2-(methoxycarbonylamino)-3-methylbutanoyl)pyrrolidin-2-yl)-1H-imidazol-5-yl)-5H-naphtho[c,g]chromeno[8,9-d]imidazol-2-yl)-4-(methoxymethyl)pyrrolidine-1-carboxylate (116 mg, 0.15 mmol), ethanol (5 mL) and concentrated HCl (1 mL) was heated to 60° C. for 1 hour. The reaction was concentrated and the crude material dissolved in DCM (10 mL). This solution was concentrated and to this material was added a solution of 2-methoxycarbonylamino-3-methylbutyric acid (38 mg, 0.22 mmol) and HATU (79 mg, 0.21 mmol) in DMF (1.4 mL). To the resulting solution was added diisopropylethylamine (270 µL, 1.5 mmol). After stirring for 18 hours at room temperature, the reaction was diluted with ethyl acetate, washed with water and brine, dried (Na$_2$SO$_4$), concentrated and purified by preparative reverse phase HPLC (Gemini, 15 to 45% ACN/H$_2$O+0.1% TFA). The product fractions were lyophilized to give methyl{1-[2-{9-[2-(1-{2-[(methoxycarbonyl)amino]-3-methylbutanoyl}pyrrolidin-2-yl)-1H-imidazol-5-yl]-1,11-dihydroisochromeno[4',3':6,7]naphtho[1,2-d]imidazol-2-yl}-4-(methoxymethyl)pyrrolidin-1-yl]-3-methyl-1-oxobutan-2-yl}carbamate (58 mg, 13%). LCMS-ESI$^+$: calculated for C$_{45}$H$_{54}$N$_8$O$_8$: 834.96; observed [M+1]$^+$: 835.70.

Example LT

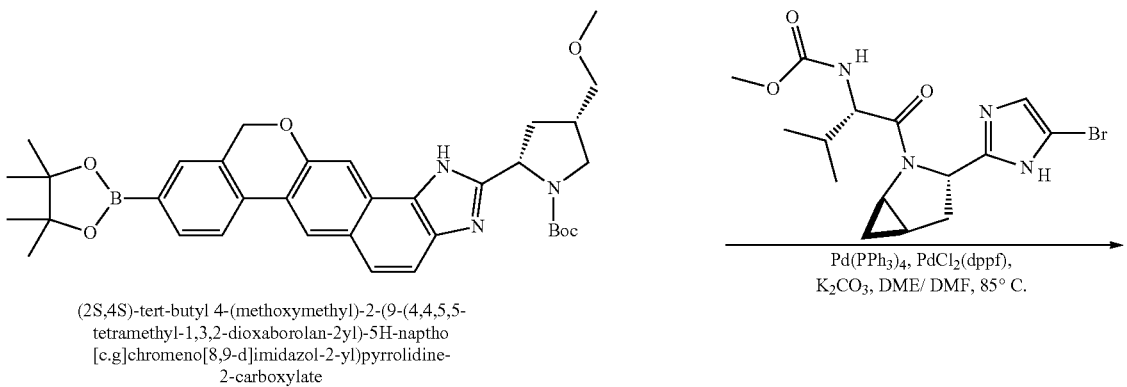

(2S,4S)-tert-butyl 4-(methoxymethyl)-2-(9-(4,4,5,5-tetramethyl-1,3,2-dioxaborolan-2yl)-5H-naptho[c,g]chromeno[8,9-d]imidazol-2-yl)pyrrolidine-2-carboxylate -continued

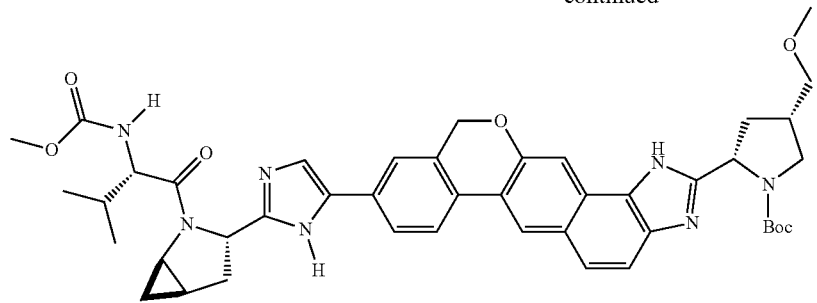

(2S,4S)-tert-butyl 2-(9-(2-((S)-1-((S)-2-(methoxycarbonylamino)-3-methylbutanoyl)azabicyclo[3.1.0]hexan-3-yl)-1H-imidazol-5-yl)-5H-naptho[c,g]chromeno[8,9-d]imidazol-2-yl)-4-(methoxymethyl)pyrrolidine-1-carboxylate 1. HCl, EtOH, 60° C.
2.

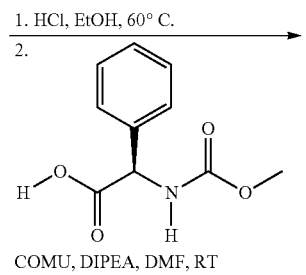

COMU, DIPEA, DMF, RT

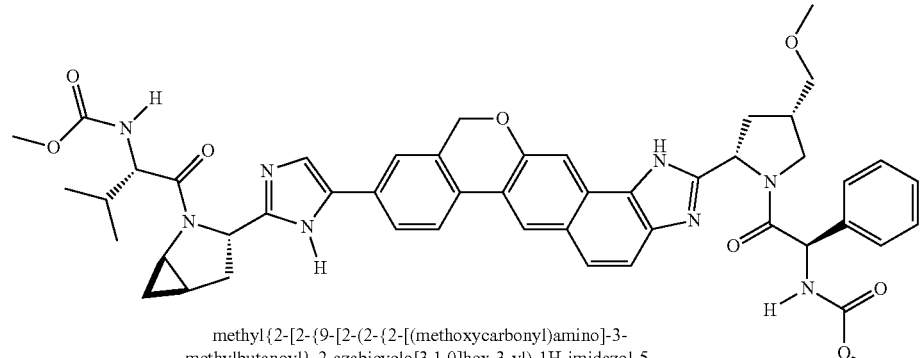

methyl{2-[2-{9-[2-(2-{2-[(methoxycarbonyl)amino]-3-methylbutanoyl}-2-azabicyclo[3.1.0]hex-3-yl)-1H-imidazol-5-yl]-1,11-dihydroisochromeno[4',3':6,7]naphtho[1,2-d]imidazol-2-yl}-4-(methoxymethyl)pyrrolidin-1-yl]-2-oxo-1-phenylethyl}carbamate

(2S,4S)-tert-butyl-2-(9-(2-((S)-1-((S)-2-(methoxycarbonylamino)-3-methylbutanoyl)azabicyclo[3.1.0]hexan-3-yl)-1H-imidazol-5-yl)-5H-naphtho[c,g]chromeno[8,9-d]imidazol-2-yl)-4-(methoxymethyl)pyrrolidine-1-carboxylate To a solution of (2S,4S)-tert-butyl 4-(methoxymethyl)-2-(9-(4,4,5,5-tetramethyl-1,3,2-dioxaborolan-2-yl)-5H-naphtho[c,g]chromeno[8,9-d]imidazol-2-yl)pyrrolidine-1-carboxylate (557 mg, 0.91 mmol), methyl(S)-1-((1S,3S,5S)-3-(5-bromo-1H-imidazol-2-yl)-2-azabicyclo[3.1.0]hexan-2-yl)-3-methyl-1-oxobutan-2-ylcarbamate (350 mg, 0.91 mmol), tetrakis(triphenylphosphine) palladium(0) (53 mg, 0.04 mmol) and dichloro[1,1'-bis(diphenylphosphino)ferrocene]palladium(II) (67 mg, 0.07 mmol) in a mixture of 1,2-dimethoxyethane (11.0 mL) and dimethylformamide (1.9 mL) was added a solution of potassium carbonate (2M in water, 1.37 mL, 2.7 mmol). The resulting mixture was degassed and then heated to 85° C. under argon for 18 hours. After cooling to room temperature, the reaction was diluted with ethyl acetate. The organics were washed with water and brine, dried ($Na_2SO_4$), and concentrated. The crude residue was purified by flash chromatography to yield (2S,4S)-tert-butyl 2-(9-(2-((S)-1-((S)-2-(methoxycarbonylamino)-3-methylbutanoyl)azabicyclo[3.1.0]hexan-3-yl)-1H-imidazol-5-yl)-5H-naphtho[c,g]chromeno[8,9-d]imidazol-2-yl)-4-(methoxymethyl)pyrrolidine-1-carboxylate (271 mg, 38%). LCMS-ESI[+]: calculated for $C_{44}H_{51}N_7O_7$. 789.92; observed [M+1][+]: 790.76.

methyl{2-[2-{9-[2-(2-{2-[(methoxycarbonyl)amino]-3-methylbutanoyl}-2-azabicyclo[3.1.0]hex-3-yl)-1H-imidazol-5-yl]-1,11-dihydroisochromeno[4',3':6,7]naphtho[1,2-d]imidazol-2-yl}-4-(methoxymethyl)pyrrolidin-1-yl]-2-oxo-1-phenylethyl}carbamate A solution of (2S,4S)-tert-butyl 2-(9-(2-((S)-1-((S)-2-(methoxycarbonylamino)-3-methylbutanoyl)azabicyclo[3.1.0]hexan-3-yl)-1H-imidazol-5-yl)-5H-naphtho[c,g]chromeno[8,9-d]imidazol-2-yl)-4-(methoxymethyl)pyrrolidine-1-carboxylate (196 mg, 0.25 mmol), ethanol (3 mL) and concentrated HCl (1 mL) was heated to 60° C. for 1 hour. The reaction was concentrated and the crude material dissolved in DCM (6 mL). This solution was concentrated and to this material was added a solution of (R)-2-(methoxycarbonylamino)-2-phenylacetic acid (69 mg, 0.33 mmol) and COMU (124 mg, 0.29 mmol) in DMF (4 mL). To the resulting solution was added diisopropylethylamine (130 μL, 0.76 mmol). After stirring for 2 hours at room temperature, the reaction was diluted with ethyl acetate, washed with water and brine, dried ($Na_2SO_4$), concentrated and purified by preparative reverse phase HPLC (Gemini, 15 to 45% ACN/$H_2O$ + 0.1% TFA). The product fractions were lyophilized to give methyl {2-[2-{9-[2-(2-{2-[(methoxycarbonyl)amino]-3-methylbutanoyl}-2-azabicyclo[3.1.0]hex-3-yl)-1H-imidazol-5-yl]-1,11-dihydroisochromeno[4',3':6,7]naphtho[1,2-d]imidazol-2-yl}-4-(methoxymethyl)pyrrolidin-1-yl]-2-oxo-1-phenylethyl}carbamate (84 mg, 39%). LCMS-ESI[+]: calculated for $C_{49}H_{52}N_8O_8$: 880.99; observed [M+1][+]: 882.09

Example LZ
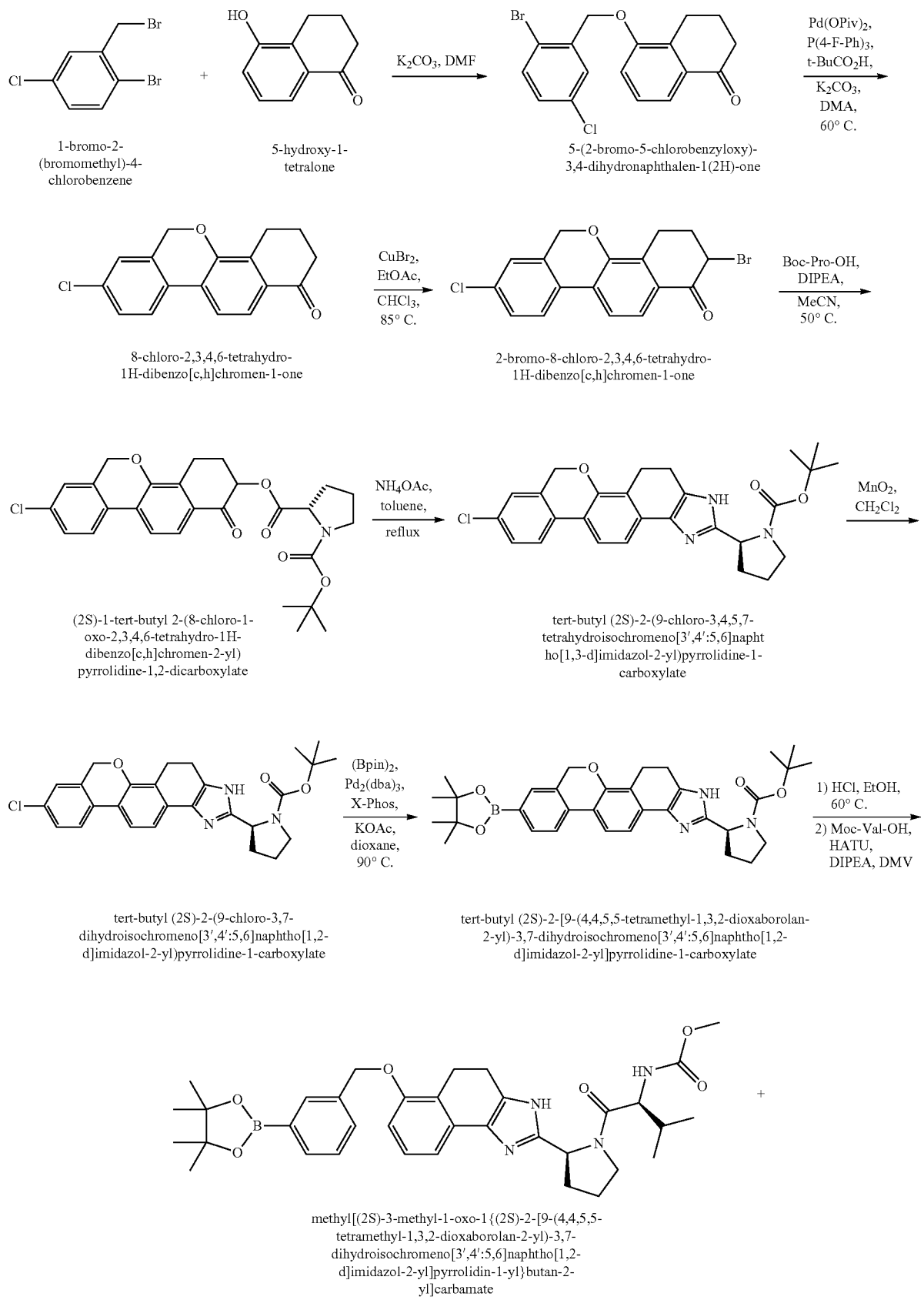

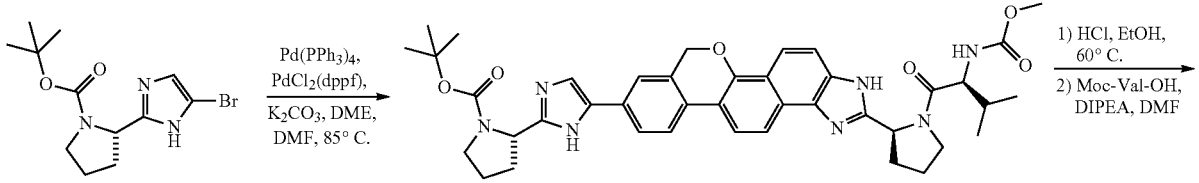

tert-butyl (2R)-2-[5-(2-{(2S)-1-[N-(methoxycarbonyl)-L-valyl]pyrrolidin-2-yl}-3,7-dihydroisochromeno[3',4':5,6]naphtho[1,2-d]imidazol-9-yl)-1H-imidazol-2-yl]pyrrolidine-1-carboxylate

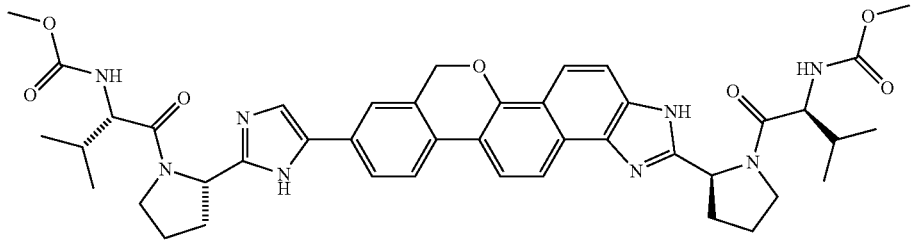

methyl {(2S)-1-[(2R)-2-(5-{2-[(2S)-1-{(2S)-2-[(methoxycarbonyl)amino]-3-methylbutanoyl}pyrrolidin-2-yl]-3,7-dihydroisochromeno[3',4':5,6]naphtho[1,2-d]imidazol-9-yl}-1H-imidazol-2-yl)pyrrolidin-1-yl]-3-methyl-1-oxobutan-2-yl}carbamate

5-(2-bromo-5-chlorobenzyloxy)-3,4-dihydronaphthalen-1(2H)-one

To a stirred solution of 5-hydroxy-1-tetralone (2.0 g, 12.3 mmol) and 1-bromo-2-(bromomethyl)-4-chlorobenzene (3.6 g, 12.7 mmol) in dimethylformamide (125 mL) was added potassium carbonate (3.5 g, 25.1 mmol). The reaction was stirred under argon for 1 hour then diluted with ethyl acetate (1 L). The organics were washed three times with water and once with brine. The organic layer was then dried with magnesium sulfate, filtered and concentrated. To the resulting oil was added methanol (100 mL) and the suspension was agitated for thirty minutes. 5-(2-bromo-5-chlorobenzyloxy)-3,4-dihydronaphthalen-1(2H)-one (4.25 g, 94% yield) was isolated by filtration.

8-chloro-2,3,4,6-tetrahydro-1H-dibenzo[c,h]chromen-1-one

To a flask containing palladium(II) pivalate (68 mg, 0.22 mmol), tri(4-fluorophenyl)phosphine (70 mg, 0.22 mmol), pivalic acid (135 mg, 1.3 mmol) and potassium carbonate (1.83 g, 13.1 mmol) was added a solution of 5-(2-bromo-5-chlorobenzyloxy)-3,4-dihydronaphthalen-1(2H)-one (1.61 g, 4.4 mmol) in dimethyacetamide (23 mL). The flask was evacuated and backfilled with argon 5 times and then stirred under argon at 60° C. for 24 hours. The reaction was poured directly onto a silica gel column and purified by flash column chromatography (hexanes/DCM) to yield 8-chloro-2,3,4,6-tetrahydro-1H-dibenzo[c,h]chromen-1-one (1.22 g, 97% yield) as an off-white solid.

2-bromo-8-chloro-2,3,4,6-tetrahydro-1H-dibenzo[c,h]chromen-1-one

To a mixture of 8-chloro-2,3,4,6-tetrahydro-JH-dibenzo[c,h]chromen-1-one (2.58 g, 9.1 mmol) in chloroform (9.1 mL) and ethyl acetate (9.1 mL) was added copper(II) bromide (4.65 g, 19.9 mmol). The reaction was heated to 80° C. for 5 hours and then cooled to room temperature. The mixture was diluted with dichloromethane and washed twice with a 5:1 solution of saturated aqueous ammonium chloride and aqueous ammonium hydroxide (~28%), and washed once with water. The organic layer was dried with magnesium sulfate, filtered and concentrated. The crude material was purified by flash column chromatography (hexanes/DCM) to yield 2-bromo-8-chloro-2,3,4,6-tetrahydro-]H-dibenzo[c,h]chromen-1-one (2.45 g, 75% yield).

(2S)-1-tert-butyl 2-(8-chloro-1-oxo-2,3,4,6-tetrahydro-1H-dibenzo[c,h]chromen-2-yl)pyrrolidine-1,2-dicarboxylate To a solution of 2-bromo-8-chloro-2,3,4,6-tetrahydro-JH-dibenzo[c,h]chromen-1-one (1.05 g, 2.9 mmol) and Boc-Pro-OH (1.75 g, 8.1 mmol) in acetonitrile (9.0 mL) was added diisopropylethylamine (1.5 mL, 8.7 mmol). The solution was stirred under argon at 50° C. for two hours. Extra Boc-Pro-OH (620 mg, 2.9 mmol) and diisopropylethylamine (0.5 mL, 2.9 mmol) were added and the reaction was stirred at 50° C. for 16 hours. The reaction was cooled to room temperature and diluted with ethyl acetate. The organics were washed with water and brine, dried with magnesium sulfate and concentrated. The crude material was purified by flash column chromatography and the product (2S)-1-tert-butyl 2-(8-chloro-1-oxo-2,3,4,6-tetrahydro-]H-dibenzo[c,h]chromen-2-yl)pyrrolidine-1,2-dicarboxylate was isolated as a mixture of diastereomers (0.99 g, 69% yield).

tert-butyl (2S)-2-(9-chloro-3,4,5,7-tetrahydroisochromeno[3',4':5,6]naphtho[1,2-d]imidazol-2-yl)pyrrolidine-1-carboxylate To a solution of (2S)-1-tert-butyl 2-(8-chloro-1-oxo-2,3,4,6-tetrahydro-1H-dibenzo[c,h]chromen-2-yl)pyrrolidine-1,2-dicarboxylate (2.2 g, 4.4 mmol) in toluene (40 mL) was added ammonium acetate (7 g, 91 mmol). The reaction mixture was vigorously refluxed for 3 hours, then cooled to room temperature and diluted with ethyl acetate. The organics were washed with water and brine, dried with magnesium sulfate and concentrated. The crude material was purified by flash column chromatography to yield tert-butyl (2S)-2-(9-chloro-3,4,5,7- tetrahydroisochromeno[3',4':5,6]naphtho[1,2-d]imidazol-2-yl)pyrrolidine-1-carboxylate (1.13 g, 54% yield) as well as recovered (2S)-1-tert-butyl 2-(8-chloro-1-oxo-2,3,4,6-tetrahydro-1H-dibenzo[c,h]chromen-2-yl)pyrrolidine-1,2-dicarboxylate (0.8 g, 36%).). LCMS-ESI$^+$: calculated for $C_{27}H_{28}N_3O_3$: 477.98; observed [M+1]$^+$: 478.54.

tert-butyl (2S)-2-(9-chloro-3,7-dihydroisochromeno[3',4':5,6]naphtho[1,2-d]imidazol-2-yl)pyrrolidine-1-carboxylate To a solution of Intermediate tert-butyl (2S)-2-(9-chloro-3,4,5,7-tetrahydroisochromeno[3',4':5,6]naphtho[1,2-d]imidazol-2-yl)pyrrolidine-1-carboxylate (1.43 g, 3.0 mmol) in dichloromethane (30 mL) was added manganese(IV) oxide (15 g, 198 mmol). The mixture was stirred for four hours at room temperature then filtered through Celite. The MnO$_2$ was thoroughly rinsed with dichloromethane and the total filtrate was concentrated to yield tert-butyl (2S)-2-(9-chloro-3,7-dihydroisochromeno[3',4':5,6]naphtho[1,2-d]imidazol-2-yl)pyrrolidine-1-carboxylate (1.37 g, 96% yield). This material was used without further purification.

tert-butyl (2S)-2-[9-(4,4,5,5-tetramethyl-1,3,2-dioxaborolan-2-yl)-3,7-dihydroisochromeno[3',4':5,6]naphtho[1,2-d]imidazol-2-yl]pyrrolidine-1-carboxylate To a solution of tert-butyl (2S)-2-(9-chloro-3,7-dihydroisochromeno[3',4':5,6]naphtho[1,2-d]imidazol-2-yl)pyrrolidine-1-carboxylate (1.4 g, 2.9 mmol) in dioxane (20 mL) was added bis(pinacolato)diboron (1.5 g, 5.9 mmol), tris(dibenzylideneacetone)dipalladium(0) (110 mg, 0.12 mmol), X-Phos (145 mg, 0.30 mmol) and potassium acetate (870 mg, 8.9 mmol). The mixture was degassed with a stream of argon for ten minutes. The degassed reaction was heated under argon to 90° C. for 2.5 hours then cooled to room temperature and diluted with ethyl acetate. The organics were washed with water and brine, dried with magnesium sulfate and concentrated. The crude material was purified by flash column chromatography (DCM/EtOAc) to yield tert-butyl (2S)-2-[9-(4,4,5,5-tetramethyl-1,3,2-dioxaborolan-2-yl)-3,7-dihydroisochromeno[3',4':5,6]naphtho[1,2-d]imidazol-2-yl]pyrrolidine-1-carboxylate (1.5 g, 90% yield).

methyl[(2S)-3-methyl-1-oxo-1-{(2S)-2-[9-(4,4,5,5-tetramethyl-1,3,2-dioxaborolan-2-yl)-3,7-dihydroisochromeno[3',4':5,6]naphtho[1,2-d]imidazol-2-yl]pyrrolidin-1-yl}butan-2-yl]carbamate A solution of tert-butyl (2S)-2-[9-(4,4,5,5-tetramethyl-1,3,2-dioxaborolan-2-yl)-3,7-dihydroisochromeno[3',4':5,6]naphtho[1,2-d]imidazol-2-yl]pyrrolidine-1-carboxylate (0.98 g, 1.7 mmol), concentrated HCl (2 mL) and ethanol (20 mL) was heated to 60° C. for 2 hours. The reaction was concentrated and redissolved in a minimal amount of methanol. An equal volume of dichloromethane was added and the solution was again concentrated. Dichloromethane was added to the resulting residue and concentrated off two more times. The resulting crude material was dissolved in dimethylformamide (17 mL). To this solution was added (S)-2-(methoxycarbonylamino)-3-methylbutanoic acid (455 mg, 2.6 mmol), HATU (955 mg, 2.5 mmol) and diisopropylethylamine (3 mL, 17 mmol). The reaction was stirred at room temperature for one hour then diluted with ethyl acetate. The organics were washed with water (x2) and brine, dried with magnesium sulfate and concentrated. The resulting residue was purified by flash column chromatography to yield Intermediate methyl[(2S)-3-methyl-1-oxo-1-{(2S)-2-[9-(4,4,5,5-tetramethyl-1,3,2-dioxaborolan-2-yl)-3,7-dihydroisochromeno[3',4':5,6]naphtho[1,2-d]imidazol-2-yl]pyrrolidin-1-yl}butan-2-yl]carbamate (780 mg, 72% yield over 2 steps).

tert-butyl (2R)-2-[5-(2-{(2S)-1-[N-(methoxycarbonyl)-L-valyl]pyrrolidin-2-yl}-3,7-dihydroisochromeno[3',4':5,6]naphtho[1,2-d]imidazol-9-yl)-1H-imidazol-2-yl]pyrrolidine-1-carboxylate A mixture of Pentacyclic Intermediate methyl[(2S)-3-methyl-1-oxo-1-{(2S)-2-[9-(4,4,5,5-tetramethyl-1,3,2-dioxaborolan-2-yl)-3,7-dihydroisochromeno[3',4':5,6]naphtho[1,2-d]imidazol-2-yl]pyrrolidin-1-yl}butan-2-yl]carbamate (780 mg, 1.3 mmol), (S)-tert-butyl 2-(5-bromo-1H-imidazol-2-yl)pyrrolidine-1-carboxylate (450 mg, 1.4 mmol), tetrakis(triphenylphosphine)palladium(0) (30 mg, 0.03 mmol), PdCl$_2$(dppf) (60 mg, 0.08 mmol), 2M aqueous potassium carbonate (1.9 mL, 3.9 mmol), dimethoxyethane (10 mL) and dimethylformamide (2 mL) was degassed with argon for 15 minutes. The reaction was then heated to 85° C. for 3 hours. Upon completion, the reaction was cooled to room temperature, diluted with ethyl acetate and filtered through Celite. The filtrate was washed with water and brine, dried (MgSO$_4$) and concentrated. The resulting crude material was purified by flash column chromatography (EtOAc/MeOH) to yield Intermediate tert-butyl (2R)-2-[5-(2-{(2S)-1-[N-(methoxycarbonyl)-L-valyl]pyrrolidin-2-yl}-3,7-dihydroisochromeno[3',4':5,6]naphtho[1,2-d]imidazol-9-yl)-1H-imidazol-2-yl]pyrrolidine-1-carboxylate (390 mg, 43% yield).

methyl {(2S)-1-[(2R)-2-(5-{2-[(2S)-1-{(2S)-2-[(methoxycarbonyl)amino]-3-methylbutanoyl}pyrrolidin-2-yl]-3,7-dihydroisochromeno[3',4':5,6]naphtho[1,2-d]imidazol-9-yl}-1H-imidazol-2-yl)pyrrolidin-1-yl]-3-methyl-1-oxobutan-2-yl}carbamate A mixture of Intermediate tert-butyl (2R)-2-[5-(2-{(2S)-1-[N-(methoxycarbonyl)-L-valyl]pyrrolidin-2-yl}-3,7-dihydroisochromeno[3',4':5,6]naphtho[1,2-d]imidazol-9-yl)-1H-imidazol-2-yl]pyrrolidine-1-carboxylate (390 mg, 0.53 mmol), concentrated HCl (2 mL) and ethanol (10 mL) was heated to 60° C. for 2 hours. The reaction was concentrated and redissolved in a minimal amount of methanol. An equal volume of dichloromethane was added and the solution was again concentrated. Dichloromethane was added to the resulting residue and concentrated off two more times. One half of the crude material (~0.27 mmol) was dissolved in dimethylformamide (2.5 mL). To this solution was added (S)-2-(methoxycarbonylamino)-3-methylbutanoic acid (66 mg, 0.38 mmol), HATU (140 mg, 0.37 mmol) and diisopropylethylamine (0.48 mL, 2.7 mmol). The reaction was stirred at room temperature for 2 hours, and then diluted with acetonitrile (2 mL) and methanol (2 mL). To this solution was added ten drops of 5M aqueous NaOH solution and stirring was continued for 30 minutes. The reaction was diluted with ethyl acetate and the organic layer was washed with water and brine. The combined aqueous washings were extracted three times with ethyl acetate, and the combined organic layers were dried (MgSO$_4$) and concentrated. The crude material was purified by reverse phase HPLC (Gemini, 15 to 45% ACN/H$_2$O+0.1% TFA) to yield methyl {(2S)-1-[(2R)-2-(5-{2-[(2S)-1-{(2S)-2-[(methoxycarbonyl)amino]-3-methylbutanoyl}pyrrolidin-2-yl]-3,7-dihydroisochromeno[3',4':5,6]naphtho[1,2-d]imidazol-9-yl}-1H-imidazol-2-yl)pyrrolidin-1-yl]-3-methyl-1-oxobutan-2-yl}carbamate (140 mg, 67% yield over 2 steps). LCMS-ESI$^|$: calculated for $C_{43}H_{50}N_8O_7$: 790.91; observed [M+1]$^+$: 791.71.

Example MA

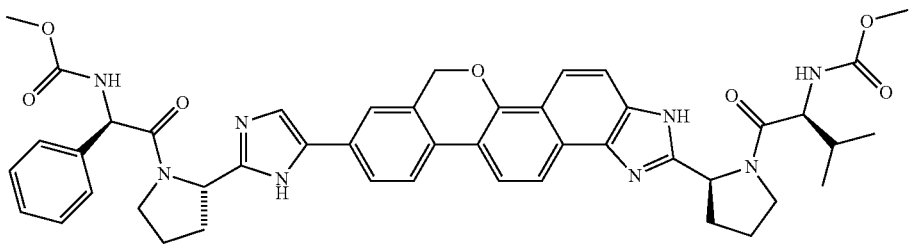

methyl {(1R)-2-[(2R)-2-(5-{2-[(2S)-1-{(2S)-2-[(methoxycarbonyl)amino]-3-methylbutanoyl}pyrrolidin-2-yl]-3,7-dihydroisochromeno[3',4':5,6]naphtho[1,2-d]imidazol-9-yl}-1H-imidazol-2-yl)pyrrolidin-1-yl]-2-oxo-1-phenylethyl}carbamate This compound was made in an analogous manner to methyl {(2S)-1-[(2R)-2-(5-{2-[(2S)-1-{(2S)-2-[(methoxycarbonyl)amino]-3-methylbutanoyl}pyrrolidin-2-yl]-3,7-dihydroisochromeno[3',4':5,6]naphtho[1,2-d]imidazol-9-yl}-1H-imidazol-2-yl)pyrrolidin-1-yl]-3-methyl-1-oxobutan-2-yl}carbamate, substituting (R)-2-(methoxycarbonylamino)-2-phenylacetic acid for (S)-2-(methoxycarbonylamino)-3-methylbutanoic acid and substituting COMU for HATU in the final amide coupling step. LCMS-ESI$^+$: calculated for $C_{46}H_{48}N_8O_7$: 824.92; observed [M+1]$^+$: 825.72.

Example MB

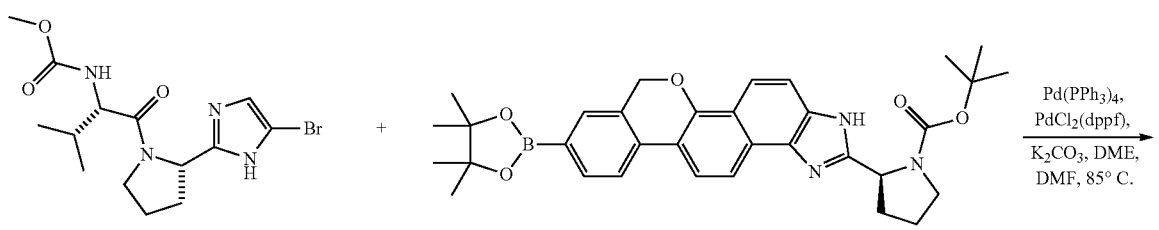

methyl (S)-1-((S)-2-(5-bromo-1H-imidazol-2-yl)pyrrolidin-1-yl)-3-methyl-1-oxobutan-2-ylcarbamate tert-butyl (2S)-2-[9-(4,4,5,5-tetramethyl-1,3,2-dioxaborlan-2-yl)-3,7-dihydroisochromeno(3',4':5,6]naphtho[1,3-d]imidazol-2-yl]pyrrolidine-1-carboxylate Pd(PPh$_3$)$_4$, PdCl$_2$(dppf), K$_2$CO$_3$, DME, DMF, 85° C.

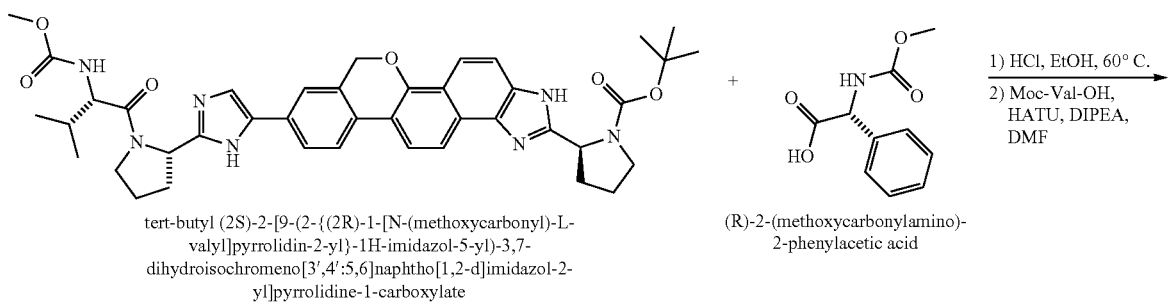

tert-butyl (2S)-2-[9-(2-{(2R)-1-[N-(methoxycarbonyl)-L-valyl]pyrrolidin-2-yl}-1H-imidazol-5-yl)-3,7-dihydroisochromeno[3',4':5,6]naphtho[1,2-d]imidazol-2-yl]pyrrolidine-1-carboxylate (R)-2-(methoxycarbonylamino)-2-phenylacetic acid 1) HCl, EtOH, 60° C.
2) Moc-Val-OH, HATU, DIPEA, DMF

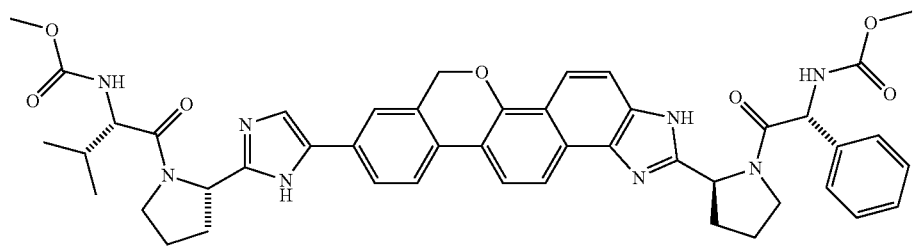

methyl {(2S)-1-[(2R)-2-(5-{(2[(2S)-1-{(2R)-2-[(methoxycarbonyl)amino]-2-phenylacetyl}pyrrolidin-2-yl]-3,7-dihydroisochromeno[3',4':5,6]naphtho[1,2-d]imidazol-9-yl}-1H-imidazol-2-yl)pyrrolidin-1-yl}-3-methyl-1-oxobutan-2-yl}carbamate tert-butyl (2S)-2-[9-(2-{(2R)-1-[N-(methoxycarbonyl)-L-valyl]pyrrolidin-2-yl}-1H-imidazol-5-yl)-3,7-dihydroisochromeno[3',4':5,6]naphtho[1,2-d]imidazol-2-yl]pyrrolidine-1-carboxylate A mixture of tert-butyl (2S)-2-[9-(4,4,5,5-tetramethyl-1,3,2-dioxaborolan-2-yl)-3,7-dihydroisochromeno[3',4':5,6]naphtho[1,2-d]imidazol-2-yl]pyrrolidine-1-carboxylate (450 mg, 0.79 mmol), methyl(S)-1-((S)-2-(5-bromo-1H-imidazol-2-yl)pyrrolidin-1-yl)-3-methyl-1-oxobutan-2-ylcarbamate (325 mg, 0.87 mmol), tetrakis(triphenylphosphine)palladium(0) (30 mg, 0.02 mmol), PdCl$_2$(dppf) (35 mg, 0.05 mmol), 2M aqueous potassium carbonate (1.2 mL, 2.4 mmol), dimethoxyethane (6.8 mL) and dimethylformamide (1.2 mL) was degassed with argon for 15 minutes. The reaction was then heated to 85° C. for 2.5 hours. Upon completion, the reaction was cooled to room temperature, diluted with ethyl acetate and filtered through Celite. The filtrate was washed with water and brine, dried (MgSO$_4$) and concentrated. The resulting crude material was purified by flash column chromatography (EtOAc/MeOH) to yield tert-butyl (2S)-2-[9-(2-{(2R)-1-[N-(methoxycarbonyl)-L-valyl]pyrrolidin-2-yl}-1H-imidazol-5-yl)-3,7-dihydroisochromeno[3',4':5,6]naphtho[1,2-d]imidazol-2-yl]pyrrolidine-1-carboxylate (270 mg, 46% yield).

methyl {(2S)-1-[(2R)-2-(5-{2-[(2S)-1-{(2R)-2-[(methoxycarbonyl)amino]-2-phenylacetyl}pyrrolidin-2-yl]-3,7-dihydroisochromeno[3',4':5,6]naphtho[1,2-d]imidazol-9-yl}-1H-imidazol-2-yl)pyrrolidin-1-yl]-3-methyl-1-oxobutan-2-yl}carbamate A mixture of tert-butyl (2S)-2-[9-(2-{(2R)-1-[N-(methoxycarbonyl)-L-valyl]pyrrolidin-2-yl}-1H-imidazol-5-yl)-3,7-dihydroisochromeno[3',4':5,6]naphtho[1,2-d]imidazol-2-yl]pyrrolidine-1-carboxylate (270 mg, 0.37 mmol), concentrated HCl (1.5 mL) and ethanol (8 mL) was heated to 60° C. for 1 hour. The reaction was concentrated and redissolved in a minimal amount of methanol. An equal volume of dichloromethane was added and the solution was again concentrated. Dichloromethane was added to the resulting residue and concentrated off two more times. The crude material was dissolved in 5:1 dichloromethane/dimethylformamide (3.8 mL). To this solution was added (R)-2-(methoxycarbonylamino)-2-phenylacetic acid (96 mg, 0.46 mmol), COMU (190 mg, 0.44 mmol) and diisopropylethylamine (0.20 mL, 1.1 mmol). The reaction was stirred at 0° C. for 30 minutes then warmed to room temperature. Upon completion, the reaction was diluted with acetonitrile (2 mL) and methanol (2 mL). To this solution was added ten drops of 5M aqueous NaOH solution and stirring was continued for 30 minutes. The reaction was diluted with ethyl acetate and the organic layer was washed with water and brine. The combined aqueous washings were extracted three times with ethyl acetate, and the combined organic layers were dried (MgSO$_4$) and concentrated. The crude material was purified by reverse phase HPLC (Gemini, 15 to 45% ACN/H$_2$O+0.1% TFA) to yield methyl {(2S)-1-[(2R)-2-(5-{2-[(2S)-1-{(2R)-2-[(methoxycarbonyl)amino]-2-phenylacetyl}pyrrolidin-2-yl]-3,7-dihydroisochromeno[3',4':5,6]naphtho[1,2-d]imidazol-9-yl}-1H-imidazol-2-yl)pyrrolidin-1-yl]-3-methyl-1-oxobutan-2-yl}carbamate (155 mg, 51% yield over 2 steps). LCMS-ESI$^+$: calculated for C$_{46}$H$_{48}$N$_8$O$_7$: 824.92; observed [M+1]$^+$: 825.67.

Example MC

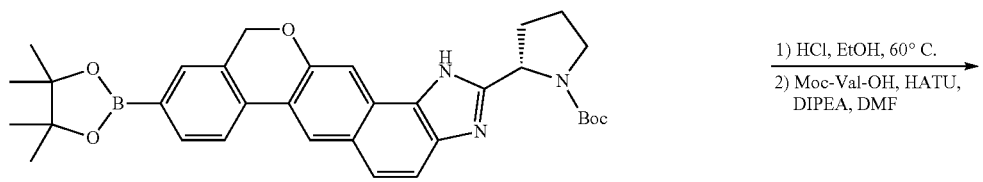

tert-butyl 2-[9-(4,4,5,5-tetramethyl-1,3,2-dioxaborolan-2-yl)-1,11-dihydroisochromeno[4',3':6,7]naphtho[1,2-d]imidazol-2-yl]pyrrolidine-1-carboxylate

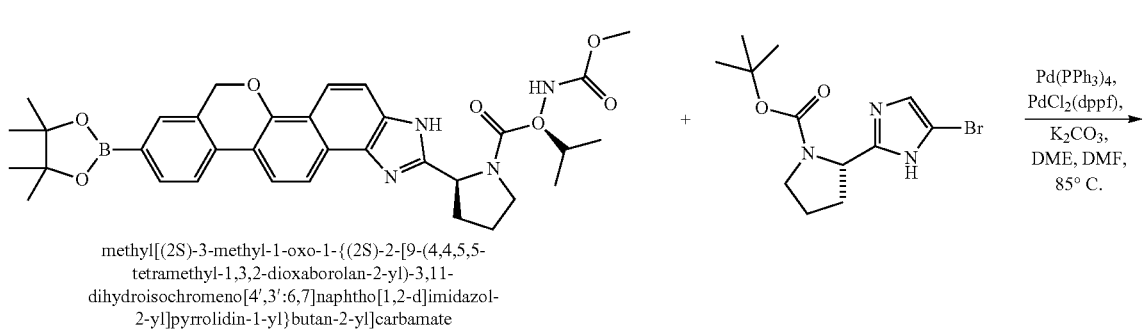

methyl[(2S)-3-methyl-1-oxo-1-{(2S)-2-[9-(4,4,5,5-tetramethyl-1,3,2-dioxaborolan-2-yl)-3,11-dihydroisochromeno[4',3':6,7]naphtho[1,2-d]imidazol-2-yl]pyrrolidin-1-yl}butan-2-yl]carbamate

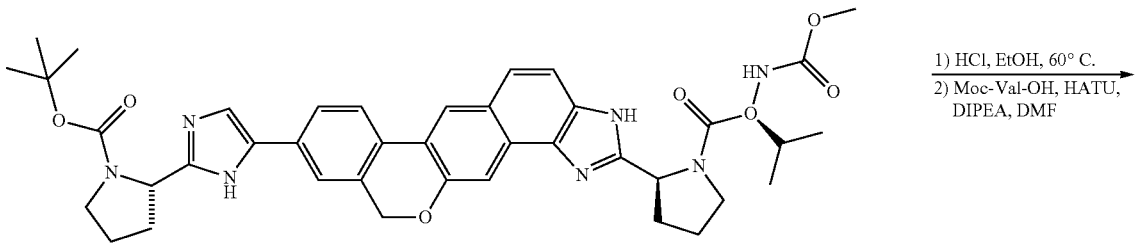

tert-butyl (2R)-2-[5-(2-{(2S)-1-[N-(methoxycarbonyl)-L-valyl]pyrrolidin-2-yl}-3,11-dihydroisochromeno[4',3':6,7]naphtho[1,2-d]imidazol-9-yl)-1H-imidazol-2-yl]pyrrolidine-1-carboxylate

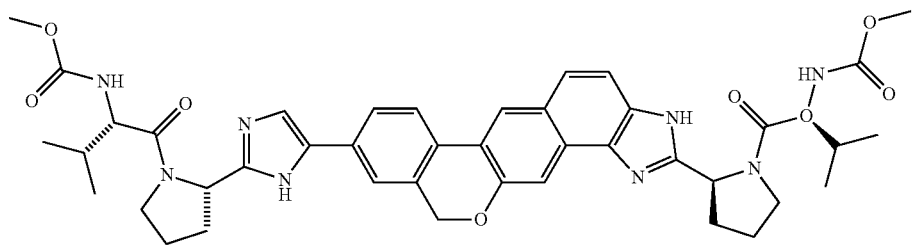

dimethyl (2S,2'S)-1,1'-((2S,2'S)-2,2'1-pyrrolidin-2-yl)-5H-naphtho[c,g]chromeno[8,9-d]imidazol-9-yl)-1H-imidazol-2-yl)pyrrolidin-1-yl))bis(3-methyl-1-oxobutane-2,1-diyl)dicarbamate dimethyl (2S,2'S)-1,1'-((2S,2'S)-2,2'1-pyrrolidin-2-yl)-5H-naphtho[c,g]chromeno[8,9-d]imidazol-9-yl)-1H-imidazol-2-yl)pyrrolidin-1-yl))bis(3-methyl-1-oxobutane-2,1-diyl)dicarbamate This compound was made in an analogous manner to methyl {(2S)-1-[(2R)-2-(5-{2-[(2S)-1-{(2S)-2-[(methoxycarbonyl)amino]-3-methylbutanoyl}pyrrolidin-2-yl]-3,7-dihydroisochromeno[3',4':5,6]naphtho[1,2-d]imidazol-9-yl}-1H-imidazol-2-yl)pyrrolidin-1-yl]-3-methyl-1-oxobutan-2-yl}carbamate, substituting 7-hydroxy-1-tetralone for 5-hydroxy-1-tetralone in the first step of the sequence. All reactions in the synthesis gave similar product yields as in the synthesis of methyl {(2S)-1-[(2R)-2-(5-{2-[(2S)-1-{(2S)-2-[(methoxycarbonyl)amino]-3-methylbutanoyl}pyrrolidin-2-yl]-3,7-dihydroisochromeno[3',4':5,6]naphtho[1,2-d]imidazol-9-yl}-1H-imidazol-2-yl)pyrrolidin-1-yl]-3-methyl-1-oxobutan-2-yl}carbamate. LCMS-ESI$^+$: calculated for $C_{43}H_{50}N_8O_7$: 790.91; observed [M+1]$^+$: 791.6.

Example MD

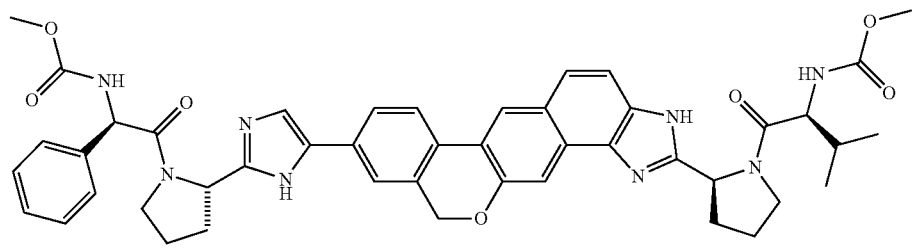

methyl [1-(2-{5-[2-(1-{[(methoxycarbonyl)amino]-3-methyl-1-oxobutan-2-yl}pyrrolidin-2-yl)-1,11-dihydroisochromeno[4',3':6,7]naphtho[1,2-d]imidazol-9-yl]-1H-imidazol-2--yl}pyrrolidin-1-yl)-phenyl-1-oxoacet-2-yl]carbamate This compound was made in an analogous manner to dimethyl (2S,2'S)-1,1'-((2S,2'S)-2,2'1-pyrrolidin-2-yl)-5H-naphtho[c,g]chromeno[8,9-d]imidazol-9-yl)-1H-imidazol-2-yl)pyrrolidin-1-yl))bis(3-methyl-1-oxobutane-2,1-diyl) dicarbamate, substituting (R)-2-(methoxycarbonylamino)-2-phenylacetic acid for (S)-2-(methoxycarbonylamino)-3-methylbutanoic acid and substituting COMU for HATU in the final amide coupling step. LCMS-ESI+: calculated for $C_{46}H_{48}N_8O_7$: 824.92; observed [M+1]+: 825.67.

Example ME

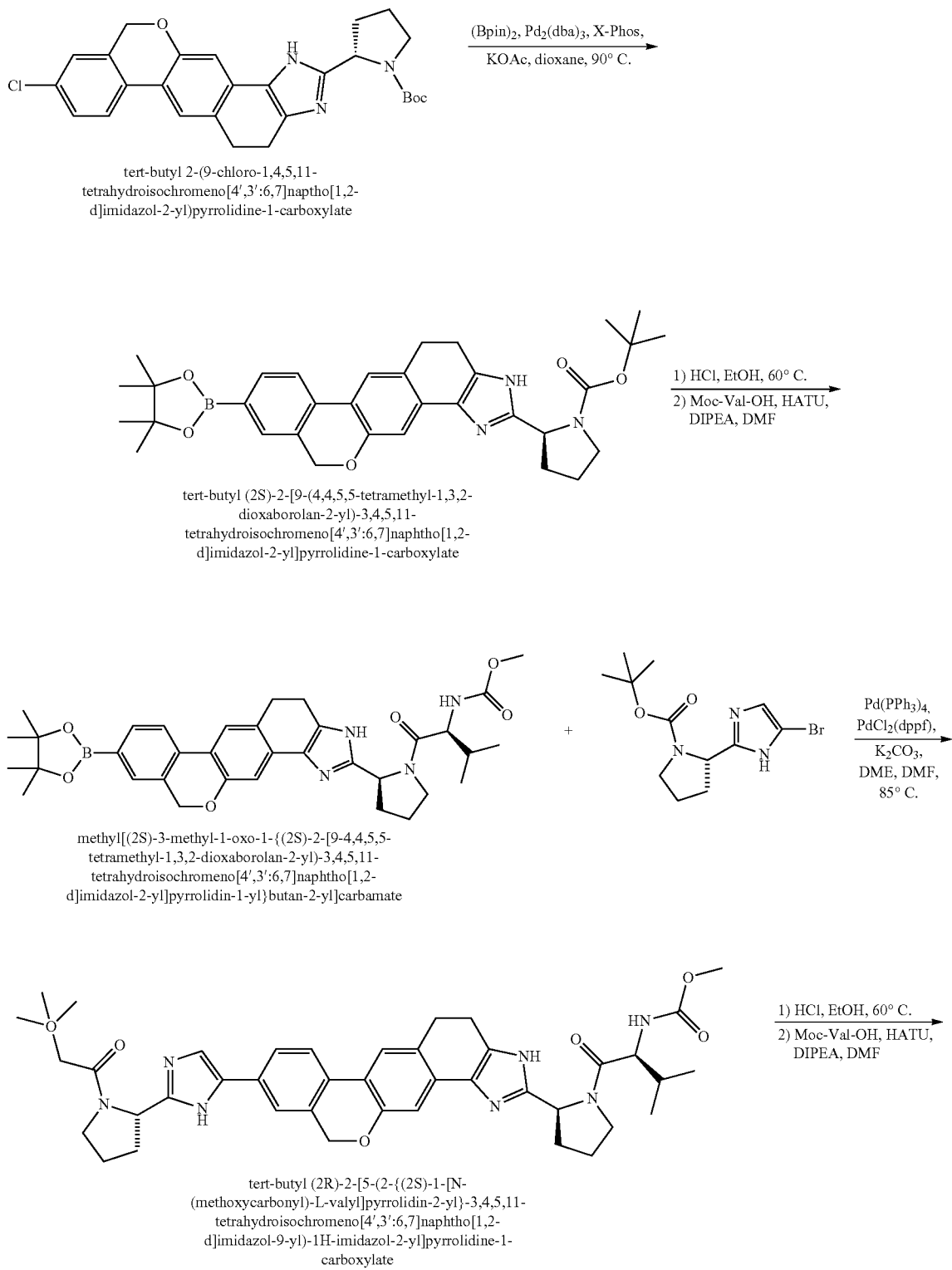

-continued

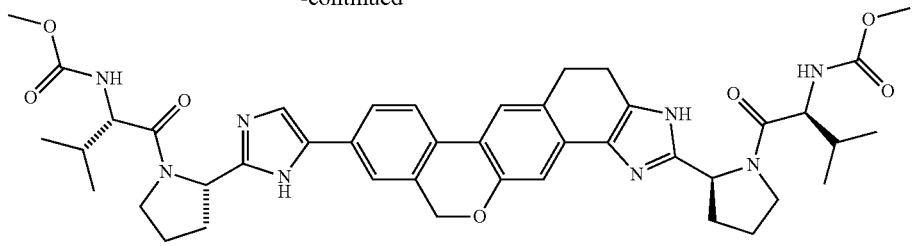

dimethyl (2S,2'S)-1,1'-((2S,2'S)-2,2'1-pyrrolidin-2-yl)-
7H-dihydro-naphtho[c,g]chromeno[8,9-d]imidazol-9-yl)-1H-imidazol-2-yl)
pyrrolidin-1-yl))bis(3-methyl-1-oxobutane-2,1-diyl)dicarbamate dimethyl (2S,2'S)-1,1'-((2S,2'S)-2,2'1-pyrrolidin-2-yl)-7H-dihydro-naphtho[c,g]chromeno[8,9-d]imidazol-9-yl)-1H-imidazol-2-yl)pyrrolidin-1-yl))bis(3-methyl-1-oxobutane-2,1-diyl)dicarbamate This compound was made in an analogous manner to dimethyl (2S,2'S)-1,1'-((2S,2'S)-2,2'1-pyrrolidin-2-yl)-5H-naphtho[c,g]chromeno[8,9-d]imidazol-9-yl)-11H-imidazol-2-yl)pyrrolidin-1-yl))bis(3-methyl-1-oxo butane-2,1-diyl)dicarbamate, omitting the MnO$_2$ oxidation of tert-butyl 2-(9-chloro-1,4,5,11-tetrahydroisochromeno[4',3':6,7]naphtho[1,2-d]imidazol-2-yl)pyrrolidine-1-carboxylate. LCMS-ESI$^+$: calculated for C$_{43}$H$_{52}$N$_8$O$_7$: 792.40; observed [M+1]$^+$: 793.69.

Example MF

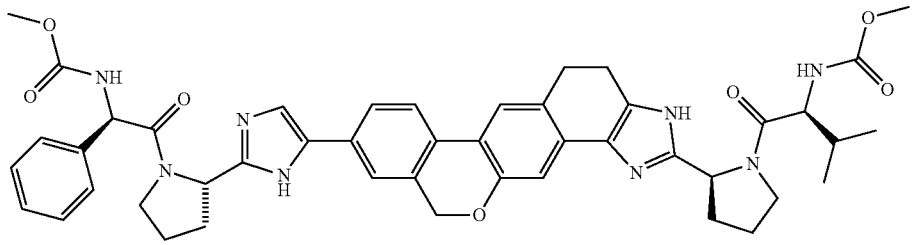

methyl [1-(2-{5-[2-(1-{[(methoxycarbonyl)amino]-3-methyl-1-oxobutan-2-yl}pyrrolidin-2-yl)-
1,4,5,11-tetrahydroisochromeno[4',3':6,7]naphtho[1,2-d]imidazol-9-yl]-1H-imidazol-2-
yl}pyrrolidin-1-yl)-phenyl-1-oxoacet-2-yl]carbamate methyl[1-(2-{5-[2-(1-{[(methoxycarbonyl)amino]-3-methyl-1-oxobutan-2-yl}pyrrolidin-2-yl)-1,4,5,11-tetrahydroisochromeno[4',3':6,7]naphtho[1,2-d]imidazol-9-yl]-1H-imidazol-2-yl}pyrrolidin-1-yl)-phenyl-1-oxoacet-2-yl]carbamate This compound was made in an analogous manner to dimethyl (2S,2'S)-1,1'-((2S,2'S)-2,2'1-pyrrolidin-2-yl)-7H-dihydro-naphtho[c,g]chromeno[8,9-d]imidazol-9-yl)-1H-imidazol-2-yl)pyrrolidin-1-yl))bis(3-methyl-1-oxo butane-2,1-diyl)dicarbamate, substituting (R)-2-(methoxycarbonylamino)-2-phenylacetic acid for (S)-2-(methoxycarbonylamino)-3-methylbutanoic acid and substituting COMU for HATU in the final amide coupling step. LCMS-ESI$^+$: calculated for C$_{46}$H$_{50}$N$_8$O$_7$: 826.94; observed [M+1]$^+$: 827.71.

Example MG

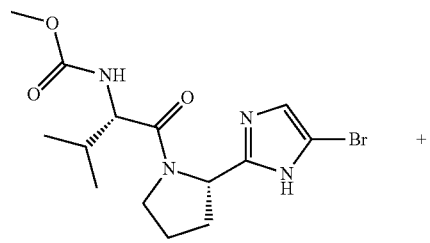 + methyl (S)-1-((S)-2-(5-bromo-1H-
imidazol-2-yl)pyrrolidin-1-yl)-3-
methyl-1-oxobutan-2-ylcarbamate

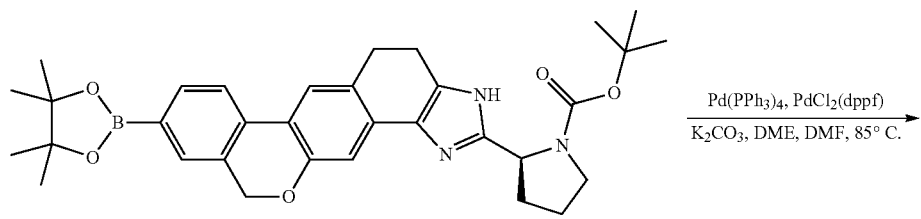

tert-butyl 2-(9-chloro-1,4,5,11-tetrahydroisochromeno[4',3';6,7]naphtho[1,2-d]imidazol-2-yl)pyrrolidine-1-carboxylate

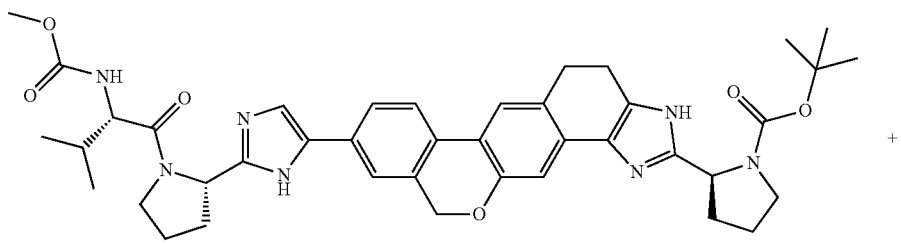

tert-butyl (2S)-2-[9-(2-{(2R)-1-[N-(moethoxycarbonyl)-L-valyl]pyrrolidin-2-yl}-1H-imidazol-5-yl)-3,4,5,11-tetrahydroisochromeno[4',3',6,7]naphtho[1,2-d]imidazol-2-yl]pyrrolidine-1-carboxylate

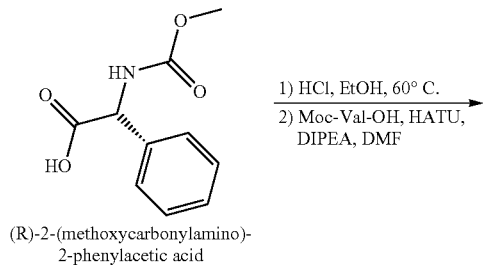

(R)-2-(methoxycarbonylamino)-2-phenylacetic acid

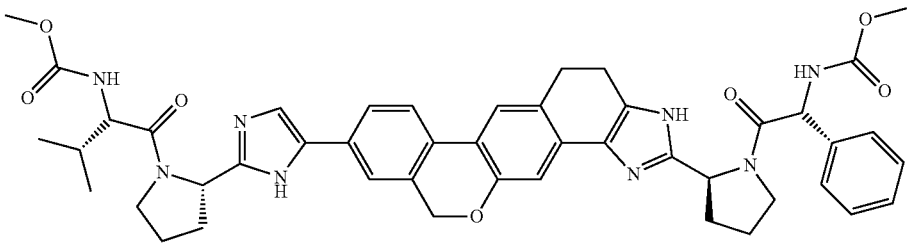

[1-(2-{5-[2-(1-{[(moethoxycarbonyl)amino](phenyl)acetyl}pyrrolidin-2-yl)-1,4,5,11-tetrahydroisochromeno[4',3',:6,7]naphtho[1,2-d]imidazol-9-yl]-1H-imidazol-2-yl}pyrrolidin-1-yl)-3-methyl-1-oxobutan-2-yl]carbamic acid This compound was made in an analogous manner to methyl {(2S)-1-[(2R)-2-(5-{2-[(2S)-1-{(2R)-2-[(methoxycarbonyl)amino]-2-phenylacetyl}pyrrolidin-2-yl]-3,7-dihydroisochromeno[3',4':5,6]naphtho[1,2-d]imidazol-9-yl}-1H-imidazol-2-yl)pyrrolidin-1-yl]-3-methyl-1-oxobutan-2-yl}carbamate, substituting tert-butyl (2S)-2-[9-(2-{(2R)-1-[N-(methoxycarbonyl)-L-valyl]pyrrolidin-2-yl}-1H-imidazol-5-yl)-3,4,5,11-tetrahydroisochromeno[4',3':6,7]naphtho[1,2-d]imidazol-2-yl]pyrrolidine-1-carboxylate for tert-butyl (2S)-2-[9-(2-{(2R)-1-[N-(methoxycarbonyl)-L-valyl]pyrrolidin-2-yl}-1H-imidazol-5-yl)-3,7-dihydroisochromeno[3',4':5,6]naphtho[1,2-d]imidazol-2-yl]pyrrolidine-1-carboxylate. LCMS-ESI$^+$: calculated for $C_{46}H_{50}N_8O_7$: 826.94; observed [M+1]$^+$: 827.64.

Example MM

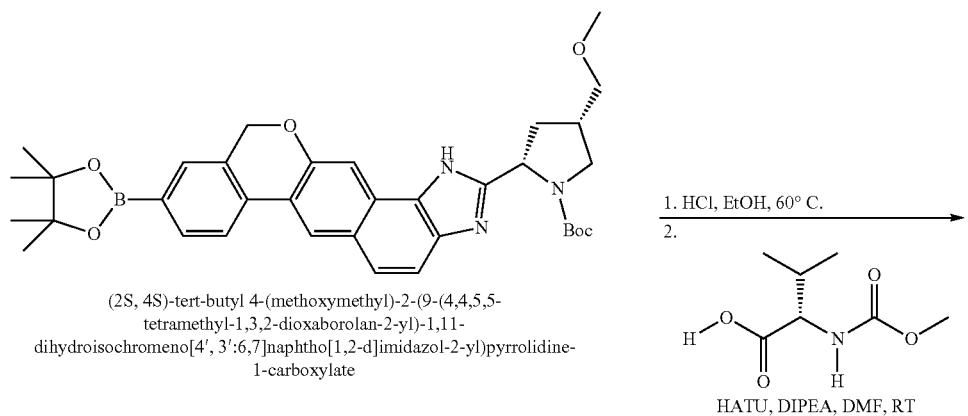

(2S, 4S)-tert-butyl 4-(methoxymethyl)-2-(9-(4,4,5,5-tetramethyl-1,3,2-dioxaborolan-2-yl)-1,11-dihydroisochromeno[4', 3':6,7]naphtho[1,2-d]imidazol-2-yl)pyrrolidine-1-carboxylate 1. HCl, EtOH, 60° C.
2. HATU, DIPEA, DMF, RT

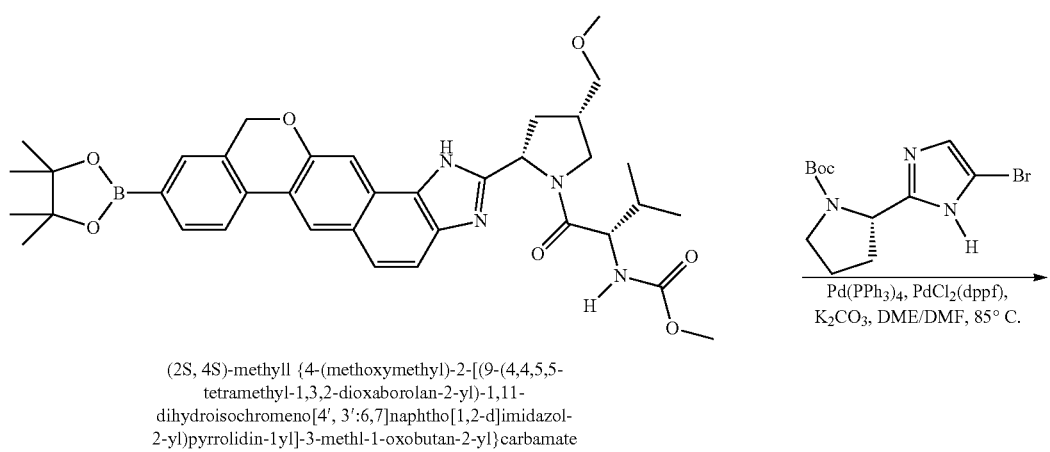

(2S, 4S)-methyl {4-(methoxymethyl)-2-[(9-(4,4,5,5-tetramethyl-1,3,2-dioxaborolan-2-yl)-1,11-dihydroisochromeno[4', 3':6,7]naphtho[1,2-d]imidazol-2-yl)pyrrolidin-1yl]-3-methl-1-oxobutan-2-yl}carbamate Pd(PPh$_3$)$_4$, PdCl$_2$(dppf), K$_2$CO$_3$, DME/DMF, 85° C.

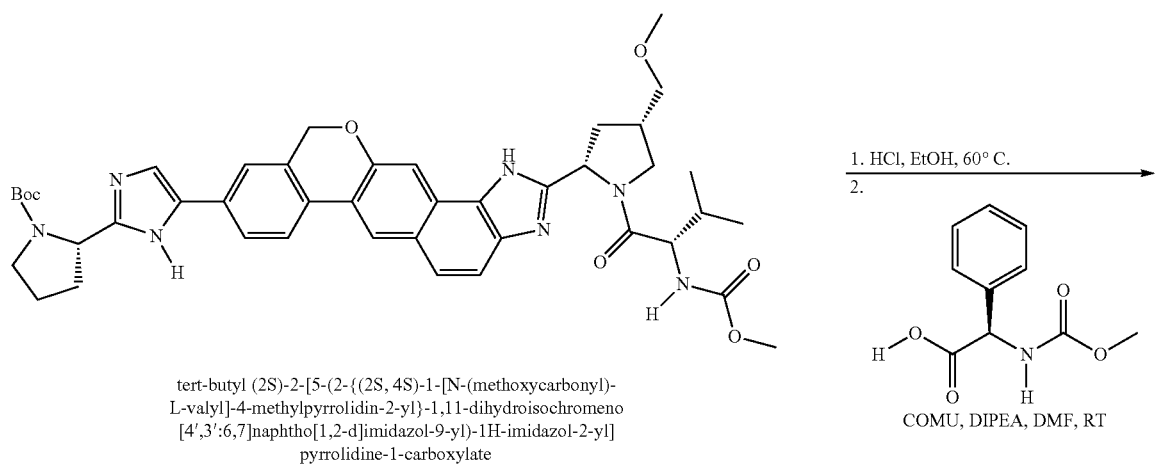

tert-butyl (2S)-2-[5-(2-{(2S, 4S)-1-[N-(methoxycarbonyl)-L-valyl]-4-methylpyrrolidin-2-yl}-1,11-dihydroisochromeno[4',3':6,7]naphtho[1,2-d]imidazol-9-yl)-1H-imidazol-2-yl]pyrrolidine-1-carboxylate 1. HCl, EtOH, 60° C.
2. COMU, DIPEA, DMF, RT

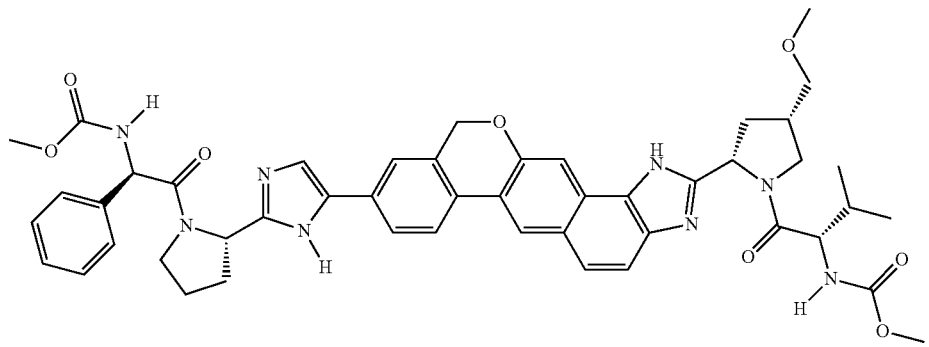

methyl {(1R)-2-[(2S)-2-(5-{2-[(2S, 4S)-1-{(2S)-2-[(methoxycarbonyl)
amino]-3-methylbutanoyl}-4-(methoxymethyl)pyrrolidin-2-yl]-1,11-
dihydroisochromeno[4',3':6,7]naphtho[1,2-d]imidazol-9-yl}-1H-imidazol-
2-yl)pyrrolidin-1-yl]-2-oxo-1-phenylethyl}carbamate (2S,4S)-methyl {4-(methoxymethyl)-2-[(9-(4,4,5,5-tetramethyl-1,3,2-dioxa borolan-2-yl)-1,11-dihydroisochromeno[4',3':6,7]naphtho[1,2-d]imidazol-2-yl)pyrrolidin-1yl]-3-methyl-1-oxobutan-2-yl}carbamate A solution of (2S,4S)-tert-butyl 4-(methoxymethyl)-2-(9-(4,4,5,5-tetramethyl-1,3,2-dioxaborolan-2-yl)-1,11-dihydroisochromeno[4',3':6,7]naphtho[1,2-d]-imidazol-2-yl)pyrrolidine-1-carboxylate (424 mg, 0.69 mmol), ethanol (6 mL) and concentrated HCl (2 mL) was heated to 60° C. for 1 hour. The reaction was concentrated and the crude material dissolved in DCM (10 mL). This solution was concentrated and to this material was added a solution of 2-methoxycarbonylamino-3-methylbutyric acid (152 mg, 0.86 mmol) and HATU (303 mg, 0.79 mmol) in DMF (6 mL). To the resulting solution was added diisopropylethylamine (360 μL, 2.08 mmol). After stirring for 2 hours at room temperature, the reaction was diluted with ethyl acetate, washed with 5% NaHCO$_3$ solution, water and brine, dried (Na$_2$SO$_4$), concentrated and dried under vacuum to give (2S,4S)-methyl {4-(methoxymethyl)-2-[(9-(4,4,5,5-tetramethyl-1,3,2-dioxaborolan-2-yl)-1,11-dihydroisochromeno[4',3':6,7]naphtho[1,2-d]imidazol-2-yl)pyrrolidin-1-yl]-3-methyl-1-oxobutan-2-yl}carbamate.

tert-butyl(2S)-2-[5-(2-{(2S,4S)-1-[N-(methoxycarbonyl)-L-valyl]-4-methylpyrrolidin-2-yl}-1,11-dihydroisochromeno[4',3':6,7]naphtho[1,2-d]imidazol-9-yl)-1H-imidazol-2-yl]pyrrolidine-1-carboxylate To a solution of (2S,4S)-methyl {4-(methoxymethyl)-2-[(9-(4,4,5,5-tetramethyl-1,3,2-dioxaborolan-2-yl)-1,11-dihydroiso chromeno[4',3':6,7]naphtho[1,2-d]imidazol-2-yl)pyrrolidin-1-yl]-3-methyl-1-oxobutan-2-yl}carbamate (0.69 mmol), (S)-tert-butyl 2-(5-bromo-1H-imidazol-2-yl)pyrrolidine-1-carboxylate (220 mg, 0.69 mmol), tetrakis(triphenylphosphine) palladium(0) (24 mg, 0.02 mmol) and dichloro[1,1'-bis(diphenylphosphino) ferrocene]palladium (II) (31 mg, 0.04 mmol) in a mixture of 1,2-dimethoxyethane (6.0 mL) and dimethylformamide (1.0 mL) was added a solution of potassium carbonate (2M in water, 1.04 mL, 2.0 mmol). The resulting mixture was degassed and then heated to 85° C. under argon for 18 hours. After cooling to room temperature, the reaction was diluted with ethyl acetate. The organics were washed with water and brine, dried (Na$_2$SO$_4$), and concentrated. The crude residue was purified by flash chromatography to yield (tert-butyl (2S)-2-[5-(2-{(2S,4S)-1-[N-(methoxycarbonyl)-L-valyl]-4-methylpyrrolidin-2-yl}-1,11-dihydroisochromeno[4',3':6,7]naphtho[1,2-d]imidazol-9-yl)-1H-imidazol-2-yl]pyrrolidine-1-carboxylate (145 mg, 27%).

methyl {(1R)-2-[(2S)-2-(5-{2-[(2S,4S)-1-{(2S)-2-[(methoxycarbonyl)amino]-3-methylbutanoyl}-4-(methoxymethyl)pyrrolidin-2-yl]-1,11-dihydroisochromeno[4',3':6,7]naphtho[1,2-d]imidazol-9-yl}-1H-imidazol-2-yl)pyrrolidin-1-yl]-2-oxo-1-phenylethyl}carbamate A solution of tert-butyl (2S)-2-[5-(2-{(2S,4S)-1-[N-(methoxycarbonyl)-L-valyl]-4-methylpyrrolidin-2-yl}-1,11-dihydroisochromeno[4',3':6,7]naphtho[1,2-d]imidazol-9-yl)-1H-imidazol-2-yl]pyrrolidine-1-carboxylate (145 mg, 0.18 mmol), ethanol (3 mL) and concentrated HCl (1 mL) was heated to 60° C. for 1 hour. The reaction was concentrated and the crude material dissolved in DCM (6 mL). This solution was concentrated and to this material was added a solution of (R)-2-(methoxycarbonylamino)-2-phenylacetic acid (51 mg, 0.24 mmol) and COMU (92 mg, 021 mmol) in DMF (3 mL). To the resulting solution was added diisopropylethylamine (100 μL, 0.56 mmol). After stirring for 2 hours at room temperature, the reaction was diluted with ethyl acetate, washed with water and brine, dried (Na$_2$SO$_4$), concentrated and purified by preparative reverse phase HPLC (Gemini, 15 to 43% ACN/H$_2$O+0.1% TFA). The product fractions were lyophilized to give methyl {(1R)-2-[(2S)-2-(5-{2-[(2S,4S)-1-{(2S)-2-[(methoxycarbonyl)amino]-3-methylbutanoyl}-4-(methoxymethyl)pyrrolidin-2-yl]-1,11-dihydroisochromeno[4',3':6,7]naphtho[1,2-d]imidazol-9-yl}-1H-imidazol-2-yl)pyrrolidin-1-yl]-2-oxo-1-phenylethyl}carbamate (68 mg, 39%). MS (ESI) m/z 870 [M+H]$^+$. 1H NMR (400 MHz, dmso) δ 8.71 (s, 1H), 8.22 (d, 1H, J=8 Hz), 8.09 (m, 1H), 7.88-7.63 (m, 6H), 7.36-7.29 (m, 6H), 5.41 (d, 1H, J=8.4 Hz), 5.30-5.24 (m, 2H), 5.14-5.10 (m, 1H), 4.13-3.09 (m, 15H), 2.47-1.80 (m, 8H), 0.80 (dd, 6H, J=6.4 Hz, J=23 Hz).

Example MN

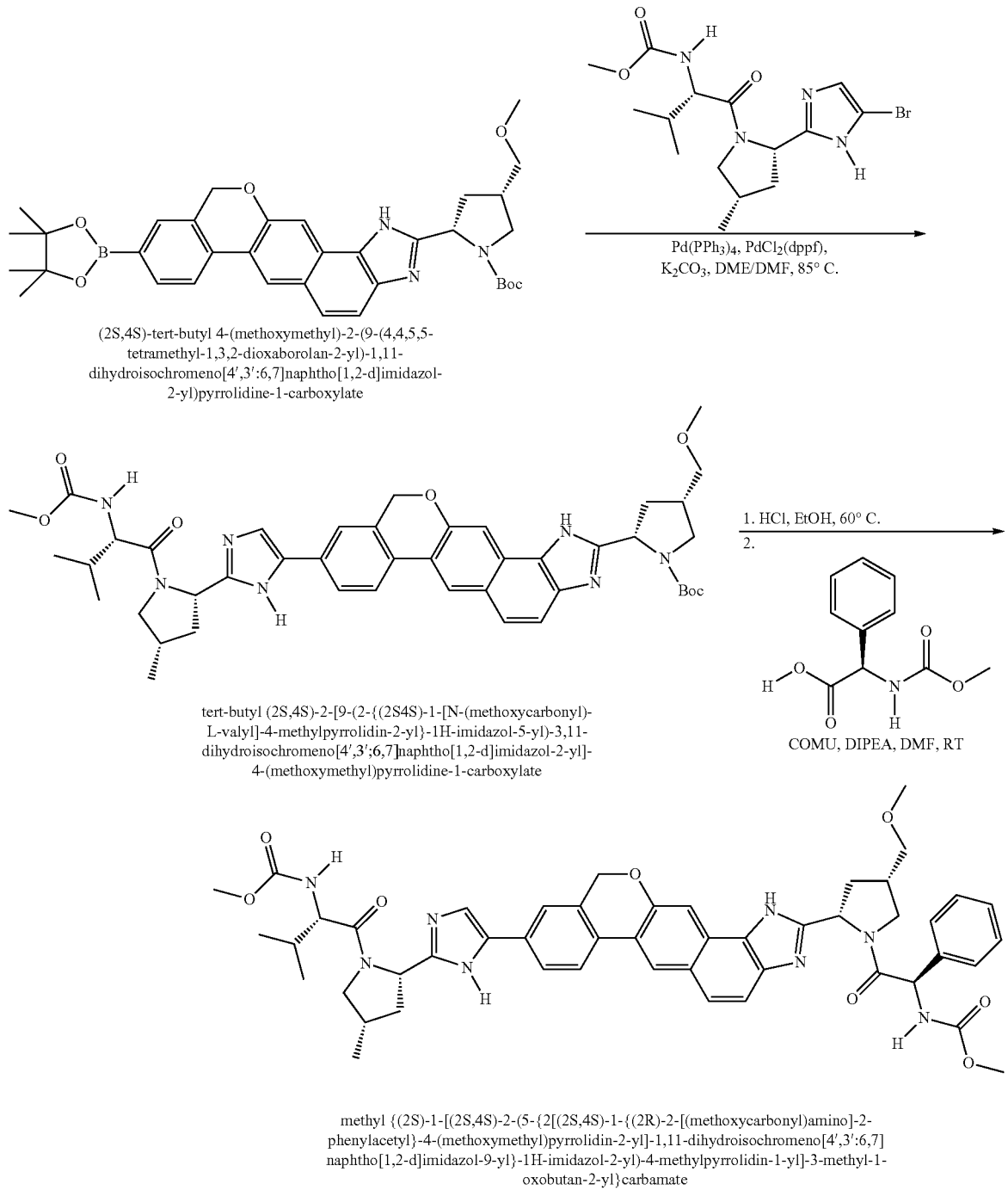

tert-butyl(2S,4S)-2-[9-(2-{(2S4S)-1-[N-(methoxy-carbonyl)-L-valyl]-4-methylpyrrolidin-2-yl}-1H-imidazol-5-yl)-3,11-dihydroisochromeno[4',3':6,7]naphtho[1,2-d]imidazol-2-yl]-4-(methoxymethyl)pyrrolidine-1-carboxylate To a solution of (2S,4S)-tert-butyl 4-(methoxymethyl)-2-(9-(4,4,5,5-tetramethyl-1,3,2-dioxaborolan-2-yl)-1,11-dihydroisochromeno[4',3':6,7]naphtho[1,2-d]imidazol-2-yl)pyrrolidine-1-carboxylate (438 mg, 0.72 mmol), methyl(S)-1-((2S,4S)-2-(5-bromo-1H-imidazol-2-yl)-4-methylpyrrolidin-1-yl)-3-methyl-1-oxobutan-2-ylcarbamate (276 mg, 0.72 mmol), tetrakis(triphenylphosphine) palladium(0) (41 mg, 0.04 mmol) and dichloro[1,1'-bis(diphenylphosphino) ferrocene]palladium(II) (52 mg, 0.07 mmol) in a mixture of 1,2-dimethoxyethane (8.6 mL) and dimethylformamide (1.5 mL) was added a solution of potassium carbonate (2M in water, 1.07 mL, 2.15 mmol). The resulting mixture was degassed and then heated to 85° C. under argon for 18 hours. After cooling to room temperature, the reaction was diluted with ethyl acetate. The organics were washed with water and brine, dried (Na$_2$SO$_4$), and concentrated. The crude residue was purified by flash chromatography to yield tert-butyl (2S,4S)-2-[9-(2-{(2S,4S)-1-[N-(methoxycarbonyl)-L-valyl]-4-methylpyrrolidin-2-yl}-1H-imidazol-5-yl)-3,11-dihydroisochromeno[4',3':6,7]naphtho[1,2-d]imidazol-2-yl]-4-(methoxymethyl)pyrrolidine-1-carboxylate (182 mg, 32%).

methyl {(2S)-1-[(2S,4S)-2-(5-{2-[(2S,4S)-1-{(2R)-2-[(methoxycarbonyl)amino]-2-phenylacetyl}-4-(methoxymethyl)pyrrolidin-2-yl]-1,11-dihydroisochromeno[4',3':6,7]naphtho[1,2-d]imidazol-9-yl}-1H-imidazol-2-yl)-4-methylpyrrolidin-1-yl]-3-methyl-1-oxobutan-2-yl}carbamate A solution of tert-butyl (2S,4S)-2-[9-(2-{(2S4S)-1-[N-(methoxycarbonyl)-L-valyl]-4-methylpyrrolidin-2-yl}-1H-imidazol-5-yl)-3,11-dihydroisochromeno[4',3':6,7]naphtho[1,2-d]imidazol-2-yl]-4-(methoxy methyl)pyrrolidine-1-carboxylate (182 mg, 0.18 mmol), ethanol (3 mL) and concentrated HCl (1 mL) was heated to 60° C. for 1 hour. The reaction was concentrated and the crude material dissolved in DCM (6 mL). This solution was concentrated and to this material was added a solution of (R)-2-(methoxycarbonylamino)-2-phenylacetic acid (47 mg, 0.23 mmol) and COMU (85 mg, 0.2 mmol) in DMF (3 mL). To the resulting solution was added diisopropylethylamine (90 μL, 0.52 mmol). After stirring for 2 hours at room temperature, the reaction was diluted with ethyl acetate, washed with water and brine, dried (Na$_2$SO$_4$), concentrated and purified by preparative reverse phase HPLC (Gemini, 15 to 49% ACN/H$_2$O+0.1% TFA). The product fractions were lyophilized to give methyl{(2S)-1-[(2S,4S)-2-(5-{2-[(2S,4S)-1-{(2R)-2-[(methoxycarbonyl)amino]-2-phenylacetyl}-4-(methoxymethyl)pyrrolidin-2-yl]-1,11-dihydroisochromeno[4',3':6,7]naphtho[1,2-d]imidazol-9-yl}-1H-imidazol-2-yl)-methylpyrrolidin-1-yl]-3-methyl-1-oxobutan-2-yl}carbamate (32 mg, 39%). MS (ESI) m/z 884 [M+H]$^+$.

1H NMR (400 MHz, dmso) δ 8.70 (s, 1H), 8.21 (d, 1H, J=8 Hz), 8.08 (s, 1H), 7.90-7.64 (m, 6H), 7.34-7.31 (m, 3H), 7.64 (d, 1H, J=8.4 Hz), 5.47 (d, 1H, J=7.6 Hz), 5.28-5.25 (m, 3H), 5.05-5.01 (m, 1H), 4.19-4.04 (m, 3H), 3.67-3.15 (m, 15H), 2.51-2.46 (m, 4H), 1.95-1.92 (m, 2H), 1.82-1.76 (m, 1H), 1.10 (d, 3H, J=6 Hz), 0.75 (dd, 6H, J=6.8 Hz, J=14 Hz).

Example MO

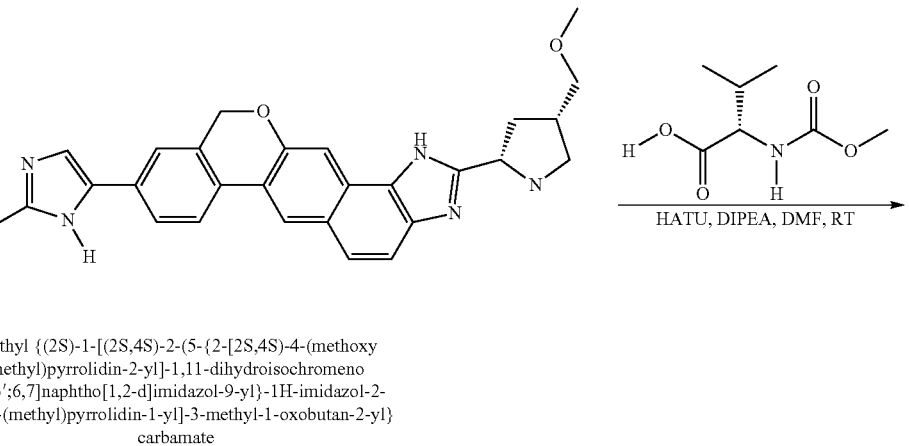

methyl {(2S)-1-[(2S,4S)-2-(5-{2-[2S,4S]-4-(methoxymethyl)pyrrolidin-2-yl}-1,11-dihydroisochromeno[4',3';6,7]naphtho[1,2-d]imidazol-9-yl}-1H-imidazol-2-yl)-4-(methyl)pyrrolidin-1-yl]-3-methyl-1-oxobutan-2-yl} carbamate

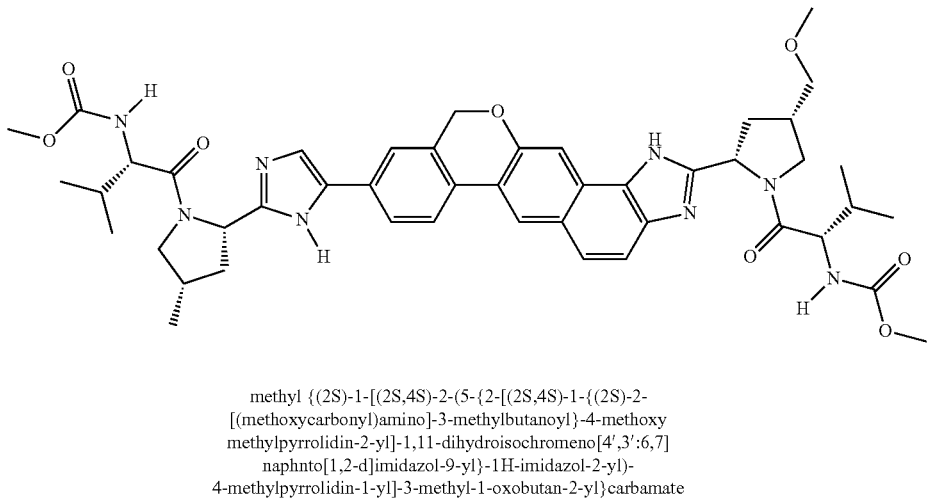

methyl {(2S)-1-[(2S,4S)-2-(5-{2-[(2S,4S)-1-{(2S)-2-[(methoxycarbonyl)amino]-3-methylbutanoyl}-4-methoxymethylpyrrolidin-2-yl]-1,11-dihydroisochromeno[4',3':6,7]naphnto[1,2-d]imidazol-9-yl}-1H-imidazol-2-yl)-4-methylpyrrolidin-1-yl]-3-methyl-1-oxobutan-2-yl}carbamate methyl {(2S)-1-[(2S,4S)-2-(5-{2-[(2S,4S)-1-{(2S)-2-[(methoxycarbonyl)amino]-3-methylbutanoyl}-4-methoxymethylpyrrolidin-2-yl]-1,11-dihydroisochromeno[4',3':6,7]naphtho[1,2-d]imidazol-9-yl}-1H-imidazol-2-yl)-4-methylpyrrolidin-1-yl]-3-methyl-1-oxobutan-2-yl}carbamate To a solution of methyl {(2S)-1-[(2S,4S)-2-(5-{2-[(2S,4S)-4-(methoxymethyl)pyrrolidin-2-yl]-1,11-dihydroisochromeno[4',3':6,7]naphtho[1,2-d]imidazol-9-yl}-1H-imidazol-2-yl)-4-(methyl)pyrrolidin-1-yl]-3-methyl-1-oxobutan-2-yl}carbamate (57 mg, 0.08 mmol), 2-methoxycarbonylamino-3-methylbutyric acid (19 mg, 0.1 mmol), HATU (303 mg, 0.79 mmol) in DMF (1 mL) was added diisopropylethylamine (43 µL, 0.24 mmol). After stirring for 2 hours at room temperature, the reaction was diluted with ethyl acetate, washed with 5% NaHCO₃ solution, water and brine, dried (Na₂SO₄), concentrated and purified by preparative reverse phase HPLC (Gemini, 15 to 43% ACN/H₂O+ 0.1% TFA). The product fractions were lyophilized to give methyl {(2S)-1-[(2S,4S)-2-(5-{2-[(2S,4S)-1-{(2S)-2-[(methoxycarbonyl)amino]-3-methyl butanoyl}-4-methoxymethylpyrrolidin-2-yl]-1,11-dihydroisochromeno[4',3':6,7]naphtho[1,2-d]imidazol-9-yl}-1H-imidazol-2-yl)-4-methylpyrrolidin-1-yl]-3-methyl-1-oxobutan-2-yl})carbamate. (13 mg, 19%). MS (ESI) m/z 850 [M+H]⁺.

1H NMR (400 MHz, dmso) δ 8.66 (s, 1H), 8.28-8.13 (m, 1H), 8.12-7.99 (m, 1H), 7.90-7.75 (m, 3H), 7.73-7.65 (m, 1H), 7.63-7.57 (m, 1H), 7.34-7.19 (m, 2H), 5.30-5.24 (m, 2H), 5.21-4.95 (m, 2H), 4.33-3.93 (m, 6H), 3.23-3.58 (m, 12H), 2.76-2.59 (m, 2H), 2.02-1.73 (m, 6H), 1.12-1.07 (m, 3H), 0.86-0.68 (m, 12H).

Example MP

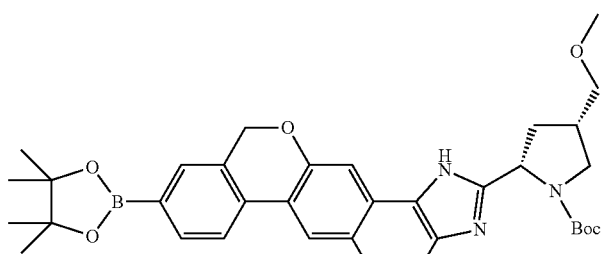

(2S,4S)-tert-butyl 4-(methoxymethyl)-2-(9-(4,4,5,5-tetramethyl-1,3,2-dioxaborolan-2-yl)-1,11-dihydroisochromeno[4',3':6,7]naphtho[1,2-d]imidazol-2-yl)pyrrolidine-1-carboxylate

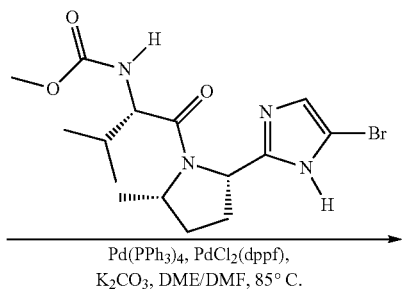

Pd(PPh₃)₄, PdCl₂(dppf), K₂CO₃, DME/DMF, 85° C.

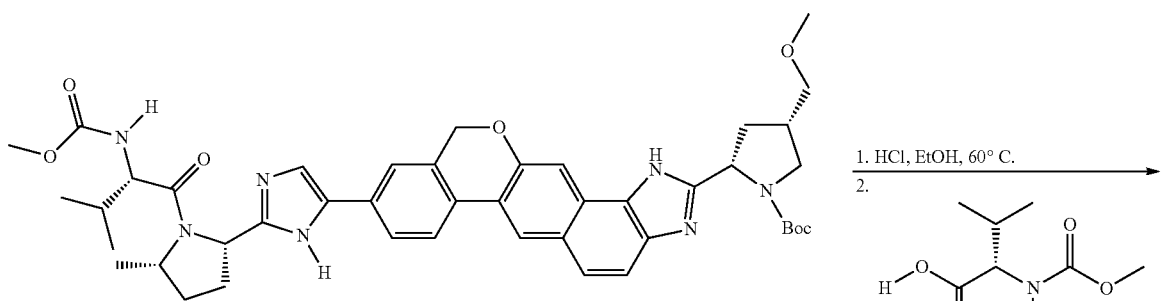

tert-butyl (2S,4S)-2-[9-(2-{(2S,5S)-1-[N-(methoxycarbonyl)-L-valyl]-5-methylpyrrolidin-2-yl}-1H-imidazol-5-yl)-3,11-dihydroisochromeno[4',3':6,7]naphtho[1,2-d]imidazol-2-yl]-4-(methoxymethyl)pyrrolidine-1-carboxylate 1. HCl, EtOH, 60° C.
2.

HATU, DIPEA, DMF, RT

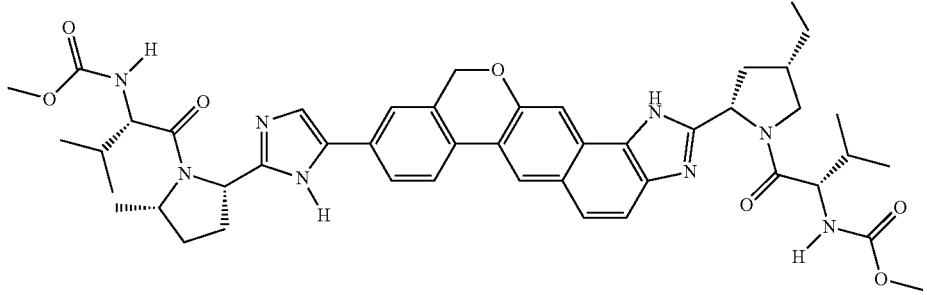

methyl {(2S)-1-[(2S,5S)-2-(5-{2-[(2S,4S)-1-{(2S)-2-[(methoxycarbonyl)amino-3-methylbutanoyl}-4-methoxy methylpyrrolidin-2-yl]-1,11-dihydroisochromeno[4',3':6,7]naphtho[1,2-d]imidazol-9-yl}-1H-imidazol-2-yl)-5-methylpyrrolidin-1-yl]-3-methyl-1-oxobutan-2-yl}carbamate tert-butyl(2S,4S)-2-[9-(2-{(2S,5S)-1-[N-(methoxy-carbonyl)-L-valyl]-5-methylpyrrolidin-2-yl}-1H-imidazol-5-yl)-3,11-dihydroisochromeno[4',3':6,7]naphtho[1,2-d]imidazol-2-yl]-4-(methoxymethyl)pyrrolidine-1-carboxylate To a solution of (2S,4S)-tert-butyl 4-(methoxymethyl)-2-(9-(4,4,5,5-tetramethyl-1,3,2-dioxaborolan-2-yl)-1,11-dihydroisochromeno[4',3':6,7]naphtho[1,2-d]imidazol-2-yl)pyrrolidine-1-carboxylate (217 mg, 0.35 mmol), methyl(S)-1-((2S,5S)-2-(5-bromo-1H-imidazol-2-yl)-5-methylpyrrolidin-1-yl)-3-methyl-1-oxobutan-2-ylcarbamate (170 mg, 0.39 mmol), tetrakis(triphenylphosphine) palladium(0) (21 mg, 0.02 mmol) and dichloro[1,1'-bis(diphenylphosphino) ferrocene]palladium(II) (26 mg, 0.04 mmol) in a mixture of 1,2-dimethoxyethane (4.3 mL) and dimethylformamide (0.75 mL) was added a solution of potassium carbonate (2M in water, 0.53 mL, 1.06 mmol). The resulting mixture was degassed and then heated to 85° C. under argon for 18 hours. After cooling to room temperature, the reaction was diluted with ethyl acetate. The organics were washed with water and brine, dried (Na$_2$SO$_4$), and concentrated. The crude residue was purified by flash chromatography to yield tert-butyl (2S,4S)-2-[9-(2-{(2S,5S)-1-[N-(methoxycarbonyl)-L-valyl]-5-methylpyrrolidin-2-yl}-1H-imidazol-5-yl)-3,11-dihydroisochromeno[4',3':6,7]naphtho[1,2-d]imidazol-2-yl]-4-(methoxy methyl)pyrrolidine-1-carboxylate (110 mg, 39%).

methyl{(2S)-1-[(2S,5S)-2-(5-{2-[(2S,4S)-1-{(2S)-2-[(methoxycarbonyl)amino]-3-methylbutanoyl}-4-methoxymethylpyrrolidin-2-yl]-1,11-dihydroisochromeno[4',3':6,7]naphtho[1,2-d]imidazol-9-yl}-1H-imidazol-2-yl)-5-methylpyrrolidin-1-yl]-3-methyl-1-oxobutan-2-yl}carbamate A solution of tert-butyl (2S,4S)-2-[9-(2-{(2S,5S)-1-[N-(methoxycarbonyl)-L-valyl]-5-methylpyrrolidin-2-yl}-1H-imidazol-5-yl)-3,11-dihydroisochromeno[4',3':6,7]naphtho[1,2-d]imidazol-2-yl]-4-(methoxy methyl)pyrrolidine-1-carboxylate (108 mg, 0.14 mmol), ethanol (2 mL) and concentrated HCl (0.7 mL) was heated to 60° C. for 1 hour. The reaction was concentrated and the crude material dissolved in DCM (10 mL). This solution was concentrated and to this material was added a solution of 2-methoxycarbonylamino-3-methylbutyric acid (31 mg, 0.18 mmol) and HATU (60 mg, 0.16 mmol) in DMF (2 mL). To the resulting solution was added diisopropylethylamine (70 μL, 0.41 nmol). After stirring for 2 hours at room temperature, the reaction was diluted with ethyl acetate, washed with 5% NaHCO$_3$ solution, water and brine, dried (Na$_2$SO$_4$). After stirring for 2 hours at room temperature, the reaction was diluted with ethyl acetate, washed with 5% NaHCO$_3$ solution, water and brine, dried (Na$_2$SO$_4$), concentrated and purified by preparative reverse phase HPLC (Gemini, 15 to 430/ACN/H$_2$O+0.1% TFA). The product fractions were lyophilized to give methyl {(2S)-1-[(2S,5S)-2-(5-{2-[(2S,4S)-1-{(2S)-2-[(methoxycarbonyl)amino]-3-methylbutanoyl}-4-methoxy methylpyrrolidin-2-yl]-1,11-dihydroisochromeno[4',3':6,7]naphtho[1,2-d]imidazol-9-yl}-1H-imidazol-2-yl)-5-methylpyrrolidin-1-yl]-3-methyl-1-oxobutan-2-yl}carbamate (52 mg, 45%). MS (ESI) m/z 850 [M+H]$^+$.

1H NMR (400 MHz, dmso) δ 8.69 (s, 1H), 8.18 (d, 1H, J=7.6 Hz), 7.99-7.86 (m, 4H), 7.72 (s, 1H), 7.64 (d, 1H, J=8.8 Hz), 7.51 (d, 1H, J=8 Hz), 7.23 (d, 1H, J=8.4 Hz), 5.29 (s, 2H), 5.22-5.18 (m, 1H), 5.01-4.70 (m, 1H), 4.64 4.61 (m, 1H), 4.21-4.17 (m, 1H), 4.09-4.05 (m, 1H), 3.92-3.88 (m, 1H), 3.59-3.08 (m, 14H), 2.67-1.83 (m, 7H), 1.43 (d, 3H, J=6.4 Hz), 0.91-0.71 (m, 12H).

Example MQ

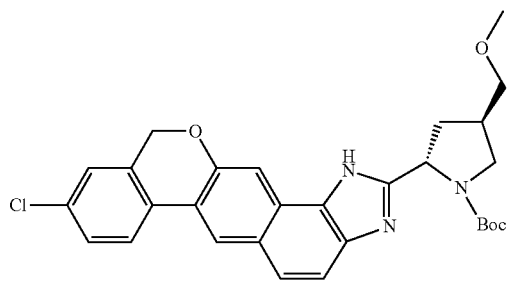

(2S,4R)-tert-butyl 2-(9-chloro-1,11-dihydroisochromeno[4', 3';6,7]naphtho[1,2-d]imidazol-2-yl)-4-(methoxymethyl)pyrrolidine-1-carboxylate

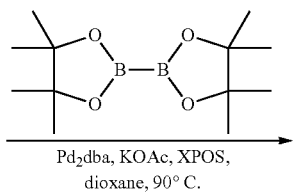

Pd$_2$dba, KOAc, XPOS, dioxane, 90° C.

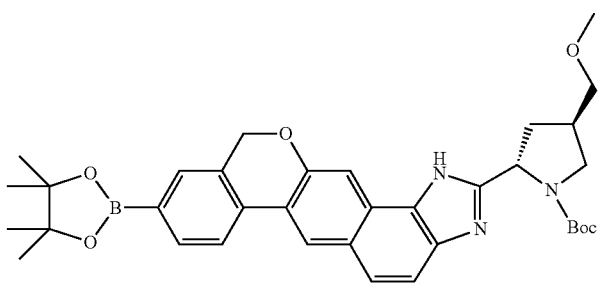

(2S,4R)-tert-butyl 4-(methoxymethyl)-2-(9-(4,4,5,5-tetramethyl-1,3,2-dioxaborolan-2-yl)-1,11-dihydroisochromeno[4', 3';6,7]naphtho[1,2-d]imidazol-2-yl)pyrrolidine-1-carboxylate

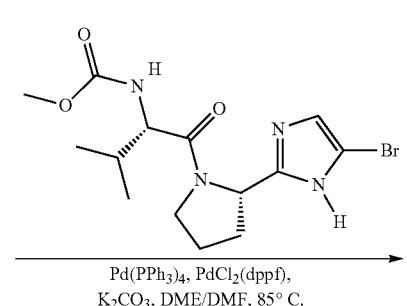

Pd(PPh$_3$)$_4$, PdCl$_2$(dppf), K$_2$CO$_3$, DME/DMF, 85° C.

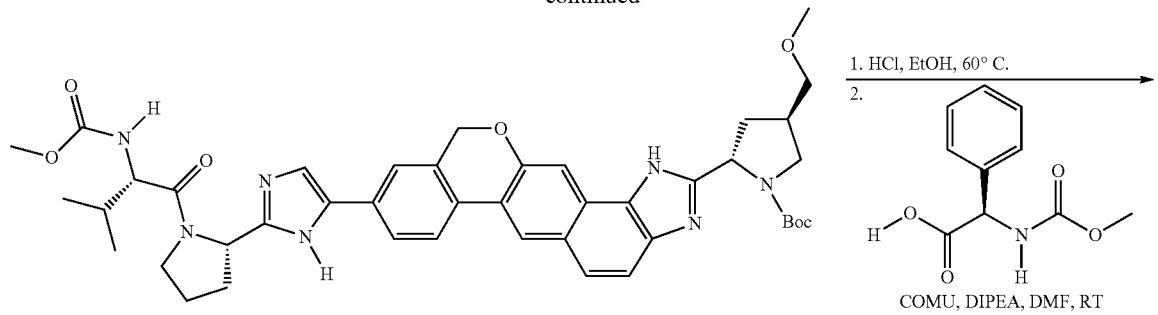

(2S,4R)-tert-butyl 2-(9-(2-((S)-1-((S)-2-(methoxycarbonyl
amino)-3-methylbutanoyl)pyrrolidin-2-yl)-1H-imidazol-5-yl)-
1,11-dihydroisochromeno[4', 3':6,7]naphtho[1,2-d]imidazol
-2-yl)-4-(methoxymethyl)pyrrolidine-1-carboxylate

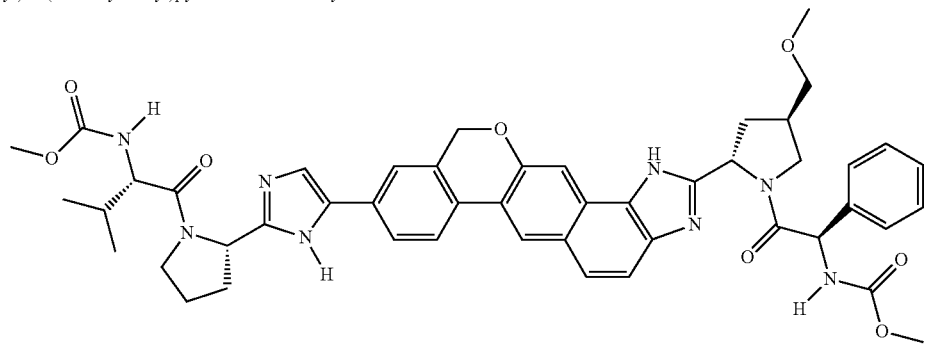

methyl {(1R)-2-[(2S,4R)-2-(9-{2-[(2S)-1-{(2S)-2-(methoxycarbonyl)
amino]-3-methylbutanoyl)pyrrolidin-2-yl)-1H-imidazol-5-yl)-
1,11-dihydroisochromeno[4', 3':6,7]naphtho[1,2-d]imidazol-2-
yl}-4-(methoxymethyl)pyrrolidin-1-yl]-2-oxo-phenylethyl}carbamate (2S,4R)-tert-butyl-4-(methoxymethyl)-2-(9-(4,4,5,5-
tetramethyl-1,3,2-dioxa borolan-2-yl)-1,11-dihy-
droisochromeno[4',3':6,7]naphtho[1,2-d]imidazol-2-
yl)pyrrolidine-1-carboxylate A degassed mixture of -(2S,4R)-tert-butyl-2-(9-chloro-1,
11-dihydroisochromeno[4',3':6,7]naphtho[1,2-d]imidazol-
2-yl)-4-(methoxymethyl)pyrrolidine-1-carboxylate (335 mg,
0.64 mmol), bis(pinacolato)diboron (246 mg, 0.96 mmol),
potassium acetate (190 mg, 1.9 mmol), tris(dibenzylideneac-
etone) palladium (24 mg, 0.02 mmol) and 2-dicyclohexy-
lphosphino-2',4',6'-tri-i-propyl-1,1'-biphenyl (31 mg, 0.06
mmol) in 1,4-dioxane (3.3 mL) was heated to 90° C. for 3
hours, cooled to room temperature and diluted with ethyl
acetate. The organics were washed with water and brine, dried
($Na_2SO_4$), and concentrated. The crude residue was purified
by flash chromatography to yield (2S,4R)-tert-butyl 4-(meth-
oxymethyl)-2-(9-(4,4,5,5-tetramethyl-1,3,2-dioxaborolan-
2-yl)-1,11-dihydroisochromeno[4',3':6,7]naphtho[1,2-d]
imidazol-2-yl)pyrrolidine-1-carboxylate (379 mg, 96%).

(2S,4R)-tert-butyl-2-(9-(2-((S)-1-((S)-2-(methoxy-
carbonylamino)-3-methyl butanoyl)pyrrolidin-2-yl)-
1H-imidazol-5-yl)-1,11-dihydroisochromeno[4',3':6,
7]naphtho[1,2-d]imidazol-2-yl)-4(methoxymethyl)
pyrrolidine-1-carboxylate To a solution of (2S,4R)-tert-butyl 4-(methoxymethyl)-2-
(9-(4,4,5,5-tetramethyl-1,3,2-dioxaborolan-2-yl)-1,11-dihy-
droisochromeno[4',3':6,7]naphtho[1,2-d]imidazol-2-yl)pyr-
rolidine-1-carboxylate (299 mg, 0.49 mmol), methyl(S)-1-
((S)-2-(5-bromo-1H-imidazol-2-yl)pyrrolidin-1-yl)-3-
methyl-1-oxobutan-2-ylcarbamate (217 mg, 0.58 mmol),
tetrakis(triphenylphosphine) palladium(0) (28 mg, 0.02
mmol) and dichloro[1,1'-bis(diphenylphosphino)ferrocene]
palladium(II) (35 mg, 0.04 mmol) in a mixture of 1,2-
dimethoxyethane (4.3 mL) and dimethylformamide (0.75
mL) was added a solution of potassium carbonate (2M in
water, 0.73 mL, 1.46 mmol). The resulting mixture was
degassed and then heated to 85° C. under argon for 18 hours.
After cooling to room temperature, the reaction was diluted
with ethyl acetate. The organics were washed with water and
brine, dried ($Na_2SO_4$), and concentrated. The crude residue
was purified by flash chromatography to yield (2S,4R)-tert-
butyl 2-(9-(2-((S)-1-((S)-2-(methoxycarbonylamino)-3-me-
thylbutanoyl)pyrrolidin-2-yl)-1H-imidazol-5-yl)-1,11-dihy-
droisochromeno[4',3':6,7]naphtho[1,2-d]imidazol-2-yl)-4-
(methoxymethyl)pyrrolidine-1-carboxylate (170 mg, 45%).

methyl{(1R)-2-[(2S,4R)-2-(9-{2-[(2S)-1-{(2S)-2-
[(methoxycarbonyl)amino]-3-
methylbutanoyl}pyrrolidin-2-yl)-1H-imidazol-5-yl]-
1,11-dihydroisochromeno[4',3':6,7]naphtho[1,2-d]
imidazol-2-yl}-4-(methoxymethyl)pyrrolidin-1-yl]-
2-oxo-phenylethyl}carbamate A solution of (2S,4R)-tert-butyl 2-(9-(2-((S)-1-((S)-2-
(methoxycarbonylamino)-3-methylbutanoyl)pyrrolidin-2-
yl)-1H-imidazol-5-yl)-1,11-dihydroisochromeno[4',3':6,7]

naphtho[1,2-d]imidazol-2-yl)-4-(methoxymethyl) pyrrolidine-1-carboxy late (170 mg, 0.22 mmol), ethanol (3 mL) and concentrated HCl (1 mL) was heated to 60° C. for 1 hour. The reaction was concentrated and the crude material dissolved in DCM (6 mL). This solution was concentrated and to this material was added a solution of (R)-2-(methoxycarbonylamino)-2-phenylacetic acid (59 mg, 0.28 mmol) and COMU (108 mg, 0.25 mmol) in DMF (3 mL). To the resulting solution was added diisopropylethylamine (110 µL, 0.66 mmol). After stirring for 2 hours at room temperature, the reaction was diluted with ethyl acetate, washed with water and brine, dried (Na₂SO₄), concentrated and purified by preparative reverse phase HPLC (Gemini, 15 to 44% ACN/H₂O+ 0.1% TFA). The product fractions were lyophilized to give methyl {(1R)-2-[(2S,4R)-2-(9-{2-[(2S)-1-(2S)-2-[(methoxycarbonyl)amino]-3-methylbutanoyl}pyrrolidin-2-yl)-1H-imidazol-5-yl]-1,11-dihydroisochromeno[4',3':6,7]-naphtho[1,2-d]imidazol-2-yl}-(methoxymethyl)pyrrolidin-1-yl]-2-oxo-phenylethyl}carbamate (67 mg, 35%). MS (ESI) m/z 870 [M+H]⁺. 1H NMR (400 MHz, dmso) δ 8.71 (s, 1H), 8.20 (d, 1H, J=8.4 Hz), 8.01 (m, 1H), 7.91-7.64 (m, 6H), 7.38-7.28 (m, 6H), 6.85 (s, 1H), 5.51 (d, 1H, J=7.2 Hz), 5.39-5.29 (m, 3H), 5.13-5.09 (m, 1H), 4.11-3.04 (m, 15H), 2.77-1.98 (m, 8H), 0.79 (dd, 6H, J=6.8 Hz, J=12.8 Hz).

Example MR

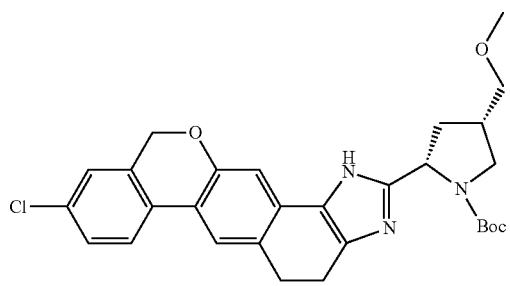

(2S,4S)-tert-butyl 2-(9-chloro-4,5-dihydro-1,11-dihydroisochromeno[4', 3';6,7]naphtho[1,2-d]imidazol-2-yl)-4-(methoxymethyl)pyrrolidine-1-carboxylate

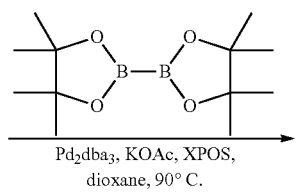

Pd₂dba₃, KOAc, XPOS, dioxane, 90° C.

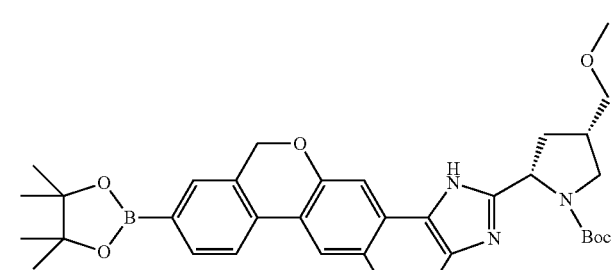

(2S,4S)-tert-butyl 4-(methoxymethyl)-2-(9-(4,4,5,5-tetramethyl-1,3,2-dioxaborolan-2-yl)-4,5-dihydro-1,11-dihydroisochromeno[4', 3';6,7]naphtho[1,2-d]imidazol-2-yl)pyrrolidine-1-carboxylate

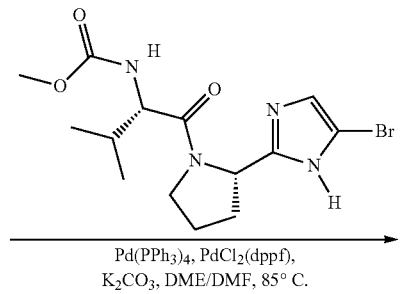

Pd(PPh₃)₄, PdCl₂(dppf), K₂CO₃, DME/DMF, 85° C.

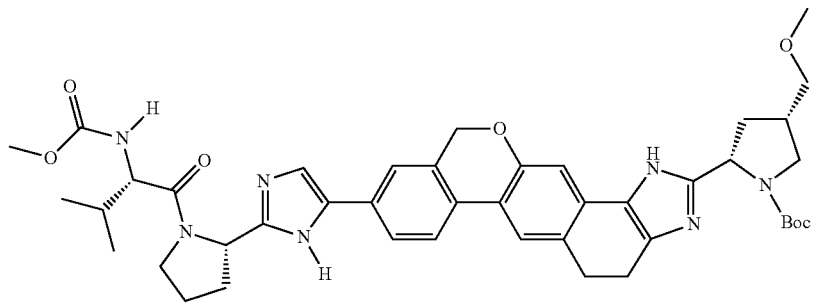

(2S,4S)-tert-butyl 2-(9-(2-((S)-1-((S)-2-(methoxycarbonyl amino)-3-methylbutanoyl)pyrrolidin-2-yl)-1H-imidazol-5-yl-4,5-dihydro-1,11-dihydroisochromeno[4', 3';6,7]naphtho [1,2-d]imidazol-2-yl)-4-(methoxymethyl)pyrrolidine-1-carboxylate

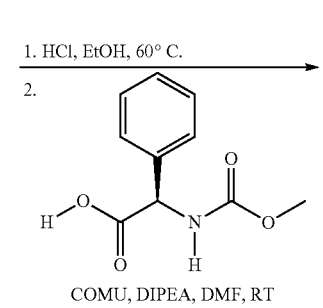

1. HCl, EtOH, 60° C.
2.

COMU, DIPEA, DMF, RT

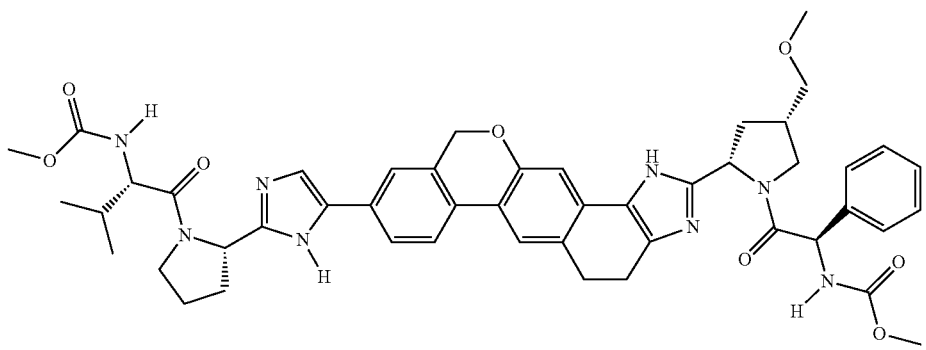

methyl {(1R)-2-[(2S,4S)-2-(9-{2-[(2S)-1-{(2S)-2-[(methoxy carbonyl)amino]-3-methylbutanoyl}pyrrolidin-2-yl)-1H-imidazol-5-yl]-1,11-dihydroisochromeno[4', 3':6,7]-4,5-dihydro-naphtho [1,2-d]imidazol-2-yl}-4-(methoxymethyl)pyrrolidin-1-yl]-2-oxo-1-phenylethyl}carbamate (2S,4S)-tert-butyl4-(methoxymethyl)-2-(9-(4,4,5,5-tetramethyl-1,3,2-dioxaborolan-2-yl)-4,5-dihydro-1, 11-dihydroisochromeno[4',3':6,7]naphtho[1,2-d] imidazol-2-yl)pyrrolidine-1-carboxylate A degassed mixture of (2S,4S)-tert-butyl 2-(9-chloro-4,5-dihydro-1,11-dihydroisochromeno[4',3':6,7]naphtho[1,2-d] imidazol-2-yl)-4-(methoxymethyl)pyrrolidine-1-carboxylate (322 mg, 0.61 mmol), bis(pinacolato)diboron (235 mg, 0.92 mmol), potassium acetate (182 mg, 1.9 mmol), tris (dibenzylideneacetone)palladium (23 mg, 0.02 mmol) and 2-dicyclohexylphosphino-2',4',6'-tri-i-propyl-1,1'-biphenyl (29 mg, 0.06 mmol) in 1,4-dioxane (3.3 mL) was heated to 90° C. for 3 hours, cooled to room temperature and diluted with ethyl acetate. The organics were washed with water and brine, dried (Na$_2$SO$_4$), and concentrated. The crude residue was purified by flash chromatography to yield (2S,4S)-tert-butyl 4-(methoxymethyl)-2-(9-(4,4,5,5-tetramethyl-1,3,2-dioxaborolan-2-yl)-4,5-dihydro-1,11-dihydroisochromeno [4',3':6,7]naphtho[1,2-d]imidazol-2-yl)pyrrolidine-1-carboxylate (267 mg, 70%).

(2S,4S)-tert-butyl-2-(9-(2-((S)-1-((S)-2-(methoxycarbonylamino)-3-methylbutanoyl)pyrrolidin-2-yl)-1H-imidazol-5-yl-4,5-dihydro-1,11-dihydroisochromeno[4',3':6,7]naphtho[1,2-d]imidazol-2-yl)-4-(methoxymethyl)pyrrolidine-1-carboxylate To a solution of (2S,4S)-tert-butyl 4-(methoxymethyl)-2-(9-(4,4,5,5-tetramethyl-1,3,2-dioxaborolan-2-yl)-4,5-dihydro-1,11-dihydroisochromeno[4',3':6,7]naphtho[1,2-d]imidazol-2-yl)pyrrolidine-1-carboxylate (267 mg, 0.52 mmol), methyl(S)-1-((S)-2-(5-bromo-1H-imidazol-2-yl)pyrrolidin-1-yl)-3-methyl-1-oxobutan-2-ylcarbamate (195 mg, 0.52 mmol), tetrakis(triphenylphosphine) palladium(0) (25 mg, 0.02 mmol) and dichloro[1,1'-bis(diphenylphosphino)ferrocene]palladium(II) (32 mg, 0.04 mmol) in a mixture of 1,2-dimethoxyethane (4.3 mL) and dimethylformamide (0.75 mL) was added a solution of potassium carbonate (2M in water, 0.65 mL, 1.3 mmol). The resulting mixture was degassed and then heated to 85° C. under argon for 18 hours. After cooling to room temperature, the reaction was diluted with ethyl acetate. The organics were washed with water and brine, dried (Na$_2$SO$_4$), and concentrated. The crude residue was purified by flash chromatography to yield (2S,4S)-tert-butyl 2-(9-(2-((S)-1-((S)-2-(methoxycarbonylamino)-3-methylbutanoyl)pyrrolidin-2-yl)-1H-imidazol-5-yl-4,5-dihydro-1,11-dihydroisochromeno[4',3':6,7]naphtho[1,2-d] imidazol-2-yl)-4-(methoxymethyl)pyrrolidine-1-carboxylate (75 mg, 22%).

methyl{(1R)-2-[(2S,4S)-2-(9-{2-[(2S)-1-{(2S)-2-[(methoxycarbonyl)amino]-3-methylbutanoyl}pyrrolidin-2-yl)-1H-imidazol-5-yl]-1,11-dihydroisochromeno[4',3':6,7]-4,5-dihydro-naphtho[1,2-d]imidazol-2-yl}-(methoxymethyl) pyrrolidin-1-yl]-2-oxo-1-phenylethyl}carbamate A solution of (2S,4S)-tert-butyl 2-(9-(2-((S)-1-((S)-2-(methoxy carbonylamino)-3-methylbutanoyl)pyrrolidin-2-yl)-1H-imidazol-5-yl-4,5-dihydro-1,11-dihydroisochromeno[4',3':6,7]naphtho[1,2-d]imidazol-2-yl)-4-(methoxymethyl)pyrrolidine-1-carboxylate (75 mg, 0.09 mmol), ethanol (2 mL) and concentrated HCl (0.6 mL) was heated to 60° C. for 1 hour. The reaction was concentrated and the crude material dissolved in DCM (6 mL). This solution was concentrated and to this material was added a solution of (R)-2-(methoxycarbonylamino)-2-phenylacetic acid (26 mg, 0.13 mmol) and COMU (47 mg, 0.11 mmol) in DMF (2 mL). To the resulting solution was added diisopropylethylamine (50 μL, 0.29 mmol). After stirring for 2 hours at room temperature, the reaction was diluted with ethyl acetate, washed with water and brine, dried (Na$_2$SO$_4$), concentrated and purified by preparative reverse phase HPLC (Gemini, 15 to 44% ACN/H$_2$O+0.1% TFA). The product fractions were lyophilized to give methyl {(1R)-2-[(2S,4S)-2-(9-{2-[(2S)-1-{(2S)-2-[(methoxycarbonyl)amino]-3-methylbutanoyl}pyrrolidin-2-yl)-1H-imidazol-5-yl]-1,11-dihydroisochromeno[4',3':6,7]-4,5-dihydro-naphtho[1,2-d]imidazol-2-yl}-4-(methoxymethyl)pyrrolidin-1-yl]-2-oxo-1-phenylethyl}carbamate (15 mg, 18%).

MS (ESI) m/z 872 [M+H]$^+$.

1H NMR (400 MHz, dmso) δ 7.95 7.63 (m, 6H), 7.35-7.25 (m, 7H), 6.97 (s, 1H), 5.42 (d, 1H, J=6.8 Hz), 5.18 (s, 2H), 5.09 (s, 2H), 4.28-2.63 (m, 19H), 2.47-1.80 (m, 8H), 0.77 (dd, 6H, J=4.8 Hz, J=12.4 Hz).

Example MS

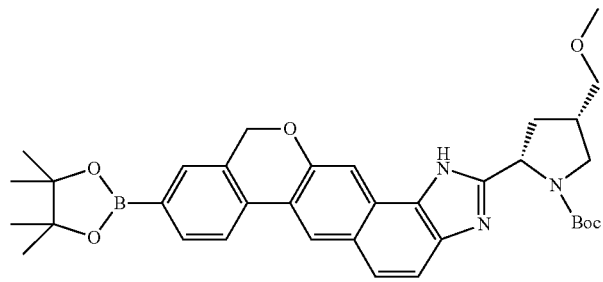

(2S,4S)-tert-butyl 4-(methoxymethyl)-2-(9-(4,4,5,5-tetramethyl-1,3,2-dioxaborolan-2-yl)-1,11-dihydroisochromeno[4',3':6,7]naphtho[1,2-d]imidazol-2-yl)pyrrolidine-1-carboxylate

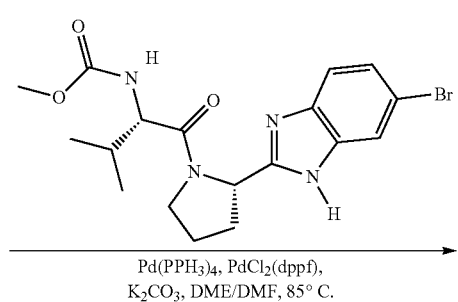

Pd(PPH$_3$)$_4$, PdCl$_2$(dppf),
K$_2$CO$_3$, DME/DMF, 85° C.

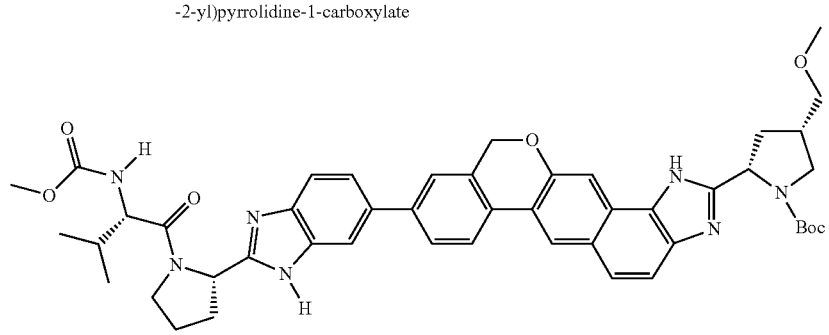

(2S,4S)-tert-butyl 2-(9-(2-((S)-1-((S)-2-(methoxycarbonyl amino)-3-methylbutanoyl)pyrrolidin-2-yl)-1H-benzo[d]imidazol-6-yl)-1,11-dihydroisochromeno[4',3':6,7]naphtho[1,2-d]imidazol-2-yl)-4-(methoxymethyl)pyrrolidine-1-carboxylate

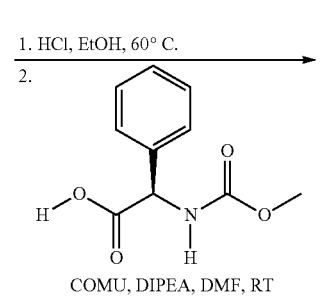

1. HCl, EtOH, 60° C.
2.

COMU, DIPEA, DMF, RT

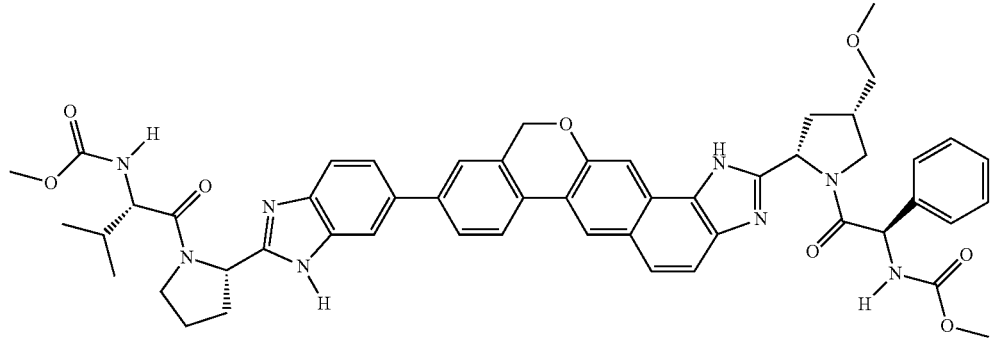

methyl {(2S)-2-[[(2S,4S)-2-{9-[2-((2S)-1-{(2S)-2[(methoxycarbonyl)amino]-3-methylbutanoyl}pyrrolidin-2-yl)-1H-benzo[d]imidazol-6-yl]-1,11-dihydroisochromeno[4',3':6,7]naphtho[1,2-d]imidazol-2-yl}-4-(methoxymethyl)pyrrolidin-1-yl]-2-oxo-1-phenylethyl}-carbamate (2S,4S)-tert-butyl-2-(9-(2-((S)-1-((S)-2-(methoxycarbonylamino)-3-methylbutanoyl)pyrrolidin-2-yl)-1H-benzo[d]imidazol-6-yl)-1,11-dihydroisochromeno[4',3':6,7]naphtho[1,2-d]imidazol-2-yl)-4-(methoxymethyl)pyrrolidine-1-carboxylate To a solution of (2S,4S)-tert-butyl 4-(methoxymethyl)-2-(9-(4,4,5,5-tetramethyl-1,3,2-dioxaborolan-2-yl)-1,11-dihydroisochromeno[4',3':6,7]naphtho[1,2-d]imidazol-2-yl)pyrrolidine-1-carboxylate (400 mg, 0.85 mmol), methyl(S)-1-((S)-2-(6-bromo-1H-benzo[d]imidazol-2-yl)pyrrolidin-1-yl)-3-methyl-1-oxobutan-2-ylcarbamate (360 mg, 0.85 mmol), tetrakis(triphenylphosphine) palladium(0) (38 mg, 0.03 mmol) and dichloro[1,1'-bis(diphenylphosphino) ferrocene]palladium(II) (48 mg, 0.07 mmol) in a mixture of 1,2-dimethoxyethane (8.0 mL) and dimethylformamide (1.4 mL) was added a solution of potassium carbonate (2M in water, 0.98 mL, 1.96 mmol). The resulting mixture was degassed and then heated to 85° C. under argon for 18 hours. After cooling to room temperature, the reaction was diluted with ethyl acetate. The organics were washed with water and brine, dried (Na$_2$SO$_4$), and concentrated. The crude residue was purified by flash chromatography to (2S,4S)-tert-butyl 2-(9-(2-((S)-1-((S)-2-(methoxycarbonylamino)-3-methylbutanoyl)pyrrolidin-2-yl)-1H-benzo[d]imidazol-6-yl)-1,11-dihydroisochromeno[4',3':6,7]naphtho[1,2-d]imidazol-2-yl)-4-(methoxymethyl)pyrrolidine-1-carboxylate (156 mg, 29%).

methyl{(2S)-2-[[(2S,4S)-2-{9-[2-((2S)-1-{(2S)-2-[(methoxycarbonyl)amino]-3-methylbutanoyl}pyrrolidin-2-yl)-1H-benzo[d]imidazol-6-yl]-1,11-dihydroisochromeno[4',3':6,7]naphtho[1,2-d]imidazol-2-yl}-4-(methoxymethyl)pyrrolidin-1-yl]-2-oxo-1-phenylethyl}carbamate A solution of (2S,4S)-tert-butyl 2-(9-(2-((S)-1-((S)-2-(methoxycarbonylamino)-3-methylbutanoyl)pyrrolidin-2-yl)-1H-benzo[d]imidazol-6-yl)-1,11-dihydroisochromeno[4',3':6,7]naphtho[1,2-d]imidazol-2-yl)-4-(methoxymethyl)

imidazol-2-yl}-4-(methoxymethyl)pyrrolidin-1-yl]-2-oxo-1-phenylethyl}carbamate (62 mg, 56%). MS (ESI) m/z 920 [M+H]+.

1H NMR (400 MHz, dmso) δ 8.73 (s, 1H), 8.17 (d, 2H, J=8.4 Hz), 7.94 (d, 3H, J=8.8 Hz), 7.84-7.67 (m, 6H), 7.37-7.29 (m, 6H), 5.48 (d, 1H, J=7.6 Hz), 5.35-5.20 (m, 5H), 4.14-3.12 (m, 15H), 2.52-1.92 (m, 8H), 0.80 (dd, 6H, J=6.8 Hz, J=6.4 Hz).

Example MT

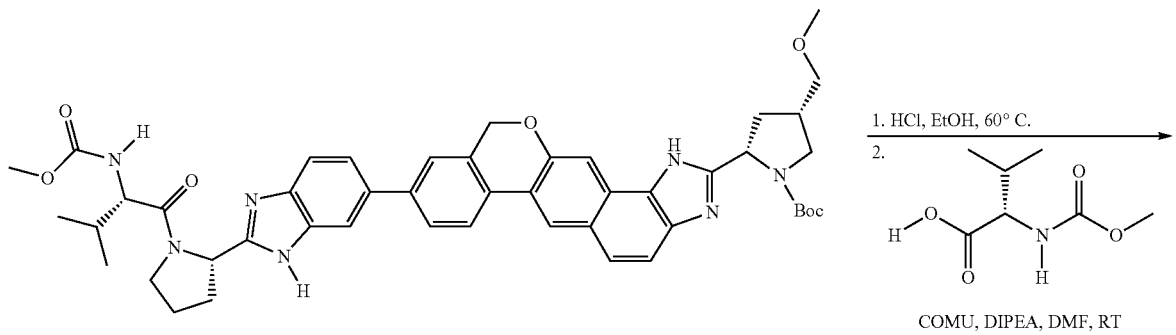

(2S,4S)-tert-butyl 2-(9-(2-((S)-1-((S)-2-(methoxycarbonyl amino)-3-methylbutanoyl)pyrrolidin-2-yl)-1H-benzo[d]imidazol-6-yl)-1,11-dihydroisochromeno[4', 3';6,7]naphtho[1,2-d]imidazol-2-yl)-4-(methoxymethyl)pyrrolidine-1-carboxylate

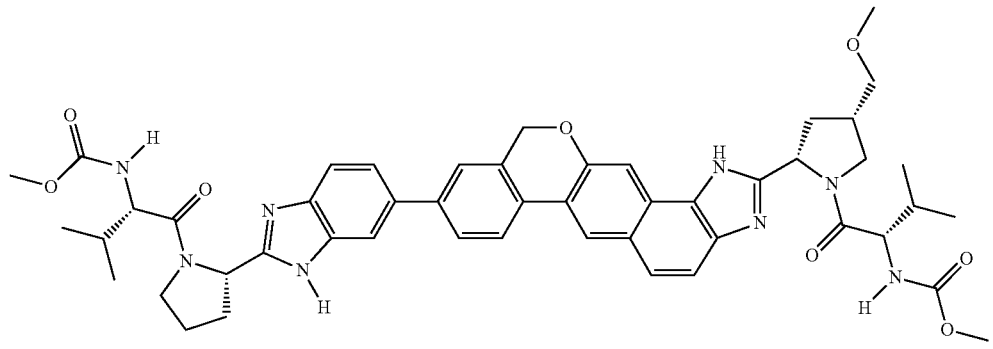

methyl {(2S)-2-[(2S,4S)-2-{9-[2-((2S)-1-{(2S)-2-[(methoxycarbonyl)amino]-3-methylbutanoyl}pyrrolidin-2-yl)-1H-benzo[d]imidazol-6-y)-1,11-dihydroisochromeno[4', 3';6,7]naphtho[1,2-d]imidazol-2-yl}-4-(methoxymethyl)pyrrolidin-1-yl]-3-methyl-1-oxobutan-2-yl}carbamate pyrrolidin-1-carboxylate (156 mg, 0.18 mmol), ethanol (3 mL) and concentrated HCl (1 mL) was heated to 60° C. for 1 hour. The reaction was concentrated and the crude material dissolved in DCM (6 mL). This solution was concentrated and to (68 mg (0.09 mmol) of this material was added a solution of (S)-2-(methoxycarbonylamino)-3-methylbutanoic acid (21 mg, 0.12 mmol) and COMU (61 mg, 014 mmol) in DMF (2 mL). To the resulting solution was added diisopropylethylamine (60 µL, 0.37 mmol). After stirring for 2 hours at room temperature, the reaction was diluted with ethyl acetate, washed with water and brine, dried (Na$_2$SO$_4$), concentrated and purified by preparative reverse phase HPLC (Gemini, 15 to 49% ACN/H$_2$O+0.1% TFA). The product fractions were lyophilized to give methyl {(2S)-2-[[(2S,4S)-2-{9-[2-((2S)-1-{(2S)-2-[(methoxycarbonyl)amino]-3-methylbutanoyl}pyrrolidin-2-yl)-1H-benzo[d]imidazol-6-yl]-1,11-dihydroisochromeno[4',3':6,7]naphtho[1,2-d]

methyl{(2S)-2-[[(2S,4S)-2-{9-[2-((2S)-1-{(2S)-2-[(methoxycarbonyl)amino]-3-methylbutanoyl}pyrrolidin-2-yl)-1H-benzo[d]imidazol-6-yl]-1,11-dihydroisochromeno[4',3':6,7]naphtho[1,2-d]imidazol-2-yl}-4-(methoxymethyl)pyrrolidin-1-yl]-3-methyl-1-oxobutan-2-yl}carbamate A solution of (2S,4S)-tert-butyl-2-(9-(2-((S)-1-((S)-2-(methoxycarbonylamino)-3-methylbutanoyl)pyrrolidin-2-yl)-1H-benzo[d]imidazol-6-yl)-1,11-dihydroisochromeno[4',3':6,7]naphtho[1,2-d]imidazol-2-yl)-4-(methoxymethyl)pyrrolidine-1-carboxylate (156 mg, 0.18 mmol), ethanol (3 mL) and concentrated HCl (1 mL) was heated to 60° C. for 1 hour. The reaction was concentrated and the crude material dissolved in DCM (6 mL). This solution was concentrated and to 68 mg (0.09 mmol) of this material was added a solution of (S)-2-(methoxycarbonylamino)-3methylbutanoic acid (21 mg, 0.12 mmol) and HATU (41 mg, 0.1 mmol) in DMF (1 mL). To the resulting solution was added diisopropylethylamine (50 μL, 0.28 mmol). After stirring for 2 hours at room temperature, the reaction was diluted with ethyl acetate, washed with water and brine, dried (Na$_2$SO$_4$), concentrated and purified by preparative reverse phase HPLC (Gemini, 15 to 44% ACN/H$_2$O+0.1% TFA). The product fractions were lyophilized to give methyl {(2S)-2-[(2S,4S)-2-{9-[2-[((2S)-1-{(2S)-2-[(methoxycarbonyl)amino]-3-methylbutanoyl}pyrrolidin-2-yl)-1H-benzo[d]imidazol-6-yl]-1,11-dihydroisochromeno[4',3':6,7]naphtho[1,2-d]imidazol-2-yl}-4-(methoxymethyl)pyrrolidin-1-yl]-3-methyl-1-oxobutan-2-yl}carbamate (32 mg, 40%). MS (ESI) m/z 886 [M+H]$^+$.

1H NMR (400 MHz, dmso) δ 8.71 (s, 1H), 8.15 (d, 1H, J=8 Hz), 7.95-7.64 (m, 8H), 7.28 (dd, 2H, J=8.8 Hz, J=14.4 Hz), 5.31 (s, 2H), 5.23-5.19 (m, 2H), 4.09-3.85 (m, 5H), 3.58-3.28 (m, 14H), 2.47-1.89 (m, 9H), 0.83-0.72 (m, 12H).

Example MU tert-butyl (2S,4S)-2-[5-(2-{(2S,4S)-1-lN-(methoxycarbonyl)-L-valyl]-pyrrolidin-2-yl}-1,11-dihydroisochromeno[4',3':6,71 naphtho[1,2-d]imidazol-9-yl)-1H-imidazol-2-yl]-4-(methoxymethyl)pyrrolidine-1-carboxylate To a solution of (2S)-methyl {-2-[(9-(4,4,5,5-tetramethyl-1,3,2-dioxaborolan-2-yl)-1,11-dihydroisochromeno[4',3':6,7]naphtho[1,2-d]imidazol-2-yl)pyrrolidin-1-yl]-3-methyl-1-oxobutan-2-yl}carbamate (460 mg, 0.74 mmol), (2S,4S)-tert-butyl 2-(5-bromo-1H-imidazol-2-yl)-4-(methoxymethyl)pyrrolidine-1-carboxylate (250 mg, 0.61 mmol), tetrakis(triphenylphosphine) palladium(0) (35 mg, 0.03 mmol) and dichloro[1,1'-bis(diphenylphosphino) ferrocene]palladium(II) (45 mg, 0.06 mmol) in a mixture of 1,2-dimethoxyethane (9.0 mL) and dimethylformamide (1.5 mL) was added a solution of potassium carbonate (2M in water, 0.92 mL, 1.84 mmol). The resulting mixture was

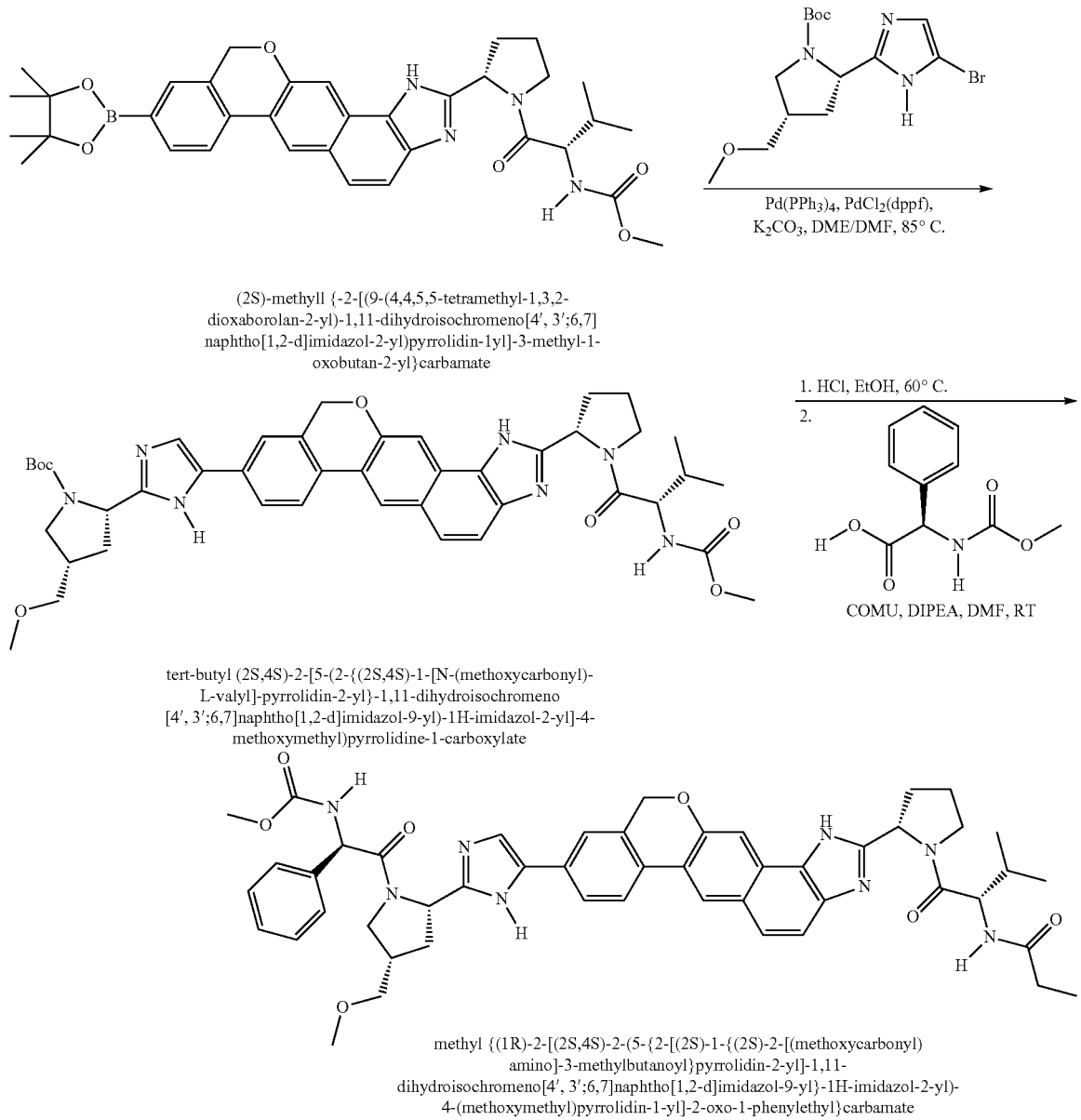

degassed and then heated to 85° C. under argon for 18 hours. After cooling to room temperature, the reaction was diluted with ethyl acetate. The organics were washed with water and brine, dried (Na₂SO₄), and concentrated. The crude residue was purified by flash chromatography to tert-butyl (2S,4S)-2-[5-(2-{(2S,4S)-1-[N-(methoxycarbonyl)-L-valyl]-pyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate (123 mg)

methyl{(1R)-2-[(2S,4S)-2-(5-{2-[(2S)-1-{(2S)-2-[(methoxycarbonyl)amino]-3-methylbutanoyl}-pyrrolidin-2-yl]-1,11-dihydroisochromeno[4',3':6,7]naphtho[1,2-d]imidazol-9-yl}-1H-imidazol-2-yl)-4-(methoxymethyl)pyrrolidin-1-yl]-2-oxo-1-phenylethyl}carbamate A solution of tert-butyl (2S,4S)-2-[5-(2-{(2S,4S)-1-[N-(methoxy carbonyl)-L-valyl]-pyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-carboxylate (122 mg, 0.16 mmol), ethanol (3 mL) and concentrated HCl (1 mL) was heated to 60° C. for 1 hour. The reaction was concentrated and the crude material dissolved in DCM (3 mL). This solution was concentrated and to this material was added a solution of (R)-2-(methoxycarbonylamino)-2-phenylacetic acid (43 mg, 0.2 mmol) and COMU (77 rmg, 018 mmol) in DMF (3 mL). To the resulting solution was added diisopropylethylamine (80 µL, 0.37 mmol). After stirring for 2 hours at room temperature, the reaction was diluted with ethyl acetate, washed with water and brine, dried (Na₂SO₄), concentrated and purified by preparative reverse phase HPLC (Gemini, 15 to 44% ACN/H₂O+0.1% TFA). The product fractions were lyophilized to give methyl {(1R)-2-[(2S,4S)-2-(5-{2-[(2S)-1-{(2S)-2-[(methoxycarbonyl)amino]-3-methylbutanoyl}-pyrrolidin-2-yl]-1,11-dihydroisochromeno[4',3':6,7]naphtho[1,2-d]imidazol-9-yl}-1H-imidazol-2-yl)-4-(methoxymethyl)pyrrolidin-1-yl]-2-oxo-1-phenylethyl}carbamate (60 mg, 44%). MS (ESI) m/z 870 [M+H]⁺.

1H NMR (400 MHz, dmso) δ 8.71 (s, 1H), 8.22 (d, 1H, J=8 Hz), 8.09 (m, 1H), 7.88-7.63 (m, 6H), 7.36-7.29 (m, 6H), 5.41 (d, 1H, J=8.4 Hz), 5.30-5.24 (m, 2H), 5.14-5.10 (m, 1H), 4.13-3.09 (m, 15H), 2.47-1.80 (m, 8H), 0.80 (dd, 6H, J=6.4 Hz, J=23 Hz).

Example MV

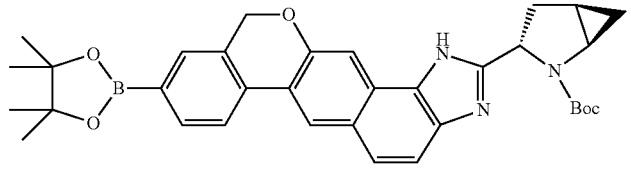

(1R,3S,5R)-tert-butyl-3-(9-(4,4,5,5-tetramethyl-1,3,2-dioxaborolan-2-yl)-1,11-dihydroisochromeno[4',3':6,7]naphtho[1,2-d]imidazol-2-yl)-2-azabicyclo[3.1.0]hexane-2-carboxylate

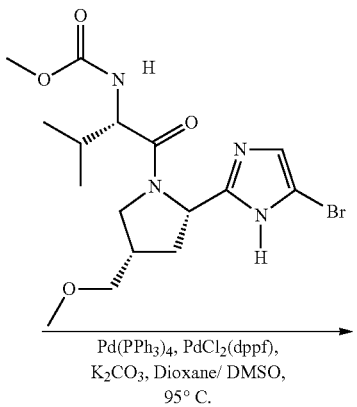

Pd(PPh₃)₄, PdCl₂(dppf), K₂CO₃, Dioxane/ DMSO, 95° C.

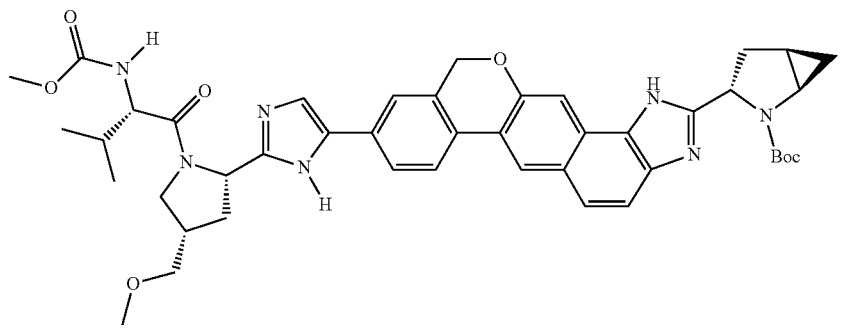

(1R,3S,5R)-tert-butyl 3-(9-(2-((S)-1-((S)-2-(methoxy carbonylamino)-3-methylbutanoyl)-4-methoxymethyl pyrrolidin-2-yl)-1H-imidazol-5-yl)-1,11-dihydroisochromeno[4',3':6,7]naphtho[1,2-d]imidazol-2-yl)-2-azabicyclo[3.1.0]hexane-2-carboxylate

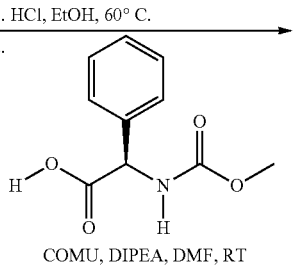

COMU, DIPEA, DMF, RT

1. HCl, EtOH, 60° C.
2.

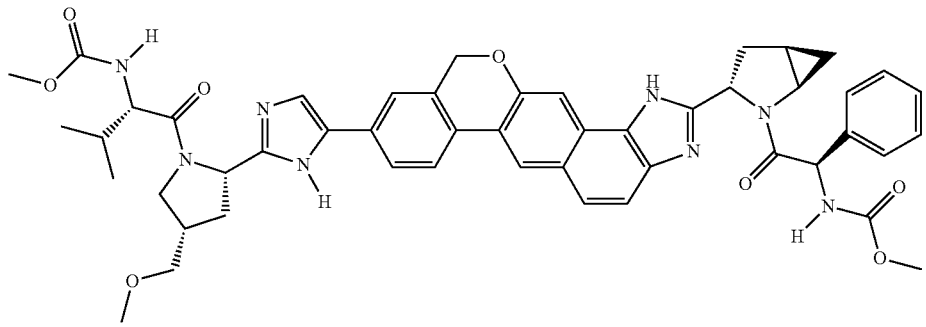

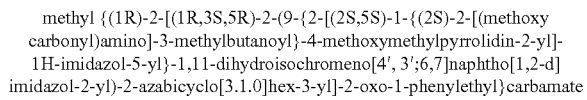

methyl {(1R)-2-[(1R,3S,5R)-2-(9-{2-[(2S,5S)-1-{(2S)-2-[(methoxy carbonyl)amino]-3-methylbutanoyl}-4-methoxymethylpyrrolidin-2-yl]-1H-imidazol-5-yl}-1,11-dihydroisochromeno[4', 3':6,7]naphtho[1,2-d] imidazol-2-yl)-2-azabicyclo[3.1.0]hex-3-yl]-2-oxo-1-phenylethyl}carbamate (1R,3S,5R)-tert-butyl-3-(9-(2-((S)-1-((S)-2-(methoxycarbonylamino)-3-methylbutanoyl)-4-methoxymethylpyrrolidin-2-yl)-1H-imidazol-5-yl)-1,11-dihydroisochromeno[4',3':6,71 naphtho 1,2-d]imidiazol-2-yl)-2-azabicyclo[3.1.0]hexane-2-carboxylate To a solution of (1R,3S,5R)-tert-butyl-3-(9-(4,4,5,5-tetramethyl-1,3,2-dioxaborolan-2-yl)-1,11-dihydroisochromeno[4',3':6,7]naphtho[1,2-d]imidazol-2-yl)-2-azabicyclo[3.1.0]hexane-2-carboxylate (213 mg, 0.37 mmol), methyl(S)-1-((2S,4S)-2-(5-bromo-1H-imidazol-2-yl)-4-(methoxymethyl)pyrrolidin-1-yl)-3-methyl-1-oxobutan-2-ylcarbamate (142 mg, 0.31 mmol), tetrakis(triphenylphosphine) palladium(0) (35 mg, 0.03 mmol) and dichloro[1,1'-bis(diphenylphosphino) ferrocene]palladium(11) (22 mg, 0.03 mmol) in a mixture of 1,4-dioxane (3.0 mL) and dimethylsulfoxide (3.0 mL) was added a solution of potassium carbonate (2M in water, 0.46 mL, 0.9 mmol). The resulting mixture was degassed and then heated to 95° C. under argon for 7 hours. After cooling to room temperature, the reaction was diluted with ethyl acetate. The organics were washed with water and brine, dried (Na$_2$SO$_4$), and concentrated. The crude residue was purified by flash chromatography to (1R,3S,5R)-tert-butyl 3-(9-(2-((S)-1-((S)-2-(methoxycarbonyl amino)-3-methylbutanoyl)-4-methoxymethylpyrrolidin-2-yl)-1H-imidazol-5-yl)-1,11-dihydroisochromeno[4',3':6,7] naphtho[1,2-d]imidazol-2-yl)-2-azabicyclo[3.1.0]hexane-2-carboxylate (101 mg, 42%).

methyl {(1R)-2-[(1R,3S,5R)-2-(9-{2-[(2S,5S)-1-{(2S)-2-[(methoxycarbonyl)amino]-3-methylbutanoyl}-4-methoxymethylpyrrolidin-2-yl]-1H-imidazol-5-yl}-1,11-dihydroisochromeno[4',3':6,7]naphtho[1,2-d]imidazol-2-yl)-azabicyclo[3.1.0]hex-3-yl]-2-oxo-1-phenylethyl}carbamate A solution (1R,3S,5R)-tert-butyl 3-(9-(2-((S)-1-((S)-2-(methoxycarbonylamino)-3-methylbutanoyl)-4-methoxymethylpyrrolidin-2-yl)-1H-imidazol-5-yl)-1,11-dihydroisochromeno[4',3':6,7]naphtho[1,2-d]imidazol-2-yl)-2-azabicyclo[3.1.0]hexane-2-carboxylate (101 mg, 0.16 mmol), ethanol (3 mL) and concentrated HCl (1 mL) was heated to 60° C. for 1 hour. The reaction was concentrated and the crude material dissolved in DCM (3 mL). This solution was concentrated and to this material was added a solution of (R)-2-(methoxycarbonylamino)-2-phenylacetic acid (35 mg, 0.17 mmol) and COMU (63 mg, 015 mmol) in DMF (3 mL). To the resulting solution was added diisopropylethylamine (70 μL, 0.38 mmol). After stirring for 2 hours at room temperature, the reaction was diluted with ethyl acetate, washed with water and brine, dried (Na$_2$SO$_4$), concentrated and purified by preparative reverse phase HPLC (Gemini, 15 to 44% ACN/H$_2$O+ 0.1% TFA). The product fractions were lyophilized to give methyl {(1R)-2-[(1R,3S,5R)-2-(9-{2-[(2S,5S)-1-{(2S)-2-[(methoxycarbonyl)amino]-3-methylbutanoyl}-4-methoxymethylpyrrolidin-2-yl]-1H-imidazol-5 yl}-1,11-dihydroisochromeno[4',3':6,7]naphtho[1,2-d]imidazol-2-yl)-2-azabicyclo[3.1.0]hex-3-yl]-2-oxo-1-phenylethyl}carbamate (71 mg, 63%).

MS (ESI) m/z 882 [M+H]$^+$.

$^1$H NMR (400 MHz, dmso) δ 8.66 (s, 1H), 8.17 (d, 1H, J=8.8 Hz), 8.04 (s, 1H), 7.87-7.59 (m, 6H), 7.39-7.22 (m, 6H), 5.72 (d, 1H, J=7.6 Hz), 5.68 (s, 1H), 5.25 (s, 1H), 5.13-5.01 (m, 2H), 4.12-4.00 (m, 2H), 3.81-3.00 (m, 13H), 2.60 (m, 1H), 2.43-2.37 (m, 3H), 1.92-1.82 (m, 3H), 0.83-0.58 (m, 7H), 0.59 (s, 1H), 0.00 (s, 1H).

Example MW

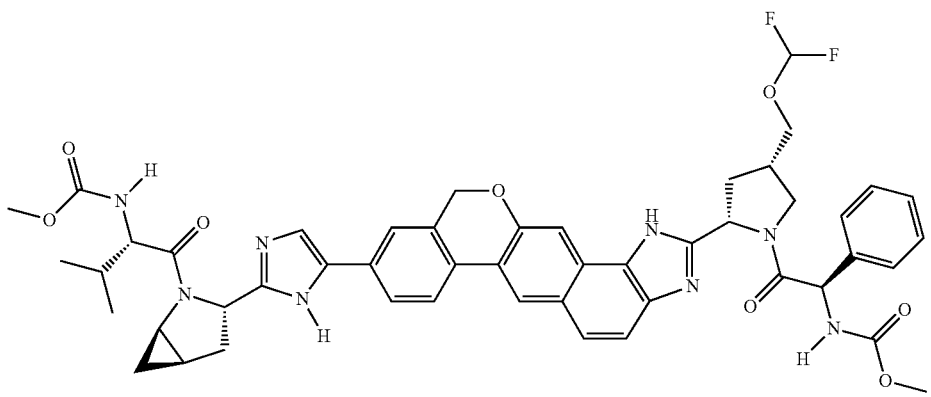

methyl {(1R)-2-[(2S,4S)-2-(9-{2-[(1R,3S,5R)-1-
{(2S)-2-[(methoxycarbonyl)amino]-3-methylbu-
tanoyl}-5-azabicyclo[3.1.0]hex-3-yl]-1H-imidazol-5-
yl}-1,11-dihydroisochromeno[4',3':6,7]naphtho[1,2-
d]imidazol-2-yl)-4-(difluoromethoxy)
methylpyrrolidin-1-yl]-2-oxo-1-
phenylethyl}carbamate This compound was synthesized using the same conditions as example OO substituting with the respective (1R,3S,5R)-2-((S)-2-(methoxycarbonylamino)-3-methylbutanoyl)-2-azabicyclo[3.1.0]hexane-3-carboxylic acid and (2S,4S)-1-(tert-butoxycarbonyl)-4-((difluoromethoxy)methyl)pyrrolidine-2-carboxylic acid as appropriate.
MS (ESI) m/z 918 [M+H]$^+$.

Example MX

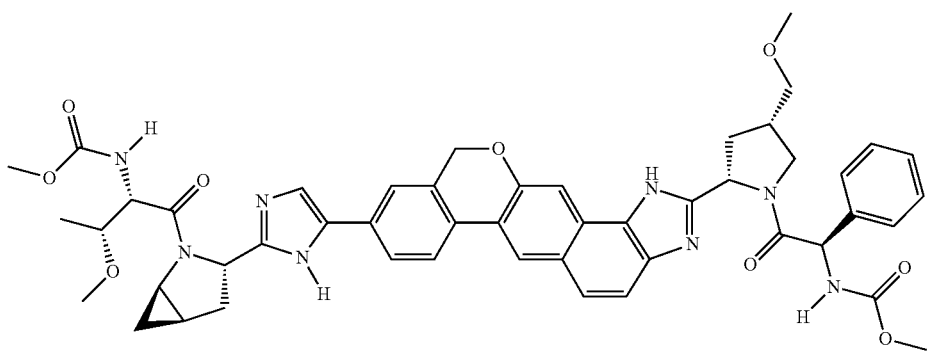

methyl {(1R)-2-[(2S,4S)-2-(9-{2-[(1R,3S,5R)-1-
{(2S,3S)-3-methoxy-2-[(methoxycarbonyl)amino]
butanoyl}-5-azabicyclo[3.1.0]hex-3-yl]-1H-imida-
zol-5-yl}-1,11-dihydroisochromeno[4',3':6,7]naph-
tho[1,2-d]imidazol-2-yl)-4-(difluoromethoxy)
methylpyrrolidin-1-yl]-2-oxo-1-
phenylethyl}carbamate This compound was synthesized using the same conditions as example OO substituting with the respective (1R,3S,5R)-2-((2S,3S)-3-methoxy-2 (methoxycarbonylamino)butanoyl)-2-azabicyclo[3.1.0]hexane-3-carboxylic acid and (2S,3R)-3-methoxy-2-(methoxycarbonylamino)butanoic acid as appropriate.
MS (ESI) m/z 898 [M+H]$^+$.

Example MY
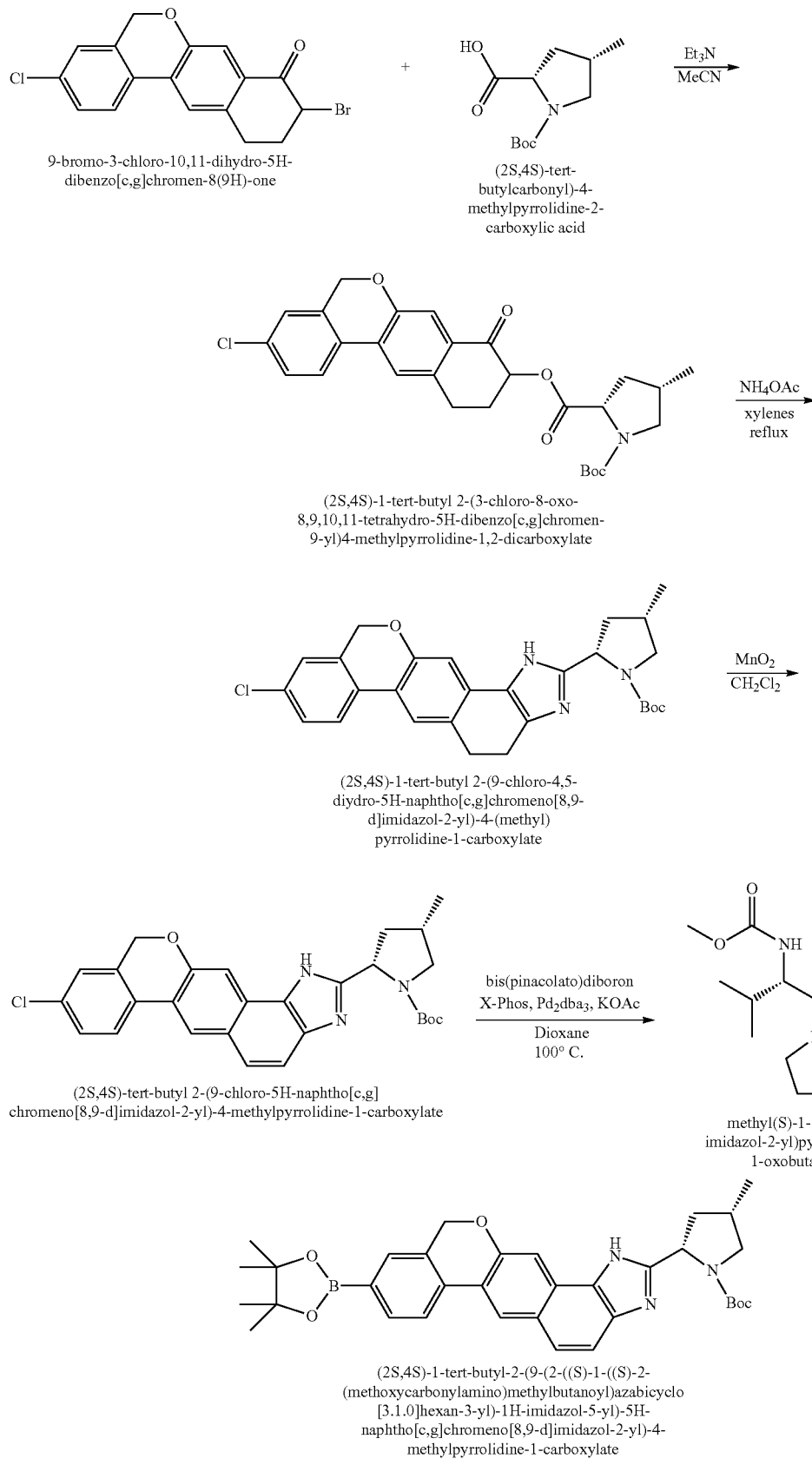

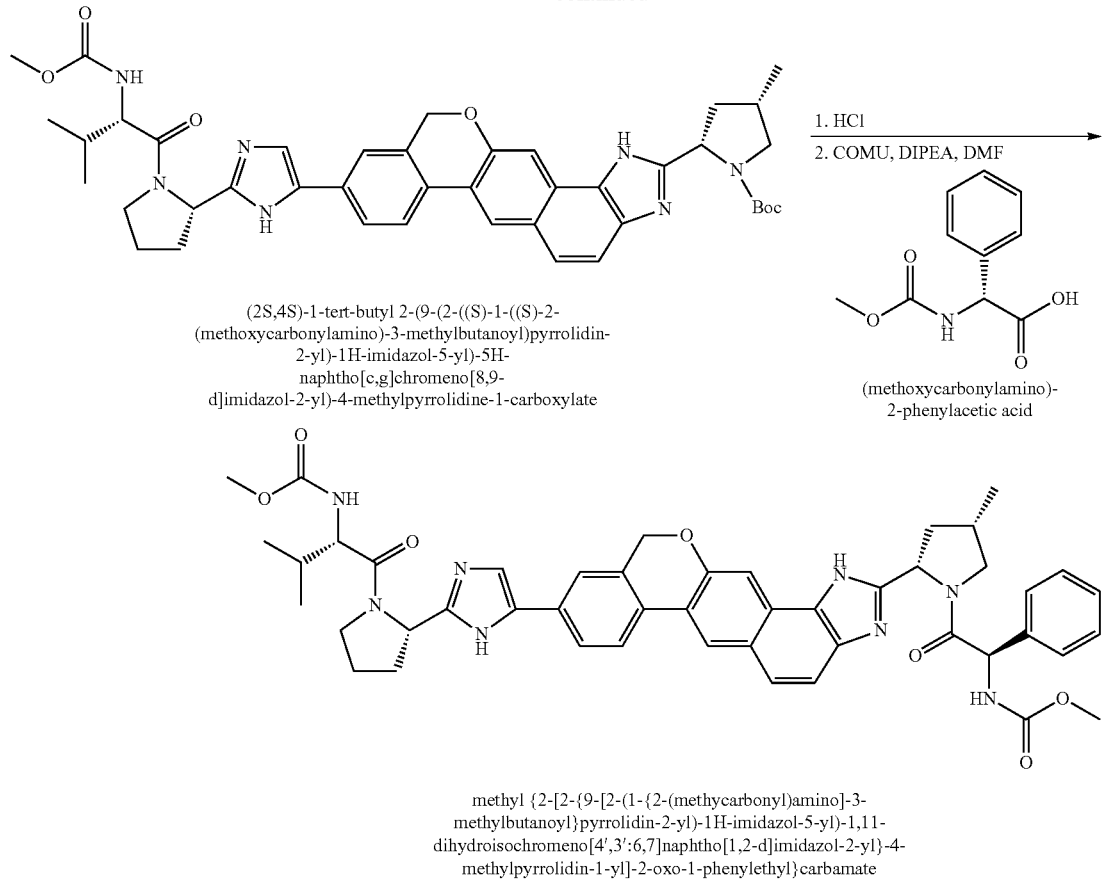

(2S,4S)-1-tert-butyl 2-(9-(2-((S)-1-((S)-2-(methoxycarbonylamino)-3-methylbutanoyl)pyrrolidin-2-yl)-1H-imidazol-5-yl)-5H-naphtho[c,g]chromeno[8,9-d]imidazol-2-yl)-4-methylpyrrolidine-1-carboxylate (methoxycarbonylamino)-2-phenylacetic acid methyl {2-[2-{9-[2-(1-{2-(methycarbonyl)amino]-3-methylbutanoyl}pyrrolidin-2-yl)-1H-imidazol-5-yl)-1,11-dihydroisochromeno[4',3':6,7]naphtho[1,2-d]imidazol-2-yl}-4-methylpyrrolidin-1-yl]-2-oxo-1-phenylethyl}carbamate

(2S,4S)-1-tert-butyl 2-(3-chloro-8-oxo-8,9,10,11-tetrahydro-5H-dibenzo[c,g]chromen-9-yl) 4-methylpyrrolidine-1,2-dicarboxylate To a solution of 9-bromo-3-chloro-10,11-dihydro-5H-dibenzo[c,g]chromen-8(9H)-one (1.32 g, 3.63 mmol) in MeCN (40 mL) was added (2S,4S)-1-(tert-butoxycarbonyl)-4-methylpyrrolidine-2-carboxylic acid (1.0 g, 4.36 mmol) and DIPEA (0.7 mL, 3.99 mmol). After stirring for 18 h, the solution was diluted with EtOAc and washed successively with saturated aqueous NaHCO$_3$ and brine. The organics were dried over MgSO$_4$, filtered and concentrated under reduced pressure. The crude residue was purified by silica column chromatography (10% to 40% EtOAc/hexanes) to afford (2S,4S)-1-tert-butyl 2-(3-chloro-8-oxo-8,9,10,11-tetrahydro-5H-dibenzo[c,g]chromen-9-yl) 4-methylpyrrolidine-1,2-dicarboxylate (1.31 g, 70%).

(2S,4S)-tert-butyl 2-(9-chloro-4,5-dihydro-5H-naphtho[c,g]chromeno[8,9-d]imidazol-2-yl)-4-methylpyrrolidine-1-carboxylate (2S,4S)-1-tert-butyl 2-(3-chloro-8-oxo-8,9,10,11-tetrahydro-5H-dibenzo[c,g]chromen-9-yl) 4-methylpyrrolidine-1,2-dicarboxylate (1.31 g, 2.56 mmol) was added xylenes (25 mL) and ammonium acetate (3.95 g, 51.2 mmol) and the solution was heated to 136° C. and stirred overnight. The following morning, the solution was cooled to rt and was diluted with EtOAc and washed successively with water, saturated aqueous NaHCO$_3$ and brine. The organics were dried over MgSO$_4$, filtered and concentrated under reduced pressure. The crude residue was purified by silica column chromatography (60% to 100% EtOAc/hexanes) to afford (2S,4S)-tert-butyl 2-(9-chloro-4,5-dihydro-5H-naphtho[c,g]chromeno[8,9-d]imidazol-2-yl)-4-methylpyrrolidine-1-carboxylate (711 mg, 56%).

(2S,4S)-tert-butyl 2-(9-chloro-5H-naphtho[c,g]chromeno[8,9-d]imidazol-2-yl)-4-methylpyrrolidine-1-carboxylate To a solution of (2S,4S)-tert-butyl 2-(9-chloro-4,5-dihydro-5H-naphtho[c,g]chromeno[8,9-d]imidazol-2-yl)-4-(methyl)pyrrolidine-1-carboxylate (935 mg, 1.9 mmol) in CH$_2$Cl$_2$ (20 mL) was added MnO$_2$ (8.25 g, 95 mmol). The reaction mixture was stirred for 3 h, and then filtered over celite. The filter cake was washed with copious CH$_2$Cl$_2$ and MeOH, and the filtrate was concentrated under reduced pressure. The crude residue was purified by silica column chromatography (0% to 10% MeOH/EtOAc) to afford (2S,4S)-tert-butyl 2-(9-chloro-5H-naphtho[c,g]chromeno[8,9-d]imidazol-2-yl)-4-methylpyrrolidine-1-carboxylate (692 mg, 74%).

(2S,4S)-tert-butyl 4methyl-2-(9-(4,4,5,5-tetramethyl-1,3,2-dioxaborolan-2-yl)-1,11-dihydroisochromeno[4',3':6,7]naphtho[1,2-d]imidazol-2-yl)pyrrolidine-1-carboxylate (2S,4S)-tert-butyl 2-(9-chloro-5H-naphtho[c,g]chromeno[8,9-d]imidazol-2-yl)-4-methylpyrrolidine-1-carboxylate (692 mg, 1.41 mmol) in dioxane (15 mL) was added bis(pinacolato)diboron (1.07 g, 4.23 mmol), KOAc (415 mg, 4.23 mmol), X-Phos (52 mg, 0.11 mmol), and Pd$_2$dba$_3$ (26 mg, 0.03 mmol). The solution was degassed with N$_2$ for 10 min, then heated to 100° C. for 16 h. The solution was cooled to rt, diluted with EtOAc, washed with saturated aqueous NaHCO$_3$, brine, dried with MgSO$_4$, and concentrated. Purified by silica gel chromatography (0% to 30% MeOH/EtOAc) to afford (2S,4S)-tert-butyl 4-methyl-2-(9-(4,4,5,5-tetramethyl-1,3,2-dioxaborolan -2-yl)-1,11-dihydroisochromeno[4',3':6,7] naphtho[1,2-d]imidazol-2-yl)pyrrolidine-1-carboxylate (821 mg, quant).

(2S,4S)-tert-butyl 2-(9-(2-((S)-1-((S)-2-(methoxycarbonylamino)-3-methylbutanoyl)pyrrolidin-2-yl)-1H-imidazol-5-yl)-5H-naphtho[c,g]chromeno[8,9-d]imidazol-2-yl)-4(methyl)pyrrolidine-1-carboxylate (821 mg, quant).

To a solution of (2S,4S)-tert-butyl 4-methyl-2-(9-(4,4,5,5-tetramethyl-1,3,2-dioxaborolan-2-yl)-1,11-dihydroisochromeno [4', 3':6,7] naphtho[1,2-d]imidazol-2-yl)pyrrolidine-1-carboxylate (821 mg, 1.41 mmol), methyl(S)-1-((S)-2-(5-bromo-1H-imidazol-2-yl)pyrrolidin-1-yl)-3-methyl-1-oxobutan-2-ylcarbamate (1.05 g, 2.82 mmol), tetrakis(triphenylphosphine) palladium(0) (162 mg, 0.14 mmol) and dichloro[1,1'-bis(diphenylphosphino)ferrocene]palladium (II) (102 mg, 0.14 mmol) in DME (15 mL) was added a solution of potassium carbonate (2M in water, 2.32 mL, 4.65 mmol). The resulting mixture was degassed and then heated to 85° C. for 18 hours. After cooling to room temperature, the reaction was diluted with ethyl acetate. The organics were washed with saturated sodium bicarbonate and brine, dried over MgSO$_4$ and concentrated. The crude residue was purified by flash chromatography to yield (2S,4S)-tert-butyl 2-(9-(2-((S)-1-((S)-2-(methoxycarbonylamino)-3-methylbutanoyl)pyrrolidin-2-yl)-1H-imidazol-5-yl)-5H-naphtho[c,g]chromeno[8,9-d]imidazol-2-yl)-4methylpyrrolidine-1-carboxylate (386 mg, 37%).

Methyl {2-[2-{9-[2-(1-{2-[(methoxycarbonyl)amino]-3-methylbutanoyl}pyrrolidin-2-yl)-1H-imidazol-5-yl]-1,11-dihydroisochromeno[4',3':6,7]naphtho[1,2-d]imidazol-2-yl}-4-(methyl)pyrrolidin-1-yl]-2-oxo-1-phenylethyl}carbamate A solution of (2S,4S)-tert-butyl 2-(9-(2-((S)-1-((S)-2-(methoxycarbonylamino)-3-methylbutanoyl)pyrrolidin-2-yl)-1H-imidazol-5-yl)-5H-naphtho[c,g]chromeno[8,9-d]imidazol-2-yl)-4methylpyrrolidine-1-carboxylate (386 mg, 0.52 mmol), CH$_2$Cl$_2$ (8 mL), MeOH (2 mL) and HCl (4M in Dioxane, 2 mL) and was stirred overnight. The reaction was concentrated and the crude material dissolved in DMF (8 mL). This solution was concentrated and to this material was added a solution of (R)-2-(methoxycarbonylamino)-2-phenylacetic acid (108 mg, 0.52 mmol) and COMU (248 mg, 0.52 mmol). To the resulting solution was added diisopropylethylamine (0.45 mL, 2.6 mmol). After stirring for 2 hours at room temperature, the reaction was diluted with 10% MeOH/EtOAc, washed with saturated NaHCO$_3$, water and brine, dried (Na$_2$SO$_4$), concentrated and purified by HPLC to give methyl {2-[2-{9-[2-(1-{2-[(methoxycarbonyl)amino]-3-methylbutanoyl}pyrrolidin-2-yl)-1H-imidazol-5-yl]-1,11-dihydroisochromeno[4',3':6,7]naphtho[1,2-d]imidazol-2-yl}-4-methylpyrrolidin-1-yl]-2-oxo-1-phenylethyl}carbamate (27 mg, 6%). LCMS-ESI$^+$: calculated for C$_{47}$H$_{50}$N$_8$O$_7$: 838.38; observed [M+1]$^+$: 840.12

Example NB

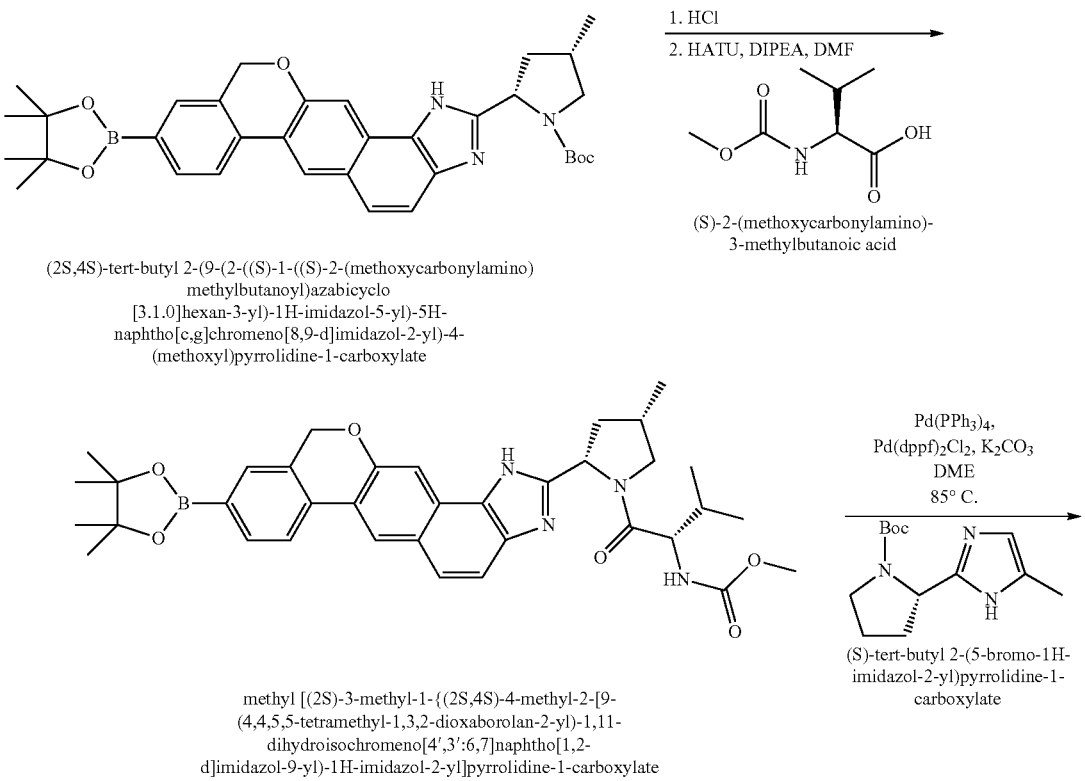

(2S,4S)-tert-butyl 2-(9-(2-((S)-1-((S)-2-(methoxycarbonylamino) methylbutanoyl)azabicyclo [3.1.0]hexan-3-yl)-1H-imidazol-5-yl)-5H-naphtho[c,g]chromeno[8,9-d]imidazol-2-yl)-4-(methoxyl)pyrrolidine-1-carboxylate (S)-2-(methoxycarbonylamino)-3-methylbutanoic acid methyl [(2S)-3-methyl-1-{(2S,4S)-4-methyl-2-[9-(4,4,5,5-tetramethyl-1,3,2-dioxaborolan-2-yl)-1,11-dihydroisochromeno[4',3':6,7]naphtho[1,2-d]imidazol-9-yl)-1H-imidazol-2-yl]pyrrolidine-1-carboxylate (S)-tert-butyl 2-(5-bromo-1H-imidazol-2-yl)pyrrolidine-1-carboxylate

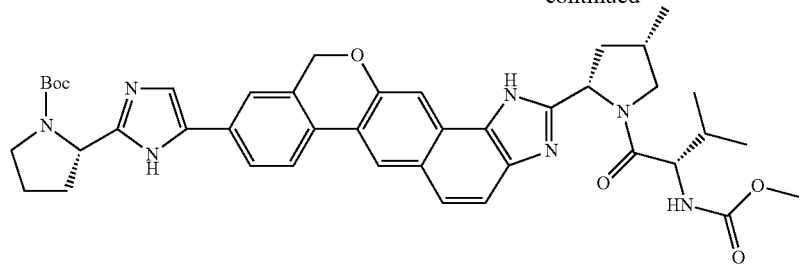

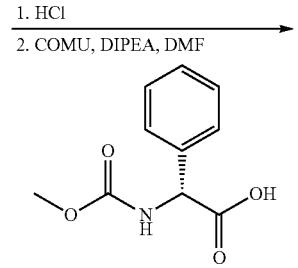

tert-butyl (2S)-2-[5-(2-{(2S,4S)-1-[N-(methoxycarbonyl)-L-valyl]-4-methylpyrrolidin-2-yl}-1,11-dihydroisochromeno[4',3':6,7]naphtho[1,2-d]imidazol-9-yl)-1H-imidazol-2-yl]pyrrolidine-1-carboxylate (R)-2-(methoxycarbonylamino)-2-phenylacetic acid

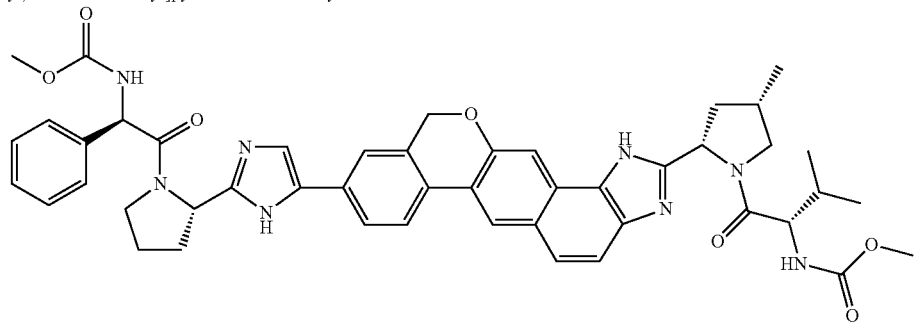

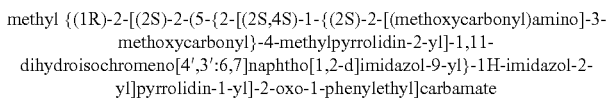

methyl {(1R)-2-[(2S)-2-(5-{2-[(2S,4S)-1-{(2S)-2-[(methoxycarbonyl)amino]-3-methoxycarbonyl}-4-methylpyrrolidin-2-yl]-1,11-dihydroisochromeno[4',3':6,7]naphtho[1,2-d]imidazol-9-yl}-1H-imidazol-2-yl]pyrrolidin-1-yl]-2-oxo-1-phenylethyl}carbamate Methyl [(2S)-3-methyl-1-{(2S,4S)-4-methyl-2-[9-(4,4,5,5-tetramethyl-1,3,2-dioxaborolan-2-yl)-1,11-dihydroisochromeno[4',3':6,7]naphtho[1,2-d]imidazol-2-yl]pyrrolidin-1-yl}-1-oxobutan-2-yl]carbamate (2S,4S)-tert-butyl 4-methyl-2-(9-(4,4,5,5-tetramethyl-1,3,2-dioxaborolan-2-yl)-1,11-dihydroisochromeno [4',3':6,7]naphto[1,2-d]imidazol-2-yl)pyrrolidine-1-carboxylate (950 mg, 1.63 mmol) was dissolved in DCM (12 mL), MeOH (3 mL) and HCl (4 M in dioxane, 3 mL) was added. The reaction mixture was stirred for 4 h and then concentrated under reduced pressure. The crude residue was treated with (S)-2-(methoxycarbonylamino)-3-methylbutanoic acid (285 mg, 1.63 mmol), HATU (620 mg, 1.63 mmol) and DMF (15 mL), then DIPEA (1.42 mL, 8.15 mmol) was added dropwise. After 1 h, the mixture was diluted with EtOAc and washed successively with saturated aqueous NaHCO$_3$ and brine. The organics were dried over MgSO$_4$, filtered and concentrated under reduced pressure. The crude residue was purified by silica column chromatography (0% to 30% MeOH/EtOAc) to afford methyl [(2S)-3-methyl-1-{(2S,4S)-4-methyl-2-[9-(4,4,5,5-tetramethyl-1,3,2-dioxaborolan-2-yl)-1,11-dihydroisochromeno[4',3':6,7]naphtho[1,2-d]imidazol-2-yl]pyrrolidin-1-yl}-1-oxobutan-2-yl]carbamate (596 mg, 57%).

Tert-butyl (2S)-2-[5-(2-{(2S,4S)-1-[N-(methoxycarbonyl)-L-valyl]-4-methylpyrrolidin-2-yl}-1,11-dihydroisochromeno[4',3':6,7]naphtho[1,2-d]imidazol-9-yl)-1H-imidazol-2-yl]pyrrolidine-1-carboxylate Methyl [(2S)-3-methyl-1-{(2S,4S)-4-methyl-2-[9-(4,4,5,5-tetramethyl-1,3,2-dioxaborolan-2-yl)-1,11-dihydroisochromeno[4',3':6,7]naphtho[1,2-d]imidazol-2-yl]pyrrolidin-1-yl}-1-oxobutan-2-yl]carbamate (298 mg, 0.47 mmol), (S)-tert-butyl 2-(5-bromo-1H-imidazol-2-yl)pyrrolidine-1-carboxylate (443 mg, 1.4 mmol), Pd(PPh$_3$)$_4$ (54 mg, 0.05 mmol), PdCl$_2$(dppf)$_2$ (36 mg, 0.05 mmol), and K$_2$CO$_3$ (2M in H$_2$O, 0.78 mL, 1.55 mmol) were combined in DME (5 mL). The mixture was degassed with bubbling N$_2$ for 10 min then heated to 85° C. for 16 h. After cooling, the reaction mixture was diluted with EtOAc, and washed successively with saturated aqueous NaHCO$_3$ and brine. The organics were dried over MgSO$_4$, filtered and concentrated under reduced pressure. The crude residue was purified by silica column chromatography (0% to 30% MeOH/EtOAc) to afford tert-butyl (2S)-2-[5-(2-{(2S,4S)-1-[N-(methoxycarbonyl)-L-valyl]-4-methylpyrrolidin-2-yl}-1,11-dihydroisochromeno[4',3':6,7]naphtho[1,2-d]imidazol-9-yl)-1H-imidazol-2-yl]pyrrolidine-1-carboxylate (84 mg, 24%).

Methyl {(1R)-2-[(2S)-2-(5-{2-[(2S,4S)-1-{(2S)-2-[(methoxycarbonyl)amino]-3-methylbutanoyl}-4-methylpyrrolidin-2-yl]-1,11-dihydroisochromeno[4',3':6,7]naphtho[1,2-d]imidazol-9-yl}-1H-imidazol-2-yl)pyrrolidin-1-yl]-2-oxo-1-phenylethyl}carbamate Tert-butyl (2S)-2-[5-(2-{(2S,4S)-1-[N-(methoxycarbonyl)-L-valyl]-4-methylpyrrolidin-2-yl}-1,11-dihydroisochromeno[4',3':6,7]naphtho[1,2-d]imidazol-9-yl)-1H-imidazol-2-yl]pyrrolidine-1-carboxylate (84 mg, 0.11 mmol) was dissolved in DCM (2.5 mL), MeOH (0.5 mL) and HCl (4 M in dioxane, 0.5 mL) was added. The reaction mixture was stirred for 18 h and then concentrated under reduced pressure.

The crude residue was treated with (R)-2-(methoxycarbonylamino)-2-phenylacetic acid (23 mg, 0.11 mmol), COMU (53 mg, 0.11 mmol) and DMF (3 mL), then DIPEA (0.10 mL, 0.56 mmol) was added dropwise. After 30 min, the mixture was diluted with 10% MeOH/EtOAc and washed successively with saturated aqueous NaHCO₃ and brine. The organics were dried over MgSO₄, filtered and concentrated under reduced pressure. The crude residue was purified by HPLC to afford methyl {(1R)-2-[(2S)-2-(5-{2-[(2S,4S)-1-{(2S)-2-[(methoxycarbonyl)amino]-3-methylbutanoyl}-4-methylpyrrolidin-2-yl]-1,11-dihydroisochromeno[4',3':6,7]naphtho[1,2-d]imidazol-9-yl}-1H-imidazol-2-yl)pyrrolidin-1-yl]-2-oxo-1-phenylethyl}carbamate (41 mg, 45%). LCMS-ESI⁺: calculated for C47H50N8O7: 838.38; observed [M+1]⁺: 839.39

Example NC yl)-1,11-dihydroisochromeno[4',3':6,7]naphtho[1,2-d]imidazol-2-yl]-4-methylpyrrolidine-1-carboxylate (164 mg, 0.23 mmol) was dissolved in DCM (2.57 mL), MeOH (0.7 mL) and HCl (4 M in dioxane, 0.7 mL) was added. The reaction mixture was stirred for 16 h and then concentrated under reduced pressure. The crude residue was treated with (S)-2-(methoxycarbonylamino)-3-methylbutanoic acid (30 mg, 0.17 mmol), HATU (65 mg, 0.17 mmol) and DMF (3 mL), then DIPEA (0.15 mL, 0.85 mmol) was added dropwise. After 45 min, the mixture was diluted with 10% MeOH/EtOAc and washed successively with saturated aqueous NaHCO₃ and brine. The organics were dried over MgSO₄, filtered and concentrated under reduced pressure. The crude residue was purified by HPLC to afford methyl {(2S)-1-[(2S,

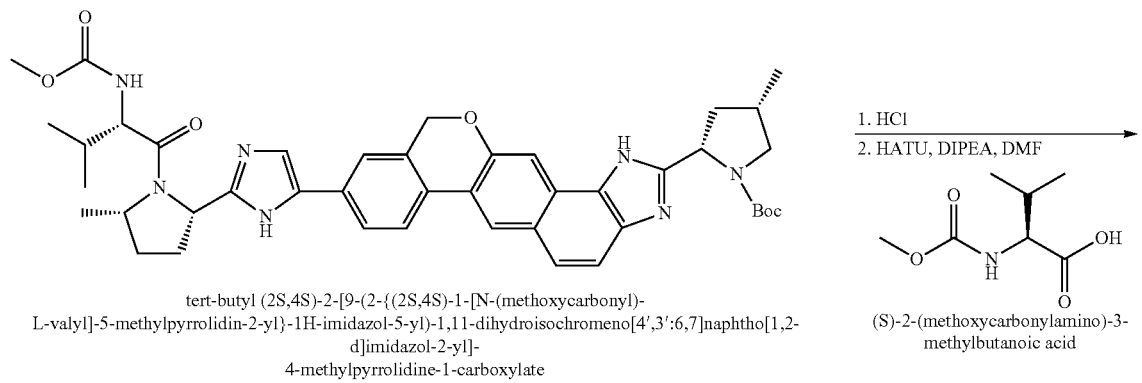

tert-butyl (2S,4S)-2-[9-(2-{(2S,4S)-1-[N-(methoxycarbonyl)-L-valyl]-5-methylpyrrolidin-2-yl}-1H-imidazol-5-yl)-1,11-dihydroisochromeno[4',3':6,7]naphtho[1,2-d]imidazol-2-yl]-4-methylpyrrolidine-1-carboxylate (S)-2-(methoxycarbonylamino)-3-methylbutanoic acid

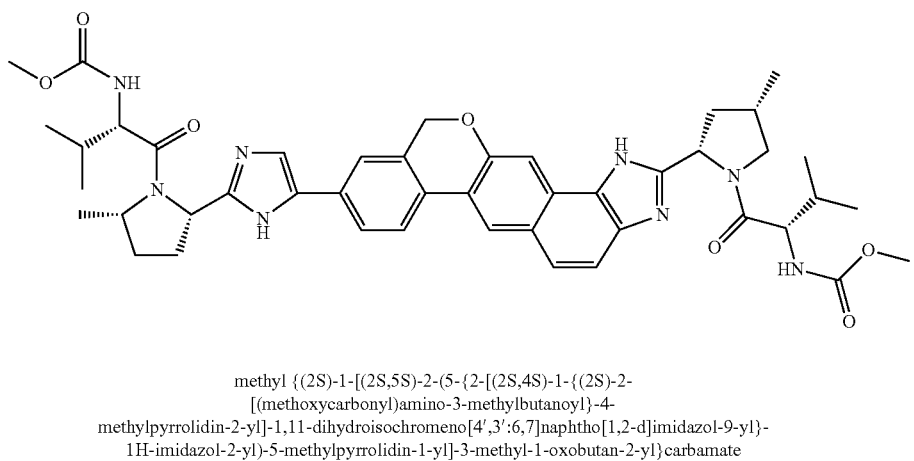

methyl {(2S)-1-[(2S,5S)-2-(5-{2-[(2S,4S)-1-{(2S)-2-[(methoxycarbonyl)amino-3-methylbutanoyl}-4-methylpyrrolidin-2-yl]-1,11-dihydroisochromeno[4',3':6,7]naphtho[1,2-d]imidazol-9-yl}-1H-imidazol-2-yl)-5-methylpyrrolidin-1-yl]-3-methyl-1-oxobutan-2-yl}carbamate Methyl {(2S)-1-[(2S,5S)-2-(5-{2-[(2S,4S)-1-{(2S)-2-[(methoxycarbonyl)amino]-3-methylbutanoyl}-4-methylpyrrolidin-2-yl]-1,11-dihydroisochromeno[4',3':6,7]naphtho[1,2-d]imidazol-9-yl}-1H-imidazol-2-yl)-5-methylpyrrolidin-1-yl]-3-methyl-1-oxobutan-2-yl}carbamate Tert-butyl (2S,4S)-2-[9-(2-{(2S,4S)-1-[N-(methoxycarbonyl)-L-valyl]-5-methylpyrrolidin-2-yl}-1H-imidazol-5-

5S)-2-(5-{2-[(2S,4S)-1-{(2S)-2-[(methoxycarbonyl)amino]-3-methylbutanoyl}-4-methylpyrrolidin-2-yl]-1,11-dihydroisochromeno[4',3':6,7]naphtho[1,2-d]imidazol-9-yl}-1H-imidazol-2-yl)-5-methylpyrrolidin-1-yl]-3-methyl-1-oxobutan-2-yl}carbamate (23 mg, 16%).

LCMS-ESI⁺: calculated for C45H54N8O7: 818.41; observed [M+1]⁺: 820.70.

Example ND

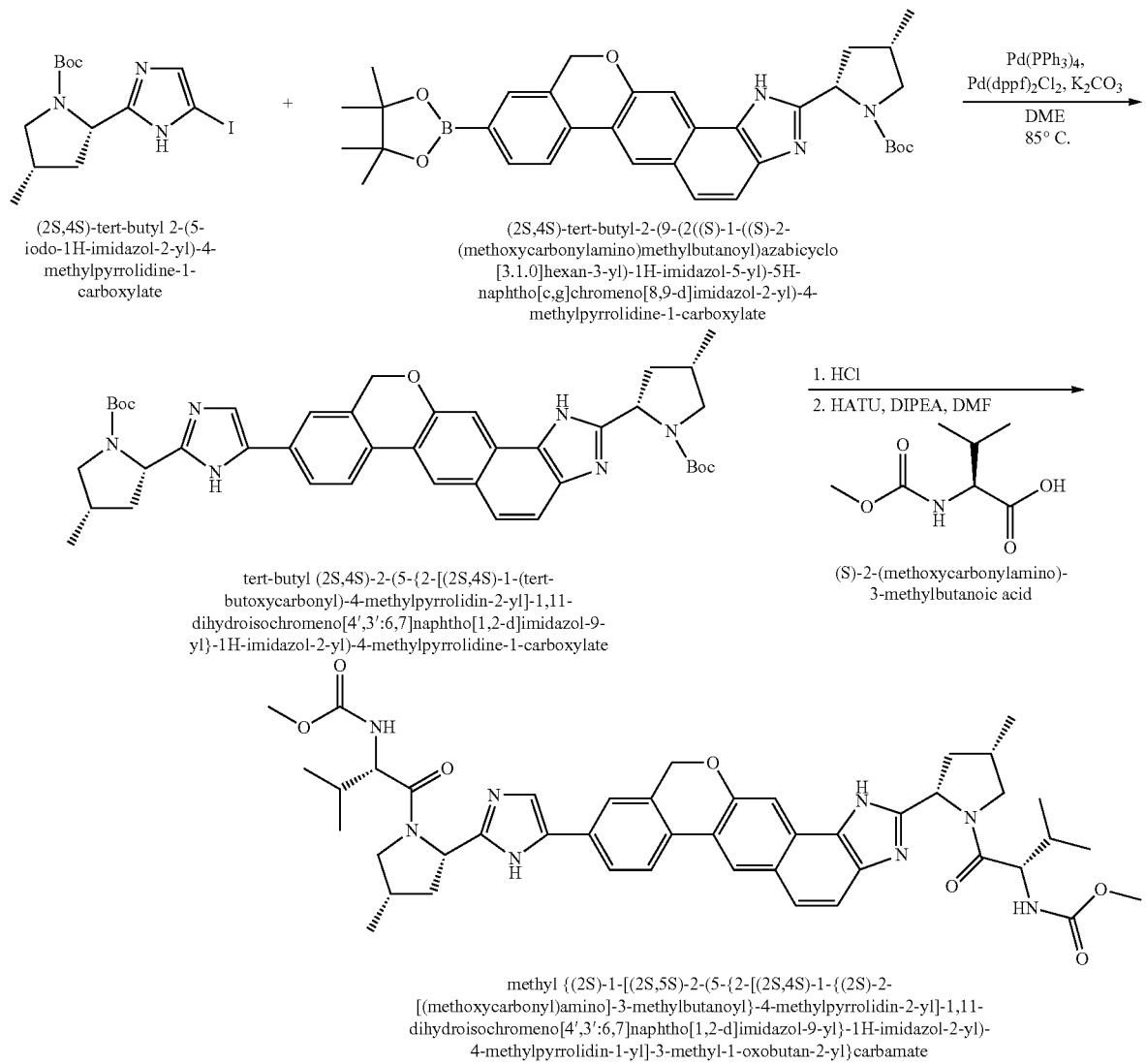

Tert-butyl (2S,4S)-2-(5-{2-[(2S,4S)-1-(tert-butoxycarbonyl)-4-methylpyrrolidin-2-yl]-1,11-9-yl}-1H-imidazol-2-yl)-4-methylpyrrolidine-1-carboxylate (2S,4S)-tert-butyl 4-methyl-2-(9-(4,4,5,5-tetramethyl-1,3,2-dioxaborolan-2-yl)-1,11-dihydroisochromeno [4',3':6,7]naphtho[1,2-d]imidazol-2-yl)pyrrolidine-1-carboxylate (293 mg, 0.78 mmol), (2S,4S)-tert-butyl 2-(5-iodo-1H-imidazol-2-yl)-4-methylpyrrolidine-1-carboxylate (300 mg, 0.52 mmol), Pd(PPh$_3$)$_4$ (60 mg, 0.052 mmol), PdCl$_2$(dppf)$_2$ (38 mg, 0.052 mmol), and K$_2$CO$_3$ (2M in H$_2$O, 0.86 mL, 1.72 mmol) were combined in DME (6 mL). The mixture was degassed with bubbling N$_2$ for 10 min then heated to 85° C. for 16 h. After cooling, the reaction mixture was diluted with EtOAc, and washed successively with saturated aqueous NaHCO$_3$ and brine. The organics were dried over MgSO$_4$, filtered and concentrated under reduced pressure. The crude residue was purified by silica column chromatography (100% EtOAc) to afford tert-butyl (2S,4S)-2-(5-{2-[(2S,4S)-1-(tert-butoxycarbonyl)-4-methylpyrrolidin-2-yl]-1,11-dihydroisochromeno[4',3':6,7]naphtho[1,2-d]imidazol-9-yl}-1H-imidazol-2-yl)-4-methylpyrrolidine-1-carboxylate (183 mg, 50%).

Methyl {(2S)-1-[(2S,5S)-2-(5-{2-[(2S,4S)-1-{(2S)-2-[(methoxycarbonyl)amino]-3-methylbutanoyl}-4-methylpyrrolidin-2-yl]-1,11-dihydroisochromeno[4',3':6,7]naphtho[1,2-d]imidazol-9-yl}-1H-imidazol-2-yl)-4-methylpyrrolidin-1-yl]-3-methyl-1-oxobutan-2-yl}carbamate Tert-butyl (2S,4S)-2-(5-{2-[(2S,4S)-1-(tert-butoxycarbonyl)-4-methylpyrrolidin-2-yl]-1,11-dihydroisochromeno[4',3':6,7]naphtho[1,2-d]imidazol-9-yl}-1H-imidazol-2-yl)-4-methylpyrrolidine-1-carboxylate (183 mg, 0.26 mmol) was dissolved in DCM (4 mL), MeOH (1 mL) and HCl (4 M in dioxane, 1 mL) was added. The reaction mixture was stirred for 2 h and then concentrated under reduced pressure. The crude residue was treated with (S)-2-(methoxycarbonylamino)-3-methylbutanoic acid (91 mg, 0.52 mmol), HATU (198 mg, 0.52 mmol) and DMF (5 mL), then DIPEA (0.45 mL, 2.6 mmol) was added dropwise. After 1 h, the mixture was diluted with 10% MeOH/EtOAc and washed successively with saturated aqueous NaHCO₃ and brine. The organics were dried over MgSO₄, filtered and concentrated under reduced pressure. The crude residue was purified by HPLC to afford methyl {(2S)-1-[(2S,5S)-2-(5-{2-[(2S,4S)-1-{(2S)-2-[(methoxycarbonyl)amino]-3-methylbutanoyl}-4-methylpyrrolidin-2-yl]-1,11-dihydroisochromeno[4',3':6,7]naphtho[1,2-d]imidazol-9-yl}-1H-imidazol-2-yl)-4-methylpyrrolidin-1-yl]-3-methyl-1-oxobutan-2-yl}carbamate (6 mg, 3%). LCMS-ESI⁺: calculated for $C_{45}H_{54}N_8O_7$: 818.41; observed [M+1]⁺: 819.41.

Example NF

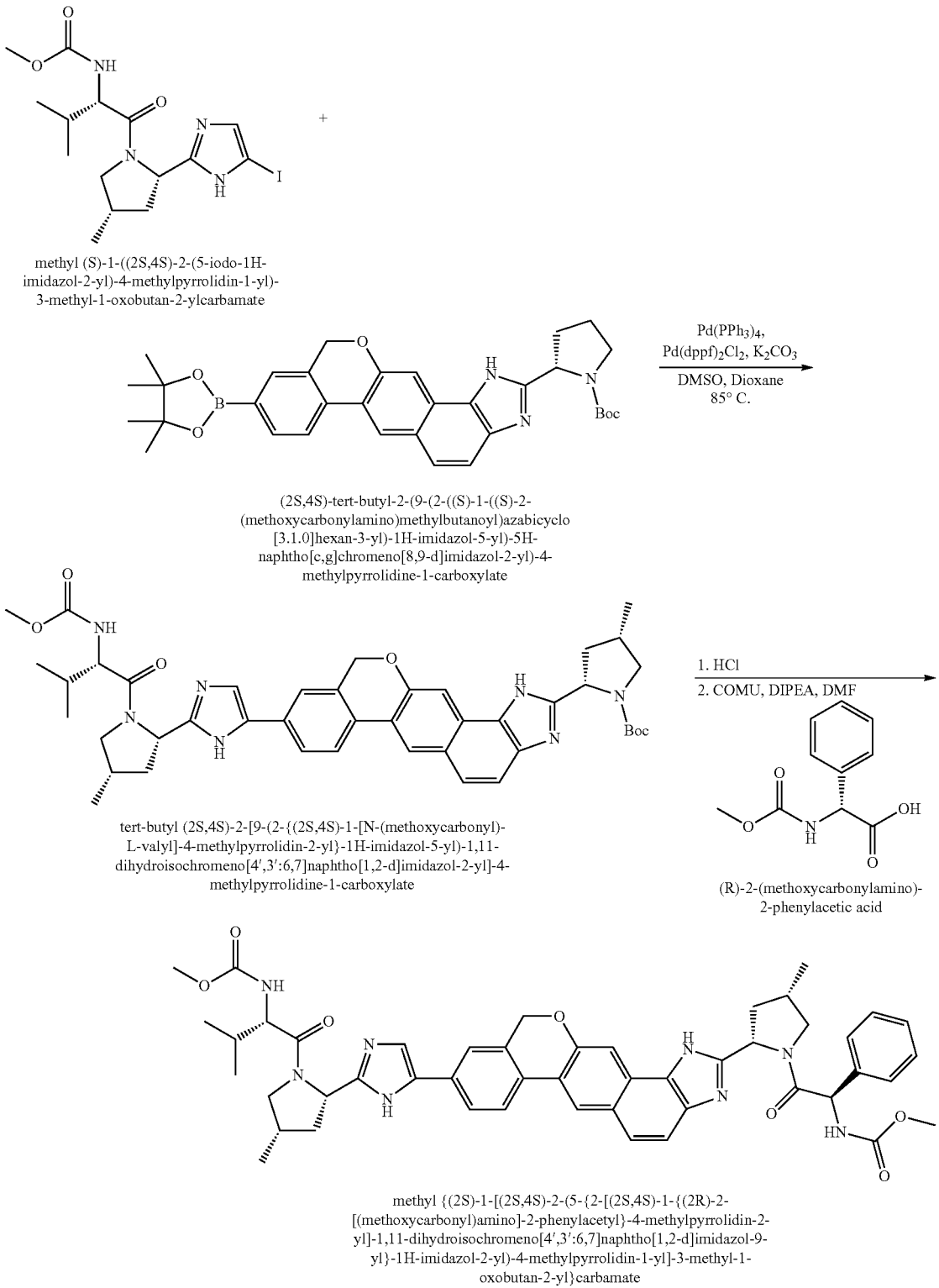

Tert-butyl (2S,4S)-2-[9-(2-{(2S,4S)-1-[N-(methoxy-carbonyl)-L-valyl]-4-methylpyrrolidin-2-yl}-1H-imidazol-5-yl)-1,11-dihydroisochromeno[4',3':6,7]naphtho[1,2-d]imidazol-2-yl]-4-methylpyrrolidine-1-carboxylate (2S,4S)-tert-butyl 4-methyl-2-(9-(4,4,5,5-tetramethyl-1,3,2-dioxaborolan-2-yl)-1,11-dihydroisochromeno [4', 3':6,7] naptho[1,2-d]imidazol-2-yl)pyrrolidine-1-carboxylate (558 mg, 0.96 mmol), methyl(S)-1-((2S,4S)-2-(5-iodo-1H-imidazol-2-yl)-4-methylpyrrolidin-1-yl)-3-methyl-1-oxobutan-2-ylcarbamate (501 mg, 1.15 mmol), Pd(PPh$_3$)$_4$ (111 mg, 0.096 mmol), PdCl$_2$(dppf)$_2$ (70 mg, 0.096 mmol), and K$_2$CO$_3$ (2M in H$_2$O, 1.6 mL, 3.17 mmoL) were combined in DMSO (6 mL) and dioxane (6 mL). The mixture was degassed with bubbling N$_2$ for 10 min then heated to 95° C. for 14 h. After cooling, the reaction mixture was diluted with EtOAc, and washed successively with saturated aqueous NaHCO$_3$ and brine. The organics were dried over MgSO$_4$, filtered and concentrated under reduced pressure. The crude residue was purified by silica column chromatography (0%-30% MeOH/EtOAc) to afford tert-butyl (2S,4S)-2-[9-(2-{(2S,4S)-1-[N-(methoxycarbonyl)-L-valyl]-4-methylpyrrolidin-2-yl}-1H-imidazol-5-yl)-1,11-dihydroisochromeno[4',3':6,7]naphtho[1,2-d]imidazol-2-yl]-4-methylpyrrolidine-1-carboxylate (257 mg, 35%).

Methyl {(2S)-1-[(2S,4S)-2-(5-{2-[(2S,4S)-1-{(2R)-2-[(methoxycarbonyl)amino]-2-phenylacetyl}-4-methylpyrrolidin-2-yl]-1,11-dihydroisochromeno[4',3':6,7]naphtho[1,2-d]imidazol-9-yl}-1H-imidazol-2-yl)-4-methylpyrrolidin-1-yl]-3-methyl-1-oxobutan-2-yl}carbamate Tert-butyl (2S,4S)-2-[9-(2-{(2S,4S)-1-[N-(methoxycarbonyl)-L-valyl]-4-methylpyrrolidin-2-yl}-1H-imidazol-5-yl)-1,11-dihydroisochromeno[4',3':6,7]naphtho[1,2-d]imidazol-2-yl]-4-methylpyrrolidine-1-carboxylate (257 mg, 0.34 mmol) was dissolved in DCM (4 mL), MeOH (1 mL) and HCl (4 M in dioxane, 1 mL) was added. The reaction mixture was stirred for 3 h and then concentrated under reduced pressure. The crude residue was treated with (R)-2-(methoxycarbonylamino)-2-phenylacetic acid (71 mg, 0.34 mmol), COMU (161 mg, 0.34 mmol) and DMF (6 mL), then DIPEA (0.3 mL, 1.67 mmol) was added dropwise. After 15 h, the mixture was diluted with 10% MeOH/EtOAc and washed successively with saturated aqueous NaHCO$_3$ and brine. The organics were dried over MgSO$_4$, filtered and concentrated under reduced pressure. The crude residue was purified by HPLC to afford methyl {(2S)-1-[(2S,4S)-2-(5-{2-[(2S,4S)-1-{(2R)-2-[(methoxycarbonyl)amino]-2-phenyl acetyl}-4-methylpyrrolidin-2-yl]-1,11-dihydroisochromeno[4',3':6,7]naphtho[1,2-d]imidazol-9-yl}-1H-imidazol-2-yl)-4-methylpyrrolidin-1-yl]-3-methyl-1-oxobutan-2-yl}carbamate (152 mg, 53%). LCMS-ESI$^+$: calculated for C48H52N8O7: 852.40; observed [M+1]$^+$: 854.26. $^1$H NMR (CD$_3$OD): 8.677 (s, 1H), 8.232-7.837 (m, 5H), 7.695-7.673 (m, 2H), 7.496-7.426 (m, 5H), 5.499 (s, 1H), 5.445-5.401 (m, 1H), 5.337 (s, 1H), 5.253-5.208 (q, 1H, J=7.2 Hz), 4.870 (m, 1H), 4.230 (d, 1H, J=7.2 Hz), 3.781 (m, 1H), 3.671 (s, 3H), 3.607 (s, 3H), 3.425 (m, 3H), 2.750-2.689 (m, 2H), 2.683 (m, 2H), 2.384 (m, 1H), 1.894 (quint, 2H, J=12 Hz), 1.249-1.151 (m, 6H), 0.974-0.890 (m, 6H).

Example NG

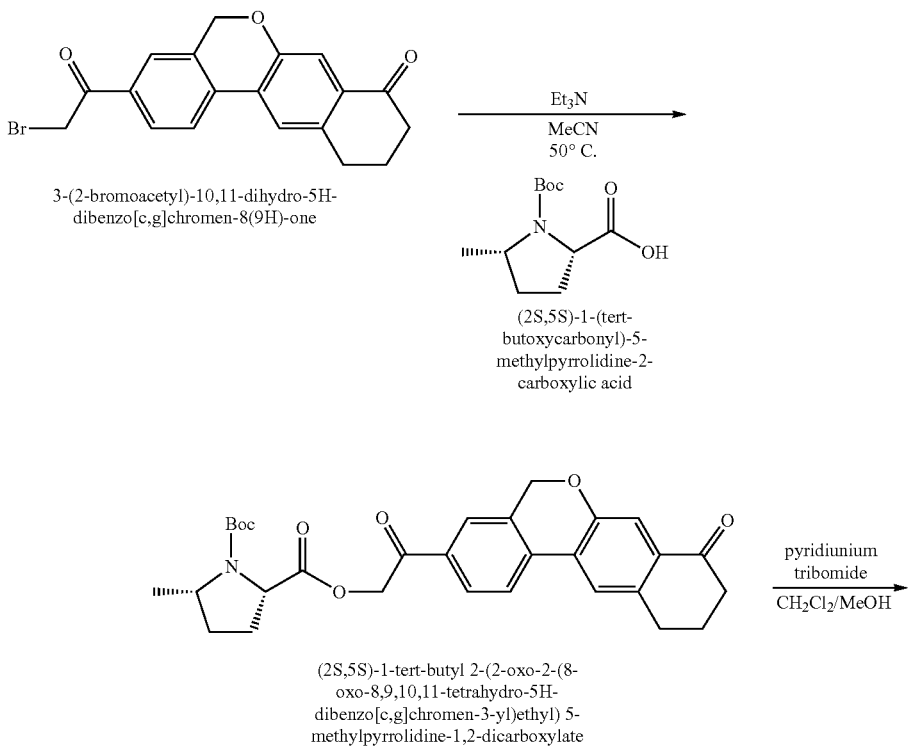

3-(2-bromoacetyl)-10,11-dihydro-5H-dibenzo[c,g]chromen-8(9H)-one (2S,5S)-1-(tert-butoxycarbonyl)-5-methylpyrrolidine-2-carboxylic acid (2S,5S)-1-tert-butyl 2-(2-oxo-2-(8-oxo-8,9,10,11-tetrahydro-5H-dibenzo[c,g]chromen-3-yl)ethyl) 5-methylpyrrolidine-1,2-dicarboxylate -continued

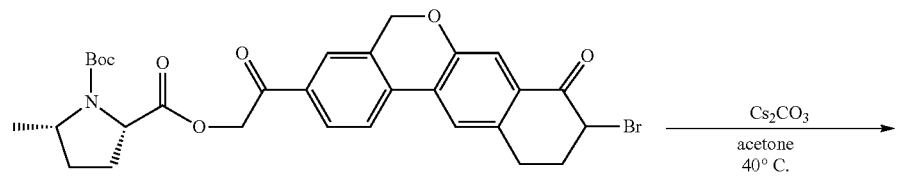

(2S,5S)-2-(2-(9-bromo-8-oxo-8,9,10,11-tetrahydro-5H-dibenzo[c,g]chromen-3-yl)ethyl)-2-oxoethyl) 1-tert-butyl 5-methylpyrrolidine-1,2-dicarboxylate Cs$_2$CO$_3$
acetone
40° C.

(2S,5S)-1-(tert-butoxycarbonyl)-5-methylpyrrolidine-2-carboxylic acid

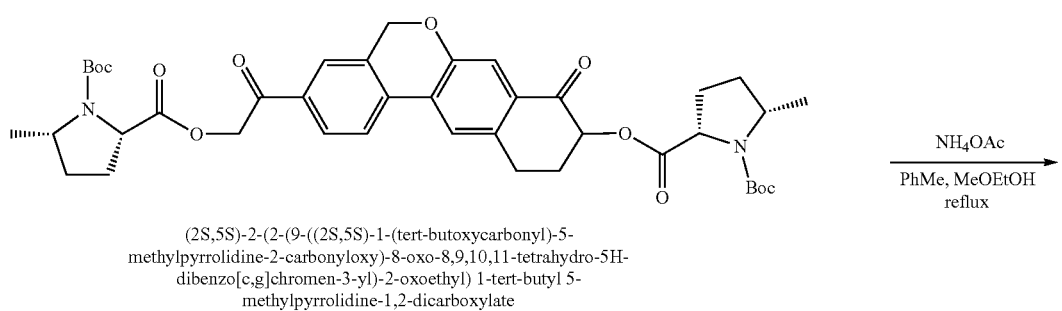

(2S,5S)-2-(2-(9-((2S,5S)-1-(tert-butoxycarbonyl)-5-methylpyrrolidine-2-carbonyloxy)-8-oxo-8,9,10,11-tetrahydro-5H-dibenzo[c,g]chromen-3-yl)-2-oxoethyl) 1-tert-butyl 5-methylpyrrolidine-1,2-dicarboxylate NH$_4$OAc
PhMe, MeOEtOH
reflux

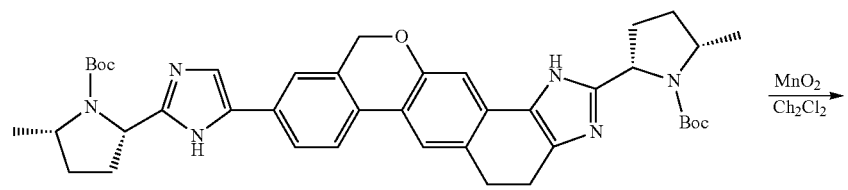

tert-butyl (2S,5S)-2-(9-{2-[(2S,5S)-1-(tert-butoxycarbonyl)-5-methylpyrrolidin-2-yl]-1H-imidazol-5-yl}-1,4,5,11-tetrahydroisochromeno[4',3':6,7]naphtho[1,2-d]imidazol-2-yl}-5-methylpyrrolidine-1-carboxylate MnO$_2$
Ch$_2$Cl$_2$

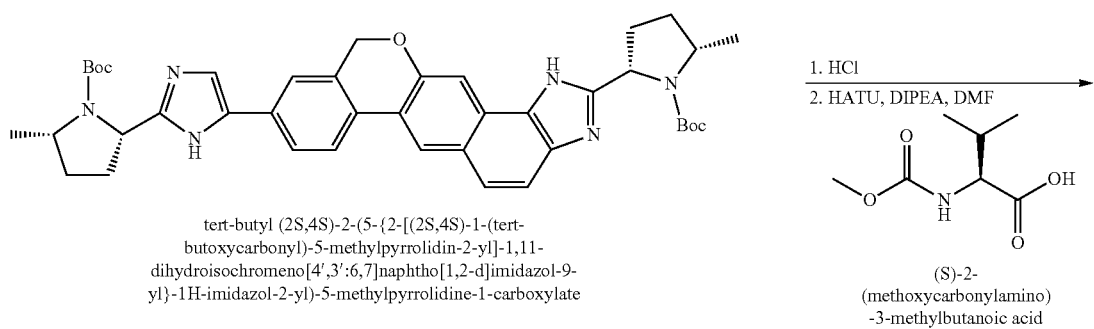

tert-butyl (2S,4S)-2-(5-{2-[(2S,4S)-1-(tert-butoxycarbonyl)-5-methylpyrrolidin-2-yl]-1,11-dihydroisochromeno[4',3':6,7]naphtho[1,2-d]imidazol-9-yl}-1H-imidazol-2-yl)-5-methylpyrrolidine-1-carboxylate 1. HCl
2. HATU, DIPEA, DMF (S)-2-(methoxycarbonylamino)-3-methylbutanoic acid

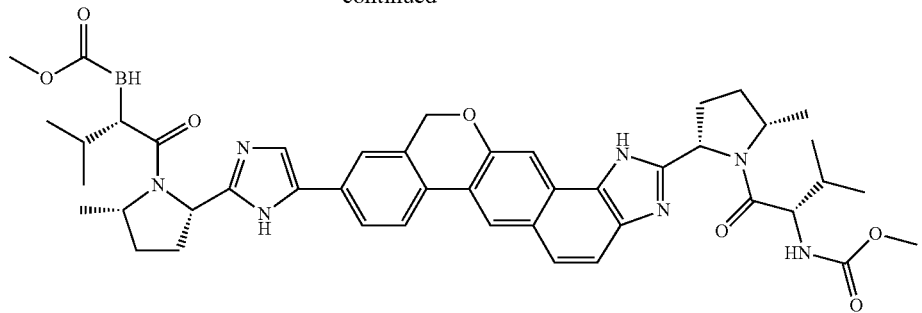

methyl {(2S)-1-[(2S,5S)-2-(5-{2-[(2S,4S)-1-{(2S)-2-
[(methoxycarbonyl)amino-3-methylbutanoyl}-5-methylpyrroldin-
2-yl]1,11-dihydroisochromeno[4',3':6,7]naphtho[1,2-d]imidazol-
9-yl}-1H-imidazol-2-yl)-5-methylpyrrolidin-1-yl]-3-methyl-1-
oxobutan-2-yl}carbamate (2S,5S)-1-tert-butyl 2-(2-oxo-2-(8-oxo-8,9,10,11-tetrahydro-5H-dibenzo[c,g]chromen-3-yl)ethyl) 5-methylpyrrolidine-1,2-dicarboxylate To a solution of 3-(2-bromoacetyl)-10,11-dihydro-5H-dibenzo[c,g]chromen-8(9H)-one in MeCN (30 mL) was added (2S,5S)-1-(tert-butoxycarbonyl)-5-methylpyrrolidine-2-carboxylic acid (1.2 g, 3.23 mmol) and triethyl amine (0.48 mL, 3.55 mmol) and the solution was heated to 50° C. After stirring for 15 h, the solution was cooled to rt, and diluted with EtOAc and washed successively with saturated aqueous NaHCO₃ and brine. The organics were dried over MgSO₄, filtered and concentrated under reduced pressure. The crude residue was purified by silica column chromatography (20% to 50% EtOAc/hexanes) to afford (2S,5S)-1-tert-butyl 2-(2-oxo-2-(8-oxo-8,9,10,11-tetrahydro-5H-dibenzo[c,g]chromen-3-yl)ethyl) 5-methylpyrrolidine-1,2-dicarboxylate (1.09 g, 65%).

(2S,5S)-2-(2-(9-bromo-8-oxo-8,9,10,11-tetrahydro-5H-dibenzo[c,g]chromen-3-yl)-2-oxoethyl) 1-tert-butyl 5-methylpyrrolidine-1,2-dicarboxylate (2S,5S)-1-tert-butyl 2-(2-oxo-2-(8-oxo-8,9,10,11-tetrahydro-5H-dibenzo[c,g]chromen-3-yl)ethyl) 5-methylpyrrolidine-1,2-dicarboxylate (1.29 g, 2.48 mmol) was dissolved in a solution of DCM (17.5 mL) and MeOH (7 mL), then treated with pyridinium tribromide (873 mg, 2.73 mmol). After stirring at RT for 1 h, the reaction mixture was diluted with DCM and 10% HCl, and extracted with DCM. The organic phase was dried over MgSO₄, filtered and concentrated under reduced pressure and the crude material was carried on without further purification.

(2S,5S)-2-(2-(9-((2S,5S)-1-(tert-butoxycarbonyl)-5-methylpyrrolidine-2-carbonyloxy)-8-oxo-8,9,10,11-tetrahydro-5H-dibenzo[c,g]chromen-3-yl)-2-oxoethyl) 1-tert-butyl 5-methylpyrrolidine-1,2-dicarboxylate (2S,5S)-2-(2-(9-bromo-8-oxo-8,9,10,11-tetrahydro-5H-dibenzo[c,g]chromen-3-yl)-2-oxoethyl) 1-tert-butyl 5-methylpyrrolidine-1,2-dicarboxylate (700 mg, 1.17 mmol) was treated with a solution of (2S,5S)-1-(tert-butoxycarbonyl)-5-methylpyrrolidine-2-carboxylic acid (375 mg, 1.64 mmol) in acetone (6 mL) and Cs₂CO₃ (267 mg, 0.82 mmol). The stirred reaction mixture was heated to 40° C. for 16 h, then cooled to RT and diluted with CH₂Cl₂ and extracted 3×. The organic phase was washed with brine, then dried over MgSO₄, filtered and concentrated under reduced pressure. The crude residue was purified by silica column chromatography (40% to 100% EtOAc/hexanes) to afford (2S,5S)-2-(2-(9-((2S,5S)-1-(tert-butoxycarbonyl)-5-methylpyrrolidine-2-carbonyloxy)-8-oxo-8,9,10,11-tetrahydro-5H-dibenzo[c,g]chromen-3-yl)-2-oxoethyl) 1-tert-butyl 5-methylpyrrolidine-1,2-dicarboxylate (464 mg, 53%).

Tert-butyl (2S,5S)-2-(9-{2-[(2S,5S)-1-(tert-butoxycarbonyl)-5-methylpyrrolidin-2-yl]-1H-imidazol-5-yl}-1,4,5,11-tetrahydroisochromeno[4',3':6,7]naphtho[1,2-d]imidazol-2-yl)-5-methylpyrrolidine-1-carboxylate (2S,5S)-2-(2-(9-((2S,5S)-1-(tert-butoxycarbonyl)-5-methylpyrrolidine-2-carbonyloxy)-8-oxo-8,9,10,11-tetrahydro-5H-dibenzo[c,g]chromen-3-yl)-2-oxoethyl) 1-tert-butyl 5-methylpyrrolidine-1,2-dicarboxylate (464 mg, 0.62 mmol) and NH₄OAc (8.48 g, 110.0 mmol) were suspended in a solution of 10:1 PhMe/2-methoxyethanol (22 mL). The stirred reaction mixture was heated to 110° C. for 20 h, then cooled to RT and diluted with EtOAc. The organic phase was washed with water, saturated aqueous NaHCO₃, and brine, then dried over MgSO₄, filtered and concentrated under reduced pressure. The crude residue was purified by silica column chromatography (0% to 30% MeOH/EtOAc) to afford tert-butyl (2S,5S)-2-(9-{2-[(2S,5S)-1-(tert-butoxycarbonyl)-5-methylpyrrolidin-2-yl]-1H-imidazol-5-yl}-1,4,5,11-tetrahydroisochromeno[4',3':6,7]naphtho[1,2-d]imidazol-2-yl)-5-methylpyrrolidine-1-carboxylate (393 mg, 90%).

Tert-butyl (2S,4S)-2-(5-{2-[(2S,4S)-1-(tert-butoxycarbonyl)-5-methylpyrrolidin-2-yl]-1,11-dihydroisochromeno[4',3':6,7]naphtho[1,2-d]imidazol-9-yl}-1H-imidazol-2-yl)-5-methylpyrrolidine-1-carboxylate Tert-butyl (2S,5S)-2-(9-{2-[(2S,5S)-1-(tert-butoxycarbonyl)-5-methylpyrrolidin-2-yl]-1H-imidazol-5-yl}-1,4,5,11-tetrahydroisochromeno[4',3':6,7]naphtho[1,2-d]imidazol-2- yl)-5-methylpyrrolidine-1-carboxylate (393 mg, 0.55 mmol) was suspended in DCM (7 mL) and activated MnO$_2$ (1.45 g, 16.7 mmol) was added in a single portion. The reaction mixture was heated to 40° C. After stirring for 2.5 h, the mixture was cooled to rt and the slurry was filtered over celite. The filter cake was washed with copious CH$_2$Cl$_2$ and MeOH and the filtrate was concentrated under reduced pressure. The crude material was taken on to the next step without further purification to afford tert-butyl (2S,5S)-2-(5-{2-[(2S,5S)-1-(tert-butoxycarbonyl)-5-methylpyrrolidin-2-yl]-1,11-dihydroisochromeno[4',3':6,7]naphtho[1,2-d]imidazol-9-yl}-1H-imidazol-2-yl)-5-methylpyrrolidine-1-carboxylate (328mg, 85%).

Methyl {(2S)-1-[(2S,5S)-2-(5-{2-[(2S,5S)-1-{(2S)-2-[(methoxycarbonyl)amino]-3-methylbutanoyl}-5-methylpyrrolidin-2-yl]-1,11-dihydroisochromeno[4',3':6,7]naphtho[1,2-d]imidazol-9-yl}-1H-imidazol-2-yl)-5-methylpyrrolidin-1-yl]-3-methyl-1-oxobutan-2-yl}carbamate Tert-butyl (2S,5S)-2-(5-{2-[(2S,5S)-1-(tert-butoxycarbonyl)-5-methylpyrrolidin-2-yl]-1,11-dihydroisochromeno[4',3':6,7]naphtho[1,2-d]imidazol-9-yl}-1H-imidazol-2-yl)-5-methylpyrrolidine-1-carboxylate (164 mg, 0.23 mmol) was dissolved in DCM (7 mL), MeOH (1.5 mL) and HCl (4 M in dioxane, 1.5 mL) was added. The reaction mixture was stirred for 16 h and then concentrated under reduced pressure. The crude residue was treated with (S)-2-(methoxycarbonylamino)-3-methylbutanoic acid (81 mg, 0.46 mmol), HATU (175 mg, 0.46 mmol) and DMF (5 mL), then DIPEA (0.4 mL, 2.34 mmol) was added dropwise. After 35 min, the mixture was diluted with 10% MeOH/EtOAc and washed successively with saturated aqueous NaHCO$_3$ and brine. The organics were dried over MgSO$_4$, filtered and concentrated under reduced pressure. The crude residue was purified by HPLC to afford methyl {(2S)-1-[(2S,5S)-2-(5-{2-[(2S,5S)-1-{(2S)-2-[(methoxycarbonyl)amino]-3-methylbutanoyl}-5-methylpyrrolidin-2-yl]-1,11-dihydroisochromeno[4',3':6,7]naphtho[1,2-d]imidazol-9-yl}-1H-imidazol-2-yl)-5-methylpyrrolidin-1-yl]-3-methyl-1-oxobutan-2-yl}carbamate (132 mg, 69%). LCMS-ESI$^+$: calculated for C45H54N8O7: 818.41; observed [M+1]$^+$: 820.19. $^1$H NMR (CD$_3$OD): 8.492 (m, 1H), 8.179-7.538 (m, 7H), 5.267-5.201 (m, 3H), 5.125-5.082 (m, 1H), 4.070 (m, 1H), 3.383-3.592 (m, 4H), 3.225 (s, 3H), 2.466-2.249 (m, 5H), 1.992-1.892 (m, 3H), 1.568 (d, 3H, J=6.4 Hz), 1.490 (d, 3H, J=6.8 Hz), 1.266 (m, 2H), 1.020-0.806 (m, 14H).

Example NI

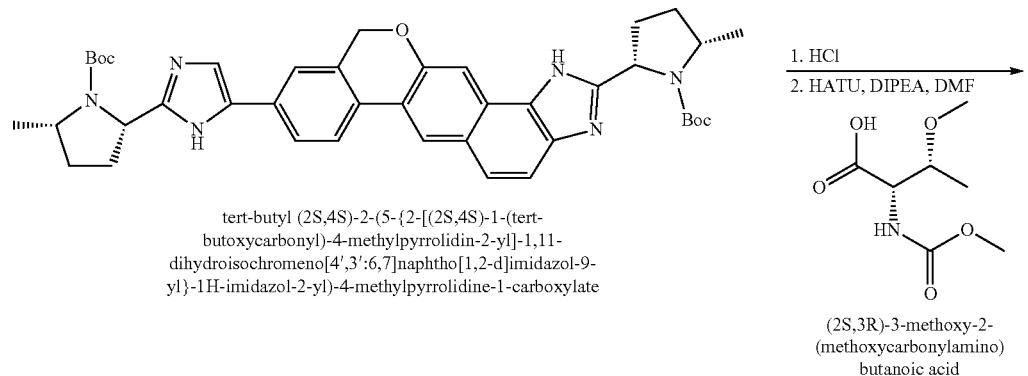

tert-butyl (2S,4S)-2-(5-{2-[(2S,4S)-1-(tert-butoxycarbonyl)-4-methylpyrrolidin-2-yl]-1,11-dihydroisochromeno[4',3':6,7]naphtho[1,2-d]imidazol-9-yl}-1H-imidazol-2-yl)-4-methylpyrrolidine-1-carboxylate (2S,3R)-3-methoxy-2-(methoxycarbonylamino) butanoic acid

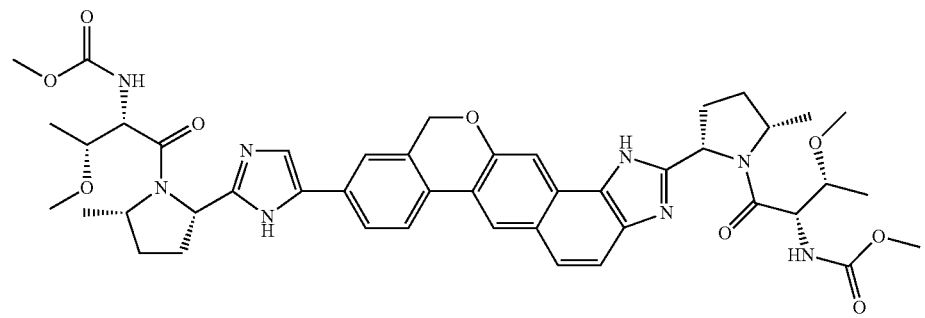

methyl [(2S,3R)-3-methoxy-1-{(2S,5S)-2-[9-(2-{(2S,5S)-1-[N-(methoxycarbonyl)-O-methyl-L-threonyl]-5-methylpyrrolidin-2-yl}-1H-imidazol-5-yl)-1,11-dihydroisochromeno[4',3':6,7]naphtho[1,2-d]imidazol-2-yl]-5-methylpyrrolidin-1-yl}-1-oxobutan-2-yl]carbamate

Methyl [(2S,3R)-3-methoxy-1-{(2S,5S)-2-[9-(2-{(2S,5S)-1-[N-(methoxycarbonyl)-O-methyl-L-threonyl]-5-methylpyrrolidin-2-yl}-1H-imidazol-5-yl)-1,11-dihydroisochromeno[4',3':6,7]naphtho[1,2-d]imidazol-2-yl]-5-methylpyrrolidin-1-yl}-1-oxobutan-2-yl]carbamate Tert-butyl (2S,5S)-2-(5-{2-[(2S,5S)-1-(tert-butoxycarbonyl)-4-methylpyrrolidin-2-yl]-1,11-dihydroisochromeno[4',3':6,7]naphtho[1,2-d]imidazol-9-yl}-1H-imidazol-2-yl)-4-methylpyrrolidine-1-carboxylate (164 mg, 0.23 mmol) was dissolved in DCM (7 mL), MeOH (1.5 mL) and HCl (4 M in dioxane, 1.5 mL) was added. The reaction mixture was stirred for 16 h and then concentrated under reduced pressure. The crude residue was treated with (2S,3R)-3-methoxy-2-(methoxycarbonylamino)butanoic acid (90 mg, 0.46 mmol), HATU (175 mg, 0.46 mmol) and DMF (6 mL), then DIPEA (0.4 mL, 2.34 mmol) was added dropwise. After 30 min, the mixture was diluted with 10% MeOH/EtOAc and washed successively with saturated aqueous NaHCO$_3$ and brine. The organics were dried over MgSO$_4$, filtered and concentrated under reduced pressure. The crude residue was purified by HPLC to afford methyl [(2S,3R)-3-methoxy-1-{(2S,5S)-2-[9-(2-{(2S,5S)-1-[N-(methoxycarbonyl)-O-methyl-L-threonyl]-5-methylpyrrolidin-2-yl}-1H-imidazol-5-yl)-1,11-dihydroisochromeno[4',3':6,7]naphtho[1,2-d]imidazol-2-yl]-5-methylpyrrolidin-1-yl}-1-oxobutan-2-yl]carbamate (97 mg, 50%). LCMS-ESI$^+$: calculated for C45H54N8O9: 850.40; observed [M+1]$^+$: 851.58. $^1$H NMR (CD$_3$OD): 8.631 (s, 1H), 8.191-7.938 (m, 7H), 6.100 (m, 1H), 5.925 (m, 1H), 5.303 (m, 3H), 5.179 (t, 1H, J=6.8 Hz), 4.406-4.358 (m, 2H), 3.754-3.598 (m, 8H), 3.376 (s, 3H), 3.263 (s, 3H), 2.625-2.256 (m, 6H), 2.038-1.955 (m, 2H), 1.598 (d, 3H, J=6.4 Hz), 1.530 (d, 3H, J=6.8 Hz), 1.302-1.099 (m, 6H).

Example NJ

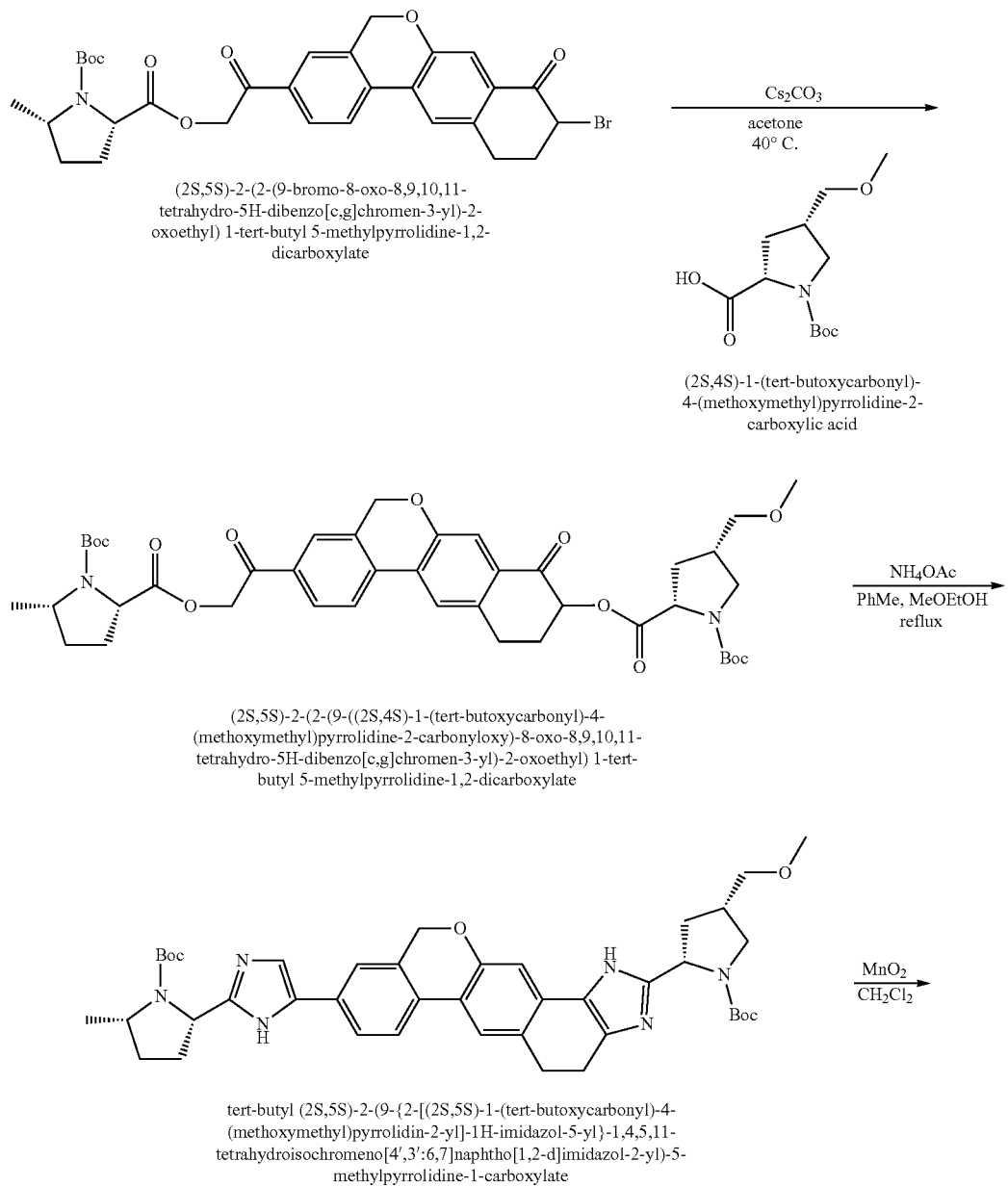

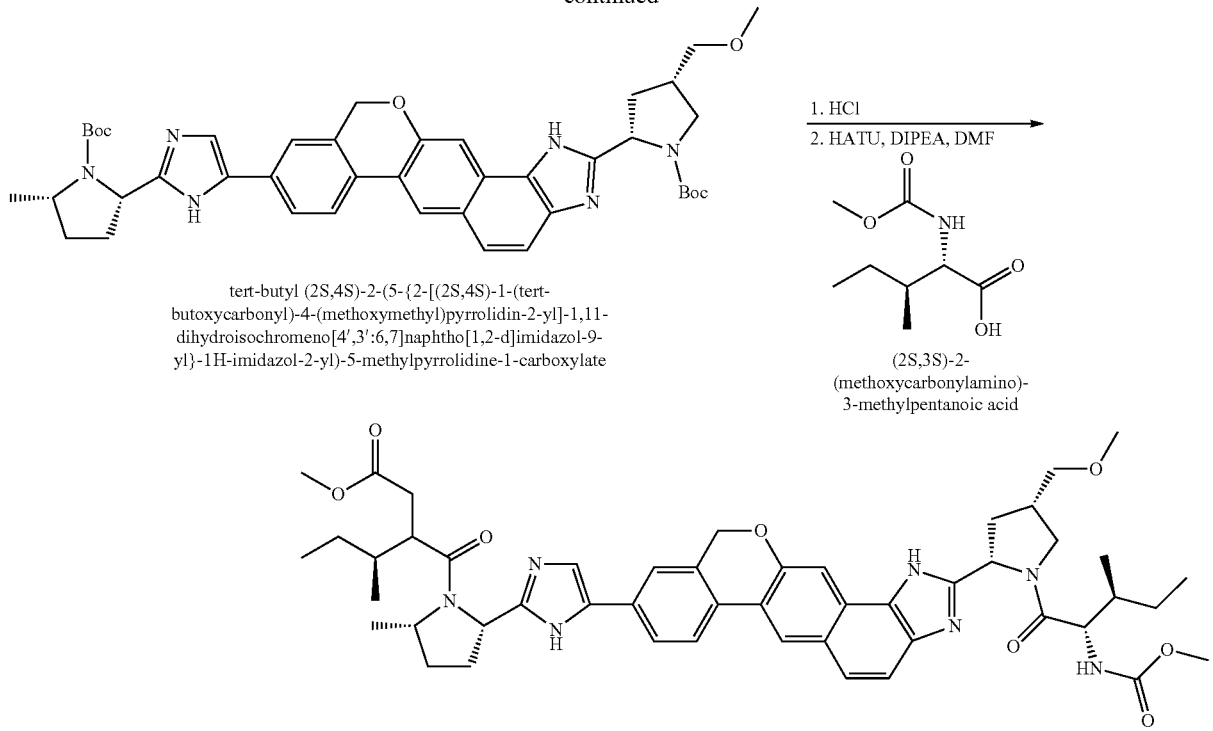

tert-butyl (2S,4S)-2-(5-{2-[(2S,4S)-1-(tert-butoxycarbonyl)-4-(methoxymethyl)pyrrolidin-2-yl]-1,11-dihydroisochromeno[4',3':6,7]naphtho[1,2-d]imidazol-9-yl}-1H-imidazol-2-yl)-5-methylpyrrolidine-1-carboxylate (2S,3S)-2-(methoxycarbonylamino)-3-methylpentanoic acid methyl {(2S,3S)-1-[(2S,5S)-2-(5-{2-[(2S,4S)-1-{[(2S,3S)-2-[(methoxycarbonyl)amino]-3-methylpentanoyl}-4-(methoxymethyl)pyrrolidin-2-yl]-1,11-dihydroisochromeno[4',3':6,7]naphtho[1,2-d]imidazol-9-yl}-1H-imidazol-2-yl)-5-methylpyrrolidin-1-yl]-3-methyl-1-oxopentan-2-yl}carbamate (2S,5S)-2-(2-(9-((2S,4S)-1-(tert-butoxycarbonyl)-4-(methoxymethyl)pyrrolidine-2-carbonyloxy)-8-oxo-8,9,10,11-tetrahydro-5H-dibenzo[c,g]chromen-3-yl)-2-oxoethyl) 1-tert-butyl 5-methylpyrrolidine-1,2-dicarboxylate (2S,5S)-2-(2-(9-bromo-8-oxo-8,9,10,11-tetrahydro-5H-dibenzo[c,g]chromen-3-yl)-2-oxoethyl) 1-tert-butyl 5-methylpyrrolidine-1,2-dicarboxylate (800 mg, 1.34 mmol) was treated with a solution of (2S,4S)-1-(tert-butoxycarbonyl)-4-(methoxymethyl)pyrrolidine-2-carboxylic acid (485 mg, 1.87 mmol) in acetone (6 mL) and Cs₂CO₃ (306 mg, 0.94 mmol). The stirred reaction mixture was heated to 40° C. for 16 h, then cooled to RT and diluted with CH₂Cl₂ and extracted 3×. The organic phase was washed with brine, then dried over MgSO₄, filtered and concentrated under reduced pressure. The crude residue was purified by silica column chromatography (40% to 100% EtOAc/hexanes) to afford (2S,5S)-2-(2-(9-((2S,4S)-1-(tert-butoxycarbonyl)-4-(methoxymethyl)pyrrolidine-2-carbonyloxy)-8-oxo-8,9,10,11-tetrahydro-5H-dibenzo[c,g]chromen-3-yl)-2-oxoethyl) 1-tert-butyl 5-methylpyrrolidine-1,2-dicarboxylate (680 mg, 65%).

Tert-butyl (2S,5S)-2-(9-{2-[(2S,4S)-1-(tert-butoxycarbonyl)-4-(methoxymethyl)pyrrolidin-2-yl]-1H-imidazol-5-yl}-1,4,5,11-tetrahydroisochromeno[4',3':6,7]naphtho[1,2-d]imidazol-2-yl)-5-methylpyrrolidine-1-carboxylate (2S,5S)-2-(2-(9-((2S,4S)-1-(tert-butoxycarbonyl)-4-methoxymethyl(pyrrolidine-2-carbonyloxy)-8-oxo-8,9,10,11-tetrahydro-5H-dibenzo[c,g]chromen-3-yl)-2-oxoethyl) 1-tert-butyl 5-methylpyrrolidine-1,2-dicarboxylate (680 mg, 0.87 mmol) and NH₄OAc (10.0 g, 130.0 mmol) were suspended in a solution of 10:1 PhMe/2-methoxyethanol (22 mL). The stirred reaction mixture was heated to 110° C. for 24 h, then cooled to RT and diluted with EtOAc. The organic phase was washed with water, saturated aqueous NaHCO₃, and brine, then dried over MgSO₄, filtered and concentrated under reduced pressure. The crude residue was purified by silica column chromatography (0% to 30% MeOH/EtOAc) to afford tert-butyl (2S,5S)-2-(9-{2-[(2S,4S)-1-(tert-butoxycarbonyl)-4-(methoxymethyl)pyrrolidin-2-yl]-1H-imidazol-5-yl}-1,4,5,11-tetrahydroisochromeno[4',3':6,7]naphtho[1,2-d]imidazol-2-yl)-5-methylpyrrolidine-1-carboxylate (461 mg, 72%).

Tert-butyl (2S,5S)-2-(5-{2-[(2S,4S)-1-(tert-butoxycarbonyl)-4-(methoxymethyl)pyrrolidin-2-yl]-1,11-dihydroisochromeno[4',3':6,7]naphtho[1,2-d]imidazol-9-yl}-1H-imidazol-2-yl)-5-methylpyrrolidine-1-carboxylate tert-butyl (2S,5S)-2-(9-{2-[(2S,4S)-1-(tert-butoxycarbonyl)-4-(methoxymethyl)pyrrolidin-2-yl]-1H-imidazol-5-yl}-1,4,5,11-tetrahydroisochromeno[4',3':6,7]naphtho[1,2-d]imidazol-2-yl)-5-methylpyrrolidine-1-carboxylate (461 mg, 0.62 mmol) was suspended in DCM (7 mL) and activated MnO₂ (1.6 g, 18.8 mmol) was added in a single portion. The reaction mixture was heated to 40° C. After stirring for 5.5 h, the mixture was cooled to rt and the slurry was filtered over celite. The filter cake was washed with copious CH₂Cl₂ and MeOH and the filtrate was concentrated under reduced pressure. The crude material was taken on to the next step without further purification to afford tert-butyl (2S,5S)-2-(5-{2-[(2S,4S)-1-(tert-butoxycarbonyl)-4-(methoxymethyl)pyrrolidin-2-yl]-1,11-dihydroisochromeno[4',3':6,7]naphtho[1,2-d]imidazol-9-yl}-1H-imidazol-2-yl)-5-methylpyrrolidine-1-carboxylate (414mg, 90%).

Methyl {(2S,3S)-1-[(2S,5S)-2-(5-{2-[(2S,4S)-1-{(2S,3S)-2-[(methoxycarbonyl)amino]-3-methylpentanoyl}-4-(methoxymethyl)pyrrolidin-2-yl]-1,11-dihydroisochromeno[4',3':6,7]naphtho[1,2-d]imidazol-9-yl}-1H-imidazol-2-yl)-5-methylpyrrolidin-1-yl]-3-methyl-1-oxopentan-2-yl}carbamate Tert-butyl (2S,5S)-2-(5-{2-[(2S,4S)-1-(tert-butoxycarbonyl)-4-(methoxymethyl)pyrrolidin-2-yl]-1,11-dihydroisochromeno[4',3':6,7]naphtho[1,2-d]imidazol-9-yl}-1H-imidazol-2-yl)-5-methylpyrrolidine-1-carboxylate (207 mg, 0.28 mmol) was dissolved in DCM (4 mL), MeOH (1 mL) and HCl (4 M in dioxane, 1 mL) was added. The reaction mixture was stirred for 1.5 h and then concentrated under reduced pressure. The crude residue was treated with (2S,3S)-2-(methoxycarbonylamino)-3-methylpentanoic acid (106 mg, 0.56 mmol), HATU (214 mg, 0.56 mmol) and DMF (5 mL), then DIPEA (0.49 mL, 2.8 mmol) was added dropwise. After 30 min, the mixture was diluted with 10% MeOH/EtOAc and washed successively with saturated aqueous NaHCO$_3$ and brine. The organics were dried over MgSO$_4$, filtered and concentrated under reduced pressure. The crude residue was purified by HPLC to afford methyl {(2S,3S)-1-[(2S,5S)-2-(5-{2-[(2S,4S)-1-{(2S,3S)-2-[(methoxycarbonyl)amino]-3-methylpentanoyl}-4-(methoxymethyl)pyrrolidin-2-yl]-1,11-dihydroisochromeno[4',3':6,7]naphtho[1,2-d]imidazol-9-yl}-1H-imidazol-2-yl)-5-methylpyrrolidin-1-yl]-3-methyl-1-oxopentan-2-yl}carbamate (132 mg, 69%). LCMS-ESI$^i$: calculated for C45H54N8O7: 876.45; observed [M+1]$^+$: 879.02

Example NK

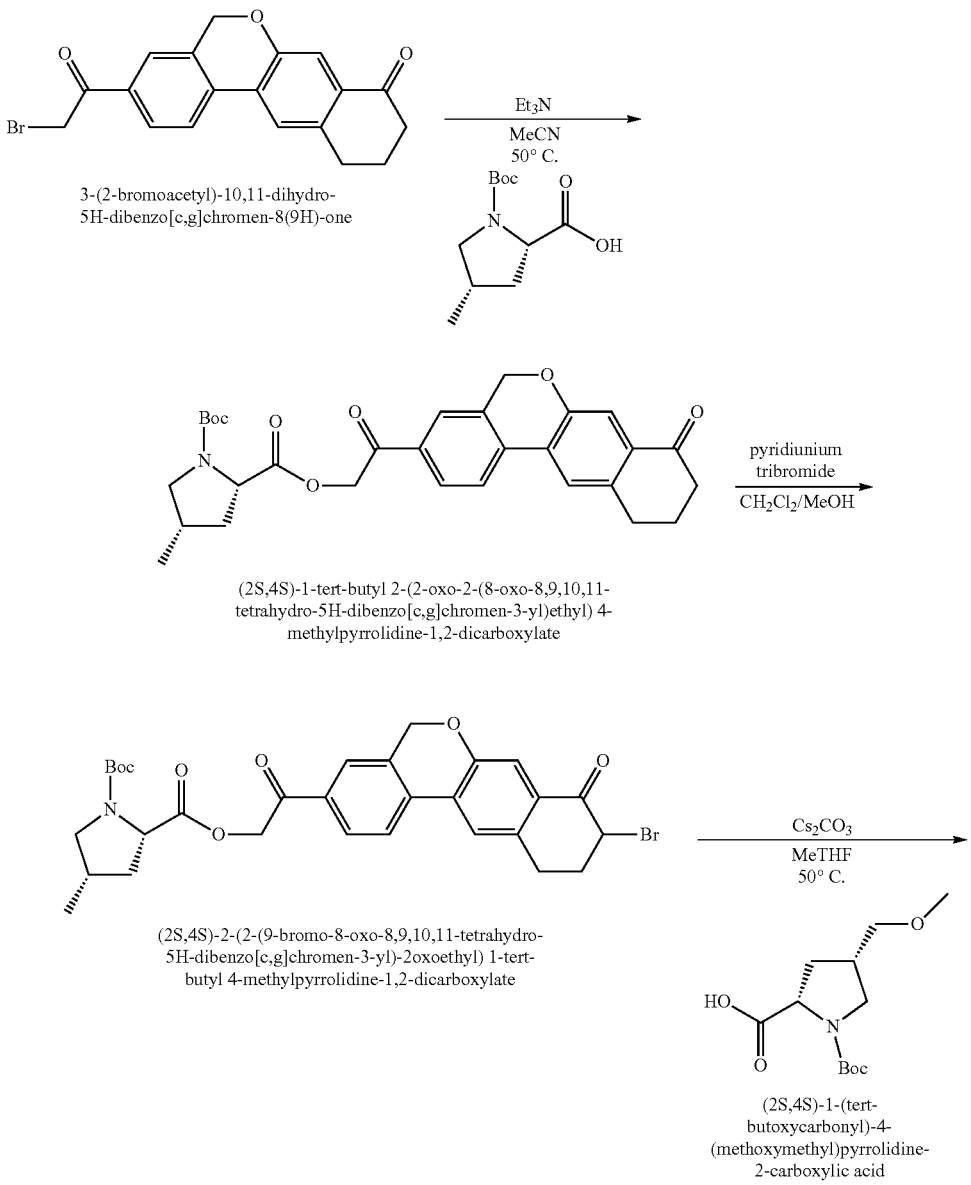

-continued

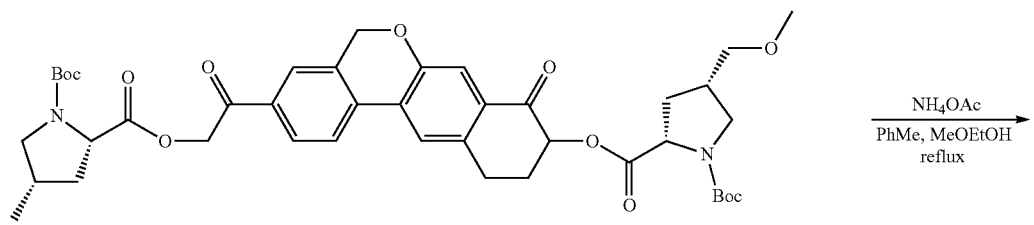

(2S,4S)-2-(2-(9-((2S,4S)-1-(tert-butoxycarbonyl)-4-(methoxymethyl)pyrrolidine-2-carbonyloxy)-8-oxo-8,9,10,11-tetrahydro-5H-dibenzo[c,g]chromen-3-yl)-2-oxoethyl) 1-tert-butyl 4-methylpyrrolidine-1,2-dicarboxylate

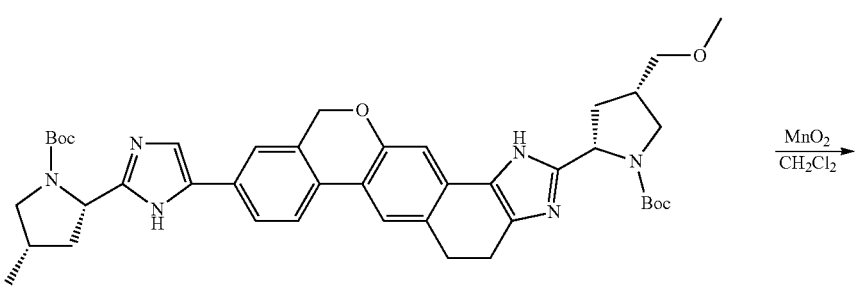

tert-butyl (2S,5S)-2-(9-{2-[(2S,5S)-1-(tert-butoxycarbonyl)-4-(methoxymethyl)pyrrolidin-2-yl]-1H-imidazol-5-yl}-1,4,5,11-tetrahydroisochromeno[4′,3′:6,7]naphtho[1,2-d]imidazol-2-yl)-4-methylpyrrolidine-1-carboxylate

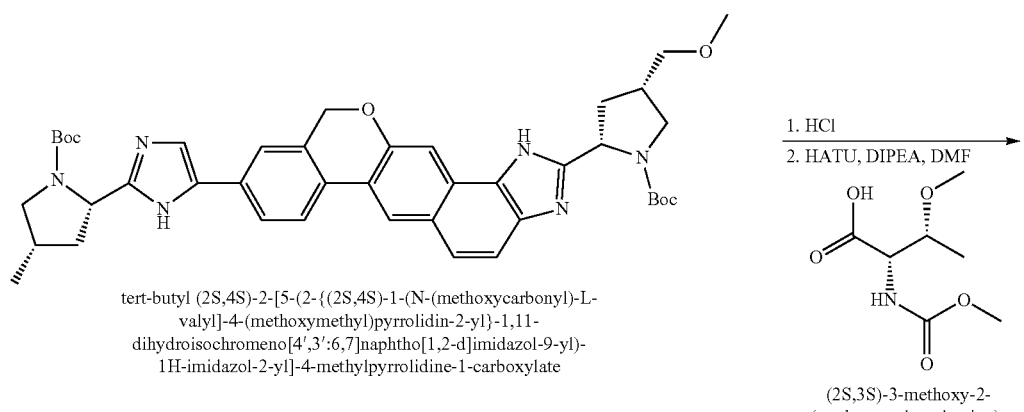

tert-butyl (2S,4S)-2-[5-(2-{(2S,4S)-1-(N-(methoxycarbonyl)-L-valyl]-4-(methoxymethyl)pyrrolidin-2-yl}-1,11-dihydroisochromeno[4′,3′:6,7]naphtho[1,2-d]imidazol-9-yl)-1H-imidazol-2-yl]-4-methylpyrrolidine-1-carboxylate (2S,3S)-3-methoxy-2-(methoxycarbonylamino)-butanoic acid

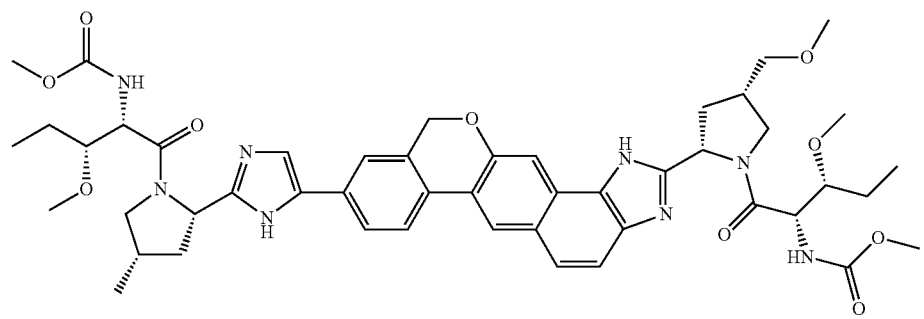

methyl {(2S,3R)-3-methoxy-1-[(2S,4S)-2-[9-(2-{(2S,4S)-1-[N-(methoxycarbonyl)-O-methyl-L-threonyl]-4-methylpyrrolidin-2-yl}-1H-imidazol-5-yl)-1,11-dihydroisochromeno[4′,3′:6,7]naphtho[1,2-d]imidazol-2-yl]-4-(methoxymethyl)pyrrolidin-1-yl]-1-oxobutan-2-yl}carbamate

(2S,4S)-1-tert-butyl 2-(2-oxo-2-(8-oxo-8,9,10,11-tetrahydro-5H-dibenzo[c,g]chromen-3-yl)ethyl) 4-methylpyrrolidine-1,2-dicarboxylate To a solution of 3-(2-bromoacetyl)-10,11-dihydro-5H-dibenzo[c,g]chromen-8(9H)-one (647 mg, 1.74 mmol) in MeCN (20 mL) was added ((2S,4S)-1-(tert-butoxycarbonyl)-4-methylpyrrolidine-2-carboxylic acid (559 mg, 2.44 mmol) and DIPEA (0.36 mL, 2.09 mmol) and the solution was heated to 60° C. After stirring for 3 h, the solution was cooled to rt, and diluted with EtOAc and washed successively with saturated aqueous NaHCO$_3$ and brine. The organics were dried over MgSO$_4$, filtered and concentrated under reduced pressure. The crude residue was purified by silica column chromatography (20% to 50% EtOAc/hexanes) to afford (2S,4S)-1-tert-butyl 2-(2-oxo-2-(8-oxo-8,9,10,11-tetrahydro-5H-dibenzo[c,g]chromen-3-yl)ethyl) 4-methylpyrrolidine-1,2-dicarboxylate (621 mg, 69%).

(2S,4S)-2-(2-(9-bromo-8-oxo-8,9,10,11-tetrahydro-5H-dibenzo[c,g]chromen-3-yl)-2-oxoethyl) 1-tert-butyl 4-methylpyrrolidine-1,2-dicarboxylate (2S,4S)-1-tert-butyl 2-(2-oxo-2-(8-oxo-8,9,10,11-tetrahydro-5H-dibenzo[c,g]chromen-3-yl)ethyl) 4-methylpyrrolidine-1,2-dicarboxylate (621 mg, 1.19 mmol) was dissolved in a solution of DCM (10 mL) and MeOH (4 mL), then treated with pyridinium tribromide (421 mg, 1.3 mmol). After stirring at RT for 1.5 h, the reaction mixture was diluted with DCM and 10% HCl, and extracted with DCM. The organic phase was dried over MgSO$_4$, filtered and concentrated under reduced pressure and the crude material was carried on without further purification.

(2S,4S)-2-(2-(9-((2S,4S)-1-(tert-butoxycarbonyl)-4-(methoxymethyl)pyrrolidine-2-carbonyloxy)-8-oxo-8,9,10,11-tetrahydro-5H-dibenzo[c,g]chromen-3-yl)-2-oxoethyl) 1-tert-butyl 4-methylpyrrolidine-1,2-dicarboxylate (2S,4S)-2-(2-(9-bromo-8-oxo-8,9,10,11-tetrahydro-5H-dibenzo[c,g]chromen-3-yl)-2-oxoethyl) 1-tert-butyl 4-methylpyrrolidine-1,2-dicarboxylate (709 mg, 1.18 mmol) was treated with a solution of (2S,4S)-1-(ter-butoxycarbonyl)-4-(methoxymethyl)pyrrolidine-2-carboxylic acid (614 mg, 2.36 mmol) in Me-THF (12 mL) and Cs$_2$CO$_3$ (384 mg, 1.18 mmol). The stirred reaction mixture was heated to 50° C. for 16 h, then cooled to RT and diluted with CH$_2$Cl$_2$ and extracted 3×. The organic phase was washed with brine, then dried over MgSO$_4$, filtered and concentrated under reduced pressure. The crude residue was purified by silica column chromatography (40% to 100% EtOAc/hexanes) to afford (2S,4S)-2-(2-(9-((2S,4S)-1-(tert-butoxycarbonyl)-4-(methoxymethyl)pyrrolidine-2-carbonyloxy)-8-oxo-8,9,10,11-tetrahydro-5H-dibenzo[c,g]chromen-3-yl)-2-oxoethyl) 1-tert-butyl 4-methylpyrrolidine-1,2-dicarboxylate (651 mg, 71%).

Tert-butyl (2S,4S)-2-(9-{2-[(2S,4S)-1-(tert-butoxycarbonyl)-4-(methoxymethyl)pyrrolidin-2-yl]-1H-imidazol-5-yl}-1,4,5,11-tetrahydroisochromeno[4',3':6,7]naphtho[1,2-d]imidazol-2-yl)-4-methylpyrrolidine-1-carboxylate (2S,4S)-2-(2-(9-((2S,4S)-1-(tert-butoxycarbonyl)-4-(methoxymethyl)pyrrolidine-2-carbonyloxy)-8-oxo-8,9,10,11-tetrahydro-5H-dibenzo[c,g]chromen-3-yl)-2-oxoethyl) 1-tert-butyl 4-methylpyrrolidine-1,2-dicarboxylate (651 mg, 0.84 mmol) and NH$_4$OAc (10.0 g, 129.7 mmol) were suspended in a solution of 10:1 PhMe/2-methoxyethanol (22 mL). The stirred reaction mixture was heated to 110° C. for 20 h, then cooled to RT and diluted with EtOAc. The organic phase was washed with water, saturated aqueous NaHCO$_3$, and brine, then dried over MgSO$_4$, filtered and concentrated under reduced pressure. The crude residue was purified by silica column chromatography (0% to 30% MeOH/EtOAc) to afford tert-butyl (2S,4S)-2-(9-{2-[(2S,4S)-1-(tert-butoxycarbonyl)-4-(methoxymethyl)pyrrolidin-2-yl]-1H-imidazol-5-yl}-1,4,5,11-tetrahydroisochromeno[4',3':6,7]naphtho[1,2-d]imidazol-2-yl)-4-methylpyrrolidine-1-carboxylate (382 mg, 62%).

Tert-butyl (2S,4S)-2-[5-(2-{(2S,4S)-1-[N-(methoxycarbonyl)-L-valyl]-4-(methoxymethyl)pyrrolidin-2-yl}-1,11-dihydroisochromeno[4',3':6,7]naphtho[1,2-d]imidazol-9-yl)-1H-imidazol-2-yl]-4-methylpyrrolidine-1-carboxylate Tert-butyl (2S,4S)-2-(9-{2-[(2S,4S)-1-(tert-butoxycarbonyl)-4-(methoxymethyl)pyrrolidin-2-yl]-1H-imidazol-5-yl}-1,4,5,11-tetrahydroisochromeno[4',3':6,7]naphtho[1,2-d]imidazol-2-yl)-4-methylpyrrolidine-1-carboxylate (382 mg, 0.52 mmol) was suspended in DCM (8 mL) and activated MnO$_2$ (1.35 g, 15.5 mmol) was added in a single portion. The reaction mixture was heated to 35° C. After stirring for 15 h, the mixture was cooled to rt and the slurry was filtered over celite. The filter cake was washed with copious CH$_2$Cl$_2$ and MeOH and the filtrate was concentrated under reduced pressure. The crude material was taken on to the next step without further purification to afford tert-butyl (2S,4S)-2-[5-(2-{(2S,4S)-1-[N-(methoxycarbonyl)-L-valyl]-4-(methoxymethyl)pyrrolidin-2-yl}-1,11-dihydroisochromeno[4',3':6,7]naphtho[1,2-d]imidazol-9-yl)-1H-imidazol-2-yl]-4-methylpyrrolidine-1-carboxylate (347mg, 91%).

Methyl {(2S,3R)-3-methoxy-1-[(2S,4S)-2-[9-(2-{(2S,4S)-1-[N-(methoxycarbonyl)-O-methyl-L-threonyl]-4-methylpyrrolidin-2-yl}-1H-imidazol-5-yl)-1,11-dihydroisochromeno[4',3':6,7]naphtho[1,2-d]imidazol-2-yl]-4-(methoxymethyl)pyrrolidin-1-yl]-1-oxobutan-2-yl}carbamate Tert-butyl (2S,4S)-2-[5-(2-{(2S,4S)-1-[N-(methoxycarbonyl)-L-valyl]-4-(methoxymethyl)pyrrolidin-2-yl}-1,11-dihydroisochromeno[4',3':6,7]naphtho[1,2-d]imidazol-9-yl)-1H-imidazol-2-yl]-4-methylpyrrolidine-1-carboxylate (174 mg, 0.24 mmol) was dissolved in DCM (4 mL), MeOH (1 mL) and HCl (4 M in dioxane, 1 mL) was added. The reaction mixture was stirred for h and then concentrated under reduced pressure. The crude residue was treated with ((2S,3R)-3-methoxy-2-(methoxycarbonylamino)butanoic acid (92 mg, 0.48 mmol), HATU (182 mg, 0.48 mmol) and DMF (5 mL), then DIPEA (0.31 mL, 2.4 mmol) was added dropwise. After 35 min, the mixture was diluted with 10% MeOH/

EtOAc and washed successively with saturated aqueous NaHCO$_3$ and brine. The organics were dried over MgSO$_4$, filtered and concentrated under reduced pressure. The crude residue was purified by HPLC to afford methyl {(2S,3R)-3-methoxy-1-[(2S,4S)-2-[9-(2-{(2S,4S)-1-[N-(methoxycarbonyl)-O-methyl-L-threonyl]-4-methylpyrrolidin-2-yl}-1H-imidazol-5-yl)-1,11-dihydroisochromeno[4',3':6,7]naphtho[1,2-d]imidazol-2-yl]-4-(methoxymethyl)pyrrolidin-1-yl]-1-oxobutan-2-yl}carbamate (72 mg, 34%). LCMS-ESI$^+$: calculated for C46H56N8O10: 880.41; observed [M+1]$^+$: 882.39. $^1$H NMR (CD$_3$OD): 8.558 (s, 1H), 8.123-7.572 (m, 7H), 5.436-5.391 (dd, 1H, J=7.2, 3.6 Hz), 5.252 (s, 2H), 5.220 (m, 1H), 4.493-4.444 (m, 2H), 4.287-4.206 (m, 2H), 3.756-3.256 (m, 21H), 2.834 (m, 1H), 2.717-2.621 (m, 2H), 2.500 (m, 1H), 2.150 (m, 1H), 1.882 (m, 1H), 1.208 (d, 3H, J=6.4 Hz), 1.159-1.099 (m, 6H).

Example NL

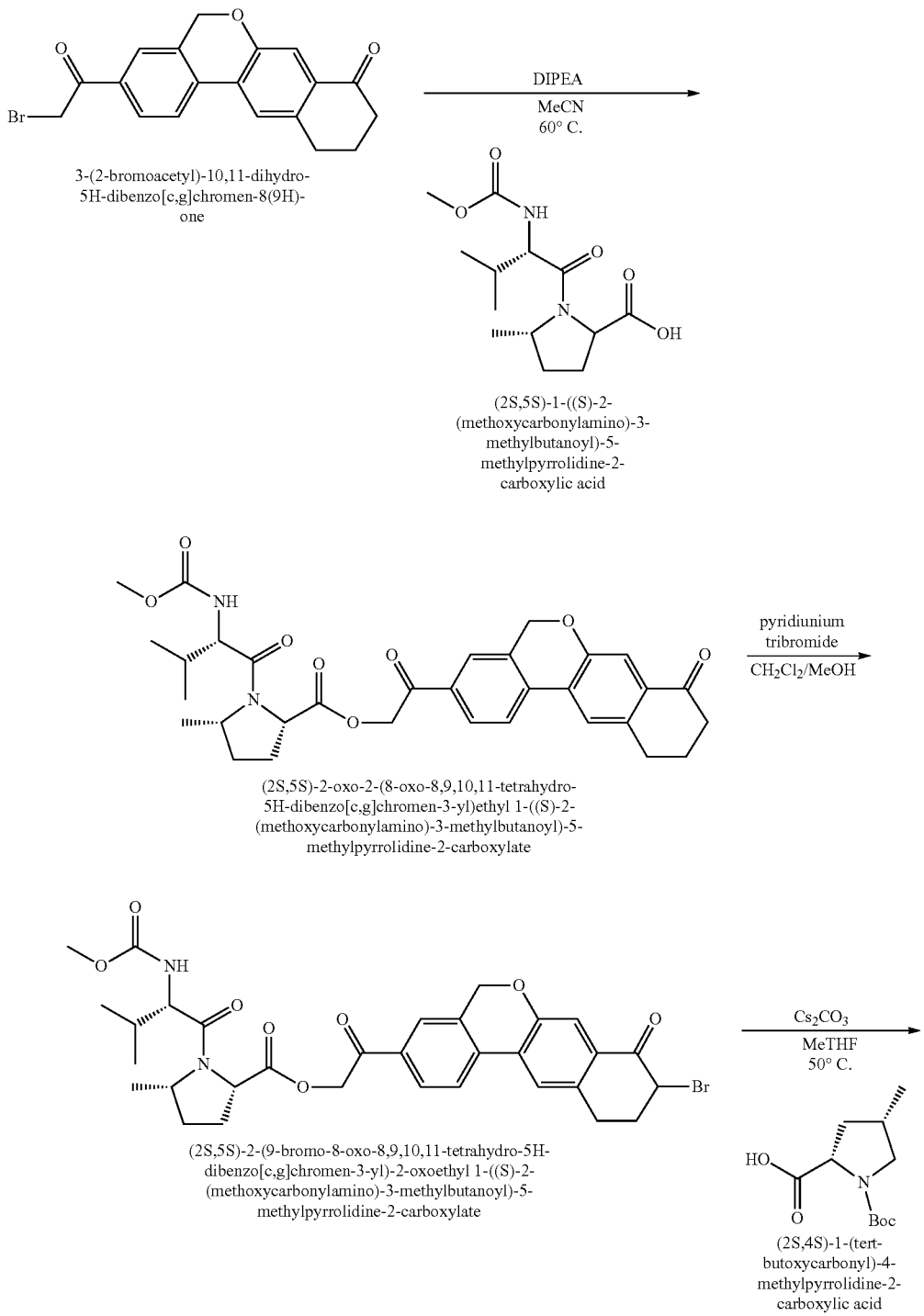

-continued

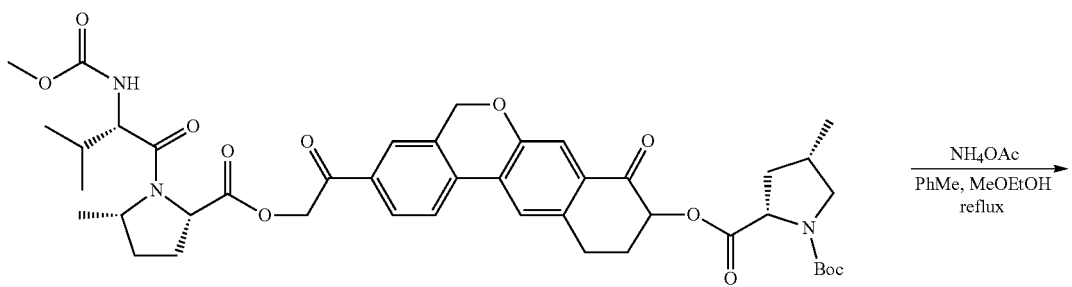

(2S,4S)-1-tert-butyl 2-(3-(2-(((2S,5S)-1-((S)-2-(methoxycarbonylamino)-3-methylbutanoyl)-5-methylpyrrolidine-2-carbonyloxy)acetyl)-8-oxo-8,9,10,11-tetrahydro-5H-dibenzo[c,g]chromen-9-yl) 4-methylpyrrolidine-1,2-dicarboxylate

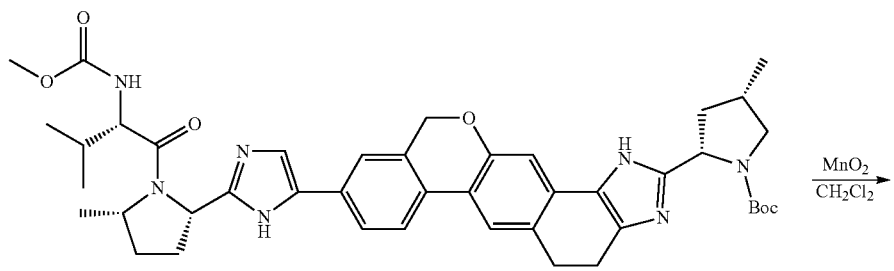

tert-butyl (2S,4S)-2-[9-(2-{(2S,5S)-1-[N-(methoxycarbonyl)-L-valyl]-5-methylpyrrolidin-2-yl}-1H-imidazol-5-yl)-1,4,5,11-tetrahydroisochromeno[4',3':6,7]naphtho[1.2-d]imidazol-2-yl]-4-methylpyrrolidine-1-carboxylate

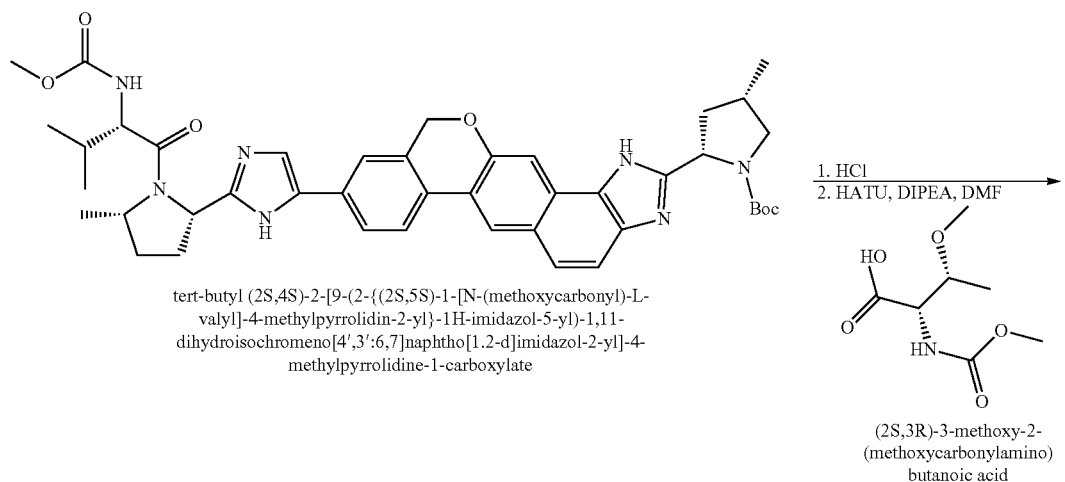

tert-butyl (2S,4S)-2-[9-(2-{(2S,5S)-1-[N-(methoxycarbonyl)-L-valyl]-4-methylpyrrolidin-2-yl}-1H-imidazol-5-yl)-1,11-dihydroisochromeno[4',3':6,7]naphtho[1.2-d]imidazol-2-yl]-4-methylpyrrolidine-1-carboxylate (2S,3R)-3-methoxy-2-(methoxycarbonylamino) butanoic acid

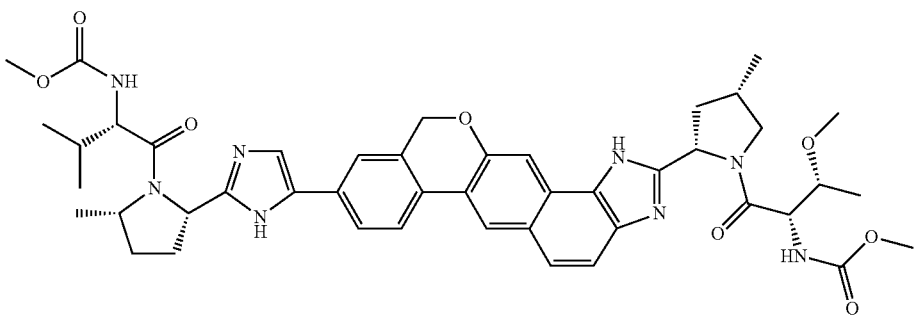

methyl {(2S)-1-[(2S,5S)-2-(5-{2-[(2S,4S)-1-{(2S,3R)-3-methoxy-2-[(methoxycarbonyl)amino]butanoyl}-4-methylpyrrolidin-2-yl]-1,11-dihydroisochromeno[4',3':6,7]naphtho[1.2-d]imidazol-9-yl}-1H-imidazol-2-yl)-5-methylpyrrolidin-1-yl]-3-methyl-1-oxobutan-2-yl}carbamate

(2S,5S)-2-oxo-2-(8-oxo-8,9,10,11-tetrahydro-5H-dibenzo[c,g]chromen-3-yl)ethyl 1-((S)-2-(methoxycarbonylamino)-3-methylbutanoyl)-5-methylpyrrolidine-2-carboxylate To a solution of 3-(2-bromoacetyl)-10,11-dihydro-5H-dibenzo[c,g]chromen-8(9H)-one (750 mg, 2.02 mmol) in MeCN (20 mL) was added (2S,5S)-1-((S)-2-(methoxycarbonylamino)-3-methylbutanoyl)-5-methylpyrrolidine-2-carboxylic acid (600 mg, 2.09 mmol) and DIPEA (0.35 mL, 2.02 mmol) and the solution was heated to 60° C. After stirring for 4 h, the solution was cooled to rt, and diluted with EtOAc and washed successively with saturated aqueous NaHCO$_3$ and brine. The organics were dried over MgSO$_4$, filtered and concentrated under reduced pressure. The crude residue was purified by silica column chromatography (40% to 80% EtOAc/hexanes) to afford (2S,5S)-2-oxo-2-(8-oxo-8,9,10,11-tetrahydro-5H-dibenzo[c,g]chromen-3-yl)ethyl 1-((S)-2-(methoxycarbonylamino)-3-methylbutanoyl)-5-methylpyrrolidine-2-carboxylate (1.16 g, quant.).

(2S,5S)-2-(9-bromo-8-oxo-8,9,10,11-tetrahydro-5H-dibenzo[c,g]chromen-3-yl)-2-oxoethyl 1-((S)-2-(methoxycarbonylamino)-3-methylbutanoyl)-5-methylpyrrolidine-2-carboxylate (2S,5S)-2-oxo-2-(8-oxo-8,9,10,11-tetrahydro-5H-dibenzo[c,g]chromen-3-yl)ethyl 1-((S)-2-(methoxycarbonylamino)-3-methylbutanoyl)-5-methylpyrrolidine-2-carboxylate (400 mg, 0.61 mmol) was dissolved in a solution of DCM (15 mL) and MeOH (6 mL), then treated with pyridinium tribromide (409 mg, 1.28 mmol). At 2 h, an additional portion of pyridinium tribromide (40 mg) was added. After stirring at RT for another 20 min, the reaction mixture was diluted with DCM and 10% HCl, and extracted with DCM. The organic phase was dried over MgSO$_4$, filtered and concentrated under reduced pressure and the crude material was carried on without further purification.

(2S,4S)-1-tert-butyl 2-(3-(2-((2S,5S)-1-((S)-2-(methoxycarbonylamino)-3-methylbutanoyl)-5-methylpyrrolidine-2-carbonyloxy)acetyl)-8-oxo-8,9,10,11-tetrahydro-5H-dibenzo[c,g]chromen-9-yl) 4-methylpyrrolidine-1,2-dicarboxylate (2S,5S)-2-(9-bromo-8-oxo-8,9,10,11-tetrahydro-5H-dibenzo[c,g]chromen-3-yl)-2-oxoethyl 1-((S)-2-(methoxycarbonylamino)-3-methylbutanoyl)-5-methylpyrrolidine-2-carboxylate) was treated with a solution of (2S,4S)-1-(tert-butoxycarbonyl)-4-methylpyrrolidine-2-carboxylic acid (280 mg, 1.22 mmol) in Me-THF (6 mL) and Cs$_2$CO$_3$ (199 mg, 0.61 mmol). The stirred reaction mixture was heated to 50° C. for 2.5 h, then cooled to RT and diluted with CH$_2$Cl$_2$ and extracted 3×. The organic phase was washed with brine, then dried over MgSO$_4$, filtered and concentrated under reduced pressure. The crude residue was purified by silica column chromatography (50% to 100% EtOAc/hexanes) to afford (2S,4S)-1-tert-butyl 2-(3-(2-((2S,5S)-1-((S)-2-(methoxycarbonylamino)-3-methylbutanoyl)-5-methylpyrrolidine-2-carbonyloxy)acetyl)-8-oxo-8,9,10,11-tetrahydro-5H-dibenzo[c,g]chromen-9-yl) 4-methylpyrrolidine-1,2-dicarboxylate (441 mg, 90%).

Tert-butyl (2S,4S)-2-[9-(2-{(2S,5S)-1-[N-(methoxycarbonyl)-L-valyl]-5-methylpyrrolidin-2-yl}-1H-imidazol-5-yl)-1,4,5,11-tetrahydroisochromeno[4',3':6,7]naphtho[1,2-d]imidazol-2-yl]-4-methylpyrrolidine-1-carboxylate (2S,4S)-1-tert-butyl 2-(3-(2-((2S,5S)-1-((S)-2-(methoxycarbonylamino)-3-methylbutanoyl)-5-methylpyrrolidine-2-carbonyloxy)acetyl)-8-oxo-8,9,10,11-tetrahydro-5H-dibenzo[c,g]chromen-9-yl) 4-methylpyrrolidine-1,2-dicarboxylate (441 mg, 0.55 mmol) and NH$_4$OAc (5 g, 65.0 mmol) were suspended in a solution of 10:1 PhMe/2-methoxyethanol (11 mL). The stirred reaction mixture was heated to 110° C. for 7 h, then cooled to RT and diluted with EtOAc. The organic phase was washed with water, saturated aqueous NaHCO$_3$, and brine, then dried over MgSO$_4$, filtered and concentrated under reduced pressure. The crude residue was purified by silica column chromatography (0% to 30% MeOH/EtOAc) to afford tert-butyl (2S,4S)-2-[9-(2-{(2S,5S)-1-[N-(methoxycarbonyl)-L-valyl]-5-methylpyrrolidin-2-yl}-1H-imidazol-5-yl)-1,4,5,11-tetrahydroisochromeno[4',3':6,7]naphtho[1,2-d]imidazol-2-yl]-4-methylpyrrolidine-1-carboxylate (266 mg, 63%).

Tert-butyl (2S,4S)-2-[9-(2-{(2S,5S)-1-[N-(methoxycarbonyl)-L-valyl]-4-methylpyrrolidin-2-yl}-1H-imidazol-5-yl)-1,11-dihydroisochromeno[4',3':6,7]naphtho[1,2-d]imidazol-2-yl]-4-methylpyrrolidine-1-carboxylate Tert-butyl (2S,4S)-2-[9-(2-{(2S,5S)-1-[N-(methoxycarbonyl)-L-valyl]-5-methylpyrrolidin-2-yl}-1H-imidazol-5-yl)-1,4,5,11 tetrahydroisochromeno[4',3':6,7]naphtho[1,2-d]imidazol-2-yl]-4-methylpyrrolidine-1-carboxylate (266 mg, 0.35 mmol) was suspended in DCM (7 mL) and activated MnO$_2$ (908 mg, 10.45 mmol) was added in a single portion. The reaction mixture was stirred overnight. After stirring for 15 h, additional activated MnO$_2$ (500 mg, 5.75 mmol) was added in a single portion.

After stirring 2 h at 35° C., the mixture was cooled to rt and the slurry was filtered over celite. The filter cake was washed with copious CH$_2$Cl$_2$ and MeOH and the filtrate was concentrated under reduced pressure. The crude material was taken on to the next step without further purification to afford tert-butyl (2S,4S)-2-[9-(2-{(2S,5S)-1-[N-(methoxycarbonyl)-L-valyl]-4-methylpyrrolidin-2-yl}-1H-imidazol-5-yl)-1,11-dihydroisochromeno[4',3':6,7]naphtho[1,2-d]imidazol-2-yl]-4-methylpyrrolidine-1-carboxylate (266 mg, quant).

Methyl {(2S)-1-[(2S,5S)-2-(5-{2-[(2S,4S)-1-{(2S,3R)-3-methoxy-2-[(methoxycarbonyl)amino]butanoyl}-4-methylpyrrolidin-2-yl]-1,11-dihydroisochromeno[4',3':6,7]naphtho[1,2-d]imidazol-9-yl}-1H-imidazol-2-yl)-5-methylpyrrolidin-1-yl]-3-methyl-1-oxobutan-2-yl}carbamate Tert-butyl (2S,4S)-2-[9-(2-{(2S,5S)-1-[N-(methoxycarbonyl)-L-valyl]-4-methylpyrrolidin-2-yl}-1H-imidazol-5-yl)-1,11-dihydroisochromeno[4',3':6,7]naphtho[1,2-d]imidazol-2-yl]-4-methylpyrrolidine-1-carboxylate (266 mg, 0.23 mmol) was dissolved in DCM (4 mL), MeOH (1 mL) and HCl (4 M in dioxane, 1 mL) was added. The reaction mixture was stirred for 1.5 h and then concentrated under reduced pressure. The crude residue was treated with (2S,3R)-3-methoxy-2-(methoxycarbonylamino)butanoic acid (44 mg, 0.23 mmol), HATU (87 mg, 0.23 mmol) and DMF (5 mL), then DIPEA (0.3 mL, 1.75 mmol) was added dropwise.

After 30 min, the mixture was diluted with 10% MeOH/EtOAc and washed successively with saturated aqueous NaHCO$_3$ and brine. The organics were dried over MgSO$_4$, filtered and concentrated under reduced pressure. The crude residue was purified by HPLC to afford methyl {(2S)-1-[(2S,5S)-2-(5-{2-[(2S,4S)-1-{(2S,3R)-3-methoxy-2-[(methoxycarbonyl)amino]butanoyl}-4-methylpyrrolidin-2-yl]-1,11-dihydroisochromeno[4',3':6,7]naphtho[1,2-d]imidazol-9-yl}-1H-imidazol-2-yl)-5-methylpyrrolidin-1-yl]-3-methyl-1-oxobutan-2-yl}carbamate (59 mg, 31%). LCMS-ESI$^+$: calculated for C45H54N8O8: 834.41; observed [M+1]$^+$: 836.89. $^1$H NMR (CD$_3$OD): 8.186 (s, 1H), 7.800-7.291 (m, 7H), 5.258-5.213 (dd, 1H, J=7.2, 3.6 Hz), 5.027-4.918 (m, 4H), 4.620 (t, 1H, J=6.8 Hz), 4.246 (m, 1H), 4.116 (m, 1H), 3.972 (d, 1H, J=8.8 Hz), 3.701-3.675 (m, 1H), 3.503 (s, 3H), 3.479 (s, 3H), 3.177 (s, 3H), 2.554-2.191 (m, 3H), 1.906-1.821 (m, 6H), 1.392 (d, 2H, J=6.4 Hz), 1.113-0.728 (m, 12H).

Example NM

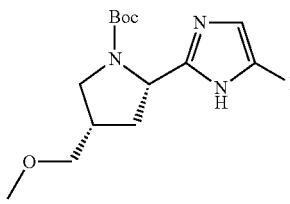

(2S,4S)-tert-butyl 2-(5-iodo-1H-imidazol-2-yl)-4-(methoxymethyl)pyrrolidine-1-carboxylate

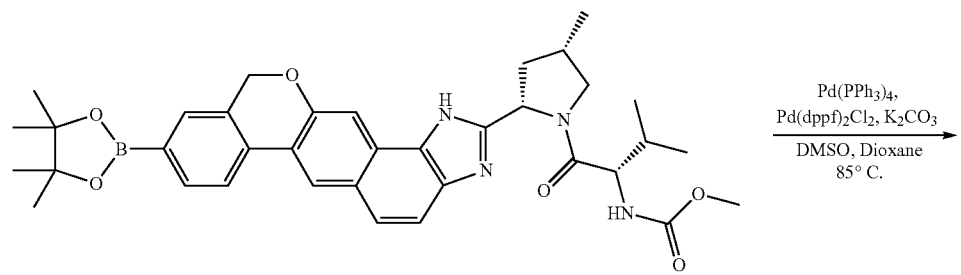

methyl [(2S)-3-methyl-1-{(2S,4S)-4-methyl-2-[9-(4,4,5,5-tetramethyl-1,3,2-dioxaborolan-2-yl)-1,11-dihydroisochromeno[4',3':6,7]naphtho[1,2-d]imidazol-2-yl]pyrrolidin-1-yl}-1-oxobutan-2-yl]carbamate

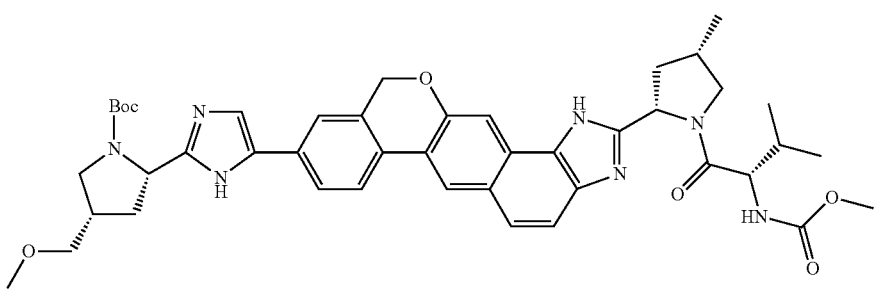

tert-butyl (2S,4S)-2-[5-(2-{(2S,4S)-1-[N-(methoxycarbonyl)-L-valyl]-4-methylpyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate

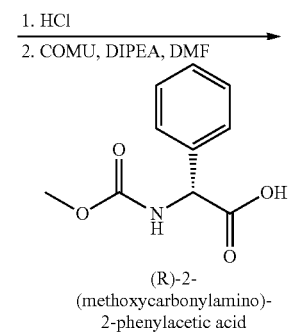

(R)-2-(methoxycarbonylamino)-2-phenylacetic acid

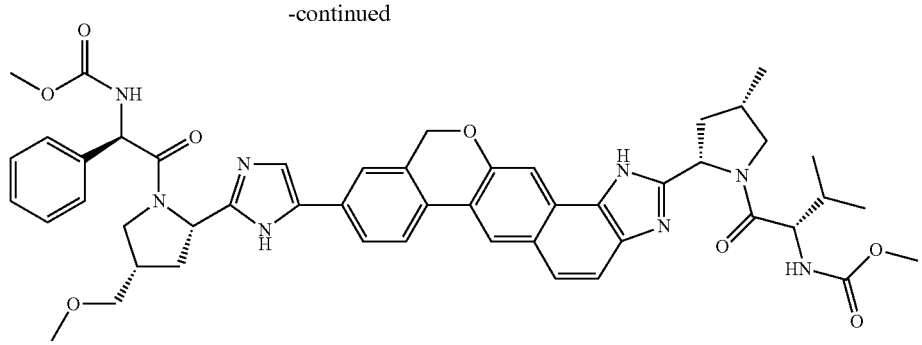

methyl {(1R)-2-[(2S,4S)-2-(5-{2-[(2S,4S)-1-{(2S)-2-[(methoxycarbonyl)amino]-
3-methylbutanoyl}-4-methylpyrrolidin-2-yl]-1,11-
dihydroisochromeno[4',3':6,7]naphtho[1,2-d]imidazol-9-yl}-1H-imidazol-2-yl)-
4-(methoxymethyl)pyrrolidin-1-yl]-2-oxo-1-phenylethyl}carbamate Tert-butyl (2S,4S)-2-[5-(2-{(2S,4S)-1-[N-(methoxy-carbonyl)-L-valyl]-4-methylpyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate Methyl [(2S)-3-methyl-1-{(2S,4S)-4-methyl-2-[9-(4,4,5,5-tetramethyl-1,3,2-dioxaborolan-2-yl)-1,11-dihydroisochromeno[4',3':6,7]naphtho[1,2-d]imidazol-2-yl]pyrrolidin-1-yl}-1-oxobutan-2-yl]carbamate (312 mg, 0.49 mmol), methyl(S)-1-((2S,4S)-2-(5-iodo-1H-imidazol-2-yl)-4-(methoxymethyl)pyrrolidin-1-yl)-3-methyl-1-oxobutan-2-ylcarbamate (219 mg, 0.54 mmol), Pd(PPh₃)₄ (58 mg, 0.05 mmol), PdCl₂(dppf)₂ (36 mg, 0.05 mmol), and K₂CO₃ (2M in H₂O, 0.8 mL, 1.6 mmoL) were combined in DMSO (5 mL) and dioxane (5 mL). The mixture was degassed with bubbling N₂ for 10 min then heated to 95° C. for 5 h. After cooling, the reaction mixture was diluted with EtOAc, and washed successively with saturated aqueous NaHCO₃ and brine. The organics were dried over MgSO₄, filtered and concentrated under reduced pressure. The crude residue was purified by silica column chromatography (0%-30% MeOH/EtOAc) to afford tert-butyl (2S,4S)-2-[5-(2-{(2S,4S)-1-[N-(methoxy-carbonyl)-L-valyl]-4-methylpyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate (166 mg, 43%).

Methyl {(1R)-2-[(2S,4S)-2-(5-{2-[(2S,4S)-1-{(2S)-2-[(methoxycarbonyl)amino]-3-methylbutanoyl}-4-methylpyrrolidin-2-yl]-1,11-dihydroisochromeno[4',3':6,7]naphtho[1,2-d]imidazol-9-yl}-1H-imidazol-2-yl)-4-(methoxymethyl)pyrrolidin-1-yl]-2-oxo-1-phenylethyl}carbamate Tert-butyl (2S,4S)-2-[5-(2-{(2S,4S)-1-[N-(methoxycarbonyl)-L-valyl]-4-methylpyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate (166 mg, 0.21 mmol) was dissolved in DCM (4 mL), MeOH (1 mL) and HCl (4 M in dioxane, 1 mL) was added. The reaction mixture was stirred for 2 h and then concentrated under reduced pressure. The crude residue was treated with (R)-2-(methoxycarbonylamino)-2-phenylacetic acid (44 mg, 0.21 mmol), COMU (100 mg, 0.21 mmol) and DMF (5 mL), then DIPEA (0.18 mL, 1.05 mmol) was added dropwise. After 1 h, the mixture was diluted with 10% MeOH/EtOAc and washed successively with saturated aqueous NaHCO₃ and brine. The organics were dried over MgSO₄, filtered and concentrated under reduced pressure. The crude residue was purified by HPLC to afford methyl {(1R)-2-[(2S,4S)-2-(5-{2-[(2S,4S)-1-{(2S)-2-[(methoxycarbonyl)amino]-3-methylbutanoyl}-4-methylpyrrolidin-2-yl]-1,11-dihydroisochromeno[4',3':6,7]naphtho[1,2-d]imidazol-9-yl}-1H-imidazol-2-yl)-4-(methoxymethyl)pyrrolidin-1-yl]-2-oxo-1-phenylethyl}carbamate (71 mg, 38%). LCMS-ESI¹: calculated for C49H54N8O8: 882.41; observed [M+1]⁺: 884.34. ¹H NMR (CD₃OD): 8.462 (s, 1H), 8.029-7.471 (m, 7H), 7.394-7.343 (m, 5H), 5.410 (d, 2H, J=6.8 Hz), 5.300 (m, 1H), 5.233 (m, 2H), 4.341 (m, 1H), 4.236 (d, 1H, J=7.2 Hz), 3.603 (s, 3H), 3.551 (s, 3H), 3.522-3.241 (m, 8H), 2.650 (m, 1H), 2.550 (m, 2H), 1.977-1.926 (m, 4H), 1.221 (d, 3H, J=3.2 Hz), 0.897-0.779 (dd, 6H, J=19.2, 6.8 Hz).

Example NO

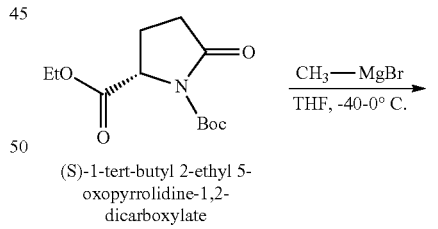

(S)-1-tert-butyl 2-ethyl 5-oxopyrrolidine-1,2-dicarboxylate

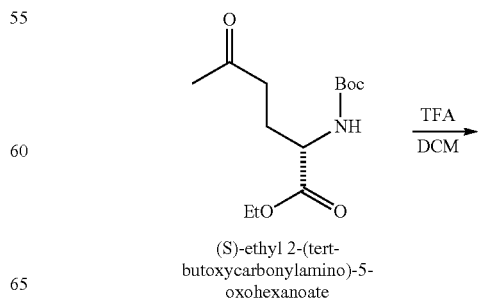

(S)-ethyl 2-(tert-butoxycarbonylamino)-5-oxohexanoate

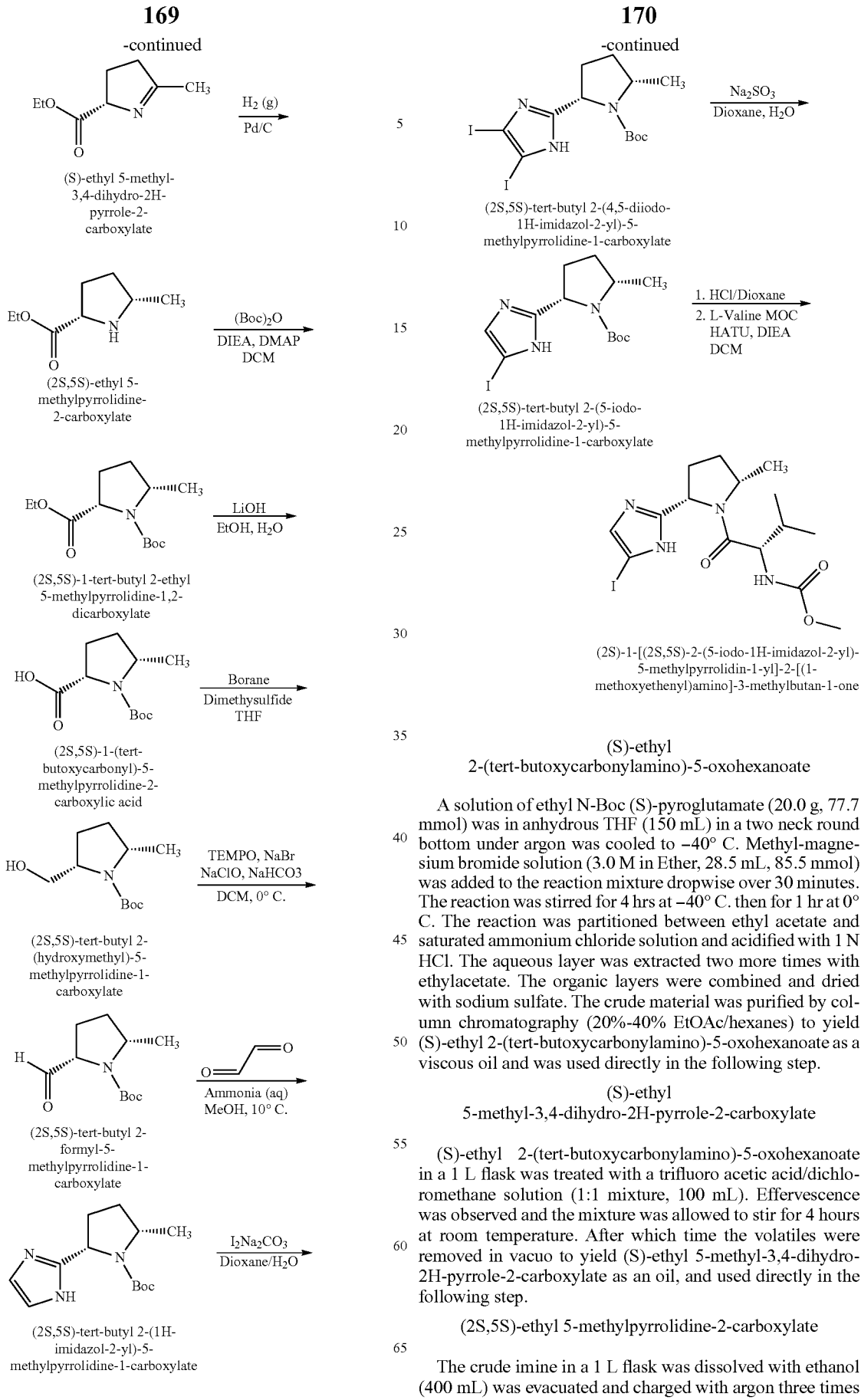

(S)-ethyl 2-(tert-butoxycarbonylamino)-5-oxohexanoate

A solution of ethyl N-Boc (S)-pyroglutamate (20.0 g, 77.7 mmol) was in anhydrous THF (150 mL) in a two neck round bottom under argon was cooled to −40° C. Methyl-magnesium bromide solution (3.0 M in Ether, 28.5 mL, 85.5 mmol) was added to the reaction mixture dropwise over 30 minutes. The reaction was stirred for 4 hrs at −40° C. then for 1 hr at 0° C. The reaction was partitioned between ethyl acetate and saturated ammonium chloride solution and acidified with 1 N HCl. The aqueous layer was extracted two more times with ethylacetate. The organic layers were combined and dried with sodium sulfate. The crude material was purified by column chromatography (20%-40% EtOAc/hexanes) to yield (S)-ethyl 2-(tert-butoxycarbonylamino)-5-oxohexanoate as a viscous oil and was used directly in the following step.

(S)-ethyl 5-methyl-3,4-dihydro-2H-pyrrole-2-carboxylate (S)-ethyl 2-(tert-butoxycarbonylamino)-5-oxohexanoate in a 1 L flask was treated with a trifluoro acetic acid/dichloromethane solution (1:1 mixture, 100 mL). Effervescence was observed and the mixture was allowed to stir for 4 hours at room temperature. After which time the volatiles were removed in vacuo to yield (S)-ethyl 5-methyl-3,4-dihydro-2H-pyrrole-2-carboxylate as an oil, and used directly in the following step.

(2S,5S)-ethyl 5-methylpyrrolidine-2-carboxylate

The crude imine in a 1 L flask was dissolved with ethanol (400 mL) was evacuated and charged with argon three times (3×). Palladium on carbon (apprx. 750 mg, 10% w/w, dry) was added and the reaction was evacuated of gas and charged with hydrogen gas (3×). The reaction was allowed to stir under atmospheric hydrogen for 16 hours. The mixture was filtered through a plug of celite and the filtrate was concentrated in vacuo. Diethyl ether was added to the oil and a precipitate formed. The mixture was filtered to yield (2S,5S)-ethyl 5-methylpyrrolidine-2-carboxylate, as a white solid (10.6 g, 67.4 mmol, 86.7% over three steps). $^1$H NMR (400 MHz, cdcl$_3$) δ 4.48 (dd, 1H), 4.27 (q, 2H), 3.92-3.80 (m, 1H), 2.52-2.36 (m, 1H), 2.32-2.13 (m, 2H), 1.75-1.60 (m, 1H), 1.51 (d, 3H), 1.30 (t, 3H).

(2S,5S)-1-tert-butyl 2-ethyl 5-methylpyrrolidine-1,2-dicarboxylate

To a solution of (2S,5S)-ethyl 5-methylpyrrolidine-2-carboxylate (7.0 g, 44.5 mmol) in dichloromethane (250 mL), ditertbutylanhydride (10.7 g, 49.0 mmol), diisopropylethylamine (17.1 mL, 98.0 mmol) dropwise over 10 minutes, and dimethyl amino pyridine (0.27 g, 2.23 mmol) were added successively. Effervescence was observed and the mixture was allowed to stir for 16 hours at room temperature. The reaction was washed with HCl (250 mL, of 1N). The organic layer was then dried with sodium sulfate. The crude material was purified by column chromatography (5%-25% EtOAc/hexanes) to yield (2S,5S)-1-tert-butyl 2-ethyl 5-methylpyrrolidine-1,2-dicarboxylate as an oil (6.46 g, 25.1 mmol, 56%). LCMS-ESI$^+$: calc'd for $C_{13}H_{23}NO_4$: 257.16 (M$^+$). Found: 258.70 (M+H$^+$).

(2S,5S)-1-(tert-butoxycarbonyl)-5-methylpyrrolidine-2-carboxylic acid

To a solution of (2S,5S)-1-tert-butyl 2-ethyl 5-methylpyrrolidine-1,2-dicarboxylate (6.46 g, 25.1 mmol) in ethanol (20 mL) was added lithium hydroxide mono hydrate (2.11 g, 50.2 mmol) and deionized water (12 mL). The mixture was allowed to stir for 16 hours then partitioned between ethylacetate and a 1:1 mixture of saturated brine and 1N HCl. The aqueous layer was extracted an additional time with ethyl acetate. The organic layers were combined, dried with sodium sulfate and the solvent was removed in vacuo to yield (2S,5S)-1-(tert-butoxycarbonyl)-5-methylpyrrolidine-2-carboxylic acid as a white solid (quant.) and was used directly in the following step.

(2S,5S)-tert-butyl 2-(hydroxymethyl)-5-methylpyrrolidine-1-carboxylate

To a solution of (2S,5S)-1-(tert-butoxycarbonyl)-5-methylpyrrolidine-2-carboxylic acid (5.91 g, 25.8 mmol) in tetrahydrofuran at 0° C., was added borane in dimethylsulfide (1.0 M, 3.4 mL, 34 mmol) dropwise. The reaction was stirred for 4 hours at 0° C. then 18 hours at room temperature. The mixture was then cooled to 0° C. and methanol (70 mL) was added dropwise. The reaction was warmed to room temperature and the solvents were removed in vacuo. The residue was taken up in dichloromethane (200 mL) and extracted with saturated sodium bicarbonate. The organic layer was dried with sodium sulfate and the solvent was removed in vacuo to yield (2S,5S)-tert-butyl 2-(hydroxymethyl)-5-methylpyrrolidine-1-carboxylate as a clear oil (5.15 g, 23.9 mmol, 93%) and was used directly in the following step.

(2S,5S)-tert-butyl 2-formyl-5-methylpyrrolidine-1-carboxylate

To a solution of (2S,5S)-tert-butyl 2-(hydroxymethyl)-5-methylpyrrolidine-1-carboxylate (5.15 g, 23.9 mmol) in dichloromethane, was added TEMPO (0.075 g, 0.48 mmol), sodium bromide (0.246 g, 2.39 mmol) and sodium bicarbonate (0.442 g, 5.26 mmol). Sodium hypochlorite (2.67 g, 35.9 mmol) of a 6% solution was added and the biphasic mixture was vigorously stirred for 2 hours at room temperature. The reaction mixture was extracted two times with dichloromethane (2×100 mL). The organic layers were combined and washed with saturated sodium thiosulfate solution, dried with sodium sulfate and the solvent was removed in vacuo to yield (2S,5S)-tert-butyl 2-formyl-5-methylpyrrolidine-1-carboxylate (3.9 g, 18.29 mmol, 77%) as a slight colored oil and was used directly in the following step.

(2S,5S)-tert-butyl 2-(1H-imidazol-2-yl)-5-methylpyrrolidine-1-carboxylate

To a solution of (2S,5S)-tert-butyl 2-formyl-5-methylpyrrolidine-1-carboxylate (3.9 g, 18.30 mmol) in MeOH (15 mL) and ammonium hydroxide (15 mL, 99.9%), glyoxal (11.7 mL, 40% w/v in water, 102.40 mmol) was added dropwise. The biphasic mixture turned orange and turbid. The reaction was stirred vigorously overnight at room temperature. The solvent was removed in vacuo. The crude mixture was redissolved in ethyl acetate and washed with water. The aqueous layer was washed an additional time with ethyl acetate. The organic layers were combined and washed with brine, dried with sodium sulfate and the solvent was removed in vacuo. The crude material was purified by column chromatography 85% to 100% ethyl acetate in hexanes to yield (2S,5S)-tert-butyl 2-(1H-imidazol-2-yl)-5-methylpyrrolidine-1-carboxylate as an off white solid (3.47 g, 13.8 mmol, 75%). LCMS-ESI$^+$: calc'd for $C_{13}H_{21}N_3O_2$: 251.16 (M$^+$). Found: 252.20 (M+H$^+$).

(2S,5S)-tert-butyl 2-(4,5-diiodo-1H-imidazol-2-yl)-5-methylpyrrolidine-1-carboxylate A 500 mL round bottom flask was charged with (2S,5S)-tert-butyl 2-(1H-imidazol-2-yl)-5-methylpyrrolidine-1-carboxylate (3.47 g, 13.8 mmol), iodine (7.7 g, 30.4 mmol) and sodium carbonate (4.54 g, 42.8 mmol). Dioxane (70 mL) and water (45 mL) was added to mixture and the reaction was stirred vigorously overnight in the dark. The reaction was then partitioned between ethyl acetate and a 10% aqueous solution of sodium thiosulfate and extracted. The aqueous layer was extracted an additional time with ethyl acetate. The organic layers were combined, dried with sodium sulfate and the solvent was removed in vacuo. The crude material was filtered through a plug of silica with 25% ethyl acetate in hexanes to yield (2S,5S)-tert-butyl 2-(4,5-diiodo-1H-imidazol-2-yl)-5-methylpyrrolidine-1-carboxylate as a white solid (4.28 g, 8.50 mmol, 62%). LCMS-ESI$^+$: calc'd for $C_{13}H_{19}I_2N_3O_2$: 502.96 (M$^l$). Found: 503.94 (M+H$^l$).

(2S,5S)-tert-butyl 2-(5-iodo-1H-imidazol-2-yl)-5-methylpyrrolidine-1-carboxylate To a solution of (2S,5S)-tert-butyl 2-(4,5-diiodo-1H-imidazol-2-yl)-5-methylpyrrolidine-1-carboxylate (4.28 g, 8.50 mmol) in ethanol (75 mL) and water (75 mL), sodium thiosulfate (10.72 g, 85.1 mmol) was added and the reaction mixture was stirred vigorously for 1 hour at 100° C., 16 hours at 90° C., and 5 hours at 100° C. The reaction mixture was partitioned between ethyl acetate and water. The aqueous layer was washed additionally with ethyl acetate and the organic layers were combined. The organic layer was dried with sodium sulfate, concentrated and the crude material was purified by column chromatography to yield (2S,5S)-tert-butyl 2-(5-iodo-1H-imidazol-2-yl)-5-methylpyrrolidine-1-carboxylate as a white solid (2.34 g, 6.20 mmol, 73%). $^1$H NMR (400 MHz, cdcl$_3$) δ 7.04 (s, 1H), 4.89 (dd, 1H), 3.92 (m, 1H), 2.91 (s, 1H), 2.18-2.06 (m, 2H), 1.78 (m, 1H), 1.52 (m, 1H), 1.48 (s, 9H), 1.13 (d, 3H).

(2S)-1-[(2S,5S)-2-(5-iodo-1H-imidazol-2-yl)-5-methylpyrrolidin-1-yl]-2-[(1-methoxyethenyl)amino]-3-methylbutan-1-one A round bottom flask was charged with (2S,5S)-tert-butyl 2-(5-iodo-1H-imidazol-2-yl)-5-methylpyrrolidine-1-carboxylate (1.5 g, 3.98 mmol) and treated with an excess of hydrochloric acid (100 mL of 4.0M in dioxane). The mixture was stirred vigorously for 3 hours in which time a precipitate formed and the solvent was removed in vacuo. To a mixture of the crude intermediate, (S)-2-(methoxycarbonylamino)-3-methylbutanoic acid (0.836 g, 4.77 mmol), HATU (1.81 g, 4.77 mmol) in dichloromethane (25 mL), diisopropylethylamine (3.46 mL, 19.9 mmol) was then added dropwise and was stirred over night under nitrogen. The reaction mixture was partitioned ethyl acetate and saturated sodium bicarbonate. The organic layer was dried with sodium sulfate, the solvent removed in vacuo. The crude product was purified by column chromatography to yield (2S)-1-[(2S,5S)-2-(5-iodo-1H-imidazol-2-yl)-5-methylpyrrolidin-1-yl]-2-[(1-methoxyethenyl)amino]-3-methylbutan-1-one as a white solid (1.63 g, 3.75 mmol, 94%). LCMS-ESI$^+$: calc'd for $C_{15}H_{23}IN_4O_3$: 434.08 (M$^+$). Found: 435.51 (M+H$^+$).

Example NP

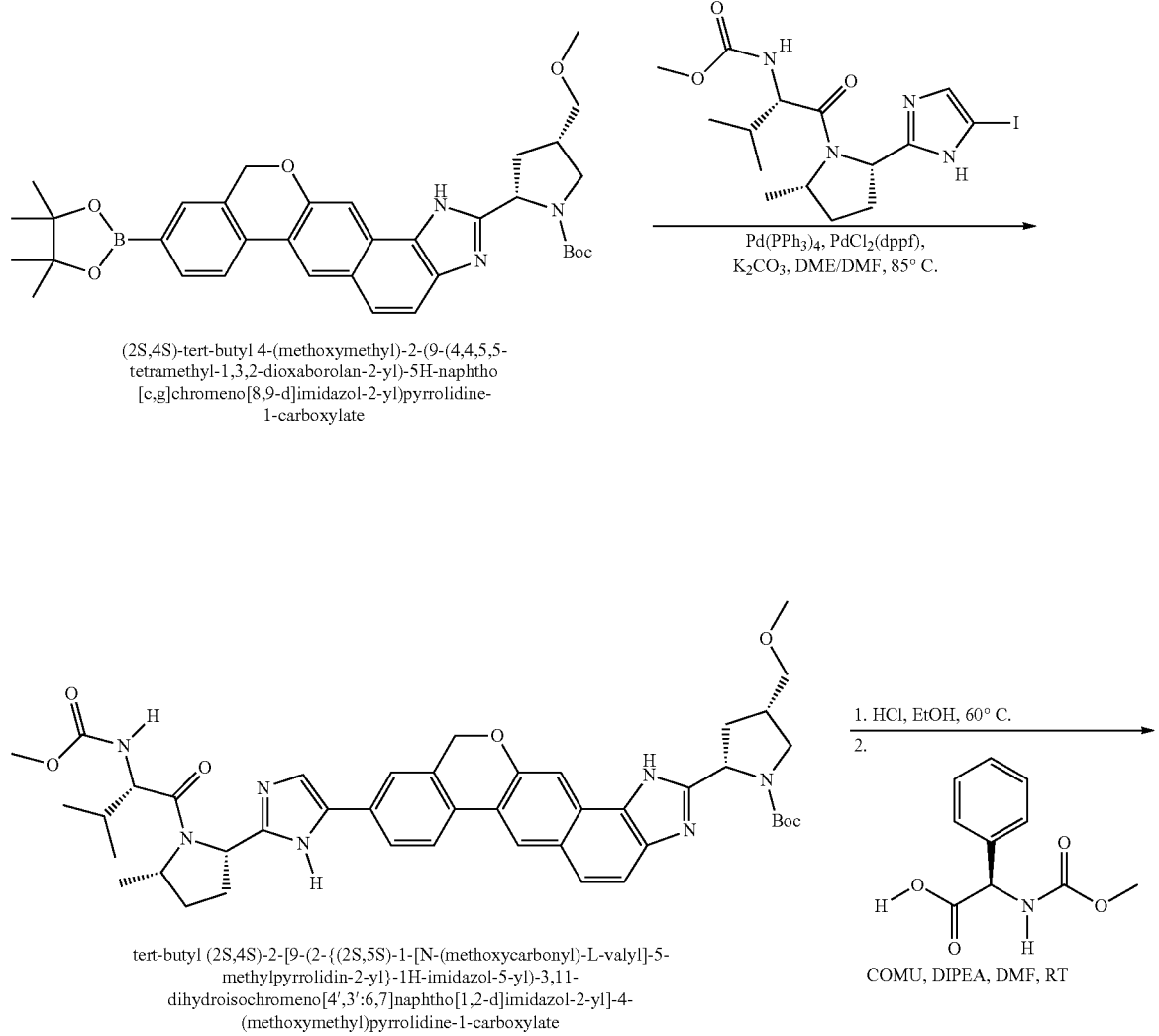

(2S,4S)-tert-butyl 4-(methoxymethyl)-2-(9-(4,4,5,5-tetramethyl-1,3,2-dioxaborolan-2-yl)-5H-naphtho[c,g]chromeno[8,9-d]imidazol-2-yl)pyrrolidine-1-carboxylate tert-butyl (2S,4S)-2-[9-(2-{(2S,5S)-1-[N-(methoxycarbonyl)-L-valyl]-5-methylpyrrolidin-2-yl}-1H-imidazol-5-yl)-3,11-dihydroisochromeno[4′,3′:6,7]naphtho[1,2-d]imidazol-2-yl]-4-(methoxymethyl)pyrrolidine-1-carboxylate

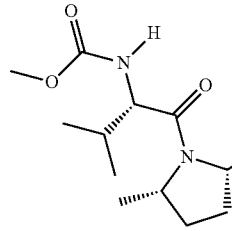
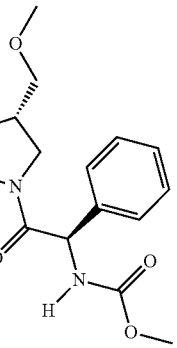

Methyl {(2S)-1-[(2S,5S)-2-(5-{2-[(2S,4S)-1-{(2R)-2-[(methoxycarbonyl)amino]-2-phenylacetyl}-4-(methoxymethyl)pyrrolidin-2-yl]-1,11 dihydroisochromeno[4',3':6,7]naphtho[1,2-d]imidazol-9-yl}-1H-imidazol-2-yl)-5-methylpyrrolidin-1-yl]-3-methyl-1-oxobutan-2-yl}carbamate

Methyl {(2S)-1-[(2S,5S)-2-(5-{2-[(2S,4S)-1-{(2R)-2-[(methoxycarbonyl)amino]-2-phenylacetyl}-4-(methoxymethyl)pyrrolidin-2-yl]-1,11 dihydroisochromeno[4',3':6,7]naphtho[1,2-d]imidazol-9-yl}-1H-imidazol-2-yl)-5-methylpyrrolidin-1-yl]-3-methyl-1-oxobutan-2-yl}carbamate The synthesis of this compound was prepared according to the procedure of example LR-1 with the following modification. During the Suzuki coupling, (2S)-1-[(2S,5S)-2-(5-iodo-1H-imidazol-2-yl)-5-methylpyrrolidin-1-yl]-2-[(1-methoxyethenyl)amino]-3-methylbutan-1-one was used in lieu of (2S)-1-[(2S)-2-(5-bromo-1H-imidazol-2-yl)pyrrolidin-1-yl]-2-[(1-methoxyethenyl)amino]-3-methylbutan-1-one.

The crude material was purified by preparative HPLC to provide methyl {(2S)-1-[(2S,5S)-2-(5-{2-[(2S,4S)-1-{(2R)-2-[(methoxycarbonyl)amino]-2-phenylacetyl}-4-(methoxymethyl)pyrrolidin-2-yl]-1,11 dihydroisochromeno[4',3':6,7]naphtho[1,2-d]imidazol-9-yl}-1H-imidazol-2-yl)-5-methylpyrrolidin-1-yl]-3-methyl-1-oxobutan-2-yl}carbamate as a white solid (17 mg, 0.019 mmol, 17%). $^1$H NMR (400 MHz, cd$_3$od) δ 8.63 (s, 1H), 8.19 (d, 1H), 8.04 (m, 1H), 7.87 (m, 2H), 7.66 (m, 2H), 7.52-7.39 (m, 6H), 5.50 (m, 2H), 5.32 (s, 2H), 5.16 (m, 1H), 4.12 (m, 1H), 3.80 (m, 4H), 3.66 (s, 6H), 3.43 (m, 4H), 3.23 (s, 3H), 2.72-1.99 (m, 9H), 1.56 (d, 3H), 1.29 (m, 1H), 0.99 (d, 3H), 0.88 (d, 3H).

Example NQ

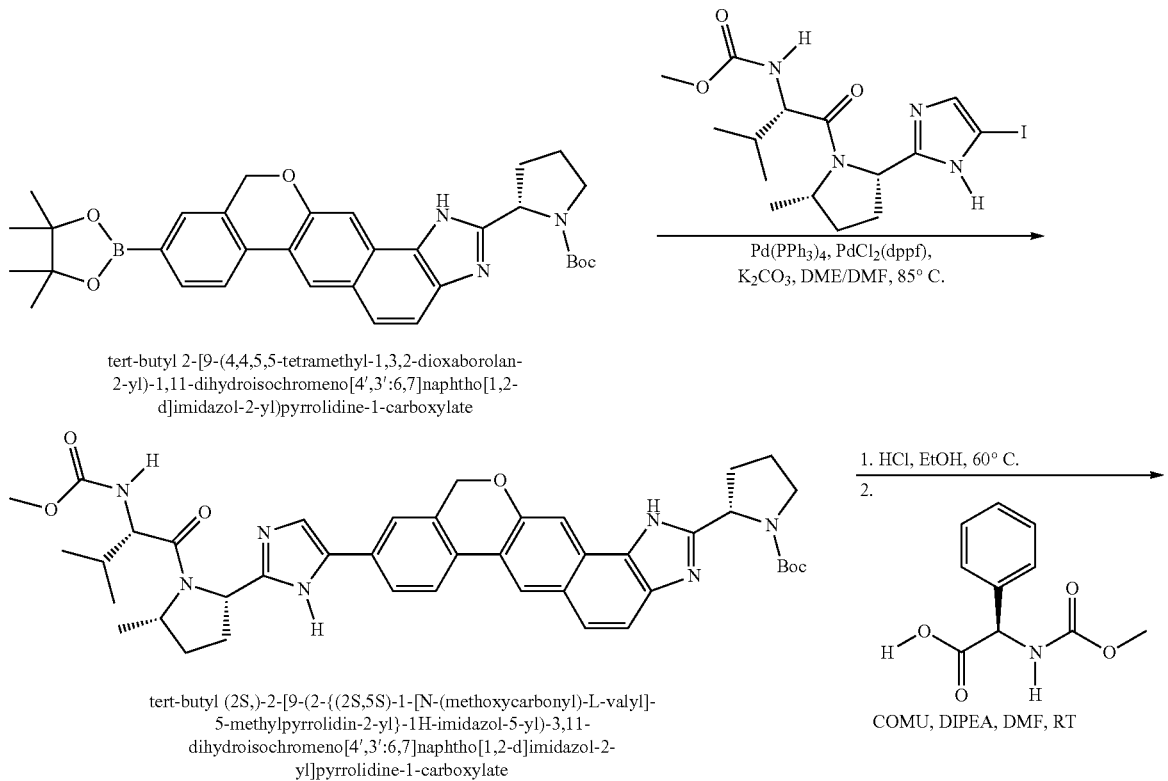

tert-butyl 2-[9-(4,4,5,5-tetramethyl-1,3,2-dioxaborolan-2-yl)-1,11-dihydroisochromeno[4',3':6,7]naphtho[1,2-d]imidazol-2-yl]pyrrolidine-1-carboxylate tert-butyl (2S,)-2-[9-(2-{(2S,5S)-1-[N-(methoxycarbonyl)-L-valyl]-5-methylpyrrolidin-2-yl}-1H-imidazol-5-yl)-3,11-dihydroisochromeno[4',3':6,7]naphtho[1,2-d]imidazol-2-yl]pyrrolidine-1-carboxylate

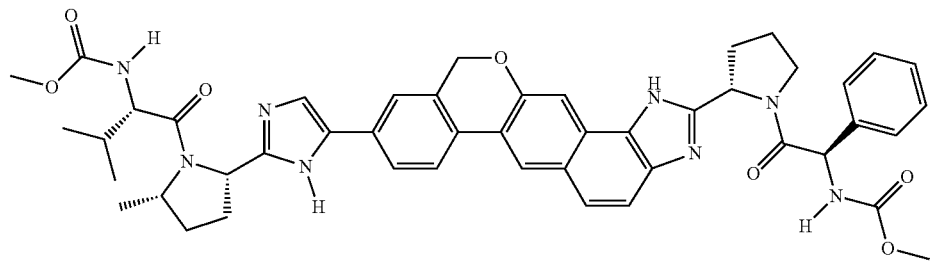

methyl {(2S)-1-[(2S,5S)-2-(5-{2-[(2S)-1-{(2R)-2-[(methoxycarbonyl)amino]-2-phenylacetyl}pyrrolidin-2-yl]-1,11 dihydroisochromeno[4',3':6,7]naphtho[1,2-d]imidazol-9-yl}-1H-imidazol-2-yl)-5-methylpyrrolidin-1-yl]-3-methyl-1-oxobutan-2-yl}carbamate Methyl {(2S)-1-[(2S,5S)-2-(5-{2-[(2S)-1-{(2R)-2-[(methoxycarbonyl)amino]-2-phenylacetyl}pyrrolidin-2-yl]-1,11-dihydroisochromeno[4',3':6,7]naphtho[1,2-d]imidazol-9-yl}-1H-imidazol-2-yl)-5-methylpyrrolidin-1-yl]-3-methyl-1-oxobutan-2-yl}carbamate The synthesis of this compound was prepared according to the procedure of example LQ with the following modification. During the Suzuki coupling, (2S)-1-[(2S,5S)-2-(5-iodo-1H-imidazol-2-yl)-5-methylpyrrolidin-1-yl]-2-[(1-methoxyethenyl)amino]-3-methylbutan-1-one was used in lieu of (2S)-1-[(2S)-2-(5-bromo-1H-imidazol-2-yl)pyrrolidin-1-yl]-2-[(1-methoxyethenyl)amino]-3-methylbutan-1-one.

The crude material was purified by preparative HPLC to provide methyl {(2S)-1-[(2S,5S)-2-(5-{2-[(2S)-1-{(2R)-2-[(methoxycarbonyl)amino]-2-phenylacetyl}pyrrolidin-2-yl]-1,11-dihydroisochromeno[4',3':6,7]naphtho[1,2-d]imidazol-9-yl}-1H-imidazol-2-yl)-5-methylpyrrolidin-1-yl]-3-methyl-1-oxobutan-2-yl}carbamate as a white solid (110 mg, 0.131 mmol, 57%). $^1$H NMR (400 MHz, cd$_3$od) δ 8.65 (s, 1H), 8.21 (d, 1H), 8.04 (m, 2H), 7.91 (s, 1H), 7.81 (m, 1H), 7.67 (m, 2H), 7.46 (m, 6H), 5.59 (s, 1H), 5.50 (dd, 1H), 5.33 (s, 2H), 5.22-5.09 (m, 1H), 4.14 (m, 2H), 3.74 (s, 1H), 3.65 (m, 6H), 3.52-3.37 (m, 2H), 2.60-1.89 (m, 11H), 1.56 (d, 3H), 1.29 (d, 1H), 0.99 (d, 3H), 0.88 (d, 3H).

Example NR

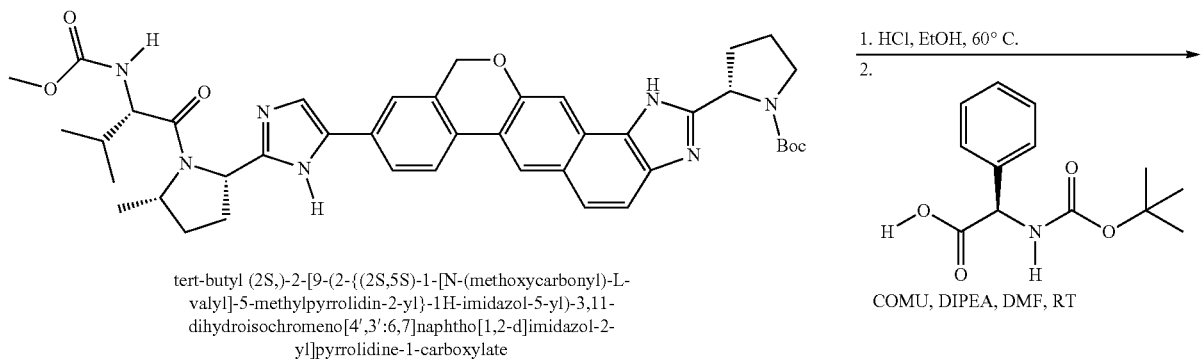

tert-butyl (2S,)-2-[9-(2-{(2S,5S)-1-[N-(methoxycarbonyl)-L-valyl]-5-methylpyrrolidin-2-yl}-1H-imidazol-5-yl)-3,11-dihydroisochromeno[4',3':6,7]naphtho[1,2-d]imidazol-2-yl]pyrrolidine-1-carboxylate

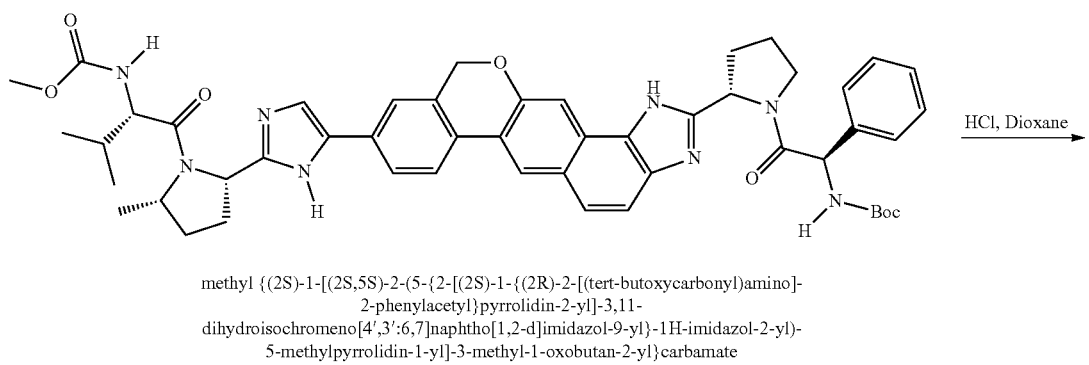

methyl {(2S)-1-[(2S,5S)-2-(5-{2-[(2S)-1-{(2R)-2-[(tert-butoxycarbonyl)amino]-2-phenylacetyl}pyrrolidin-2-yl]-3,11-dihydroisochromeno[4',3':6,7]naphtho[1,2-d]imidazol-9-yl}-1H-imidazol-2-yl)-5-methylpyrrolidin-1-yl]-3-methyl-1-oxobutan-2-yl}carbamate

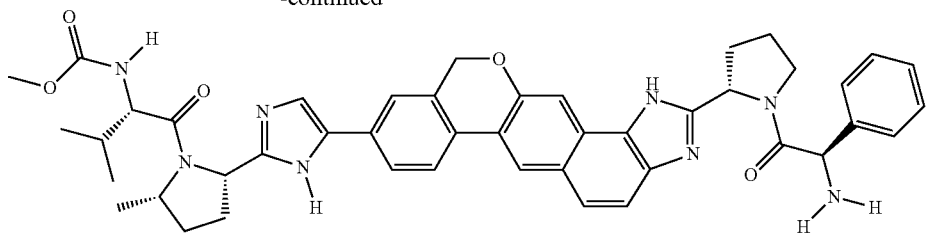

methyl [(2S)-1-[(2S,5S)-2-[5-(2-{(2S)-1-[(2R)-2-amino-
2-phenylacetyl]pyrrolidin-2-yl}-
1,11-dihydroisochromeno[4',3':6,7]naphtho[1,2-d]imidazol-9-yl)-1H-imidazol-2-yl]-5-
methylpyrrolidin-1-yl}-3-methyl-1-oxobutan-2-yl]carbamate Methyl [(2S)-1-{(2S,5S)-2-[5-(2-{(2S)-1-[(2R)-2-
amino-2-phenylacetyl]pyrrolidin-2-yl}-1,11-dihy-
droisochromeno[4',3':6,7]naphtho[1,2-d]imidazol-9-
yl)-1H-imidazol-2-yl]-5-methylpyrrolidin-1-yl}-3-
methyl-1-oxobutan-2-yl]carbamate The synthesis of this compound was prepared according to Example NQ with the following modifications. During the amide coupling, (R)-2-(tert-butoxycarbonylamino)-2-phenylacetic acid was used in lieu of (R)-2-(methoxycarbonylamino)-2-phenylacetic acid. This was then treated with an excess of hydrochloric acid (15 mL, 4.0 M in Dioxane) for 2 hours. The crude product was purified by HPLC to provide methyl [(2S)-1-{(2S,5S)-2-[5-(2-{(2S)-1-[(2R)-2-amino-2-phenylacetyl]pyrrolidin-2-yl}-1,11-dihydroisochromeno[4',3':6,7]naphtho[1,2-d]imidazol-9-yl)-1H-imidazol-2-yl]-5-methylpyrrolidin-1-yl}-3-methyl-1-oxobutan-2-yl] carbamate as a white solid (153 mg, 0.196 mmol, 74%). $^1$H NMR (400 MHz, cd$_3$od) δ 8.63 (s, 1H), 8.20 (d, 1H), 7.99 (m, 1H), 7.93 (m, 2H), 7.80 (m, 2H), 7.72-7.64 (m, 2H), 7.63-7.52 (m, 5H), 5.52 (dd, 1H), 5.44 (m, 1H), 5.33 (s, 2H), 5.21-5.10 (m, 1H), 4.80 (m, 2H), 4.14 (m, 1H), 4.02 (m, 1H), 3.75 (s, 1H), 3.67 (s, 3H), 3.12 (dd, 1H), 2.72-2.13 (m, 7H), 2.00 (m, 3H), 1.56 (d, 3H), 1.30 (d, 1H), 0.98 (d, 3H), 0.88 (d, 3H).

Example OE

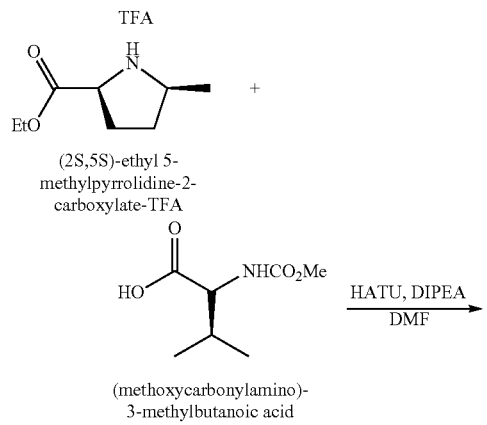

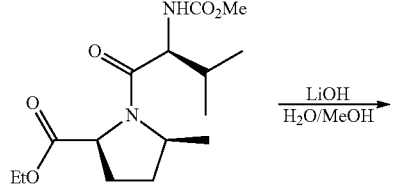

(2S,5S)-ethyl 1-((S)-2-
(methoxycarbonylamino)-3-
methylbutanoyl)-5-
methylpyrrolidine-2-carboxylate (2S,5S)-1-((S)-2-
(methoxycarbonylamino)-3-
methylbutanoyl)-5-
methylpyrrolidine-2-
carboxylate acid (2S,5S)-Ethyl 1-((S)-2-(methoxycarbonylamino)-3-
methylbutanoyl)-5-methylpyrrolidine-2-carboxylate (2S,5S)-Ethyl 5-methylpyrrolidine-2-carboxylate-TFA (10.0 g, 39.3 mmol), (S)-2-(methoxycarbonylamino)-3-methylbutanoic acid (6.88 g, 39.3 mmol) and HATU (14.9 g, 39.3 mmol) were combined in DMF (100 mL) and DIPEA (15.0 mL, 86.5 mmol) was added. After stirring for 1 h at RT, the reaction mixture was diluted with EtOAc. The organic phase was washed successively with 10% HCl, saturated aqueous NaHCO$_3$ and brine, then dried over MgSO$_4$, filtered and concentrated under reduced pressure to afford (2S,5S)-ethyl 1-((S)-2-(methoxycarbonylamino)-3-methylbutanoyl)-5-methylpyrrolidine-2-carboxylate. The crude material was carried on without further purification.

(2S,5S)-1-((S)-2-(Methoxycarbonylamino)-3-meth-
ylbutanoyl)-5-methylpyrrolidine-2-carboxylic acid (2S,5S)-Ethyl 1-((S)-2-(methoxycarbonylamino)-3-methylbutanoyl)-5-methylpyrrolidine-2-carboxylate (39.3 mmol, assuming complete conversion from the previous transformation) was suspended in MeOH (200 mL) and aqueous LiOH (1.0 M, 100 mL, 100 mmol) was added. The reaction mixture was stirred o/n, then concentrated under reduced pressure to remove most of the MeOH. The aqueous solution was washed 2× with DCM before being acidified to pH~1-2 with 10% HCl. The acidic aqueous phase was then extracted 5× with EtOAc. The combined EtOAc extracts were dried over MgSO₄ filtered and concentrated under reduced pressure to afford (2S,5S)-1-((S)-2-(Methoxycarbonylamino)-3-methylbutanoyl)-5-methylpyrrolidine-2-carboxylic acid (6.89 g, 56% over 2 steps).

Example OF

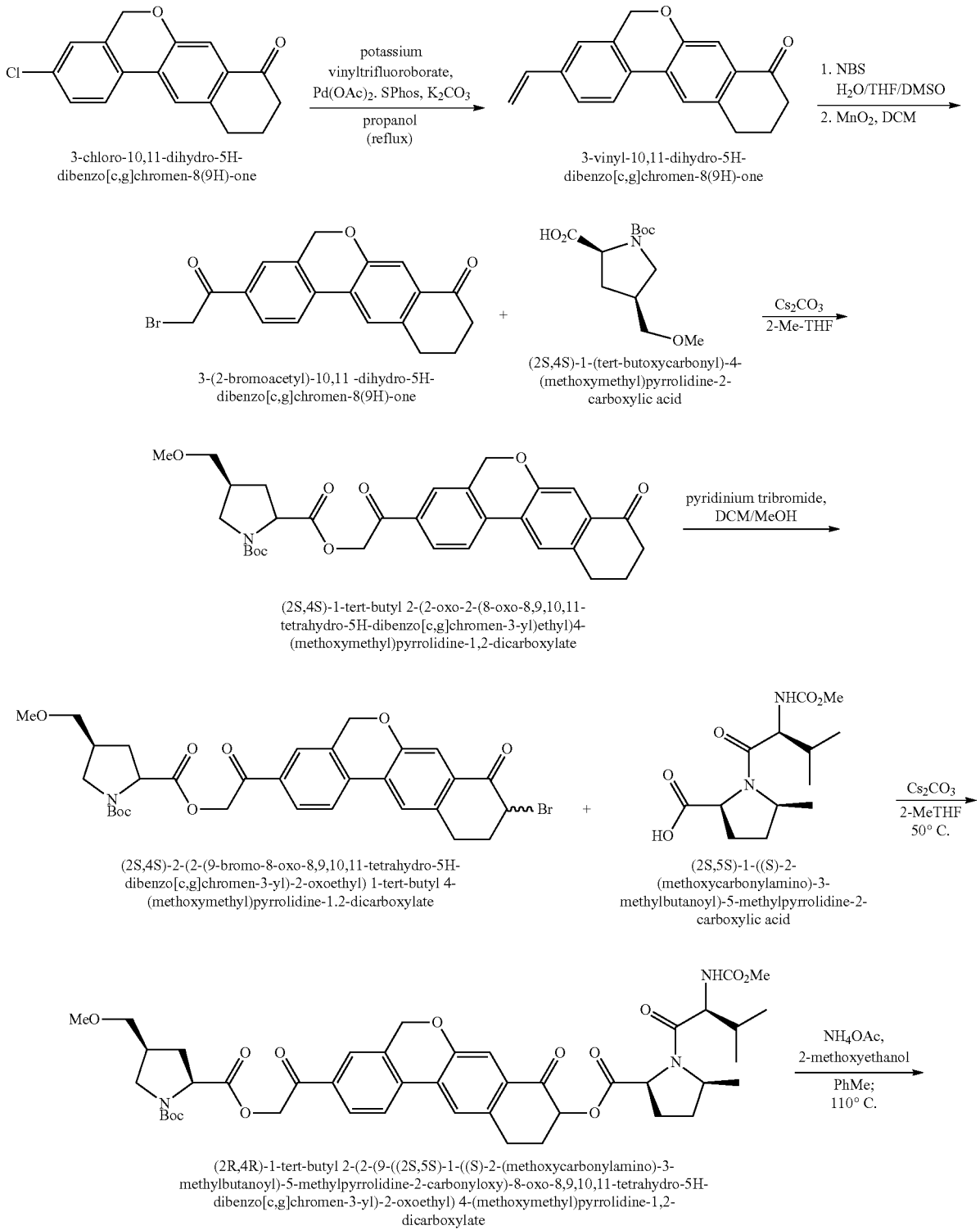

-continued

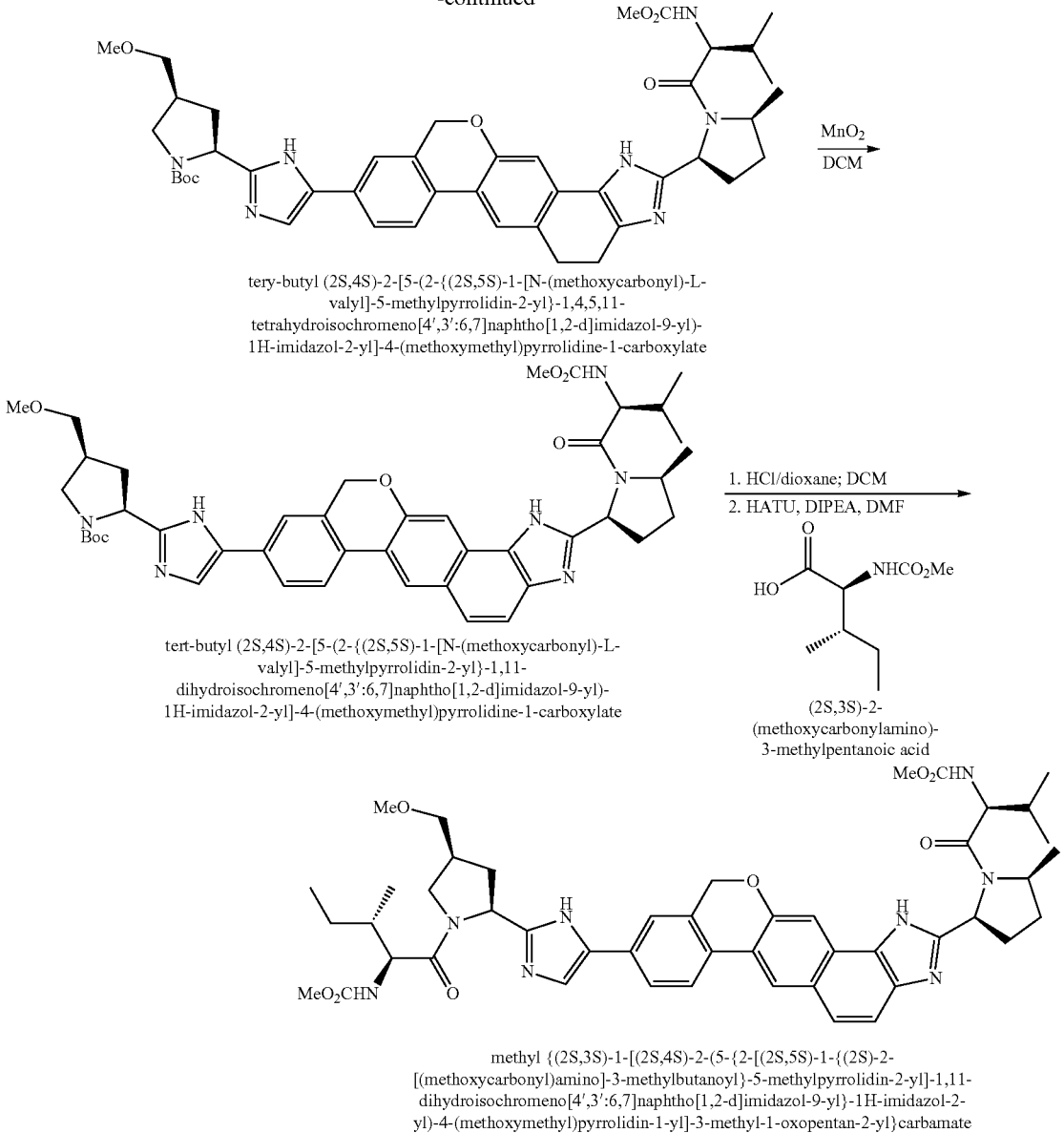

tert-butyl (2S,4S)-2-[5-(2-{(2S,5S)-1-[N-(methoxycarbonyl)-L-valyl]-5-methylpyrrolidin-2-yl}-1,4,5,11-tetrahydroisochromeno[4',3':6,7]naphtho[1,2-d]imidazol-9-yl)-1H-imidazol-2-yl]-4-(methoxymethyl)pyrrolidine-1-carboxylate tert-butyl (2S,4S)-2-[5-(2-{(2S,5S)-1-[N-(methoxycarbonyl)-L-valyl]-5-methylpyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate (2S,3S)-2-(methoxycarbonylamino)-3-methylpentanoic acid methyl {(2S,3S)-1-[(2S,4S)-2-(5-{2-[(2S,5S)-1-{(2S)-2-[(methoxycarbonyl)amino]-3-methylbutanoyl}-5-methylpyrrolidin-2-yl]-1,11-dihydroisochromeno[4',3':6,7]naphtho[1,2-d]imidazol-9-yl}-1H-imidazol-2-yl)-4-(methoxymethyl)pyrrolidin-1-yl]-3-methyl-1-oxopentan-2-yl}carbamate

3-Vinyl-10,11-dihydro-5H-dibenzo[c,g]chromen-8(9H)-one

A 3-neck oven-dried 500 mL round-bottom flask was cooled under Ar, then charged with 3-Chloro-10,11-dihydro-5H-dibenzo[c,g]chromen-8(9H)-one (12.0 g, 42.1 mmol), potassium vinyltrifluoroborate (8.47 g, 6.32 mmol), Pd(OAc)$_2$ (473 mg, 2.11 mmol), SPhos (1.74 g, 4.25 mmol), K$_2$CO$_3$ (17.5 g, 126 mmol) and anhydrous propanol (120 mL). The reaction mixture was sparged with Ar for 16 min, then heated to reflux for 5.5 h. Upon completion, the reaction mixture was cooled to RT and concentrated under reduced pressure. The crude residue was suspended in DCM, then washed with H$_2$O and brine. The organic solution was dried over MgSO$_4$, filtered and concentrated under reduced pressure. The resulting residue was further purified via silica plug, eluting with DCM to afford 3-vinyl-10,11-dihydro-5H-dibenzo[c,g]chromen-8(9H)-one (10.2 g, 87%).

3-(2-Bromoacetyl)-10,11-dihydro-5H-dibenzo[c,g]chromen-8(9H)-one

3-Vinyl-10,11-dihydro-5H-dibenzo[c,g]chromen-8(9H)-one (9.98 g, 36.1 mmol) was dissolved in a stirred solution of THF (70 mL), DMSO (70 mL) and H$_2$O (35 mL). NBS (6.75 g, 37.9 mmol) was added in a single portion and the reaction mixture was stirred at RT for 33 min. Upon completion, the reaction medium was diluted with EtOAc and washed twice with H$_2$O and once with brine. The organic phase was dried over MgSO$_4$, filtered and concentrated under reduced pressure. The resulting crude bromohydrin was suspended in DCM (200 mL) and treated with activated MnO$_2$ (62.7 g, 722 mmol). After stirring for 15 h at RT, the reaction mixture was filtered over celite and the filter cake was rinsed several times with DCM. The combined filtrate (~400 mL) was treated with MeOH (~100 mL) and the mixture was gradually concentrated under reduced pressure, causing solid material to precipitate from solution. When the liquid volume reached ~200 mL, the solid was filtered off and rinsed with MeOH. The concentration/precipitation/filtration/rinsing sequence was performed 2× more, resulting in the collection of 3 crops of powdered 3-(2-bromoacetyl)-10,11-dihydro-5H-dibenzo[c,g]chromen-8(9H)-one (7.49 g, 56% over 2 steps).

(2S,4S)-1-tert-Butyl 2-(2-oxo-2-(8-oxo-8,9,10,11-tetrahydro-5H-dibenzo[c,g]chromen-3-yl)ethyl) 4-(methoxymethyl)pyrrolidine-1,2-dicarboxylate 3-(2-Bromoacetyl)-10,11-dihydro-5H-dibenzo[c,g]chromen-8(9H)-one (7.47 g, 20.1 mmol) and (2S,4S)-1-(tert-butoxycarbonyl)-4-(methoxymethyl)pyrrolidine-2-carboxylic acid (5.22 g, 20.1 mmol) were suspended in 2-Me-THF (75 mL) and treated with $Cs_2CO_3$ (3.27 g, 10.1 mmol). After stirring 4 h at RT, the reaction mixture was diluted with DCM. The organic layer was washed with $H_2O$. The aqueous layer was then back extracted 2× with DCM. The combined organics were dried over $MgSO_4$, filtered and concentrated under reduced pressure. The crude residue was purified by silica column chromatography (10% to 50% EtOAc/DCM) to afford (2S, 4S)-1-tert-butyl 2-(2-oxo-2-(8-oxo-8,9, 10,11-tetrahydro-5H-dibenzo[c,g]chromen-3-yl)ethyl) 4-(methoxymethyl)pyrrolidine-1,2-dicarboxylate (7.73 g, 70%).

(2S,4S)-2-(2-(9-Bromo-8-oxo-8,9,10,11-tetrahydro-5H-dibenzo[c,g]chromen-3-yl)-2-oxoethyl) 1-tert-butyl 4-(methoxymethyl)pyrrolidine-1,2-dicarboxylate (2S,4S)-1-tert-Butyl 2-(2-oxo-2-(8-oxo-8,9,10,11-tetrahydro-5H-dibenzo[c,g]chromen-3-yl)ethyl) 4-(methoxymethyl)pyrrolidine-1,2-dicarboxylate (7.66 g, 13.9 mmol) was dissolved in a solution of DCM (100 mL) and MeOH (40 mL), then treated with pyridinium tribromide (4.90 g, 15.3 mmol). After stirring at RT for 1.75 h, the reaction mixture was diluted with DCM and washed successively with 10% HCl, saturated aqueous $NaHCO_3$ and brine. The organic phase was dried over $MgSO_4$, filtered and concentrated under reduced pressure and the crude material was carried on without further purification.

(2S,4S)-1-tert-Butyl 2-(2-(9-((2S,5S)-1-((S)-2-(methoxycarbonylamino)-3-methylbutanoyl)-5-methylpyrrolidine-2-carbonyloxy)-8-oxo-8,9,10,11-tetrahydro-5H-dibenzo[c,g]chromen-3-yl)-2-oxoethyl) 4-(methoxymethyl)pyrrolidine-1,2-dicarboxylate (2S,4S)-2-(2-(9-Bromo-8-oxo-8,9,10,11-tetrahydro-5H-dibenzo[c,g]chromen-3-yl)-2-oxoethyl) 1-tert-butyl 4-(methoxymethyl)pyrrolidine-1,2-dicarboxylate (8.76 g, 13.94 mmol) was treated with a solution of (2S,5S)-1-((S)-2-(methoxycarbonylamino)-3-methylbutanoyl)-5-methylpyrrolidine-2-carboxylic acid (6.85 g, 23.92 mmol) in 2-Me-THF (70 mL) and $Cs_2CO_3$ (3.63 g, 11.15 mmol). The stirred reaction mixture was heated to 50° C. for 20 h, then cooled to RT and diluted with EtOAc. The organic phase was washed with $H_2O$ and brine, then dried over $MgSO_4$, filtered and concentrated under reduced pressure. The crude residue was purified by silica column chromatography (0% to 30% MeOH/EtOAc) to afford (2S,4S)-1-tert-butyl 2-(2-(9-((2S, 5S)-1-((S)-2-(methoxycarbonylamino)-3-methylbutanoyl)-5-methylpyrrolidine-2-carbonyloxy)-8-oxo-8,9,10,11-tetrahydro-5H-dibenzo[c,g]chromen-3-yl)-2-oxoethyl) 4-(methoxymethyl)pyrrolidine-1,2-dicarboxylate (10.47 g, 90%).

tert-Butyl (2S,4S)-2-[5-(2-{(2S,5S)-1-[N-(methoxycarbonyl)-L-valyl]-5-methylpyrrolidin-2-yl}-1,4,5,11-tetrahydroisochromeno[4',3':6,7]naphtho[1,2-d]imidazol-9-yl)-1H-imidazol-2-yl]-4-(methoxymethyl)pyrrolidine-1-carboxylate (2S,4S)-1-tert-Butyl 2-(2-(9-((2S,5S)-1-((S)-2-(methoxycarbonylamino)-3-methylbutanoyl)-5-methylpyrrolidine-2-carbonyloxy)-8-oxo-8,9,10,11-tetrahydro-5H-dibenzo[c,g]chromen-3-yl)-2-oxoethyl) 4-(methoxymethyl)pyrrolidine-1,2-dicarboxylate (10.47 g, 12.56 mmol) and $NH_4OAc$ (50.9 g, 660 mmol) were suspended in a solution of 10:1 PhMe/2-methoxyethanol (132 mL). The stirred reaction mixture was heated to 110° C. for 4.5 h, then cooled to RT and diluted with EtOAc. The organic phase was washed 3× with saturated aqueous $NaHCO_3$, then dried over $MgSO_4$, filtered and concentrated under reduced pressure. The crude residue was purified by silica column chromatography (0% to 30% MeOH/EtOAc) to afford tert-butyl (2S,4S)-2-[5-(2-{(2S,5S)-1-[N-(methoxycarbonyl)-L-valyl]-5-methylpyrrolidin-2-yl}-1,4,5,11-tetrahydroisochromeno[4',3':6,7]naphtho[1,2-d]imidazol-9-yl)-1H-imidazol-2-yl]-4-(methoxymethyl)pyrrolidine-1-carboxylate (8.33 g, 84%).

tert-Butyl (2S,4S)-2-[5-(2-{(2S,5S)-1-[N-(methoxycarbonyl)-L-valyl]-5-methylpyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate tert-Butyl (2S,4S)-2-[5-(2-{(2S,5S)-1-[N-(methoxycarbonyl)-L-valyl]-5-methylpyrrolidin-2-yl}-1,4,5,11-tetrahydroisochromeno[4',3':6,7]naphtho[1,2-d]imidazol-9-yl)-1H-imidazol-2-yl]-4-(methoxymethyl)pyrrolidine-1-carboxylate (8.33 g, 1.049 mmol) was suspended in DCM and activated $MnO_2$ (55.0 g, 630 mmol) was added in a single portion. After 13 h, MeOH (200 mL) was added and the slurry was filtered over celite. The filter cake was washed with MeOH (600 mL) and the filtrate was concentrated under reduced pressure. The crude material was purified by silica column chromatography (0% to 45% MeOH/EtOAc) to afford tert-butyl (2S,4S)-2-[5-(2-{(2S,5S)-1-[N-(methoxycarbonyl)-L-valyl]-5-methylpyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate (4.85 g, 58%).

Methyl {(2S,3S)-1-[(2S,4S)-2-(5-{2-[(2S,5S)-1-{(2S)-2-[(methoxycarbonyl)amino]-3-methylbutanoyl}-5-methylpyrrolidin-2-yl]-1,11-dihydroisochromeno[4',3':6,7]naphtho[1,2-d]imidazol-9-yl}-1H-imidazol-2-yl)-4-(methoxymethyl)pyrrolidin-1-yl]-3-methyl-1-oxopentan-2-yl}carbamate tert-Butyl (2S,4S)-2-[5-(2-{(2S,5S)-1-[N-(methoxycarbonyl)-L-valyl]-5-methylpyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate (179 mg, 0.226 mmol) was dissolved in DCM (4 mL) and HCl (4.0 M in dioxane, 1 mL) was added. The reaction mixture was stirred for 1 h at RT then concentrated under reduced pressure. The resulting residue was treated with (2S,3S)-2-(methoxycarbonylamino)-3-methylpentanoic acid (51 mg, 0.27 mmol), HATU (95 mg, 0.25 mmol), DMF (2 mL) and DIPEA (0.39 mL, 2.3 mmol). After stirring for 6 min, the reaction was quenched with $H_2O$, filtered and purified by reverse phase HPLC to afford methyl {(2S,3S)-1-[(2S,4S)-2-

(5-{2-[(2S,5S)-1-{(2S)-2-[(methoxycarbonyl)amino]-3-methylbutanoyl}-5-methylpyrrolidin-2-yl]-1,11-dihydroisochromeno[4',3':6,7]naphtho[1,2-d]imidazol-9-yl}-1H-imidazol-2-yl)-4-(methoxymethyl)pyrrolidin-1-yl]-3-methyl-1-oxopentan-2-yl}carbamate (116 mg, 59%). MS (ESI) m/z 864 [M+H]$^+$. $^1$H NMR (400 MHz, cd$_3$od) δ 8.57 (d, J=14.7 Hz, 1H), 8.45 (s, 1H), 8.20 (d, J=14.4 Hz, 1H), 8.15-7.98 (m, 2H), 7.91 (dd, J=21.8, 14.1 Hz, 2H), 7.85-7.69 (m, 2H), 7.69-7.48 (m, 2H), 5.42-5.12 (m, 5H), 4.34 (dd, J=22.3, 13.7 Hz, 1H), 4.30-4.10 (m, 2H), 3.87-3.73 (m, 1H), 3.73-3.63 (m, 7H), 3.62-3.48 (m, 2H), 3.48-3.38 (m, 4H), 3.35 (s, 3H), 2.95-2.70 (m, 1H), 2.70-2.55 (m, 2H), 2.55-2.20 (m, 2H), 2.20-1.91 (m, 3H), 1.77 (d, J=42.0 Hz, 1H), 1.65 (d, J=6.6 Hz, 3H), 1.43 (t, J=24.6 Hz, 1H), 1.28 (d, J=6.2 Hz, 1H), 1.23-1.01 (m, 3H), 0.98 (d, J=6.6 Hz, 3H), 0.90 (dd, J=13.1, 5.9 Hz, 10H).

Example OG nyl)-L-valyl]-5-methylpyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate by the same method employed in the synthesis of methyl {(2S, 3S)-1-[(2S,4S)-2-(5-{2-[(2S,5S)-1-{(2S)-2-[(methoxycarbonyl)amino]-3-methylbutanoyl}-5-methylpyrrolidin-2-yl]-1,11-dihydroisochromeno[4',3':6,7]naphtho[1,2-d]imidazol-9-yl)-1H-imidazol-2-yl)-4-(methoxymethyl)pyrrolidin-1-yl]-3-methyl-1-oxopentan-2-yl}carbamate, replacing (2S,3S)-2-(methoxycarbonylamino)-3-methylpentanoic acid with (2S,3R)-2-(methoxycarbonylamino)-3-methylpentanoic acid. MS (ESI) m/z 864 [M+H]$^+$. $^1$H NMR (400 MHz, cd$_3$od) δ 8.62-8.41 (m, 1H), 8.22 (s, 1H), 8.07 (dt, J=20.1, 10.0 Hz, 1H), 7.89 (dt, J=35.6, 15.6 Hz, 2H), 7.77 (dd, J=20.3, 7.0 Hz, 2H), 7.68-7.48 (m, 2H), 5.95 (d, J=5.0 Hz, 1H), 5.42-5.13 (m, 4H), 4.47 (t, J=5.5 Hz, 1H), 4.40-4.09 (m, 2H), 3.80-3.73 (m, 1H), 3.73-3.62 (m, 6H), 3.57 (dt, J=16.1, 9.7

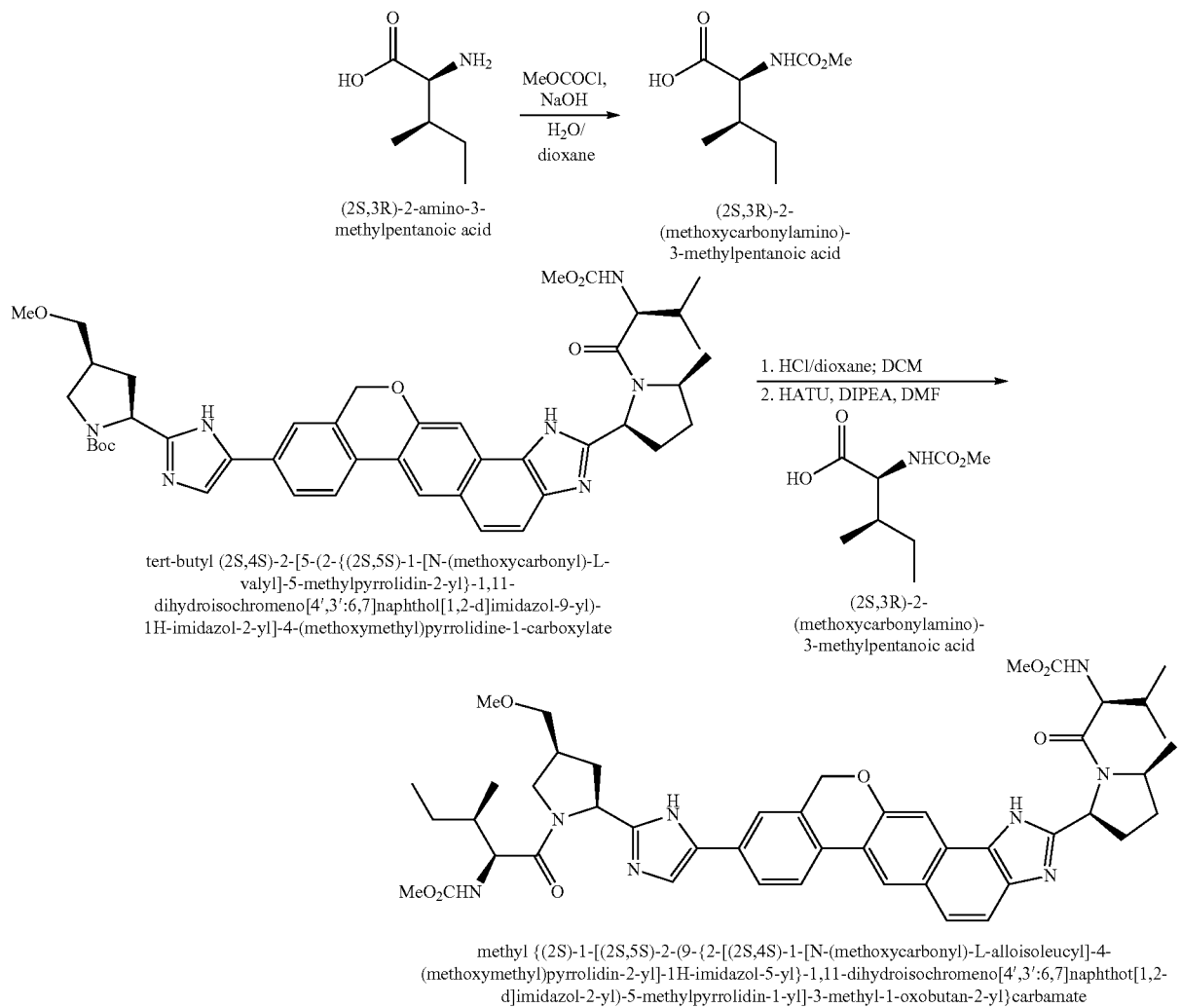

Methyl {(2S)-1-[(2S,5S)-2-(9-{2-[(2S,4S)-1-[N-(methoxycarbonyl)-L-alloisoleucyl]-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate was prepared from tert-butyl (2S,4S)-2-[5-(2-{(2S,5S)-1-[N-(methoxycarbo- Hz, 2H), 3.40 (s, 3H), 3.34 (d, J=7.5 Hz, 1H), 2.81 (dd, J=18.4, 12.5 Hz, 1H), 2.63 (td, J=13.3, 6.8 Hz, 2H), 2.55-2.18 (m, 2H), 2.16-1.77 (m, 4H), 1.65 (d, J=6.6 Hz, 3H), 1.50-1.31 (m, 1H), 1.26 (dd, J=15.6, 6.7 Hz, 2H), 1.17-1.03 (m, 2H), 0.98 (dd, J=6.7, 4.5 Hz, 5H), 0.89 (dd, J=15.5, 7.8 Hz, 3H), 0.86-0.74 (m, 3H).

Example OH

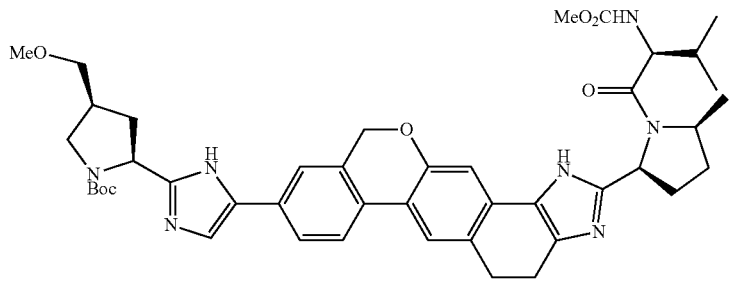

tert-butyl (2S,4S)-2-[5-(2-{(2S,5S)-1-[N-(methoxycarbonyl)-L-valyl]-5-methylpyrrolidin-2-yl}-1,4,5,11-tetrahydroisochromeno[4',3':6,7]naphtho[1,2-d]imidazol-9-yl)-1H-imidazol-2-yl]-4-(methoxymethyl)pyrrolidine-1-carboxylate 1. HCl/dioxane; DCM
2. COMU, DIPEA, DMF

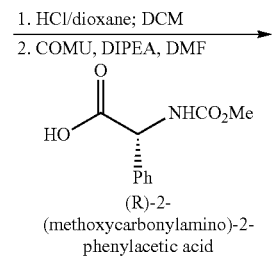

(R)-2-(methoxycarbonylamino)-2-phenylacetic acid

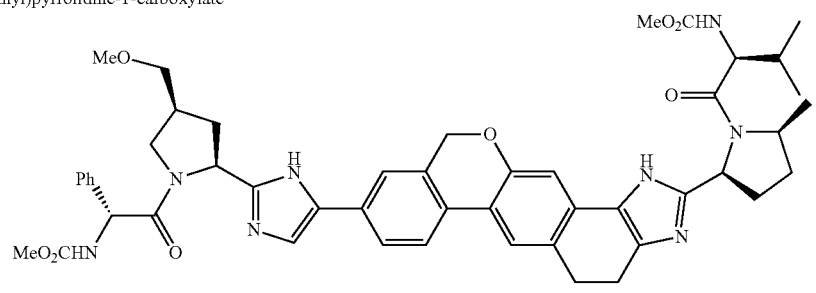

methyl {(1R)-2-[(2S,4S)-2-(5-{2-[(2S,5S)-1-{(2S)-2-[(methoxycarbonyl)amino]-3-methylbutanoyl}-5-methylpyrrolidin-2-yl]-1,4,5,11-tetrahydroisochromeno[4',3':6,7]naphtho[1,2-d]imidazol-9-yl}-1H-imidazol-2-yl)-4-(methoxymethyl)pyrrolidin-1-yl]-2-oxo-1-phenylethyl}carbamate Methyl {(1R)-2-[(2S,4S)-2-(5-{2-[(2S,5S)-1-{(2S)-2-[(methoxycarbonyl)amino]-3-methylbutanoyl}-5-methylpyrrolidin-2-yl]-1,4,5,11-tetrahydroisochromeno[4',3':6,7]naphtho[1,2-d]imidazol-9-yl}-1H-imidazol-2-yl)-4-(methoxymethyl)pyrrolidin-1-yl-2-oxo-1-phenylethyl}carbamacetic tert-Butyl (2S,4S)-2-[5-(2-{(2S,5S)-1-[N-(methoxycarbonyl)-L-valyl]-5-methylpyrrolidin-2-yl}-1,4,5,11-tetrahydroisochromeno[4',3':6,7]naphtho-[1,2-d]imidazol-9-yl)-1H-imidazol-2-yl]-4-(methoxymethyl)pyrrolidine-1-carboxylate (102 mg, 0.128 mmol) was dissolved in DCM (4 mL) and HCl (4.0 M in dioxane, 2.0 mL, 8.0 mmol) was added. After stirring at RT for 30 min, the solution was concentrated under reduced pressure. The residue was treated with (R)-2-(methoxycarbonylamino)-2-phenylacetic acid (29mg, 0.141 mmol), COMU (60 mg, 0.141 mmol), DMF (3.0 mL) and DIPEA (0.223 mL, 1.28 mmol). After stirring at RT for 20 min, the reaction mixture was diluted with EtOAc. The organic solution was washed with saturated aqueous NaHCO₃ and brine, then dried over MgSO₄, filtered and concentrated under reduced pressure. The crude material was purified by reverse-phase HPLC to afford methyl {(1R)-2-[(2S,4S)-2-(5-{2-[(2S,5S)-1-{(2S)-2-[(methoxycarbonyl)amino]-3-methylbutanoyl}-5-methylpyrrolidin-2-yl]-1,4,5,11-tetrahydroisochromeno[4',3':6,7]naphtho[1,2-d]imidazol-9-yl}-1H-imidazol-2-yl)-4-(methoxymethyl)pyrrolidin-1-yl]-2-oxo-1-phenylethyl}carbamate as the bis-TFA salt (82.4 mg, 60%). MS (ESI) m/z 866 [M+H]⁺. ¹H NMR (400 MHz, cd₃od) δ 7.94-7.67 (m, 4H), 7.59 (d, J=9.1 Hz, 1H), 7.52 (s, 1H), 7.48-7.33 (m, 4H), 7.11 (d, J=18.7 Hz, 1H), 5.68 (d, J=6.3 Hz, 1H), 5.48-5.33 (m, 1H), 5.23 (dd, J=24.1, 15.7 Hz, 1H), 5.17-5.03 (m, 3H), 4.22 (dd, J=17.0, 9.6 Hz, 1H), 4.16-4.01 (m, 1H), 3.91 (d, J=24.1 Hz, 1H), 3.83-3.68 (m, 1H), 3.68-3.59 (m, 3H), 3.59-3.49 (m, 3H), 3.38 (ddd, J=15.9, 9.6, 5.7 Hz, 2H), 3.28-3.14 (m, 5H), 3.10 (dd, J=14.0, 8.2 Hz, 1H), 3.00 (dd, J=17.8, 9.6 Hz, 1H), 2.92 (dd, J=14.5, 6.7 Hz, 1H), 2.73-2.41 (m, 2H), 2.40-2.11 (m, 2H), 2.11-1.83 (m, 2H), 1.54 (t, J=9.7 Hz, 2H), 1.24 (d, J=6.2 Hz, 1H), 1.06 (t, J=8.0 Hz, 1H), 0.99 (d, J=6.8 Hz, 1H), 0.94 (d, J=6.6 Hz, 2H), 0.85 (d, J=6.7 Hz, 2H).

Example OI

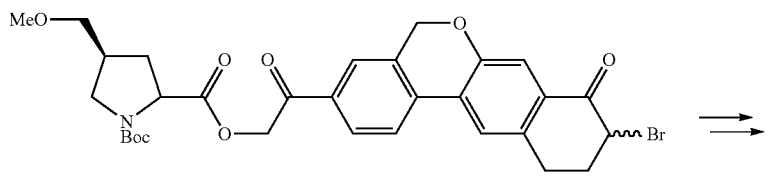

(2S,4S)-2-(2-(9-bromo-8-oxo-8,9,10,11-tetrahydro-5H-dibenzo[c,g]chromen-3-yl)-2-oxoethyl) 1-tert-butyl 4-(methoxymethyl)pyrrolidine-1,2-dicarboxylate

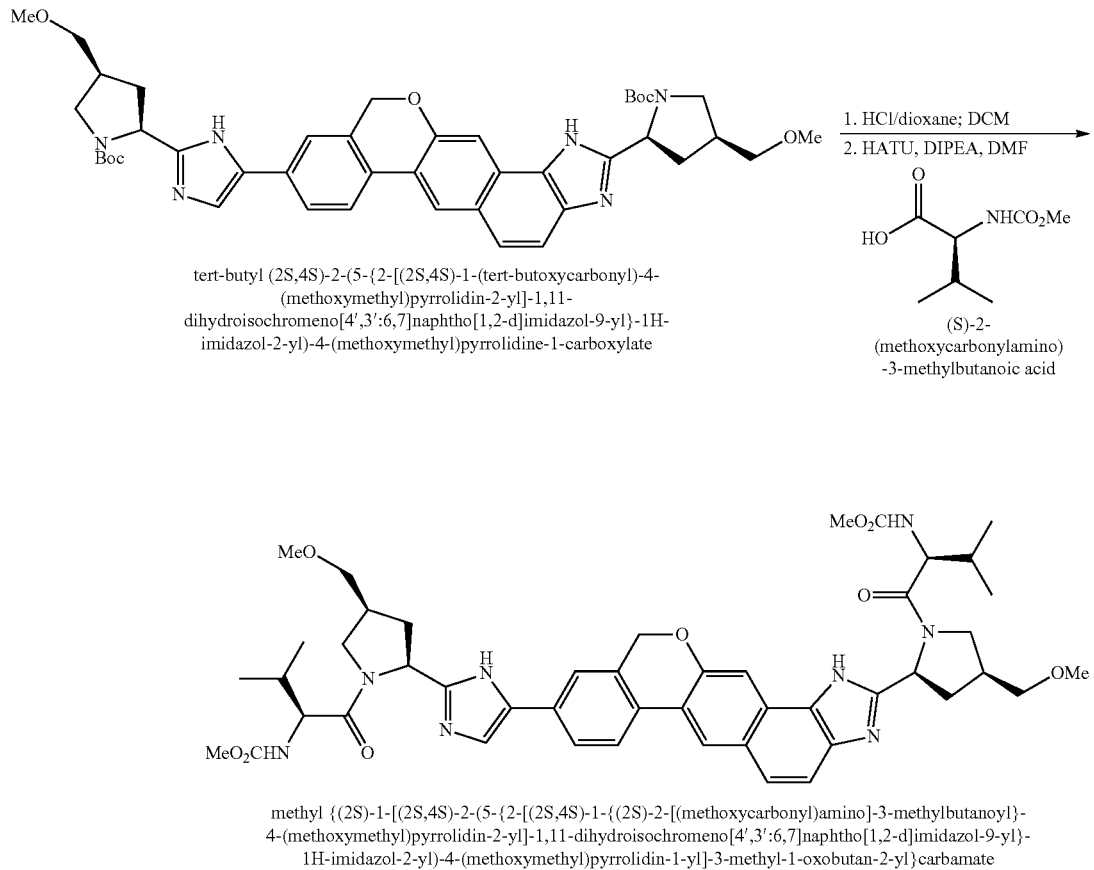

tert-Butyl (2S,4S)-2-(5-{2-[(2S,4S)-1-(tert-butoxycarbonyl)-4-(methoxymethyl)pyrrolidin-2-yl]-1,11-dihydroisochromeno[4',3':6,7]naphtho[1,2-d]imidazol-9-yl}-1H-imidazol-2-yl)-4-(methoxymethyl)pyrrolidine-1-carboxylate was prepared from (2S,4S)-2-(2-(9-bromo-8-oxo-8,9,10,11-tetrahydro-5H-dibenzo[c,g]chromen-3-yl)-2-oxoethyl) 1-tert-butyl 4-(methoxymethyl)pyrrolidine-1,2-dicarboxylate by the same method employed in the synthesis of tert-butyl (2S,4S)-2-[5-(2-{(2S,5S)-1-[N-(methoxycarbonyl)-L-valyl]-5-methylpyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate, replacing (2S,5S)-1-((S)-2-(methoxycarbonylamino)-3-methylbutanoyl)-5-methylpyrrolidine-2-carboxylic acid with (2S,4S)-1-(tert-butoxycarbonyl)-4-(methoxymethyl)pyrrolidine-2-carboxylic acid.

Methyl {(2S)-1-[(2S,4S)-2-(5-{2-[(2S,4S)-1-{(2S)-2-[(methoxycarbonyl)amino]-3-methylbutanoyl}-4-(methoxymethyl)pyrrolidin-2-yl]-1,11-dihydroisochromeno[4',3':6,7]naphtho[1,2-d]imidazol-9-yl}-1H-imidazol-2-yl)-4-(methoxymethyl)pyrrolidin-1-yl]-3-methyl-1-oxobutan-2-yl}carbamate tert-Butyl (2S,4S)-2-(5-{2-[(2S,4S)-1-(tert-butoxycarbonyl)-4-(methoxymethyl)pyrrolidin-2-yl]-1,11-dihydroisochromeno[4',3':6,7]naphtho[1,2-d]imidazol-9-yl}-1H-imidazol-2-yl)-4-(methoxymethyl)pyrrolidine-1-carboxylate (137 mg, 0.179 mmol) was dissolved in DCM (5 mL) and HCl (4.0 M in dioxane, 1 mL) was added. After stirring at RT for 1.5 h, the reaction mixture was concentrated under reduced pressure. The crude residue was treated with (S)-2-(methoxycarbonylamino)-3-methylbutanoic acid (69 mg, 0.39 mmol), HATU (149 mg, 0.393 mmol), DMF (2.0 mL) and DIPEA (0.31 mL, 1.8 mmol). After stirring for 15 min at RT, the reaction mixture was quenched with water and purified by HPLC to provide methyl {(2S)-1-[(2S,4S)-2-(5-{2-[(2S,4S)-1-{(2S)-2-[(methoxycarbonyl)amino]-3-methylbutanoyl}-4-(methoxymethyl)pyrrolidin-2-yl]-1,11-dihydroisochromeno[4',3':6,7]naphtho[1,2-d]imidazol-9-yl}-1H-imidazol-2-yl)-4-(methoxymethyl)pyrrolidin-1-yl]-3-methyl-1-oxobutan-2-yl}carbamate (123 mg). MS (ESI) m/z 880 [M+H]$^+$. $^1$H NMR (400 MHz, cd$_3$od) δ 8.48 (s, 1H), 8.05 (t, J=11.2 Hz, 1H), 7.92 (dd, J=19.7, 10.1 Hz, 2H), 7.74 (s, 2H), 7.59-7.44 (m, 2H), 5.49 (s, 1H), 5.40 (dt, J=16.3, 8.1 Hz, 1H), 5.31-5.15 (m, 3H), 4.47-4.10 (m, 4H), 3.86-3.44 (m, 12H), 3.39 (dd, J=13.2, 7.1 Hz, 6H), 2.94-2.57 (m, 4H), 2.25-1.94 (m, 4H), 1.02-0.82 (m, 12H).

Example OJ

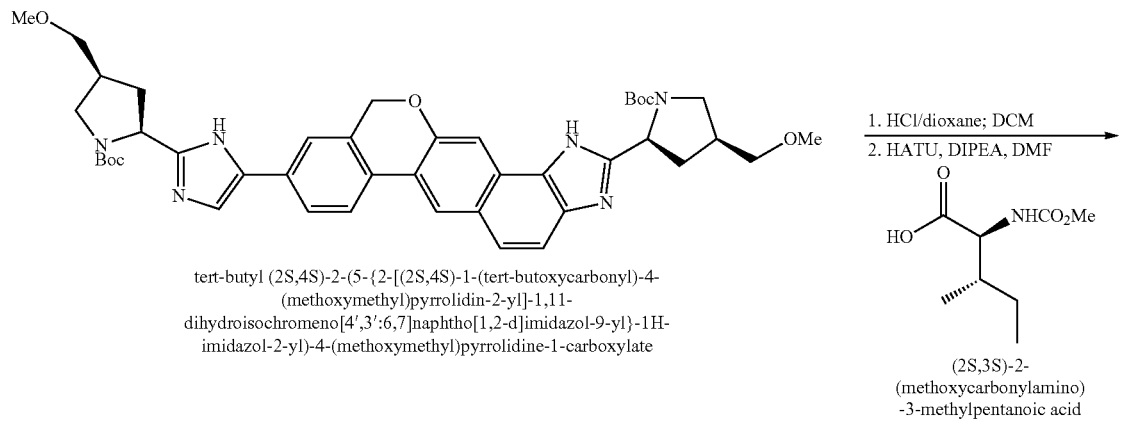

tert-butyl (2S,4S)-2-(5-{2-[(2S,4S)-1-(tert-butoxycarbonyl)-4-(methoxymethyl)pyrrolidin-2-yl]-1,11-dihydroisochromeno[4',3':6,7]naphtho[1,2-d]imidazol-9-yl}-1H-imidazol-2-yl)-4-(methoxymethyl)pyrrolidine-1-carboxylate (2S,3S)-2-(methoxycarbonylamino)-3-methylpentanoic acid

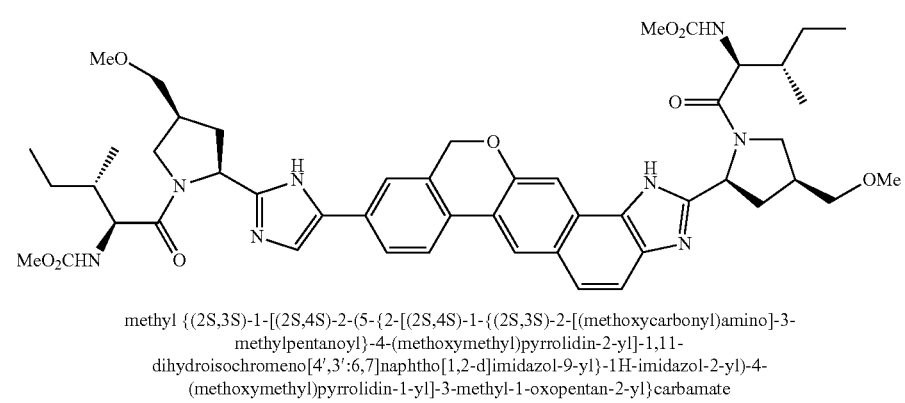

methyl {(2S,3S)-1-[(2S,4S)-2-(5-{2-[(2S,4S)-1-{(2S,3S)-2-[(methoxycarbonyl)amino]-3-methylpentanoyl}-4-(methoxymethyl)pyrrolidin-2-yl]-1,11-dihydroisochromeno[4',3':6,7]naphtho[1,2-d]imidazol-9-yl}-1H-imidazol-2-yl)-4-(methoxymethyl)pyrrolidin-1-yl]-3-methyl-1-oxopentan-2-yl}carbamate Methyl {(2S,3S)-1-[(2S,4S)-2-(5-{2-[(2S,4S)-1-({(2S,3S)-2-[(methoxycarbonyl)amino]-3-methylpentanoyl}-4-(methoxymethyl)pyrrolidin-2-yl]-1,11-dihydroisochromeno[4',3':6,7]naphtho[1,2-d]imidazol-9-yl}-1H-imidazol-2-yl)-4-(methoxymethyl)pyrrolidin-1-yl]-3-methyl-1-oxopentan-2-yl}carbamate was prepared from tert-Butyl (2S,4S)-2-(5-{2-[(2S,4S)-1-(tert-butoxycarbonyl)-4-(methoxymethyl)pyrrolidin-2-yl]-1,11-dihydroisochromeno[4',3':6,7]naphtho[1,2-d]imidazol-9-yl}-1H-imidazol-2-yl)-4-(methoxymethyl)pyrrolidine-1-carboxylate using the same method employed in the synthesis of methyl {(2S)-1-[(2S,4S)-2-(5-{2-[(2S,4S)-1-{(2S)-2-[(methoxycarbonyl)amino]-3-methylbutanoyl}-4-(methoxymethyl)pyrrolidin-2-yl]-1,11-dihydroisochromeno[4',3':6,7]naphtho[1,2-d]imidazol-9-yl}-1H-imidazol-2-yl)-4-(methoxymethyl)pyrrolidin-1-yl]-3-methyl-1-oxobutan-2-yl}carbamate, replacing with (S)-2-(methoxycarbonylamino)-3-methylbutanoic acid with (2S,3S)-2-(methoxycarbonylamino)-3-methylpentanoic acid. MS (ESI) m/z 908 [M+H]$^+$.

Example OK

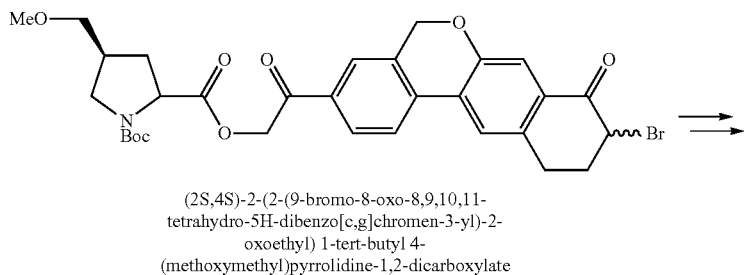

(2S,4S)-2-(2-(9-bromo-8-oxo-8,9,10,11-tetrahydro-5H-dibenzo[c,g]chromen-3-yl)-2-oxoethyl) 1-tert-butyl 4-(methoxymethyl)pyrrolidine-1,2-dicarboxylate

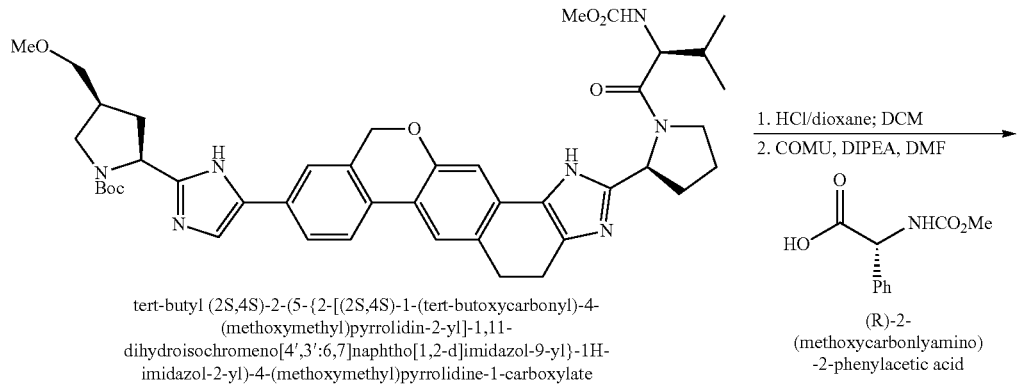

tert-butyl (2S,4S)-2-(5-{2-[(2S,4S)-1-(tert-butoxycarbonyl)-4-
(methoxymethyl)pyrrolidin-2-yl]-1,11-
dihydroisochromeno[4',3':6,7]naphtho[1,2-d]imidazol-9-yl}-1H-
imidazol-2-yl)-4-(methoxymethyl)pyrrolidine-1-carboxylate (R)-2-
(methoxycarbonlyamino)
-2-phenylacetic acid

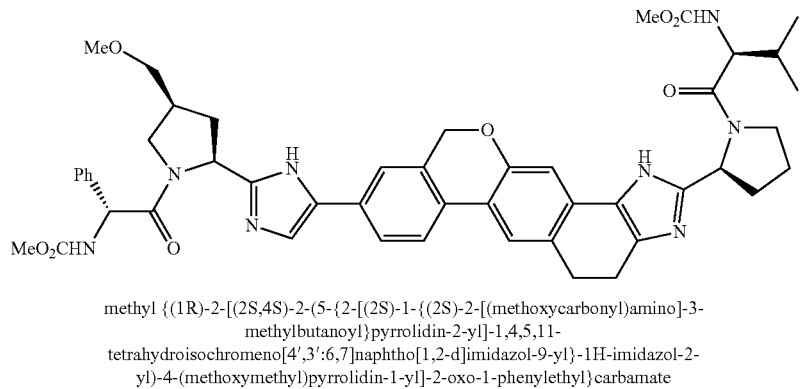

methyl {(1R)-2-[(2S,4S)-2-(5-{2-[(2S)-1-{(2S)-2-[(methoxycarbonyl)amino]-3-
methylbutanoyl}pyrrolidin-2-yl]-1,4,5,11-
tetrahydroisochromeno[4',3':6,7]naphtho[1,2-d]imidazol-9-yl}-1H-imidazol-2-
yl)-4-(methoxymethyl)pyrrolidin-1-yl]-2-oxo-1-phenylethyl}carbamate tert-Butyl (2S,4S)-2-[5-(2-{(2S)-1-[N-(methoxycarbonyl)-L-valyl]pyrrolidin-2-yl}-1,4,5,11-tetrahydroisochromeno[4',3':6,7]naphtho[1,2-d]imidazol-9-yl)-1H-imidazol-2-yl]-4-(methoxymethyl)pyrrolidine-1-carboxylate was synthesized from (2S,4S)-2-(2-(9-bromo-8-oxo-8,9,10,11-tetrahydro-5H-dibenzo[c,g]chromen-3-yl)-2-oxoethyl) 1-tert-butyl 4-(methoxymethyl)pyrrolidine-1,2-dicarboxylate using the same methods described for the synthesis of tert-butyl (2S,4S)-2-[5-(2-{(2S,5S)-1-[N-(methoxycarbonyl)-L-valyl]-5-methylpyrrolidin-2-yl}-1,4,5,11-tetrahydroisochromeno[4',3':6,7]naphtho[1,2-d]imidazol-9-yl)-1H-imidazol-2-yl]-4-(methoxymethyl)pyrrolidine-1-carboxylate, substituting (S)-1-((S)-2-(methoxycarbonylamino)-3-methylbutanoyl)pyrrolidine-2-carboxylic acid for (2S,5S)-1-((S)-2-(methoxycarbonylamino)-3-methylbutanoyl)-5-methylpyrrolidine-2-carboxylic acid.

Methyl {(1R)-2-[(2S,4S)-2-(5-{2-[(2S)-1-{(2S)-2-[(methoxycarbonyl)amino]-3-methylbutanoyl}pyrrolidin-2-yl]-1,4,5,11-tetrahydroisochromeno[4',3':6,7]naphtho[1,2-d]imidazol-9-yl}-1H-imidazol-2-yl)-4-(methoxymethyl)pyrrolidin-1-yl]-2-oxo-1-phenylethyl}carbamate was synthesized from tert-butyl (2S,4S)-2-[5-(2-{(2S)-1-[N-(methoxycarbonyl)-L-valyl]pyrrolidin-2-yl}-1,4,5,11-tetrahydroisochromeno[4',3':6,7]naphtho[1,2-d]imidazol-9-yl)-1H-imidazol-2-yl]-4-(methoxymethyl)pyrrolidine-1-carboxylate using the same method employed for the synthesis of methyl {(1R)-2-[(2S,4S)-2-(5-{2-[(2S,5S)-1-{(2S)-2-[(methoxycarbonyl)amino]-3-methylbutanoyl}-5-methylpyrrolidin-2-yl]-1,4,5,11-tetrahydroisochromeno[4',3':6,7]naphtho[1,2-d]imidazol-9-yl}-1H-imidazol-2-yl)-4-(methoxymethyl)pyrrolidin-1-yl]-2-oxo-1-phenylethyl}carbamate substituting tert-butyl (2S,4S)-2-[5-(2-{(2S)-1-[N-(methoxycarbonyl)-L-valyl]pyrrolidin-2-yl}-1,4,5,11-tetrahydroisochromeno[4',3':6,7]naphtho[1,2-d]imidazol-9-yl)-1H-imidazol-2-yl]-4-(methoxymethyl)pyrrolidine-1-carboxylate for tert-Butyl (2S,4S)-2-[5-(2-{(2S,5S)-1-[N-(methoxycarbonyl)-L-valyl]-5-methylpyrrolidin-2-yl}-1,4,5,11-tetrahydroisochromeno[4',3':6,7]naphtho[1,2-d]imidazol-9-yl)-1H-imidazol-2-yl]-4-(methoxymethyl)pyrrolidine-1-carboxylate. MS (ESI) m/z 871 [M+H]+.
$^1$H NMR (400 MHz, cd$_3$od) δ 7.87 (ddd, J=20.5, 15.3, 6.8 Hz, 4H), 7.65 (s, 1H), 7.50-7.38 (m, 5H), 7.17 (s, 1H), 5.41 (d, J=24.5 Hz, 1H), 5.28 (t, J=8.3 Hz, 1H), 5.20 (d, J=7.3 Hz, 3H), 4.24 (d, J=7.2 Hz, 1H), 4.12 (d, J=10.3 Hz, 1H), 4.03-3.94 (m, 1H), 3.89 (dd, J=15.4, 8.6 Hz, 1H), 3.77 (t, J=9.6 Hz, 1H), 3.72-3.64 (m, 4H), 3.63-3.52 (m, 4H), 3.43 (qd, J=9.5, 5.6 Hz, 3H), 3.30 (s, 3H), 3.24-3.08 (m, 2H), 2.97 (dd, J=11.6, 5.4 Hz, 2H), 2.59 (dt, J=21.1, 7.8 Hz, 3H), 2.29 (s, 1H), 2.24-2.14 (m, 2H), 2.11-1.85 (m, 2H), 0.92 (dd, J=15.8, 6.7 Hz, 6H).

Example OL

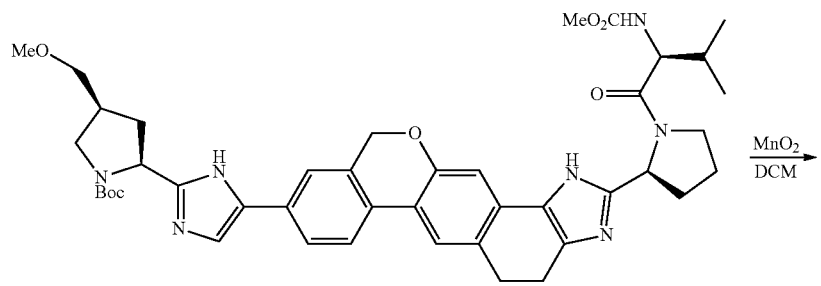

tert-butyl (2S,4S)-2-[5-(2-{(2S)-1-[N-(methoxycarbonyl)-L-valyl]pyrrolidin-2-yl}-1,4,5,11-tetrahydroisochromeno[4',3':6,7]naphtho[1,2-d]imidazol-9-yl)-1H-imidazol-2-yl]-4-(methoxymethyl)pyrrolidine-1-carboxylate

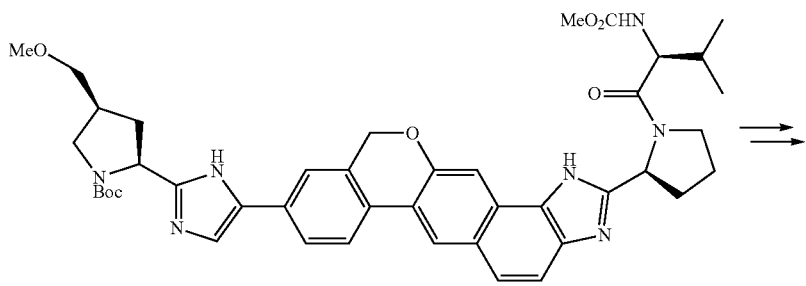

tert-butyl (2S,4S)-2-[5-(2-{(2S)-1-[N-(methoxycarbonyl)-L-valyl]pyrrolidin-2-yl}-1,11-dihydroisochromeno[4',3':6,7]naptho[1,2-d]imidazol-9-yl)-1H-imidazol-2-yl]-4-(methoxymethyl)pyrrolidine-1-carboxylate

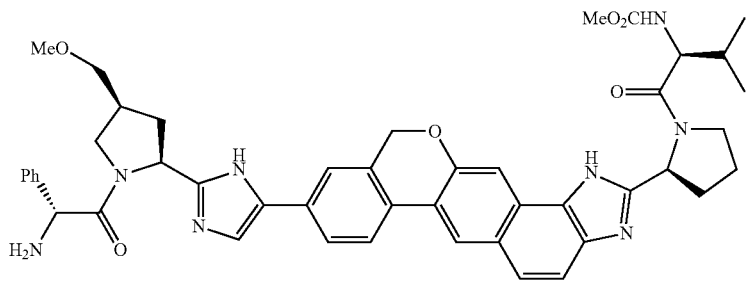

methyl {(2S)-1-[(2S)-1-[(2S)-2-(9-{2-[(2S,4S)-1-[(2R)-2-amino-2-phenylacetyl]-4-(methoxymethyl)pyrrolidin-2-yl]-1H-imidazol-5-yl}-1,11-dihydroisochromeno[4',3':6,7]naphtho[1,2-d]imidazol-2-yl)pyrrolidin-1-yl]-3-methyl-1-oxobutan-2-yl}carbamate tert-Butyl (2S,4S)-2-[5-(2-{(2S)-1-[N-(methoxycarbonyl)-L-valyl]pyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate was prepared according to the method described for the synthesis of tert-butyl (2S,4S)-2-[5-(2-{(2S,5S)-1-[N-(methoxycarbonyl)-L-valyl]-5-methylpyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate, substituting tert-butyl (2S,4S)-2-[5-(2-{(2S)-1-[N-(methoxycarbonyl)-L-valyl]pyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate for tert-Butyl (2S,4S)-2-[5-(2-{(2S,5S)-1-[N-(methoxycarbonyl)-L-valyl]-5-methylpyrrolidin-2-yl}-1,4,5,11-tetrahydroisochromeno[4',3':6,7]naphtho[1,2-d]imidazol-9-yl)-1H-imidazol-2-yl]-4-(methoxymethyl)pyrrolidine-1-carboxylate.

Methyl {(2S)-1-[(2S)-2-(9-{2-[(2S,4S)-[(2R)-2-amino-2-phenylacetyl]-4-(methoxymethyl)pyrrolidin-2-yl]-1H-imidazol-5-yl}-1,11-dihydroisochromeno[4',3':6,7]naphtho[1,2-d]imidazol-2-yl)pyrrolidin-1-yl]-3-methyl-1-oxobutan-2-yl}carbamate was prepared according to the method described for the synthesis of methyl(S)-1-((2S,4S)-2-(2'-((2S,4S)-1-((R)-2-amino-2-phenylacetyl)-4-(methoxymethyl)pyrrolidin-2-yl)-1H,1'H-7,7'-binaphtho[1,2-d]imidazol-2-yl)-4-methylpyrrolidin-1-yl)-3-methyl-1-oxobutan-2-ylcarbamate, substituting methyl(S)-1-((2S,4S)-2-(2'-((2S,4S)-1-((R)-2-tert-butoxycarbonylamino-2-phenylacetyl)-4-(methoxymethyl)pyrrolidin-2-yl)-1H,1'H-7,7'-binaphtho[1,2-d]imidazol-2-yl)-4-methylpyrrolidin-1-yl)-3-methyl-1-oxobutan-2-ylcarbamate with tert-butyl (2S,4S)-2-[5-(2-{(2S)-1-[N-(methoxycarbonyl)-L-valyl]pyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate. MS (ESI) m/z 811 [M+H]$^+$.

Example OM

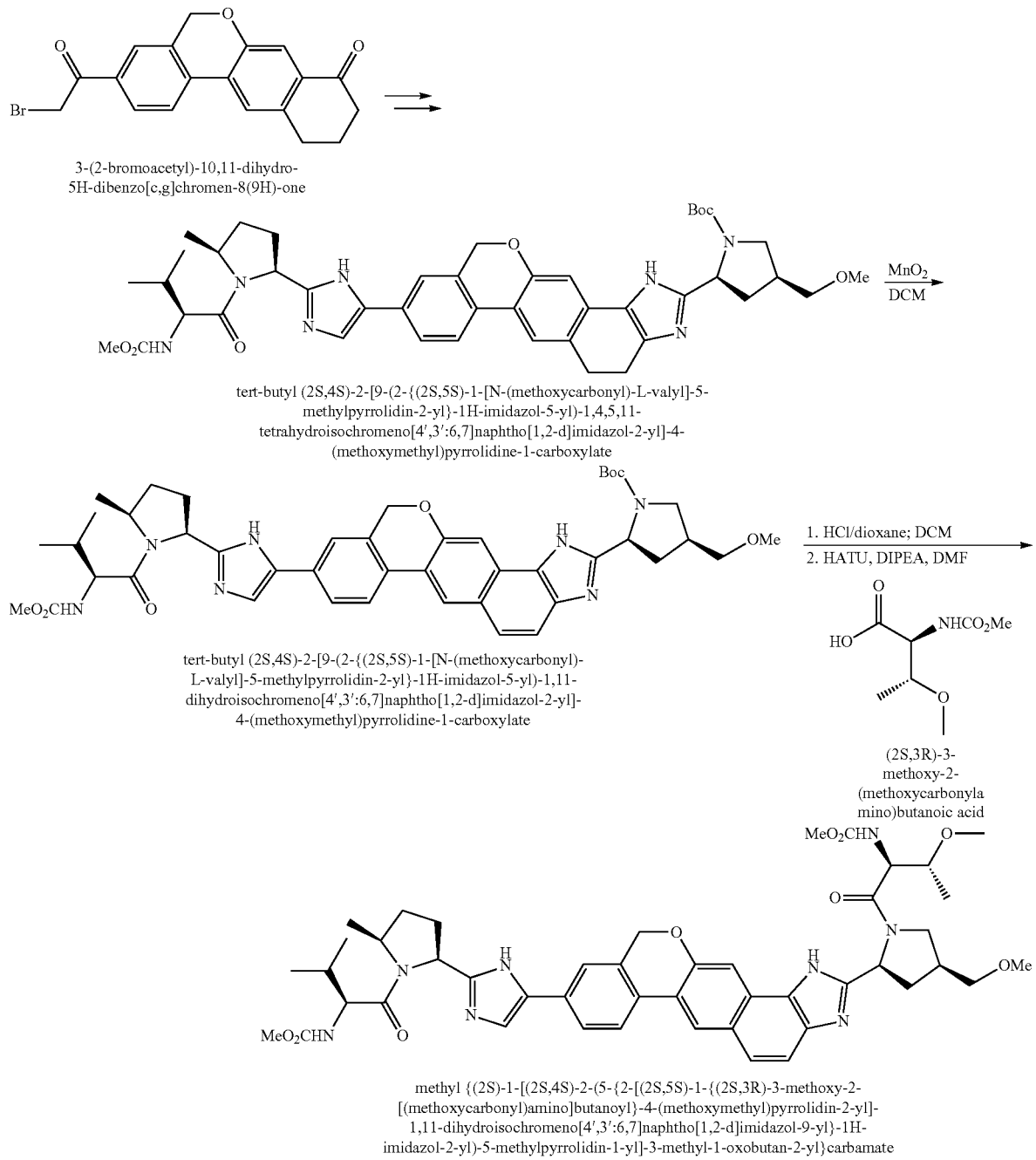

tert-Butyl (2S,4S)-2-[9-(2-{(2S,5S)-1-[N-(methoxycarbonyl)-L-valyl]-5-methylpyrrolidin-2-yl}-1H-imidazol-5-yl)-1,4,5,11-tetrahydroisochromeno[4',3':6,7]naphtho[1,2-d]imidazol-2-yl]-4-(methoxymethyl)pyrrolidine-1-carboxylate was synthesized from 3-(2-bromoacetyl)-10,11-dihydro-5H-dibenzo[c,g]chromen-8(9H)-one, by the same methods employed in the synthesis of tert-butyl (2S,4S)-2-[5-(2-{(2S,5S)-1-[N-(methoxycarbonyl)-L-valyl]-5-methylpyrrolidin-2-yl}-1,4,5,11-tetrahydroisochromeno[4',3':6,7]naphtho[1,2-d]imidazol-9-yl]-1H-imidazol-2-yl]-4-(methoxymethyl)pyrrolidine-1-carboxylate, substituting (2S,5S)-1-((S)-2-(methoxycarbonylamino)-3-methylbutanoyl)-5-methylpyrrolidine-2-carboxylic acid for (2S,4S)-1-(tert-butoxycarbonyl)-4-(methoxymethyl)pyrrolidine-2-carboxylic acid and (2S,4S)-1-(tert-butoxycarbonyl)-4-(methoxymethyl)pyrrolidine-2-carboxylic acid for (2S,5S)-1-((S)-2-(methoxycarbonylamino)-3-methylbutanoyl)-5-methylpyrrolidine-2-carboxylic acid.

tert-Butyl (2S,4S)-2-[9-(2-{(2S,5S)-1-[N-(methoxycarbonyl)-L-valyl]-5-methylpyrrolidin-2-yl}-1H-imidazol-5-yl)-1,11-dihydroisochromeno[4',3':6,7]naphtho[1,2-d]imidazol-2-yl]-4-(methoxymethyl)pyrrolidine-1-carboxylate was prepared according to the method described for the synthesis of tert-butyl (2S,4S)-2-[5-(2-{(2S,5S)-1-[N-(methoxycarbonyl)-L-valyl]-5-methylpyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate, substituting tert-butyl (2S,4S)-2-[9-(2-{(2S,5S)-1-[N-(methoxycarbonyl)-L-valyl]-5-methylpyrrolidin-2-yl}-1H-imidazol-5-yl)-1,4,5,11-tetrahydroisochromeno[4',3':6,7]naphtho[1,2-d]imidazol-2-yl]-4-(methoxymethyl)pyrrolidine-1-carboxylate for tert-butyl (2S,4S)-2-[5-(2-{(2S,5S)-1-[N-(methoxycarbonyl)-L-valyl]-5-methylpyrrolidin-2-yl}-1,4,5,11-tetrahydroisochromeno[4',3':6,7]naphtho[1,2-d]imidazol-9-yl)-1H-imidazol-2-yl]-4-(methoxymethyl)pyrrolidine-1-carboxylate.

Methyl {(2S)-1-[(2S,4S)-2-(5-{2-[(2S,5S)-1-{(2S,3R)-3-methoxy-2-[(methoxycarbonyl)amino]butanoyl}-4-(methoxymethyl)pyrrolidin-2-yl]-1,11-dihydroisochromeno[4',3':6,7]naphtho[1,2-d]imidazol-9-yl}-1H-imidazol-2-yl)-5-methylpyrrolidin-1-yl]-3-methyl-1-oxobutan-2-yl}carbamate was prepared from tert-butyl (2S,4S)-2-[9-(2-{(2S,5S)-1-[N-(methoxycarbonyl)-L-valyl]-5-methylpyrrolidin-2-yl}-1H-imidazol-5-yl)-1,11-dihydroisochromeno[4',3':6,7]naphtho[1,2-d]imidazol-2-yl]-4-(methoxymethyl)pyrrolidine-1-carboxylate according to the same method described for the synthesis of methyl(S)-1-((2S,4S)-2-(2'-((2S,4S)-1-((2S,3R)-2-methoxycarbonylamino-3-methoxybutanoyl)-4-(methoxymethyl)pyrrolidin-2-yl)-1H,1'H-7,7'-binaphtho[1,2-d]imidazol-2-yl)-4-methylpyrrolidin-1-yl)-3-methyl-1-oxobutan-2-ylcarbamate, substituting (2S,4S)-tert-Butyl 2-(2'-((2S,4S)-1-((S)-2-(methoxycarbonylamino)-3-methylbutanoyl)-4-methylpyrrolidin-2-yl)-1H,1'H-7,7'-binaphtho[1,2-d]imidazol-2-yl)-4-(methoxymethyl)pyrrolidine-1-carboxylate with tert-butyl (2S,4S)-2-[9-(2-(2S,5S)-1-[N-(methoxycarbonyl)-L-valyl]-5-methylpyrrolidin-2-yl}-1H-imidazol-5-yl)-1,11-dihydroisochromeno[4',3':6,7]naphtho[1,2-d]imidazol-2-yl]-4-(methoxymethyl)pyrrolidine-1-carboxylate. MS (ESI) m/z 866 [M+H]+. 1H NMR (400 MHz, cd3od) δ 8.44 (d, J=19.8 Hz, 1H), 8.02 (t, J=8.6 Hz, 2H), 7.98-7.81 (m, 3H), 7.74 (dd, J=22.2, 13.6 Hz, 2H), 7.63-7.41 (m, 2H), 5.79 (d, J=6.0 Hz, 1H), 5.42 (dt, J=43.3, 21.5 Hz, 2H), 5.31-5.10 (m, 5H), 4.85-4.70 (m, 1H), 4.52 (d, J=3.8 Hz, 1H), 4.31 (t, J=8.2 Hz, 1H), 4.17 (dd, J=20.8, 8.8 Hz, 1H), 3.80 (dt, J=19.0, 7.3 Hz, 2H), 3.73 3.63 (m, 7H), 3.63 3.49 (m, 3H), 3.39 (d, J=9.7 Hz, 4H), 3.35 (s, 5H), 3.28 (d, J=4.4 Hz, 3H), 2.84 (d, J=8.8 Hz, 1H), 2.72 (dd, J=12.5, 6.6 Hz, 1H), 2.59-2.45 (m, 1H), 2.45-2.11 (m, 4H), 2.11-1.82 (m, 2H), 1.56 (d, J=6.6 Hz, 3H), 1.35-1.21 (m, 1H), 1.22-1.12 (m, 4H), 1.10-1.01 (m, 2H), 0.99 (d, J=6.6 Hz, 3H), 0.91 (d, J=6.7 Hz, 3H).

Example ON methyl {(2S)-1-[(2S,4S)-2-(5-{2-[(2S,5S)-1-{(2S,3S)-2-[(methoxycarbonyl)amino]-3-methylpentanoyl}-4-(methoxymethyl)-2-yl]-1,11-dihydroisochromeno[4',3':6,7]naphtho[1,2-d]imidazol-9-yl)-1H-imidazol-2-yl)-5-methylpyrrolidin-1-yl]-3-methyl-1-oxobutan-2-yl}carbamate Methyl {(2S)-1-[(2S,4S)-2-(5-{2-[(2S,5S)-1-{(2S,3S)-2-[(methoxycarbonyl)amino]-3-methylpentanoyl}-4-(methoxymethyl)-2-yl]-1,11-dihydroisochromeno[4',3':6,7]naphtho[1,2-d]imidazol-9-yl}-1H-imidazol-2-yl)-5-methylpyrrolidin-1-yl]-3-methyl-1-oxobutan-2-yl}carbamate was prepared according to the method described for the synthesis of methyl {(2S,3S)-1-[(2S,4S)-2-(5-{2-[(2S,4S)-1-{(2S,3S)-2-[(methoxycarbonyl)amino]-3-methylpentanoyl}-4-(methoxymethyl)pyrrolidin-2-yl]-1,11-dihydroisochromeno[4',3':6,7]naphtho[1,2-d]imidazol-9-yl}-1H-imidazol-2-yl)-4-(methoxymethyl)pyrrolidin-1-yl]-3-methyl-1-oxopentan-2-yl}carbamate substituting tert-butyl (2S,4S)-2-[9-(2-{(2S)-1-[N-(methoxycarbonyl)-L-valyl]pyrrolidin-2-yl}-1H-imidazol-5-yl)-1,11-dihydroisochromeno[4',3':6,7]naphtho[1,2-d]imidazol-2-yl]-4-(methoxymethyl)pyrrolidine-1-carboxylate for tert-Butyl (2S,4S)-2-[5-(2-{(2S,5S)-1-[N-(methoxycarbonyl)-L-valyl]-5-methylpyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate. MS (ESI) m/z 863 [M+H]+. 1H NMR (400 MHz, cd3od) δ 8.43 (d, J=24.6 Hz, 1H), 8.01 (dt, J=16.1, 8.0 Hz, 1H), 7.95-7.78 (m, 2H), 7.77-7.64 (m, 2H), 7.59-7.41 (m, 2H), 5.79 (d, J=5.8 Hz, 1H), 5.39 (dt, J=46.2, 23.1 Hz, 1H), 5.27-5.07 (m, 3H), 4.85-4.72 (m, 1H), 4.42 (t, J=8.6 Hz, 1H), 4.31 (d, J=7.9 Hz, 1H), 4.17 (dd, J=19.7, 8.7 Hz, 1H), 3.81 (dd, J=23.6, 13.3 Hz, 1H), 3.69 (d, J=10.0 Hz, 5H), 3.60 (dd, J=14.7, 7.8 Hz, 2H), 3.42 (s, 3H), 3.17 (d, J=6.1 Hz, 1H), 3.07 (s, 1H), 2.99-2.91 (m, 1H), 2.85 (s, 1H), 2.73 (dd, J=12.5, 6.4 Hz, 1H), 2.62-2.48 (m, 1H), 2.45-2.14 (m, 3H), 2.10-1.91 (m, 2H), 1.83 (s, 1H), 1.57 (d, J=6.6 Hz, 3H), 1.44 (d, J=7.4 Hz, 1H), 1.34-1.23 (m, 1H), 1.20-0.96 (m, 5H), 0.90 (dt, J=14.8, 6.7 Hz, 9H).

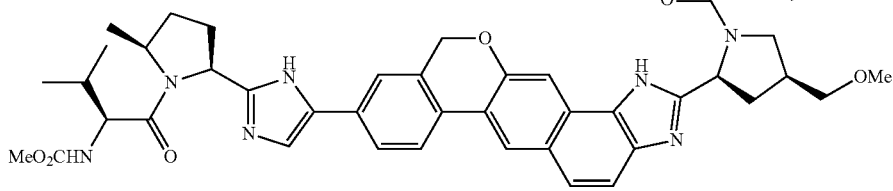

Example OO

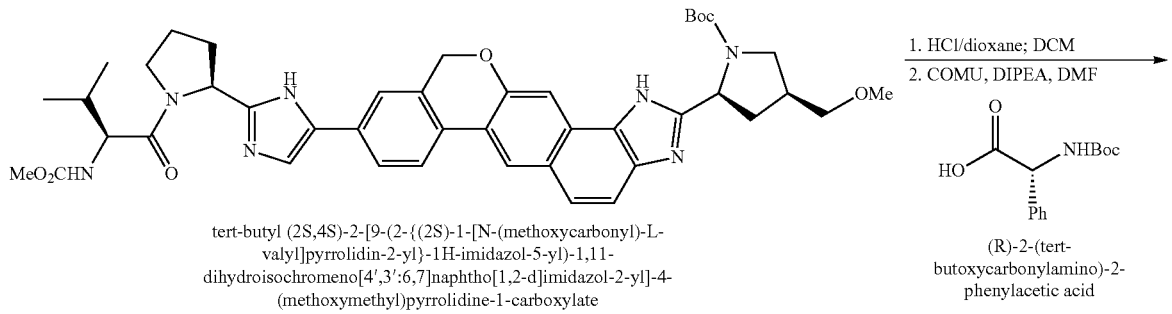

tert-butyl (2S,4S)-2-[9-(2-{(2S)-1-[N-(methoxycarbonyl)-L-valyl]pyrrolidin-2-yl}-1H-imidazol-5-yl)-1,11-dihydroisochromeno[4',3':6,7]naphtho[1,2-d]imidazol-2-yl]-4-(methoxymethyl)pyrrolidine-1-carboxylate (R)-2-(tert-butoxycarbonylamino)-2-phenylacetic acid

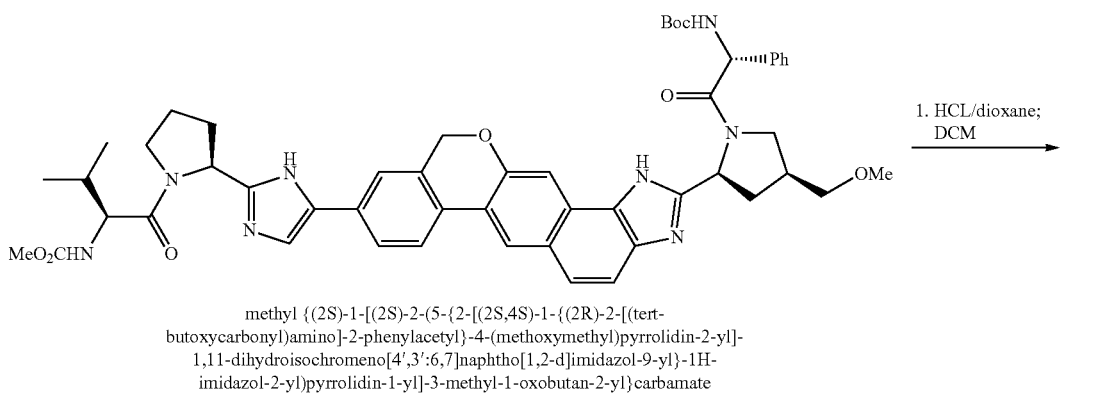

methyl {(2S)-1-[(2S)-2-(5-{2-[(2S,4S)-1-{(2R)-2-[(tert-butoxycarbonyl)amino]-2-phenylacetyl}-4-(methoxymethyl)pyrrolidin-2-yl]-1,11-dihydroisochromeno[4',3':6,7]naphtho[1,2-d]imidazol-9-yl}-1H-imidazol-2-yl)pyrrolidin-1-yl]-3-methyl-1-oxobutan-2-yl}carbamate

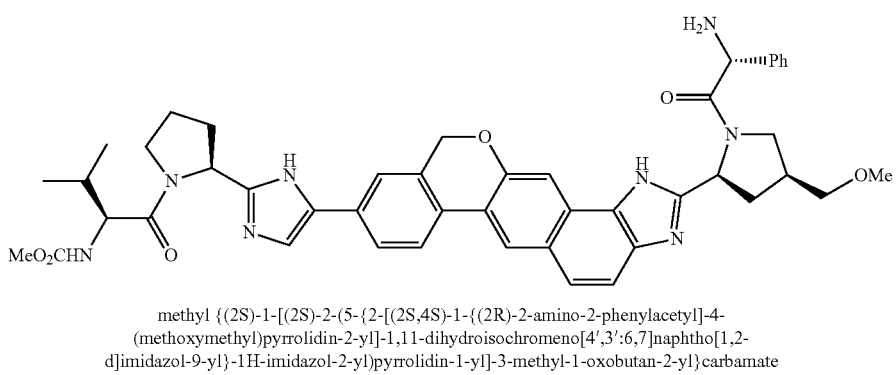

methyl {(2S)-1-[(2S)-2-(5-{2-[(2S,4S)-1-{(2R)-2-amino-2-phenylacetyl}-4-(methoxymethyl)pyrrolidin-2-yl]-1,11-dihydroisochromeno[4',3':6,7]naphtho[1,2-d]imidazol-9-yl}-1H-imidazol-2-yl)pyrrolidin-1-yl]-3-methyl-1-oxobutan-2-yl}carbamate Methyl {(2S)-1-[(2S)-2-(5-{2-[(2S,4S)-1-[(2R)-2-amino-2-phenylacetyl]-4-(methoxymethyl)pyrrolidin-2-yl]-1,11-dihydroisochromeno[4',3':6,7]naphtho[1,2-d]imidazol-9-yl}-1H-imidazol-2-yl)pyrrolidin-1-yl]-3-methyl-1-oxobutan-2-yl}carbamate was prepared according to the method described for the synthesis of methyl(S)-1-((2S,4S)-2-(2'-((2S,4S)-1-((R)-2-amino-2-phenylacetyl)-4-(methoxymethyl)pyrrolidin-2-yl)-1H,1'H-7,7'-binaphtho[1,2-d]imidazol-2-yl)-4-methylpyrrolidin-1-yl)-3-methyl-1-oxobutan-2-ylcarbamate, substituting tert-butyl (2S,4S)-2-[9-(2-{(2S)-1-[N-(methoxycarbonyl)-L-valyl]pyrrolidin-2-yl}-1H-imidazol-5-yl)-1,11-dihydroisochromeno[4',3':6,7]naphtho[1,2-d]imidazol-2-yl]-4-(methoxymethyl)pyrrolidine-1-carboxylate for (2S,4S)-tert-butyl 2-(2'-((2S,4S)-1-((S)-2-(methoxycarbonylamino)-3-methylbutanoyl)-4-methylpyrrolidin-2-yl)-1H,1'H-7,7'-binaphtho[1,2-d]imidazol-2-yl)-4-(methoxymethyl)pyrrolidine-1-carboxylate. MS (ESI) m/z 811 [M+H]$^+$.

Example OP

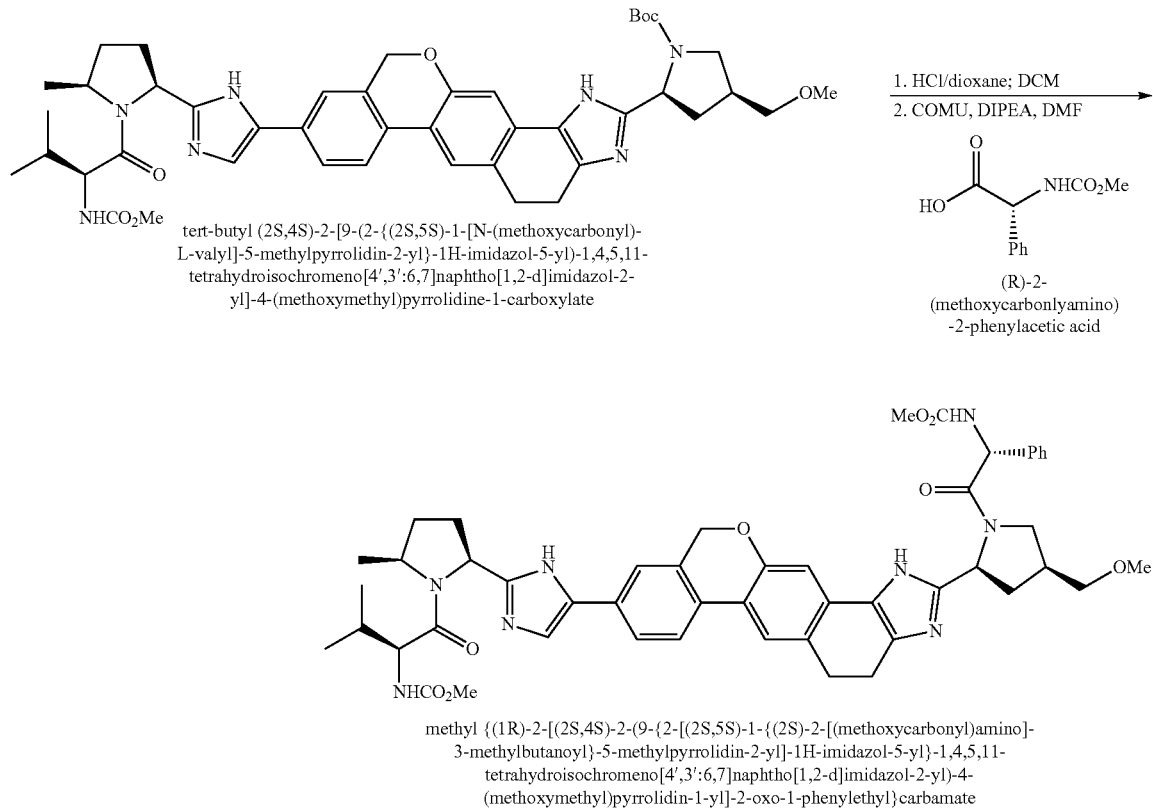

Methyl {(1R)-2-[(2S,4S)-2-(9-{2-[(2S,5S)-1-{(2S)-2-[(methoxycarbonyl)amino]-3-methylbutanoyl}-5-methylpyrrolidin-2-yl]-1H-imidazol-5-yl}-1,4,5,11-tetrahydroisochromeno[4',3':6,7]naphtho[1,2-d]imidazol-2-yl)-4-(methoxymethyl)pyrrolidin-1-yl]-2-oxo-1-phenylethyl}carbamate was synthesized according to the protocol described for the preparation of methyl {(1R)-2-[(2S,4S)-2-(5-{2-[(2S)-1-{(2S)-2-[(methoxycarbonyl)amino]-3-methylbutanoyl}pyrrolidin-2-yl]-1,4,5,11-tetrahydroisochromeno[4',3':6,7]naphtho[1,2-d]imidazol-9-yl}-1H-imidazol-2-yl)-4-(methoxymethyl)pyrrolidin-1-yl]-2-oxo-1-phenylethyl}carbamate, substituting tert-butyl (2S,4S)-2-[9-(2-{(2S,5S)-1-[N-(methoxycarbonyl)-L-valyl]-5-methylpyrrolidin-2-yl}-1H-imidazol-5-yl)-1,4,5,11-tetrahydroisochromeno[4',3':6,7]naphtho[1,2-d]imidazol-2-yl]-4-(methoxymethyl)pyrrolidine-1-carboxylate for tert-butyl (2S,4S)-2-[5-(2-{(2S)-1-[N-(methoxycarbonyl)-L-valyl]pyrrolidin-2-yl}-1,4,5,11 tetrahydroisochromeno[4',3':6,7]naphtho[1,2-d]imidazol-9-yl)-1H-imidazol-2-yl]-4-(methoxymethyl)pyrrolidine-1-carboxylate. MS (ESI) m/z 886 [M+H]⁺. ¹H NMR (400 MHz, cd₃od) δ 8.02-7.85 (m, 2H), 7.85-7.68 (m, 2H), 7.58 (d, J=21.5 Hz, 1H), 7.55-7.35 (m, 4H), 7.31 (d, J=13.6 Hz, 1H), 5.43 (d, J=19.1 Hz, 1H), 5.28 (t, J=8.3 Hz, 1H), 5.25-5.10 (m, 3H), 4.13 (t, J=9.5 Hz, 1H), 3.93-3.54 (m, 7H), 3.42 (qd, J=9.5, 5.5 Hz, 2H), 3.34 (d, J=7.9 Hz, 1H), 3.28 (s, 3H), 3.19 (t, J=7.8 Hz, 2H), 3.00 (t, J=7.8 Hz, 2H), 2.74-2.46 (m, 3H), 2.44-2.15 (m, 2H), 2.12-1.86 (m, 2H), 1.56 (d, J=6.7 Hz, 2H), 1.29 (d, J=6.3 Hz, 1H), 1.15-1.01 (m, 1H), 0.98 (d, J=6.7 Hz, 2H), 0.88 (d, J=6.8 Hz, 2H).

Example OQ

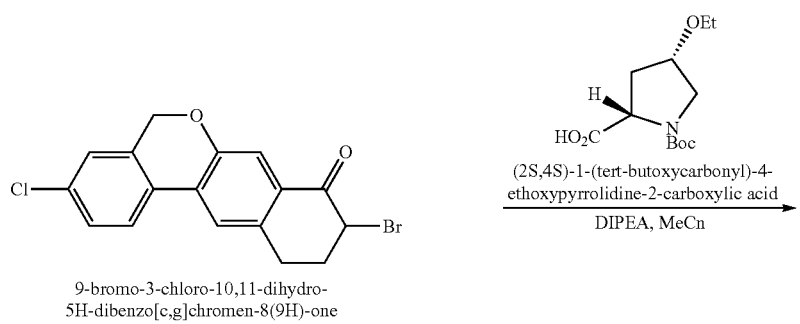

-continued

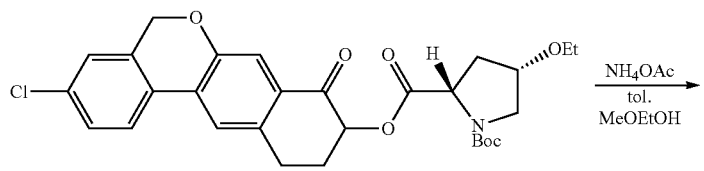

(2S,4S)-1-tert-butyl 2-(3-chloro-8-oxo-
8,9,10,11-tetrahydro-5H-dibenzo[c,g]chromen-
9-yl) 4-ethoxypyrrolidine-1,2-dicarboxylate

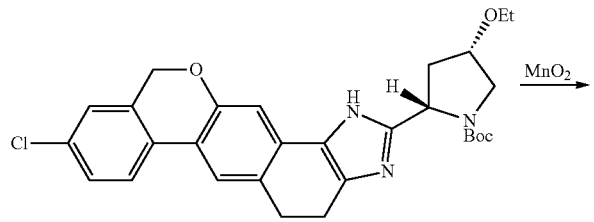

tert-butyl (2S,4S)-2-(9-chloro-1,4,5,11-
tetrahydroisochromeno[4',3':6,7]naphtho[1,2-
d]imidazol-2-yl)-4-ethoxypyrrolidine-1-carboxylate

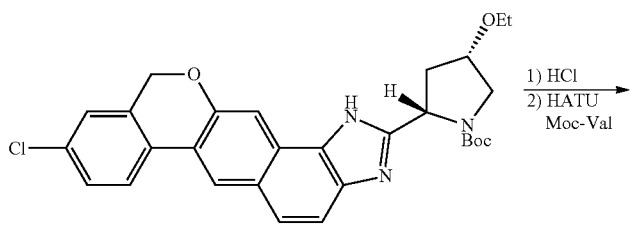

tert-butyl (2S,4S)-2-(9-chloro-1,11-
dihydroisochromeno[4',3':6,7]naphtho[1,2-
d]imidazol-2-yl)-4-ethoxypyrrolidine-1-carboxylate

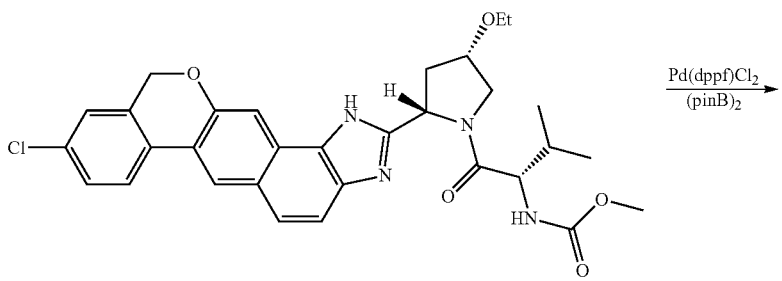

methyl {(2S)-1-[(2S,4S)-2-(9-chloro-1,11-
dihydroisochromeno[4',3':6,7]naphtho[1,2-d]imidazol-2-yl)-4-
ethoxypyrrolidin-1-yl]-3-methyl-1-oxobutan-2-yl}carbamate

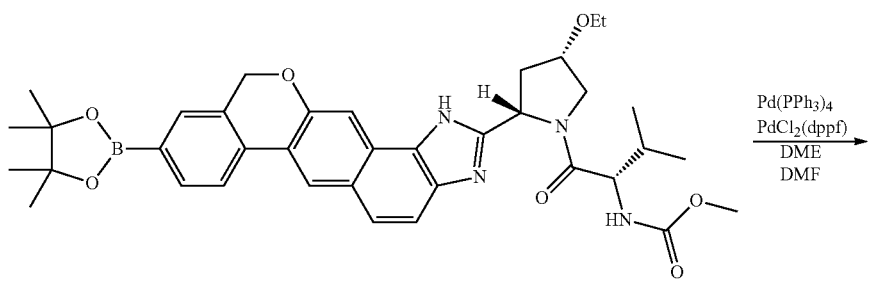

methyl [(2S)-1-{(2S,4S)-4-ethoxy-2-[9-(4,4,5,5-
tetramethyl-1,3,2-dioxaborolan-2-yl)-1,11-
dihydroisochromeno[4',3':6,7]naphtho[1,2-d]imidazol-2-
yl]pyrrolidin-1-yl}-3-methyl-1-oxobutan-2-yl]carbamate -continued

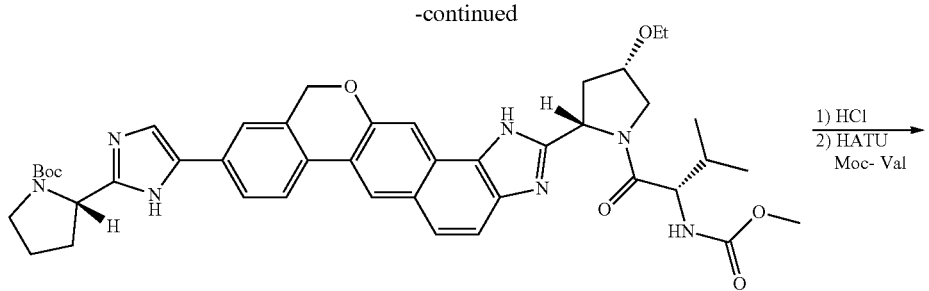

tert-butyl (2S)-2-[5-(2-{(2S,4S)-4-ethoxy-1-[N-(methoxycarbonyl)-L-valyl]pyrrolidin-2-yl}-1,11-dihydroisochromeno[4',3':6,7]naphtho[1,2-d]imidazol-9-yl)-1H-imidazol-2-yl]pyrrolidine-1-carboxylate

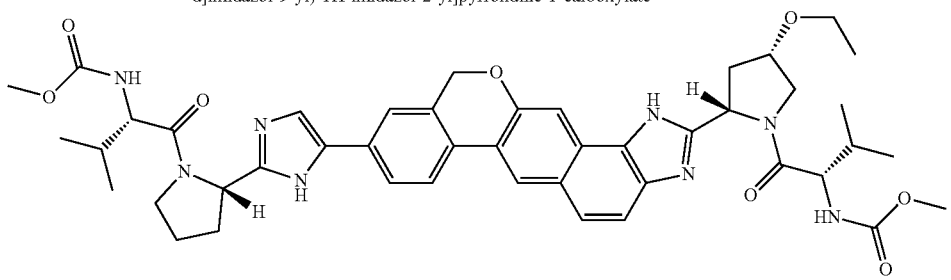

methyl {(2S)-1-[(2S)-2-(5-{2-[(2S,4S)-4-ethoxy-1-[(2S)-2-[(methoxycarbonyl)amino]-3-methylbutanoyl}pyrrolidin-2-yl]-1,11-dihydroisochromeno[4',3':6,7]naphtho[1,2-d]imidazol-9-yl}-1H-imidazol-2-yl)pyrrolidin-1-yl]-3-methyl-1-oxobutan-2-yl}carbamate

(2S,4S)-1-Tert-butyl 2-(3-chloro-8-oxo-8,9,10,11-tetrahydro-5H-dibenzo[c,g]chromen-9-yl) 4-ethoxypyrrolidine-1,2-dicarboxylate To a slurry of 9-bromo-3-chloro-10,11-dihydro-5H-dibenzo[c,g]chromen-8(9H)-one (2.50 g, 6.8 mmol) in MeCN (20 mL) was added (2S,4S)-1-(tert-butoxycarbonyl)-4-ethoxypyrrolidine-2-carboxylic acid (2.68 g, 10.3 mmol) and DIPEA (1.3 mL, 7.5 mmol). The reaction was heated with stirring to 50° C. for 18 h. The reaction was then cooled to room temperature and diluted with EtOAc. The solution was washed with HCl (1N) and brine. The aqueous layers were backextracted with EtOAc and the resulting organic layers were combined, dried ($Na_2SO_4$) and concentrated under reduced pressure. The crude residue was purified by silica column chromatography (15% to 50% EtOAc/Hexanes) to afford (2S,4S)-1-tert-butyl 2-(3-chloro-8-oxo-8,9,10,11-tetrahydro-5H-dibenzo[c,g]chromen-9-yl) 4-ethoxypyrrolidine-1,2-dicarboxylate (2.08 g, 56%).

Tert-butyl (2S,4S)-2-(9-chloro-1,4,5,11-tetrahydroisochromeno[4',3':6,7]naphtho[1,2-d]imidazol-2-yl)-4-ethoxypyrrolidine-1-carboxylate To a solution of (2S,4S)-1-tert-butyl 2-(3-chloro-8-oxo-8,9,10,11-tetrahydro-5H-dibenzo[c,g]chromen-9-yl) 4-ethoxypyrrolidine-1,2-dicarboxylate (2.08 g, 3.8 mmol) in a mixture of toluene (30 mL) and methoxyethanol (4 mL) was added ammonium acetate (2.90 g, 37.7 mmol). The solution was heated with stirring to 80° C. for 18 h. The reaction was then cooled to room temperature and diluted with EtOAc. The solution was washed with brine, and the resulting aqueous layer was backextracted with EtOAc. The resulting organic layers were combined, dried ($Na_2SO_4$), and concentrated under reduced pressure. The crude residue was purified by silica column chromatography (10% to 75% EtOAc(w/5% MeOH)/Hexanes) to afford tert-butyl (2S,4S)-2-(9-chloro-1,4,5,11-tetrahydroisochromeno[4',3':6,7]naphtho[1,2-d]imidazol-2-yl)-4-ethoxypyrrolidine-1-carboxylate (0.99 g, 50%).

Tert-butyl (2S,4S)-2-(9-chloro-1,11-dihydroisochromeno[4',3':6,7]naphtho[1,2-d]imidazol-2-yl)-4-ethoxypyrrolidine-1-carboxylate To a solution of (2S,4S)-2-(9-chloro-1,4,5,11-tetrahydroisochromeno[4',3':6,7]naphtho[1,2-d]imidazol-2-yl)-4-ethoxypyrrolidine-1-carboxylate (0.99 g, 1.9 mmol) in $CH_2Cl_2$ (18 mL) was added $MnO_2$ (4.52 g, 52.0 mmol). The resulting slurry was stirred at room temperature for 18 h. The reaction was filtered through celite, washed with $CH_2Cl_2$, and concentrated under reduced pressure. The crude residue was purified by silica column chromatography (10% to 75% EtOAc(w/5% MeOH)/Hexanes) to afford tert-butyl (2S,4S)-2-(9-chloro-1,11-dihydroisochromeno[4',3':6,7]naphtho[1,2-d]imidazol-2-yl)-4-ethoxypyrrolidine-1-carboxylate (0.71 g, 72%)

Methyl {(2S)-1-[(2S,4S)-2-(9-chloro-1,11-dihydroisochromeno[4',3':6,7]naphtho[1,2-d]imidazol-2-yl)-4-ethoxypyrrolidin-1-yl]-3-methyl-1-oxobutan-2-yl}carbamate To a solution of tert-butyl (2S,4S)-2-(9-chloro-1,11-dihydroisochromeno[4',3':6,7]naphtho[1,2-d]imidazol-2-yl)-4-ethoxypyrrolidine-1-carboxylate (0.46 g, 0.9 mmol) in a mixture of $CH_2Cl_2$ (9.0 mL) and MeOH (1.5 mL) was added HCl (in dioxanes, 4M, 6.5 mL, 26.0 mmol). The resulting solution was stirred at room temperature for 2 h. The solution was concentrated to dryness under reduced pressure. To the crude intermediate in $CH_2Cl_2$ (10.0 mL) was added (S)-2-(methoxycarbonylamino)-3-methylbutanoic acid (0.17 g, 0.9 mmol), HATU (0.41 g, 1.1 mmol), and DIPEA (0.5 mL, 2.9 mmol). The resulting solution was stirred at room temperature for 48 h and diluted with $CH_2Cl_2$. The solution was washed with aqueous HCl (IN) and brine. The aqueous layers were backextracted with $CH_2Cl_2$ (2×). The resulting organic layers were combined, dried ($Na_2SO_4$), and concentrated under reduced pressure. The crude residue was purified by silica column chromatography (20% to 100% EtOAc(w/5% MeOH)/Hexanes to 80% MeOH/EtOAc) to afford methyl {(2S)-1-[(2S,4S)-2-(9-chloro-1,11-dihydroisochromeno[4', 3':6,7]naphtho[1,2-d]imidazol-2-yl)-4-ethoxypyrrolidin-1-yl]-3-methyl-1-oxobutan-2-yl}carbamate (0.46 g, 90%).

Methyl [(2S)-1-{(2S,4S)-4-ethoxy-2-[9-(4,4,5,5-tetramethyl-1,3,2-dioxaborolan-2-yl)-1,11-dihydroisochromeno[4',3':6,7]naphtho[1,2-d]imidazol-2-yl]pyrrolidin-1-yl}-3-methyl-1-oxobutan-2-yl]carbamate To a solution of methyl {(2S)-1-[(2S,4S)-2-(9-chloro-1,11-dihydroisochromeno[4',3':6,7]naphtho[1,2-d]imidazol-2-yl)-4-ethoxypyrrolidin-1-yl]-3-methyl-1-oxobutan-2-yl}carbamate (0.46 g, 0.84 mmol) in dioxane (8.5 mL) was added 4,4,4',4',5,5,5',5'-octamethyl-2,2'-bi(1,3,2-dioxaborolane) (0.32 g, 1.3 mmol), potassium acetate (0.25 g, 2.5 mmol), bis(dibenzylideneacetone)palladium (0.032 g, 0.035 mmol), and 2-dicyclohexylphosphino-2',4',6'-triisopropylbiphenyl (Xphos, 0.032 g, 0.067 mmol). The resulting solution was degassed with argon for 5 min and heated, with stirring, to 90° C. for 6 h. The reaction was cooled to room temperature, diluted with EtOAc, and filtered through celite. The crude residue was purified by silica column chromatography (20% to 100% EtOAc(w/5% MeOH)/Hexanes to 90% MeOH/EtOAc) to afford methyl [(2S)-1-{(2S,4S)-4-ethoxy-2-[9-(4,4,5,5-tetramethyl-1,3,2-dioxaborolan-2-yl)-1,11-dihydroisochromeno[4',3':6,7]naphtho[1,2-d]imidazol-2-yl]pyrrolidin-1-yl}-3-methyl-1-oxobutan-2-yl]carbamate (0.41 g, 73%).

Tert-butyl (2S)-2-[5-(2-{(2S,4S)-4-ethoxy-1-[N-(methoxycarbonyl)-L-valyl]pyrrolidin-2-yl}-1,11-dihydroisochromeno[4',3':6,7]naphtho[1,2-d]imidazol-9-yl)-1H-imidazol-2-yl]pyrrolidine-1-carboxylate To a solution of methyl [(2S)-1-{(2S,4S)-4-ethoxy-2-[9-(4,4,5,5-tetramethyl-1,3,2-dioxaborolan-2-yl)-1,11-dihydroisochromeno[4',3':6,7]naphtho[1,2-d]imidazol-2-yl]pyrrolidin-1-yl}-3-methyl-1-oxobutan-2-yl]carbamate (0.41 g, 0.61 mmol) in a mixture of DME (6.1 mL) and DMF (1.0 mL) was added (S)-tert-butyl 2-(5-bromo-1H-imidazol-2-yl)pyrrolidine-1-carboxylate (0.39 g, 1.2 mmol), tetrakis(triphenylphosphine)palladium (0.021 g, 0.018 mmol), [1,1'-bis(diphenylphosphino)ferrocene]dichloropalladium (0.030 g, 0.041 mmol), and aqueous potassium carbonate (2M, 1.0 mL, 2.0 mmol). The solution was degassed with argon for 5 min and heated, with stirring, to 85° C. for 6 h. The solution was cooled to room temperature and diluted with EtOAc. The organic layer was washed with water and brine. The aqueous layers were backextracted with EtOAc (3×). The combined organic layers were dried over $Na_2SO_4$ and concentrated under reduced pressure. The crude residue was purified by silica column chromatography (20% to 100% EtOAc(w/5% MeOH)/Hexanes to 80% MeOH/EtOAc) to afford tert-butyl (2S)-2-[5-(2-{(2S,4S)-4-ethoxy-1-[N-(methoxycarbonyl)-L-valyl]pyrrolidin-2-yl}-1,11-dihydroisochromeno[4',3':6, 7]naphtho[1,2-d]imidazol-9-yl)-1H-imidazol-2-yl]pyrrolidine-1-carboxylate (0.16 g, 33%).

Methyl {(2S)-1-[(2S)-2-(5-{2-[(2S,4S)-4-ethoxy-1-{(2S)-2-[(methoxycarbonyl)amino]-3-methylbutanoyl}pyrrolidin-2-yl]-1,11-dihydroisochromeno[4',3':6,7]naphtho[1,2-d]imidazol-9-yl}-1H-imidazol-2-yl)pyrrolidin-1-yl]-3-methyl-1-oxobutan-2-yl}carbamate To a solution of tert-butyl (2S)-2-[5-(2-{(2S,4S)-4-ethoxy-1-[N-(methoxycarbonyl)-L-valyl]pyrrolidin-2-yl}-1,11-dihydroisochromeno[4',3':6,7]naphtho[1,2-d]imidazol-9-yl)-1H-imidazol-2-yl]pyrrolidine-1-carboxylate (0.048 g, 0.062 mmol) in a mixture of $CH_2Cl_2$ (1.0 mL) and MeOH (0.25 mL) was added HCl (in dioxanes, 4M, 0.47 mL, 1.9 mmol). The solution was stirred at room temperature for 3 h, and then concentrated to dryness under reduced pressure. To the crude intermediate suspended in $CH_2Cl_2$ (1.5 mL) was added (S)-2-(methoxycarbonylamino)-3-methylbutanoic acid (0.012 g, 0.069 mmol), HATU (0.029 g, 0.076 mmol), and DIPEA (0.050 mL, 0.28 mmol). The resulting solution was stirred at room temperature for 1.5 h. The reaction was diluted with DMF and aqueous LiOH (2.5 M, 4 drops) was added. The solution was concentrated to remove the $CH_2Cl_2$ and the crude residue was purified by preparative reverse phase HPLC (10% to 52% MeCN/water with 0.1% TFA). The desired fractions were combined and concentrated under reduced pressure to remove volatile organics. The addition of aqueous sodium bicarbonate with stirring resulted in precipitation of a white solid. The precipitate was filtered through a membrane filter and washed with water. Drying under reduced pressure afforded methyl {(2S)-1-[(2S)-2-(5-{2-[(2S,4S)-4-ethoxy-1-{(2S)-2-[(methoxycarbonyl)amino]-3-methylbutanoyl}pyrrolidin-2-yl]-1,11-dihydroisochromeno[4',3':6,7]naphtho[1,2-d]imidazol-9-yl}-1H-imidazol-2-yl)pyrrolidin-1-yl]-3-methyl-1-oxobutan-2-yl}carbamate (0.008 g, 17%). $^1$H-NMR: 400 MHz, (MeOD) δ: (Mixture of rotamers) 8.37 (s, 1H), 7.97 (s, 2H), 7.37-7.76 (m, 5H), 5.38-5.54 (m, 1H), 5.18 (s, 2H), 5.14-5.16 (m, 1H), 4.21-4.31 (m, 4H), 3.87-4.09 (m, 1H), 3.79-3.85 (m, 2H), 3.66 (s, 3H), 3.64 (s, 3H), 3.46-3.55 (m, 2H), 2.30-2.35 (m, 3H), 2.04-2.06 (m, 3H), 1.11 (m, 2H), 0.95 (d, 3H), 0.88 (d, 3H). MS (ESI) m/z 836.02 [M+H]$^+$.

Example OR

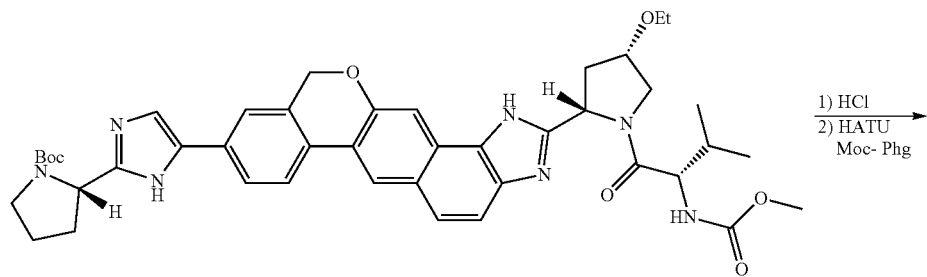

tert-butyl (2S)-2-[5-(2-{(2S,4S)-4-ethoxy-1-[N-(methoxycarbonyl)-L-valyl]pyrrolidin-2-yl}-1,11-dihydroisochromeno[4',3':6,7]naphtho[1,2-d]imidazol-9-yl)-1H-imidazol-2-yl]pyrrolidine-1-carboxylate

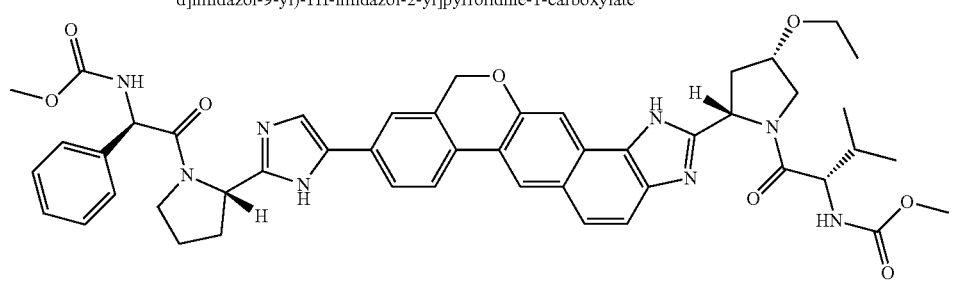

methyl {(1R)-2-[(2S)-2-(5-{2-[(2S,4S)-4-ethoxy-1-{(2S)-2-[(methoxycarbonyl)amino]-3-methylbutanoyl}pyrrolidin-2-yl]-1,11-dihydroisochromeno[4',3':6,7]naphtho[1,2-d]imidazol-9-yl}-1H-imidazol-2-yl)pyrrolidin-1-yl]-2-oxo-1-phenylethyl}carbamate Methyl {(1R)-2-[(2S)-2-(5-{2-[(2S,4S)-4-ethoxy-1-{(2S)-2-[(methoxycarbonyl)amino]-3-methylbutanoyl}pyrrolidin-2-yl]-1,11-dihydroisochromeno[4',3':6,7]naphtho[1,2-d]imidazol-9-yl}-1H-imidazol-2-yl)pyrrolidin-1-yl]-2-oxo-1-phenylethyl}carbamate To a solution of tert-butyl (2S)-2-[5-(2-{(2S,4S)-4-ethoxy-1-[N-(methoxycarbonyl)-L-valyl]pyrrolidin-2-yl}-1,11-dihydroisochromeno[4',3':6,7]naphtho[1,2-d]imidazol-9-yl)-1H-imidazol-2-yl]pyrrolidine-1-carboxylate (0.11 g, 0.14 mmol) in a mixture of $CH_2Cl_2$ (2.0 mL) and MeOH (0.5 mL) was added HCl (in dioxanes, 4M, 1.0 mL, 4.0 mmol). The solution was stirred at room temperature for 3 h, and then concentrated to dryness under reduced pressure. To the crude intermediate suspended in $CH_2Cl_2$ (1.5 mL) was added (R)-2-(methoxycarbonylamino)-2-phenylacetic acid (0.044 g, 0.21 mmol) and DIPEA (0.075 mL, 0.43 mmol). The resulting solution was cooled to −40° C. and COMU (0.096 g, 0.22 mmol) was added. The reaction was allowed to slowly warm to 0° C. over 1 h. The reaction was diluted with DMF. The solution was concentrated to remove the $CH_2Cl_2$ and the crude residue was purified by preparative reverse phase HPLC (10% to 55% MeCN/water with 0.1% TFA). The desired fractions were combined and concentrated under reduced pressure to remove volatile organics. The addition of aqueous sodium bicarbonate with stirring resulted in precipitation of a white solid. The precipitate was filtered through a membrane filter and washed with water. Drying under reduced pressure afforded methyl {(1R)-2-[(2S)-2-(5-{2-[(2S,4S)-4-ethoxy-1-{(2S)-2-[(methoxycarbonyl)amino]-3-methylbutanoyl}pyrrolidin-2-yl]-1,11-dihydroisochromeno[4',3':6,7]naphtho[1,2-d]imidazol-9-yl}-1H-imidazol-2-yl)pyrrolidin-1-yl]-2-oxo-1-phenylethyl}carbamate (0.022 g, 18%). $^1$H-NMR: 400 MHz, (MeOD) δ: (Mixture of rotamers) 8.28 (d, 1H), 7.88 (d, 1H), 7.52-7.70 (m, 3H), 7.28-7.38 (m, 5H), 6.90-6.96 (m, 2H), 5.44-5.47 (m, 1H), 5.31 (s, 1H), 5.12 (s, 2H), 4.16-4.48 (m, 3H), 3.81-3.19 (m, 1H), 3.62-3.76 (m, 2H), 3.58 (s, 3H), 2.56 (s, 3H), 2.42-2.57 (m, 1H), 2.31 (m, 1H), 1.81-2.41 (m, 5H), 1.04 (t, 3H), 0.87 (d, 3H), 0.81 (d, 3H). MS (ESI) m/z 869.55 [M+H]$^+$.

Example OS

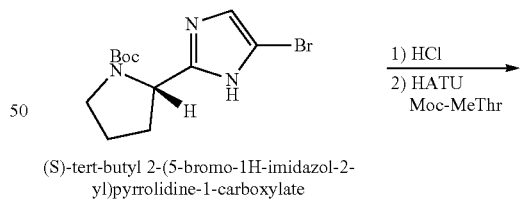

(S)-tert-butyl 2-(5-bromo-1H-imidazol-2-yl)pyrrolidine-1-carboxylate

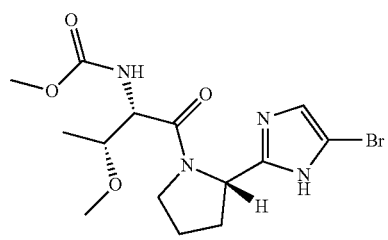

methyl (2S,3R)-1-((S)-2-(5-bromo-1H-imidazol-2-yl)pyrrolidin-1-yl)-3-methoxy-1-oxobutan-2-ylcarbamate

Methyl (2S,3R)-1-((S)-2-(5-bromo-1H-imidazol-2-yl)pyrrolidin-1-yl)-3-methoxy-1-oxobutan-2-ylcarbamate To a solution of (S)-tert-butyl 2-(5-bromo-1H-imidazol-2-yl)pyrrolidine-1-carboxylate (1.00 g, 3.2 mmol) in a mixture of CH$_2$Cl$_2$ (30 mL) and MeOH (5 mL) was added HCl (in dioxane, 4 M, 11.5 mL, 46.0 mmol). The solution was stirred at 40° C. for 1 h, cooled to room temperature, and concentrated to dryness under reduced pressure. To the crude intermediate suspended in CH$_2$Cl$_2$ (30 mL) was added (2S,3R)-3-methoxy-2-(methoxycarbonylamino)butanoic acid (0.67 g, 3.5 mmol), HATU (1.47 g, 3.8 mmol), and DIPEA (1.00 mL, 6.0 mmol). The resulting solution was stirred at room temperature for 24 h. DMF (2 mL) and aqueous LiOH (2.5 M, 1 mL) were added and the reaction was concentrated to dryness under reduced pressure. The crude material was diluted with EtOAc and washed with H$_2$O and brine. The aqueous layers were backextracted with EtOAc. The combined organic layers were dried over Na$_2$SO$_4$ and concentrated under reduced pressure. The crude residue was purified by silica column chromatography (20% to 100% EtOAc(w/5% MeOH)/CH$_2$Cl$_2$) to afford methyl (2S,3R)-1-((S)-2-(5-bromo-1H-imidazol-2-yl)pyrrolidin-1-yl)-3-methoxy-1-oxobutan-2-ylcarbamate (1.2 g, 100%).

Example OT

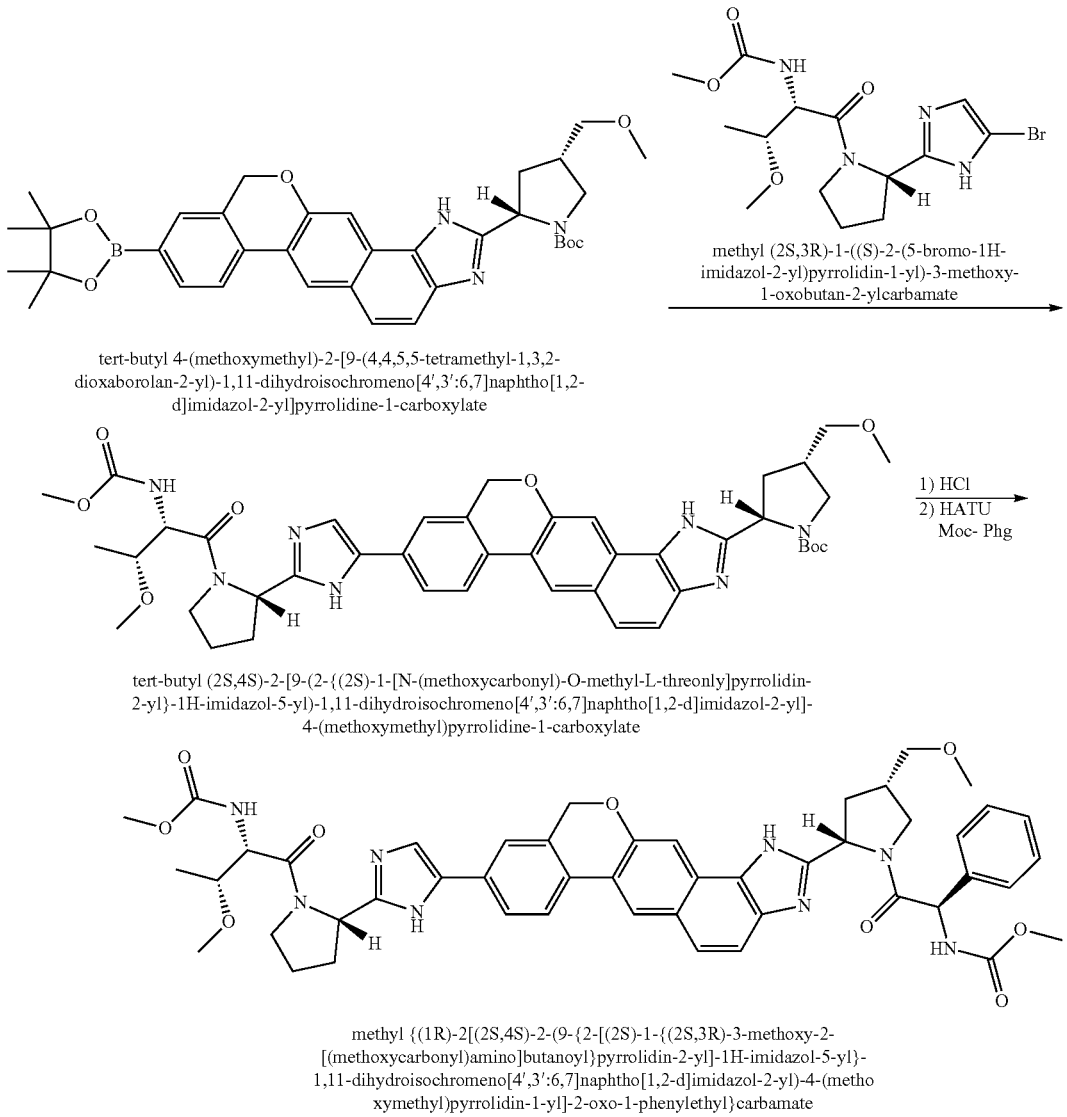

Tert-butyl (2S,4S)-2-[9-(2-{(2S)-1-[N-(methoxycarbonyl)-O-methyl-L-threonyl]pyrrolidin-2-yl}-1H-imidazol-5-yl)-1,11-dihydroisochromeno[4',3':6,7]naphtho[1,2-d]imidazol-2-yl]-4-(methoxymethyl)pyrrolidine-1-carboxylate To a solution of tert-butyl 4-(methoxymethyl)-2-[9-(4,4,5,5-tetramethyl-1,3,2-dioxaborolan-2-yl)-1,11-dihydroisochromeno[4',3':6,7]-naphtho[1,2-d]imidazol-2-yl]pyrrolidine-1-carboxylate (1.0 g, 3.2 mmol) in a mixture of DMSO (2.0 mL) and dioxanes (2.0 mL) was added methyl (2S,3R)-1-((S)-2-(5-bromo-1H-imidazol-2-yl)pyrrolidin-1-yl)-3-methoxy-1-oxobutan-2-ylcarbamate (0.24 g, 0.62 mmol), tetrakis(triphenylphosphine)palladium (0.050 g, 0.043 mmol), [1,1'- bis(diphenylphosphino)ferrocene]dichloropalladium (0.030 g, 0.041 mmol), and aqueous potassium carbonate (2M, 0.65 mL, 1.3 mmol). The solution was degassed with argon for 5 min and heated, with stirring, to 85° C. for 6 h. The solution was cooled to room temperature and diluted with EtOAc. The organic layer was washed with water and brine. The aqueous layers were backextracted with EtOAc (3×). The combined organic layers were dried over $Na_2SO_4$ and concentrated under reduced pressure. The crude residue was purified by silica column chromatography (20% to 100% EtOAc(w/5% MeOH)/Hexanes to 60% MeOH/EtOAc) to afford tert-butyl (2S,4S)-2-[9-(2-{(2S)-1-[N-(methoxycarbonyl)-O-methyl-L-threonyl]pyrrolidin-2-yl}-1H-imidazol-5-yl)-1,11-dihydroisochromeno[4',3':6,7]naphtho[1,2-d]imidazol-2-yl]-4-(methoxymethyl)pyrrolidine-1-carboxylate (0.20 g, 63%).

Methyl {(1R)-2-[(2S,4S)-2-(9-{2-[(2S)-1-{(2S,3R)-3-methoxy-2-[(methoxycarbonyl)amino]butanoyl}pyrrolidin-2-yl]-1H-imidazol-5-yl}-1,11-dihydroisochromeno[4',3':6,7]naphtho[1,2-d]imidazol-2-yl)-4-(methoxymethyl)pyrrolidin-1-yl]-2-oxo-1-phenylethyl}carbamate To a solution of tert-butyl (2S,4S)-2-[9-(2-{(2S)-1-[N-(methoxycarbonyl)-O-methyl-L-threonyl]pyrrolidin-2-yl}-1H-imidazol-5-yl)-1,11-dihydroisochromeno[4',3':6,7]naphtho[1,2-d]imidazol-2-yl]-4-(methoxymethyl)pyrrolidine-1-carboxylate (0.20 g, 0.26 mmol) in a mixture of $CH_2Cl_2$ (3.0 mL) and MeOH (0.5 mL) was added HCl (in dioxanes, 4M, 2.0 mL, 8.0 mmol). The solution was stirred at 40° C. for 1 h, and then cooled to room temperature and concentrated to dryness under reduced pressure. To the crude intermediate suspended in $CH_2Cl_2$ (3.0 mL) was added (R)-2-(methoxycarbonylamino)-2-phenylacetic acid (0.081 g, 0.39 mmol) and DIPEA (0.150 mL, 0.86 mmol). The resulting solution was cooled to −40° C. and COMU (0.180 g, 0.42 mmol) was added. The reaction was allowed to slowly warm to room temperature over 30 min and maintained for 1.5 h. The solution was diluted with $CH_2Cl_2$ and washed with aqueous bicarbonate. The aqueous layer was backextracted with $CH_2Cl_2$. The combined organic layers were dried over $Na_2SO_4$ and concentrated under reduced pressure. The crude residue was purified by preparative reverse phase HPLC (10% to 50% MeCN/water with 0.1% TFA). The desired fractions were combined and concentrated under reduced pressure to remove volatile organics. The addition of aqueous sodium bicarbonate with stirring resulted in precipitation of a white solid. The precipitate was filtered through a membrane filter and washed with water. Drying under reduced pressure afforded methyl {(1R)-2-[(2S,4S)-2-(9-{2-[(2S)-1-{((2S,3R)-3-methoxy-2-[(methoxycarbonyl)amino]butanoyl}pyrrolidin-2-yl]-1H-imidazol-5-yl}-1,11-dihydroisochromeno[4',3':6,7]naphtho[1,2-d]imidazol-2-yl)-4-(methoxymethyl)pyrrolidin-1-yl]-2-oxo-1-phenylethyl}carbamate (0.10 g, 46%). 1H-NMR: 400 MHz, (MeOD) δ: (Mixture of rotamers) 8.34 (s, 1H), 7.92-7.97 (m, 2H), 7.33-7.69 (m, 10H), 5.53 (s, 1H), 5.36-5.39 (m, 1H), 5.15-5.21 (m, 3H), 4.44 (d, 1H), 3.86-3.93 (m, 2H), 3.68-3.75 (m, 2H), 3.66 (s, 3H), 3.65 (s, 3H), 3.46-3.57 (m, 2H), 3.28 (s, 3H), 3.19 (s, 3H), 2.47-2.60 (m, 3H), 2.22-2.36 (m, 4H), 1.99-2.08 (m, 3H), 1.15 (d, 3H). MS (ESI) m/z 886.19 $[M+H]^+$.

Example OU

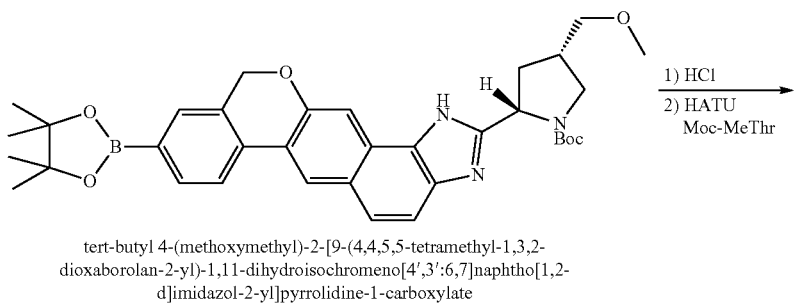

tert-butyl 4-(methoxymethyl)-2-[9-(4,4,5,5-tetramethyl-1,3,2-dioxaborolan-2-yl)-1,11-dihydroisochromeno[4',3':6,7]naphtho[1,2-d]imidazol-2-yl]pyrrolidine-1-carboxylate

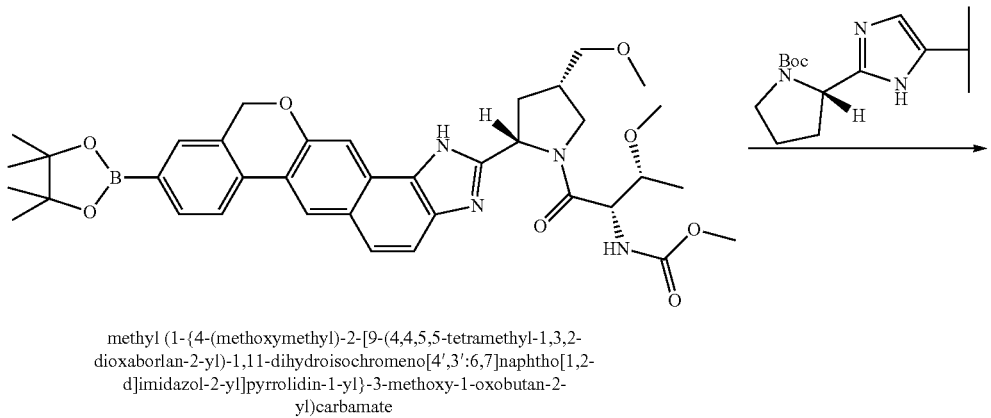

methyl (1-{4-(methoxymethyl)-2-[9-(4,4,5,5-tetramethyl-1,3,2-dioxaborlan-2-yl)-1,11-dihydroisochromeno[4',3':6,7]naphtho[1,2-d]imidazol-2-yl]pyrrolidin-1-yl}-3-methoxy-1-oxobutan-2-yl)carbamate

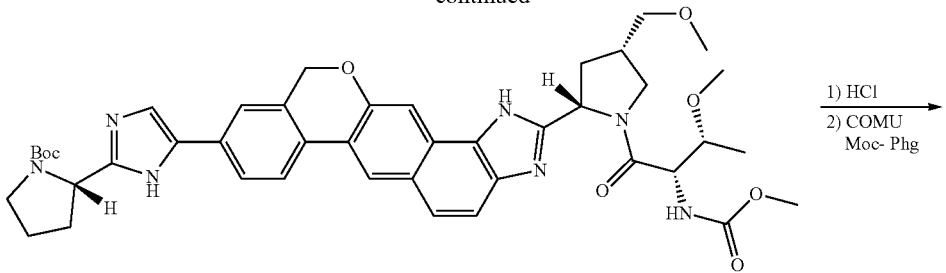

tert-butyl (2S)-2-(5-{2-[(2S,4S)-1-[N-methoxycarbonyl)-O-methyl-L-threonyl]-4-(methoxymethyl)pyrrolidin-2-yl]-1,11-dihydroisochromeno[4',3':6,7]naphtho[1,2-d]imidazol-9-yl}-1H-imidazol-2-yl)pyrrolidine-1-carboxylate

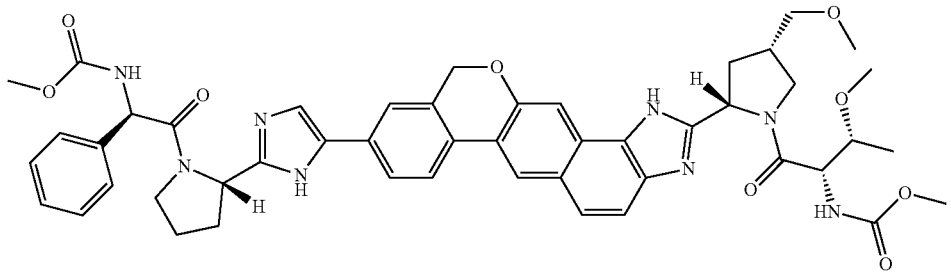

methyl {(1R)-2-[(2S)-2-(5-{2-[(2S,4S)-1-{(2S)-2-[(methoxycarbonyl)amino]-3-methoxybutanoyl}-4-(methoxymethyl)pyrrolidin-2-yl]-1,11-dihydroisochromeno[4',3':6,7]naphtho[1,2-d]imidazol-9-yl}-1H-imidazol-2-yl)pyrrolidin-1-yl]-2-oxo-1-phenylethyl}carbamate Methyl (1-{4-(methoxymethyl)-2-[9-(4,4,5,5-tetramethyl-1,3,2-dioxaborolan-2-yl)-1,11-dihydroisochromeno[4',3':6,7]naphtho[1,2-d]imidazol-2-yl]pyrrolidin-1-yl}-3-methoxy-1-oxobutan-2-yl)carbamate To a solution of tert-butyl 4-(methoxymethyl)-2-[9-(4,4,5,5-tetramethyl-1,3,2-dioxaborolan-2-yl)-1,11-dihydroisochromeno[4',3':6,7]naphtho[1,2-d]imidazol-2-yl]pyrrolidine-1-carboxylate (0.25 g, 0.41 mmol) in a mixture of $CH_2Cl_2$ (4.0 mL) and MeOH (1.0 mL) was added HCl (in dioxanes, 4M, 3.0 mL, 12.0 mmol). The resulting solution was stirred at 40° C. for 45 min. The solution was cooled to room temperature and concentrated to dryness under reduced pressure. To the crude intermediate in $CH_2Cl_2$ (4.0 mL) was added (2S,3R)-3-methoxy-2-(methoxycarbonylamino)butanoic acid (0.08 g, 0.42 mmol), HATU (0.17 g, 0.45 mmol), and DIPEA (0.4 mL, 2.3 mmol). The resulting solution was stirred at room temperature for 48 h and diluted with $CH_2Cl_2$. The solution was washed with brine. The aqueous layer was backextracted with $CH_2Cl_2$ (2×). The resulting organic layers were combined, dried ($Na_2SO_4$), and concentrated under reduced pressure. The crude residue was purified by silica column chromatography (30% to 100% EtOAc(w/5% MeOH)/Hexanes to 80% MeOH/EtOAc) to afford methyl (1-{4-(methoxymethyl)-2-[9-(4,4,5,5-tetramethyl-1,3,2-dioxaborolan-2-yl)-1,11-dihydroisochromeno[4',3':6,7]naphtho[1,2-d]imidazol-2-yl]pyrrolidin-1-yl}-3-methoxy-1-oxobutan-2-yl)carbamate (0.24 g, 92%).

Tert-butyl (2S)-2-(5-{2-[(2S,4S)-1-[N-(methoxycarbonyl)-O-methyl-L-threonyl]-4-(methoxymethyl)pyrrolidin-2-yl]-1,11-dihydroisochromeno[4',3':6,7]naphtho[1,2-d]imidazol-9-yl}-1H-imidazol-2-yl)pyrrolidine-1-carboxylate To a solution of methyl (1-{4-(methoxymethyl)-2-[9-(4,4,5,5-tetramethyl-1,3,2-dioxaborolan-2-yl)-1,11-dihydroisochromeno[4',3':6,7]naphtho[1,2-d]imidazol-2-yl]pyrrolidin-1-yl}-3-methoxy-1-oxobutan-2-yl)carbamate (0.15 g, 0.22 mmol) in a mixture of DMSO (2.0 mL) and dioxane (2.0 mL) was added (S)-tert-butyl 2-(5-iodo-1H-imidazol-2-yl)pyrrolidine-1-carboxylate (0.15 g, 0.40 mmol), tetrakis(triphenylphosphine)palladium (0.028 g, 0.024 mmol), [1,1'-bis(diphenylphosphino)ferrocene]dichloropalladium (0.018 g, 0.025 mmol), and aqueous potassium carbonate (2M, 0.35 mL, 0.70 mmol). The solution was degassed with argon for 5 min and heated, with stirring, to 90° C. for 6 h. The solution was cooled to room temperature and diluted with EtOAc. The organic layer was washed with water and brine. The aqueous layers were backextracted with EtOAc (3×). The combined organic layers were dried over $Na_2SO_4$ and concentrated under reduced pressure. The crude residue was purified by preparative reverse phase HPLC (10% to 55% MeCN/water with 0.1% TFA). The desired fractions were combined and concentrated under reduced pressure to remove volatile organics. The remaining solution was basified with aqueous bicarbonate and extracted with $CH_2Cl_2$ (3×). The combined organic layers were dried over $Na_2SO_4$ and concentrated under reduced pressure to provide tert-butyl (2S)-2-(5-{2-[(2S,4S)-1-[N-(methoxycarbonyl)-O-methyl-L-threonyl]-4-(methoxymethyl)pyrrolidin-2-yl]-1,11-dihydroisochromeno[4',3':6,7]naphtho[1,2-d]imidazol-9-yl}-1H-imidazol-2-yl)pyrrolidine-1-carboxylate (0.013 g, 7%).

Methyl {(1R)-2-[(2S)-2-(5-{2-[(2S,4S)-1-{(2S)-2-[(methoxycarbonyl)amino]-3-methoxybutanoyl}-4-(methoxymethyl)pyrrolidin-2-yl]-1,11-dihydroisochromeno[4',3':6,7]naphtho[1,2-d]imidazol-9-yl}-1H-imidazol-2-yl)pyrrolidin-1-yl]-2-oxo-1-phenylethyl}carbamate To a solution of tert-butyl (2S)-2-(5-{2-[(2S,4S)-1-[N-(methoxycarbonyl)-O-methyl-L-threonyl]-4-(methoxymethyl)pyrrolidin-2-yl]-1,11-dihydroisochromeno[4',3':6,7]naphtho[1,2-d]imidazol-9-yl}-1H-imidazol-2-yl)pyrrolidine-1-carboxylate (0.013 g, 0.016 mmol) in a mixture of $CH_2Cl_2$ (0.5 mL) and MeOH (0.02 mL) was added HCl (in dioxanes, 4M, 0.20 mL, 0.80 mmol). The solution was stirred at room temperature for 1 h, and then concentrated to dryness under reduced pressure. To the crude intermediate suspended in $CH_2Cl_2$ (0.5 mL) was added (R)-2-(methoxycarbonylamino)-2-phenylacetic acid (0.006 g, 0.029 mmol) and DIPEA (0.05 mL, 0.28 mmol). The resulting solution was cooled to 0° C. and COMU (0.012 g, 0.028 mmol) was added. The reaction was stirred at 0° C. for 30 min. The solution was diluted with DMF and aqueous LiOH (2.5 M, 2 drops) and concentrated under reduced pressure to remove the $CH_2Cl_2$. The crude residue was purified by preparative reverse phase HPLC (10% to 55% MeCN/water with 0.1% TFA). The desired fractions were combined and concentrated under reduced pressure to remove volatile organics. The addition of aqueous sodium bicarbonate with stirring resulted in precipitation of a white solid. The precipitate was filtered through a membrane filter and washed with water. Drying under reduced pressure afforded methyl {(1R)-2-[(2S)-2-(5-{2-[(2S,4S)-1-{(2S)-2-[(methoxycarbonyl)amino]-3-methoxybutanoyl}-4-(methoxymethyl)pyrrolidin-2-yl]-1,11-dihydroisochromeno[4',3':6,7]naphtho[1,2-d]imidazol-9-yl}-1H-imidazol-2-yl)pyrrolidin-1-yl]-2-oxo-1-phenylethyl}carbamate (0.008 g, 61%). $^1$H-NMR: 400 MHz, (MeOD) δ: (Mixture of rotamers) 8.37 (m, 1H), 7.96-7.98 (m, 2H), 7.60-7.79 (m, 3H), 7.35-7.52 (m, 6H), 6.98-7.03 (m, 1H), 5.52 (s, 1H), 5.26-5.39 (m, 2H), 5.20 (s, 2H), 4.44 (m, 1H), 4.27 (m, 1H), 3.64 (s, 6H), 3.50-3.57 (m, 3H), 3.37 (s, 3H), 3.29-3.44 (m, 3H), 3.20 (s, 3H), 2.68-2.72 (m, 2H), 2.57-2.62 (m, 2H), 1.89-2.15 (m, 6H), 1.18 (d, 3H). MS (ESI) m/z 885.73 $[M+H]^+$.

Example OV

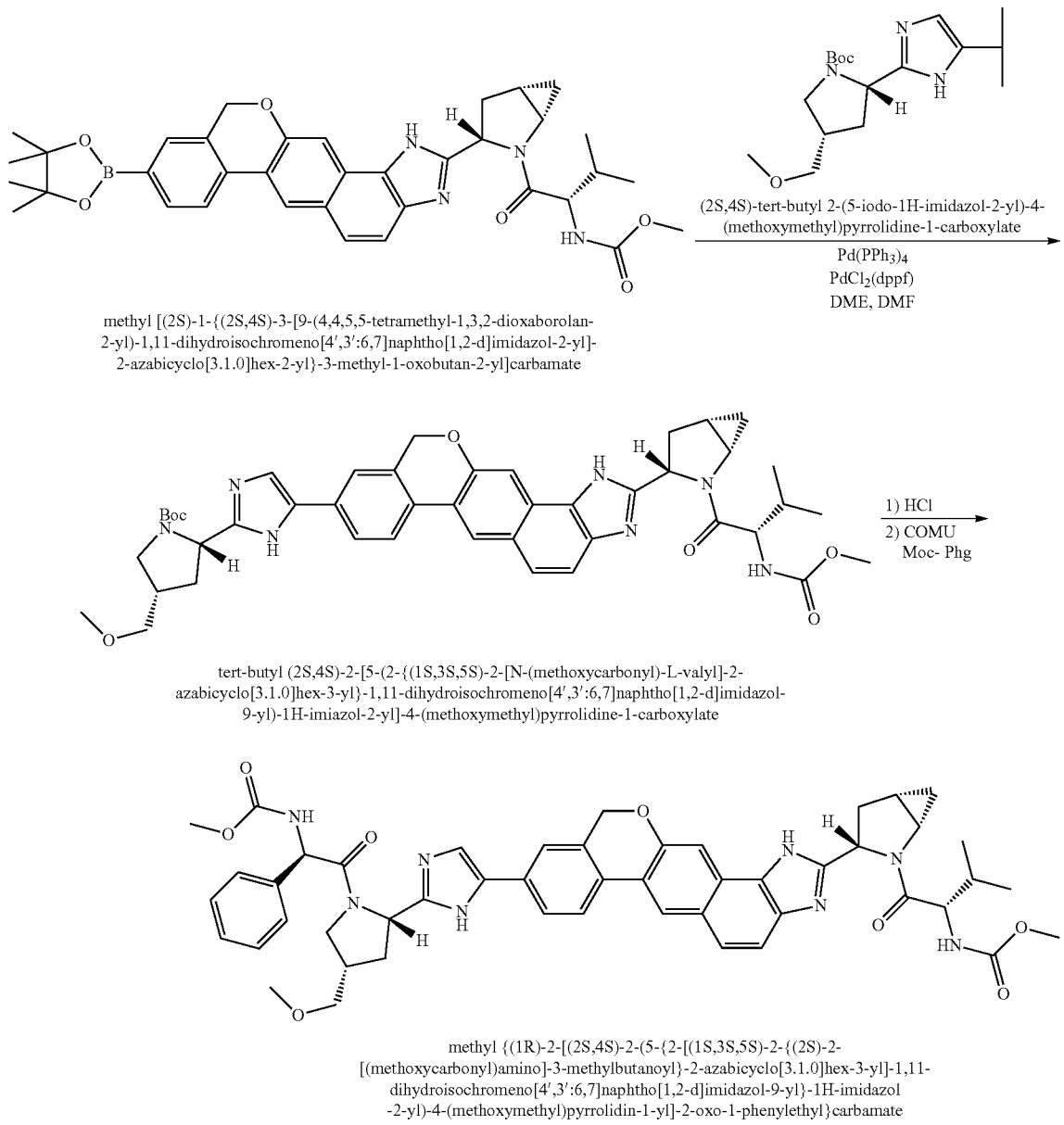

methyl [(2S)-1-{(2S,4S)-3-[9-(4,4,5,5-tetramethyl-1,3,2-dioxaborolan-2-yl)-1,11-dihydroisochromeno[4',3':6,7]naphtho[1,2-d]imidazol-2-yl]-2-azabicyclo[3.1.0]hex-2-yl}-3-methyl-1-oxobutan-2-yl]carbamate tert-butyl (2S,4S)-2-[5-(2-{(1S,3S,5S)-2-[N-(methoxycarbonyl)-L-valyl]-2-azabicyclo[3.1.0]hex-3-yl}-1,11-dihydroisochromeno[4',3':6,7]naphtho[1,2-d]imidazol-9-yl)-1H-imidazol-2-yl]-4-(methoxymethyl)pyrrolidine-1-carboxylate methyl {(1R)-2-[(2S,4S)-2-(5-{2-[(1S,3S,5S)-2-{(2S)-2-[(methoxycarbonyl)amino]-3-methylbutanoyl}-2-azabicyclo[3.1.0]hex-3-yl]-1,11-dihydroisochromeno[4',3':6,7]naphtho[1,2-d]imidazol-9-yl}-1H-imidazol-2-yl)-4-(methoxymethyl)pyrrolidin-1-yl]-2-oxo-1-phenylethyl}carbamate

223

Methyl [(2S)-1-{(2S,4S)-3-[9-(4,4,5,5-tetramethyl-1,3,2-dioxaborolan-2-yl)-1,11-dihydroisochromeno[4',3':6,7]naphtho[1,2-d]imidazol-2-yl]-2-azabicyclo[3.1.01 hex-2-yl}-3-methyl-1-oxobutan-2-yl] carbamate

Methyl [(2S)-1-{(2S,4S)-3-[9-(4,4,5,5-tetramethyl-1,3,2-dioxaborolan-2-yl)-1,11-dihydroisochromeno[4',3':6,7]naphtho[1,2-d]imidazol-2-yl]-2-azabicyclo[3.1.0]hex-2-yl}-3-methyl-1-oxobutan-2-yl]carbamate was prepared following the procedure for methyl [(2S)-1-{(2S,4S)-4-ethoxy-2-[9-(4,4,5,5-tetramethyl-1,3,2-dioxaborolan-2-yl)-1,11-dihydroisochromeno[4',3':6,7]naphtho[1,2-d]imidazol-2-yl]pyrrolidin-1-yl}-3-methyl-1-oxobutan-2-yl]carbamate by substitution of (1S,3S,5S)-2-(tert-butoxycarbonyl)-2-azabicyclo[3.1.0]hexane-3-carboxylic acid for (2S,4S)-1-(tert-butoxycarbonyl)-4-ethoxypyrrolidine-2-carboxylic acid.

Tert-butyl (2S,4S)-2-[5-(2-{(1S,3S,5S)-2-[N-(methoxycarbonyl)-L-valyl]-2-azabicyclo[3.1.0]hex-3-yl}-1,11-dihydroisochromeno[4',3':6,7]naphtho[1,2-d]imidazol-9-yl)-1H-imidazol-2-yl]-4-(methoxymethyl)pyrrolidine-1-carboxylate

To a solution of methyl [(2S)-1-{(2S,4S)-3-[9-(4,4,5,5-tetramethyl-1,3,2-dioxaborolan-2-yl)-1,11-dihydroisochromeno[4',3':6,7]naphtho[1,2-d]imidazol-2-yl]-2-azabicyclo[3.1.0]hex-2-yl}-3-methyl-1-oxobutan-2-yl]carbamate (0.19 g, 0.30 mmol) in a mixture of DMSO (2.0 mL) and dioxane (2.0 mL) was added (2S,4S)-tert-butyl 2-(5-iodo-1H-imidazol-2-yl)-4-(methoxymethyl)pyrrolidine-1-carboxylate (0.20 g, 0.55 mmol), tetrakis(triphenylphosphine) palladium (0.035 g, 0.030 mmol), [1,1'-bis(diphenylphosphino)ferrocene]dichloropalladium (0.025 g, 0.034 mmol), and aqueous potassium carbonate (2M, 0.5 mL, 1.0 mmol). The solution was degassed with argon for 5 min and heated, with stirring, to 90° C. for 6 h. The solution was cooled to room temperature, diluted with EtOAc, and filtered through celite. The filtrate was concentrated under reduced pressure and purified by silica column chromatography (2% to 25% CH$_2$Cl$_2$/MeOH) and preparative reverse phase HPLC (10% to 55% MeCN/water with 0.1% TFA). The desired fractions were combined and concentrated under reduced pressure to remove volatile organics. The aqueous layer was basified with aqueous sodium bicarbonate and extracted with CH$_2$Cl$_2$ (3×). The organic layers were combine, dried over Na$_2$SO$_4$, and concentrated under reduced pressure to afford tert-butyl (2S,4S)-2-[5-(2-{(1S,3S,5S)-2-[N-(methoxycarbonyl)-L-valyl]-2-azabicyclo[3.1.0]hex-3-yl}-1,11-dihydroisochromeno[4',3':6,7]naphtho[1,2-d]imidazol-9-yl)-1H-imidazol-2-yl]-4-(methoxymethyl)pyrrolidine-1-carboxylate (0.025 g, 11%).

224

Methyl {(1R)-2-[(2S,4S)-2-(5-{2-[(1S,3S,5S)-2-{(2S)-2-[(methoxycarbonyl)amino]-3-methylbutanoyl}-2-azabicyclo[3.1.0]hex-3-yl]-1,11-dihydroisochromeno[4',3':6,7]naphtho[1,2-d]imidazol-9-yl}-1H-imidazol-2-yl)-4-(methoxymethyl)pyrrolidin-1-yl]-2-oxo-1-phenylethyl}carbamate

To a solution of tert-butyl (2S,4S)-2-[5-(2-{(1S,3S,5S)-2-[N-(methoxycarbonyl)-L-valyl]-2-azabicyclo[3.1.0]hex-3-yl}-1,11-dihydroisochromeno[4',3':6,7]naphtho[1,2-d]imidazol-9-yl)-1H-imidazol-2-yl]-4-(methoxymethyl)pyrrolidine-1-carboxylate (0.025 g, 0.032 mmol) in a mixture of CH$_2$Cl$_2$ (1.0 mL) and MeOH (0.25 mL) was added HCl (in dioxanes, 4M, 0.50 mL, 2.0 mmol). The solution was stirred at room temperature for 12 h, and then concentrated to dryness under reduced pressure. To the crude intermediate suspended in CH$_2$Cl$_2$ (0.5 mL) was added (R)-2-(methoxycarbonylamino)-2-phenylacetic acid (0.012 g, 0.057 mmol) and DIPEA (0.05 mL, 0.28 mmol). The resulting solution was cooled to 0° C. and COMU (0.023 g, 0.054 mmol) was added. The reaction was stirred at 0° C. for 30 min. The solution was diluted with DMF and aqueous LiOH (2.5 M, 2 drops) and concentrated under reduced pressure to remove the CH$_2$Cl$_2$. The crude residue was purified by preparative reverse phase HPLC (10% to 55% MeCN/water with 0.1% TFA). The desired fractions were combined and concentrated under reduced pressure to remove volatile organics. The addition of aqueous sodium bicarbonate with stirring resulted in precipitation of a white solid. The precipitate was filtered through a membrane filter and washed with water. Drying under reduced pressure afforded methyl {(1R)-2-[(2S,4S)-2-(5-{2-[(1S,3S,5S)-2-{(2S)-2-[(methoxycarbonyl)amino]-3-methylbutanoyl}-2-azabicyclo[3.1.0]hex-3-yl]-1,11-dihydroisochromeno[4',3':6,7]naphtho[1,2-d]imidazol-9-yl}-1H-imidazol-2-yl)-4-(methoxymethyl)pyrrolidin-1-yl]-2-oxo-1-phenylethyl}carbamate (0.015 g, 55%). $^1$H-NMR: 400 MHz, (MeOD) δ: (Mixture of rotamers) 8.35 (m, 1H), 7.94-7.96 (m, 2H), 7.54-7.78 (m, 6H), 6.93-7.00 (m, 1H), 5.72 (m, 1H), 5.46 (s, 1H), 5.19 (s, 2H), 5.14-5.16 (m, 1H), 3.95 (m, 1H), 3.67 (s, 3H), 3.63 (s, 3H), 3.42-3.49 (m, 2H), 3.24 (s, 3H), 2.67-2.78 (m, 2H), 2.41-2.62 (m, 3H), 2.01-2.13 (m, 2H), 1.86-1.99 (m, 3H), 0.99-1.03 (m, 2H), 0.90 (d, 3H). MS (ESI) m/z 882.23 [M+H]$^+$.

Example OW

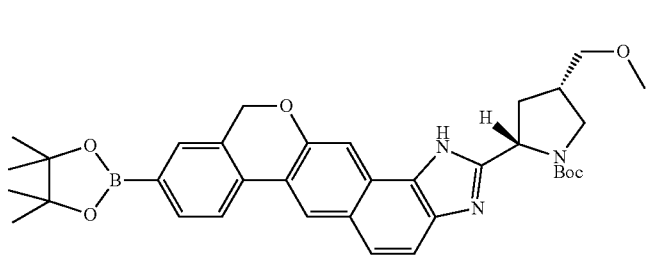

methyl (1-{4-(methoxymethyl)-2-[9-(4,4,5,5-tetramethyl-1,3,2-dioxaborolan-2-yl)-1,11-dihydroisochromeno[4',3':6,7]naphtho[1,2-d]imidazol-2-yl]pyrrolidin-1-yl}-3-methyl-1-oxobutan-2-yl)carbamate

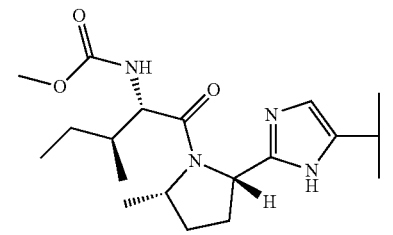

methyl (2S,3S)-1-((2S,5S)-2-(5-iodo-1H-imidazol-2-yl)-5-methylpyrrolidin-1-yl)-3-methyl-1-oxopentan-2-ylcarbamate Pd(PPh$_3$)$_4$
PdCl$_2$(dppf)
DME, DMF

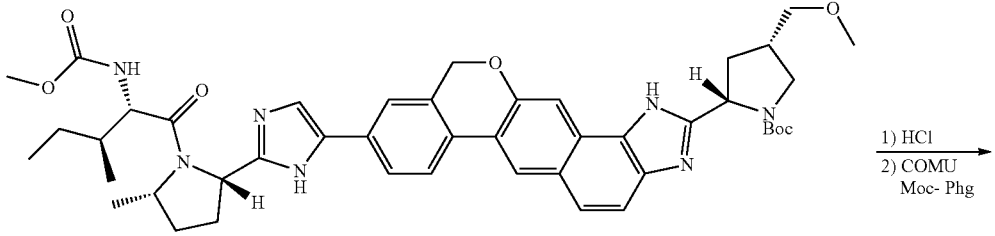

tert-butyl (2S,4S)-2-[9-(2-{(2S,5S)-1-[N-(methoxycarbonyl)-L-isoleucyl]-5-
methylpyrrolidin-2-yl}-1H-imidazol-5-yl)-1,11-dihydroisochromeno[4',3':6,7]naphtho[1,2-
d]imidazol-2-yl]-4-(methoxymethyl)pyrrolidine-1-carboxylate

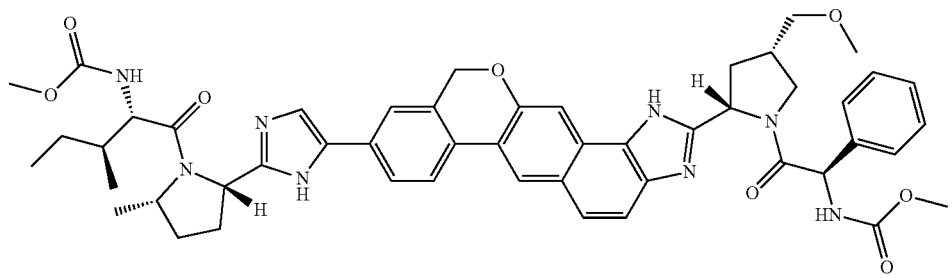

methyl {(1R)-2-[(2S,4S)-2-(9-{2-[(2S,5S)-1-{(2S,3S)-2-[(methoxycarbonyl)amino]-3-
methylbutanoyl}-5-methylpyrrolidin-2-yl]-1H-imidazol-5-yl}-1,11-
dihydroisochromeno[4',3':6,7]naphtho[1,2-d]imidazol-2-
yl)-4-(methoxymethyl)pyrrolidin-1-yl]-2-oxo-1-phenylethyl}carbamate Tert-butyl (2S,4S)-2-[9-(2-{(2S,5S)-1-[N-(methoxy-carbonyl)-L-isoleucyl]-5-methylpyrrolidin-2-yl}-1H-imidazol-5-yl)-1,11-dihydroisochromeno[4',3':6,7] naphtho[1,2-d]imidazol-2-yl]-4-(methoxymethyl) pyrrolidine-1-carboxylate To a solution of methyl (1-{4-(methoxymethyl)-2-[9-(4,4,5,5-tetramethyl-1,3,2-dioxaborolan-2-yl)-1,11-dihydroisochromeno[4',3':6,7]naphtho[1,2-d]imidazol-2-yl]pyrrolidin-1-yl}-3-methyl-1-oxobutan-2-yl)carbamate (0.47 g, 0.78 mmol) in a mixture of DMSO (4.0 mL) and dioxane (4.0 mL) was added methyl (2S,3S)-1-((2S,5S)-2-(5-iodo-1H-imidazol-2-yl)-5-methylpyrrolidin-1-yl)-3-methyl-1-oxopentan-2-ylcarbamate (0.26 g, 0.72 mmol), tetrakis(triphenylphosphine)palladium (0.090 g, 0.078 mmol), [1,1'-bis(diphenylphosphino)ferrocene]dichloropalladium (0.061 g, 0.083 mmol), and aqueous potassium carbonate (2M, 1.2 mL, 2.4 mmol). The solution was degassed with argon for 5 min and heated, with stirring, to 90° C. for 6 h. The solution was cooled to room temperature, diluted with EtOAc, and filtered through celite. The filtrate was concentrated under reduced pressure and diluted with EtOAc. The organic solution was washed with water and brine and the aqueous layers were backextracted with EtOAc. The combined organic layers were dried over Na$_2$SO$_4$ and concentrated under reduced pressure. The crude residue was purified by silica column chromatography (10% to 100% EtOAc (5% MeOH)/CH$_2$Cl$_2$) to afford tert-butyl (2S,4S)-2-[9-(2-{(2S,5S)-1-[N-(methoxycarbonyl)-L-isoleucyl]-5-methylpyrrolidin-2-yl}-1H-imidazol-5-yl)-1,11-dihydroisochromeno[4',3':6,7]naphtho[1,2-d]imidazol-2-yl]-4-(methoxymethyl)pyrrolidine-1-carboxylate (0.25 g, 40%).

Methyl {(1R)-2-[(2S,4S)-2-(9-{2-[(2S,3S)-2-[(methoxycarbonyl)amino]-3-methylpentanoyl}-5-methylpyrrolidin-2-yl]-1H-imidazol-5-yl}-1,11-dihydroisochromeno[4',3':6,71naphtho[1,2-d]imidazol-2-yl)-4-(methoxymethyl)pyrrolidin-1-yl]-2-oxo-1-phenylethyl}carbamate To a solution of tert-butyl (2S,4S)-2-[9-(2-{(2S,5S)-1-[N-(methoxycarbonyl)-L-isoleucyl]-5-methylpyrrolidin-2-yl}-1H-imidazol-5-yl)-1,11-dihydroisochromeno[4',3':6,7]naphtho[1,2-d]imidazol-2-yl]-4-(methoxymethyl)pyrrolidine-1-carboxylate (0.175 g, 0.21 mmol) in a mixture of CH$_2$Cl$_2$ (2.0 mL) and MeOH (0.5 mL) was added HCl (in dioxanes, 4M, 1.6 mL, 6.4 mmol). The solution was stirred at 40° C. for 1 h, cooled to room temperature, and then concentrated to dryness under reduced pressure. To the crude intermediate suspended in CH$_2$Cl$_2$ (3.0 mL) was added (R)-2-(methoxycarbonylamino)-2-phenylacetic acid (0.070 g, 0.34 mmol) and DIPEA (0.15 mL, 0.86 mmol). The resulting solution was cooled to −40° C. and COMU (0.15 g, 0.35 mmol) was added. The reaction was warmed to room temperature over 30 min and diluted with CH$_2$Cl$_2$. The solution was washed with saturated aqueous sodium bicarbonate. The aqueous layer was backextracted with CH$_2$Cl$_2$, and the combined organic layers were dried over Na$_2$SO$_4$ and concentrated under reduced pressure. The crude residue was purified by preparative reverse phase HPLC (10% to 58% MeCN/water with 0.1% TFA). The desired fractions were combined and concentrated under reduced pressure to remove volatile organics. The addition of aqueous sodium bicarbonate with stirring resulted in precipitation of a white solid. The precipitate was filtered through a membrane filter and washed with water. Drying under reduced pressure afforded methyl {(1R)-2-[(2S,4S)-2-(9-{2-[(2S,5S)-1-{(2S,3S)-2-[(methoxycarbonyl)amino]-3-methylpentanoyl})-5-methylpyrrolidin-2-yl]-1H-imidazol-5-yl}-1,11-dihydroisochromeno[4',3':6,7]

naphtho[1,2-d]imidazol-2-yl)-4-(methoxymethyl)pyrrolidin-1-yl]-2-oxo-1-phenylethyl}carbamate (0.079 g, 41%). ¹H-NMR: 400 MHz, (McOD) δ: (Mixture of rotamers) 8.36 (m, 1H), 7.93-7.98 (m, 2H), 7.66-7.84 (m, 3H), 7.35-7.48 (m, 7H), 5.53 (s, 1H), 5.36-5.39 (m, 1H), 5.17 (d, 2H), 5.08 (m, 1H), 4.14-4.35 (m, 1H), 3.74 (m, 4H), 3.64 (s, 3H), 3.62 (s, 3H), 3.46 (m, 1H), 3.19 (s, 3H), 2.76 (m, 1H), 2.46-2.60 (m, 3H), 2.24-2.35 (m, 1H), 2.08-2.18 (m, 2H), 1.91 (m, 1H), 1.61-1.87 (m, 2H), 1.48 (d, 3H), 1.13-1.21 (m, 3H), 0.80-0.97 (m, 3H). MS (ESI) m/z 898.24 [M+H]⁺.

Example OX

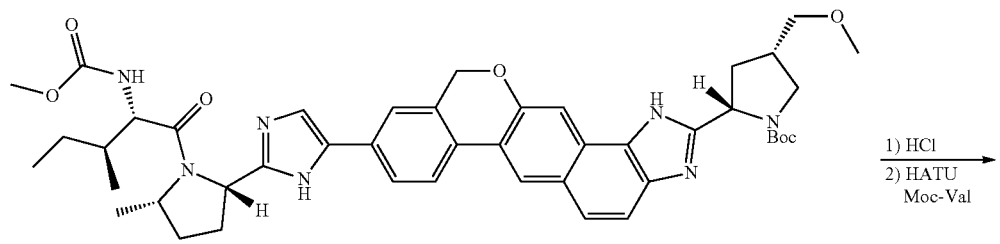

tert-butyl (2S,4S)-2-[9-(2-{(2S,5S)-1-[N-(methoxycarbonyl)-L-isoleucyl]-5-methylpyrrolidin-2-yl}-1H-imidazol-5-yl)-1,11-dihydroisochromeno[4',3':6,7]naphtho[1,2-d]imidazol-2-yl]-4-(methoxymethyl)pyrrolidine-1-carboxylate

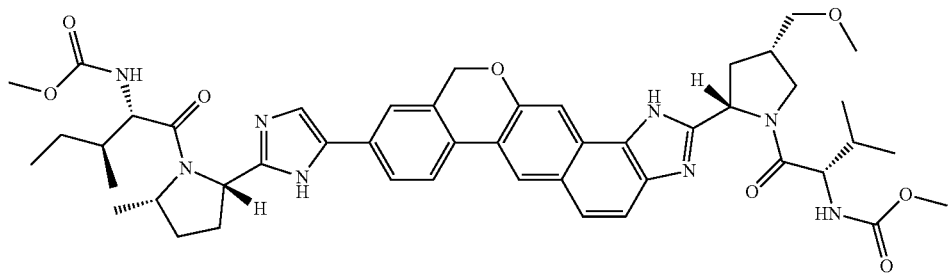

methyl {(2S)-1-[(2S,4S)-2-(9-{2-[(2S,5S)-1-{(2S,3S)-2-[(methoxycarbonyl)amino]-3-methylpentanonyl}-5-methylpyrrolidin-2-yl]-1H-imidazol-5-yl}-1,11-dihyroisochromeno[4',3':6,7]naphtho[1,2-d]imidazol-2-yl)-4-(methoxymethyl)pyrrolidin-1-yl]-3-methyl-1-oxobutan-2-yl}carbamate Methyl {(2S)-1-[(2S,4S)-2-(9-{2-[(2S,5S)-1-{(2S,3S)-2-[(methoxycarbonyl)amino]-3-methylpentanoyl}-5-methylpyrrolidin-2-yl]-1H-imidazol-5-yl}-1,11-dihydroisochromeno[4',3':6,7]naphtho[1,2-d]imidazol-2-yl)-4-(methoxymethyl)pyrrolidin-1-yl]-3-methyl-1-oxobutan-2-yl}carbamate To a solution of tert-butyl (2S,4S)-2-[9-(2-{(2S,5S)-1-[N-(methoxycarbonyl)-L-isoleucyl]-5-methylpyrrolidin-2-yl}-1H-imidazol-5-yl)-1,11-dihydroisochromeno[4',3':6,7]naphtho[1,2-d]imidazol-2-yl]-4-(methoxymethyl)pyrrolidine-1-carboxylate (0.075 g, 0.09 mmol) in a mixture of CH₂Cl₂ (1.0 mL) and MeOH (0.25 mL) was added HCl (in dioxanes, 4M, 0.7 mL, 2.8 mmol). The solution was stirred at 40° C. for 1 h, cooled to room temperature, and then concentrated to dryness under reduced pressure. To the crude intermediate suspended in CH₂Cl₂ (3.0 mL) was added (S)-2-(methoxycarbonylamino)-3-methylbutanoic acid (0.020 g, 0.14 mmol), HATU (0.043 g, 0.11 mmol) and DIPEA (0.10 mL, 0.57 mmol). The reaction was stirred at room temperature for 2 h. The reaction was diluted with DMF and aqueous LiOH (2.5 M, 3 drops) and the CH₂Cl₂ was removed under reduced pressure. The crude residue was purified by preparative reverse phase HPLC (10% to 58% MeCN/water with 0.1% TFA). The desired fractions were combined and concentrated under reduced pressure to remove volatile organics. The addition of aqueous sodium bicarbonate with stirring resulted in precipitation of a white solid. The precipitate was filtered through a membrane filter and washed with water. Drying under reduced pressure afforded methyl {(2S)-1-[(2S,4S)-2-(9-{2-[(2S,5S)-1-{(2S,3S)-2-[(methoxycarbonyl)amino]-3-methylpentanoyl}-5-methylpyrrolidin-2-yl]-1H-imidazol-5-yl}-1,11-dihydroisochromeno[4',3':6,7]naphtho[1,2-d]imidazol-2-yl)-4-(methoxymethyl)pyrrolidin-1-yl]-3-methyl-1-oxobutan-2-yl}carbamate (0.031 g, 38%). ¹H-NMR: 400 MHz, (MeOD) δ: (Mixture of rotamers) 8.34 (m, 1H), 7.91-9.97 (m, 2H), 7.50-7.81 (m, 3H), 7.35-7.38 (m, 2H), 5.17-5.26 (m, 3H), 5.08 (m, 1H), 4.14-4.33 (m, 4H), 3.64 (s, 3H), 3.63 (s, 3H), 3.51-3.59 (m, 3H), 3.37 (s, 3H), 2.71 (m, 1H), 2.55-2.59 (m, 1H), 2.23-2.33 (m, 1H), 1.92-2.10 (m, 2H), 1.77-1.89 (m, 1H), 1.60 (m, 1H), 1.48 (d, 1H), 1.11-1.22 (m, 2H), 0.81-0.98 (m, 12H). MS (ESI) m/z 864.27 [M+H]⁺.

Example PF

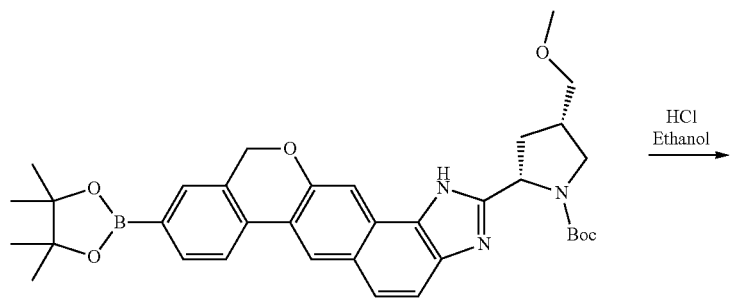

tert-butyl (2S,4S)-4-(methoxymethyl)-2-[9-(4,4,5,5-tetramethyl-1,3,2-dioxaborolan-2-yl)-1,11-dihydroisochromeno[4',3':6,7]naphtho[1,2-d]imidazol-2-yl]pyrrolidine-1-carboxylate

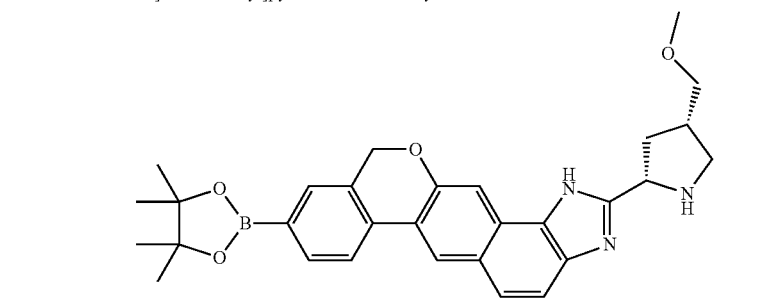

2-[4-(methoxymethyl)pyrrolidin-2-yl]-9-(4,4,5,5-tetramethyl-1,3,2-dioxaborolan-2-yl)-1,11-dihydroisochromeno[4',3':6,7]naphtho[1,2-d]imidazole

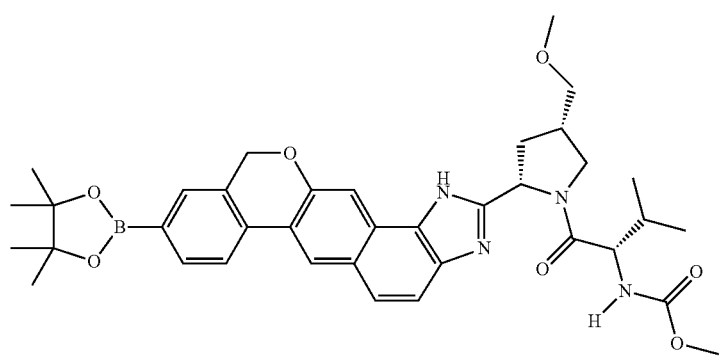
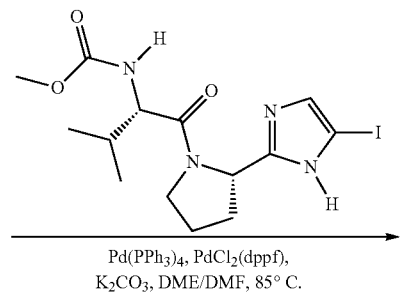

methyl [(2S)-1-{(2S,4S)-4-ethoxy-2-[9-(4,4,5,5-tetramethyl-1,3,2-dioxaborolan-2-yl)-1,11-dihydroisochromeno[4',3':6,7]naphtho[1,2-d]imidazol-2-yl]pyrrolidin-1-yl}-3-methyl-1-oxobutan-2-yl]carbamate

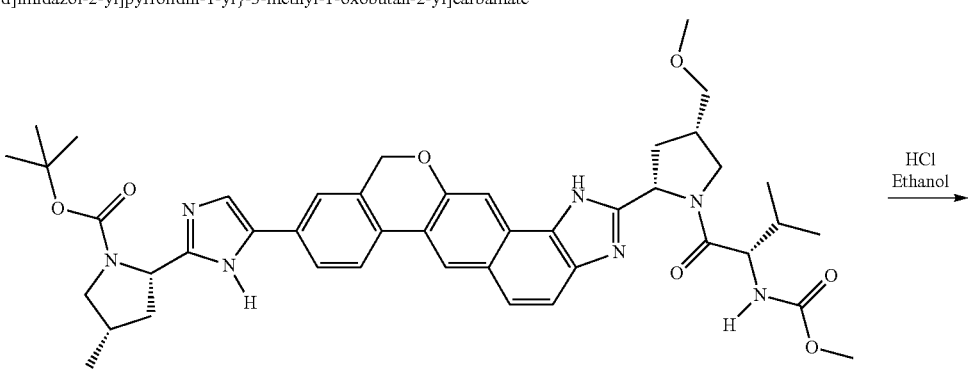

tert-butyl 2-[5-(2-{1-[N-(methoxycarbonyl)valyl]-4-(methoxymethyl)pyrrolidin-2-yl}-1,11-dihydroisochromeno[4',3':6,7]naphtho[1,2-d]imidazol-9-yl)-1H-imidazol-2-yl]-4-methylpyrrolidine-1-carboxylate

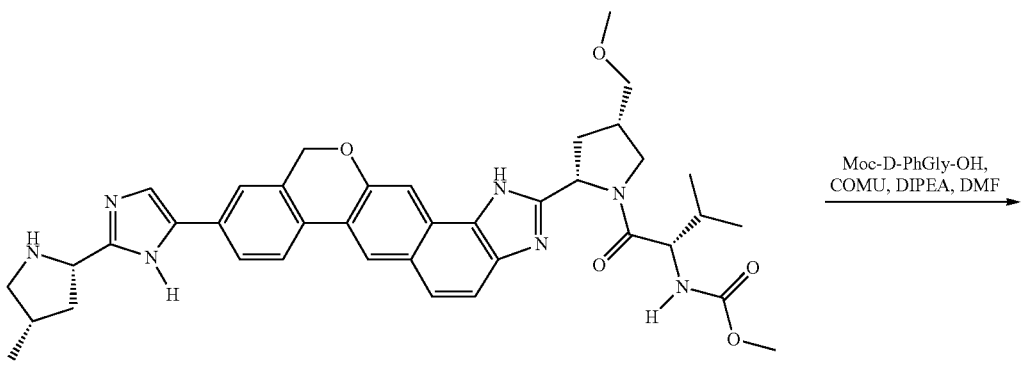

methyl {1-[4-(methoxymethyl)-2-{9-[2-(4-methylpyrrolidin-2-yl)-1H-imidazol-5-yl]-1,11-dihydroisochromeno[4',3':6,7]naphtho[1,2-d]imidazol-2-yl}pyrrolidin-1-yl]-3-methyl-1-oxobutan-2-yl}carbamate Moc-D-PhGly-OH, COMU, DIPEA, DMF

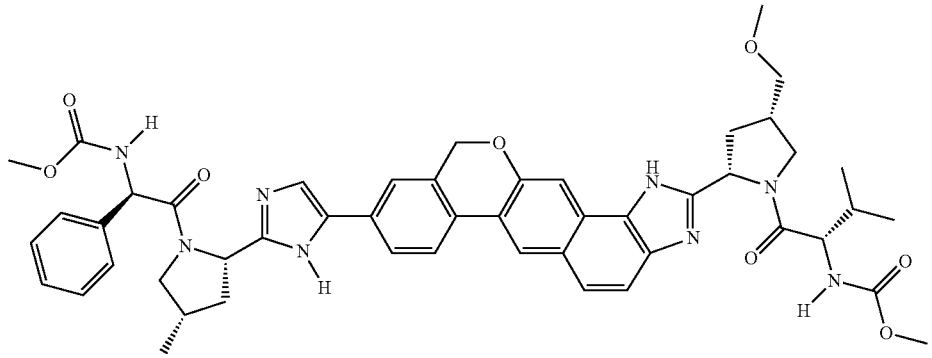

methyl {1-[2-{9-[2-(1-{[(methoxycarbonyl)amino](phenyl)acetyl}-4-methylpyrrolidin-2-yl)-1H-imidazol-5-yl]-1,11-dihydroisochromeno[4',3':6,7]naphtho[1,2-d]imidazol-2-yl}-4-(methoxymethyl)pyrrolidin-1-yl]-3-methyl-1-oxobutan-2-yl}carbamate tert-butyl (2S,4S)-4-(methoxymethyl)-2-[9-(4,4,5,5-tetramethyl-1,3,2-dioxaborolan-2-yl)-1,11-dihydroisochromeno[4',3':6,7]naphtho[1,2-d]imidazol-2-yl]pyrrolidine-1-carboxylate The title compound was obtained as in example LQ but using (2S,4S)-1-(tert-butoxycarbonyl)-4-(methoxymethyl)pyrrolidine-2-carboxylic acid in place of (S)-1-(tert-butoxycarbonyl)pyrrolidine-2-carb oxylic acid.

2-[4-(methoxymethyl)pyrrolidin-2-yl]-9-(4,4,5,5-tetramethyl-1,3,2-dioxaborolan-2-yl)-1,11-dihydroisochromeno[4',3':6,7]naphtho[1,2-d]imidazole Tert-butyl (2S,4S)-4-(methoxymethyl)-2-[9-(4,4,5,5-tetramethyl-1,3,2-dioxaborolan-2-yl)-1,11-dihydroisochromeno[4',3':6,7]naphtho[1,2-d]imidazol-2-yl]pyrrolidine-1-carboxylate (310 mg, 0.507 mmol) was treated with 2 mL 1.25N HCl in ethanol and stirred at room temperature for 2 h then at 50° C. for 2 h. The reaction mixture was concentrated under reduced pressure to give a dark yellow solid that was directly in the next step.

methyl [(2S)-1-{(2S,4S)-4-ethoxy-2-[9-(4,4,5,5-tetramethyl-1,3,2-dioxaborolan-2-yl)-1,11-dihydroisochromeno[4',3':6,7]naphtho[1,2-d]imidazol-2-yl]pyrrolidin-1-yl}-3-methyl-1-oxobutan-2-yl]carbamate A mixture of (S)-2-(methoxycarbonylamino)-3-methylbutanoic acid (107 mg, 0.608 mmol), HATU (231 mg, 0.608 mmol) and 6 mL 10% DIPEA in DMF was pre-activated for 5 minutes, then it was added to the amine salt from the step above and allowed to stir overnight. The reaction mixture was partitioned between ethyl acetate and saturated sodium bicarbonate. The organic phase was concentrated and purified by silica gel chromatography. (103 mg)

tert-butyl 2-[5-(2-{1-[N-(methoxycarbonyl)valyl]-4-(methoxymethyl)pyrrolidin-2-yl}-1,11-dihydroisochromeno[4',3':6,7]naphthol 1,2-d]imidazol-9-yl)-1H-imidazol-2-yl]-4-methylpyrrolidine-1-carboxylate The title compound was obtained as in example LQ but using methyl [(2S)-1-{(2S,4S)-4-ethoxy-2-[9-(4,4,5,5-tetramethyl-1,3,2-dioxaborolan-2-yl)-1,11-dihydroisochromeno[4',3':6,7]naphtho[1,2-d]imidazol-2-yl]pyrrolidin-1- yl}-3-methyl-1-oxobutan-2-yl]carbamate (103 mg, 0.154 mmol) in place of tert-butyl 2-[9-(4,4,5,5-tetramethyl-1,3,2-dioxaborolan-2-yl)-1,11-dihydroisochromeno[4',3':6,7]naphtho[1,2-d]imidazol-2-yl]pyrrolidine-1-carboxylate and methyl (S)-1-((2S,4S)-2-(5-iodo-1H-imidazol-2-yl)-4-methylpyrrolidin-1-yl)-3-methyl-1-oxobutan-2-ylcarbamate (58 mg, 0.154 mmol) in place of methyl(S)-1-((S)-2-(5-bromo-1H-imidazol-2-yl)pyrrolidin-1-yl)-3-methyl-1-oxobutan-2-ylcarbamate. (50.0 mg)

methyl {1-[4-(methoxymethyl)-2-{9-[2-(4-methylpyrrolidin-2-yl)-1H-imidazol-5-yl]-1,11-dihydroisochromeno[4',3':6,7]naphtho[1,2-d]imidazol-2-yl}pyrrolidin-1-yl]-3-methyl-1-oxobutan-2-yl}carbamate tert-butyl 2-[5-(2-{1-[N-(methoxycarbonyl)valyl]-4-(methoxymethyl)pyrrolidin-2-yl}-1,11-dihydroisochromeno[4',3':6,7]naphtho[1,2-d]imidazol-9-yl)-1H-imidazol-2-yl]-4-methylpyrrolidine-1-carboxylate (50 mg, 0.063 mmol) was treated with 2 mL 1.25N HCl in ethanol and heated at 60° C. for 2 h, then it was concentrated under reduced pressure and pumped dry under high vacuum and used directly in the next step.

methyl {1-[2-{9-[2-(1-{[(methoxycarbonyl)amino](phenyl)acetyl}-4-methylpyrrolidin-2-yl)-1H-imidazol-5-yl]-1,11-dihydroisochromeno[4',3':6,7]naphtho[1,2-d]imidazol-2-yl}-4-(methoxymethyl)pyrrolidin-1-yl]-3-methyl-1-oxobutan-2-yl}carbamate A mixture of (R)-2-(methoxycarbonylamino)-2-phenylacetic acid (13 mg, 0.063 mmol), COMU (30 mg, 0.069 mmol) in 0.500 mL DMF and DIPEA (0.033 mL, 0.189 mmol) was allowed to preactivate for 15 minutes before it was added to the solid crude amine salt from the previous step and stirred overnight. The product was purified by reverse phase HPLC. The product was converted to the free base by dissolution in 2 mL 1:1 acetonitrile:methanol and passage through a prepacked cartridge of polymer supported carbonate. Concentration and drying gave an off white powder. (23.3 mg).

MS (ESI) m/z 883.8 [M+H]+

$^1$H NMR (CD$_3$CN) 8.176 (s, 1H), 7.778 (m, 1H), 7.596-7.521 (m, 4H), 7.455-7.347 (m, 6H), 7.218 (s, 1H), 5.482 (s, 1H), 5.310 (m, 1H), 5.192 (m, 1H), 4.999 (q, 2H, J=14 Hz), 4.372 (d, 1H, J=6.4 Hz), 4.279 (m, 1H), 3.800-3.697 (m, 2H), 3.632 (s, 3H) 3.597-3.445 (m, 7H), 3.355 (s, 3H), 2.876 (m, 2H), 2.761 (m, 1H), 2.583 (m, 2H), 2.220 (m, 2H), 1.764 (m, 1H), 1.070 (d, 3H, J=6.4 Hz), 1.020 (d, 3H, J=6.4 Hz), 0.898 (d, 3H, J=6.4 Hz).

Example PG

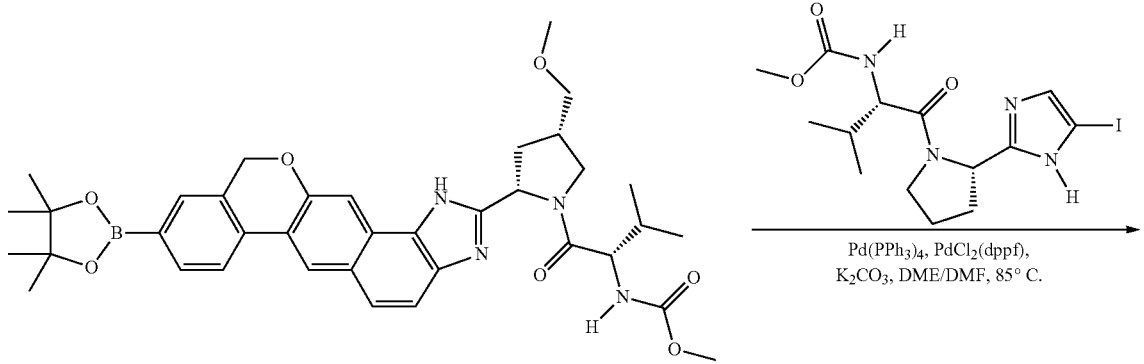

methyl [(2S)-3-methyl-1-{(2S,4S)-4-methyl-2-[9-(4,4,5,5-tetramethyl-1,3,2-dioxaborolan-2-yl)-1,11-dihydroisochromeno[4',3':6,7]naphtho[1,2-d]imidazole-2-yl]pyrrolidin-1-yl}-3-methyl-1-oxobutan-2-yl]carbamate

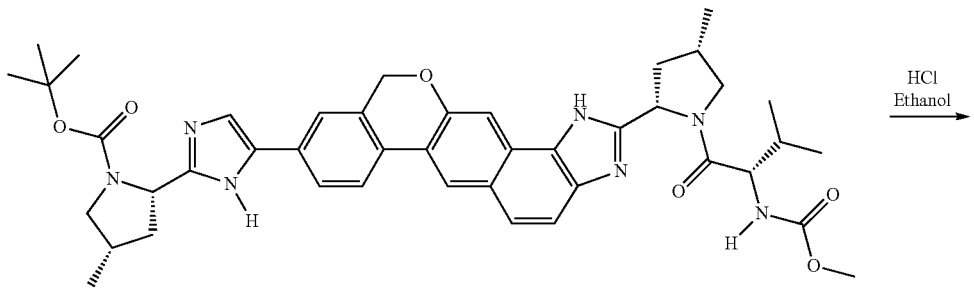

tert-butyl (2S,4S)-2-[5-(2-{(2S,4S)-1-[N-(methoxycarbonyl)-L-valyl]-4-methylpyrrolidin-2-yl}-1,11-dihydroisochromeno[4',3':6,7]naphtho[1,2-d]imidazol-9-yl)-1H-imidazol-2-yl]-4-methylpyrrolidine-1-carboxylate

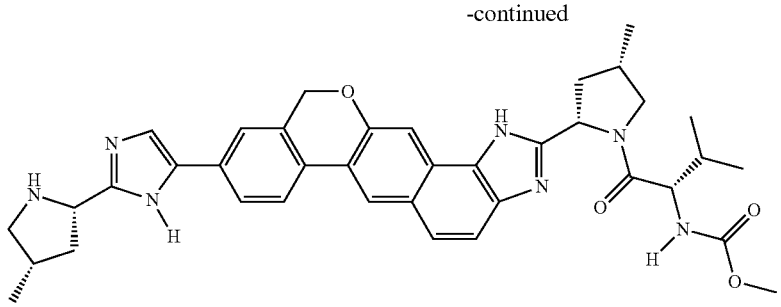

methyl {(2S)-3-methyl-1-[(2S,4S)-4-methyl-2-(9-{2-[(2S,4S)-4-methylpyrrolidin-2-yl)-1H-imidazol-5-yl}-1,11-dihydroisochromeno[4',3':6,7]naphtho[1,2-d]imidazol-2-yl)pyrrolidin-1-yl]-1-oxobutan-2-yl}carbamate

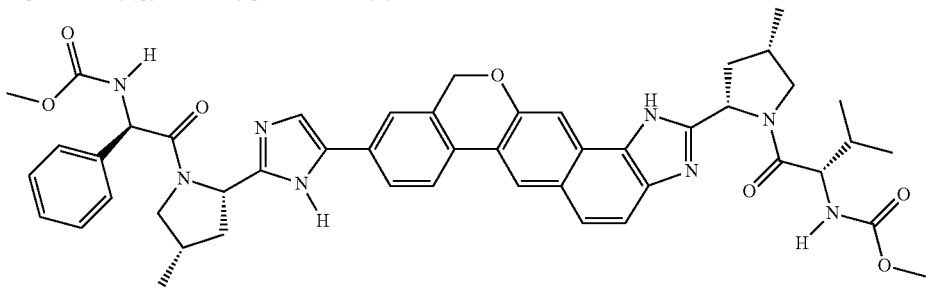

methyl {(1R)-2-[(2S,4S)-2-(5-{2-[(2S,4S)-1-{(2S)-2-[(methoxycarbonyl)amino]-3-methylbutanoyl}-4-methylpyrrolidin-2-yl]-1,11-dihydroisochromeno[4',3':6,7]naphtho[1,2-d]imidazol-9-yl}-1H-imidazol-2-yl)-4-methylpyrrolidin-1-yl]-2-oxo-1-phenylethyl}carbamate tert-butyl (2S,4S)-2-[5-(2-{(2S,4S)-1-IN-(methoxycarbonyl)-L-valyl]-4-methylpyrrolidin-2-yl}-1,11-dihydroisochromeno[4',3':6,7]naphtho[1,2-d]imidazol-9-yl)-1H-imidazol-2-yl]-4-methylpyrrolidine-1-carboxylate The title compound was obtained as in example LQ but using methyl [(2S)-3-methyl-1-{(2S,4S)-4-methyl-2-[9-(4,4,5,5-tetramethyl-1,3,2-dioxaborolan-2-yl)-1,11-dihydroisochromeno[4',3':6,7]naphtho[1,2-d]imidazol-2-yl]pyrrolidin-1-yl}-1-oxobutan-2-yl]carbamate (307 mg, 0.481 mmol) in place of tert-butyl 2-[9-(4,4,5,5-tetramethyl-1,3,2-dioxaborolan-2-yl)-1,11-dihydroisochromeno[4',3':6,7]naphtho[1,2-d]imidazol-2-yl]pyrrolidine-1-carboxylate and methyl (S)-1-((2S,4S)-2-(5-iodo-1H-imidazol-2-yl)-4-methylpyrrolidin-1-yl)-3-methyl-1-oxobutan-2-ylcarbamate (181 mg, 0.481 mmol)in place of methyl(S)-1-((S)-2-(5-bromo-1H-imidazol-2-yl)pyrrolidin-1-yl)-3-methyl-1-oxobutan-2-ylcarbamate. (200.8 mg)

methyl {(2S)-3-methyl-1-[(2S,4S)-4-methyl-2-(9-{2-[(2S,4S)-4-methylpyrrolidin-2-yl]-1H-imidazol-5-yl}-1,11-dihydroisochromeno[4',3':6,7]naphtho[1,2-d]imidazol-2-yl)pyrrolidin-1-yl]-1-oxobutan-2-yl}carbamate Tert-butyl (2S,4S)-2-[5-(2-{(2S,4S)-1-[N-(methoxycarbonyl)-L-valyl]-4-methylpyrrolidin-2-yl}-1,11-dihydroisochromeno[4',3':6,7]naphtho[1,2-d]imidazol-9-yl)-1H-imidazol-2-yl]-4-methylpyrrolidine-1-carboxylate (200 mg, 0.262 mmol) was treated with 2 mL 1.25N HCl in ethanol and heated at 60° C. for 2 h, then it was concentrated under reduced pressure and pumped dry under high vacuum and used directly in the next step.

methyl {(1R)-2-[(2S,4S)-2-(5-{2-[(2S,4S)-1-{(2S)-2-[(methoxycarbonyl)amino]-3-methylbutanoyl}-4-methylpyrrolidin-2-yl]-1,11-dihydroisochromeno[4',3':6,7]naphtho[1,2-d]imidazol-9-yl}-1H-imidazol-2-yl)-4-methylpyrrolidin-1-yl]-2-oxo-1-phenylethyl}carbamate A mixture of (R)-2-(methoxycarbonylamino)-2-phenylacetic acid (13 mg, 0.063 mmol), COMU (30 mg, 0.069 mmol) in 1.5 mL DMF was allowed to preactivate for 5 minutes before it was added to a solution of the amine from the previous salt in 1.5 mL DMF and DIPEA (0.137 mL, 0.786 mmol) and stirred overnight. The product was purified by reverse phase HPLC. The product was converted to the free base by dissolution in 2 mL 1:1 acetonitrile:methanol and passage through a prepacked cartridge of polymer supported carbonate. Concentration and drying gave an off white powder. (25.8 mg).

MS (ESI) m/z 853.8 [M+H]$^+$.

$^1$H NMR (CD$_3$CN) 8.164 (s, 1H), 7.781 (m, 1H), 7.609 (m, 2H), 7.535 (m, 2H), 7.433-7.305 (m, 6H), 7.229 (s, 1H), 5.482 (s, 1H), 5.290 (m, 1H), 5.191 (m, 1H), 4.997 (m, 2H), 4.372 (d, 1H, J=6.4 Hz), 4.267 (m, 1H), 3.735-3.445 (m, 10H), 2.573 (m, 4H), 2.197 (m, 2H), 2.017 (m, 1H), 1.760 (m, 1H), 1.204 (d, 3H, J=6.4 Hz), 1.068 (d, 3H, J=6.4 Hz), 1.010 (d, 3H, J=6.8 Hz), 0.887 (d, 3H, J=6.8 Hz).

Example PH

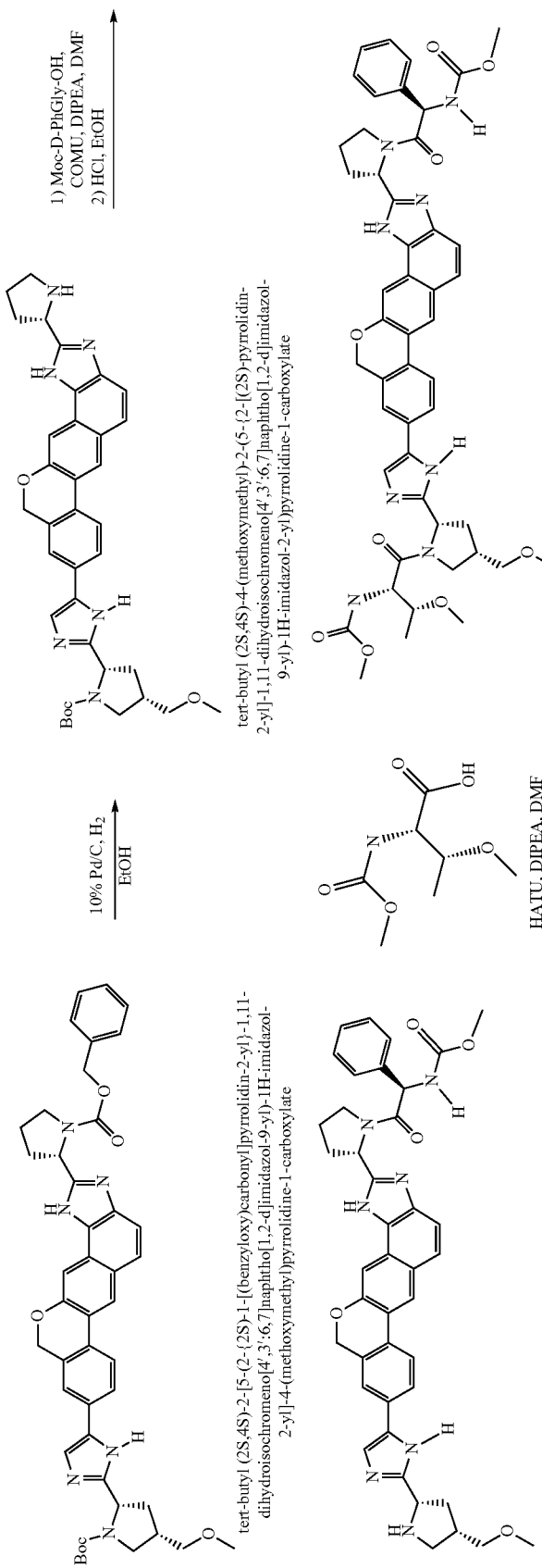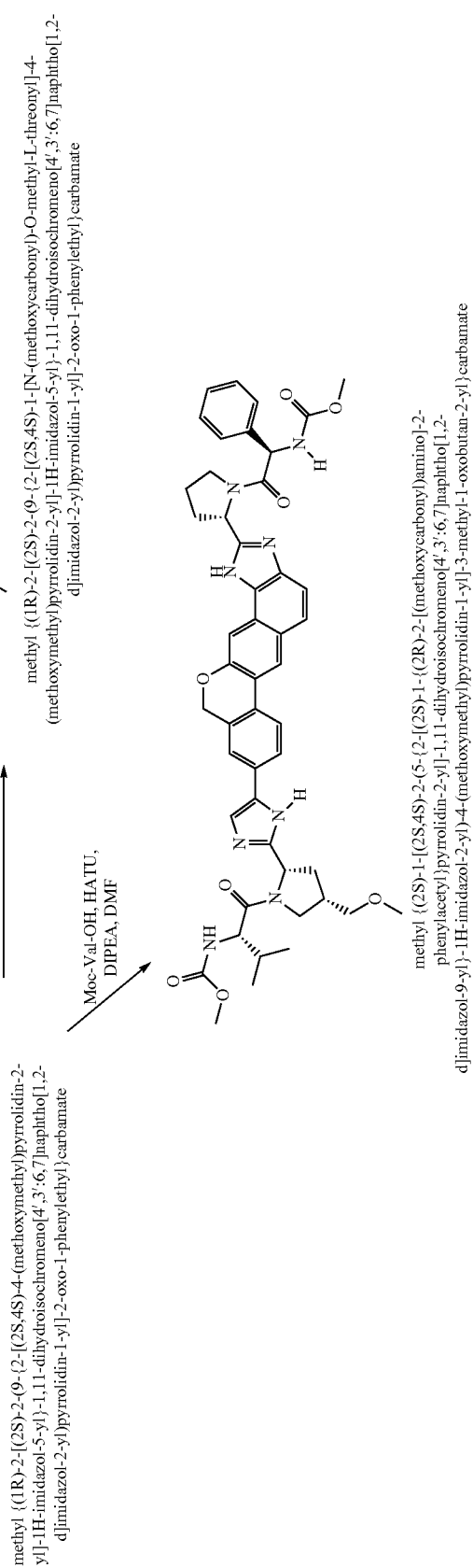

tert-butyl (2S,4S)-2-[5-(2-{(2S)-1-[(benzyloxy)carbonyl]pyrrolidin-2-yl}-1,11-dihydroisochromeno[4',3':6,7]naphtho[1,2-d]imidazol-9-yl)-1H-imidazol-2-yl[-4-(methoxymethyl)pyrrolidine-1-carboxylate The title compound was obtained as in example OF (compound tert-butyl (2S,4S)-2-[5-(2-{(2S,5S)-1-[N-(methoxycarbonyl)-L-valyl]-5-methylpyrrolidin-2-yl}-1,4,5,11-tetrahydroisochromeno[4',3':6,7]naphtho[1,2-d]imidazol-9-yl)-1H-imidazol-2-yl]-4-(methoxymethyl)pyrrolidine-1-carboxylate) but using (S)-1-(benzyloxycarbonyl)pyrrolidine-2-carboxylic acid in place of (2S,5S)-1-((S)-2-(methoxycarbonylamino)-3-methylbutanoyl)-5-methylpyrrolidine-2-carboxylic acid.

tert-butyl (2S,4S)-4-(methoxymethyl)-2-(5-{2-[(2S)-pyrrolidin-2-yl]-1,11-dihydroisochromeno[4',3':6,7]naphtho[1,2-d]imidazol-9-yl}-1H-imidazol-2-yl)pyrrolidine-1-carboxylate A mixture of tert-butyl (2S,4S)-2-[5-(2-{(2S)-1-[(benzyloxy)carbonyl]pyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate (724 mg, 0.96 mmol) and 70 mg 10% Pd/C in 20 mL ethanol was hydrogenated at 1atm overnight. Additional 10% Pd/C (300 mg) and a portion of solid NaHCO3 was added and hydrogenation continued for 4 hours. Filtration through celite and concentration of the filtrate under reduced pressure gave the product as a dark brown solid, 454 mg. Purification by reverse phase HPLC gave 65 mg purified product.

methyl {(1R)-2-[(2S)-2-(9-{2-[(2S,4S)-4-(methoxymethyl)pyrrolidin-2-yl]-1H-imidazol-5-yl}-1,11-dihydroisochromeno[4',3':6,7]naphtho[1,2-d]imidazol-2-yl)pyrrolidin-1-yl]-2-oxo-1-phenylethyl}carbamate A mixture of (R)-2-(methoxycarbonylamino)-2-phenylacetic acid (22 mg, 0.105 mmol), COMU (45 mg, 0.069 mmol), and tert-butyl (2S,4S)-4-(methoxymethyl)-2-(5-{2-[(2S)-pyrrolidin-2-yl]-1,11-dihydroisochromeno[4',3':6,7]naphtho[1,2-d]imidazol-9-yl}-1H-imidazol-2-yl)pyrrolidine-1-carboxylate (65 mg, 0.105 mmol) in 1.5 mL 10% DIPEA in DMF was stirred for 1.5h. The reaction mixture was partitioned between ethyl acetate and saturated sodium bicarbonate. The organic phase was dried over sodium sulphate, filtered and concentrated under reduced pressure. The crude intermediate was treated with 8 mL 1.25N HCl in ethanol at 50° C. for 4 h. Added saturated sodium bicarbonate and extracted the free base into dichloromethane. (106 mg).

methyl {(2S)-1-[(2S,4S)-2-(5-{2-[(2S)-1-{(2R)-2-[(methoxycarbonyl)amino]-2-phenylacetyl}pyrrolidin-2-yl]-1,11-dihydroisochromeno[4',3':6,7]naphtho[1,2-d]imidazol-9-yl}-1H-imidazol-2-yl)-4-(methoxymethyl)pyrrolidin-1-yl]-3-methyl-1-oxobutan-2-yl}carbamate A mixture of methyl {(1R)-2-[(2S)-2-(9-{2-[(2S,4S)-4-(methoxymethyl)pyrrolidin-2-yl]-1H-imidazol-5-yl}-1,11-dihydroisochromeno[4',3':6,7]naphtho[1,2-d]imidazol-2-yl)pyrrolidin-1-yl]-2-oxo-1-phenylethyl}carbamate (55 mg, 0.077 mmol), (S)-2-(methoxycarbonylamino)-3-methylbutanoic acid (14 mg, 0.077 mmol), HATU (32 mg, 0.085 mmol) and 0.4 mL 10% DIPEA in DMF was stirred at room temperature for 1 hour. The product was purified by reverse phase HPLC. The product was converted to the free base by dissolution in 2 mL 1:1 acetonitrile:methanol and passage through a prepacked cartridge of polymer supported carbonate. The eluent was concentrated, the taken up in 10% TFA in 1:1 acetonitrile:water, frozen, and lyophilized to give the product as a trifluoroacetate salt. (30.7 mg)

MS (ESI) m/z 869.9 [M+H]+.

methyl {(1R)-2-[(2S)-2-(9-{2-[(2S,4S)-1-[N-(methoxycarbonyl)-O-methyl-L-threonyl]-4-(methoxymethyl)pyrrolidin-2-yl]-1H-imidazol-5-yl}-1,11-dihydroisochromeno[4',3':6,7]naphtho[1,2-d]imidazol-2-yl)pyrrolidin-1-yl]-2-oxo-1-phenylethyl}carbamate A mixture of methyl {(1R)-2-[(2S)-2-(9-{2-[(2S,4S)-4-(methoxymethyl)pyrrolidin-2-yl]-1H-imidazol-5-yl}-1,11-dihydroisochromeno[4',3':6,7]naphtho[1,2-d]imidazol-2-yl)pyrrolidin-1-yl]-2-oxo-1-phenylethyl}carbamate (51 mg, 0.072 mmol), (2S,3R)-3-methoxy-2-(methoxycarbonylamino)butanoic acid (14 mg, 0.072 mmol), HATU (30 mg, 0.079 mmol) and 0.4 mL 10% DIPEA in DMF was stirred at room temperature for 1 hour. The product was purified by reverse phase HPLC. The product was converted to the free base by dissolution in 2 mL 1:1 acetonitrile:methanol and passage through a prepacked cartridge of polymer supported carbonate. The eluent was concentrated, the taken up in 1% TFA in 1:1 acetonitrile:water, frozen, and lyophilized to give the product as a trifluoroacetate salt. (24 mg)

MS (ESI) m/z 885.8 [M+H]+;

1H NMR (CD3CN) 7.635 (s, 1H), 7.434 (m, 3H), 7.330 (m, 4H), 7.233 (m, 1H), 7.164 (m, 1H), 6.983 (m, 1H), 6.747 (m, 2H), 6.127 (m, 1H), 5.584 (d, 1H, J=6.4 Hz), 5.431 (m, 1H), 5.145 (m, 1H), 4.729 (s, 2H), 4.442 (m, 1H), 4.029 (m, 2H), 3.838 (m, 1H), 3.662-3.534 (m, 2H), 3.572 (s, 3H) 3.552 (s, 3H), 3.444-3.310 (m, 3H), 3.240 (s, 3H), 3.225 (s, 3H), 2.618 (m, 1H), 2.464 (m, 1H), 2.304 (m, 1H), 2.129 (m, 1H), 2.041 (m, 1H), 1.899 (m, 2H), 1.107 (d, 3H, J=6.4 Hz).

Example PI

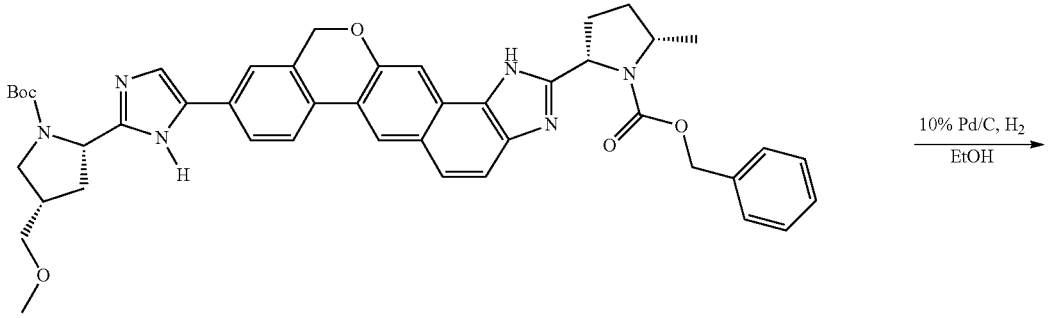

tert-butyl (2S,4S)-2-[5-(2-{(2S,5S)-1-[(benzyloxy)carbonyl]-5-methylpyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate -continued

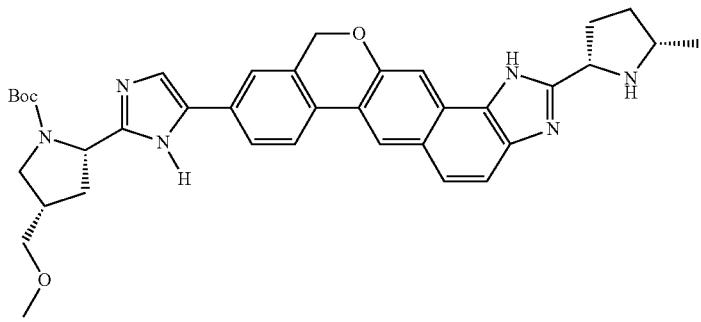

tert-butyl (2S,4S)-4-(methoxymethyl)-2-(5-{2-[(2S,5S)-5-methylpyrrolidin-2-yl]-1,11-dihydroisochromeno[4',3':6,7]naphtho[1,2-d]imidazol-9-yl}-1H-imidazol-2-yl)pyrrolidine-1-carboxylate

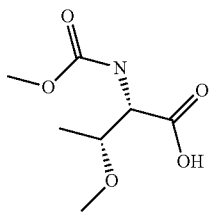

(2S,3R)-3-methoxy-2-(methoxycarbonylamino) butanoic acid

1) HATU, DIPEA, DMF
2) HCl in Ethanol
→

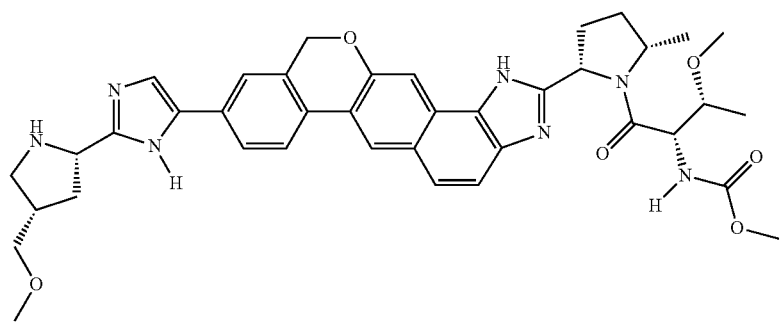

methyl {(2S,3R)-3-methoxy-1-[(2S,5S)-2-(9-{2-[(2S,4S)-4-methoxymethyl)pyrrolidin-2-yl]-1H-imidazol-5-yl}-1,11-dihydroisochromeno[4',3':6,7]naphtho[1,2-d]imidazol-2-yl]-5-methylpyrrolidin-1-yl]-1-oxobutan-2-yl}carbamate Mov-Val-OH, HATU
DIPEA, DMF
→

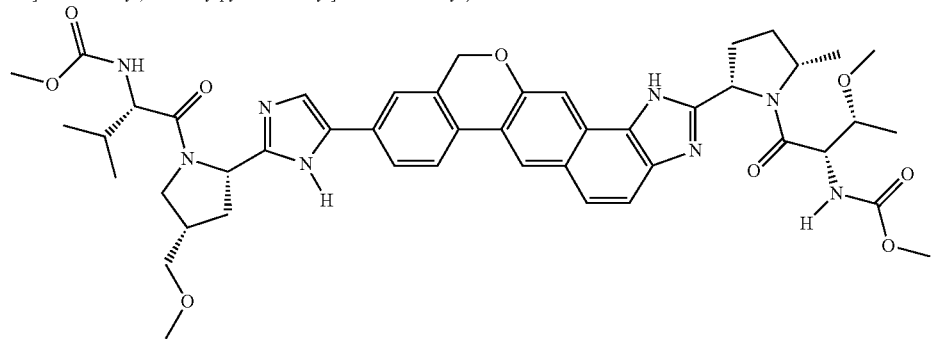

methyl {(2S)-1-[(2S,4S)-2-(5-{2-[(2S,5S)-1-{(2S,3R)-3-methoxy-2-[(methoxycarbonyl)amino]butanoyl}-5-methylpyrrolidin-2-yl]-1,11-dihydroisochromeno[4',3':6,7]naphtho[1,2-d]imidazol-9-yl}-1H-imidazol-2-yl]-4-(methoxymethyl)pyrrolidin-1-yl]-3-methyl-1-oxobutan-2-yl}carbamate tert-butyl (2S,4S)-2-[5-(2-{(2S,5S)-1-[(benzyloxy)carbonyl]-5-methylpyrrolidin-2-yl}-1,11-dihydroisochromeno[4',3':6,7]naphtho[1,2-d]imidazol-9-yl)-1H-imidazol-(methoxymethyl)pyrrolidine-1-carboxylate The title compound was obtained as in example OF (compound tert-butyl (2S,4S)-2-[5-(2-(2S,5S)-1-[N-(methoxycarbonyl)-L-valyl]-5-methylpyrrolidin-2-yl}-1,4,5,11-tetrahydroisochromeno[4',3':6,7]naphtho[1,2-d]imidazol-9-yl)-1H-imidazol-2-yl]-4-(methoxymethyl)pyrrolidine-1-carboxylate) but using (2S,5S)-1-(benzyloxycarbonyl)-5-methylpyrrolidine-2-carboxylic acid in place of (2S,5S)-1-((S)-2-(methoxycarbonylamino)-3-methylbutanoyl)-5-methylpyrrolidine-2-carboxylic acid.

tert-butyl (2S,4S)-4-(methoxymethyl)-2-(5-{2-[(2S,5S)-5-methylpyrrolidin-2-yl]-1,11-dihydroisochromeno[4',3':6,7]naphtho[1,2-d]imidazol-9-yl}-1H-imidazol-2-yl)pyrrolidine-1-carboxylate A mixture of tert-butyl (2S,4S)-2-[5-(2-{(2S,5S)-1-[(benzyloxy)carbonyl]-5-methylpyrrolidin-2-yl}-1,11-dihydroisochromeno[4',3':6,7]naphtho[1,2-d]imidazol-9-yl)-1H- imidazol-2-yl]-4-(methoxymethyl)pyrrolidine-1-carboxylate (830 mg, 1.08 mmol) and 100 mg 10% Pd/C in 20 mL ethanol was hydrogenated at 1atm overnight. Additional 10% Pd/C (300 mg) and a portion of solid NaHCO3 was added and hydrogenation continued for 4 hours. Filtration through celite and concentration of the filtrate under reduced pressure gave the product as a dark brown solid, 722 mg. Purification by reverse phase HPLC gave 100 mg purified product.

methyl {(2S,3R)-3-methoxy-1-[(2S,5S)-2-(9-{2-[(2S,4S)-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidine-1-yl]-1-oxobutan-2-yl}carbamate A mixture of tert-butyl (2S,4S)-4-(methoxymethyl)-2-(5-{2-[(2S,5S)-5-methylpyrrolidin-2-yl]-1,11-dihydroisochromeno[4',3':6,7]naphtho[1,2-d]imidazol-9-yl}-1H-imidazol-2-yl)pyrrolidine-1-carboxylate (101 mg, 0.159 mmol), (2S,3R)-3-methoxy-2-(methoxycarbonylamino)butanoic acid (30 mg, 0.159 mmol), HATU (61 mg, 0.159 mmol) and 2 mL 10% DIPEA in DMF was stirred at room temperature for 1.5 hours. Saturated sodium bicarbonate was added and the product was extracted into dichloromethane, dried over sodium sulphate, filtered and concentrated under reduced pressure. This crude product was treated with 5 mL 1.25N HCl in ethanol at 50° C. for 4 h and then it was concentrated under reduced pressure. Saturated sodium bicarbonate was added and the product was extracted into dichloromethane, dried over sodium sulphate, filtered and concentrated under reduced pressure. (74.6 mg)

methyl {(2S)-1-[(2S,4S)-2-(5-{2-[(2S,5S)-1-{(2S,3R)-3-methoxy-2-[(methoxycarbonyl)amino]butanoyl}-5-methylpyrrolidin-2-yl]-1,11-dihydroisochromeno[4',3':6,7]naphtho[1,2-d]imidazol-9-yl]-1H-imidazol-2-yl)-4-(methoxymethyl)pyrrolidin-1-yl]-3-methyl-1-oxobutan-2-yl}carbamate A mixture of methyl {(2S,3R)-3-methoxy-1-[(2S,5S)-2-(9-{2-[(2S,4S)-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-1-oxobutan-2-yl}carbamate (74.6 mg, 0.105 mmol), (S)-2-(methoxycarbonylamino)-3-methylbutanoic acid (18.5 mg, 0.105 mmol), HATU (44 mg, 0.116 mmol) and 0.6 mL 10% DIPEA in DMF was stirred at room temperature for 1 hour. The product was purified by reverse phase HPLC. (48.1 mg) MS (ESI) m/z 866.1 [M+H]+.

Example PJ

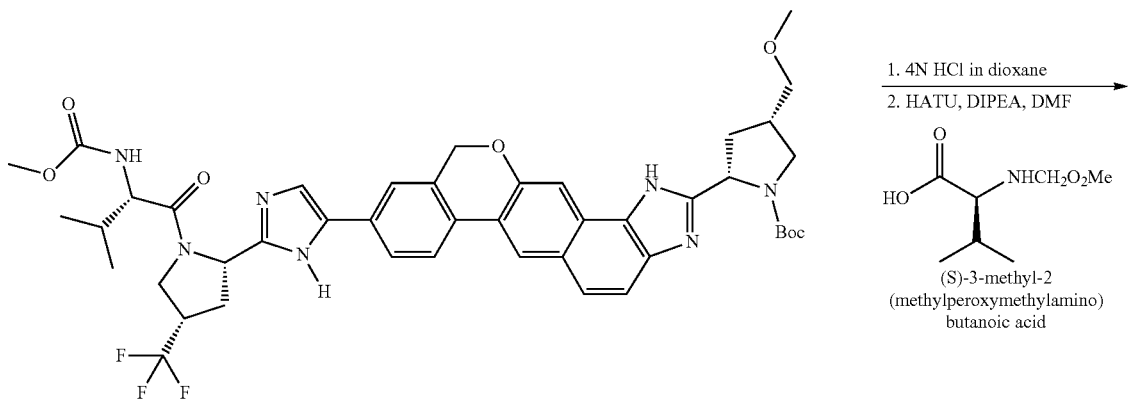

tert-butyl (2S,4S)-2-(9-{2-[(2S,4S)-1-[N-(methoxycarbonyl)-L-valyl]-4-(trifluoromethyl)pyrrolidin-2-yl]-1H-imidazol-5-yl}-1,11-dihydroisochromeno[4',3':6,7]naphtho[1,2-d]imidazol-2-yl)-4-(methoxymethyl)pyrrolidine-1-carboxylate

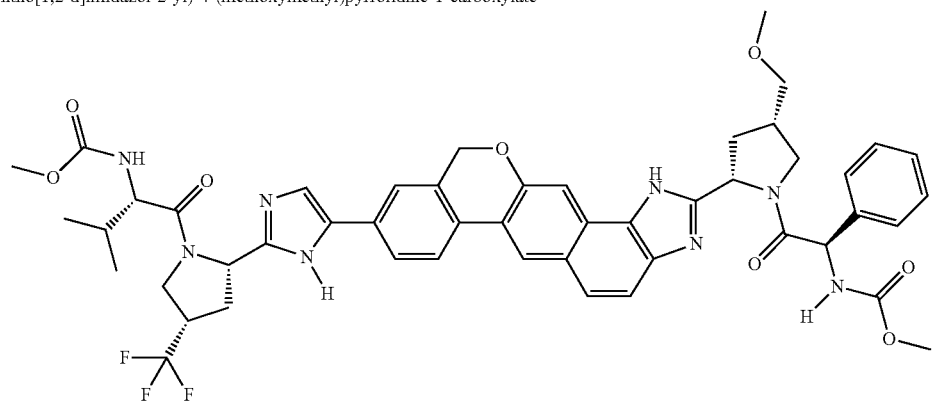

methyl {(1R)-2-[(2S,4S)-2-(9-{2-[(2S,4S)-1-{(2S)-2-[(methoxycarbonyl)amino]-3-methylbutanoyl}-4-(trifluoromethyl)pyrrolidin-2-yl]-1H-imidazol-5-yl}-1,11-dihydroisochromeno[4',3':6,7]naphtho[1,2-d]imidazol-2-yl)-4-(methoxymethyl)pyrrolidin-1-yl]-2-oxo-1-phenylethyl}carbamate tert-butyl (2S,4S)-2-(9-{2-[(2S,4S)-1-[N-(methoxycarbonyl)-L-valyl]-4-(trifluoromethyl)pyrrolidin-2-yl}-1H-imidazol-5-yl}-1,11-dihydroisochromeno[4',3':6,7]naphtho[1,2-d]imidazol-2-yl)-4-(methoxymethyl)pyrrolidine-1-carboxylate The title compound was prepared as in example OF for compound tert-butyl (2S,4S)-2-[5-(2-{(2S,5S)-1-[N-(methoxycarbonyl)-L-valyl]-5-methylpyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate, by using (2S,4S)-1-((S)-2-(methoxycarbonylamino)-3-methylbutanoyl)-4-(trifluoromethyl)pyrrolidine-2-carboxylic acid in place of (2S,4S)-1-(tert-butoxycarbonyl)-4-(methoxymethyl)pyrrolidine-2-carboxylic acid and (2S,4S)-1-(tert-butoxycarbonyl)-4-(methoxymethyl)pyrrolidine-2-carboxylic acid in place of (2S,5S)-1-((S)-2-(methoxycarbonylamino)-3-methylbutanoyl)-5-methylpyrrolidine-2-carboxylic acid.

methyl {(1R)-2-[(2S,4S)-2-(9-{2-[(2S,4S)-1-{(2S)-2-[(methoxycarbonyl)amino]-3-methylbutanoyl}-4-(trifluoromethyl)pyrrolidin-2-yl]-1H-imidazol-5-yl}-1,11-dihydroisochromeno[4',3':6,7]naphtho[1,2-d]imidazol-2-yl)-4-(methoxymethyl)pyrrolidin-1-yl]-2-oxo-1-phenylethyl}carbamate tert-butyl (2S,4S)-2-(9-{2-[(2S,4S)-1-[N-(methoxycarbonyl)-L-valyl]-4-(trifluoromethyl)pyrrolidin-2-yl]-1H-imidazol-5-yl}-1,11-dihydroisochromeno[4',3':6,7]naphtho[1,2-d]imidazol-2-yl)-4-(methoxymethyl)pyrrolidine-1-carboxylate (<0.412 mmol, crude from previous step) was treated with 6 mL 4N HCl in dioxane at room temperature overnight and then at 50° C. for 1 hour. Diethyl ether (20 mL) was added and the precipitate of hydrochloride salt was collected by vacuum filtration. (126 mg, 0.16 mmol). This material was combined with (R)-2-(methoxycarbonylamino)-2-phenylacetic acid (34 mg, 0.16 mmol), COMU (70 mg, 0.16 mmol), and 1.6 mL of 10% DIPEA in DMF. After 1 hour at room temperature, the mixture was added dropwise into 25 mL saturated sodium bicarbonate, with stirring and the resulting precipitate was collected by vacuum filtration and washed with 2 mL water. The product was purified, then re-purified by reverse phase HPLC. (3.5 mg).
MS (ESI) m/z 938.1 [M+H]⁺.

Example PK

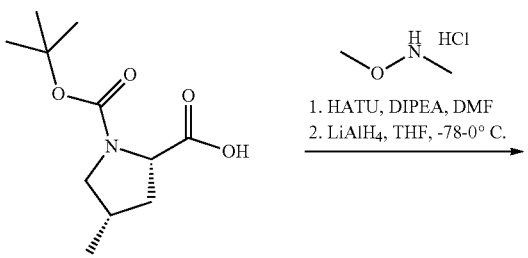

(2S,4S)-1-tert-butoxycarbonyl-4-methylpyrrolidine-2-carboxylic acid

1. HATU, DIPEA, DMF
2. LiAlH₄, THF, −78-0° C.

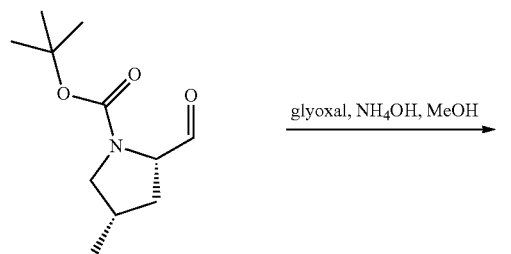

(2S,4S)-tert-butyl 2-formyl-4-methylpyrrolidine-1-carboxylate glyoxal, NH₄OH, MeOH

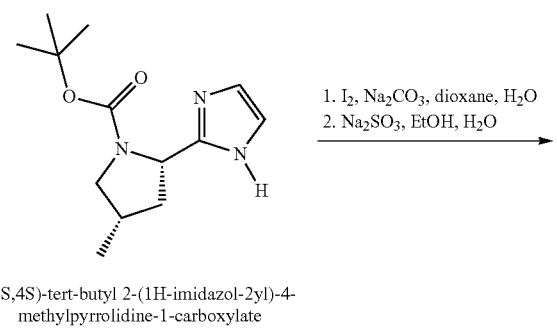

(2S,4S)-tert-butyl 2-(1H-imidazol-2yl)-4-methylpyrrolidine-1-carboxylate

1. I₂, Na₂CO₃, dioxane, H₂O
2. Na₂SO₃, EtOH, H₂O

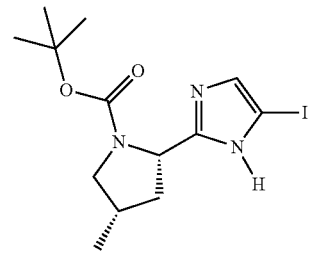

(2S,4S)-tert-butyl 2-(5-iodo-1H-imidazol-2yl)-4-methylpyrrolidine-1-carboxylate (2S,4S)-tert-butyl 2-formyl-4-methylpyrrolidine-1-carboxylate A mixture of (2S,4S)-1-(tert-butoxycarbonyl)-4-methylpyrrolidine-2-carboxylic acid (5.2 g, 22.7 mmol), O,N-dimethylhydroxylamine hydrochloride (2.4 g, 24.9 mmol), HATU (10.4 g, 27.2 mmol) and DIPEA (9.5 mL, 54.5 mmol) in 114 mL DMF was stirred at room temperature overnight. The mixture was extracted into ethyl acetate and washed with saturated bicarbonate and water, dried over sodium sulphate, filtered, and concentrated. It was then dissolved in diethyl ether (100 mL) and washed with water to remove residual DMF, dried, filtered, and concentrated to a pale yellow oil (5.30 g, 19.5 mmol) of (2S,4S)-tert-butyl 2-(methoxy(methyl)carbamoyl)-4-methylpyrrolidine-1-carboxylate.

(2S,4S)-tert-butyl 2-(methoxy(methyl)carbamoyl)-4-methylpyrrolidine-1-carboxylate (5.30 g, 19.5 mmol) was dissolved in 120 mL THF, cooled to −78° C. and treated with lithium aluminum hydride (1M in THF, 19.5 mL, 19.5 mmol) dropwise via addition funnel. After 1 hour, the mixture was brought to 0° C. and kept at that temperature for 2 hours. It was quenched by dropwise addition of a 50 mL solution of 3.0 g KHSO4 in water, removed from the ice bath, and stirred 15 minutes at room temperature. The product was extracted with three 75 mL portions of ethyl acetate and washed with brine. The organic phase was dried over sodium sulphate, filtered, and concentrated to give crude (2S,4S)-tert-butyl 2-formyl-4-methylpyrrolidine-1-carboxylate. (4.89 g)

(2S,4S)-tert-butyl 2-(1H-imidazol-2-yl)-4-methylpyrrolidine-1-carboxylate

To a solution of (2S,4S)-tert-butyl 2-formyl-4-methylpyrrolidine-1-carboxylate (4.89 g, 22.9 mmol), ammonium hydroxide (17 mL) and water (17 mL) was added, dropwise, glyoxal (40% in water, 14.6 mL, 128 mmol) and the resulting mixture was stirred at room temperature overnight. Saturated sodium bicarbonate (100 mL) was added and the mixture was extracted with four 75 mL portions of dichloromethane. The organic phase was washed with water, dried over sodium sulphate, filtered and concentrated, and then purified by silica gel chromatography to give a total of 3.76 g product.

(2S,4S)-tert-butyl 2-(5-iodo-1H-imidazol-2-yl)-4-methylpyrrolidine-1-carboxylate A mixture of (2S,4S)-tert-butyl 2-(1H-imidazol-2-yl)-4-methylpyrrolidine-1-carboxylate (1.0 g, 3.97 mmol), iodine (2.22 g, 8.75 mmol) and sodium carbonate (1.3 g, 12.31 mmol) in 20 mL dioxane and 13.25 mL water was covered in foil and stirred at room temperature overnight. The mixture was diluted with ethyl acetate and treated with 10% sodium thiosulfate (5 mL) and stirred for 10 minutes. The organic phase was washed with brine, and then the aqueous phase was back extracted with ethyl acetate. The combined organic phases were dried over sodium sulphate, filtered and concentrated to provide crude (2S,4S)-tert-butyl 2-(4,5-diiodo-1H-imidazol-2-yl)-4-methylpyrrolidine-1-carboxylate (2.25 g) as a pale yellow solid.

A solution of (2S,4S)-tert-butyl 2-(4,5-diiodo-1H-imidazol-2-yl)-4-methylpyrrolidine-1-carboxylate (2.25 g, 4.4 mmol) in 18 mL ethanol and 18 mL water was treated with sodium sulfite (5.59 g, 44.4 mmol) and heated at 90° C. overnight. The mixture was partitioned between ethyl acetate and water. The aqueous phase was extracted with more ethyl acetate and the combined organic phase was washed with brine, dried over sodium sulphate, filtered, concentrated, and purified by silica gel chromatography to give 766 mg (2S,4S)-tert-butyl 2-(5-iodo-1H-imidazol-2-yl)-4-methylpyrrolidine-1-carboxylate.

Example PL

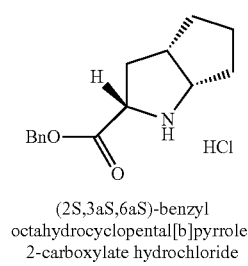 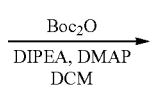

(2S,3aS,6aS)-benzyl octahydrocyclopental[b]pyrrole-2-carboxylate hydrochloride

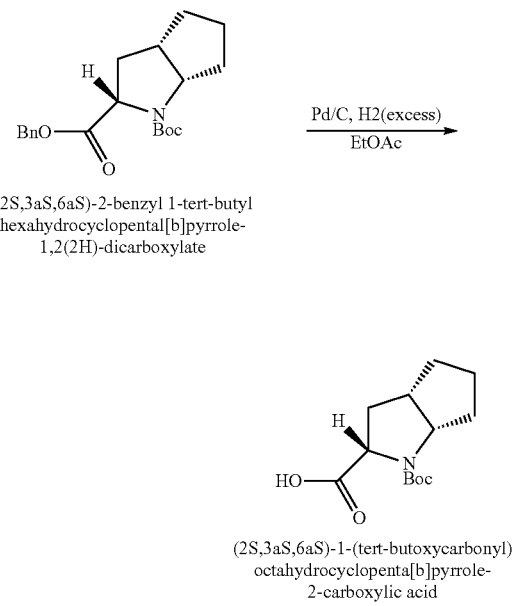

(2S,3aS,6aS)-2-benzyl 1-tert-butyl hexahydrocyclopental[b]pyrrole-1,2(2H)-dicarboxylate (2S,3aS,6aS)-1-(tert-butoxycarbonyl)octahydrocyclopenta[b]pyrrole-2-carboxylic acid (2S,3aS,6aS)-1-(tert-butoxycarbonyl)octahydrocyclopenta[b]pyrrole-2-carboxylic acid To a solution of commercially available (2S,3aS,6aS)-benzyl octahydrocyclopenta[b]pyrrole-2-carboxylate hydrochloride (4.70 g, 16.68 mmol) in methylene chloride (42 mL) was added Di-tert-butyl dicarbonate (7.28 g, 33.36 mmol), N,N-diisopropylethylamine (5.82 mL, 33.36 mmol) and 4-(Dimethylamino)pyridine (0.20 g, 1.67 mmol). The solution was stirred under air for 16 hours. Upon completion, the reaction was concentrated in vacuo, diluted in ethyl acetate, and washed with 1N HCl. The aqueous layers were backextracted twice with ethyl acetate and the combined organic layers were dried over sodium sulfate, filtered and concentrated. The resulting residue was purified by silica gel chromatography (5-40% ethyl acetate in hexanes) to afford (2S,3aS,6aS)-1-tert-butoxycarbonyl)octahydrocyclopenta[b]pyrrole-2-carboxylic acid which was used without further purification. MS (ESI) m/z 368.47 [M+Na]$^+$.

(2S,3aS,6aS)-1-(tert-butoxycarbonyl)octahydrocyclopenta[b]pyrrole-2-carboxylic acid To a 250 mL round bottom flask charged with a stir bar and (2S,3aS,6aS)-2-benzyl 1-tert-butyl hexahydrocyclopenta[b]pyrrole-1,2(2H)-dicarboxylate (5.76 g, 16.68 mmol) was added 10% Palladium on carbon (1.77 g). Ethanol was poured over the mixture and the reaction mixture was evacuated and flushed with hydrogen gas three times. The suspension was stirred at room temperature under an atmosphere of hydrogen for 24 hours. Upon completion, the reaction mixture was filtered through celite and concentrated to give (2S,3aS,6aS)-1-(tert-butoxycarbonyl)octahydrocyclopenta[b]pyrrole-2-carboxylic acid (4.45 g, >99%). MS (ESI) m/z 256.21 [M+H]$^+$.

Example PM

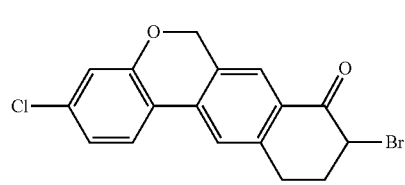
9-bromo-3-chloro-10,11-
dihydro-6H-naphtho[2,3-c]
chromen-8(9H)-one

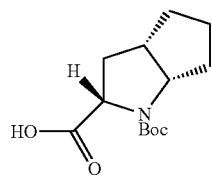
(2S,3aS,6aS)-1-(tert-butoxycarbonyl)
octahydrocyclopenta[b]pyrrole-
2-carboxylic acid

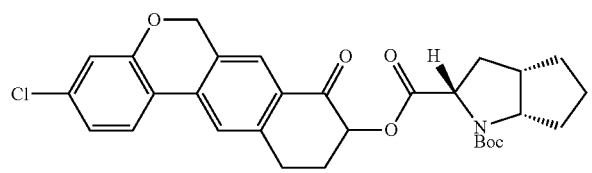
(2S,3aS,6aS)-1-tert-butyl 2-(3-chloro-8-oxo-8,9,10,11-
tetrahydro-6H-naphtho[2,3-c]chromen-9-yl)
hexahydrocyclopenta[b]pyrrole-1,2(2H)-dicarboxylate $NH_4OAc$ →

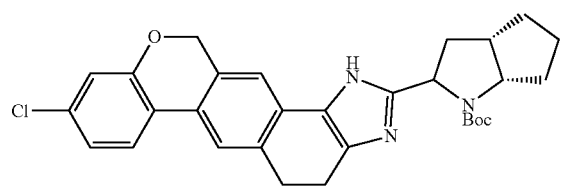
tert-butyl (3aS,6aS)-2-(9-chloro-1,4,5,12-
tetrahydrochromeno[4',3':6,7]naphtho[1,2-d]imidazol-2-yl)
hexahydrocyclopenta[b]pyrrole-1(2H)-carboxylate $MnO_2$ →

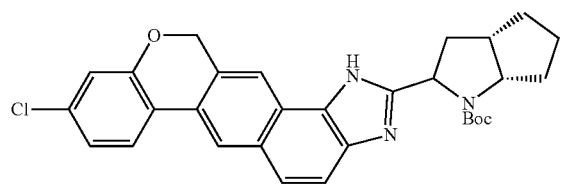
tert-butyl (3aS,6aS)-2-(9-chloro-1,12-
dihydrochromeno[4',3':6,7]naphtho[1,2-d]imidazol-2-yl)
hexahydrocyclopenta[b]pyrrole-1(2H)-carboxylate 1. HCl
2. HATU
MocVal →

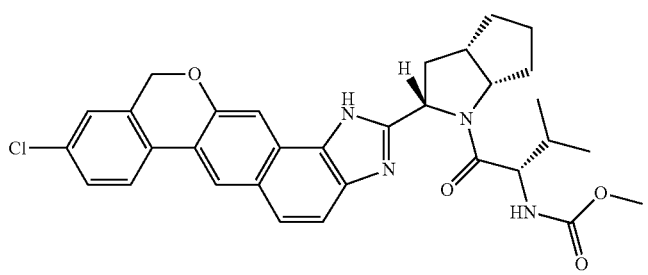
methyl {(2S)-1-[(2S,3aS,6aS)-2-9-chloro-1,11-
dihydroisochromeno[4'3':6,7]naphtho[1,2-
d]imidazol-2-yl)hexahydrocyclopenta[b]pyrrol-1(2H)-yl]-3-
methyl-1-oxobutan-2-yl}carbamate $Pd_2dba_3$
Bis-PinB
XPhos

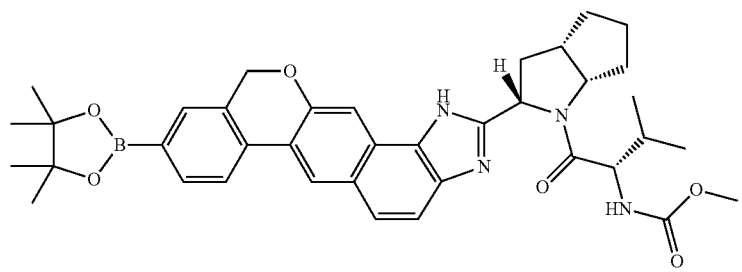

methyl {(2S)-3-methyl-1-oxo-1-[(2S,3aS,6aS)-2-[9-(4,4,5,5-tetramethyl-1,3,2-dioxaborolan-2-yl)-1,11-dihydroisochromeno[4',3':6,7]naphtho[1,2-d]imidazol-2-yl]hexahydrocyclopenta[b]pyrrol-1(2H)-yl]butan-2-yl}carbamate

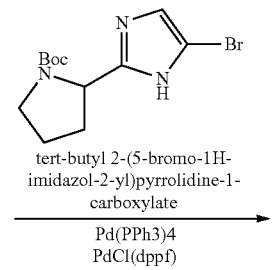

tert-butyl 2-(5-bromo-1H-imidazol-2-yl)pyrrolidine-1-carboxylate

Pd(PPh3)4
PdCl(dppf)

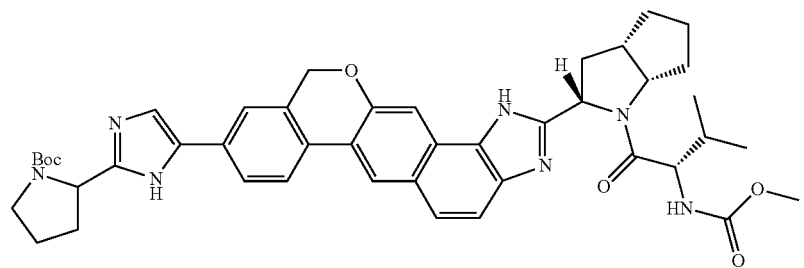

tert-butyl 2-[5-(2-{(2S,3aS,6aS)-1-[N-(methoxycarbonyl)-L-valyl]octahydrocyclopenta[b]pyrrol-2-yl}-1,11-dihydroisochromeno[4',3':6,7]naphtho[1,2-d]imidazol-9-yl)-1H-imidazol-2-yl]pyrrolidine-1-carboxylate tert-butyl 2-[5-(2-{(2S,3aS,6aS)-1-[N-(methoxycarbonyl)-L-valyl]octahydrocyclopenta[b]pyrrol-2-yl}-1,11-dihydroisochromeno[4',3':6,7]naphtho[1,2-d]imidazol-9-yl)-1H-imidazol-2-yl]pyrrolidine-1-carboxylate This compound was made in an analogous manner to tert-butyl (2R)-2-[5-(2-{(2S)-1-[N-(methoxycarbonyl)-L-valyl]pyrrolidin-2-yl}-3,11-dihydroisochromeno[4',3':6,7]naphtho[1,2-d]imidazol-9-yl)-1H-imidazol-2-yl]pyrrolidine-1-carboxylate substituting (2S,3aS,6aS)-1-(tert-butoxycarbonyl)octahydrocyclopenta[b]pyrrole-2-carboxylic acid for the initial alkylation of 9-bromo-3-chloro-10,11-dihydro-6H-naphtho[2,3-c]chromen-8(9H)-one. Reactions in the synthesis of tert-butyl 2-[5-(2-{(2S,3aS,6aS)-1-[N-(methoxycarbonyl)-L-valyl]octahydrocyclopenta[b]pyrrol-2-yl}-1,11-dihydroisochromeno[4',3':6,7]naphtho[1,2-d]imidazol-9-yl)-1H-imidazol-2-yl]pyrrolidine-1-carboxylate gave similar product yields as in the synthesis of tert-butyl (2R)-2-[5-(2-{(2S)-1-[N-(methoxycarbonyl)-L-valyl]pyrrolidin-2-yl}-3,11-dihydroisochromeno[4',3':6,7]naphtho[1,2-d]imidazol-9-yl)-1H-imidazol-2-yl]pyrrolidine-1-carboxylate. MS (ESI) m/z 774.1 [M+H]+.

Example PN

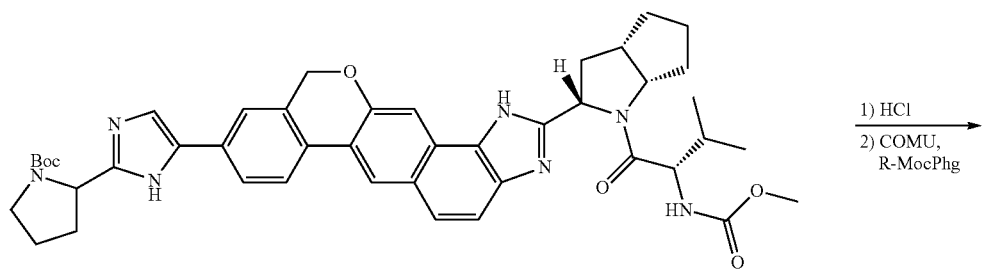

tert-butyl 2-[5-(2-{(2S,3aS,6aS)-1-[N-(methoxycarbonyl)-L-valyl]octahydrocyclopenta[b]pyrrol-2-yl}-1,11-dihydroisochromeno[4',3':6,7]naphtho[1,2-d]imidazol-9-yl)-1H-imidazol-2-yl]pyrrolidine-1-carboxylate 1) HCl
2) COMU, R-MocPhg

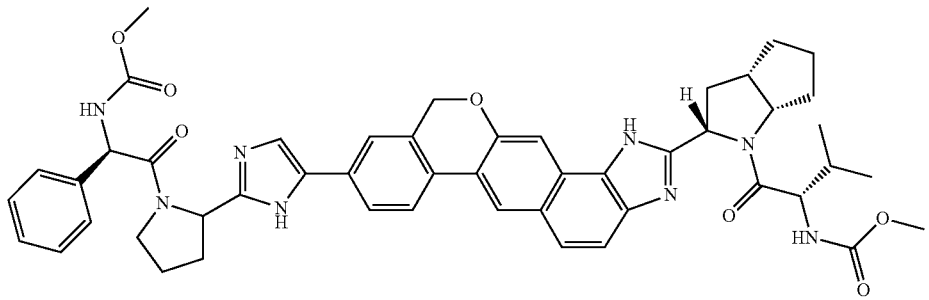

methyl {(1R)-2-[2-(5-{2-[(2S,3aS,6aS)-1-{(2S)-2-[(methoxycarbonyl)amino]-3-methylbutanoyl}octahydrocyclopenta[b]pyrrol-2-yl]-1,11-dihydroisochromeno[4',3':6,7]naphtho[1,2-d]imidazol-9-yl}-1H-imidazol-2-yl)pyrrolidin-1-yl]-2-oxo-1-phenylethyl}carbamate methyl {(1R)-2-[2-(5-{2-[(2S,3aS,6aS)-1-{(2S)-2-[(methoxycarbonyl)amino]-3-methylbutanoyl}octahydrocyclopenta[b]pyrrol-2-yl]-1,11-dihydroisochromeno[4',3':6,7]naphtho[1,2-d]imidazol-9-yl}-1H-imidazol-2-yl)pyrrolidin-1-yl]-2-oxo-1-phenylethyl}carbamate To a solution of tert-butyl 2-[5-(2-{(2S,3aS,6aS)-1-[N-(methoxycarbonyl)-L-valyl]octahydrocyclopenta[b]pyrrol-2-yl}-1,11-dihydroisochromeno[4',3':6,7]naphtho[1,2-d]imidazol-9-yl)-1H-imidazol-2-yl]pyrrolidine-1-carboxylate (0.128 g, 0.165 mmol) in a mixture of CH$_2$Cl$_2$ (1.6 mL) and MeOH (0.33 mL) was added HCl (4M in 1,4-dioxane, 1.24 mL, 4.9 mmol). The solution was stirred at room temperature for 1.5 h and concentrated to dryness.

The intermediate was dissolved in CH$_2$Cl$_2$ (1.6 mL). (R)-2-(methoxycarbonylamino)-2-phenylacetic acid (0.052 g, 0.25 mmol) and DIPEA (0.087 mL, 0.496 mmol) were then added to the solution. The reaction mixture was cooled to −40° C. (external temperature, MeCN/CO$_2$(s) bath). COMU (0.113 g, 0.265 mmol) was then added and solution was allowed to warm to 0° C. over 1.5 h. Upon completion by LCMS, the solution was diluted with DMF and concentrated.

The crude product was purified by preparative HPLC (Gemini column, 10-47% MeCN/H$_2$O with 0.1% TFA) and the desired fractions were combined. The solution was concentrated until the aqueous layer remained and aqueous bicarbonate (sat.) was slowly added until the solution was basic. The resulting slurry was stirred at room temperature for 2 h and filtered. The resulting solid was dried in vacuo to provide methyl {(1R)-2-[2-(5-{2-[(2S,3aS,6aS)-1-{(2S)-2-[(methoxycarbonyl)amino]-3-methylbutanoyl}octahydrocyclopenta[b]pyrrol-2-yl]-1,11-dihydroisochromeno[4',3':6,7]naphtho[1,2-d]imidazol-9-yl}-1H-imidazol-2-yl)pyrrolidin-1-yl]-2-oxo-1-phenylethyl}carbamate (0.068 g, 48%).

MS (ESI) m/z 865.7 [M+H]$^+$. $^1$H NMR (400 MHz, cd$_3$od) δ 8.44-8.30 (m, 1H), 8.02-7.82 (m, 2H), 7.81-7.58 (m, 4H), 7.50-7.11 (m, 6H), 7.09-6.83 (m, 2H), 5.72-5.45 (m, 2H), 5.41 (s, 1H), 5.34-5.28 (m, 1H), 5.22 (s, 3H), 4.69-4.64 (m, 1H), 4.26-4.19 (m, 1H), 4.03-3.98 (m, 1H), 3.96-3.91 (m, 1H), 3.66 (d, 4H), 2.98-2.91 (m, 1H), 2.88-2.83 (m, 1H), 2.58-2.48 (m, 1H), 2.27-2.12 (m, 4H), 2.11-2.00 (m, 3H), 2.00-1.89 (m, 2H), 1.77-1.72 (m, 1H), 1.31-1.04 (m, 3H), 0.93 (d, 6H).

Example PO

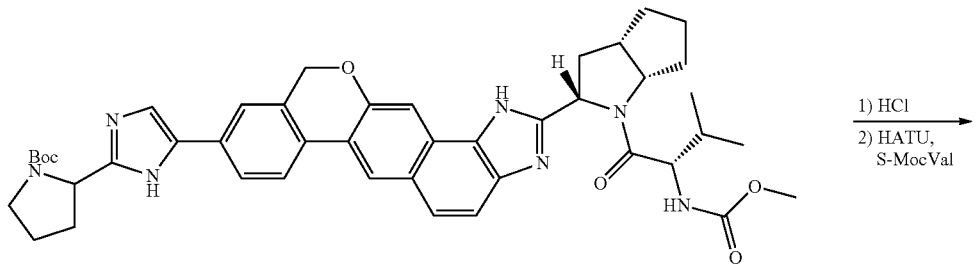

tert-butyl 2-[5-(2-{(2S,3aS,6aS)-1-[N-(methoxycarbonyl)-L-valyl]octahydrocyclopenta[b]pyrrol-2-yl}-1,11-dihydroisochromeno[4',3':6,7]naphtho[1,2-d]imidazol-9-yl)-1H-imidazol-2-yl]pyrrolidine-1-carboxylate 1) HCl
2) HATU, S-MocVal

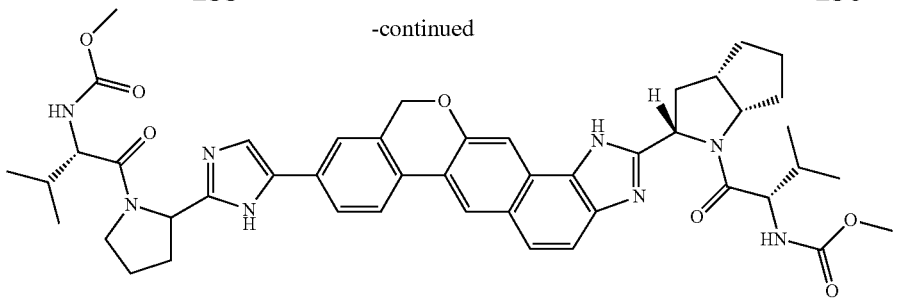

methyl {(2S)-1-[2-(5-{2-[(2S,3aS,6aS)-1-{(2S)-2-[(methoxycarbonyl)amino]-
3-methylbutanoyl}octahydrocyclopenta[b]pyrrol-2-yl]-1,11-
dihydroisochromeno[4',3':6,7]naphtho[1,2-d]imidazol-9-
yl}-1H-imidazol-2-yl)pyrrolidin-1-yl]-3-methyl-1-oxobutan-2-yl}carbamate methyl {(2S)-1-[2-(5-{2-[(2S,3aS,6aS)-1-{(2S)-2-
[(methoxycarbonyl)amino]-3-
methylbutanoyl}octahydrocyclopenta[b]pyrrol-2-yl]-
1,11-dihydroisochromeno[4',3':6,7]naphtho[1,2-d]
imidazol-9-yl}-1H-imidazol-2-yl)pyrrolidin-1-yl]-3-
methyl-1-oxobutan-2-yl}carbamate To a solution of tert-butyl 2-[5-(2-{(2S,3aS,6aS)-1-[N-(methoxycarbonyl)-L-valyl]octahydrocyclopenta[b]pyrrol-2-yl}-1,11-dihydroisochromeno[4',3':6,7]naphtho[1,2-d]imidazol-9-yl)-1H-imidazol-2-yl]pyrrolidine-1-carboxylate (0.030 g, 0.039 mmol) in a mixture of CH$_2$Cl$_2$ (0.39 mL) and MeOH (0.078 mL) was added HCl (4M in 1,4-dioxane, 0.29 mL, 1.16 mmol). The solution was stirred at room temperature for 1.5 h and concentrated to dryness.

The intermediate was dissolved in CH$_2$Cl$_2$ (0.39 mL). (S)-2-(methoxycarbonylamino)-3-methylbutanoic acid (0.007 g, 0.043 mmol) and DIPEA (0.020 mL, 0.116 mmol) were then added to the solution. HATU (0.018 g, 0.047 mmol) was added and solution was allowed to stir at room temp. Upon completion, the solution was diluted with DMF and concentrated. The crude product was purified by preparative HPLC (Gemini column, 10-47% MeCN/H$_2$O with 0.1% TFA) and the desired fractions were combined and lyophilized to provide methyl {(2S)-1-[2-(5-{2-[(2S,3aS,6aS)-1-{(2S)-2-[(methoxycarbonyl)amino]-3-methylbutanoyl}octahydrocyclopenta[b]pyrrol-2-yl]-1,11-dihydroisochromeno[4',3':6,7]naphtho[1,2-d]imidazol-9-yl}-1H-imidazol-2-yl)pyrrolidin-1-yl]-3-methyl-1-oxobutan-2-yl}carbamate (0.010 g, 31%). MS (ESI) m/z 832.2 [M+H]$^+$.

Example PP

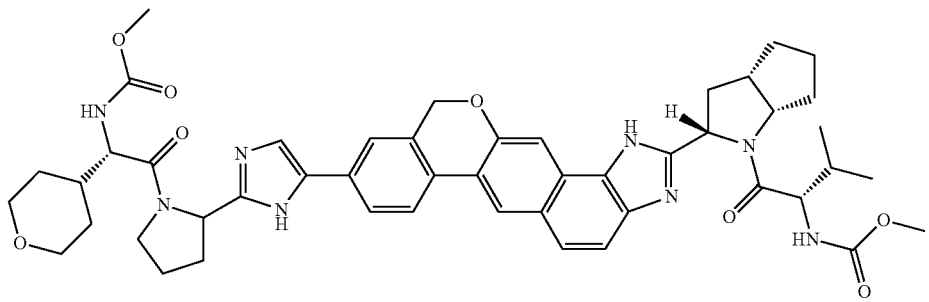

methyl [(1S)-2-[2-(5-{2-[(2S,3aS,6aS)-1-{(2S)-2-
[(methoxycarbonyl)amino]-3-
methylbutanoyl}octahydrocyclopenta[b]pyrrol-2-yl]-1,11-
dihydroisochromeno[4',3':6,7]naphtho[1,2-d]imidazol-9-yl}-1H-imidazol-
2-yl)pyrrolidin-1-yl]-2-oxo-1-(tetrahydro-2H-pyran-4-yl)ethyl]carbamate methyl [(1S)-2-[2-(5-{2-[(2S,3aS,6aS)-1-{(2S)-2-
[(methoxycarbonyl)amino]-3-
methylbutanoyl}octahydrocyclopenta[b]pyrrol-2-yl]-
1,11-dihydroisochromeno[4',3':6,7]naphtho[1,2-d]
imidazol-9-yl}-1H-imidazol-2-yl)pyrrolidin-1-yl]-2-
oxo-1-(tetrahydro-2H-pyran-4-yl)ethyl]carbamate This compound was made in an analogous manner to methyl {(2S)-1-[2-(5-{2-[(2S,3aS,6aS)-1-{(2S)-2-[(methoxycarbonyl)amino]-3-methylbutanoyl}octahydrocyclopenta[b]pyrrol-2-yl]-1,11-dihydroisochromeno[4',3':6,7]naphtho[1,2-d]imidazol-9-yl}-1H-imidazol-2-yl)pyrrolidin-1-yl]-3-methyl-1-oxobutan-2-yl}carbamate, substituting (S)-2-(methoxycarbonylamino)-2-(tetrahydro-2H-pyran-4-yl) acetic acid for (S)-2-(methoxycarbonylamino)-3-methylbutanoic acid to give methyl [(1S)-2-[2-(5-{2-[(2S,3aS,6aS)-1-{(2S)-2-[(methoxycarbonyl)amino]-3-methylbutanoyl}octahydrocyclopenta[b]pyrrol-2-yl]-1,11- dihydroisochromeno[4',3':6,7]naphtho[1,2-d]imidazol-9-yl}-1H-imidazol-2-yl)pyrrolidin-1-yl]-2-oxo-1-(tetrahydro-2H-pyran-4-yl)ethyl]carbamate (0.039 g, 56%). MS (ESI) m/z 874.34 [M+H]⁺. ¹H NMR (400 MHz, cd₃od) δ 8.58 (s, 2H), 8.26-8.08 (m, 2H), 7.96-7.75 (m, 4H), 7.65-7.54 (m, 5H), 5.36-5.11 (m, 4H), 4.34-4.04 (m, 4H), 3.97-3.79 (m, 4H), 3.65 (s, 4H), 3.53-3.44 (m, 2H), 2.68-2.47 (m, 4H), 2.32-2.02 (m, 7H), 1.95-1.82 (m, 3H), 1.77-1.54 (m, 4H), 1.49-1.24 (m, 5H), 1.10-0.99 (m, 3H), 0.92-0.85 (m, 4H).

Example PQ imidazol-2-yl]pyrrolidine-1-carboxylate substituting (2S,4S)-1-(tert-butoxycarbonyl)-4-((difluoromethoxy)methyl)pyrrolidine-2-carboxylic acid for the initial alkylation of 9-bromo-3-chloro-10,11-dihydro-6H-naphtho[2,3-c]chromen-8(9H)-one. Reactions in the synthesis of tert-butyl 2-[5-(2-{(2S,4S)-4-[(difluoromethoxy)methyl]-1-[N-(methoxycarbonyl)-L-valyl]pyrrolidin-2-yl}-1,11-dihydroisochromeno[4',3':6,7]naphtho[1,2-d]imidazol-9-yl)-1H-imidazol-2-yl]pyrrolidine-1-carboxylate gave similar product yields as in the synthesis of tert-butyl 2-[5-(2-{(2S,3aS,6aS)-1-[N-(methoxycarbonyl)-L-valyl]octahydrocyclopenta[b]

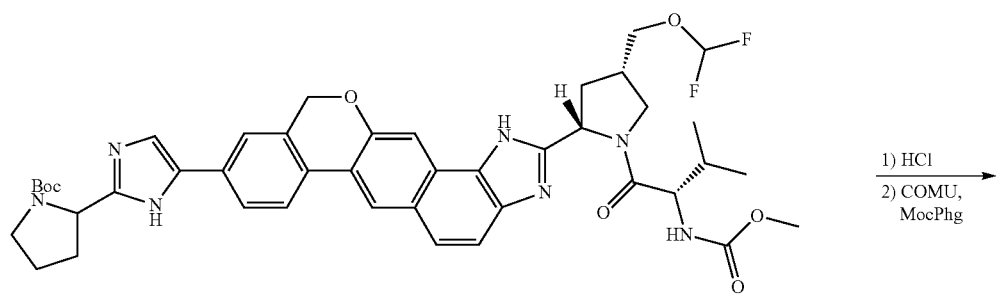

tert-butyl 2-[5-(2-{(2S,4S)-4-[(difluoromethoxy)methyl]-1-[N-(methoxycarbonyl)-L-valyl]pyrrolidin-2-yl}-1,11-dihydroisochromeno[4',3':6,7]naphtho[1,2-d]imidazol-9-yl)-1H-imidazol-2-yl]pyrrolidine-1-carboxylate

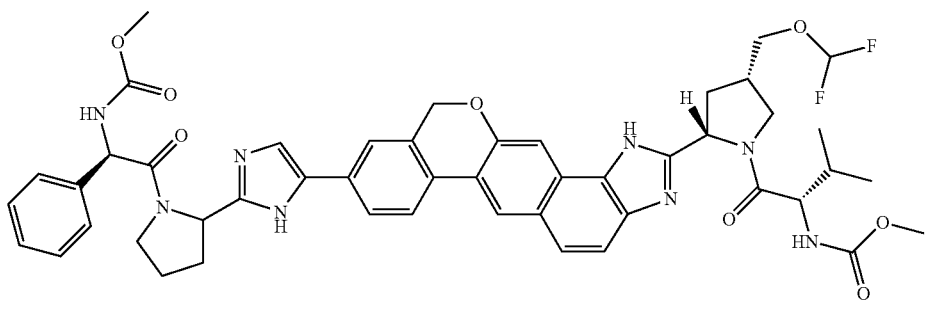

methyl {(1R)-2-[2-(5-{2-[(2S,4S)-4-[(difluoromethoxy)methyl]-1-{(2S)-2-[(methoxycarbonyl)amino]-3-methylbutanoyl}pyrrolidin-2-yl]-1,11-dihydroisochromeno[4',3':6,7]naphtho[1,2-d]imidazol-9-yl}-1H-imidazol-2-yl)pyrrolidin-1-yl]-2-oxo-1-phenylethyl}carbamate tert-butyl 2-[5-(2-{(2S,4S)-4-[(difluoromethoxy)methyl]-1-[N-(methoxycarbonyl)-L-valyl]pyrrolidin-2-yl}-1,11-dihydroisochromeno[4',3':6,7]naphtho[1,2-d]imidazol-9-yl)-1H-imidazol-2-yl]pyrrolidine-1-carboxylate This compound was made in an analogous manner to tert-butyl 2-[5-(2-{(2S,3aS,6aS)-1-[N-(methoxycarbonyl)-L-valyl]octahydrocyclopenta[b]pyrrol-2-yl}-1,11-dihydroisochromeno[4',3':6,7]naphtho[1,2-d]imidazol-9-yl)-1H-pyrrol-2-yl}-1,11-dihydroisochromeno[4',3':6,7]naphtho[1,2-d]imidazol-9-yl)-1H-imidazol-2-yl]pyrrolidine-1-carboxylate. MS (ESI) m/z 815.04 [M+H]⁺. ¹H NMR (400 MHz, cd₃od) δ 8.58 (s, 1H), 8.18 (d, 1H), 7.96-7.85 (m, 3H), 7.70 (s, 1H), 7.60 (d, 1H), 7.50-7.38 (m, 4H), 7.10 (s, 1H), 6.46 (t, 1H), 5.51 (s, 1H), 5.39-5.36 (m, 1H), 5.31-5.28 (m, 2H), 4.43-4.36 (m, 1H), 4.24 (d, 1H), 4.13-4.02 (m, 3H), 3.75-3.62 (m, 7H), 3.51-3.47 (m, 1H), 3.18-3.11 (m, 2H), 2.93-2.83 (m, 2H), 2.75-2.69 (m, 1H), 2.47-2.36 (m, 2H), 2.23-2.09 (m, 3H), 2.01-1.94 (m, 2H), 0.87 (dd, 6H).

Example PR

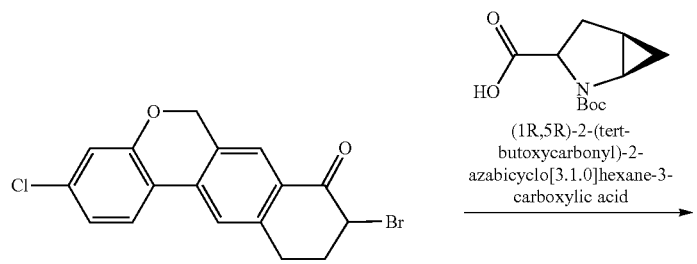

9-bromo-3-chloro-10,11-dihydro-6H-naphtho[2,3-c]chromen-8(9H)-one (1R,5R)-2-(tert-butoxycarbonyl)-2-azabicyclo[3.1.0]hexane-3-carboxylic acid

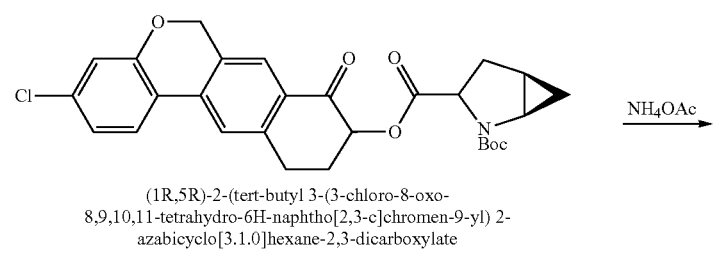

(1R,5R)-2-(tert-butyl 3-(3-chloro-8-oxo-8,9,10,11-tetrahydro-6H-naphtho[2,3-c]chromen-9-yl) 2-azabicyclo[3.1.0]hexane-2,3-dicarboxylate NH₄OAc

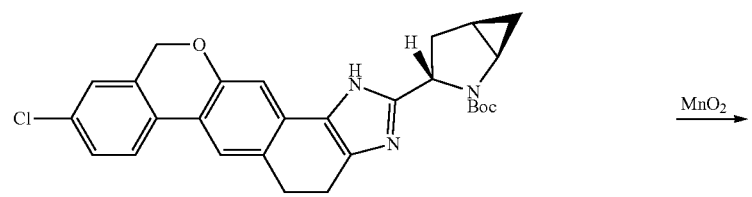

tert-butyl (1R,3S,5R)-3-(9-chloro-1,4,5,11-tetrahydroisochromeno[4',3':6,7]naphtho[1,2-d]imidazol-2-yl)-2-azabicyclo[3.1.0]hexane-2-carboxylate MnO₂

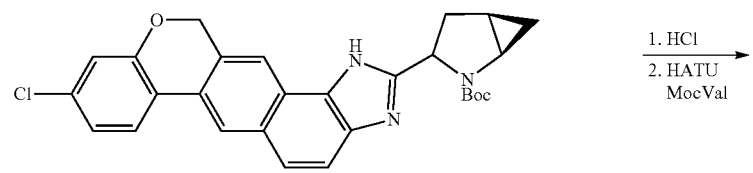

tert-butyl (1R,5R)-3-(9-chloro-1,12-dihydrochromeno[4',3':6,7]naphtho[1,2-d]imidazol-2-yl)-2-azabicyclo[3.1.0]hexane-2-carboxylate 1. HCl
2. HATU MocVal

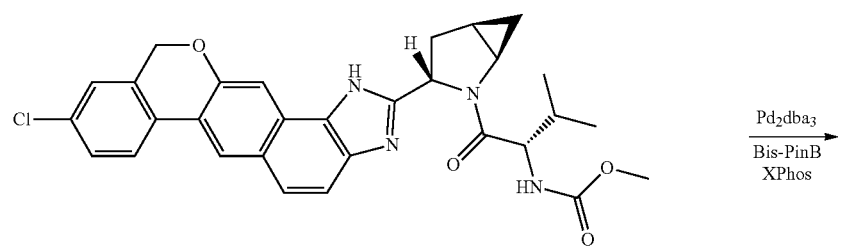

methyl {(2S)-1-[(1R,3S,5R)-3-(9-chloro-1,11-dihydroisochromeno[4',3':6,7]naphtho[1,2-d]imidazol-2-yl)-2-azabicyclo[3.1.0]hex-2-yl]-3-methyl-1-oxobutan-2-yl}carbamate Pd₂dba₃
Bis-PinB
XPhos

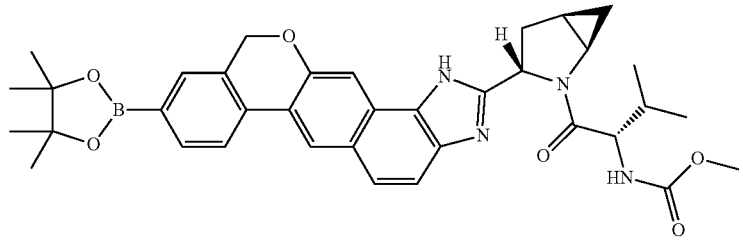

methyl [(2S)-3-methyl-1-oxo-1-{(1R,3S,5R)-3-[9-(4,4,5,5-tetramethyl-1,3,2-dioxaborolan-2-yl)-1,11-dihydroisochromeno[4',3':6,7]naphtho[1,2-d]imidazol-2-yl]-2-azabicyclo[3.1.0]hex-2-yl}butan-2-yl]carbamate

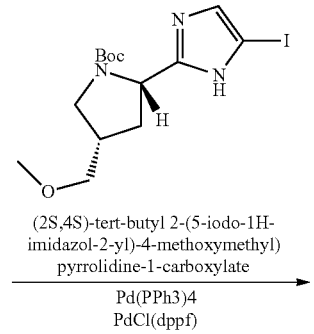

(2S,4S)-tert-butyl 2-(5-iodo-1H-imidazol-2-yl)-4-methoxymethyl)pyrrolidine-1-carboxylate Pd(PPh3)4
PdCl(dppf)

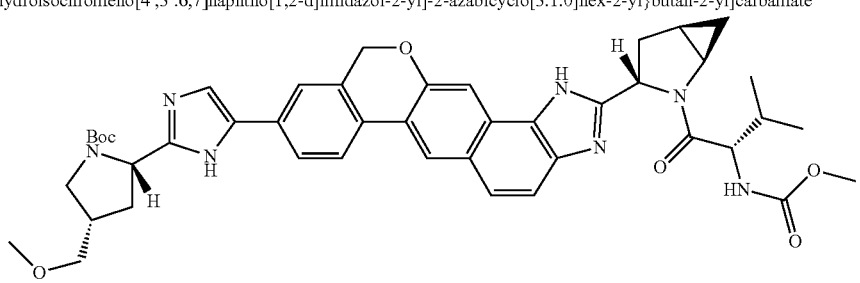

tert-butyl (2S,4S)-2-[5-(2-{(1R,3S,5R)-2-[N-(methoxycarbonyl)-L-valyl]-2-azabicyclo[3.1.0]hex-3-yl)-1,11-dihydroisochromeno[4',3':6,7]naphtho[1,2-d]imidazol-9-yl]-1H-imidazol-2-yl]-4-(methoxymethyl)pyrrolidine-1-carboxylate 1) HCl/dioxane
2) R-MocPhg, COMU
DIPEA, DCM

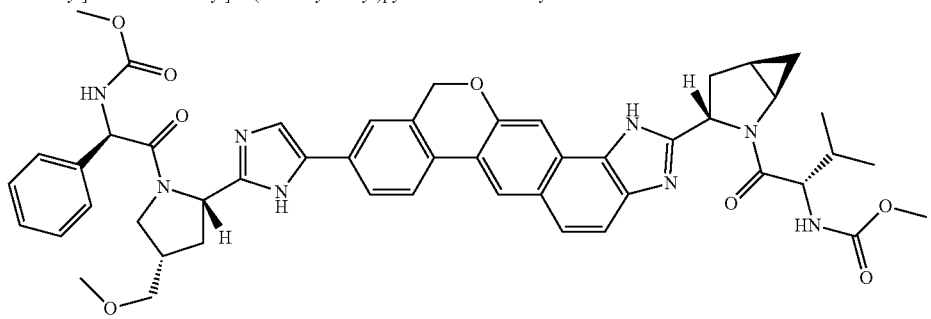

methyl {(1R)-2-[(2S,4S)-2-(5-{2-[(1R,3S,5R)-2-{(2S)-2-[(methoxycarbonyl)amino]-3-methylbutanoyl}-2-azabicyclo[3.1.0]hex-3-yl]-1,11-dihydroisochromeno[4',3':6,7]naphtho[1,2-d]imidazol-9-yl}-1H-imidazol-2-yl)-4-(methoxymethyl)pyrrolidin-1-yl]-2-oxo-1-phenylethyl}carbamate tert-butyl (2S,4S)-2-[5-(2-{(1R,3S,5R)-2-[N-(methoxycarbonyl)-L-valyl]-2-azabicyclo[3.1.0]hex-3-yl}-1,11-dihydroisochromeno[4',3':6,7]naphtho[1,2-d]imidazol-9-yl)-1H-imidazol-2-yl]-4-(methoxymethyl)pyrrolidine-1-carboxylate This compound was made in an analogous manner to tert-butyl (2R)-2-[5-(2-{(2S)-1-[N-(methoxycarbonyl)-L-valyl]pyrrolidin-2-yl}-3,11-dihydroisochromeno[4',3':6,7]naphtho[1,2-d]imidazol-9-yl)-1H-imidazol-2-yl]pyrrolidine-1-carboxylate substituting (1R,5R)-2-(tert-butoxycarbonyl)-2-azabicyclo[3.1.0]hexane-3-carboxylic acid for the initial alkylation of 9-bromo-3-chloro-10,11-dihydro-5H-dibenzo[c,g]chromen-8(9H)-one, and substituting (2S,4S)-tert-butyl 2-(5-iodo-1H-imidazol-2-yl)-4-(methoxymethyl)pyrrolidine-1-carboxylate for the Suzuki-Miyara coupling. Reactions in the synthesis of tert-butyl (2S,4S)-2-[5-(2-{(1R,3S,5R)-2-[N-(methoxycarbonyl)-L-valyl]-2-azabicyclo[3.1.0]hex-3-yl}-1,11-dihydroisochromeno[4',3':6,7]naphtho[1,2-d]imidazol-9-yl)-1H-imidazol-2-yl]-4-(methoxymethyl) pyrrolidine-1-carboxylate gave similar product yields as in the synthesis of tert-butyl (2R)-2-[5-(2-{(2S)-1-[N-(methoxycarbonyl)-L-valyl]pyrrolidin-2-yl}-3,11-dihydroisochromeno[4',3':6,7]naphtho[1,2-d]imidazol-9-yl)-1H-imidazol-2-yl]pyrrolidine-1-carboxylate. MS (ESI) m/z 791.0 [M+H]$^+$.

methyl {(1R)-2-[(2S,4S)-2-(5-{2-[(1R,3S,5R)-2-{(2S)-2-[(methoxycarbonyl)amino]-3-methylbutanoyl}-2-azabicyclo[3.1.0]hex-3-yl]-1,11-dihydroisochromeno[4',3':6,7]naphtho[1,2-d]imidazol-9-yl}-1H-imidazol-2-yl)-4-(methoxymethyl)pyrrolidin-1-yl]-2-oxo-1-phenylethyl}carbamate To a solution of tert-butyl (2S,4S)-2-[5-(2-{(1R,3S,5R)-2-[N-(methoxycarbonyl)-L-valyl]-2-azabicyclo[3.1.0]hex-3-yl}-1,11-dihydroisochromeno[4',3':6,7]naphtho[1,2-d]imidazol-9-yl)-1H-imidazol-2-yl]-4-(methoxymethyl) pyrrolidine-1-carboxylate (0.060 g, 0.076 mmol) in a mixture of $CH_2Cl_2$ (0.76 mL) and MeOH (0.15 mL) was added HCl (4M in 1,4-dioxane, 0.570 mL, 2.28 mmol). The solution was stirred at room temperature for 2 h and concentrated to dryness.

The intermediate was dissolved in CH$_2$Cl$_2$ (0.76 mL). (R)-2-(methoxycarbonylamino)-2-phenylacetic acid (0.024 g, 0.114 mmol) and DIPEA (0.040 mL, 0.228 mmol) were then added to the solution. The reaction mixture was cooled to −40° C. (external temperature, MeCN/CO$_2$(s) bath). COMU (0.052 g, 0.122 mmol) was then added and solution was allowed to warm to 0° C. over 1.5 h. Upon completion by LCMS, the solution was diluted with DMF and concentrated. The crude product was purified by preparative HPLC (Gemini column, 10-45% MeCN/H$_2$O with 0.1% TFA) and lyophilized to provide methyl {(1R)-2-[(2S,4S)-2-(5-{2-[(1R,3S,5R)-2-{(2S)-2-[(methoxycarbonyl)amino]-3-methylbutanoyl}-2-azabicyclo[3.1.0]hex-3-yl]-1,11-dihydroisochromeno[4',3':6,7]naphtho[1,2-d]imidazol-9-yl}-1H-imidazol-2-yl)-4-(methoxymethyl)pyrrolidin-1-yl]-2-oxo-1-phenylethyl}carbamate (0.028 g, 42%). MS (ESI) m/z 881.8 [M+H]$^+$. $^1$H NMR (400 MHz, cd$_3$od) δ 8.45-8.33 (m, 1H), 8.02-7.94 (m, 1H), 7.91-7.75 (m, 2H), 7.72-7.67 (m, 1H), 7.61 (s, 1H), 7.59-7.34 (m, 6H), 7.09-6.91 (m, 2H), 5.62-5.38 (m, 2H), 5.29 (t, 1H), 5.24-5.09 (m, 3H), 4.61 (d, 1H), 4.37-4.26 (m, 1H), 3.83-3.73 (m, 1H), 3.69-3.56 (m, 6H), 3.50-3.40 (m, 1H), 3.20-3.11 (m, 1H), 2.99 (s, 1H), 2.83 (d, 1H), 2.63-2.50 (m, 2H), 2.47-2.34 (m, 2H), 2.29-2.13 (m, 2H), 2.10-1.95 (m, 2H), 1.37-1.23 (m, 3H), 1.19-1.10 (m, 1H), 1.03-0.78 (m, 7H).

Example PS tert-butyl (2S,4S)-2-(9-{2-[(2S,5S)-1-(tert-butoxycarbonyl)-5-methylpyrrolidin-2-yl]-1H-imidazol-5-yl}-1,11-dihydroisochromeno[4',3':6,7]naphtho[1,2-d]imidazol-2-yl)-4-[(difluoromethoxy)methyl]pyrrolidine-1-carboxylate This compound was made in an analogous manner to tert-butyl (2S,4S)-2-[5-(2-{(2S,5S)-1-[N-(methoxycarbonyl)-L-valyl]-5-methylpyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate substituting (2S,5S)-1-(tert-butoxycarbonyl)-5-methylpyrrolidine-2-carboxylic acid for the initial alkylation of 3-(2-bromoacetyl)-10,11-dihydro-5H-dibenzo[c,g]chromen-8(9H)-one, and substituting (2S,4S)-1-(tert-butoxycarbonyl)-4-((difluoromethoxy)methyl)pyrrolidine-2-carboxylic acid for the other alkylation in the sequence. Reactions in the synthesis of tert-butyl (2S,4S)-2-(9-{2-[(2S,5S)-1-(tert-butoxycarbonyl)-5-methylpyrrolidin-2-yl]-1H-imidazol-5-yl}-1,11-dihydroisochromeno[4',3':6,7]naphtho[1,2-d]imidazol-2-yl)-4-[(difluoromethoxy)methyl]pyrrolidine-1-carboxylate gave similar product yields as in the synthesis of tert-butyl (2S,4S)-2-[5-(2-{(2S,5S)-1-[N-(methoxycarbonyl)-L-valyl]-5-methylpyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate. MS (ESI) m/z 772.03 [M+H]$^+$.

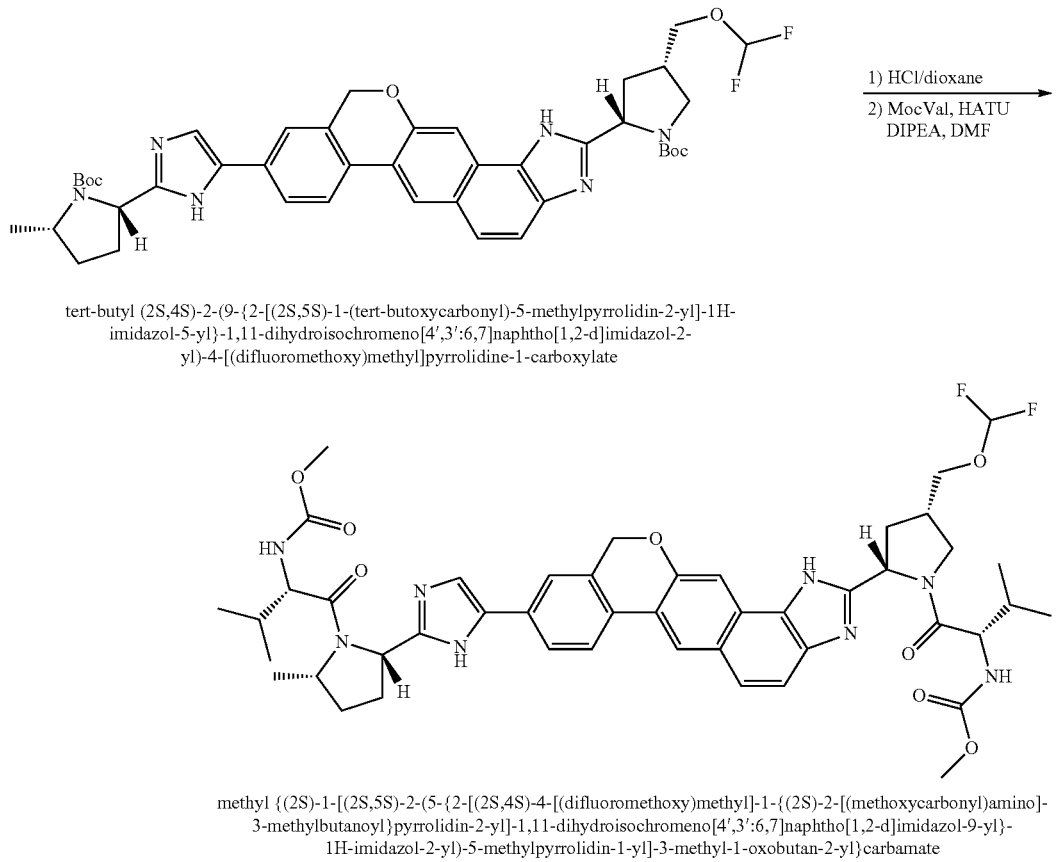

tert-butyl (2S,4S)-2-(9-{2-[(2S,5S)-1-(tert-butoxycarbonyl)-5-methylpyrrolidin-2-yl]-1H-imidazol-5-yl}-1,11-dihydroisochromeno[4',3':6,7]naphtho[1,2-d]imidazol-2-yl)-4-[(difluoromethoxy)methyl]pyrrolidine-1-carboxylate 1) HCl/dioxane
2) MocVal, HATU DIPEA, DMF methyl {(2S)-1-[(2S,5S)-2-(5-{2-[(2S,4S)-4-[(difluoromethoxy)methyl]-1-{(2S)-2-[(methoxycarbonyl)amino]-3-methylbutanoyl}pyrrolidin-2-yl]-1,11-dihydroisochromeno[4',3':6,7]naphtho[1,2-d]imidazol-9-yl}-1H-imidazol-2-yl)-5-methylpyrrolidin-1-yl]-3-methyl-1-oxobutan-2-yl}carbamate methyl {(2S)-1-[(2S,5S)-2-(5-{2-[(2S,4S)-4-[(difluoromethoxy)methyl]-1-{(2S)-2-[(methoxycarbonyl)amino]-3-methylbutanoyl}pyrrolidin-2-yl]-1,11-dihydroisochromeno[4',3':6,7]naphtho[1,2-d]imidazol-9-yl}-1H-imidazol-2-yl)-5-methylpyrrolidin-1-yl]-3-methyl-1-oxobutan-2-yl}carbamate To a solution of tert-butyl (2S,4S)-2-(9-{2-[(2S,5S)-1-(tert-butoxycarbonyl)-5-methylpyrrolidin-2-yl]-1H-imidazol-5-yl}-1,11-dihydroisochromeno[4',3':6,7]naphtho[1,2-d]imidazol-2-yl)-4-[(difluoromethoxy)methyl]pyrrolidine-1-carboxylate (0.081 g, 0.105 mmol) in a mixture of CH$_2$Cl$_2$ (1.05 mL) and MeOH (0.210 mL) was added HCl (4M in 1,4-dioxane, 0.788 mL, 3.15 mmol). The solution was stirred at room temperature for 2 h and concentrated to dryness.

The intermediate was dissolved in CH$_2$Cl$_2$ (1.05 mL). (S)-2-(methoxycarbonylamino)-3-methylbutanoic acid (0.040 g, 0.231 mmol) and DIPEA (0.055 mL, 0.315 mmol) were then added to the solution. HATU (0.176 g, 0.462 μmol) was added and solution was allowed to stir at room temp. Upon completion, the solution was diluted with DMF and concentrated. The crude product was purified by preparative HPLC (Gemini column, 10-45% MeCN/H$_2$O with 0.1% TFA) and the desired fractions were combined. The solution was concentrated until the aqueous layer remained and aqueous bicarbonate (sat.) was slowly added until the solution was basic. The resulting slurry was stirred at room temperature for 2 h and filtered. The resulting solid was dried in vacuo to provide methyl {(2S)-1-[(2S,5S)-2-(5-{2-[(2S,4S)-4-[(difluoromethoxy)methyl]-1-{(2S)-2-[(methoxycarbonyl)amino]-3-methylbutanoyl}pyrrolidin-2-yl]-1,11-dihydroisochromeno[4',3':6,7]naphtho[1,2-d]imidazol-9-yl}-1H-imidazol-2-yl)-5-methylpyrrolidin-1-yl]-3-methyl-1-oxobutan-2-yl}carbamate (0.025 g, 27%). MS (ESI) m/z 886.1 [M+H]$^+$. $^1$H NMR (400 MHz, cd$_3$od) δ 8.49-8.25 (m, 2H), 8.08-7.82 (m, 2H), 7.79-7.27 (m, 5H), 6.45 (t, 1H), 5.36-5.26 (m, 1H), 5.22-5.07 (m, 3H), 4.78-4.49 (m, 2H), 4.45-4.19 (m, 3H), 4.16-4.05 (m, 2H), 3.99-3.92 (m, 1H), 3.85-3.71 (m, 2H), 3.66 (s, 3H), 2.88-2.70 (m, 2H), 2.69-2.49 (m, 2H), 2.42-2.26 (m, 2H), 2.23-2.10 (m, 2H), 2.07-1.87 (m, 3H), 1.51 (d, 2H), 1.34-1.20 (m, 2H), 1.17-0.76 (m, 12H).

Example PT

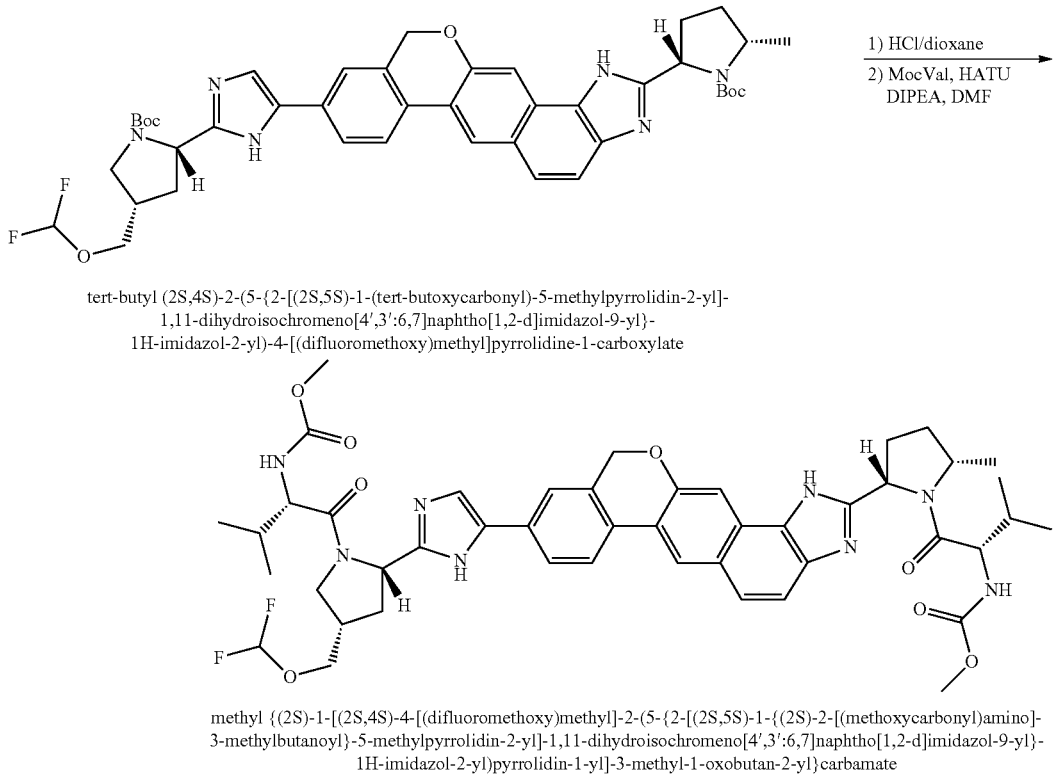

tert-butyl (2S,4S)-2-(5-{2-[(2S,5S)-1-(tert-butoxycarbonyl)-5-methylpyrrolidin-2-yl]-1,11-dihydroisochromeno[4',3':6,7]naphtho[1,2-d]imidazol-9-yl}-1H-imidazol-2-yl)-4-[(difluoromethoxy)methyl]pyrrolidine-1-carboxylate methyl {(2S)-1-[(2S,4S)-4-[(difluoromethoxy)methyl]-2-(5-{2-[(2S,5S)-1-{(2S)-2-[(methoxycarbonyl)amino]-3-methylbutanoyl}-5-methylpyrrolidin-2-yl]-1,11-dihydroisochromeno[4',3':6,7]naphtho[1,2-d]imidazol-9-yl}-1H-imidazol-2-yl)pyrrolidin-1-yl]-3-methyl-1-oxobutan-2-yl}carbamate methyl {(2S)-1-[(2S,4S)-4-[(difluoromethoxy)methyl]-2-(5-{2-[(2S,5S)-1-{(2S)-2-[(methoxycarbonyl)amino]-3-methylbutanoyl}-5-methylpyrrolidin-2-yl]-1,11-dihydroisochromeno[4',3':6,7]naphtho[1,2-d]imidazol-9-yl}-1H-imidazol-2-yl)pyrrolidin-1-yl]-3-methyl-1-oxobutan-2-yl}carbamate This compound was made in an analogous manner to tert-butyl (2S,4S)-2-[5-(2-{(2S,5S)-1-[N-(methoxycarbonyl)-L-valyl]-5-methylpyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate substituting (2S,4S)-1-(tert-butoxycarbonyl)-4-((difluoromethoxy)methyl)pyrrolidine-2-carboxylic acid for the initial alkylation of 3-(2-bromoacetyl)-10,11-dihydro-5H-dibenzo[c,g]chromen-8(9H)-one, and substituting (2S,5S)-1-(tert-butoxycarbonyl)-5-methylpyrrolidine-2-carboxylic acid for the other alkylation in the sequence. Reactions in the synthesis of tert-butyl (2S,4S)-2-(5-{2-[(2S,5S)-1-(tert-butoxycarbonyl)-5-methylpyrrolidin-2-yl]-1,11-dihydroisochromeno[4',3':6,7]naphtho[1,2-d]imidazol-9-yl}-1H-imidazol-2-yl)-4-[(difluoromethoxy)methyl]pyrrolidine-1-carboxylate gave similar product yields as in the synthesis of tert-butyl (2S, 4S)-2-[5-(2-{(2S,5S)-1-[N-(methoxycarbonyl)-L-valyl]-5-methylpyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate. MS (ESI) m/z 772.31 [M+H].

methyl {(2S)-1-[(2S,4S)-4-[(difluoromethoxy)methyl]-2-(5-{2-[(2S,5S)-1-{(2S)-2-[(methoxycarbonyl)amino]-3-methylbutanoyl}-5-methylpyrrolidin-2-yl]-1,11-dihydroisochromeno[4',3':6,7]naphtho[1,2-d]imidazol-9-yl}-1H-imidazol-2-yl)pyrrolidin-1-yl]-3-methyl-1-oxobutan-2-yl}carbamate To tert-butyl (2S,4S)-2-(5-{2-[(2S,5S)-1-(tert-butoxycarbonyl)-5-methylpyrrolidin-2-yl]-1,11-dihydroisochromeno[4',3':6,7]naphtho[1,2-d]imidazol-9-yl}-1H-imidazol-2-yl)-4-[(difluoromethoxy)methyl]pyrrolidine-1-carboxylate (0.057 g, 0.074 mmol) in a mixture of CH$_2$Cl$_2$ (0.739 mL) and HPLC (Gemini column, 10-46% MeCN/H$_2$O with 0.1% TFA) and the desired fractions were combined and lyophilized to provide methyl {(2S)-1-[(2S,4S)-4-[(difluoromethoxy)methyl]-2-(5-{2-[(2S,5S)-1-{(2S)-2-[(methoxycarbonyl)amino]-3-methylbutanoyl}-5-methylpyrrolidin-2-yl]-1,11-dihydroisochromeno[4',3':6,7]naphtho[1,2-d]imidazol-9-yl}-1H-imidazol-2-yl)pyrrolidin-1-yl]-3-methyl-1-oxobutan-2-yl}carbamate (0.011 g, 17%). MS (ESI) m/z 886.1 [M+H]$^{1}$. $^1$H NMR (400 MHz, cd$_3$od) δ 8.67-8.51 (m, 1H), 8.26-8.11 (m, 1H), 8.04-7.75 (m, 3H), 7.69-7.58 (m, 2H), 6.43 (t, 1H), 5.41-5.15 (m, 4H), 4.48-3.90 (m, 6H), 3.82 (s, 1H), 3.71-3.57 (m, 5H), 3.53-3.43 (m, 1H), 3.20-3.01 (m, 2H), 2.92-2.63 (m, 3H), 2.60-2.25 (m, 4H), 2.15-1.86 (m, 4H), 1.57 (d, 3H), 1.24 (d, 2H), 1.07 (dd, 2H), 0.98-0.77 (m, 9H).

Example PU

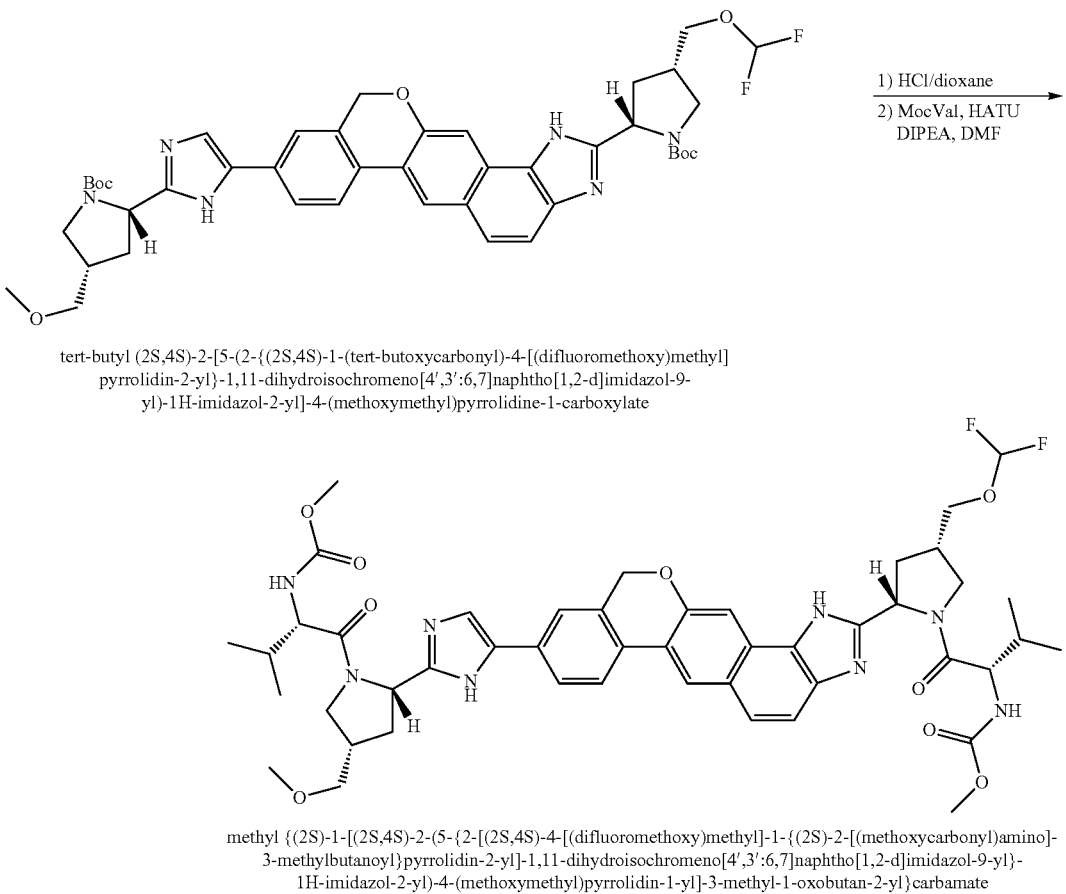

tert-butyl (2S,4S)-2-[5-(2-{(2S,4S)-1-(tert-butoxycarbonyl)-4-[(difluoromethoxy)methyl]pyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate methyl {(2S)-1-[(2S,4S)-2-(5-{2-[(2S,4S)-4-[(difluoromethoxy)methyl]-1-{(2S)-2-[(methoxycarbonyl)amino]-3-methylbutanoyl}pyrrolidin-2-yl]-1,11-dihydroisochromeno[4',3':6,7]naphtho[1,2-d]imidazol-9-yl}-1H-imidazol-2-yl)-4-(methoxymethyl)pyrrolidin-1-yl]-3-methyl-1-oxobutan-2-yl}carbamate MeOH (0.148 mL) was added HCl (4M in 1,4-dioxane, 0.555 mL, 2.218 mmol). The solution was stirred at room temperature for 2 h and concentrated to dryness.

The intermediate was dissolved in CH$_2$Cl$_2$ (0.739 mL). (S)-2-(methoxycarbonylamino)-3-methylbutanoic acid (0.028 g, 0.163 mmol) and DIPEA (0.039 mL, 0.222 mmol) were then added to the solution. HATU (0.124 g, 0.325 mmol) was added and solution was allowed to stir at room temp. Upon completion, the solution was diluted with DMF and concentrated. The crude product was purified by preparative tert-butyl (2S,4S)-2-[5-(2-{(2S,4S)-1-(tert-butoxycarbonyl)-4-[(difluoromethoxy)methyl]pyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate This compound was made in an analogous manner to tert-butyl (2S,4S)-2-[5-(2-{(2S,5S)-1-[N-(methoxycarbonyl)-L-valyl]-5-methylpyrrolidin-2-yl}-1,11-dihydroisochromeno[4',3':6,7]naphtho[1,2-d]imidazol-9-yl)-1H-imidazol-2-yl]-

4-(methoxymethyl)pyrrolidine-1-carboxylate substituting (2S,4S)-1-(tert-butoxycarbonyl)-4-(methoxymethyl)pyrrolidine-2-carboxylic acid for the initial alkylation of 3-(2-bromoacetyl)-10,11-dihydro-5H-dibenzo[c,g]chromen-8(9H)-one, and substituting (2S,4S)-1-(tert-butoxycarbonyl)-4-((difluoromethoxy)methyl)pyrrolidine-2-carboxylic acid for the other alkylation in the sequence. Reactions in the synthesis of tert-butyl (2S,4S)-2-[5-(2-(2S,4S)-1-(tert-butoxycarbonyl)-4-[(difluoromethoxy)methyl]pyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate gave similar product yields as in the synthesis of tert-butyl (2S,4S)-2-[5-(2-{(2S,5S)-1-[N-(methoxycarbonyl)-L-valyl]-5-methylpyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate. MS (ESI) m/z 801.1 [M+H]⁺.

methyl {(2S)-1-[(2S,4S)-2-(5-{2-[(2S,4S)-4-[(difluoromethoxy)methyl]-1-{(2S)-2-[(methoxycarbonyl)amino]-3-methylbutanoyl}pyrrolidin-2-yl]-1,11-dihydroisochromeno[4',3':6,7]naphtho[1,2-d]imidazol-9-yl}-1H-imidazol-2-yl)-4-(methoxymethyl)pyrrolidin-1-yl]-3-methyl-1-oxobutan-2-yl}carbamate To tert-butyl (2S,4S)-2-[5-(2-{(2S,4S)-1-(tert-butoxycarbonyl)-4-[(difluoromethoxy)methyl]pyrrolidin-2-yl}-1,11 dihydroisochromeno[4',3':6,7]naphtho[1,2-d]imidazol-9-yl)-1H-imidazol-2-yl]-4-(methoxymethyl)pyrrolidine-1-carboxylate (0.092 g, 0.115 mmol) in a mixture of $CH_2Cl_2$ (1.15 mL) and MeOH (0.230 mL) was added HCl (4M in 1,4-dioxane, 0.862 mL, 3.446 mmol). The solution was stirred at room temperature for 2 h and concentrated to dryness.

The intermediate was dissolved in $CH_2Cl_2$ (1.149 mL). (S)-2-(methoxycarbonylamino)-3-methylbutanoic acid (0.044g, 0.253 mmol) and DIPEA (0.060 mL, 0.345 mmol) were then added to the solution. HATU (0.192 g, 0.505 mmol) was added and solution was allowed to stir at room temp. Upon completion, the solution was diluted with DMF and concentrated. The crude product was purified by preparative HPLC (Gemini column, 10-45% MeCN/$H_2O$ with 0.1% TFA) and the desired fractions were combined. The solution was concentrated until the aqueous layer remained and aqueous bicarbonate (sat.) was slowly added until the solution was basic. The resulting slurry was stirred at room temperature for 2 h and filtered. The resulting solid was dried in vacuo to provide methyl {(2S)-1-[(2S,4S)-2-(5-{2-[(2S,4S)-4-[(difluoromethoxy)methyl]-1-{(2S)-2-[(methoxycarbonyl)amino]-3-methylbutanoyl}pyrrolidin-2-yl]-1,11-dihydroisochromeno[4',3':6,7]naphtho[1,2-d]imidazol-9-yl}-1H-imidazol-2-yl)-4-(methoxymethyl)pyrrolidin-1-yl]-3-methyl-1-oxobutan-2-yl}carbamate (0.042 g, 40%). MS (ESI) m/z 916.30 [M+H]⁺. ¹H NMR (400 MHz, cd₃od) δ 8.55-8.25 (m, 1H), 8.15-7.85 (m, 2H), 7.83-7.26 (m, 5H), 6.44 (t, 1H), 5.37-5.02 (m, 4H), 4.47-4.35 (m, 1H), 4.33-4.18 (m, 3H), 4.15-3.90 (m, 3H), 3.81-3.45 (m, 11H), 3.39 (s, 3H), 2.90-2.27 (m, 5H), 2.22-1.92 (m, 4H), 1.12-0.73 (m, 13H).

Example PX

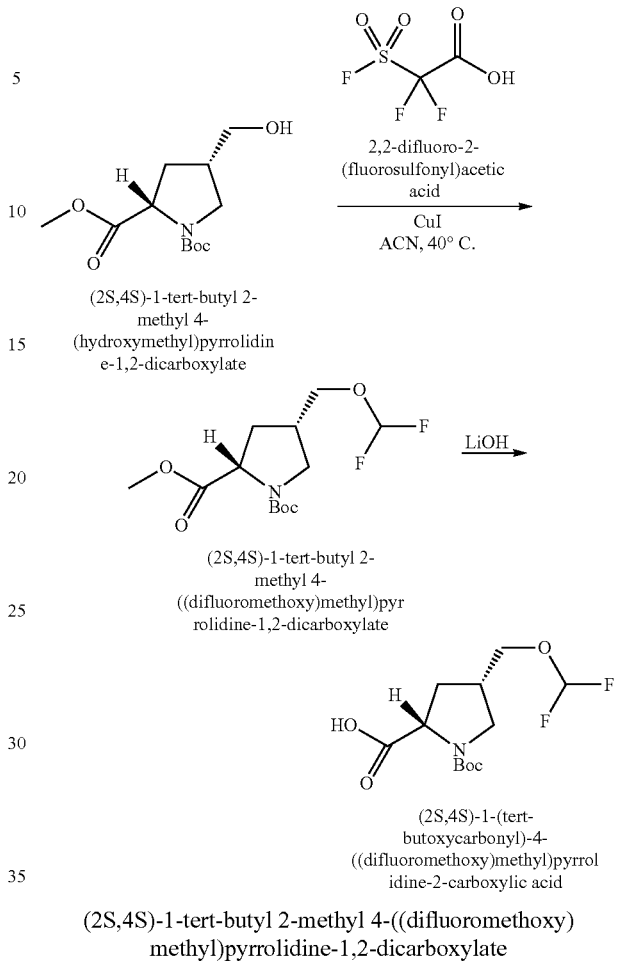

(2S,4S)-1-tert-butyl 2-methyl 4-(hydroxymethyl)pyrrolidine-1,2-dicarboxylate (2S,4S)-1-tert-butyl 2-methyl 4-((difluoromethoxy)methyl)pyrrolidine-1,2-dicarboxylate (2S,4S)-1-(tert-butoxycarbonyl)-4-((difluoromethoxy)methyl)pyrrolidine-2-carboxylic acid (2S,4S)-1-tert-butyl 2-methyl 4-((difluoromethoxy)methyl)pyrrolidine-1,2-dicarboxylate A 100 mL round-bottom flask was charged with (2S,4S)-1-tert-butyl 2-methyl 4-(hydroxymethyl)pyrrolidine-1,2-dicarboxylate (3.33 g, 12.84 mmol), CuI (0.489 g, 2.56 mmol), and anhydrous acetonitrile (57.1 mL). The reaction was heated to 45° C. (ext. oil bath). 2,2-difluoro-2-(fluorosulfonyl)acetic acid (2.655 mL, 25.68 mmol) was added at 45° C. over 30 minutes via syringe pump. The reaction was heated for 30 minutes. Upon completion as monitored by TLC, the reaction mixture was cooled to room temperature and concentrated in vacuo. The crude residue was diluted in EtOAc and washed with sodium bicarbonate (aq). The bicarbonate layer was back extracted with ethyl acetate twice. Combined organic layers were washed with brine, dried over sodium sulphate, filtered and concentrated. The resulting residue was further purified via silica gel chromatography (10 to 40% EtOAc/Hexanes) to afford (2S,4S)-1-tert-butyl 2-methyl 4-((difluoromethoxy)methyl)pyrrolidine-1,2-dicarboxylate (2.41 g, 61%). MS (ESI) m/z 210.21 [M+H–Boc]⁺.

(2S,4S)-1-(tert-butoxycarbonyl)-4-((difluoromethoxy)methyl)pyrrolidine-2-carboxylic acid To a solution of (2S,4S)-1-tert-butyl 2-methyl 4-((difluoromethoxy)methyl)pyrrolidine-1,2-dicarboxylate (2.41 g, 7.79 mmol) in a mixture of THF (39 mL) and MeOH (15.6 mL) was added LiOH (2.5 M aqueous, 15.6 mL, 38.9 mmol). The resulting solution was stirred at room temperature for 1 h. Upon completion by TLC the reaction mixture was acidified with aqueous HCl (1N). The desired product was extracted with CH$_2$Cl$_2$ (3×). The combined organic layers were dried over Na$_2$SO$_4$ and concentrated to provide (2S,4S)-1-(tert-butoxycarbonyl)-4-((difluoromethoxy)methyl)pyrrolidine-2-carboxylic acid (2.4 g, 99%). MS (ESI) m/z 294.96 [M–H]$^-$. $^1$H-NMR: 400 MHz, (acetone-d$_6$) δ (mixture of rotamers): 6.50 (t, 1H), 4.36-4.17 (m, 1H), 3.93 (d, 2H), 3.77-3.67 (m, 1H), 3.63-3.59 (m, 1H), 3.26-3.12 (m, 1H), 2.72-2.41 (m, 2H), 1.89-1.73 (m, 2H), 1.41 (s, 9H).

Example PY

HPLC. After lyophilization, the TFA salt was dissolved in EtOAc and washed with saturated NaHCO$_3$. The organic phase was dried over Na$_2$SO$_4$ and concentrated. The free base was then dissolved in MeCN/H$_2$O and lyophilized to afford methyl {(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate (65 mg, 39%). LCMS-ESI$^+$: calculated for C$_{49}$H$_{54}$N$_8$O$_8$: 882.4; observed [M+1]$^+$: 884.1. Diagnostic

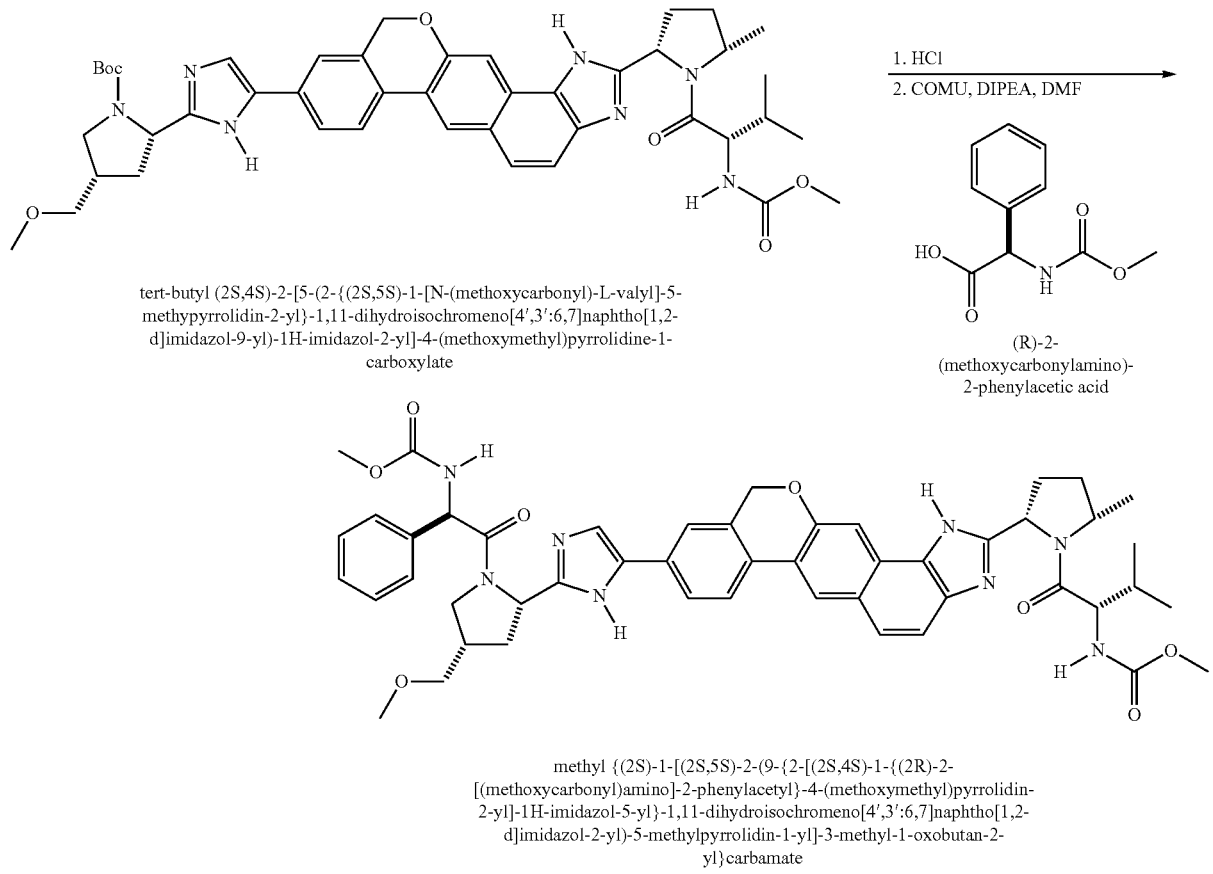

tert-butyl (2S,4S)-2-[5-(2-{(2S,5S)-1-[N-(methoxycarbonyl)-L-valyl]-5-methypyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate (R)-2-(methoxycarbonylamino)-2-phenylacetic acid methyl {(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate Methyl {(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate A solution of tert-butyl (2S,4S)-2-[5-(2-{(2S,5S)-1-[N-(methoxycarbonyl)-L-valyl]-5-methylpyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate (150 mg, 0.19 mmol) in 1.25 N HCl in EtOH (3 mL) was stirred overnight then heated to 50° C. for 3 h. The reaction was concentrated and the crude material dissolved in DMF (2 mL). To this solution was added a solution of (R)-2-(methoxycarbonylamino)-2-phenylacetic acid (52 mg, 0.25 mmol) and COMU (90 mg, 0.21 mmol). To the resulting solution was added diisopropylethylamine (0.099 mL, 0.57 mmol). After stirring for 2 h at room temperature, the reaction was quenched with 1N HCl (0.200 mL) and purified by peaks in NMR $^1$HNMR (CD$_3$OD): 8.28 (s, 1H), 8.21 (s, 1H), 8.04 (s, 1H), 7.91-7.01 (m, 10H), 3.62 (s, 3H), 3.34 (s, 3H), 3.23 (s, 3H), 1.56 (d, 3H), 1.03 (d, 3H), 0.94 (d, 3H).

Example PY-1

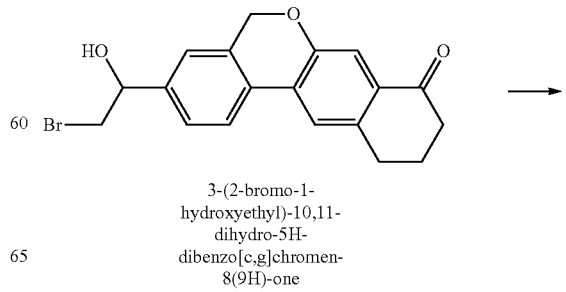

3-(2-bromo-1-hydroxyethyl)-10,11-dihydro-5H-dibenzo[c,g]chromen-8(9H)-one

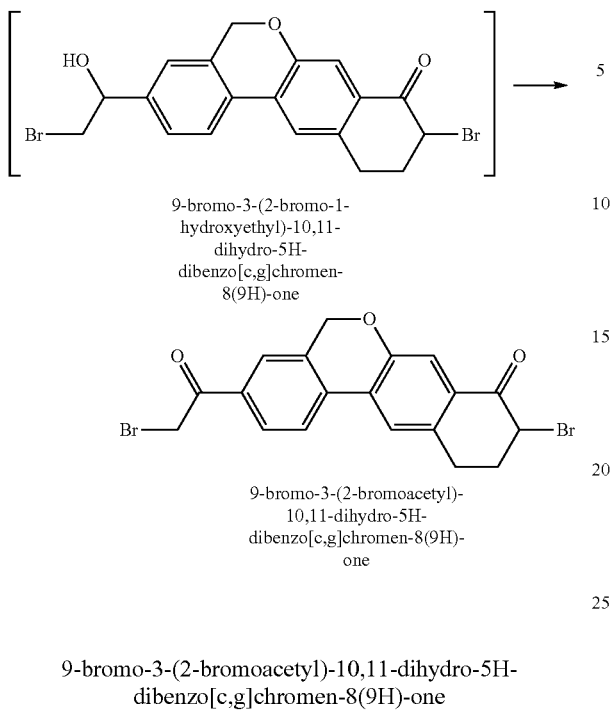

9-bromo-3-(2-bromo-1-hydroxyethyl)-10,11-dihydro-5H-dibenzo[c,g]chromen-8(9H)-one 9-bromo-3-(2-bromoacetyl)-10,11-dihydro-5H-dibenzo[c,g]chromen-8(9H)-one 9-bromo-3-(2-bromoacetyl)-10,11-dihydro-5H-dibenzo[c,g]chromen-8(9H)-one To 3-(2-bromo-1-hydroxyethyl)-10,11-dihydro-5H-dibenzo[c,g]chromen-8(9H)-one (20.3 g, 54.4 mmol) in DCM (365 mL) was added MeOH (22 mL) and pyridinium tribromide (18.24 g, 57.0 mmol). After 2h, water was added (100 mL) and after briefly agitating the layers split and the bottom organic layer was collected. The organic layer was then washed with 1M HCl (100 mL) and the bottom organic layer containing 9-bromo-3-(2-bromo-1-hydroxyethyl)-10,11-dihydro-5H-dibenzo[c,g]chromen-8(9H)-one was collected. 400 MHz $^1$H NMR (CDCl$_3$) 7.75 (d, J=8.1 Hz, 1H), 7.68 (s, 1H), 7.61 (s, 1H), 7.42 (d, J=7.5 Hz, 1H), 7.24 (s, 1H), 5.13 (s, 2H), 4.99-4.96 (m, 1H), 4.73 (dd, J=4.1, 4.1 Hz, 1H), 3.69-3.66 (m, 1H), 3.58-3.53 (m, 1H), 3.35-3.27 (m, 1H), 2.96-2.90 (m, 1H), 2.58-2.44 (m, 2H), C—OH not observed.

To 9-bromo-3-(2-bromo-1-hydroxyethyl)-10,11-dihydro-5H-dibenzo[c,g]chromen-8(9H)-one (approx. 54.4 mmol) in DCM (365 mL) was added sodium bicarbonate (5.45 g), sodium bromide (6.14 g), TEMPO (16.55 mg) and water (60 mL). The solution was cooled between 0-5° C. and 6% bleach (91.5 mL) was added. After 1 h isopropyl alcohol (20 mL) was added and the reaction mixture was warmed to room temperature. Agitation was stopped, the layers separated and the lower organic layer was collected and concentrated removing approximately 345g of solvent. The slurry was filtered and the cake washed with 50 mL water and then 50 mL DCM (precooled to 5° C.). The solids were collected and dried under vacuum to obtain 9-bromo-3-(2-bromoacetyl)-10,11-dihydro-5H-dibenzo[c,g]chromen-8(9H)-one (18.6 g, 76% yield). 400 MHz $^1$H NMR (CDCl$_3$) δ 8.03-8.01 (m, 1H), 7.85 (d, J=8.2 Hz, 1H), 7.82 (s, 1H), 7.71 (s, 1H), 7.67 (s, 1H), 5.19 (s, 2H), 4.74 (dd, J=4.1, 4.1 Hz, 1H), 4.45 (s, 2H), 3.37-3.29 (m, 1H), 2.99-2.92 (m, 1H), 2.59-2.46 (m, 2H); 100 MHz $^{13}$C NMR (CDCl$_3$) δ 190.4, 189.6, 154.2, 136.6, 134.1, 133.9, 132.9, 131.8, 129.3, 127.2, 125.6, 124.2, 123.3, 117.0, 68.1, 49.9, 31.8, 30.4, 25.5.

Example PY-2

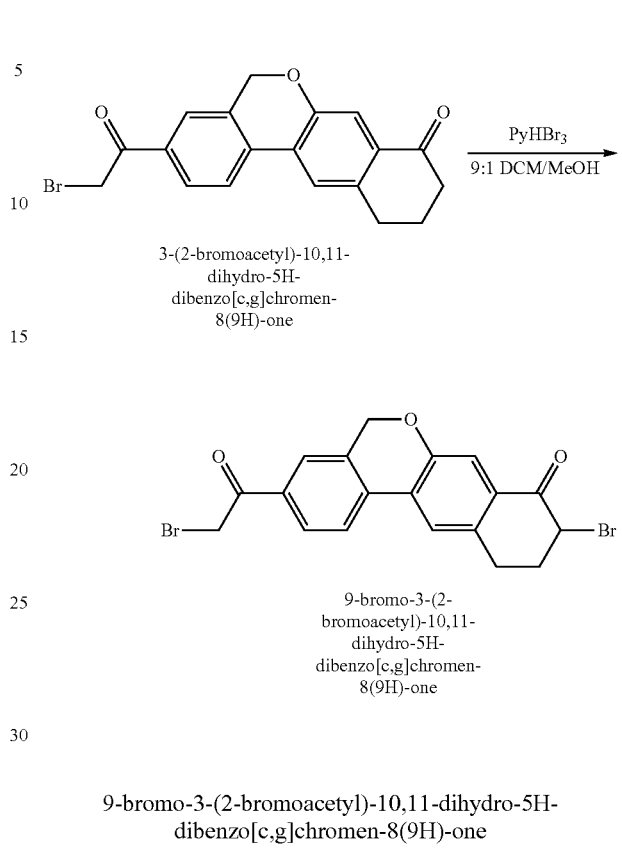

3-(2-bromoacetyl)-10,11-dihydro-5H-dibenzo[c,g]chromen-8(9H)-one 9-bromo-3-(2-bromoacetyl)-10,11-dihydro-5H-dibenzo[c,g]chromen-8(9H)-one 9-bromo-3-(2-bromoacetyl)-10,11-dihydro-5H-dibenzo[c,g]chromen-8(9H)-one A mixture of 3-(2-bromoacetyl)-10,11-dihydro-5H-dibenzo[c,g]chromen-8(9H)-one (2.58 g, 6.95 mmol), pyridinium tribromide (2.56 g, 8.0 mmol), dichloromethane (22 mL) and methanol (2.5 mL) was stirred at about 20° C. for 3 hours to obtain a slurry. The precipitated product was filtered, washed with dichloromethane (10 mL) and dried in a vacuum oven at 40° C. to give 9-bromo-3-(2-bromoacetyl)-10,11-dihydro-5H-dibenzo[c,g]chromen-8(9H)-one (2.62 g, 84% yield). 400 MHz $^1$H NMR (CDCl$_3$) δ 8.03-8.01 (m, 1H), 7.85 (d, J=8.2 Hz, 1H), 7.82 (s, 1H), 7.71 (s, 1H), 7.67 (s, 1H), 5.19 (s, 2H), 4.74 (dd, J=4.1, 4.1 Hz, 1H), 4.45 (s, 2H), 3.37-3.29 (m, 1H), 2.99-2.92 (m, 1H), 2.59-2.46 (m, 2H).

Example PY-3

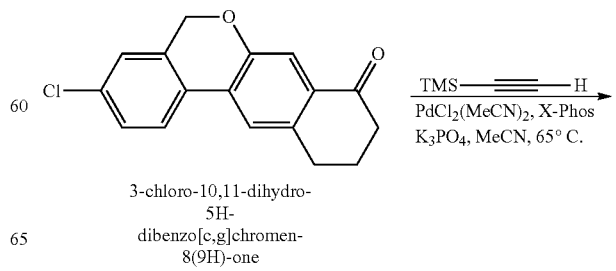

3-chloro-10,11-dihydro-5H-dibenzo[c,g]chromen-8(9H)-one

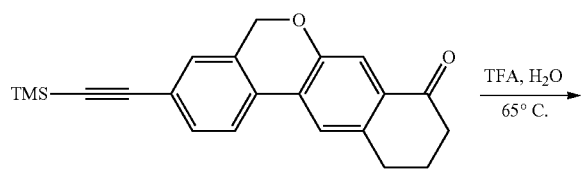

3-((trimethylsilyl)ethynyl)-
10,11-dihydro-5H-
dibenzo[c,g]chromen-8(9H)-
one

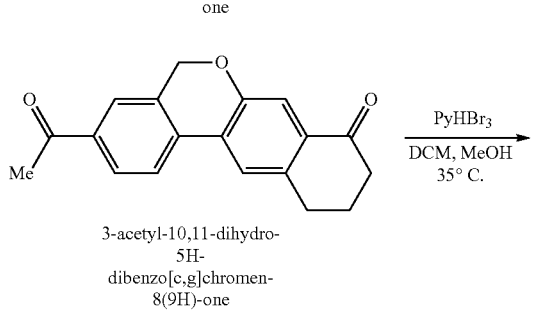

3-acetyl-10,11-dihydro-
5H-
dibenzo[c,g]chromen-
8(9H)-one

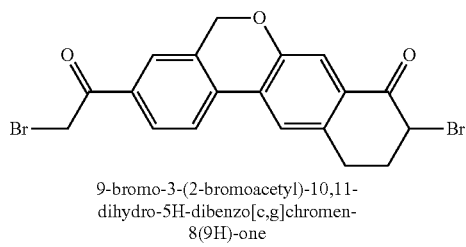

9-bromo-3-(2-bromoacetyl)-10,11-
dihydro-5H-dibenzo[c,g]chromen-
8(9H)-one

3-((trimethylsilyl)ethynyl)-10,11-dihydro-5H-dibenzo[c,g]chromen-8(9H)-one

A 300 mL flask equipped with an overhead stirrer and a reflux condenser under an atmosphere of nitrogen was charged with 3-chloro-10,11-dihydro-5H-dibenzo[c,g]chromen-8(9H)-one (10.0 g, 35.12 mmol), powdered anhydrous tripotassium phosphate (22.4 g, 105.4 mmol), XPhos (1.34 g, 2.81 mmol), and PdCl$_2$(MeCN)$_2$ (364 mg, 1.40 mmol). Acetonitrile (140 mL) was added followed by TMSacetylene (18 mL, 141 mmol). The mixture was heated to 65° C. After 6h, the reaction was judged complete, and the mixture was cooled to 20° C. The mixture was filtered through a fritted funnel, and the filtercake was washed with acetonitrile. The filtrate was concentrated to about 150 mL under reduced pressure and extracted with heptane (50 mL, 3×100 mL). N-Acetyl cysteine (15g) was added to the acetonitrile phase, and the mixture was agitated for 5 h at 45° C. The mixture was cooled to ambient temperature, filtered through a fritted funnel, and the filtercake was washed with acetonitrile. The filtrate was concentrated to about 120 mL under reduced pressure. Water (120 mL) was added and the mixture was agitated for 40 minutes at 45° C. and then cooled to ambient temperature. After 30 minutes the mixture was filtered through a fritted funnel to provide 3-((trimethylsilyl)ethynyl)-10,11-dihydro-5H-dibenzo[c,g]chromen-8(9H)-one (4.07 g, 33.4% yield) as a yellow solid: 400 MHz $^1$H NMR (CDCl$_3$) δ 7.65 (d, J=8.1 Hz, 1H), 7.60 (s, 1H), 7.55 (s, 1H), 7.47 (dd, J=8.1, 1.4 Hz, 1H), 7.27 (s, 1H), 5.06 (s, 2H), 2.95 (t, J=6.1 Hz, 2H), 2.67-2.59 (m, 2H), 2.18-2.08 (m, 2H), 0.26 (s, 9H).

3-acetyl-10,11-dihydro-5H-dibenzo[c,g]chromen-8(9H)-one

A 20 mL vial with stir bar was charged with 3-((trimethylsilyl)ethynyl)-10,11-dihydro-5H-dibenzo[c,g]chromen-8(9H)-one (850 mg, 2.44 mmol) and TFA (9.8 mL). The solution was heated to 65° C. After 3 h, the reaction was judged complete. The mixture was concentrated under reduced pressure; the resulting residue was taken up in CH$_2$Cl$_2$ and loaded onto a prepacked 25g silica gel cartridge. The product was purified by chromatography on a prepacked 80g silica gel column eluting with a solvent gradient from 5% to 85% EtOAc/hexanes. The product containing fractions were combined and concentrated to provide 3-acetyl-10,11-dihydro-5H-dibenzo[c,g]chromen-8(9H)-one (616 mg, 86%): 400 MHz $^1$H NMR (CDCl$_3$) δ 8.00-7.94 (m, 1H), 7.81 (d, J=8.2 Hz, 1H), 7.77 (s, 1H), 7.64 (s, 2H), 5.16 (s, 2H), 2.98 (t, J=6.1 Hz, 2H), 2.69-2.64 (m, 2H), 2.63 (s, 3H), 2.21-2.09 (m, 2H).

9-bromo-3-(2-bromoacetyl)-10,11-dihydro-5H-dibenzo[c,g]chromen-8(9H)-one

A 20 mL vial with a stir bar was charged with 3-acetyl-10,11-dihydro-5H-dibenzo[c,g]chromen-8(9H)-one (100 mg, 0.366 mmol), 9:1 CH$_2$Cl$_2$/MeOH (3.4 mL) and pyridinium tribromide (246 mg, 0.769 mmol). The solution was heated to 35° C. After 30 minutes, the reaction was judged complete. The mixture was cooled to ambient temperature, diluted with EtOAc (50 mL) and sequentially washed with saturated aqueous Na$_2$S$_2$O$_3$ (20 mL), 2% aqueous NaHCO$_3$ (20 mL), water (20 mL), and brine (10 mL). The organic phase was dried over MgSO$_4$, filtered and concentrated under reduced pressure resulting in 9-bromo-3-(2-bromoacetyl)-10,11-dihydro-5H-dibenzo[c,g]chromen-8(9H)-one (68 mg, 41%): 400 MHz $^1$H NMR (CDCl$_3$) δ 8.03-8.01 (m, 1H), 7.85 (d, J=8.2 Hz, 1H), 7.82 (s, 1H), 7.71 (s, 1H), 7.67 (s, 1H), 5.19 (s, 2H), 4.74 (dd, J=4.1, 4.1 Hz, 1H), 4.45 (s, 2H), 3.37-3.29 (m, 1H), 2.99-2.92 (m, 1H), 2.59-2.46 (m, 2H).

Example PY-4

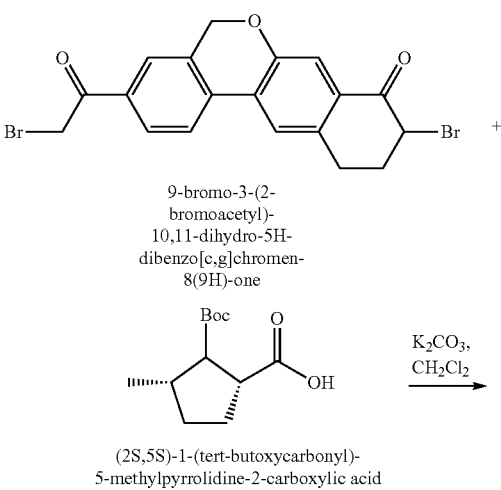

9-bromo-3-(2-
bromoacetyl)-
10,11-dihydro-5H-
dibenzo[c,g]chromen-
8(9H)-one (2S,5S)-1-(tert-butoxycarbonyl)-
5-methylpyrrolidine-2-carboxylic acid

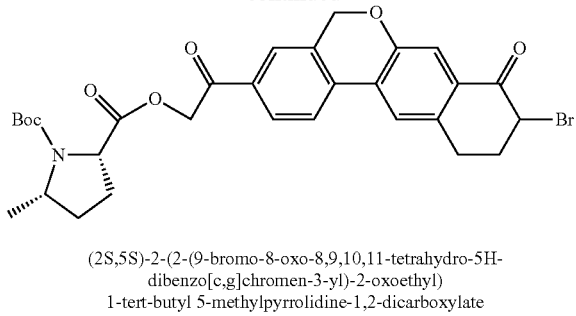

(2S,5S)-2-(2-(9-bromo-8-oxo-8,9,10,11-tetrahydro-5H-dibenzo[c,g]chromen-3-yl)-2-oxoethyl) 1-tert-butyl 5-methylpyrrolidine-1,2-dicarboxylate

(2S,5S)-2-(2-(9-bromo-8-oxo-8,9,10,11-tetrahydro-5H-dibenzo[c,g]chromen-3-yl)-2-oxoethyl) 1-tert-butyl 5-methylpyrrolidine-1,2-dicarboxylate 9-bromo-3-(2-bromoacetyl)-10,11-dihydro-5H-dibenzo[c,g]chromen-8(9H)-one (1.43 g, 3.17 mmol) was treated with a solution of (2S,5S)-1-(tert-butoxycarbonyl)-5-methylpyrrolidine-2-carboxylic acid (800 mg, 3.49 mmol) in dichloromethane (14 mL) and K$_2$CO$_3$ (658 mg, 1.18 mmol). The stirred reaction mixture was stirred at RT and diluted with CH$_2$Cl$_2$ and extracted 3×. The organic phase was washed with brine, then dried over MgSO$_4$, filtered and concentrated under reduced pressure to afford ((2S,5S)-2-(2-(9-bromo-8-oxo-8,9,10,11-tetrahydro-5H-dibenzo[c,g]chromen-3-yl)-2-oxoethyl) 1-tert-butyl 5-methylpyrrolidine-1,2-dicarboxylate (1.61 g, 84%).

This synthesis may be used to make a variety of compounds described herein, including the compound exemplified in PY.

Example PZ

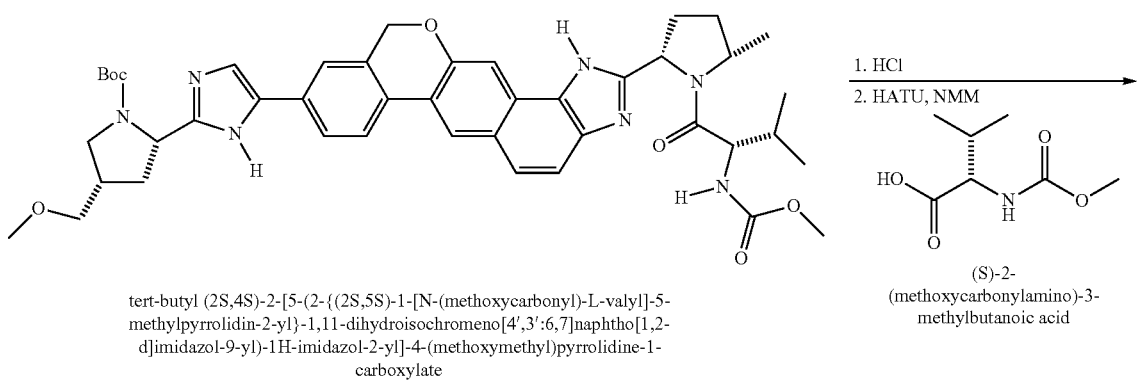

tert-butyl (2S,4S)-2-[5-(2-{(2S,5S)-1-[N-(methoxycarbonyl)-L-valyl]-5-methylpyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate (S)-2-(methoxycarbonylamino)-3-methylbutanoic acid

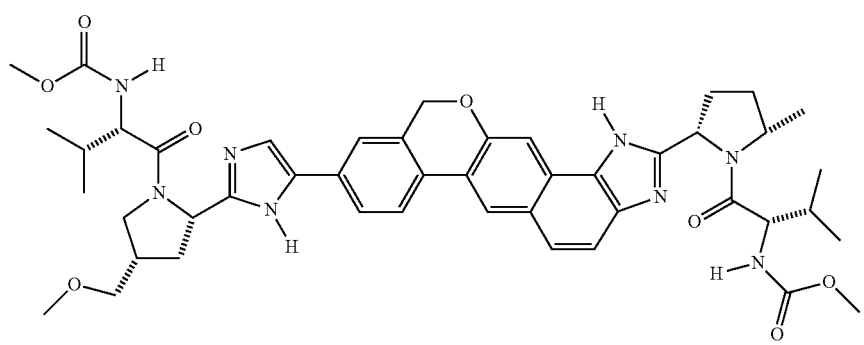

methyl {(2S)-1-[(2S,5S)-2-(9-{2-[(2S,4S)-1-{(2S)-2-[(methoxycarbonyl)amino]-3-methylbutanoyl}-4-(methyoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate Methyl {(2S)-1-[(2S,5S)-2-(9-{2-[(2S,4S)-1-{(2S)-2-[(methoxycarbonyl)amino]-3-methylbutanoyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate Tert-butyl (2S,4S)-2-[5-(2-{(2S,5S)-1-[N-(methoxycarbonyl)-L-valyl]-5-methylpyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate (100 mg, 0.13 mmol) in 1.25 N HCl in EtOH (3 mL) was heated to 50° C. for 3 h and then concentrated under reduced pressure. The crude residue was treated with (S)-2-(methoxycarbonylamino)-3-methylbutanoic acid (34 mg, 0.20 mmol), HATU (54 mg, 0.14 mmol) and DMF (1.3 mL), then N-methylmorpholine (0.043 mL, 0.39 mmol) was added dropwise. After 3h, the mixture was quenched with 1N HCl (0.100 mL) and then purified by HPLC to afford methyl {(2S)-1-[(2S,5S)-2-(9-{2-[(2S,4S)-1-{(2S)-2-[(methoxycarbonyl)amino]-3-methylbutanoyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate (91 mg, 82%).

LCMS-ESI$^+$: calculated for $C_{46}H_{56}N_8O_8$: 848.4; observed [M+1]$^+$: 850.2.

Example QA

Methyl {(2S)-1-[(2S,5S)-2-(9-{2-[(2S,4S)-1-{(2S,3S)-3-methoxy-2-[(methoxycarbonyl)amino]butanoyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate Tert-butyl (2S,4S)-2-[5-(2-{(2S,5S)-1-[N-(methoxycarbonyl)-L-valyl]-5-methylpyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate (119 mg, 0.15 mmol) in 1.25 N HCl in EtOH (3 mL) was heated to 50° C. for 3 h and then concentrated under reduced pressure. The crude residue was treated with (2S,3R)-3-methoxy-2-(methoxycarbonylamino)butanoic acid (43 mg, 0.23 mmol), HATU (63 mg, 0.17 mmol) and DMF (2 mL), then N-methylmorpholine (0.050 mL, 0.45 mmol) was added dropwise. After 3 hr, the mixture was quenched with 1N HCl (0.100 mL) and then purified by HPLC to afford methyl {(2S)-1-[(2S,5S)-2-(9-{2-[(2S,4S)-1-{(2S,3S)-3-methoxy-2-[(methoxycarbonyl)amino]butanoyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate (76 mg, 59%).

LCMS-ESI$^+$: calculated for $C_{46}H_{56}N_8O_9$: 864.4; observed [M+1]$^+$: 866.1.

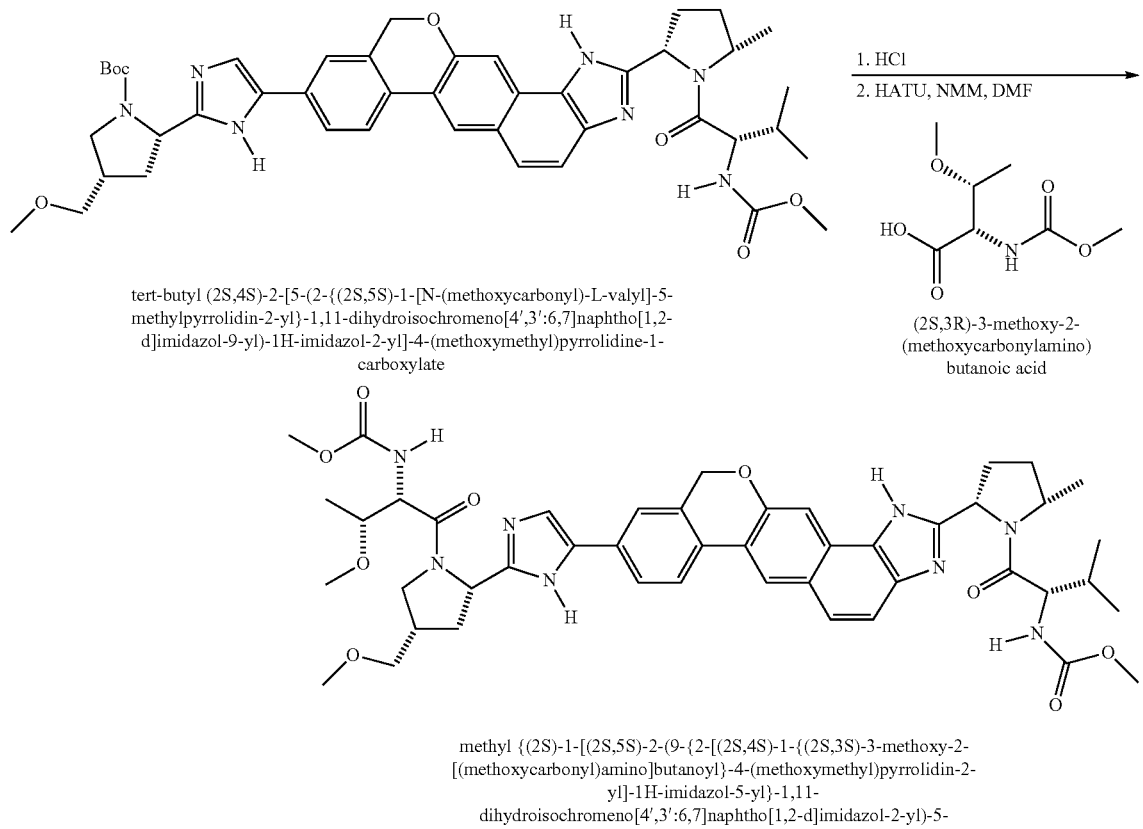

tert-butyl (2S,4S)-2-[5-(2-{(2S,5S)-1-[N-(methoxycarbonyl)-L-valyl]-5-methylpyrrolidin-2-yl}-1,11-dihydroisochromeno[4',3':6,7]naphtho[1,2-d]imidazol-9-yl)-1H-imidazol-2-yl]-4-(methoxymethyl)pyrrolidine-1-carboxylate (2S,3R)-3-methoxy-2-(methoxycarbonylamino) butanoic acid methyl {(2S)-1-[(2S,5S)-2-(9-{2-[(2S,4S)-1-{(2S,3S)-3-methoxy-2-[(methoxycarbonyl)amino]butanoyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate

Example QB
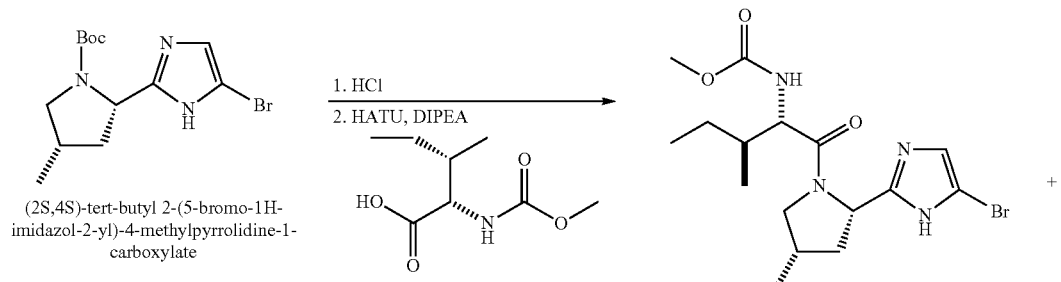
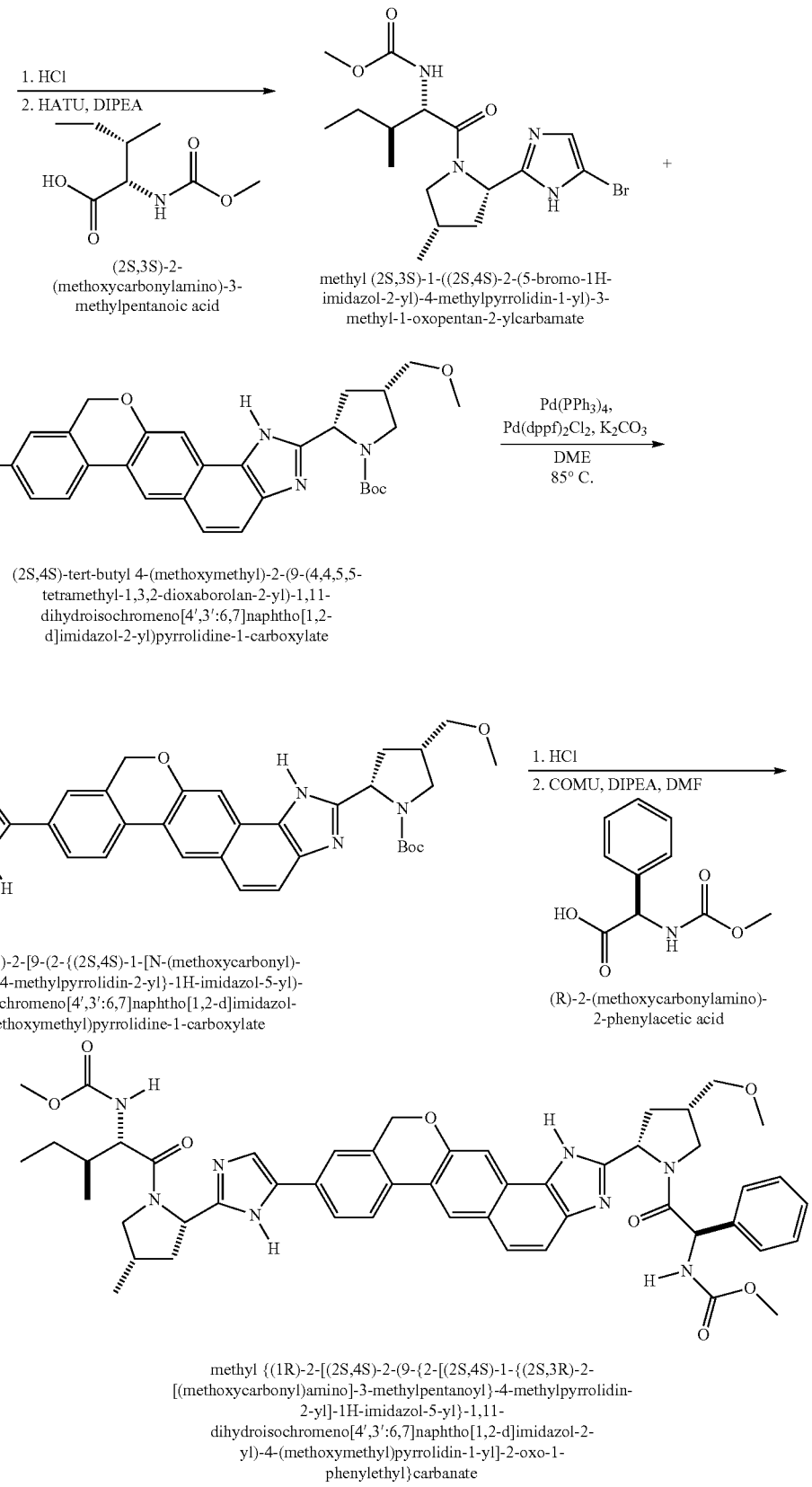

Methyl (2S,3S)-1-((2S,4S)-2-(5-bromo-1H-imidazol-2-yl)-4-methylpyrrolidin-1-yl)-3-methyl-1-oxopentan-2-ylcarbamate (2S,4S)-tert-butyl 2-(5-bromo-1H-imidazol-2-yl)-4-methylpyrrolidine-1-carboxylate (100 mg, 0.13 mmol) in 1.25 N HCl in EtOH (15 mL) was heated to 50° C. for 3 h and then concentrated under reduced pressure. The crude residue was treated with (2S,3S)-2-(methoxycarbonylamino)-3-methylpentanoic acid (625 mg, 3.30 mmol), HATU (1.05 g, 2.77 mmol) and DMF (10 mL), then DIPEA (1.33 mL, 7.62 mmol) was added dropwise. After 2h, the mixture was poured into saturated aqueous $NaHCO_3$ and then extracted with EtOAc. The organic phase was washed successively with 5% aqueous LiCl and Brine. The organics were dried over $Na_2SO_4$, filtered and concentrated under reduced pressure. The crude residue was purified by silica column chromatography (30 to 90% of 10% MeOH/EtoAc to Hexanes) afforded methyl (2S,3S)-1-((2S,4S)-2-(5-bromo-1H-imidazol-2-yl)-4-methylpyrrolidin-1-yl)-3-methyl-1-oxopentan-2-ylcarbamate (932 mg, 81%).

Tert-butyl (2S,4S)-2-[9-(2-{(2S,4S)-1-[N-(methoxycarbonyl)-L-alloisoleucyl]-4-methylpyrrolidin-2-yl}-1H-imidazol-5-yl)-1,11-dihydroisochromeno[4',3':6,7]naphtho[1,2-d]imidazol-2-yl]-4-(methoxymethyl)pyrrolidine-1-carboxylate (2S,4S)-Tert-butyl 4-(methoxymethyl)-2-(9-(4,4,5,5-tetramethyl-1,3,2-dioxaborolan-2-yl)-1,11-dihydroisochromeno[4',3':6,7]naphtho[1,2-d]imidazol-2-yl)pyrrolidine-1-carboxylate (856 mg, 1.4 mmol), methyl (2S,3S)-1-((2S,4S)-2-(5-bromo-1H-imidazol-2-yl)-4-methylpyrrolidin-1-yl)-3-methyl-1-oxopentan-2-ylcarbamate (932 mg, 2.1 mmol), $Pd(PPh_3)_4$ (162 mg, 0.14 mmol), $PdCl_2(dppf)_2$ (102 mg, 0.14 mmol), and $K_2CO_3$ (2M in $H_2OO$, 2.31 mL, 4.62 mmol) were combined in DMSO (8 mL) and dioxanes (8 mL). The mixture was degassed with bubbling Argon for 10 min then heated to 95° C. for 1 h. After cooling, the reaction mixture was diluted with EtOAc, and washed successively with saturated aqueous $NaHCO_3$ and brine. The organics were dried over $Na_2SO_4$, filtered and concentrated under reduced pressure. The crude residue was purified by silica column chromatography (1% to 20% MeOH/EtOAc) to afford tert-butyl (2S,4S)-2-[9-(2-{(2S,4S)-1-[N-(methoxycarbonyl)-L-alloisoleucyl]-4-methylpyrrolidin-2-yl}-1H-imidazol-5-yl)-1,11-dihydroisochromeno[4',3':6,7]naphtho[1,2-d]imidazol-2-yl]-4-(methoxymethyl)pyrrolidine-1-carboxylate (701 mg, 62%).

Methyl {(1R)-2-[(2S,4S)-2-(9-{2-[(2S,4S)-1-{(2S,3R)-2-[(methoxycarbonyl)amino]-3-methylpentanoyl}-4-methylpyrrolidin-2-yl]-1H-imidazol-5-yl}-1,11-dihydroisochromeno[4',3':6,7]naphtho[1,2-d]imidazol-2-yl)-4-(methoxymethyl)pyrrolidin-1-yl]-2-oxo-1-phenylethyl}carbamate A solution of tert-butyl (2S,4S)-2-[9-(2-{(2S,4S)-1-[N-(methoxycarbonyl)-L-alloisoleucyl]-4-methylpyrrolidin-2-yl}-1H-imidazol-5-yl)-1,11-dihydroisochromeno[4',3':6,7]naphtho[1,2-d]imidazol-2-yl]-4-(methoxymethyl)pyrrolidine-1-carboxylate (218 mg, 0.27 mmol) in 1.25 N HCl in EtOH (3 mL) was heated to 50° C. for 3 h. The reaction was concentrated and the crude material dissolved in DMF (3 mL). To this solution was added a solution of (R)-2-(methoxycarbonylamino)-2-phenylacetic acid (73 mg, 0.35 mmol) and COMU (127 mg, 0.30 mmol). To the resulting solution was added diisopropylethylamine (0.141 mL, 0.81 mmol). After stirring for 2 h at room temperature, the reaction was quenched with 1N HCl (0.200 mL) and purified by HPLC. After lyophilization, the TFA salt was dissolved in EtOAc and washed with saturated $NaHCO_3$. The organic phase was dried over $Na_2SO_4$ and concentrated. The free base was then dissolved in $MeCN/H_2O$ and lyophilized to afford methyl {(1R)-2-[(2S,4S)-2-(9-{2-[(2S,4S)-1-{(2S,3R)-2-[(methoxycarbonyl)amino]-3-methylpentanoyl}-4-methylpyrrolidin-2-yl]-1H-imidazol-5-yl}-1,11-dihydroisochromeno[4',3':6,7]naphtho[1,2-d]imidazol-2-yl)-4-(methoxymethyl)pyrrolidin-1-yl]-2-oxo-1-phenylethyl}carbamate (121 mg, 50%). LCMS-ESI$^+$: calculated for $C_{50}H_{56}N_8O_8$: 896.4; observed $[M+1]^+$: 897.5.

Example QC

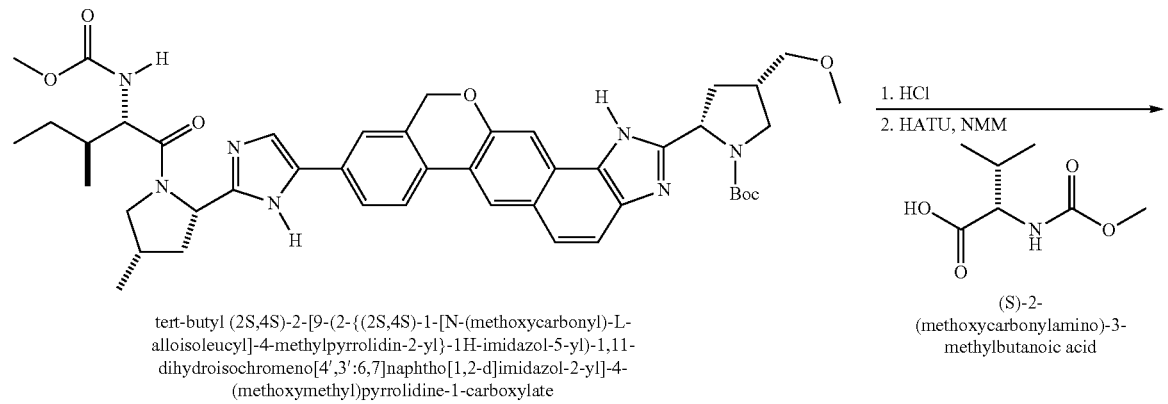

tert-butyl (2S,4S)-2-[9-(2-{(2S,4S)-1-[N-(methoxycarbonyl)-L-alloisoleucyl]-4-methylpyrrolidin-2-yl}-1H-imidazol-5-yl)-1,11-dihydroisochromeno[4',3':6,7]naphtho[1,2-d]imidazol-2-yl]-4-(methoxymethyl)pyrrolidine-1-carboxylate (S)-2-(methoxycarbonylamino)-3-methylbutanoic acid

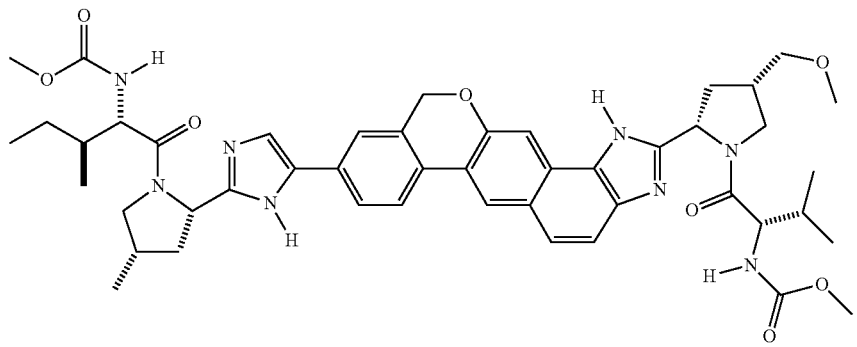

methyl {(2S)-1-[(2S,4S)-2-(9-{2-[(2S,4S)-1-{(2S,3R)-2-[(methoxycarbonyl)amino]-3-methylpentanoyl}-4-methylpyrrolidin-2-yl]-1H-imidazol-5-yl}-1,11-dihydroisochromeno[4',3':6,7]naphtho[1,2-d]imidazol-2-yl)-4-(methoxymethyl)pyrrolidin-1-yl]-3-methyl-1-oxobutan-2-yl}carbanate Methyl {(2S)-1-[(2S,4S)-2-(9-{2-[(2S,3R)-2-[(methoxycarbonyl)amino]-3-methylpentanoyl}-4-methylpyrrolidin-2-yl]-1H-imidazol-5-yl}-1,11-dihydroisochromeno[4',3':6,7]naphtho[1,2-d]imidazol-2-yl)-4-(methoxymethyl)pyrrolidin-1-yl]-3-methyl-1-oxobutan-2-yl}carbamate tert-butyl (2S,4S)-2-[9-(2-{(2S,4S)-1-[N-(methoxycarbonyl)-L-alloisoleucyl]-4-methylpyrrolidin-2-yl}-1H-imidazol-5-yl)-1,11-dihydroisochromeno[4',3':6,7]naphtho[1,2-d]imidazol-2-yl]-4-(methoxymethyl)pyrrolidine-1-carboxylate (105 mg, 0.13 mmol) in 1.25 N HCl in EtOH (3 mL) was heated to 50° C. for 3 h and then concentrated under reduced pressure. The crude residue was treated with (S)-2-(methoxycarbonylamino)-3-methylbutanoic acid (32 mg, 0.18 mmol), HATU (59 mg, 0.16 mmol) and DMF (1.3 mL), then N-methylmorpholine (0.043 mL, 0.39 mmol) was added dropwise. After 3h, the mixture was quenched with 1N HCl (0.100 mL) and then purified by HPLC to afford methyl {(2S)-1-[(2S,4S)-2-(9-{2-[(2S,4S)-1-{(2S,3R)-2-[(methoxycarbonyl)amino]-3-methylpentanoyl}-4-methylpyrrolidin-2-yl]-1H-imidazol-5-yl}-1,11-dihydroisochromeno[4',3':6,7]naphtho[1,2-d]imidazol-2-yl)-4-(methoxymethyl)pyrrolidin-1-yl]-3-methyl-1-oxobutan-2-yl}carbamate (80 mg, 71%).

LCMS-ESI$^+$: calculated for $C_{47}H_{58}N_8O_8$: 862.4; observed [M+1]$^+$: 864.2.

Example QD

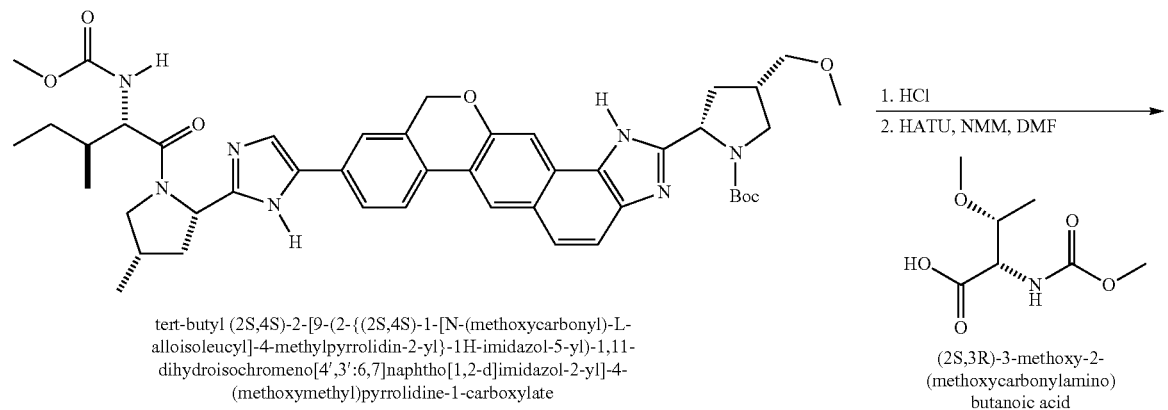

tert-butyl (2S,4S)-2-[9-(2-{(2S,4S)-1-[N-(methoxycarbonyl)-L-alloisoleucyl]-4-methylpyrrolidin-2-yl}-1H-imidazol-5-yl)-1,11-dihydroisochromeno[4',3':6,7]naphtho[1,2-d]imidazol-2-yl]-4-(methoxymethyl)pyrrolidine-1-carboxylate (2S,3R)-3-methoxy-2-(methoxycarbonylamino) butanoic acid

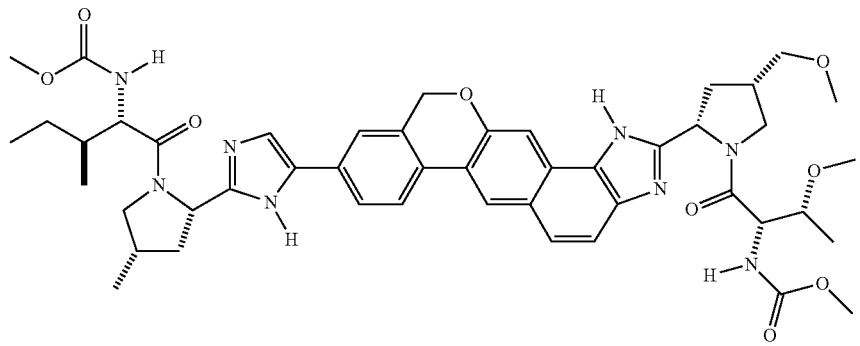

methyl {(2S,3R)-1-[(2S,4S)-2-(5-{2-[(2S,4S)-1-[N-(methoxycarbonyl)amino]-O-methyl-L-allothreonyl]-4-(methoxymethyl)pyrrolidin-2-yl]-1,11-dihydroisochromeno[4',3':6,7]naphtho[1,2-d]imidazol-2-yl)-5-methylpyrrolidin-1-yl]-3-methyl-1-oxobutan-2-yl}carbamate Methyl {(2S,3R)-1-[(2S,4S)-2-(5-{2-[(2S,4S)-1-[N-(methoxycarbonyl)-O-methyl-L-allothreonyl]-4-(methoxymethyl)pyrrolidin-2-yl]-1,11-dihydroisochromeno[4',3':6,7]naphtho[1,2-d]imidazol-9-yl}-1H-imidazol-2-yl)-4-methylpyrrolidin-1-yl]-3-methyl-1-oxopentan-2-yl}carbamate tert-butyl (2S,4S)-2-[9-(2-{(2S,4S)-1-[N-(methoxycarbonyl)-L-alloisoleucyl]-4-methylpyrrolidin-2-yl}-1H-imidazol-5-yl)-1,11-dihydroisochromeno[4',3':6,7]naphtho[1,2-d]imidazol-2-yl]-4-(methoxymethyl)pyrrolidine-1-carboxylate (105 mg, 0.13 mmol) in 1.25 N HCl in EtOH (3 mL) was heated to 50° C. for 3 h and then concentrated under reduced pressure. The crude residue was treated with (2S,3R)-3-methoxy-2-(methoxycarbonylamino)butanoic acid (35 mg, 0.18 mmol), HATU (59 mg, 0.16 mmol) and DMF (1.3 mL), then N-methylmorpholine (0.043 mL, 0.39 mmol) was added dropwise. After 3 hr, the mixture was quenched with 1N HCl (0.100 mL) and then purified by HPLC to afford methyl {(2S,3R)-1-[(2S,4S)-2-(5-{2-[(2S,4S)-1-[N-(methoxycarbonyl)-O-methyl-L-allothreonyl]-4-(methoxymethyl)pyrrolidin-2-yl]-1,11-dihydroisochromeno[4',3':6,7]naphtho[1,2-d]imidazol-9-yl}-1H-imidazol-2-yl)-4-methylpyrrolidin-1-yl]-3-methyl-1-oxopentan-2-yl}carbamate (92 mg, 81%).

LCMS-ESI+: calculated for $C_{47}H_{58}N_8O_9$: 878.4; observed [M+1]+: 879.3.

Example QE

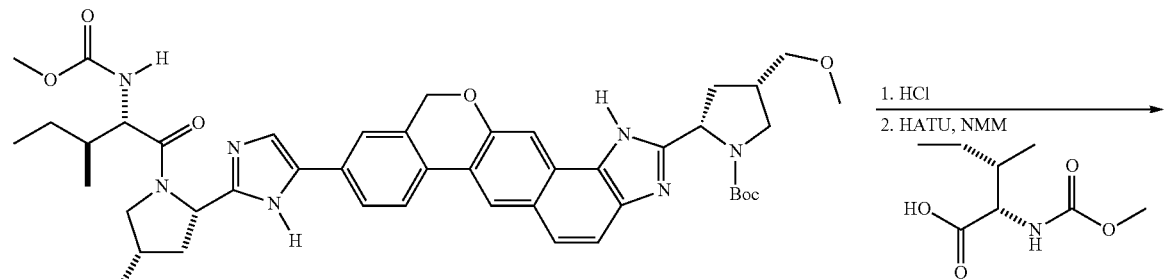

tert-butyl (2S,4S)-2-[9-(2-{(2S,4S)-1-[N-(methoxycarbonyl)-L-alloisoleucyl]-4-methylpyrrolidin-2-yl}-1H-imidazol-5-yl)-1,11-dihydroisochromeno[4',3':6,7]naphtho[1,2-d]imidazol-2-yl]-4-(methoxymethyl)pyrrolidine-1-carboxylate (2S,3S)-2-(methoxycarbonylamino)-3-methylpentanoic acid

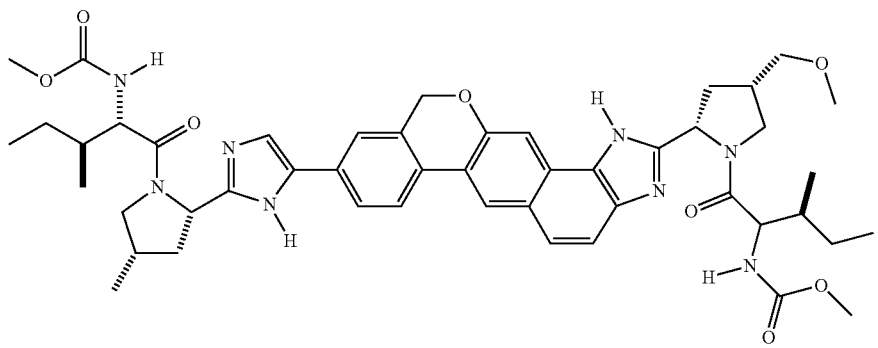

methyl {(3R)-1-[(2S,4S)-2-(9-{2-[(2S,4S)-1-{(2S,3R)-2-[(methoxycarbonyl)amino]-3-methylpentanoyl}-4-methylpyrrolidin-2-yl]-1H-imidazol-5-yl}-1,11-dihydroisochromeno[4',3':6,7]naphtho[1,2-d]imidazol-2-yl)-4-(methoxymethyl)pyrrolidin-1-yl]-3-methyl-1-oxopentan-2-yl}carbamate Methyl {(3R)-1-[(2S,4S)-2-(9-{2-[(2S,3R)-2-[(methoxycarbonyl)amino]-3-methylpentanoyl}-4-methylpyrrolidin-2-yl]-1H-imidazol-5-yl}-1,11-dihydroisochromeno[4',3':6,7]naphtho[1,2-d]imidazol-2-yl)-4-(methoxymethyl)pyrrolidin-1-yl]-3-methyl-1-oxopentan-2-yl}carbamate tert-butyl (2S,4S)-2-[9-(2-{(2S,4S)-1-[N-(methoxycarbonyl)-L-alloisoleucyl]-4-methylpyrrolidin-2-yl}-1H-imidazol-5-yl)-1,11-dihydroisochromeno[4',3':6,7]naphtho[1,2-d]imidazol-2-yl]-4-(methoxymethyl)pyrrolidine-1-carboxylate (105 mg, 0.13 mmol) in 1.25 N HCl in EtOH (3 mL) was heated to 50° C. for 3 h and then concentrated under reduced pressure. The crude residue was treated with (2S,3S)-2-(methoxycarbonylamino)-3-methylpentanoic acid (34 mg, 0.18 mmol), HATU (59 mg, 0.16 mmol) and DMF (1.3 mL), then N-methylmorpholine (0.043 mL, 0.39 mmol) was added dropwise. After 3h, the mixture was quenched with 1N HCl (0.100 mL) and then purified by HPLC to afford methyl {(3R)-1-[(2S,4S)-2-(9-{2-[(2S,4S)-1-{(2S,3R)-2-[(methoxycarbonyl)amino]-3-methylpentanoyl}-4-methylpyrrolidin-2-yl]-1H-imidazol-5-yl}-1,11-dihydroisochromeno[4',3':6,7]naphtho[1,2-d]imidazol-2-yl)-4-(methoxymethyl)pyrrolidin-1-yl]-3-methyl-1-oxopentan-2-yl}carbamate (98 mg, 86%).

LCMS-ESI$^+$: calculated for $C_{48}H_{60}N_8O_8$: 876.5; observed [M+1]$^+$: 878.2.

Example QF

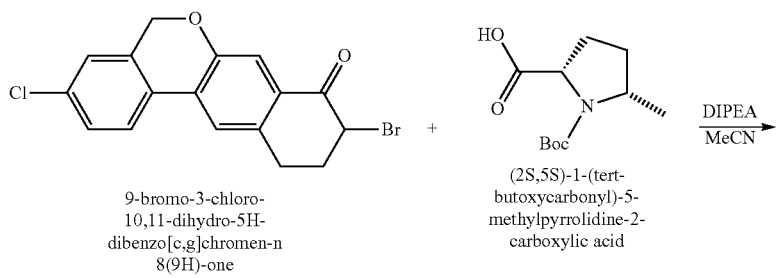

9-bromo-3-chloro-10,11-dihydro-5H-dibenzo[c,g]chromen-8(9H)-one (2S,5S)-1-(tert-butoxycarbonyl)-5-methylpyrrolidine-2-carboxylic acid

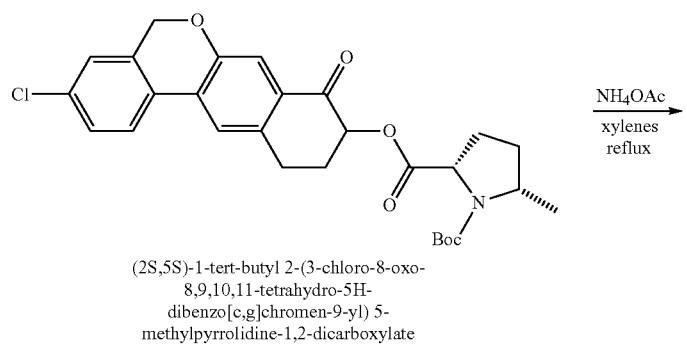

(2S,5S)-1-tert-butyl 2-(3-chloro-8-oxo-8,9,10,11-tetrahydro-5H-dibenzo[c,g]chromen-9-yl) 5-methylpyrrolidine-1,2-dicarboxylate -continued

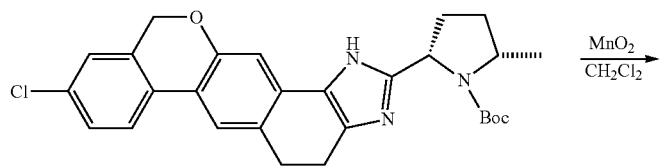

(2S,5S)-tert-butyl 2-(9-chloro-4,5-dihydro-5H-naphtho[c,g]chromeno[8,9-d]imidazol-2-yl)-5-(methyl)pyrrolidine-1-carboxylate

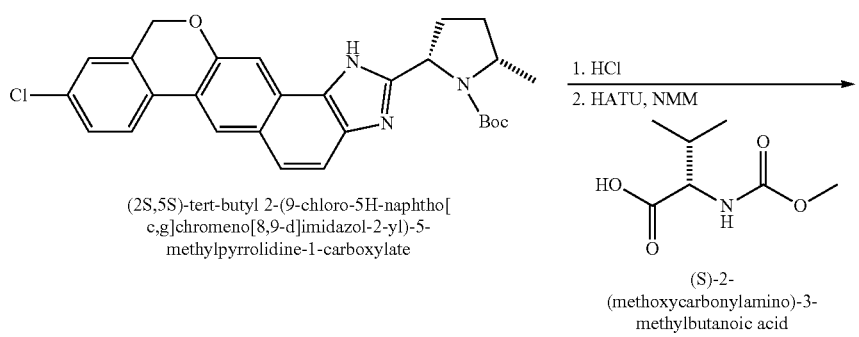

(2S,5S)-tert-butyl 2-(9-chloro-5H-naphtho[c,g]chromeno[8,9-d]imidazol-2-yl)-5-methylpyrrolidine-1-carboxylate (S)-2-(methoxycarbonylamino)-3-methylbutanoic acid

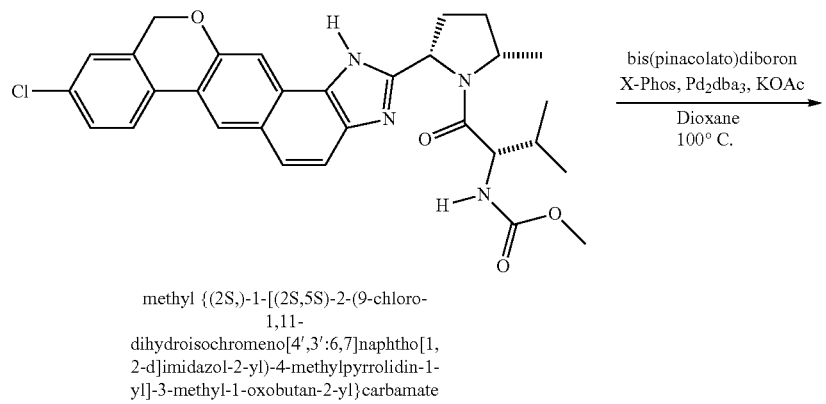

methyl {(2S,)-1-[(2S,5S)-2-(9-chloro-1,11-dihydroisochromeno[4′,3′:6,7]naphtho[1,2-d]imidazol-2-yl)-4-methylpyrrolidin-1-yl]-3-methyl-1-oxobutan-2-yl}carbamate

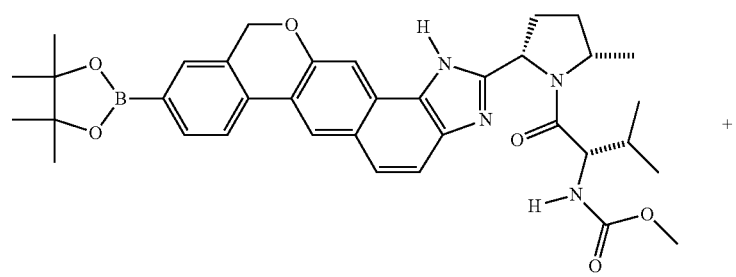

methyl [(2S)-3-methyl-1-{(2S,5S)-2-methyl-5-[9-(4,4,5,5-tetramethyl-1,3,2-dioxaborolan-2-yl)-1,11-dihydroisochromeno[4′,3′:6,7]naphtho[1,2-d]imidazol-2-yl]pyrrolidin-1-yl}-1-oxobutan-2-yl]carbamate

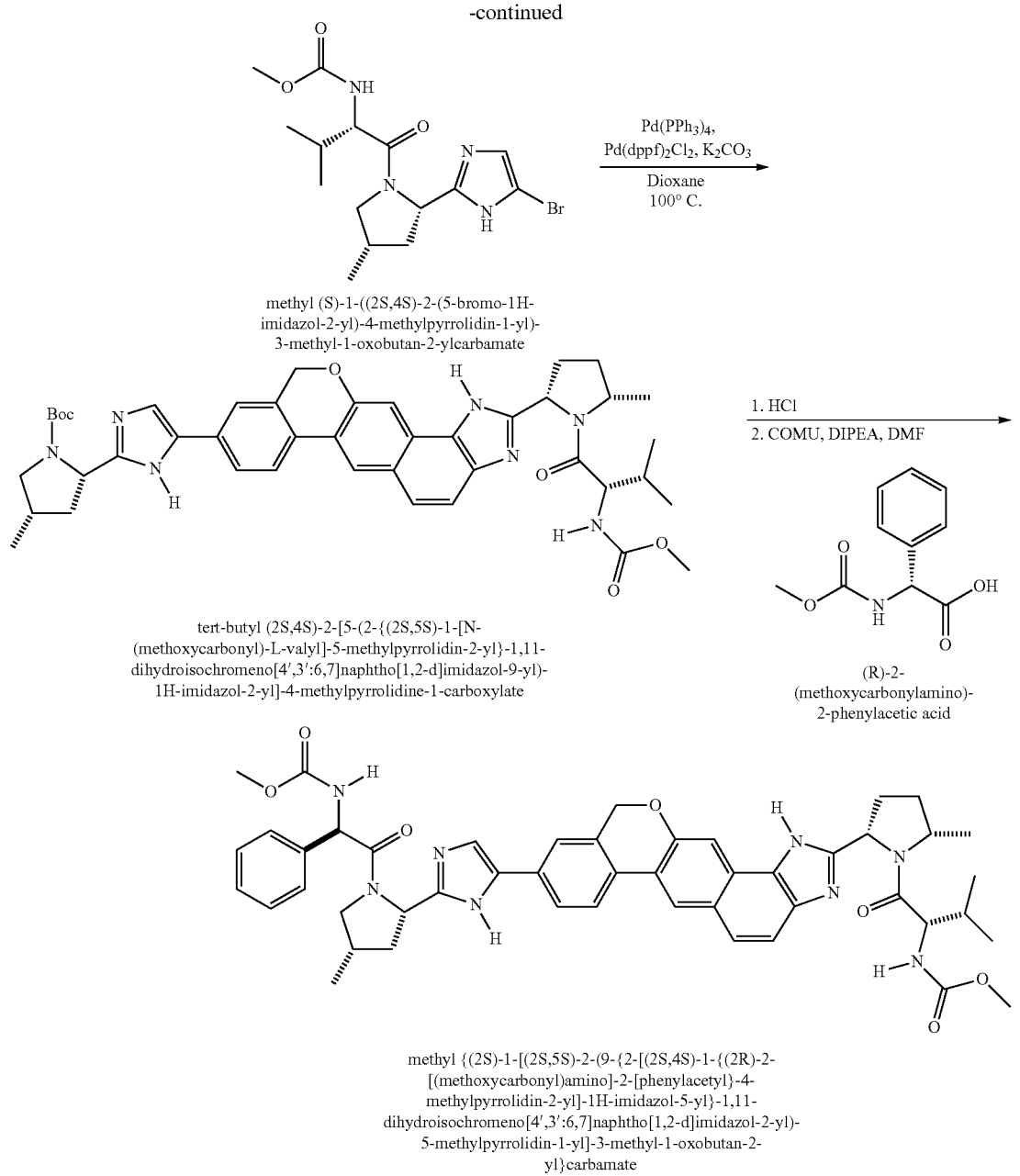

(2S,5S)-1-tert-butyl 2-(3-chloro-8-oxo-8,9,10,11-tetrahydro-5H-dibenzo[c,g]chromen-9-yl) 5-methylpyrrolidine-1,2-dicarboxylate To a solution of 9-bromo-3-chloro-10,11-dihydro-5H-dibenzo[c,g]chromen-8(9H)-one (1.41 g, 3.88 mmol) in MeCN (17 mL) was added (2S,5S)-1-(tert-butoxycarbonyl)-5-methylpyrrolidine-2-carboxylic acid (980 mg, 4.27 mmol) and DIPEA (1.49 mL, 8.54 mmol). After stirring for 18 h at 50° C., the solution was diluted with EtOAc and washed successively with 1N HCl, saturated aqueous NaHCO₃ and brine. The organics were dried over Na₂SO₄, filtered and concentrated under reduced pressure. The crude residue was purified by silica column chromatography (10% to 30% EtOAc/hexanes) to afford (2S,5S)-1-tert-butyl 2-(3-chloro-8-oxo-8,9,10,11-tetrahydro-5H-dibenzo[c,g]chromen-9-yl) 5-methylpyrrolidine-1,2-dicarboxylate (1.63 g, 81%).

(2S,5S)-tert-butyl 2-(9-chloro-4,5-dihydro-5H-naphtho[c,g]chromeno[8,9-d]imidazol-2-yl)-5-(methyl) pyrrolidine-1-carboxylate (2S,5S)-1-tert-butyl 2-(3-chloro-8-oxo-8,9,10,11-tetrahydro-5H-dibenzo[c,g]chromen-9-yl) 5-methylpyrrolidine-1,2-dicarboxylate (1.63 g, 3.18 mmol) was added toluene (30 mL), 2-methoxyethanol (3 mL), and ammonium acetate (3.68 g, 77.1 mmol) and the solution was heated to reflux overnight. The following morning, the solution was cooled to rt and was diluted with EtOAc and washed successively with water, saturated aqueous NaHCO₃ and brine. The organics were dried over Na₂SO₄, filtered and concentrated under reduced pressure. The crude residue was purified by silica column chromatography (40% to 80% EtOAc/hexanes) to afford (2S,5S)-tert-butyl 2-(9-chloro-4,5-dihydro-5H-naphtho[c,g]chromeno[8,9-d]imidazol-2-yl)-5-methylpyrrolidine-1-carboxylate (1.13 g, 72%).

((2S,5S)-tert-butyl 2-(9-chloro-5H-naphtho[c,g]chromeno[8,9-d]imidazol-2-yl)-5-methylpyrrolidine-1-carboxylate To a solution of (2S,5S)-tert-butyl 2-(9-chloro-4,5-dihydro-5H-naphtho[c,g]chromeno[8,9-d]imidazol-2-yl)-5-(methyl)pyrrolidine-1-carboxylate (1.13 g, 2.3 mmol) in $CH_2Cl_2$ (25 mL) was added $MnO_2$ (9.98 g, 115 mmol). The reaction mixture was stirred overnight then filtered over celite. The filter cake was washed with copious $CH_2Cl_2$ and MeOH, and the filtrate was concentrated under reduced pressure to afford the crude product (2S,5S)-tert-butyl 2-(9-chloro-5H-naphtho[c,g]chromeno[8,9-d]imidazol-2-yl)-5-methylpyrrolidine-1-carboxylate (931 mg, 83%).

Methyl {(2S)-1-[(2S,5S)-2-(9-chloro-1,11-dihydroisochromeno[4',3':6,7]naphtho[1,2-d]imidazol-2-yl)-5-methylpyrrolidin-1-yl]-3-methyl-1-oxobutan-2-yl}carbamate (2S,5S)-tert-butyl 2-(9-chloro-5H-naphtho[c,g]chromeno[8,9-d]imidazol-2-yl)-5-methylpyrrolidine-1-carboxylate (931 mg, 1.9 mmol) in 1.25 N HCl in EtOH (8 mL) was heated to 50° C. for 3 h and then concentrated under reduced pressure. The crude residue was treated with (S)-2-(methoxycarbonylamino)-3-methylbutanoic acid (499 mg, 2.9 mmol), HATU (795 mg, 2.1 mmol) and DMF (10 mL), then N-methylmorpholine (0.627 mL, 5.7 mmol) was added dropwise. After stirring for 1 h, the reaction was diluted with EtOAc and washed successively with saturated aqueous $NaHCO_3$, 5% LiCl, and brine. The organics were dried over $Na_2SO_4$, filtered and concentrated under reduced pressure. The crude residue was purified by silica column chromatography (50% to 100% EtOAc/hexanes) to afford methyl {(2S)-1-[(2S,5S)-2-(9-chloro-1,11-dihydroisochromeno[4',3':6,7]naphtho[1,2-d]imidazol-2-yl)-5-methylpyrrolidin-1-yl]-3-methyl-1-oxobutan-2-yl}carbamate (950 mg, 91%).

Methyl [(2S)-3-methyl-1-{(2S,5S)-2-methyl-5-[9-(4,4,5,5-tetramethyl-1,3,2-dioxaborolan-2-yl)-1,11-dihydroisochromeno[4',3':6,7]naphtho[1,2-d]imidazol-2-yl]pyrrolidin-1-yl}-1-oxobutan-2-yl]carbamate To methyl {(2S)-1-[(2S,5S)-2-(9-chloro-1,11-dihydroisochromeno[4',3':6,7]naphtho[1,2-d]imidazol-2-yl)-5-methylpyrrolidin-1-yl]-3-methyl-1-oxobutan-2-yl}carbamate (950 mg, 1.74 mmol) in dioxane (17 mL) was added bis(pinacolato)diboron (662 mg, 2.61 mmol), KOAc (512 mg, 5.22 mmol), X-Phos (25 mg, 0.05 mmol), and $Pd_2 dba_3$ (80 mg, 0.08 mmol). The solution was degassed with $N_2$ for 10 min, then heated to 90° C. for 16 h. The solution was cooled to rt, diluted with EtOAc, washed with saturated aqueous $NaHCO_3$, brine, dried with $Na_2SO_4$, and concentrated. Purification by silica gel chromatography (30% to 75% gradient using 5% MeOH/EtOAc to Hexanes) to afford methyl [(2S)-3-methyl-1-{(2S,5S)-2-methyl-5-[9-(4,4,5,5-tetramethyl-1,3,2-dioxaborolan-2-yl)-1,11-dihydroisochromeno[4',3':6,7]naphtho[1,2-d]imidazol-2-yl]pyrrolidin-1-yl}-1-oxobutan-2-yl]carbamate (800 mg, 72%).

tert-butyl (2S,4S)-2-[5-(2-{(2S,5S)-1-[N-(methoxycarbonyl)-L-valyl]-5-methylpyrrolidin-2-yl}-1,11-dihydroisochromeno[4',3':6,7]naphtho[1,2-d]imidazol-9-yl)-1H-imidazol-2-yl]-4-methylpyrrolidine-1-carboxylate To a solution of [(2S)-3-methyl-1-{(2S,5S)-2-methyl-5-[9-(4,4,5,5-tetramethyl-1,3,2-dioxaborolan-2-yl)-1,11-dihydroisochromeno[4',3':6,7]naphtho[1,2-d]imidazol-2-yl]pyrrolidin-1-yl}-1-oxobutan-2-yl]carbamate (269 mg, 0.42 mmol), (2S,4S)-tert-butyl 2-(5-bromo-1H-imidazol-2-yl)-4-methylpyrrolidine-1-carboxylate (206 mg, 0.54 mmol), tetrakis(triphenylphosphine) palladium(0) (49 mg, 0.042 mmol) and dichloro[1,1'-bis(diphenylphosphino)ferrocene] palladium(II) (31 mg, 0.042 mmol) in DMSO (3 mL) and dioxanes (3 mL) was added a solution of potassium carbonate (2M in water, 0.69 mL, 1.39 mmol). The resulting mixture was degassed and then heated to 95° C. for 2 h. After cooling to room temperature, the reaction was diluted with ethyl acetate. The organics were washed with saturated sodium bicarbonate and brine, dried over $Na_2SO_4$ and concentrated. The crude residue was purified by flash chromatography (1 to 20% MeOH/EtOAc) to yield tert-butyl (2S,4S)-2-[5-(2-{(2S,5S)-1-[N-(methoxycarbonyl)-L-valyl]-5-methylpyrrolidin-2-yl}-1,11-dihydroisochromeno[4',3':6,7]naphtho[1,2-d]imidazol-9-yl)-1H-imidazol-2-yl]-4-methylpyrrolidine-1-carboxylate (202 mg, 63%).

Methyl {(2S)-1-[(2S,5S)-2-(9-{2-[(2S,4S)-1-{(2R)-2-[(methoxycarbonyl)amino]-2-phenylacetyl}-4-methylpyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate A solution of tert-butyl (2S,4S)-2-[5-(2-{(2S,5S)-1-[N-(methoxycarbonyl)-L-valyl]-5-methylpyrrolidin-2-yl}-1,11-dihydroisochromeno[4',3':6,7]naphtho[1,2-d]imidazol-9-yl)-1H-imidazol-2-yl]-4-methylpyrrolidine-1-carboxylate (80 mg, 0.11 mmol) in 1.25 N HCl in EtOH (2 mL) was heated to 50° C. for 3 h. The reaction was concentrated and the crude material dissolved in DMF (1.5 mL). To this solution was added a solution of (R)-2-(methoxycarbonylamino)-2-phenylacetic acid (29 mg, 0.14 mmol) and COMU (52 mg, 0.12 mmol). To the resulting solution was added diisopropylethylamine (0.057 mL, 0.33 mmol). After stirring for 2 h at room temperature, the reaction was quenched with 1N HCl (0.200 mL) and purified by HPLC. After lyophilization, the TFA salt was dissolved in EtOAc and washed with saturated $NaHCO_3$. The organic phase was dried over $Na_2SO_4$ and concentrated. The free base was then dissolved in $MeCN/H_2O$ and lyophilized to afford methyl {(2S)-1-[(2S,5S)-2-(9-{2-[(2S,4S)-1-{(2R)-2-[(methoxycarbonyl)amino]-2-phenylacetyl}-4-methylpyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate: (42 mg, 45%).

LCMS-ESI$^+$: calculated for $C_{48}H_{52}N_8O_7$: 852.4; observed [M+1]$^+$: 854.2.

Example QG

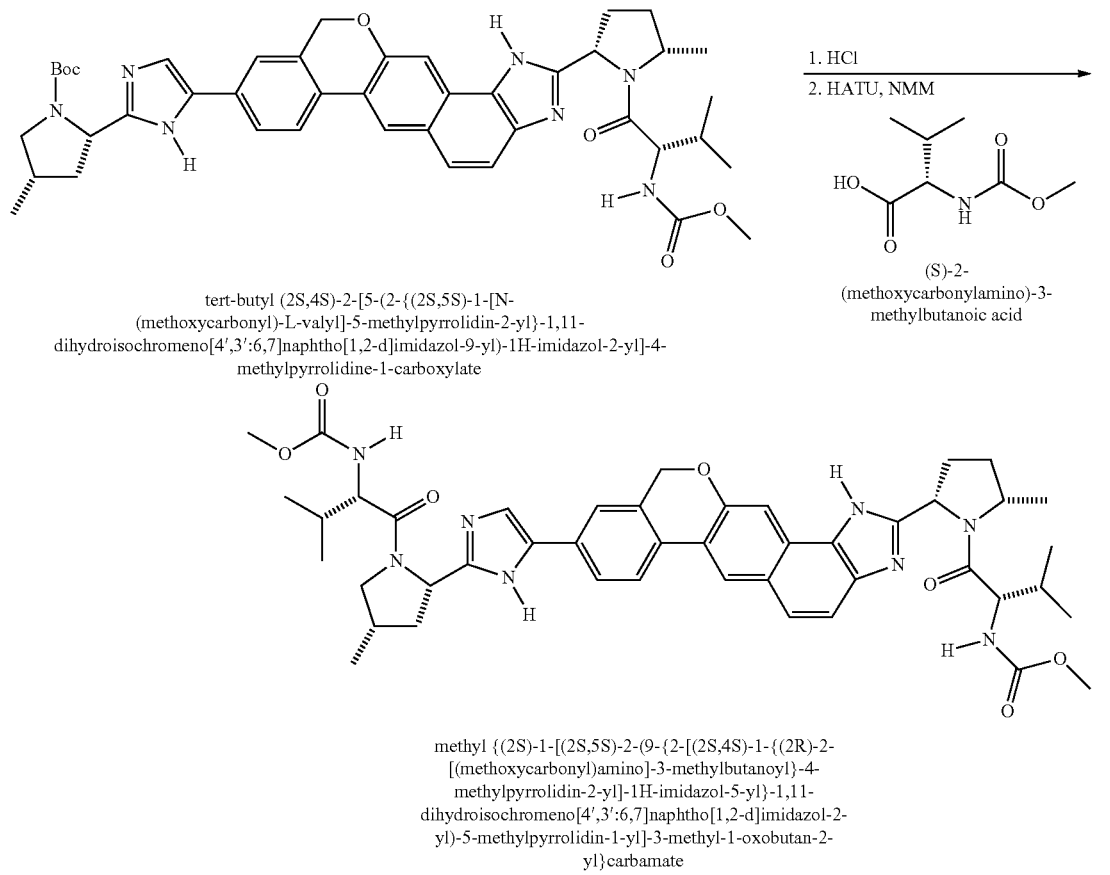

tert-butyl (2S,4S)-2-[5-(2-{(2S,5S)-1-[N-(methoxycarbonyl)-L-valyl]-5-methylpyrrolidin-2-yl}-1,11-dihydroisochromeno[4',3':6,7]naphtho[1,2-d]imidazol-9-yl)-1H-imidazol-2-yl]-4-methylpyrrolidine-1-carboxylate (S)-2-(methoxycarbonylamino)-3-methylbutanoic acid methyl {(2S)-1-[(2S,5S)-2-(9-{2-[(2S,4S)-1-{(2R)-2-[(methoxycarbonyl)amino]-3-methylbutanoyl}-4-methylpyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate Methyl {(2S)-1-[(2S,5S)-2-(9-{2-[(2S,4S)-1-{(2S)-2-[(methoxycarbonyl)amino]-3-methylbutanoyl}-4-methylpyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate tert-butyl (2S,4S)-2-[5-(2-{(2S,5S)-1-[N-(methoxycarbonyl)-L-valyl]-5-methylpyrrolidin-2-yl}-1,11-dihydroisochromeno[4',3':6,7]naphtho[1,2-d]imidazol-9-yl)-1H-imidazol-2-yl]-4-methylpyrrolidine-1-carboxylate (60 mg, 0.079 mmol) in 1.25 N HCl in EtOH (2 mL) was heated to 50° C. for 3 h and then concentrated under reduced pressure. The crude residue was treated with (S)-2-(methoxycarbonylamino)-3-methylbutanoic acid (21 mg, 0.12 mmol), HATU (36 mg, 0.095 mmol) and DMF (1.5 mL), then N-methylmorpholine (0.027 mL, 0.24 mmol) was added dropwise. After 3h, the mixture was quenched with 1N HCl (0.100 mL) and then purified by HPLC to afford methyl {(2S)-1-[(2S,5S)-2-(9-{2-[(2S,4S)-1-{(2S)-2-[(methoxycarbonyl)amino]-3-methylbutanoyl}-4-methylpyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate (33 mg, 51%).

LCMS-ESI[+]: calculated for $C_{45}H_{54}N_8O_7$: 818.4; observed [M+1][+]: 820.2.

Example QH tert-butyl (2S,4S)-2-[5-(2-{(2S,5S)-1-[N-(methoxycarbonyl)-L-valyl]-5-methylpyrrolidin-2-yl}-1,11-dihydroisochromeno[4',3':6,7]naphtho[1,2-d]imidazol-9-yl)-1H-imidazol-2-yl]-4-methylpyrrolidine-1-carboxylate A name could not be generated for this structure.

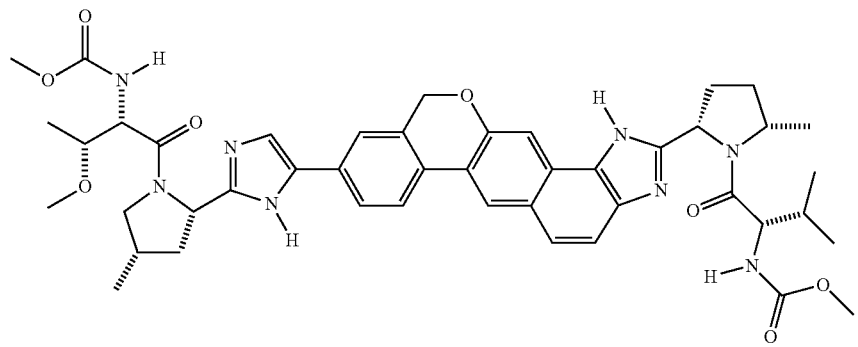

methyl {(2S)-1-[(2S,5S)-2-(9-{2-[(2S,4S)-1-{(2S,3S)-3-methoxy-
2-[(methoxycarbonyl)amino]butanoyl}-4-methylpyrrolidin-2-yl]-
1H-imidazol-5-yl}-1,11-
dihydroisochromeno[4',3':6,7]naphtho[1,2-d]imidazol-2-yl)-5-
methylpyrrolidin-1-yl]-3-methyl-1-oxobutan-2-yl}carbamate Methyl {(2S)-1-[(2S,5S)-2-(9-{2-[(2S,4S)-1-{(2S,3R)-3-methoxy-2-[(methoxycarbonyl)amino]butanoyl}-4-methylpyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate tert-butyl (2S,4S)-2-[5-(2-{(2S,5S)-1-[N-(methoxycarbonyl)-L-valyl]-5-methylpyrrolidin-2-yl}-1,11-dihydroisochromeno[4',3':6,7]naphtho[1,2-d]imidazol-9-yl)-1H-imidazol-2-yl]-4-methylpyrrolidine-1-carboxylate (20 mg, 0.079 mmol) in 1.25 N HCl in EtOH (2 mL) was heated to 50° C. for 3 h and then concentrated under reduced pressure. The crude residue was treated with (2S,3R)-3-methoxy-2-(methoxycarbonylamino)butanoic acid (8 mg, 0.04 mmol), HATU (12 mg, 0.03 mmol) and DMF (0.5 mL), then N-methylmorpholine (0.009 mL, 0.078 mmol) was added dropwise. After 3h, the mixture was quenched with 1N HCl (0.100 mL) and then purified by HPLC to afford methyl {(2S)-1-[(2S,5S)-2-(9-{2-[(2S,4S)-1-{(2S)-2-[(methoxycarbonyl)amino]-3-methylbutanoyl}-4-methylpyrrolidin-2-yl]-1H-imidazol-5-yl}-1,11-dihydroisochromeno[4',3':6,7]naphtho[1,2-d]yl)-5-methylpyrrolidin-1-yl]-3-methyl-1-oxobutan-2-yl}carbamate (7.5 mg, 35%).

LCMS-ESI$^+$: calculated for $C_{45}H_{54}N_8O_8$: 834.4; observed [M+1]$^+$: 835.7.

Compounds 478-647

Using procedures similar to those described herein, the following compounds of the disclosure were prepared.

| # | Compound | LCMS (observed) (M + H)$^+$ |
|---|----------|---------|
| 478 | Chiral | 879.4 |

US 8,575,135 B2
-continued
| # | Compound | LCMS (observed) (M + H)+ |
|---|----------|--------------------------|
| 493 | 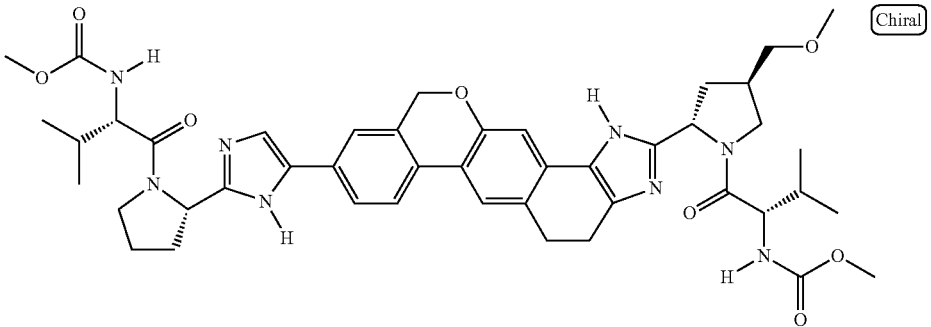 | 838.2 |
| 494 | 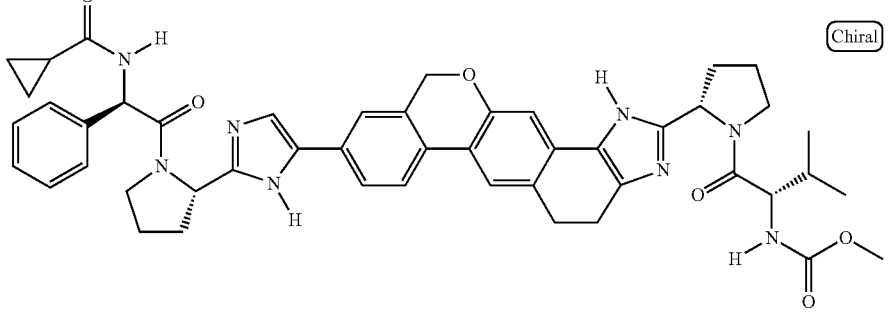 | 837.3 |
| 495 | 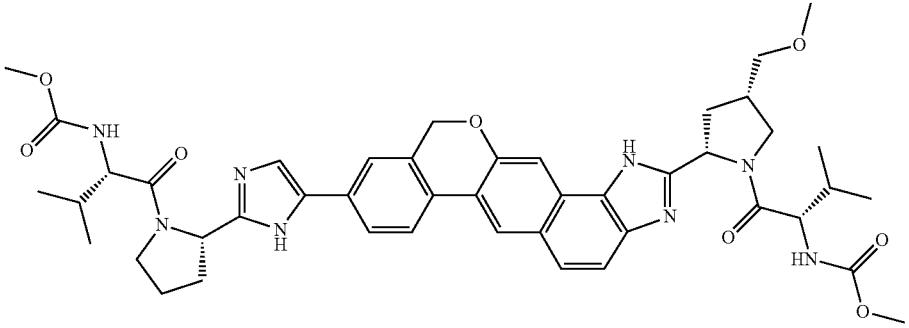 | 835.73 |
| 498 | 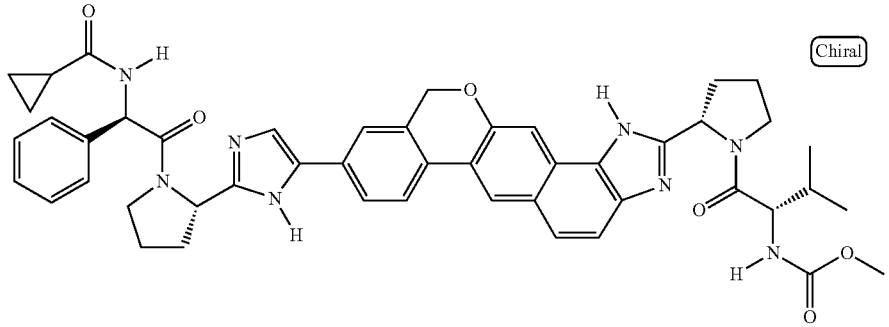 [SMILES: COC(=O)N[C@H](C(=O)N1CCC[C@H]1c1nc2ccc3cc4c(cc3c2[nH]1)OCc1cc(-c2cnc([C@@H]3CCCN3C(=O)[C@H](NC(=O)C3CC3)c3ccccc3)[nH]2)ccc1-4)C(C)C] | 835.34 |

US 8,575,135 B2

303 304

-continued

| # | Compound | LCMS (observed) (M + H)+ |
|---|---|---|
| 499 | | 823.35 |
| 503 | | 837.35 |
| 507 | | 865.32 |
| 510 | | 880.0 |
| 516 | | 836.04 |

-continued

| # | Compound | LCMS (observed) (M + H)+ |
|---|---|---|
| 518 | | 803.2 Chiral |
| 526 | | 806.11 Chiral |
| 536 | | 838.29 |
| 588 | | 842.10 Chiral |
| 602 | | 847.99 |

| # | Compound | LCMS (observed) (M + H)+ |
|---|---|---|
| 603 | | 822.02 |
| 617 | | 854.19 |
| 626 | | 885.80 |
| 643 | | 878.15 |

| # | Compound | LCMS (observed) (M + H)+ |
|---|---|---|
| 646 | 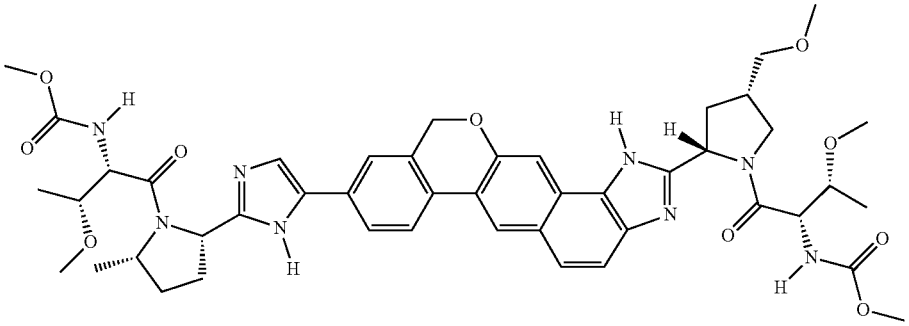 | 881.66 |

Biological Assays

Effect of Serum Proteins on Replicon Potency:

Replicon assays are conducted in normal cell culture medium (DMEM+10% FBS) supplemented with physiologic concentrations of human serum albumin (40 mg/mL) or α-acid glycoprotein (1 mg/mL). $EC_{50}$s in the presence of human serum proteins are compared to the $EC_{50}$ in normal medium to determine the fold shift in potency.

MT-4 Cell Cytotoxicity:

MT4 cells are treated with serial dilutions of compounds for a five day period. Cell viability is measured at the end of the treatment period using the Promega CellTiter-Glo assay and non-linear regression is performed to calculate $CC_{50}$.

Compound Concentration Associated with Cells at $EC_{50}$:

Huh-luc cultures are incubated with compound at concentrations equal to $EC_{50}$. At multiple time points (0-72 hours), cells are washed 2× with cold medium and extracted with 85% acetonitrile; a sample of the media at each time-point will also be extracted. Cell and media extracts are analyzed by LC/MS/MS to determine the Molar concentration of compounds in each fraction. Representative compounds of the disclosure have shown activity.

Solubility and Stability:

Solubility is determined by taking an aliquot of 10 mM DMSO stock solution and preparing the compound at a final concentration of 100 M in the test media solutions (PBS, pH 7.4 and 0.1 N HCl, pH 1.5) with a total DMSO concentration of 1%. The test media solutions are incubated at room temperature with shaking for 1 hr. The solutions will then be centrifuged and the recovered supernatants are assayed on the HPLC/UV. Solubility will be calculated by comparing the amount of compound detected in the defined test solution compared to the amount detected in DMSO at the same concentration. Stability of compounds after an 1 hour incubation with PBS at 37° C. will also be determined.

Stability in Cryopreserved Human, Dog, and Rat Hepatocytes:

Each compound is incubated for up to 1 hour in hepatocyte suspensions (100 μl, 80,000° Cells per well) at 37° C. Cryopreserved hepatocytes are reconstituted in the serum-free incubation medium. The suspension is transferred into 96-well plates (50 μL/well). The compounds are diluted to 2 μM in incubation medium and then are added to hepatocyte suspensions to start the incubation. Samples are taken at 0, 10, 30 and 60 minutes after the start of incubation and reaction will be quenched with a mixture consisting of 0.3% formic acid in 90% acetonitrile/10% water. The concentration of the compound in each sample is analyzed using LC/MS/MS. The disappearance half-life of the compound in hepatocyte suspension is determined by fitting the concentration-time data with a monophasic exponential equation. The data will also be scaled up to represent intrinsic hepatic clearance and/or total hepatic clearance.

Stability in Hepatic S9 Fraction from Human, Dog, and Rat:

Each compound is incubated for up to 1 hour in S9 suspension (500 μl, 3 mg protein/mL) at 37° C. (n=3). The compounds are added to the S9 suspension to start the incubation. Samples are taken at 0, 10, 30, and 60 minutes after the start of incubation. The concentration of the compound in each sample is analyzed using LC/MS/MS. The disappearance half-life of the compound in S9 suspension is determined by fitting the concentration-time data with a monophasic exponential equation.

Caco-2 Permeability:

Compounds are assayed via a contract service (Absorption Systems, Exton, Pa.). Compounds are provided to the contractor in a blinded manner. Both forward (A-to-B) and reverse (B-to-A) permeability will be measured. Caco-2 monolayers are grown to confluence on collagen-coated, microporous, polycarbonate membranes in 12-well Costar TRANSWELL® plates. The compounds are dosed on the apical side for forward permeability (A-to-B), and are dosed on the basolateral side for reverse permeability (B-to-A). The cells are incubated at 37° C. with 5% $CO_2$ in a humidified incubator. At the beginning of incubation and at 1 hr and 2 hr after incubation, a 200-μL aliquot is taken from the receiver chamber and replaced with fresh assay buffer. The concentration of the compound in each sample is determined with LC/MS/MS. The apparent permeability, Papp, is calculated.

Plasma Protein Binding:

Plasma protein binding is measured by equilibrium dialysis. Each compound is spiked into blank plasma at a final concentration of 2 μM. The spiked plasma and phosphate buffer is placed into opposite sides of the assembled dialysis cells, which will then be rotated slowly in a 37° C. water bath. At the end of the incubation, the concentration of the compound in plasma and phosphate buffer is determined. The percent unbound is calculated using the following equation:

$$\% \text{ Unbound} = 100 \cdot \left(\frac{C_f}{C_b + C_f}\right)$$

Where $C_f$ and $C_b$ are free and bound concentrations determined as the post-dialysis buffer and plasma concentrations, respectively.

CYP450 Profiling:

Each compound is incubated with each of 5 recombinant human CYP450 enzymes, including CYP1A2, CYP2C9, CYP3A4, CYP2D6 and CYP2C19 in the presence and absence of NADPH. Serial samples will be taken from the incubation mixture at the beginning of the incubation and at 5, 15, 30, 45 and 60 minutes after the start of the incubation. The concentration of the compound in the incubation mixture is determined by LC/MS/MS. The percentage of the compound remaining after incubation at each time point is calculated by comparing with the sampling at the start of incubation.

Stability in Rat, Dog, Monkey and Human Plasma:

Compounds will be incubated for up to 2 hours in plasma (rat, dog, monkey, or human) at 37° C. Compounds are added to the plasma at final concentrations of 1 and 10 µg/mL. Aliquots are taken at 0, 5, 15, 30, 60, and 120 minutes after adding the compound. Concentration of compounds and major metabolites at each time point are measured by LC/MS/MS.

Evaluation of Cell-Based Anti-HCV Activity:

Antiviral potency ($EC_{50}$) was determined using a Renilla luciferase (RLuc)-based HCV replicon reporter assay. To perform the assay for genotype 1 and 2a JFH-1, stable HCV 1a RLuc replicon cells (harboring a dicistronic genotype 1a H77 replicon that encodes a RLuc reporter), stable HCV 1b RLuc replicon cells (harboring a dicistronic genotype 1b Con1 replicon that encodes a RLuc reporter), or stable HCV 2a JFH-1 Rluc replicon cells (harboring a dicistronic genotype 2a JFH-1 replicon that encodes a RLuc reporter; with L31 present in NS5A) were dispensed into 384-well plates for $EC_{50}$ assays. To perform the assay for genotype 2a (with M31 present in NS5A) or 2b, NS5A chimeric genotype 2a JFH-1 replicons that encodes a RLuc-Neo reporter and either genotype 2a J6 strain NS5A gene or genotype 2b MD2b-1 strain NS5A gene (both with M31 present) respectively, were either transiently transfected (t) into Huh-Lunet cells or were established as stably replicating replicon cells (s) is provided. Either cells were dispensed into 384-well plates for $EC_{50}$ assays. To perform the assay for genotype 3 and 4, NS5A chimeric genotype 1b Con1 replicons that encodes a Pi-RLuc reporter and either genotype 3a S52 strain NS5A gene or genotype 4a ED43 strain NS5A gene respectively, were transiently transfected (t) into Huh-Lunet cells, which were subsequently dispensed into 384-well plates. Compounds were dissolved in DMSO at a concentration of 10 mM and diluted in DMSO either manually or using an automated pipeting instrument. Serially 3-fold diluted compounds were either manually mixed with cell culture media and added to the seeded cells or directly added to the cells using an automated instrument. DMSO was used as a negative (solvent; no inhibition) control, and the protease inhibitor ITMN-191 was included at a concentration >100×$EC_{50}$ as a positive control. 72 hours later, cells were lysed and Renilla luciferase activity quantified as recommended by the manufacturer (Promega-Madison, Wis.). Non-linear regression was performed to calculate $EC_{50}$ values.

To determine the antiviral potency ($EC_{50}$) against resistance mutants, resistance mutations, including M28T, Q30R, Q30H, L31M, and Y93C in genotype 1a NS5A and Y93H in genotype 1b NS5A, were introduced individually into either 1a Pi-Rluc or 1b Pi-Rluc replicons by site directed mutagenesis. Replicon RNA of each resistant mutant was transiently transfected into Huh-7-derived cured-51 cells and antiviral potency was determined on these transfected cells as described above.

The $EC_{50}$ ranges for genotype 1a, 1a Q30R, and 2a JFH are as follows: A ≥44 nM, B=1 nM to 43.99 nM, C<1 nM. The $EC_{50}$ ranges for genotype 2a J6, 2b, 3a, and 4a are as follows: A ≥5 nM, B=1 nM to 4.99 nM, C<1 nM. The $EC_{50}$ ranges for genotype 2a J6, 2b, and 4a correspond to the assay of transiently transfected cells (t). If this data is unavailable, the $EC_{50}$ range for the stably replicating cells (s) is provided.

IV and PO Single Dose Pharmacokinetic Studies in SD Rats:

The pharmacokinetics of selected compounds was characterized in male Sprague-Dawley (SD) rats (250-300g). In this study, two groups of naïve purebred SD rats (N=3 per group, fasted over night) received the selected compound either as an intravenous (IV) infusion (1 mg/kg over 30 minutes) via the jugular vein or by oral gavage (2 mg/kg). The intravenous (IV) dosing vehicle was 5% ethanol, 35% polyethylene glycol 400 (PEG 400) and 60% water pH 2.0. The oral dosing vehicle was 5% ethanol, 55% PEG 400 and 40% citrate buffer pH 2.2.

Serial blood samples (approximately 0.3 mL each) were collected from jugular vein or other suitable vein at specified time points. For the IV infusion group, the blood samples were collected predose and at 0.25, 0.48, 0.58, 0.75, 1.5, 3, 6, 8, 12 and 24 hours after the start of infusion. For the oral group, the blood samples were collected predose and at 0.25, 0.50, 1, 2, 4, 6, 8, 12 and 24 hours after dosing. The blood samples were collected into Vacutainer™ tubes containing EDTA-$K_3$ as the anti-coagulant and were centrifuged at approximately 4° C. to obtain plasma. The plasma samples were stored at −20° C. until analysis by LC/MS/MS.

A bioanalytical method utilizing high performance liquid chromatography coupled to tandem mass spectrometry (LC/MS/MS) was developed for analysis of the selected compound in rat plasma. Detection was performed using selected reaction monitoring (SRM); Ions representing the precursor (M+H) species was selected in quadrupole 1 (Q1) and collided with argon gas in the collision cell (Q2) to generate specific product ion, which was subsequently monitored by quadrupole 3 (Q3). Standard curve and quality control samples were prepared in male rat plasma and processed in the same way as the test samples to generate quantitative data.

Pharmacokinetic parameters were generated using non-compartmental pharmacokinetic analysis (Phoenix WinNonlin, version 6.3). Values below the lower limit of quantification (LLOQ) were assigned a value of zero if predose and treated as missing thereafter. Area under the curve (AUC) was calculated using the linear trapezoidal rule. The oral bioavailability (% F) was determined by comparison of the area under the curve (AUC) of the compound and/or a metabolite generated in plasma following oral administration to that generated following intravenous administration.

| # | Example No. | 1b (nM) | 1a | 1a Q30R | 2a JFH | 2a J6 | 2b | 3a | 4a | 1a (nM) | 1a Q30R (nM) | 2a JFH (nM) | 2a Jb (t) (nM) | 2a J6 (s) (nM) | 2b (t) (nM) | 2b (s) (nM) | 3a (nM) | 4a (t) (nM) | 4a (s) (nM) | Rat % F |
|---|---|---|---|---|---|---|---|---|---|---|---|---|---|---|---|---|---|---|---|---|
| 422 | MC | 0.017 | C | C | C | B | C | C | C | 0.016 | 0.990 | 0.004 | 1.155 | 3.523 | 0.162 | 0.375 | 0.004 | 0.008 | 0.028 | |
| 423 | LQ | 0.020 | C | C | C | C | C | C | C | 0.022 | 0.135 | 0.004 | 0.134 | 0.543 | 0.012 | 0.035 | 0.005 | 0.008 | 0.02 | |
| 426 | MD | 0.033 | C | C | C | C | C | C | C | 0.035 | 0.192 | 0.006 | 0.073 | 0.439 | 0.016 | 0.038 | 0.006 | 0.011 | 0.035 | |
| 427 | ME | 0.049 | C | B | C | B | C | C | C | 0.033 | 2.514 | 0.012 | 3.428 | 16.075 | 0.198 | 0.701 | 0.015 | 0.016 | 0.029 | |
| 434 | MG | 0.055 | C | C | C | C | C | C | C | 0.054 | 0.663 | 0.012 | 0.337 | 2.288 | | 0.070 | 0.010 | 0.024 | 0.08 | |
| 435 | MF | 0.058 | C | C | C | C | C | C | C | 0.059 | 0.768 | 0.012 | 0.476 | 2.136 | | 0.083 | 0.011 | 0.025 | | |
| 478 | 478 | 0.048 | C | | C | B | C | C | C | 0.045 | | 0.011 | | 3.654 | | 0.820 | 0.065 | 0.023 | 0.019 | |
| 493 | 493 | 0.030 | C | | C | A | C | C | C | 0.036 | | 0.008 | | 5.036 | | 0.650 | 0.050 | 0.013 | 0.018 | |
| 494 | 494 | 0.021 | C | C | C | C | C | C | C | 0.037 | 0.118 | 0.005 | | 0.098 | | 0.017 | 0.005 | 0.017 | 0.031 | |
| 495 | 495 | 0.026 | C | C | C | C | C | C | C | 0.021 | 0.201 | 0.008 | 0.280 | 1.016 | 0.135 | 0.541 | 0.024 | 0.014 | 0.014 | |
| 498 | 498 | 0.016 | C | C | C | C | C | C | C | 0.030 | 0.040 | 0.004 | 0.012 | 0.039 | 0.010 | 0.013 | 0.005 | 0.011 | 0.004 | |
| 499 | 499 | 0.032 | C | | C | C | C | C | C | 0.057 | | 0.008 | | 0.206 | | 0.040 | 0.010 | 0.021 | 0.005 | |
| 503 | 503 | 0.041 | C | | C | C | C | C | C | 0.062 | | 0.012 | | 0.155 | | 0.037 | 0.015 | 0.028 | 0.025 | |
| 507 | 507 | 1.503 | B | | C | A | B | C | C | 3.698 | 0.297 | | | 20.096 | | 1.561 | 0.382 | 0.594 | 0.025 | |
| 510 | 510 | 0.050 | C | | C | C | C | C | C | 0.021 | | 0.009 | 0.007 | 0.018 | 0.017 | 0.020 | 0.008 | 0.016 | 0.072 | |
| 516 | 516 | 0.024 | C | | C | C | C | C | C | 0.015 | | 0.009 | | 0.043 | | 0.013 | 0.005 | 0.010 | 0.025 | |
| 518 | 518 | 0.010 | C | | C | B | C | C | C | 0.005 | | 0.006 | | 2.493 | | 0.643 | 0.005 | 0.004 | 0.011 | |
| 526 | 526 | 0.018 | C | C | C | C | C | C | C | 0.011 | 0.095 | 0.007 | 0.443 | 1.639 | 0.132 | 0.404 | 0.018 | 0.011 | 0.011 | |
| 536 | 536 | 0.013 | C | C | C | C | C | C | C | 0.008 | 0.048 | 0.004 | 0.040 | 0.154 | 0.011 | 0.037 | 0.009 | 0.005 | 0.01 | |
| 538 | LR-1 | 0.016 | C | C | C | C | C | C | C | 0.011 | 0.015 | 0.005 | 0.018 | 0.048 | 0.010 | 0.024 | 0.013 | 0.010 | 0.012 | |
| 539 | LT | 0.016 | C | C | C | C | C | C | C | 0.009 | 0.010 | 0.004 | 0.010 | 0.047 | 0.009 | 0.039 | 0.012 | 0.015 | 0.009 | |
| 543 | MY | 0.015 | C | C | C | C | C | C | C | 0.016 | 0.024 | 0.005 | 0.047 | 0.165 | 0.016 | 0.047 | 0.010 | 0.008 | 0.02 | |
| 544 | MM | 0.026 | C | C | C | C | C | C | C | 0.022 | 0.044 | 0.007 | 0.018 | 0.064 | 0.015 | 0.042 | 0.020 | 0.017 | 0.016 | |
| 551 | OQ | 0.018 | C | C | C | C | C | C | C | 0.015 | 0.102 | 0.007 | 0.378 | 1.492 | 0.265 | 0.982 | 0.048 | 0.020 | 0.016 | |
| 552 | OR | 0.033 | C | C | C | C | C | C | C | 0.030 | 0.059 | 0.011 | 0.068 | 0.160 | 0.037 | 0.109 | 0.031 | 0.036 | 0.006 | |
| 555 | MN | 0.021 | C | C | C | C | C | C | | 0.014 | 0.018 | 0.008 | 0.017 | 0.071 | 0.013 | 0.040 | 0.034 | 0.024 | 0.007 | 1.5 |
| 556 | MS | 0.008 | C | | C | A | A | | C | 0.008 | | 0.005 | | 15.564 | | 9.562 | | 0.014 | 0.02 | |
| 558 | PQ | 0.014 | C | C | C | C | C | | C | 0.014 | 0.106 | 0.005 | 0.025 | 0.155 | 0.032 | 0.057 | | 0.015 | 0.017 | |
| 561 | MP | 0.010 | C | C | C | C | C | C | C | 0.006 | 0.031 | 0.004 | 0.039 | 0.336 | 0.032 | 0.184 | 0.015 | 0.015 | 0.013 | 24.2 |
| 562 | MO | 0.019 | C | C | C | C | C | C | C | 0.013 | 0.052 | 0.007 | 0.089 | 0.471 | 0.137 | 0.427 | 0.051 | 0.022 | 0.018 | 7.46 |
| 563 | MT | 0.007 | C | | C | A | A | B | C | 0.003 | | 0.021 | | 44.444 | | 44.444 | 1.092 | 0.015 | 0.025 | |
| 565 | NB | 0.017 | C | C | C | C | C | C | C | 0.010 | 0.034 | 0.004 | 0.020 | 0.138 | 0.007 | 0.039 | 0.011 | 0.023 | 0.025 | |
| 566 | NC | 0.009 | C | C | C | C | C | C | C | 0.007 | 0.060 | 0.005 | 0.089 | 0.762 | 0.068 | 0.191 | 0.014 | 0.011 | 0.026 | |
| 569 | ND | 0.024 | C | C | C | C | C | C | C | 0.020 | 0.057 | 0.014 | 0.314 | 2.338 | 0.270 | 1.319 | 0.035 | 0.031 | 0.044 | |
| 571 | OO | 0.114 | C | C | C | C | C | C | C | 0.072 | 0.139 | 0.015 | 0.028 | 0.259 | 0.020 | 0.076 | 0.028 | 0.086 | 0.018 | |
| 572 | PF | 0.044 | C | C | C | C | C | C | C | 0.032 | 0.034 | 0.014 | 0.025 | 0.127 | 0.023 | 0.117 | 0.072 | 0.050 | 0.018 | 4.3 |
| 573 | PG | 0.030 | C | C | C | C | C | C | C | 0.033 | 0.043 | 0.018 | 0.045 | 0.335 | 0.027 | 0.119 | 0.050 | 0.063 | 0.008 | |
| 574 | PN | 0.016 | C | C | C | C | C | C | C | 0.015 | 0.030 | 0.009 | 0.027 | 0.277 | 0.014 | 0.035 | 0.016 | 0.014 | 0.02 | |
| 575 | PP | 0.029 | C | C | C | C | C | C | C | 0.014 | 0.043 | 0.011 | 0.061 | 0.403 | 0.038 | 0.110 | 0.019 | 0.027 | 0.011 | |
| 576 | PO | 0.014 | C | | C | B | C | C | C | 0.013 | | 0.011 | | 3.135 | | 0.470 | 0.012 | 0.013 | 0.013 | |
| 579 | OI | 0.034 | C | C | C | C | C | C | C | 0.024 | 0.086 | 0.010 | 0.061 | 0.326 | 0.178 | 0.629 | 0.206 | 0.036 | 0.007 | |
| 580 | OJ | 0.017 | C | | C | C | C | C | C | 0.018 | | 0.013 | | 0.502 | | 0.813 | 0.259 | 0.026 | 0.017 | |
| 582 | NF | 0.010 | C | C | C | C | C | C | C | 0.011 | 0.017 | 0.006 | 0.031 | 0.218 | 0.018 | 0.064 | 0.017 | 0.009 | 0.012 | |
| 585 | NG | 0.009 | C | C | C | C | C | C | | 0.006 | 0.243 | 0.010 | 0.370 | 1.672 | 0.063 | 0.135 | 0.020 | 0.008 | | |
| 587 | MR | 0.041 | C | C | C | C | C | C | | 0.028 | 0.128 | 0.017 | 0.079 | 0.176 | 0.039 | 0.053 | 0.078 | 0.045 | | |
| 588 | 588 | 0.017 | C | C | C | C | C | C | | 0.012 | 0.087 | 0.004 | 0.038 | 0.140 | 0.012 | 0.017 | 0.027 | 0.019 | | |
| 589 | MQ | 0.011 | C | C | C | C | C | C | | 0.008 | 0.023 | 0.004 | 0.017 | 0.095 | 0.009 | 0.023 | 0.016 | 0.011 | | |
| 590 | MU | 0.014 | C | C | C | C | C | C | | 0.008 | 0.023 | 0.004 | 0.013 | 0.046 | 0.009 | 0.025 | 0.017 | 0.011 | | |
| 592 | NI | 0.015 | C | C | C | C | C | C | C | 0.015 | 0.059 | 0.007 | 0.026 | 0.169 | 0.019 | 0.054 | 0.022 | 0.020 | | 24.1 |
| 594 | NP | 0.013 | C | C | C | C | C | C | C | 0.014 | 0.032 | 0.007 | 0.010 | 0.096 | 0.011 | 0.043 | 0.020 | | 0.028 | 26.1 |
| 597 | NJ | 0.005 | C | C | C | C | C | C | C | 0.007 | 0.025 | 0.007 | 0.099 | 0.939 | 0.094 | 0.416 | 0.019 | | 0.017 | |
| 599 | PY | 0.009 | C | C | C | C | C | C | C | 0.012 | 0.013 | 0.006 | 0.009 | 0.098 | 0.007 | 0.030 | 0.017 | | 0.018 | 27.7 |
| 600 | PZ | 0.007 | C | C | C | C | C | C | | 0.009 | 0.057 | 0.005 | 0.175 | 1.712 | 0.071 | 0.386 | | | 0.025 | |
| 601 | MV | 0.014 | C | C | C | C | C | C | | 0.010 | 0.012 | 0.004 | 0.047 | 0.034 | 0.041 | | 0.011 | | 0.011 | |
| 602 | 602 | 0.025 | C | | C | C | C | | C | 0.025 | | 0.010 | 0.053 | | 0.036 | 0.036 | | | 0.013 | |
| 603 | 603 | 0.015 | C | C | C | C | C | C | | 0.009 | 0.146 | 0.007 | 0.194 | | 0.067 | 0.088 | 0.015 | | 0.022 | |
| 604 | NR | 0.020 | C | | C | C | C | | C | 0.026 | | 0.006 | 0.118 | | 0.017 | 0.017 | | | 0.007 | |
| 605 | NQ | 0.015 | C | C | C | C | C | C | | 0.017 | 0.039 | 0.006 | 0.064 | | 0.013 | 0.012 | 0.013 | | | |
| 606 | OK | 0.034 | C | C | C | C | C | C | | 0.026 | 0.039 | 0.011 | 0.076 | | 0.036 | 0.045 | 0.028 | | | |
| 607 | OL | 0.067 | C | | C | C | C | | | 0.047 | | 0.012 | 0.070 | | 0.052 | 0.052 | | | | |
| 608 | OH | 0.017 | C | C | C | C | C | C | | 0.016 | 0.031 | 0.007 | 0.054 | | 0.023 | 0.022 | 0.026 | | | 22.7 |
| 609 | QF | 0.005 | C | C | C | C | C | C | | 0.008 | 0.032 | 0.004 | 0.053 | | 0.015 | 0.011 | 0.020 | | | |
| 610 | QA | 0.013 | C | C | C | C | C | C | | 0.012 | 0.045 | 0.007 | 0.094 | | 0.052 | 0.040 | 0.038 | | | 7.46 |
| 612 | QH | 0.005 | C | C | C | C | C | C | | 0.007 | 0.051 | 0.005 | 0.182 | | 0.051 | 0.049 | 0.020 | | | |
| 613 | QG | 0.005 | C | C | C | C | C | C | | 0.005 | 0.071 | 0.004 | 0.551 | | 0.065 | 0.043 | 0.016 | | | |
| 614 | OP | 0.013 | C | C | C | C | C | C | | 0.013 | 0.026 | 0.008 | 0.018 | | 0.011 | 0.007 | 0.027 | | | 15.1 |
| 615 | OM | 0.019 | C | C | C | C | C | C | | 0.014 | 0.035 | 0.009 | 0.045 | | 0.053 | 0.054 | 0.035 | | | 12.2 |
| 617 | 617 | 0.005 | C | C | C | C | C | C | | 0.009 | 0.024 | 0.004 | 0.032 | | 0.013 | 0.011 | 0.019 | | | 14.4 |
| 618 | OT | 0.020 | C | C | C | C | C | C | | 0.011 | 0.041 | 0.005 | 0.013 | | 0.012 | | 0.024 | | | |
| 619 | OF | 0.007 | C | | C | C | C | | | 0.010 | | 0.008 | 0.445 | | 0.196 | | | | | |
| 620 | NK | 0.081 | C | | C | C | C | | | 0.049 | | 0.018 | 0.056 | | 0.154 | | | | | |
| 621 | NL | 0.013 | C | | C | C | C | | | 0.011 | | 0.007 | 0.043 | | 0.034 | | | | | |
| 622 | NM | 0.016 | C | C | C | C | C | C | | 0.011 | 0.028 | 0.006 | 0.012 | | 0.013 | | 0.024 | | | 6.93 |
| 623 | ON | 0.006 | C | C | C | C | C | | | 0.005 | | 0.004 | 0.068 | | 0.086 | | | | | |
| 625 | PH | 0.031 | C | C | C | C | C | C | | 0.024 | 0.051 | 0.014 | 0.055 | | 0.042 | | 0.029 | | | |
| 626 | 626 | 0.030 | C | C | C | C | C | C | | 0.021 | 0.041 | 0.009 | 0.021 | | 0.021 | | 0.027 | | | |

-continued

| # | Example No. | 1b (nM) | 1a | 1a Q30R | 2a JFH | 2a J6 | 2b | 3a | 4a | 1a (nM) | 1a Q30R (nM) | 2a JFH (nM) | 2a Jb (t) (nM) | 2a J6 (s) (nM) | 2b (t) (nM) | 2b (s) (nM) | 3a (nM) | 4a (t) (nM) | 4a (s) (nM) | Rat % F |
|---|---|---|---|---|---|---|---|---|---|---|---|---|---|---|---|---|---|---|---|---|
| 627 | PI | 0.039 | C | C | C | C | C | C |  | 0.031 | 0.094 | 0.020 | 0.129 |  | 0.090 |  | 0.065 |  |  | 8.7 |
| 628 | OG | 0.009 | C |  | C | C | C |  |  | 0.009 |  | 0.008 | 0.601 |  | 0.437 |  |  |  |  |  |
| 631 | PS | 0.006 | C |  | C | C | C | A |  | 0.005 |  | 0.004 | 0.077 |  | 0.113 |  | 44.444 |  |  |  |
| 632 | PT | 0.008 | C |  | C | C | C |  |  | 0.007 |  | 0.007 | 0.383 |  | 0.182 |  |  |  |  |  |
| 633 | PR | 0.020 | C | C | C | C | C | C |  | 0.013 | 0.045 | 0.007 | 0.022 |  | 0.028 |  | 0.018 |  |  |  |
| 634 | PU | 0.015 | C |  | C | C | C |  |  | 0.012 |  | 0.006 | 0.068 |  | 0.442 |  |  |  |  |  |
| 635 | OU | 0.041 | C |  | C | C | C |  |  | 0.047 |  | 0.016 | 0.040 |  | 0.035 |  |  |  |  |  |
| 636 | OV | 0.011 | C | C | C | C | C | C |  | 0.010 | 0.031 | 0.007 | 0.113 |  | 0.046 |  | 0.013 |  |  |  |
| 637 | OW | 0.009 | C | C | C | C | C | C |  | 0.009 | 0.019 | 0.006 | 0.009 |  | 0.008 |  | 0.013 |  |  | 13.3 |
| 638 | OX | 0.009 | C |  | C | C | C |  |  | 0.007 |  | 0.006 | 0.113 |  | 0.107 |  |  |  |  |  |
| 639 | QB | 0.011 | C | C | C | C | C | C |  | 0.011 | 0.029 | 0.008 | 0.021 |  | 0.022 |  | 0.028 |  |  | 9.56 |
| 640 | QE | 0.015 | C |  | C | C | C |  |  | 0.013 |  | 0.011 | 0.291 |  | 0.563 |  |  |  |  |  |
| 641 | QD | 0.030 | C |  | C | C | C |  |  | 0.025 |  | 0.013 | 0.103 |  | 0.193 |  |  |  |  |  |
| 642 | QC | 0.014 | C |  | C | C | C |  |  | 0.012 |  | 0.008 | 0.157 |  | 0.317 |  |  |  |  |  |
| 643 | 643 | 0.015 | C |  | C | C | C |  |  | 0.015 |  | 0.013 | 0.206 |  | 0.607 |  |  |  |  |  |
| 644 | MW | 0.026 | C |  | C | C | C |  | C | 0.012 |  | 0.012 | 0.020 |  | 0.043 | 0.123 |  |  | 0.011 |  |
| 645 | MX | 0.076 | C |  | C | C | C |  | C | 0.036 |  | 0.024 | 0.035 |  | 0.070 | 0.139 |  |  | 0.033 |  |
| 646 | 646 | 0.109 | C |  | C | C | C |  | C | 0.058 |  | 0.030 | 0.042 |  | 0.112 | 0.262 |  |  | 0.034 |  |
| 648 | PJ | 0.088 | C |  | C | C | C |  | C | 0.068 |  | 0.058 | 0.136 |  | 0.335 | 0.854 |  |  | 0.056 |  |

The invention claimed is:

1. A compound of the formula:

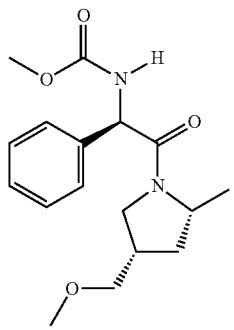

or a pharmaceutically acceptable salt thereof.

2. A pharmaceutical composition comprising a compound of the formula:

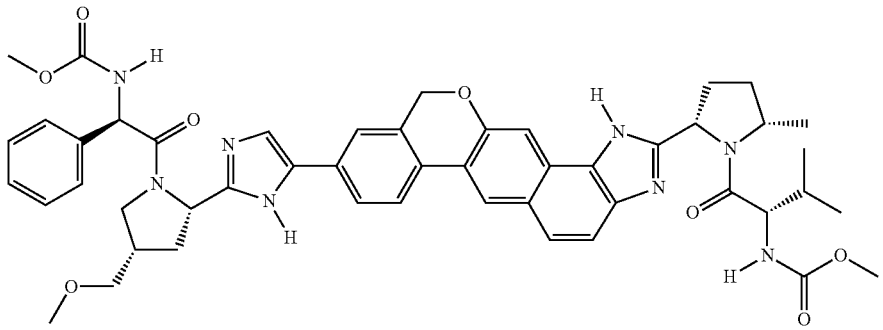 [SMILES: COC[C@H]1C[C@@H](c2ncc(-c3ccc4c(c3)COc3cc5c(ccc6nc([C@@H]7CC[C@H](C)N7C(=O)[C@@H](NC(=O)OC)C(C)C)[nH]c65)cc3-4)[nH]2)N(C(=O)[C@H](NC(=O)OC)c2ccccc2)C1]

or a pharmaceutically acceptable salt thereof; and a pharmaceutically acceptable carrier.

3. The pharmaceutical composition of claim 2, further comprising nucleoside or nucleotide inhibitors of hepatitis C virus NS5B polymerase.

4. A method of treating hepatitis C in a human patient in need thereof, said method comprising administering to the human patient in need thereof a pharmaceutical composition which comprises a therapeutically effective amount of the compound of the formula:

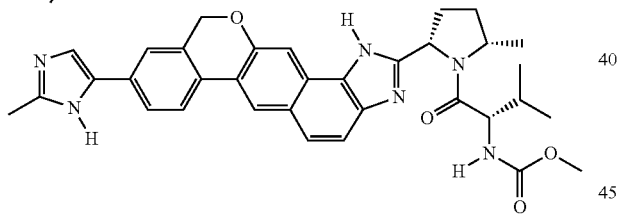

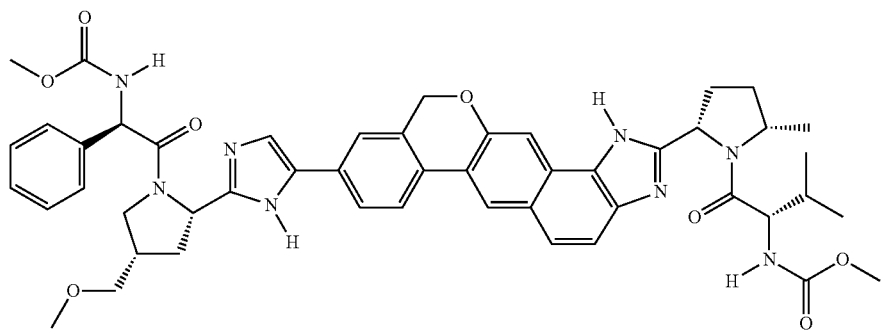 [SMILES: COC[C@H]1C[C@@H](c2ncc(-c3ccc4c(c3)COc3cc5c(ccc6nc([C@@H]7CC[C@H](C)N7C(=O)[C@@H](NC(=O)OC)C(C)C)[nH]c65)cc3-4)[nH]2)N(C(=O)[C@H](NC(=O)OC)c2ccccc2)C1]

or a pharmaceutically acceptable salt thereof.

5. The method of claim 4, further comprising administering a nucleoside or nucleotide inhibitor of hepatitis C virus NS5B polymerase to the patient.

6. The method of claim 5, further comprising administering an interferon or pegylated interferon to the patient.

7. The method of claim 5, further comprising administering ribavirin to the patient.

* * * * *

UNITED STATES PATENT AND TRADEMARK OFFICE
CERTIFICATE OF CORRECTION

PATENT NO. : 8,575,135 B2
APPLICATION NO. : 13/783056
DATED : November 5, 2013
INVENTOR(S) : Bacon et al.

Page 1 of 2

It is certified that error appears in the above-identified patent and that said Letters Patent is hereby corrected as shown below:

IN THE CLAIMS

Column 315, Line 25, Claim 1, please replace the structure of:

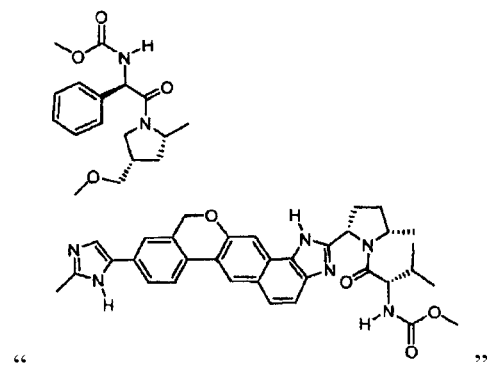

"         "

with the structure shown below:

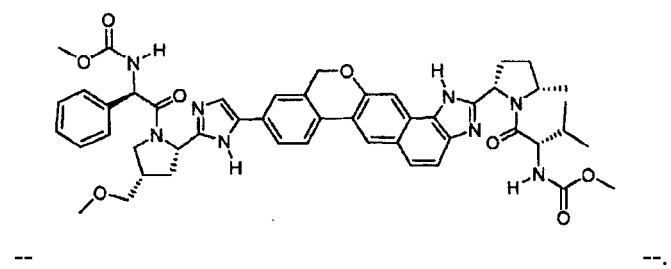

--         --.

Column 316, Line 25, Claim 3, please replace "comprising nucleoside or nucleotide inhibitors" with --comprising a nucleoside or nucleotide inhibitor--.

Column 316, Line 27, Claim 4, delete "hepatitis C in a human" and replace with --hepatitis C virus in a human--.

Signed and Sealed this
Eighth Day of July, 2014

Michelle K. Lee
*Deputy Director of the United States Patent and Trademark Office*

CERTIFICATE OF CORRECTION (continued)
U.S. Pat. No. 8,575,135 B2

IN THE CLAIMS

Column 316, Line 29, Claim 4, please replace "human patient in need thereof a pharmaceutical" with --human patient a pharmaceutical--.